United States Patent
Dasseux

(10) Patent No.: US 11,634,387 B2
(45) Date of Patent: Apr. 25, 2023

(54) COMPOUNDS USEFUL FOR TREATING LIVER DISEASES

(71) Applicant: ABIONYX PHARMA SA, Balma (FR)

(72) Inventor: Jean-Louis Henri Dasseux, Toulouse (FR)

(73) Assignee: Abionyx Pharma SA, Balma (FR)

( * ) Notice: Subject to any disclaimer, the term of this patent is extended or adjusted under 35 U.S.C. 154(b) by 0 days.

(21) Appl. No.: 17/219,058

(22) Filed: Mar. 31, 2021

(65) Prior Publication Data

US 2022/0363632 A1 Nov. 17, 2022

Related U.S. Application Data

(63) Continuation-in-part of application No. 17/195,334, filed on Mar. 8, 2021, now abandoned, and a continuation-in-part of application No. PCT/IB2020/000808, filed on Sep. 25, 2020.

(60) Provisional application No. 62/906,288, filed on Sep. 26, 2019.

(51) Int. Cl.
| | |
|---|---|
| *C07C 323/19* | (2006.01) |
| *A61P 13/12* | (2006.01) |
| *A61P 3/06* | (2006.01) |
| *A61P 3/10* | (2006.01) |

(52) U.S. Cl.
CPC ............. *C07C 323/19* (2013.01); *A61P 3/06* (2018.01); *A61P 3/10* (2018.01); *A61P 13/12* (2018.01)

(58) Field of Classification Search
CPC .................................................. C07C 323/19
See application file for complete search history.

(56) References Cited

U.S. PATENT DOCUMENTS

| | | |
|---|---|---|
| 7,265,137 B2 | 9/2007 | Sakuma et al. |
| 7,632,870 B2 | 12/2009 | Najib et al. |
| 7,648,999 B2 | 1/2010 | Sakuma et al. |
| 7,652,045 B2 | 1/2010 | Sakuma et al. |
| 8,258,182 B2 | 9/2012 | Delhomel et al. |
| 2019/0274982 A1 | 9/2019 | Laruelle et al. |
| 2020/0157074 A1 | 5/2020 | Downes et al. |
| 2020/0347037 A1 | 11/2020 | Lagu et al. |
| 2021/0283116 A1 | 9/2021 | Lagu et al. |

FOREIGN PATENT DOCUMENTS

| | | |
|---|---|---|
| EP | 1310494 A1 | 5/2003 |
| EP | 1424330 A1 | 6/2004 |
| EP | 1445258 A1 | 8/2004 |
| EP | 1897872 A1 | 3/2008 |
| EP | 2277874 A1 | 1/2011 |
| WO | 2001/000603 A1 | 1/2001 |
| WO | 2002/092590 A1 | 11/2002 |
| WO | 2003/072100 A1 | 11/2003 |
| WO | 2008/154023 | 12/2008 |
| WO | 2011/020001 A2 | 2/2011 |
| WO | 2019/076190 A1 | 4/2019 |
| WO | 2021/059023 A1 | 4/2021 |

OTHER PUBLICATIONS

International Search Report and Written Opinion dated Jan. 25, 2021 in connection with PCT/IB2020/000808.
International Search Report and Written Opinion dated Jul. 29, 2022 in connection with PCT/IB2022/000106.
Wang et al. 2013 "Differential sensitivities of the vascular KATP channel to various PPAR activators" Biochemical Pharmacology 85(10): 1495-1503.

*Primary Examiner* — Shawquia Jackson
(74) *Attorney, Agent, or Firm* — Biospark Intellectual Property Law

(57) ABSTRACT

This invention provides compounds, for example, of Formulae (A)-(H) and (J)-(AA) and pharmaceutically acceptable salts, solvates, esters, amides, and prodrugs thereof. The invention further provides pharmaceutical compositions comprising a compound of the invention, and a pharmaceutically acceptable carrier or vehicle. The compounds and compositions disclosed herein are useful for treating or preventing various diseases and conditions, for example liver disease such as liver fibrosis, fatty liver disease, non-alcoholic fatty liver disease (NAFLD) or non-alcoholic steatohepatitis (NASH), and kidney diseases such as acute kidney injury (AKI).

20 Claims, No Drawings

COMPOUNDS USEFUL FOR TREATING LIVER DISEASES

1. CROSS-REFERENCE TO RELATED APPLICATIONS

This application is a continuation in part of U.S. application Ser. No. 17/195,334, filed Mar. 8, 2021, and is a continuation-in part of, and claims the priority benefit of, international application no. PCT/IB2020/000808, filed Sep. 25, 2020, which claims the priority benefit of U.S. provisional application No. 62/906,288, filed Sep. 26, 2019, the contents of each of which are incorporated herein in their entireties by reference thereto.

2. FIELD OF THE INVENTION

This invention provides novel compounds, for example compounds of Formulae (A)-(H) and (J)-(AA), and pharmaceutically acceptable salts, solvates, esters, amides, and prodrugs thereof, such as 2-(4-(3-hydroxy-3-(4-(methylthio) phenyl)prop-1-en-1-yl)-2,6-dimethylphenoxy)-2-methyl-propanoic acid ("Compound I"), 3-(4-((1-hydroxy-2-methylpropan-2-yl)oxy)-3,5-dimethylphenyl)-1-(4-(methylthio) phenyl)prop-2-en-1-one ("Compound II"), and 3-(4-((1-hydroxy-2-methylpropan-2-yl)oxy)-3,5-dimethylphenyl)-1-(4-(methylthio)phenyl)prop-2-en-1-ol ("Compound III"), and pharmaceutically acceptable salts, solvates, esters, amides, and prodrugs thereof. The invention further provides pharmaceutical compositions comprising a novel compound described herein, for example a compound of Formulae (A)-(H) and (J)-(AA) or a pharmaceutically acceptable salt, solvate, ester, amide, or prodrug thereof, such as Compound I, Compound II or Compound III, or a pharmaceutically acceptable salt, solvate, ester, amide, or prodrug thereof, and a pharmaceutically acceptable carrier or vehicle. The compounds and compositions disclosed herein are useful for treating or preventing conditions, for example, liver disease such as liver fibrosis, fatty liver disease, non-alcoholic fatty liver disease (NAFLD) or non-alcoholic steatohepatitis (NASH).

3. BACKGROUND

Elevated levels of low-density lipoprotein cholesterol (LDL-C) and triglycerides are associated with mixed dyslipidemia. Type IIb hyperlipidemia, a type of mixed dyslipidemia, is characterized by elevation of apolipoprotein B, very low-density lipoprotein cholesterol (VLDL-C), intermediate density lipoprotein cholesterol (IDL), and small dense low-density lipoprotein (LDL) levels, in addition to elevation in LDL-C and triglyceride levels.

Liver diseases, such as a non-alcoholic fatty liver disease (NAFLD) comprise a spectrum of conditions ranging from relatively benign steatosis to more severe non-alcoholic steatohepatitis (NASH), the latter of which, if untreated, can lead to fibrosis, cirrhosis, liver failure, or hepatocellular carcinoma. NAFLD and NASH can develop due to hepatic triglyceride overproduction and accumulation. NAFLD is strongly associated with features of obesity, diabetes, dyslipidemia, hyperlipidemia and metabolic syndrome, including obesity, insulin resistance, type-2 diabetes mellitus, and dyslipidemia. NASH can cause the liver to swell, become inflamed, become fibrotic, become damaged and become ultimately less functional. NASH tends to develop in people who are overweight or obese, or have diabetes, mixed dyslipidemia, high cholesterol or high triglycerides or an inflammatory condition. NASH is marked by hepatocyte ballooning and liver inflammation, which can lead to liver damage and progress to scarring and irreversible changes, similar to the damage caused by heavy alcohol use.

Liver steatosis and fibrosis can also be induced by drugs, such as amiodarone, valproate, tamoxifen, methotrexate, and some chemotherapeutic and antiretroviral agents (Amacher, D. E., et al. Semin. Liver Dis., 2014, 34, 205). Drug-induced hepatic steatosis can be reversible and may involve drug accumulation in the liver.

NAFLD, NASH, fatty liver, or drug-induced liver steatosis can lead to metabolic complications including elevation of liver enzymes, fibrosis, cirrhosis, hepatocellular carcinoma, and liver failure. Liver failure is life-threatening and therefore there is a need to develop therapies to delay development, prevent formation or reverse the condition of a fatty liver.

Peroxisome proliferator-activated receptors (PPARs) have been identified as targets for the treatment of cardiometabolic diseases including diabetes, insulin resistance, dyslipidemia, and liver diseases such as NAFLD and NASH. There are three types of PPARs: PPARα, PPARγ and PPARδ. Several PPAR agonists have been marketed, including fenofibrate (a PPARα agonist), bezafibrate (a PPAR pan agonist), pioglitazone (a PPARγ agonist), and rosiglitazone (a PPARγ agonist). Recently, PPAR agonists such as seladelpar (a PPARδ agonist), lanifibranor (a pan agonist), and elafibranor (a dual PPARα/δ agonist) have been studied for the treatment of NASH and primary biliary cholangitis (PBC). However, several clinical trials involving such PPAR agonists have failed due to toxicity or failure to meet primary endpoint. For example, in a Phase 3 trial in adults with NASH and fibrosis, elafibranor did not demonstrate a statistically significant effect on the primary endpoint of NASH resolution without worsening of fibrosis (ir.genfit.com/news-releases/news-release-details/genfit-announces-results-interim-analysis-resolve-it-phase-3).

PPARδ agonists have also been proposed as a treatment for acute kidney injury (AKI). See, e.g., WO 2018/067857. AKI is a common occurrence in ICU patients, with an estimated incidence of >50% (Hoste et al., 2015, Intensive Care Med; 41:1411-1423). Furthermore, increasing AKI severity is associated with increased mortality. Sepsis is the major cause of AKI, accounting for 45% to 70% of cases, and approximately 25% of sepsis is of intra-abdominal origin (Seymour et al., 2016, JAMA, 315:762-774; Bagshaw et al., 2007, Clin J Am Soc Nephrol, 2:431-439). Ischemia/reperfusion injury (IRI) can cause AKI and is a common complication in subjects receiving an organ transplant, with an incidence of 50-75% after lung and heart transplantation (Gueler et al., 2014, Transplantation 98:337-338). The PPARδ agonist ASP1128 (also known as MA-0217) (Astellas) is being studied as a possible treatment for AKI following coronary artery bypass graft surgery and/or valve surgery (ClinicalTrials.gov identifier NCT03941483). To date, however, no PPARδ agonist has been approved and marketed as a treatment for AKI There remains a need for new preventions and treatments for liver disorders, kidney disorders and other conditions associated with PPARs.

4. SUMMARY OF THE INVENTION

The present invention provides novel compounds and their use to treat various disorders, for example, liver disorders such as NASH, kidney disorders such as AKI, and other conditions associated with PPARs. Without being bound by theory, the inventor believes that the clinical usefulness of PPAR agonists such as elafibranor are limited by their toxicity such that doses often cannot be increased sufficiently to reach an effective dose. The subject invention provides novel compounds, including derivatives of elafibranor and related compounds, and derivatives of PPAR modulators described in WO 2011/020001, WO 2017/06246, WO 2017/180818, and WO 2018/067857. Without being bound by theory, the inventor believes that the compounds described herein can act as PPAR agonists and/or as PPAR agonist prodrugs, which have advantageous properties that result in improved bioavailability and/or half-life and/or safety and/or efficacy and/or improved therapeutic indexes, following administration. In particular, the compound may thus have an improved therapeutic index. The therapeutic index (TI) is a ratio that compares the dose at which a compound becomes toxic against the dose at which it is effective. One common measure of TI is $TD_{50}/ED_{50}$, wherein $TD_{50}$ and $ED_{50}$ are the toxic and effective doses, respectively, for 50% of the population. The larger the TI, the safer a compound is. Compounds with a low TI can be difficult to use in clinical practice and often require monitoring of plasma concentration in order to prevent toxicity. The one or more advantageous properties of the compounds of the disclosure (compared to known PPAR agonists, such as elafibranor or one or more PPAR agonists described in WO 2011/020001, WO 2011/020001, WO 2017/06246, WO 2017/180818, and/or WO 2018/067857) can include, for example, better solubility, better kinetics, better absorption, better PPAR receptor selectivity at pharmaceutically effective doses, reduced drug metabolism by cytochrome P450 or other enzymes such as reductases, reduced glucuronidation, reduced toxicity, or a combination thereof.

In various aspects, the invention provides compounds of Formula (A)-(H) and (J)-(AA) and pharmaceutically acceptable salts, solvates, esters, amides, and prodrugs thereof.

In one aspect, the present invention provides compounds of Formula (A):

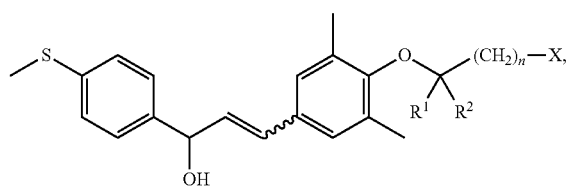

(A)

and pharmaceutically acceptable salts, solvates, esters, amides, and prodrugs thereof, wherein:
each $R^1$ and $R^2$ is independently —$C_1$-$C_6$ alkyl, —$C_2$-$C_6$ alkenyl, —$C_2$-$C_6$ alkynyl, phenyl, or benzyl; or alternatively, $R^1$ and $R^2$ together with the carbon atom to which $R^1$ and $R^2$ are attached form a $C_3$-$C_7$ cycloalkyl group;
X is —$CH_2OH$, —COOH, —COH, —$COOR^3$, —$COOCH_2CONR^4R^5$, —$SO_3H$,

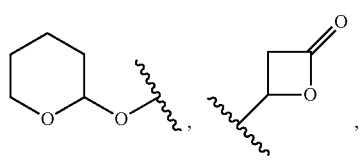

-continued

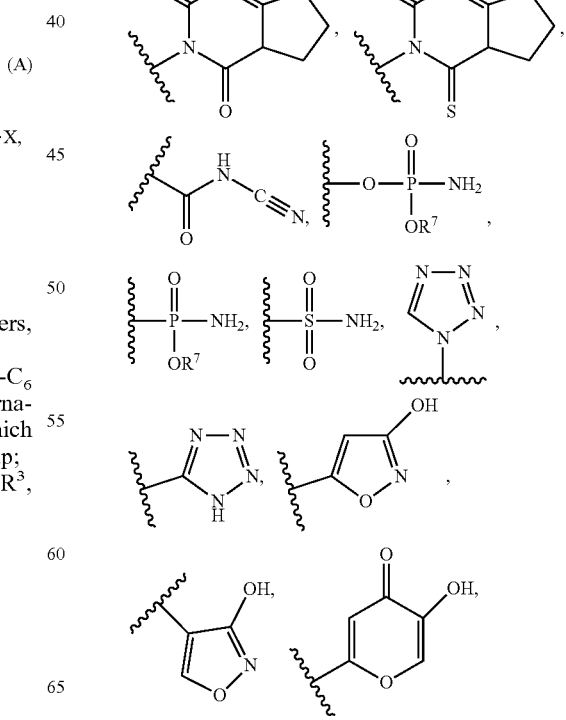

-continued

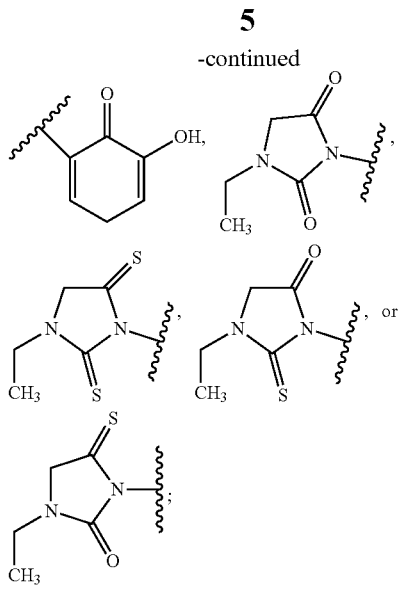

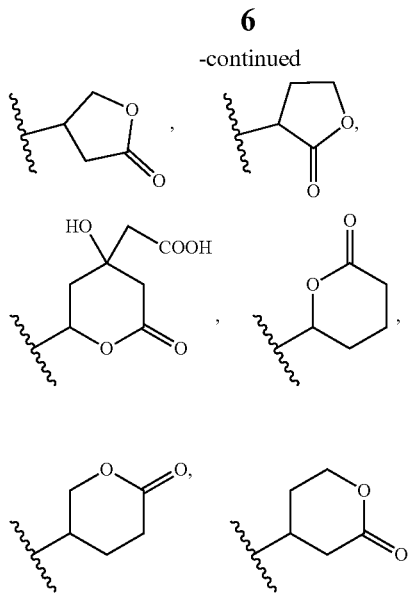

R[3] is —$C_1$-$C_6$ alkyl, —$C_2$-$C_6$ alkenyl, —$C_2$-$C_6$ alkynyl, phenyl, or benzyl;

each R[4] and R[5] is independently alkyl, aryl, or heteroaryl; or alternatively, R[4] and R[5] together with the carbon atom to which R[4] and R[5] are attached form a heterocycle;

each R[6] and R[7] is independently H, —$C_1$-$C_6$ alkyl, —$C_2$-$C_6$ alkenyl, or —$C_2$-$C_6$ alkynyl; and n is 0, 1, 2, 3, or 4.

In another aspect, the present invention also provides compounds of Formula (B):

(B)

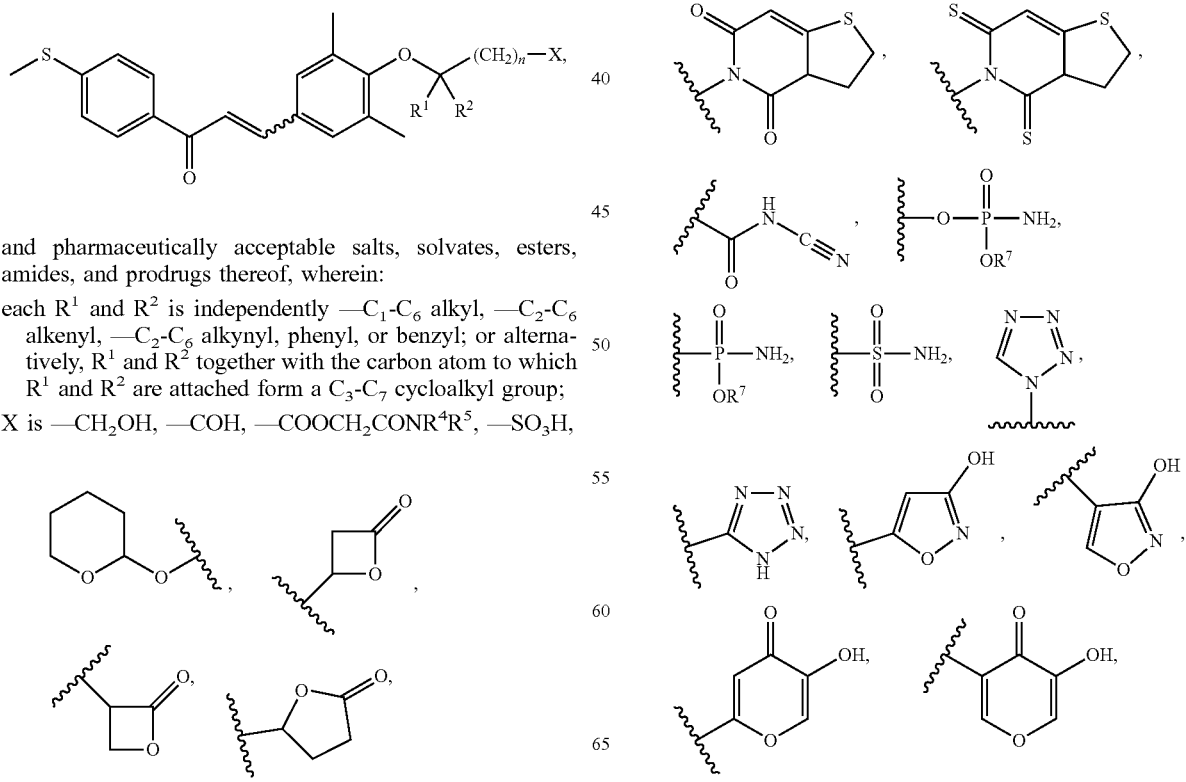

and pharmaceutically acceptable salts, solvates, esters, amides, and prodrugs thereof, wherein:

each R[1] and R[2] is independently —$C_1$-$C_6$ alkyl, —$C_2$-$C_6$ alkenyl, —$C_2$-$C_6$ alkynyl, phenyl, or benzyl; or alternatively, R[1] and R[2] together with the carbon atom to which R[1] and R[2] are attached form a $C_3$-$C_7$ cycloalkyl group;

X is —$CH_2OH$, —COH, —COOCH$_2$CONR[4]R[5], —$SO_3H$,

-continued

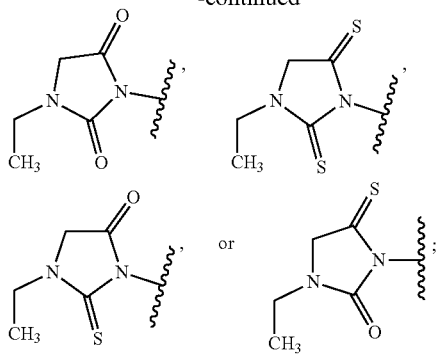

R³ is —C₁-C₆ alkyl, —C₂-C₆ alkenyl, —C₂-C₆ alkynyl, phenyl, or benzyl;

each R⁴ and R⁵ is independently alkyl, aryl, or heteroaryl; or alternatively, R⁴ and R⁵ together with the carbon atom to which R⁴ and R⁵ are attached form a heterocycle;

each R⁶ and R⁷ is independently H, —C₁-C₆ alkyl, —C₂-C₆ alkenyl, or —C₂-C₆ alkynyl; and n is 0, 1, 2, 3, or 4.

The present invention provides 2-(4-(3-hydroxy-3-(4-(methylthio)phenyl)prop-1-en-1-yl)-2,6-dimethylphenoxy)-2-methylpropanoic acid ("Compound I") and pharmaceutically acceptable salts, solvates, esters, amides, and prodrugs, thereof, wherein Compound I has the structure:

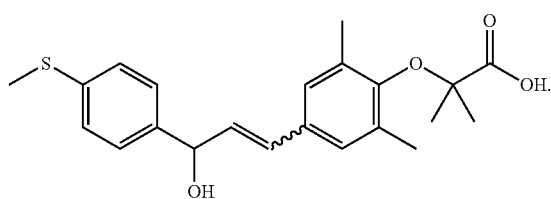

The present invention also provides 3-(4-((1-hydroxy-2-methylpropan-2-yl)oxy)-3,5-dimethylphenyl)-1-(4-(methylthio)phenyl)prop-2-en-1-one ("Compound II") and pharmaceutically acceptable salts, solvates, esters, amides, and prodrugs thereof, wherein Compound II has the structure:

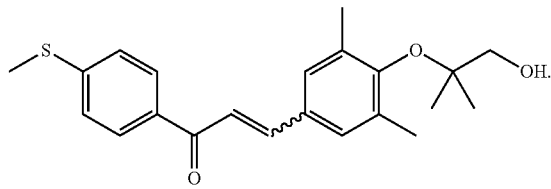

The present invention further provides 3-(4-((1-hydroxy-2-methylpropan-2-yl)oxy)-3,5-dimethylphenyl)-1-(4-(methylthio)phenyl)prop-2-en-1-ol ("Compound III") and pharmaceutically acceptable salts, solvates, esters, amides, and prodrugs thereof, wherein Compound III has the structure

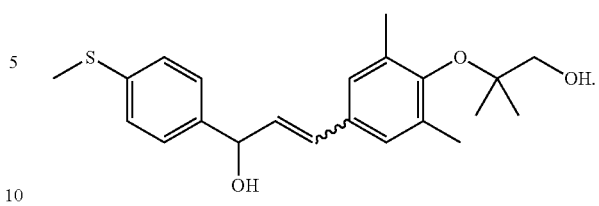

In another aspect, the present invention provides compounds of Formula (C)

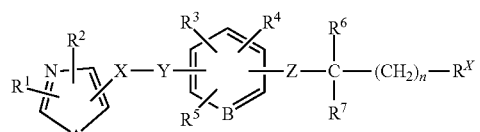

and pharmaceutically acceptable salts, solvates, esters, amides, and prodrugs thereof wherein:

R¹ is phenyl, naphthyl, pyridyl, thienyl, furyl, quinolyl or benzothienyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

R² is $C_{2-8}$ alkyl, $C_{1-8}$ haloalkyl, $C_{2-8}$ alkenyl, $C_{2-8}$ alkynyl, 3-7 membered cycloalkyl, $C_{1-8}$ alkyl substituted with a 3-7 membered cycloalkyl, or $C_{1-6}$ alkyl substituted with phenyl, naphthyl or pyridyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

A is oxygen, sulfur or NR⁹ in which R⁹ is hydrogen or $C_{1-8}$ alkyl;

X is a $C_{1-8}$ alkylene chain which is unsubstituted or substituted with $C_{1-8}$ alkyl, $C_{1-8}$ alkoxy or hydroxyl, and which has 0 or 1 double bonds;

Y is C(=O), C(=N—OR¹⁰), CH(OR¹¹), CH=CH, C≡C, or C(=CH₂) in which each of R¹⁰ and R¹¹ is hydrogen or $C_{1-8}$ alkyl;

each of R³, R⁴ and R⁵ is independently hydrogen, $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl, or pyridyl; optionally wherein at least one of R³, R⁴, and R⁵ is not hydrogen;

B is CH or nitrogen;

Z is oxygen or sulfur;

each of R⁶ and R⁷ is independently hydrogen, $C_{1-8}$ alkyl, or $C_{1-8}$ haloalkyl;

$R^X$ is CH₂OH, COH, COOCH₂CONR$^{X4}$R$^{X5}$, SO₃H,

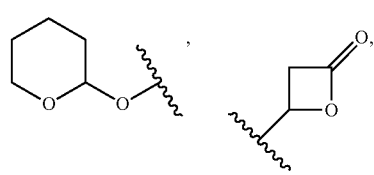

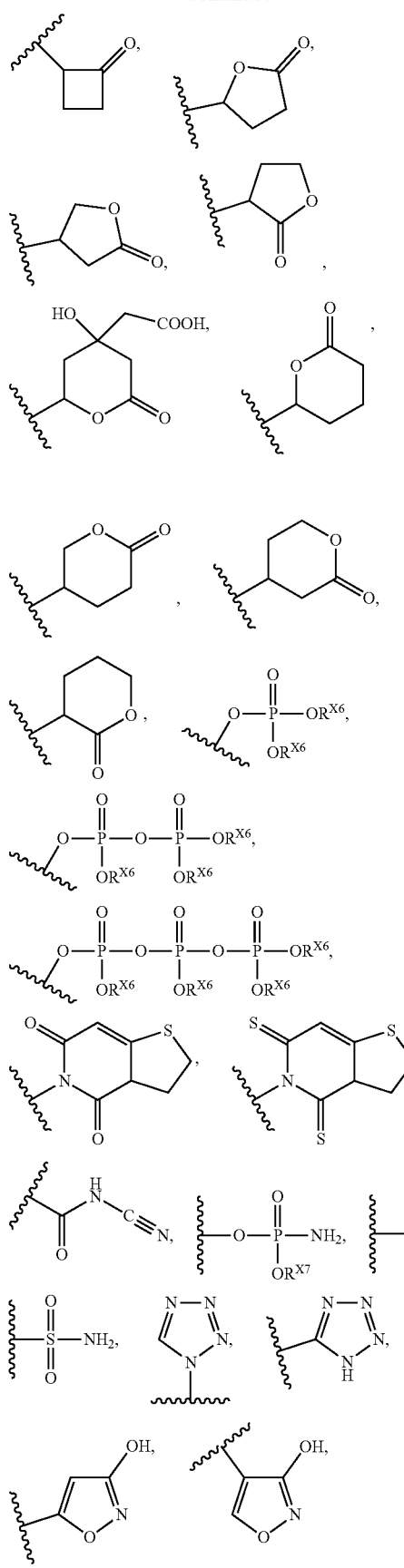

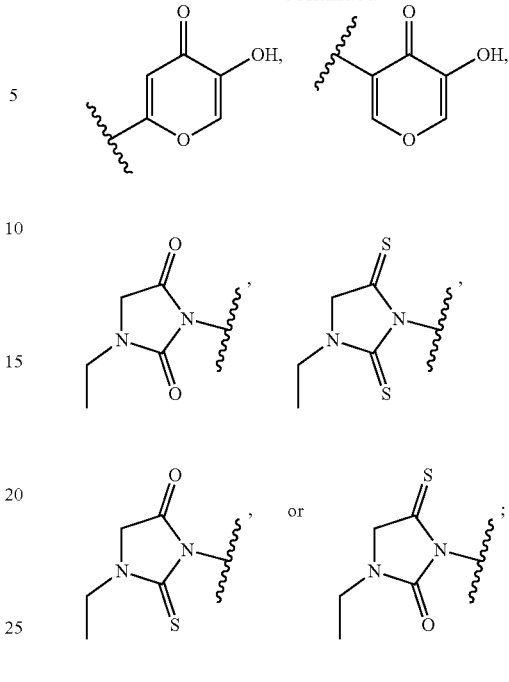

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In other aspects, the invention provides compounds of Formula (D)-(H) and (J)-(AA) and pharmaceutically acceptable salts, solvates, esters, amides, and prodrugs thereof.

The present invention further provides a compound having the structure

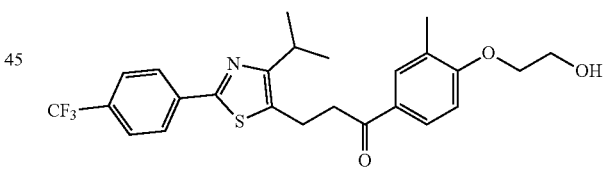

("Compound IV") and pharmaceutically acceptable salts, solvates, esters, amides, and prodrugs thereof.

The present invention further provides a compound having the structure

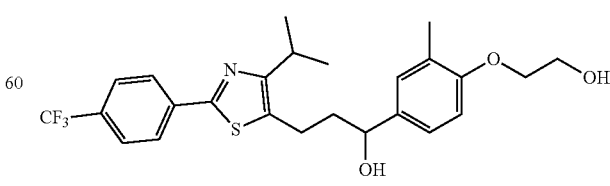

("Compound V") and pharmaceutically acceptable salts, solvates, esters, amides, and prodrugs thereof.

The present invention further provides a compound having the structure

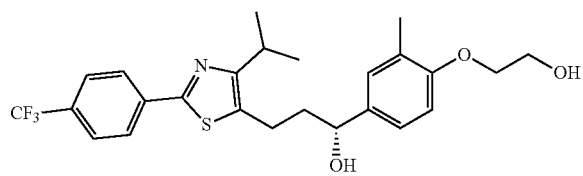

("Compound Va") and pharmaceutically acceptable salts, solvates, esters, amides, and prodrugs thereof.

The present invention further provides a compound having the structure

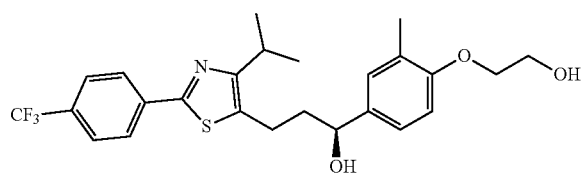 [SMILES: Cc1cc([C@@H](O)CCc2sc(-c3ccc(C(F)(F)F)cc3)nc2C(C)C)ccc1OCCO]

("Compound Vb") and pharmaceutically acceptable salts, solvates, esters, amides, and prodrugs thereof.

In further aspects, the invention provides compounds of Formula (D)-(H) and (J)-(AA), e.g., as described in Section 5.2 (including subparts) and pharmaceutically acceptable salts, solvates, esters, amides, and prodrugs thereof.

The present invention further provides a compound having the structure

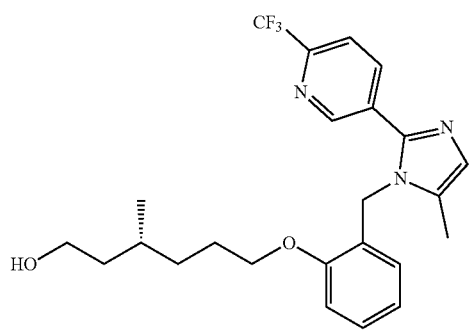 [SMILES: Cc1cnc(-c2ccc(C(F)(F)F)nc2)n1Cc1ccccc1OCCC[C@@H](C)CCO]

("Compound VI") and pharmaceutically acceptable salts, solvates, esters, amides, and prodrugs thereof.

The present invention further provides a compound having the structure

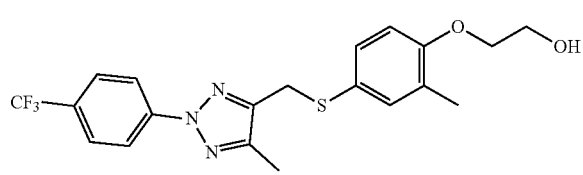 [SMILES: Cc1cc(SCc2nn(-c3ccc(C(F)(F)F)cc3)nc2C)ccc1OCCO]

("Compound VII") and pharmaceutically acceptable salts, solvates, esters, amides, and prodrugs thereof.

The present invention further provides a compound having the structure

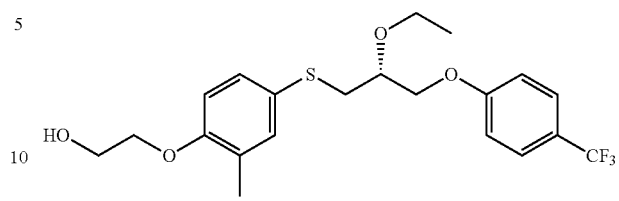

("Compound VIII") and pharmaceutically acceptable salts, solvates, esters, amides, and prodrugs thereof.

Each compound of Formula (A)-(H) and (J)-(AA), each compound of Compounds I, II, III, IV, V, Va, Vb, VI, VII, and VIII, and each compound described in Sections 5-7 (including their subparts), or a pharmaceutically acceptable salt, solvate, ester, amide, and prodrug thereof is a "compound of the invention". Exemplary features of compounds of the invention are described in Section 5.2 and specific embodiments 1 to 50 in Section 7.1 and 1 to 209 in Section 7.2, infra.

The present invention also provides compositions comprising i) an effective amount of a compound of the invention and ii) a pharmaceutically acceptable carrier or vehicle (each composition being a "composition of the invention"). Exemplary features of pharmaceutical compositions of the disclosure are described in Section 5.3 and specific embodiments 51 to 54 in Section 7.1 and 210 to 213 in Section 7.2, infra.

The present invention further provides methods for treating or preventing a liver disorder, dyslipidemia, dyslipoproteinemia, a renal disease, a disorder of glucose metabolism, a disorder of lipid metabolism, a disorder of glucid metabolism, a cardiovascular disease, a vascular disease, a metabolic syndrome, a complication associated with metabolic syndrome, a PPAR-associated disorder, septicemia, a thrombotic disorder, obesity, diabetic nephropathy, diabetic retinopathy, atherosclerosis, pancreatitis, a cerebrovascular disease, a disorder related to neovascularization, hypertension, cancer, inflammation, an inflammatory disease, a neurodegenerative disease, an autoimmune disease, a neoplastic disease, muscle atrophy, cholestasis, mitochondrial dysfunction, an ocular disease, a lysosomal storage disease, a kidney disease (e.g., acute kidney injury), or impotence, comprising administering to a subject in need thereof an effective amount of a compound of the invention or a composition of the invention.

The present invention further provides methods for treating or preventing hyperlipemia, hyperlipidemia, hyperlipoproteinemia, hypercholesterolemia, hypertriglyceridemia, or dyslipidemia, comprising administering to a subject in need thereof an effective amount of a compound of the invention or a composition of the invention.

The present invention further provides methods for treating a subject having or preventing a subject from having an abnormally high concentration in a subject's blood plasma or blood serum of high low-density lipoprotein (LDL), apolipoprotein B (apo B), lipoprotein(a) (Lp(a)), apolipoprotein (a), or very low-density lipoprotein (VLDL), comprising administering to a subject in need thereof an effective amount of a compound of the invention or a composition of the invention.

The present invention further provides methods for treating a subject having or preventing a subject from having an abnormally low concentration in a subject's blood plasma or blood serum of high-density lipoprotein (HDL), comprising administering to a subject in need thereof an effective amount of the compound of the invention or the composition of the invention.

The present invention further provides methods for treating a subject having or preventing a subject from having an abnormally reduced or deficient lipoprotein lipase concentration or activity in a subject's blood plasma or blood serum, comprising administering to a subject in need thereof an effective amount of a compound of the invention or a composition of the invention.

The present invention provides methods for treating or preventing hypoalphalipoproteinemia, a lipoprotein abnormality associated with diabetes, a lipoprotein abnormality associated with obesity, a lipoprotein abnormality associated with Alzheimer's Disease, or familial combined hyperlipidemia, comprising administering to a subject in need thereof an effective amount of a compound of the invention or a composition of the invention.

The present invention further provides methods for reducing in a subject's blood plasma or blood serum an abnormally high concentration of triglycerides, low-density lipoprotein cholesterol (LDL-C), very low-density lipoprotein cholesterol (VLDL-C), non-high-density lipoprotein cholesterol, (non-HDL-C), lipoprotein(a) (Lp(a)), apolipoprotein B, HDL/(VLDL+LDL) ratio, apolipoprotein C-II or apolipoprotein C-III, comprising administering to a subject in need thereof an effective amount of a compound of the invention or a composition of the invention.

The present invention further provides methods for elevating in a subject's blood plasma or blood serum an abnormally low concentration of a high-density lipoprotein (HDL) associated protein, HDL-cholesterol, apolipoprotein A-I, or apolipoprotein E, comprising administering to a subject in need thereof an effective amount of a compound of the invention or a composition of the invention.

The present invention further provides methods for promoting clearance of triglycerides from a subject's blood plasma or blood serum, comprising administering to a subject in need thereof an effective amount of a compound of the invention or a composition of the invention.

The present invention further provides methods for increasing abnormally low glucose metabolism or increasing abnormally low lipid metabolism in a subject, comprising administering to a subject in need thereof an effective amount of a compound of the invention or a composition of the invention.

The present invention further provides methods for treating or preventing one or more symptoms of inflammation, systemic lupus erythematosus, lupus nephritis, or arthritis, comprising administering to a subject in need thereof an effective amount of a compound of the invention or a composition of the invention.

The present invention further provides methods for reducing the fat content of meat in livestock, comprising administering to livestock an effective amount of a compound of the invention or a composition of the invention.

The present invention further provides methods for reducing cholesterol content of a fowl egg, comprising administering to a fowl species an effective amount of a compound of the invention or a composition of the invention.

Exemplary uses of the compounds and compositions of the disclosure are described in specific embodiments 55 to 163 in Section 7.1 and specific embodiments 214 to 322 in Section 7.2, infra.

5. DETAILED DESCRIPTION OF THE INVENTION

5.1. Definitions

The term "about" when immediately preceding a numerical value means ±up to 20% of the numerical value. For example, "about" a numerical value means ±up to 20% of the numerical value, in some embodiments, ±up to 19%, ±up to 18%, ±up to 17%, up to 16%, +up to 15%, up to 14%, ±up to 13%, ±up to 12%, up to 11%, ±up to 10%, ±up to 9%, up to 8%, ±up to 7%, ±up to 6%, up to 5%, ±up to 4%, ±up to 3%, ±up to 2%, ±up to 1%, +up to less than 1%, or any other value or range of values therein.

Throughout the present specification, numerical ranges are provided for certain quantities. These ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "pharmaceutically acceptable salt" includes both an acid and a base addition salt. Pharmaceutically acceptable salts can be obtained by reacting the compound of the invention functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Pharmaceutically acceptable salts can also be obtained by reacting a compound of the invention functioning as an acid, with an inorganic or organic base to form a salt, for example, salts of sodium, potassium, lithium, ammonium, calcium, magnesium, iron, zinc, copper, manganese, aluminum, ammonia, isopropylamine, trimethylamine, choline, betaine, etc. Inorganic base can include, but are not limited to, calcium hydroxide, potassium hydroxide, sodium hydroxide, and sodium carbonate. Organic base can include, but are not limited to, primary amines, secondary amines, tertiary amines, substituted amines including naturally-occurring substituted amines, and cyclic amines, such as isopropylamine, trimethylamine, diethylamine, triethylamine, tripropylamine, ethanolamine, 2-dimethylaminoethanol, tromethamine, lysine, arginine, histidine, caffeine, procaine, hydrabamine, glucosamine, N-alkylglucamines, theobromine, purines, piperazine, piperidine, N-ethylpiperidine, and the like. Those skilled in the art will further recognize that pharmaceutically acceptable salts can be prepared by reaction of the compounds of the invention with an appropriate inorganic or organic acid or base via any of a number of known methods.

The term "solvate" refers to a solvation complex. Solvates can be formed by solvation (the combination of solvent molecules with molecules or ions of the compounds of the invention), or a solvate can be an aggregate that comprises a solute ion or molecule or a solvent molecules. The solvent can be water, in which case the solvate is a hydrate. Examples of hydrates include, but are not limited to, a hemihydrate, monohydrate, dihydrate, trihydrate, hexahydrate, etc. The solvate can be formed via hydration, including via absorption of moisture. A pharmaceutically acceptable salt can also be a solvate. Where a solvate is obtained via crystallization from a solvent, the solvent can be an alcohol, such as methanol or ethanol; an aldehyde; a ketone, such as acetone; or an ester, such as ethyl acetate.

The compounds of the invention can have one or more asymmetric centers and can thus be enantiomers, racemates, diastereomers, other stereoisomers and mixtures thereof. The compounds of the invention include all such possible isomers (including geometric isomers), as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation or isolation of individual enantiomers include chiral synthesis from a suitable optically pure precursor or resolution of the racemate using, for example, chiral high pressure liquid chromatography (HPLC). Likewise, the compounds of the invention include all tautomeric forms.

The language "substantially free of its corresponding opposite enantiomer" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of its corresponding opposite enantiomer.

The language "substantially free of its corresponding opposite stereoisomer" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of its corresponding opposite stereoisomer.

The language "substantially free of its corresponding other olefin configuration" means having no more than about 10 mol %, in another embodiment no more than about 5 mol %, in another embodiment no more than about 2 mol %, in another embodiment no more than about 1 mol %, in another embodiment no more than about 0.5 mol % and in another embodiment no more than about 0.1 mol %, of its corresponding other olefin configuration.

An "effective amount" when used in connection with a compound of the invention means an amount of the compound of the invention that, when administered to a subject is effective to treat or prevent a disorder or condition disclosed herein, alone or with another pharmaceutically active agent.

An "effective amount" when used in connection with another pharmaceutically active agent means an amount of the other pharmaceutically active agent that is effective to treat or prevent a disorder or condition disclosed herein, alone or in combination with a compound of the invention.

A "subject" is a human or non-human mammal, e.g., a bovine, horse, feline, canine, rodent, or non-human primate. The human can be a male or female, child, adolescent or adult. The female can be premenarcheal or postmenarcheal.

"Mammal" includes a human, domestic animal such as a laboratory animal (e.g., mouse, rat, rabbit, monkey, dog, etc.) and household pet (e.g., cat, dog, swine, cattle, sheep, goat, horse, rabbit), and a non-domestic, wild animal.

All weight percentages (i.e., "% by weight" and "wt. %" and w/w) referenced herein, unless otherwise indicated, are relative to the total weight of the mixture or composition, as the case can be.

"Alkyl" refers to a fully saturated, straight or branched hydrocarbon chain having from one to twelve carbon atoms, and which is attached to an atom by a single bond. Alkyls with a number of carbon atoms ranging from 1 to 12 are included. An alkyl group with 1 to 12 carbon atoms is a $C_1$-$C_{12}$ alkyl (alternatively represented as $C_{1-12}$ alkyl), an alkyl group with 1 to 10 carbon atoms is a $C_1$-$C_{10}$ alkyl (alternatively represented as $C_{1-10}$ alkyl), an alkyl group with 1 to 6 carbon atoms is a $C_1$-$C_6$ alkyl (alternatively represented as $C_{1-6}$ alkyl), an alkyl group with 1 to 5 carbon atoms is a $C_1$-$C_5$ alkyl (alternatively represented as $C_{1-5}$ alkyl), and so on. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes C alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise, an alkyl group can be unsubstituted or substituted with a substituent disclosed herein. In some embodiments, an alkyl group is unsubstituted.

Alkoxy" refers to RO in which R is alkyl.

"Alkenyl" refers to a straight or branched hydrocarbon chain having from two to twelve carbon atoms, and having one or more carbon-carbon double bonds. Each alkenyl group is attached to an atom by a single bond. Alkenyl groups with a number of carbon atoms ranging from 2 to 12 are included. An alkenyl group with 2 to 12 carbon atoms is a $C_2$-$C_{12}$ alkenyl (alternatively represented as $C_{2-12}$ alkenyl), an alkenyl group with 2 to 10 carbon atoms is a $C_2$-$C_{10}$ alkenyl (alternatively represented as $C_{2-10}$ alkenyl), an alkenyl group with 2 to 6 carbon atoms is a $C_2$-$C_6$ alkenyl (alternatively represented as $C_{2-6}$ alkenyl) and an alkenyl group with 2 to 5 carbon atoms is a $C_2$-$C_5$ alkenyl (alternatively represented as $C_{2-6}$ alkenyl) and so on. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise, an alkyl group can be unsubstituted or substituted with a substituent disclosed herein. In some embodiments, an alkenyl group is unsubstituted.

"Alkynyl" refers to a straight or branched hydrocarbon chain radical having from two to twelve carbon atoms, and having one or more carbon-carbon triple bonds. Each alkynyl group is attached to an atom by a single bond. Alkynyl groups with a number of carbon atoms ranging from 2 to 12 are included. An alkynyl group having 2 to 12 carbon atoms is a $C_2$-$C_{12}$ alkynyl (alternatively represented as $C_{2-12}$ alkynyl), an alkynyl group with 2 to 10 carbon atoms is a $C_2$-$C_{10}$ alkynyl (alternatively represented as $C_{2-10}$ alkynyl), an alkynyl group with 2 to 6 carbon atoms is a $C_2$-$C_6$ alkynyl (alternatively represented as $C_{2-6}$ alkynyl) and an alkynyl group with 2 to 5 carbon atoms is a $C_2$-$C_5$ alkynyl (alternatively represented as $C_{2-6}$ alkynyl). A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise, an alkyl group can be unsubstituted or substituted with a substituent disclosed herein. In some embodiments, an alkynyl group is unsubstituted.

"Aryl" refers to a hydrocarbon ring system radical comprising hydrogen, 6 to 18 carbon atoms and at least one aromatic ring. The aryl radical can be a monocyclic, bicyclic, tricyclic or tetracyclic ring system, which can include fused or bridged ring systems. Aryl radicals include, but are not limited to, aceanthrylenyl, acenaphthylenyl, acephenanthrylenyl, anthracenyl, azulenyl, chrysenyl, fluoranthenyl, fluorenyl, as-indacenyl, s-indacenyl, indanyl, indenyl, naphthalenyl, phenalenyl, phenanthrenyl, phenyl, pleiadenyl, pyrenyl, and triphenylenyl. Unless stated otherwise, the aryl can be unsubstituted or substituted with a substituent disclosed herein. In some embodiments, an aryl group is unsubstituted.

"Cycloalkyl" refers to a non-aromatic monocyclic or polycyclic fully saturated hydrocarbon radical consisting of carbon and hydrogen atoms, which can include fused or bridged ring systems, having from three to twenty carbon atoms, preferably having from three to ten carbon atoms, and which is attached to an atom by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless stated otherwise, a cycloalkyl group can be unsubstituted or substituted with a substituent disclosed herein. In some embodiments, a cycloalkyl group is unsubstituted.

"Halo" or "halogen" represents chloro, fluoro, bromo or iodo.

"Haloalkyl" refers to an alkyl group in which one or more hydrogen atoms are replaced by halogen. Examples of haloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$).

"Haloalkoxy" refers to RO in which R is a haloalkyl group.

"Heteroaryl" refers to a 5- to 20-membered ring system radical including hydrogen atoms, one to thirteen carbon atoms, one to six nitrogen, oxygen or sulfur heteroatoms, and at least one aromatic ring. The heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples of heteroaryl include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thienyl). Unless stated otherwise, a heteroaryl group can be unsubstituted or substituted. In some embodiments, a heteroaryl group is unsubstituted.

"Heterocyclyl" refers to a 3- to 20-membered non-aromatic, partially unsaturated, or aromatic ring radical which includes two to twelve carbon atoms and from one to six nitrogen, oxygen or sulfur heteroatoms. Heterocycly include heteroaryls as defined herein. Unless stated otherwise, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise, a heterocyclyl group can be unsubstituted or substituted with a substituent disclosed herein. In some embodiments, a heterocyclyl groups is unsubstituted.

As used herein, the symbol

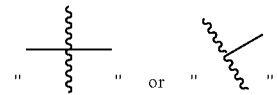

(a "point of attachment bond") denotes a bond that is a point of attachment between two chemical entities, one of which is depicted as being attached to the point of attachment bond and the other of which is not depicted as being attached to the point of attachment bond. For example,

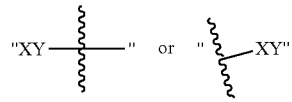

5.2. The Compounds of the Invention

5.2.1. Compounds of Formula (A)

In some embodiments, the compound of the invention is a compound of Formula (A):

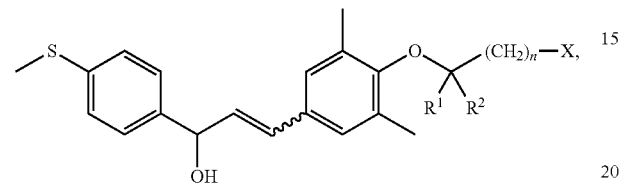

(A)

or a pharmaceutically acceptable salt, solvate, ester, amide, or prodrug thereof, wherein:

each $R^1$ and $R^2$ is independently —$C_1$-$C_6$ alkyl, —$C_2$-$C_6$ alkenyl, —$C_2$-$C_6$ alkynyl, phenyl, or benzyl; or alternatively, $R^1$ and $R^2$ together with the carbon atom to which $R^1$ and $R^2$ are attached form a $C_3$-$C_7$ cycloalkyl group;

X is —$CH_2OH$, —COOH, —COH, —$COOR^3$, —$COOCH_2CONR^4R^5$, —$SO_3H$,

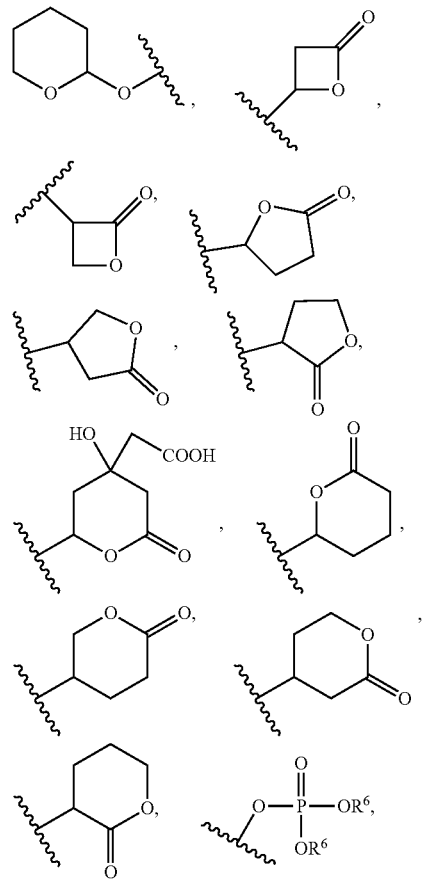

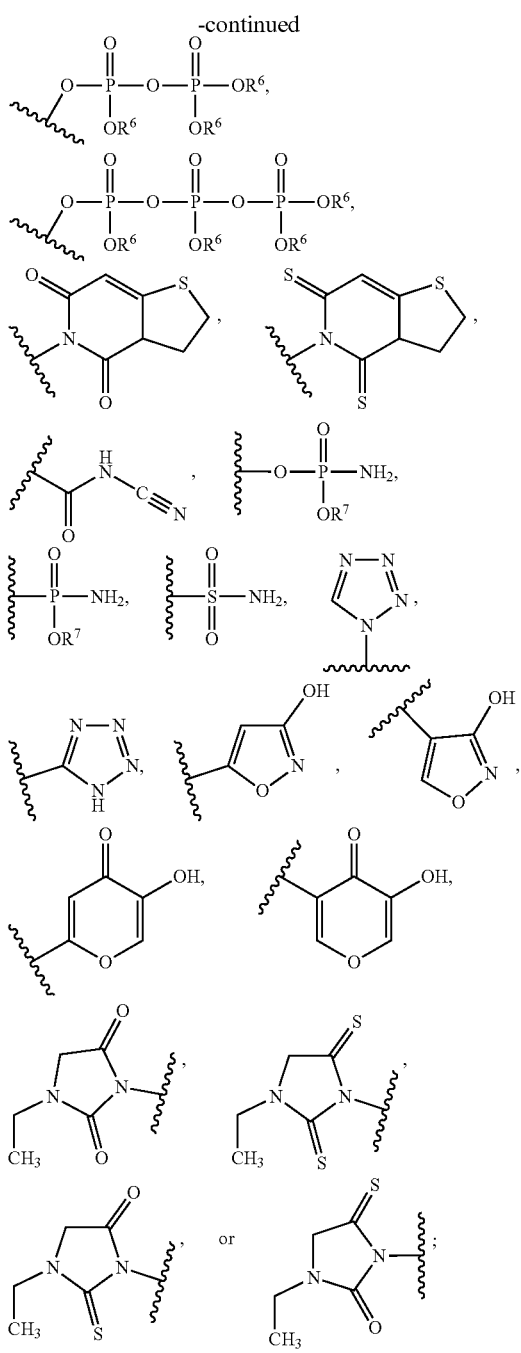

$R^3$ is —$C_1$-$C_6$ alkyl, —$C_2$-$C_6$ alkenyl, —$C_2$-$C_6$ alkynyl, phenyl, or benzyl;

each $R^4$ and $R^5$ is independently alkyl, aryl, or heteroaryl; or alternatively, $R^4$ and $R^5$ together with the carbon atom to which $R^4$ and $R^5$ are attached form a heterocycle;

each $R^6$ and $R^7$ is independently H, —$C_1$-$C_6$ alkyl, —$C_2$-$C_6$ alkenyl, or —$C_2$-$C_6$ alkynyl; and n is 0, 1, 2, 3, or 4.

In some embodiments, the compound of Formula (A) is a racemate or a mixture of enantiomers or diastereomers. In some embodiments, the compound of Formula (A) has an olefin isomer configuration of (Z) or (E). In some embodiments, the hydroxyl-bearing allylic carbon atom of the compound of Formula (A) has an (R)- or an (S)-stereochemistry.

In some embodiments, the compound of Formula (A) is a (Z)-isomer (or cis) and has the structure:

((Z)-A)

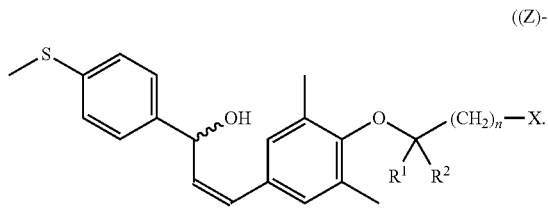

In some embodiments, the compound of Formula ((Z)-A) is substantially free of its corresponding other olefin configuration (i.e., (E)-isomer).

In some embodiments, the compound of formula (A) is an (E)-isomer (or trans) and has the structure:

((E)-A)

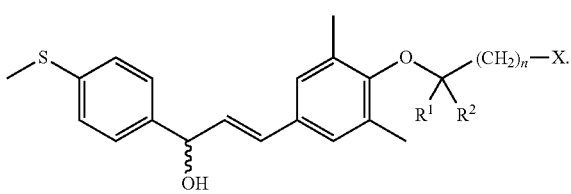

In some embodiments, the compound of Formula ((E)-A) is substantially free of its corresponding other olefin configuration (i.e., (Z)-isomer).

In some embodiments, the compound of Formula (A) has an hydroxyl-bearing allylic carbon atom having (R)-stereochemistry and has the structure:

((R)-A)

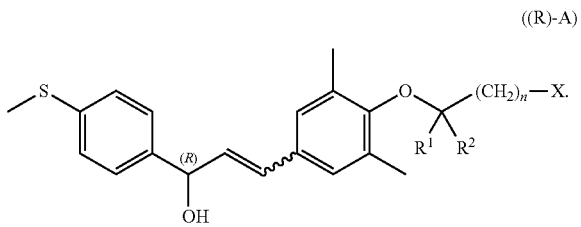

In some embodiments, the compound of Formula ((R)-A) is substantially free of its corresponding opposite stereoisomer, i.e., a compound of Formula (A) whose hydroxyl-bearing allylic carbon atom has an (S)-stereochemistry.

In some embodiments, the hydroxyl-bearing allylic carbon atom of the compound of Formula (A) has an (S)-stereochemistry and has the structure:

((S)-A)

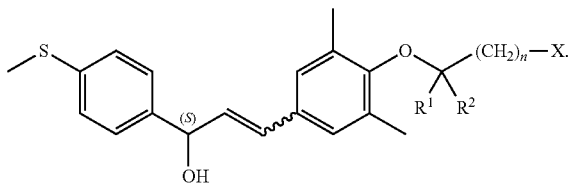

In some embodiments, the compound of Formula ((S)-A) is substantially free of its corresponding opposite stereoisomer, i.e., a compound of Formula (A) whose hydroxyl-bearing allylic carbon atom has an (R)-stereochemistry.

In some embodiments, the compound of Formula (A) is a (Z)-isomer (or cis), has an hydroxyl-bearing allylic carbon atom having an (R)-stereochemistry and has the structure:

((Z)-(R)-A)

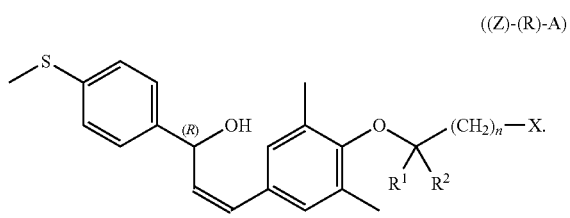

In some embodiments, the compound of Formula ((Z)-(R)-A) is substantially free of compounds of Formulae ((Z)-(S)-A), ((E)-(R)-A), or ((E)-(S)-A).

In some embodiments, the compound of Formula (A) is a (Z)-isomer (or cis), has an hydroxyl-bearing allylic carbon atom having an (S)-stereochemistry and has the structure:

((Z)-(S)-A)

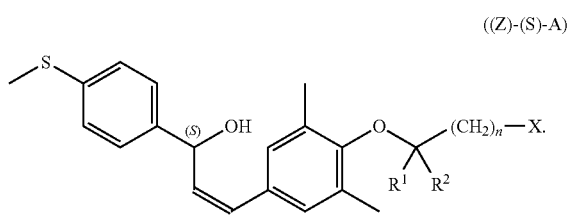

In some embodiments, the compound of Formula ((Z)-(S)-A) is substantially free of compounds of Formulae ((Z)-(R)-A), ((Z)-(R)-A), or ((Z)-(S)-A).

In some embodiments, the compound of Formula (A) is an (E)-isomer (or cis), has an hydroxyl-bearing allylic carbon atom having an (R)-stereochemistry and has the structure:

((E)-(R)-A)

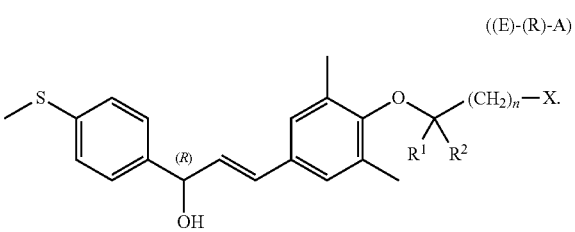

In some embodiments, the compound of Formula ((E)-(R)-A) is substantially free of compounds of Formulae ((E)-(S)-A), ((Z)-(R)-A), or ((Z)-(S)-A).

In some embodiments, the compound of Formula (A) is an (E)-isomer (or cis), has an hydroxyl-bearing allylic carbon atom having an (S)-stereochemistry and has the structure:

((E)-(S)-A)

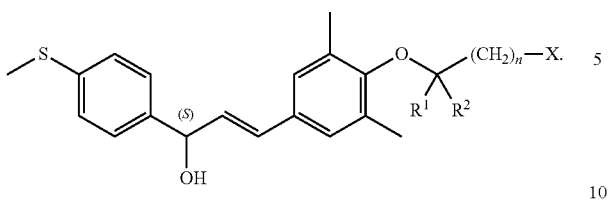

In some embodiments, the compound of Formula ((E)-(S)-A) is substantially free of compounds of Formulae ((E)-(R)-A), ((Z)-(R)-A), or ((Z)-(S)-A).

In some embodiments of compounds of Formula (A), ((Z)-A), ((E)-A), ((R)-A), ((S)-A), ((E)-(R)-A), ((E)-(S)-A), ((Z)-(R)-A), or ((Z)-(S)-A) each $R^1$ and $R^2$ is independently —$C_1$-$C_6$ alkyl. In some embodiments, each $R^1$ and $R^2$ is independently —$C_1$-$C_3$ alkyl. In some embodiments, each $R^1$ and $R^2$ is independently methyl.

In some embodiments of compounds of formula (A), ((Z)-A), ((E)-A), ((R)-A), ((S)-A), ((E)-(R)-A), ((E)-(S)-A), ((Z)-(R)-A), or ((Z)-(S)-A), X is —$CH_2OH$, —COOH, —COH, or —$COOR^3$, or —$COOCH_2CONR^4R^5$. In some embodiments, X is —$CH_2OH$, —COOH, —$COOR^3$, —$COOCH_2CONR^4R^5$. In some embodiments, X is —$CH_2OH$ or —COOH.

In some embodiments of compounds of Formula (A), ((Z)-A), ((E)-A), ((R)-A), ((S)-A), ((E)-(R)-A), ((E)-(S)-A), ((Z)-(R)-A), or ((Z)-(S)-A), $R^3$ is —$C_1$-$C_6$ alkyl. In some embodiments, $R^3$ is methyl, ethyl, n-propyl, isopropyl, n-butyl, s-butyl, or t-butyl.

In some embodiments of compounds of Formula (A), ((Z)-A), ((E)-A), ((R)-A), ((S)-A), ((E)-(R)-A), ((E)-(S)-A), ((Z)-(R)-A), or ((Z)-(S)-A), n is 0, 1, 2, or 3. In some embodiments, n is 0, 1, or 2. In some embodiments, n is 0 or 1.

5.2.1.1. Compound I

In some embodiments, the compound of the invention is Compound I having the structure:

(I)

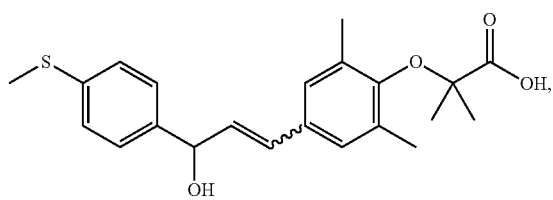

or a pharmaceutically acceptable salt, solvate, ester, amide, or prodrug thereof.

In some embodiments, Compound I is a racemate or a mixture of enantiomers. In some embodiments, Compound I has an olefin isomer configuration of (Z) or (E). In some embodiments, Compound I has an hydroxyl-bearing allylic carbon atom having an (R)- or an (S)-stereochemistry.

In some embodiments, Compound I is a (Z)-isomer (or cis) and has the structure:

((Z)-I)

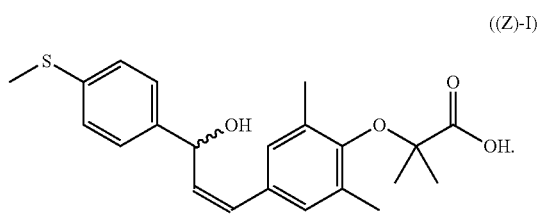 [SMILES: CSc1ccc(C(O)/C=C\c2cc(C)c(OC(C)(C)C(=O)O)c(C)c2)cc1]

In some embodiments, Compound I is a (Z)-isomer and is substantially free of its corresponding other olefin configuration (i.e., (E)-isomer).

In some embodiments, Compound I is an (E)-isomer (or trans) and has the structure:

((E)-I)

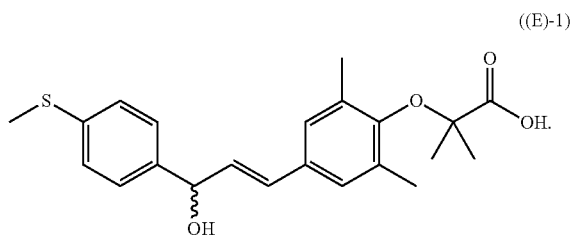 [SMILES: CSc1ccc(C(O)/C=C/c2cc(C)c(OC(C)(C)C(=O)O)c(C)c2)cc1]

In some embodiments, Compound I is an (E)-isomer and is substantially free of its corresponding other olefin configuration (i.e., (Z)-isomer).

In some embodiments, Compound I has an hydroxyl-bearing allylic carbon atom having an (R)-enantiomer and has the structure:

((R)-I)

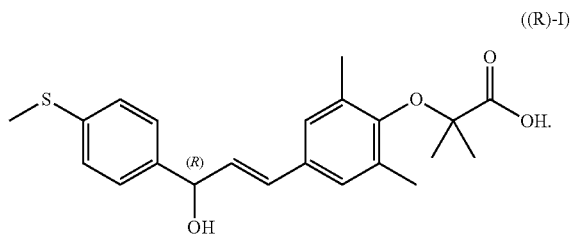

In some embodiments, Compound I has an hydroxyl-bearing allylic carbon atom having an (R)-enantiomer and is substantially free of its corresponding opposite enantiomer (i.e., (S)-enantiomer).

In some embodiments, Compound I has an hydroxyl-bearing allylic carbon atom having an (S)-enantiomer and has the structure:

((S)-I)

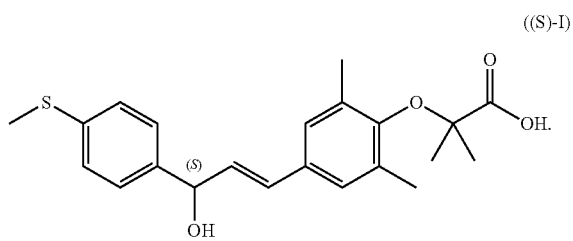

In some embodiments, Compound I has an hydroxyl-bearing allylic carbon atom having an (S)-enantiomer and is substantially free of its corresponding opposite enantiomer (i.e., (R)-enantiomer). In some embodiments, Compound I is a non-racemic mixture of its (R)-enantiomer and (S)-enantiomer. In some embodiments, the non-racemic mixture has an excess of (R)-enantiomer relative to (S)-enantiomer. In some embodiments, the non-racemic mixture has an excess of (S)-enantiomer relative to (R)-enantiomer.

In some embodiments, Compound I is a (Z)-isomer (or cis), has an hydroxyl-bearing allylic carbon atom having an (R)-enantiomer and has the structure:

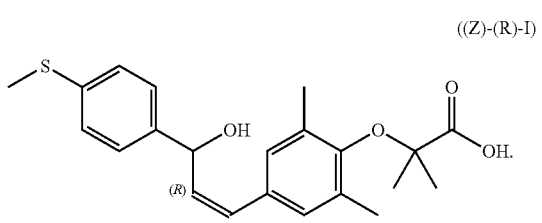

((Z)-(R)-I)

In some embodiments, Compound ((Z)-(R)-I) is substantially free of Compounds ((Z)-(S)-I), ((E)-(R)-I), or ((E)-(S)-I).

In some embodiments, Compound I is a (Z)-isomer, has an hydroxyl-bearing allylic carbon atom having an (S)-enantiomer and has the structure:

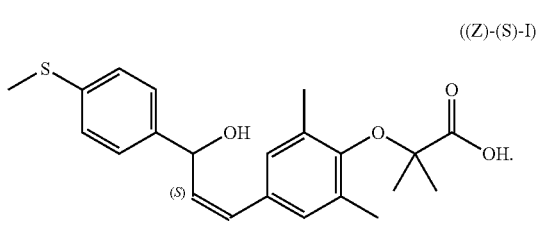

((Z)-(S)-I)

In some embodiments, Compound ((Z)-(S)-I) is substantially free of Compounds ((Z)-(R)-I), ((E)-(R)-I), or ((E)-(S)-I).

In some embodiments, Compound I is an (E)-isomer (or trans), has an hydroxyl-bearing allylic carbon atom having an (R)-enantiomer and has the structure:

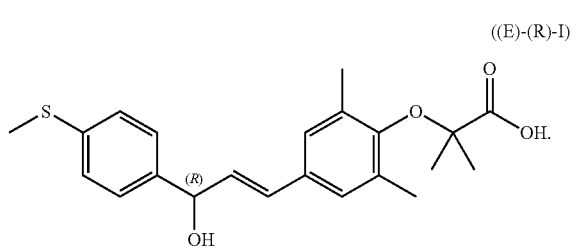

((E)-(R)-I)

In some embodiments, Compound ((E)-(R)-I) is substantially free of Compounds (E)-(S)-I), ((Z)-(R)-I), or ((Z)-(S)-I).

In some embodiments, Compound I is an (E)-isomer, has an hydroxyl-bearing allylic carbon atom having an (S)-enantiomer and has the structure:

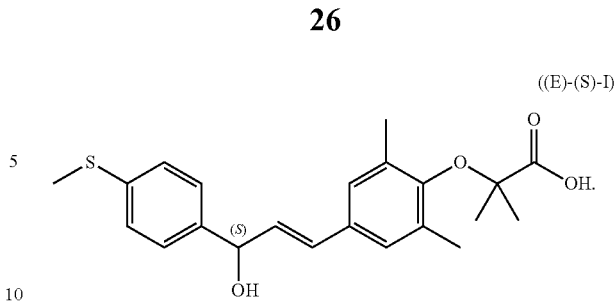

((E)-(S)-I)

In some embodiments, Compound ((E)-(S)-I) is substantially free of Compounds ((E)-(R)-I), ((Z)-(R)-I), or ((Z)-(S)-I).

5.2.1.2. Compound III

In some embodiments, the compound of the invention is Compound III having the structure:

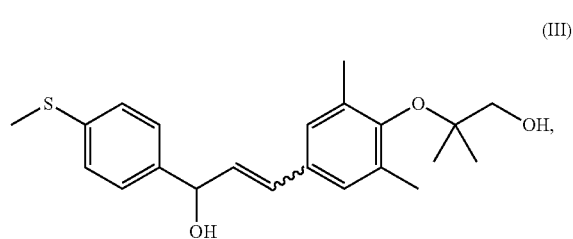 [SMILES: CSc1ccc(C(O)C=Cc2cc(C)c(OC(C)(C)CO)c(C)c2)cc1]

(III)

or a pharmaceutically acceptable salt, solvate, ester, amide, or prodrug thereof.

In some embodiments, Compound III is a racemate or a mixture of enantiomers. In some embodiments, Compound III has an olefin isomer configuration of (Z) or (E). In some embodiments, Compound III has an hydroxyl-bearing allylic carbon atom having an (R)- or an (S)-stereochemistry.

In some embodiments, Compound III is a (Z)-isomer (or cis) and has the structure:

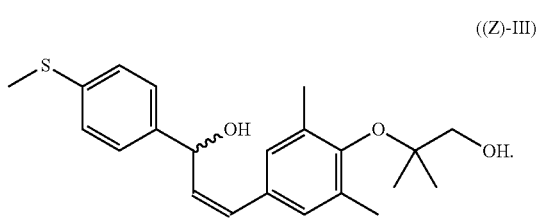 [SMILES: CSc1ccc(C(O)/C=C\c2cc(C)c(OC(C)(C)CO)c(C)c2)cc1]

((Z)-III)

In some embodiments, Compound III is a (Z)-isomer and is substantially free of its corresponding other olefin configuration (i.e., (E)-isomer).

In some embodiments, Compound III is an (E)-isomer (or trans) and has the structure:

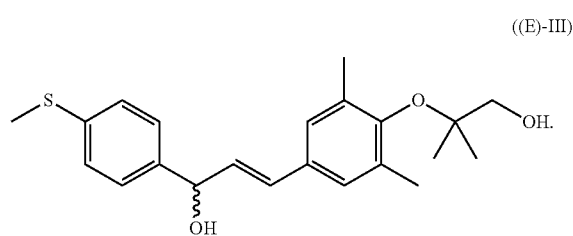

((E)-III)

In some embodiments, Compound III is an (E)-isomer and is substantially free of its corresponding other olefin configuration (i.e., (Z)-isomer).

In some embodiments, Compound III has an hydroxyl-bearing allylic carbon atom having an (R)-enantiomer and has the structure:

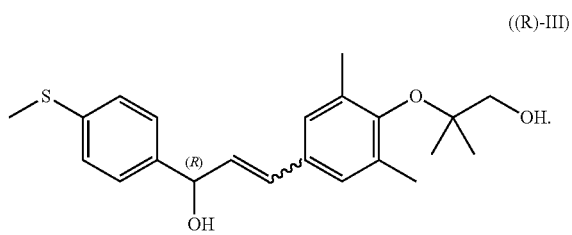

((R)-III)

In some embodiments, Compound III has an hydroxyl-bearing allylic carbon atom having an (R)-enantiomer and is substantially free of its corresponding opposite enantiomer (i.e., (S)-enantiomer).

In some embodiments, Compound III has an hydroxyl-bearing allylic carbon atom having an (S)-enantiomer and has the structure:

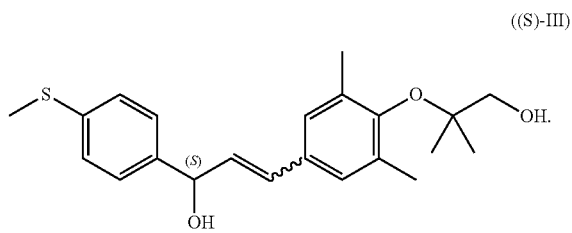

((S)-III)

In some embodiments, Compound III has an hydroxyl-bearing allylic carbon atom having an (S)-enantiomer and is substantially free of its corresponding opposite enantiomer (i.e., (R)-enantiomer). In some embodiments, Compound III is a non-racemic mixture of its (R)-enantiomer and (S)-enantiomer. In some embodiments, the non-racemic mixture has an excess of (R)-enantiomer relative to (S)-enantiomer. In some embodiments, the non-racemic mixture has an excess of (S)-enantiomer relative to (R)-enantiomer.

In some embodiments, Compound III is an (Z)-isomer (or cis), has an hydroxyl-bearing allylic carbon atom having an (R)-enantiomer and has the structure:

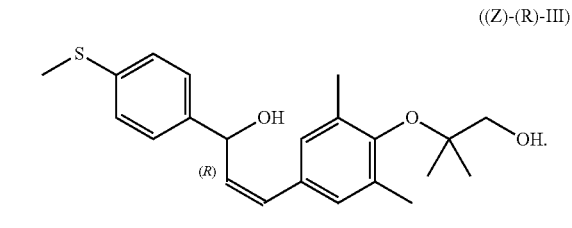

((Z)-(R)-III)

In some embodiments, Compound ((Z)-(R)-III) is substantially free of Compounds ((Z)-(S)-III), ((E)-(R)-III), or ((E)-(S)-III).

In some embodiments, Compound III is an (Z)-isomer, has an hydroxyl-bearing allylic carbon atom having an (S)-enantiomer and has the structure:

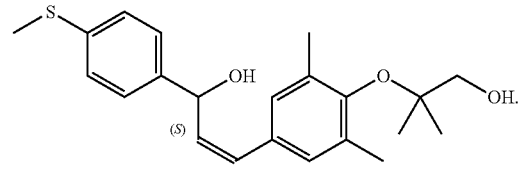

((Z)-(S)-III)

In some embodiments, Compound ((Z)-(S)-III) is substantially free of Compounds ((Z)-(R)-III), ((E)-(R)-III), or ((E)-(S)-III).

In some embodiments, Compound I is an (E)-isomer (or trans), has an hydroxyl-bearing allylic carbon atom having an (R)-enantiomer and has the structure:

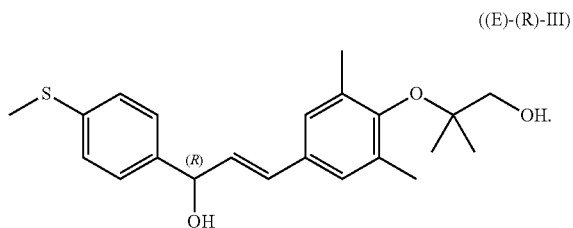

((E)-(R)-III)

In some embodiments, Compound ((E)-(R)-III) is substantially free of Compounds ((E)-(S)-III), ((Z)-(R)-III), or ((Z)-(S)-III).

In some embodiments, Compound III is an (E)-isomer, has an hydroxyl-bearing allylic carbon atom having an (S)-enantiomer and has the structure:

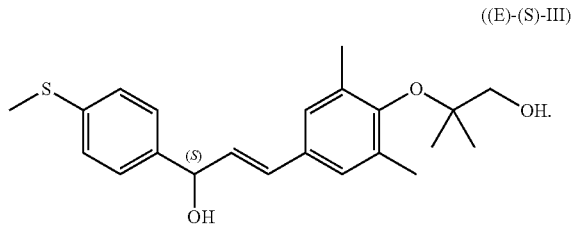

((E)-(S)-III)

In some embodiments, Compound ((E)-(S)-III) is substantially free of Compounds ((E)-(R)-III), ((Z)-(R)-III), or ((Z)-(S)-III).

5.2.2. Compounds of Formula (B)

In some embodiments, the compounds of the invention are compounds of Formula (B):

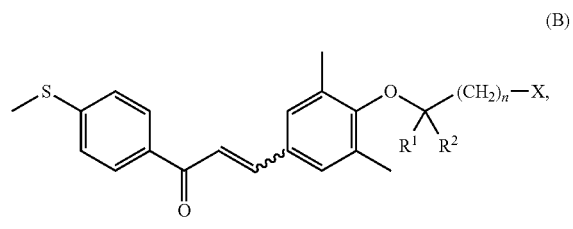

(B)

or a pharmaceutically acceptable salt, solvate ester, amide, or prodrug thereof, wherein:

each $R^1$ and $R^2$ is independently —$C_1$-$C_6$ alkyl, —$C_2$-$C_6$ alkenyl, —$C_2$-$C_6$ alkynyl, phenyl, or benzyl; or alternatively, $R^1$ and $R^2$ together with the carbon atom to which $R^1$ and $R^2$ are attached form a $C_3$-$C_7$ cycloalkyl group;

X is —$CH_2OH$, —COH, —$COOCH_2CONR^4R^5$, —$SO_3H$,

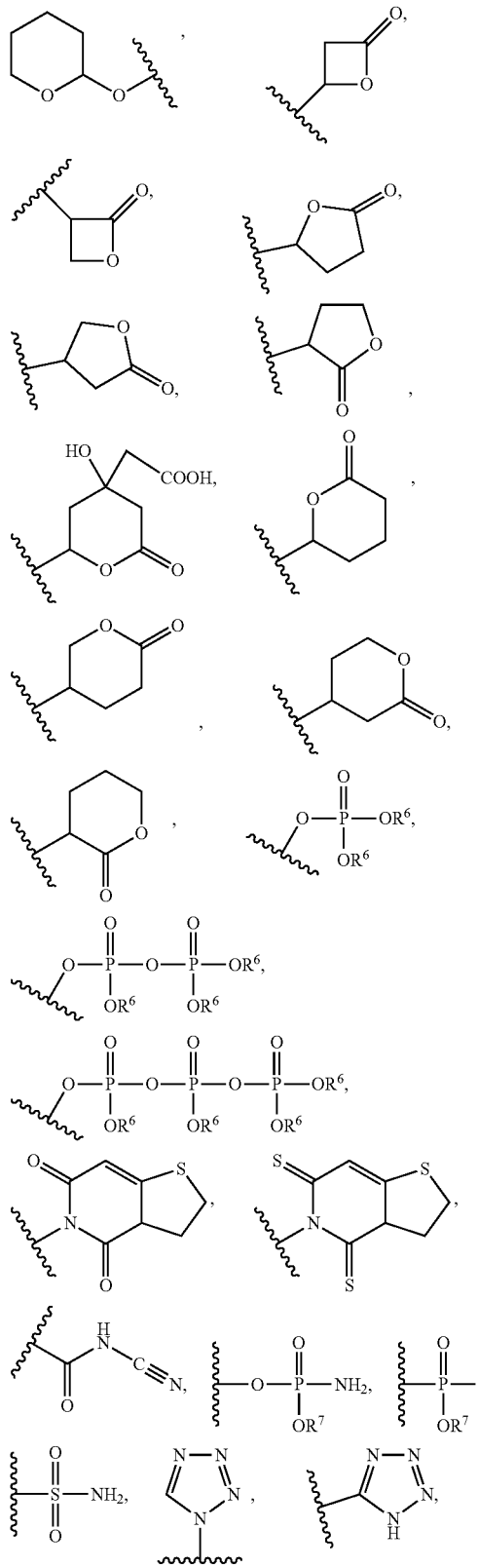

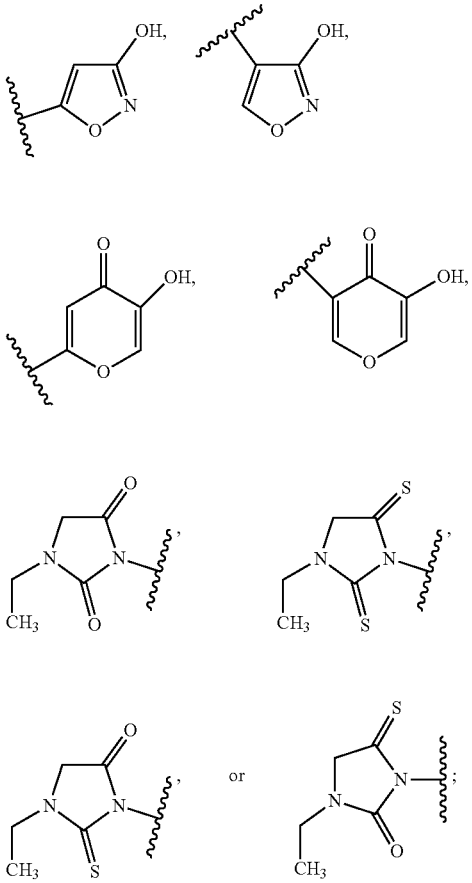

$R^3$ is —$C_1$-$C_6$ alkyl, —$C_2$-$C_6$ alkenyl, —$C_2$-$C_6$ alkynyl, phenyl, or benzyl;

each $R^4$ and $R^5$ is independently alkyl, aryl, or heteroaryl; or alternatively, $R^4$ and $R^5$ together with the carbon atom to which $R^4$ and $R^5$ are attached form a heterocycle;

each $R^6$ and $R^7$ is independently H, —$C_1$-$C_6$ alkyl, —$C_2$-$C_6$ alkenyl, or —$C_2$-$C_6$ alkynyl; and n is 0, 1, 2, 3, or 4.

In some embodiments, the compound of Formula (B) is a racemate or a mixture of enantiomers. In some embodiments, the compounds of Formula (B) has an olefin isomer configuration of (Z) or (E).

In some embodiments, the compounds of Formula (B) is a (Z)-isomer (or cis) and has the structure:

((Z)-B)

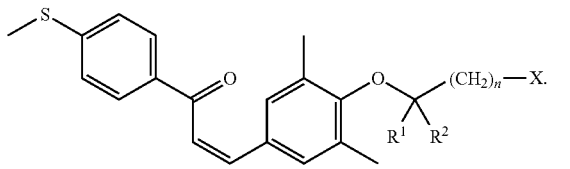

In some embodiments, the compounds of Formula (B) is a (Z)-isomer and is substantially free of its corresponding other olefin configuration (i.e., (E)-isomer).

In some embodiments, the compounds of Formula (B) is an (E)-isomer (or trans) and has the structure:

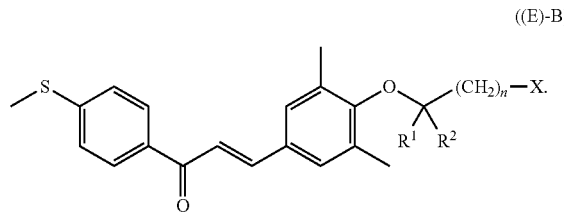

((E)-B)

In some embodiments, the compounds of Formula (B) is an (E)-isomer and is substantially free of its corresponding other olefin configuration (i.e., (Z)-isomer).

In some embodiments of compounds of Formula (B), each $R^1$ and $R^2$ is independently —$C_1$-$C_6$ alkyl. In some embodiments, each $R^1$ and $R^2$ is independently —$C_1$-$C_3$ alkyl. In some embodiments, each $R^1$ and $R^2$ is independently methyl.

In some embodiments of compounds of Formula (B), X is —$CH_2OH$, —COH, or —$COOCH_2CONR^4R^5$. In some embodiments, X is —$CH_2OH$.

In some embodiments of compounds of Formula (B), $R^3$ is —$C_1$-$C_6$ alkyl. In some embodiments, $R^3$ is methyl, ethyl, n-propyl, isopropyl, n-butyl, s-butyl, or t-butyl.

In some embodiments of compounds of Formula (B), n is 0, 1, 2, or 3. In some embodiments, n is 0, 1, or 2. In some embodiments, n is 0 or 1.

5.2.2.1. Compound II

In some embodiments, the compound of the invention is Compound II having the structure:

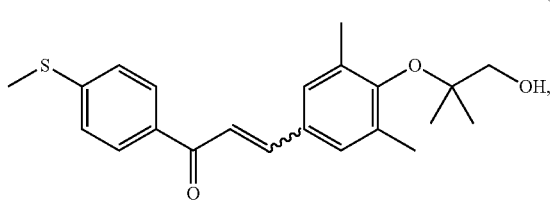

(II)

or a pharmaceutically acceptable salt, solvate, ester, amide, or prodrug thereof.

In some embodiments, Compound II has an olefin isomer configuration of (Z) or (E).

In some embodiments, Compound II is a (Z)-isomer (or cis) and has the structure:

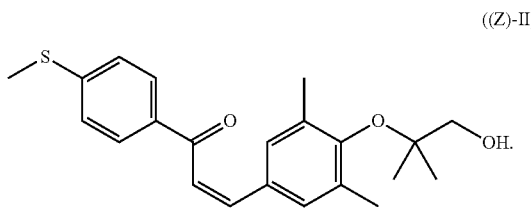

((Z)-II)

In some embodiments, Compound II is a (Z)-isomer and is substantially free of its corresponding other olefin configuration (i.e., (E)-isomer).

In some embodiments, Compound II is an (E)-isomer (or trans) and has the structure:

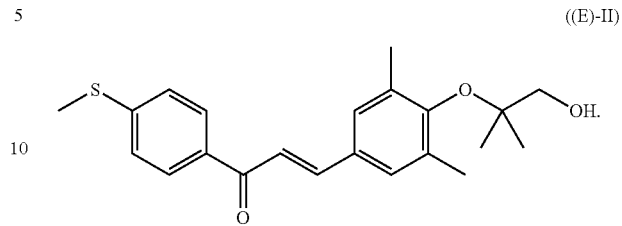

((E)-II)

In some embodiments, Compound II is an (E)-isomer and is substantially free of its corresponding other olefin configuration (i.e., (Z)-isomer).

5.2.3. Compounds of Formula (C)

In some embodiments, the compounds of the invention are compounds of Formula (C):

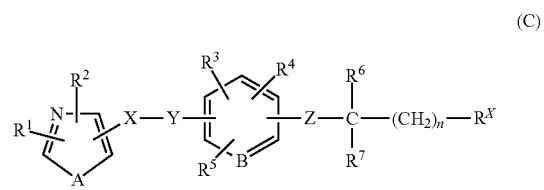

(C)

or a pharmaceutically acceptable salt, solvate, ester, amide, or prodrug thereof, wherein:

$R^1$ is phenyl, naphthyl, pyridyl, thienyl, furyl, quinolyl or benzothienyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

$R^2$ is $C_{2-8}$ alkyl, $C_{1-8}$ haloalkyl, $C_{2-8}$ alkenyl, $C_{2-8}$ alkynyl, 3-7 membered cycloalkyl, $C_{1-8}$ alkyl substituted with a 3-7 membered cycloalkyl, or $C_{1-6}$ alkyl substituted with phenyl, naphthyl or pyridyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

A is oxygen, sulfur or $NR^9$ in which $R^9$ is hydrogen or $C_{1-8}$ alkyl;

X is a $C_{1-8}$ alkylene chain which is unsubstituted or substituted with $C_{1-8}$ alkyl, $C_{1-8}$ alkoxy or hydroxyl, and which has 0 or 1 double bonds;

Y is C(=O), C(=N—$OR^{10}$), CH($OR^{11}$), CH=CH, C≡C, or C(=$CH_2$) in which each of $R^{10}$ and $R^{11}$ is hydrogen or $C_{1-8}$ alkyl;

each of $R^3$, $R^4$ and $R^5$ is independently hydrogen, $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl, or pyridyl; optionally wherein at least one of $R^3$, $R^4$, and $R^5$ is not hydrogen;

B is CH or nitrogen;

Z is oxygen or sulfur;

each of $R^6$ and $R^7$ is independently hydrogen, $C_{1-8}$ alkyl, or $C_{1-8}$ haloalkyl;

$R^X$ is $CH_2OH$, COH, $COOCH_2CONR^{X4}R^{X5}$, $SO_3H$,

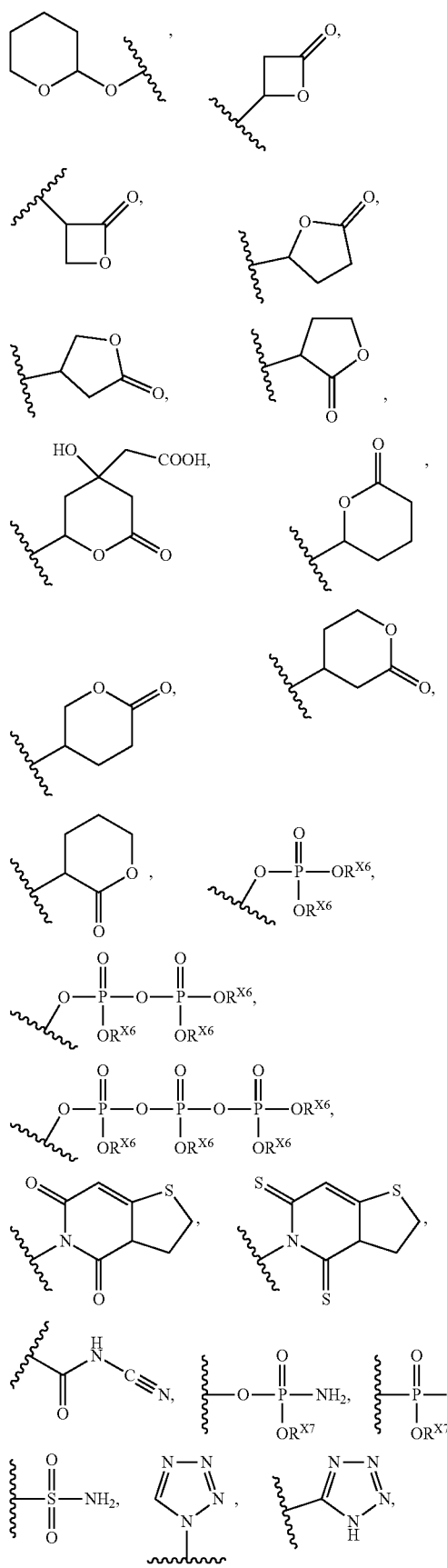
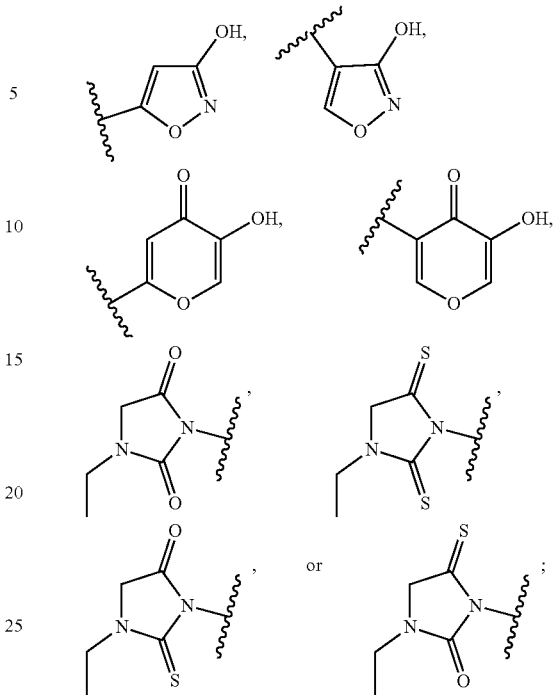

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In the Formula (C), examples of the alkyl groups having 1-8 carbon atoms include methyl, ethyl, propyl, isopropyl, butyl, isobutyl, t-butyl and pentyl.

Examples of the alkyl groups having 1-8 carbon atoms and a halogen substituent include methyl, ethyl, propyl, isopropyl, butyl, and t-butyl which are substituted with 1-3 halogens such as fluorine, chlorine, and bromine. Examples include trifluoromethyl, chloromethyl, 2-chloroethyl, 2-bromoethyl and 2-fluoroethyl.

Examples of the alkoxy groups having 1-8 carbon atoms include methoxy, ethoxy, propoxy, isopropoxy, butoxy, isobutoxy, t-butoxy and pentyloxy.

Examples of the alkoxy groups having 1-8 carbon atoms and a halogen substituent include methoxy, ethoxy, propoxy, isopropoxy, butoxy and t-butoxy groups substituted with 1-3 halogen atoms such as fluorine atom, chlorine atom or bromine atom. Trifluoromethoxy, chloromethoxy, 2-chloroethoxy, 2-bromoethoxy and 2-fluoroethoxy are included.

Examples of the alkenyl groups having 2-8 carbon atoms include vinyl and allyl.

Examples of the alkynyl groups having 2-8 carbon atoms include propargyl.

Examples of 3-7 membered cycloalkyl groups include cyclohexyl and cyclopentyl.

Examples of the alkyl groups having 1-8 carbon atoms and a 3-7 membered cycloalkyl substituent include cyclohexylmethyl and cyclopentylmethyl.

The compound of the Formula (C) can be present in the form of geometrical isomers such as cis and trans and optical isomers. These isomers are included in the compounds provided. Further, the compounds provided can be in the form of pharmaceutically acceptable salts, such as alkali metal salts, e.g., sodium or potassium salt.

In some embodiments, $R^x$ is $CH_2OH$, $COH$, or $COOCH_2CONR^4R^5$. In other embodiments, $R^x$ is $CH_2OH$.

In some embodiments, the compound of Formula (C) is

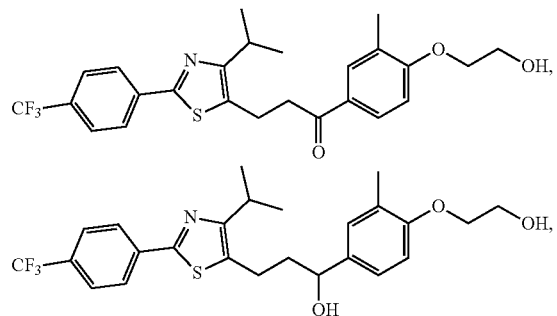

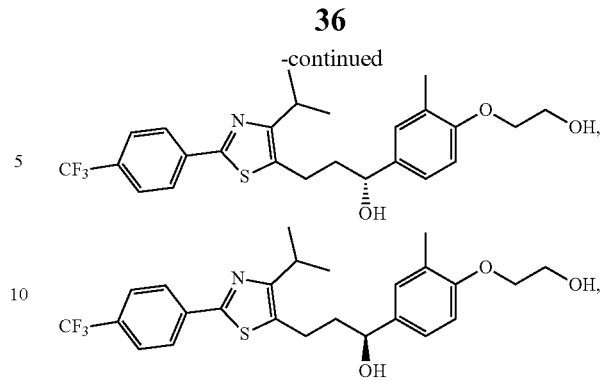

or pharmaceutically acceptable salt, solvate, ester, amide, or prodrug thereof.

In some embodiments, the compound of Formula (C) is a compound shown in Table 1 or pharmaceutically acceptable salt, solvate, ester, amide, or prodrug thereof.

TABLE 1

| Structure | Name |
| --- | --- |
| 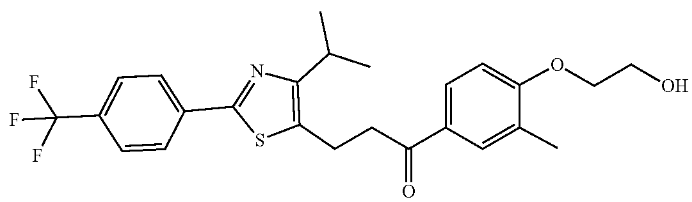 [SMILES: Cc1cc(C(=O)CCc2sc(-c3ccc(C(F)(F)F)cc3)nc2C(C)C)ccc1OCCO] | 1-(4-(2-hydroxyethoxy)-3-methylphenyl)-3-(4-isopropyl-2-(4-(trifluoromethyl)phenyl)thiazol-5-yl)propan-1-one |
| 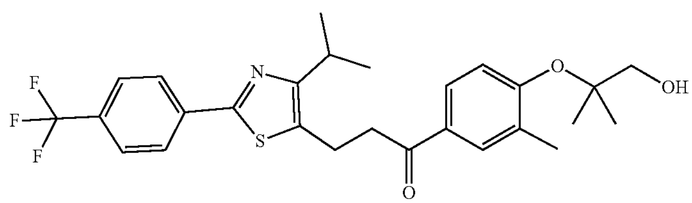 [SMILES: Cc1cc(C(=O)CCc2sc(-c3ccc(C(F)(F)F)cc3)nc2C(C)C)ccc1OC(C)(C)CO] | 1-(4-((1-hydroxy-2-methylpropan-2-yl)oxy)-3-methylphenyl)-3-(4-isopropyl-2-(4-(trifluoromethyl)phenyl)thiazol-5-yl)propan-1-one |
| 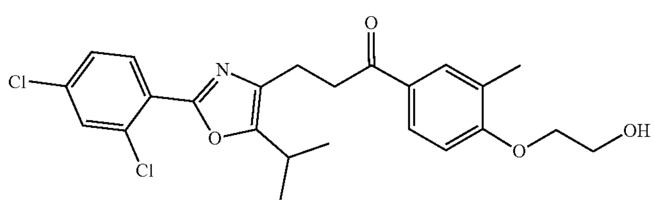 [SMILES: Cc1cc(C(=O)CCc2nc(-c3ccc(Cl)cc3Cl)oc2C(C)C)ccc1OCCO] | 3-(2-(2,4-dichlorophenyl)-5-isopropyloxazol-4-yl)-1-(4-(2-hydroxyethoxy)-3-methylphenyl)propan-1-one |
| 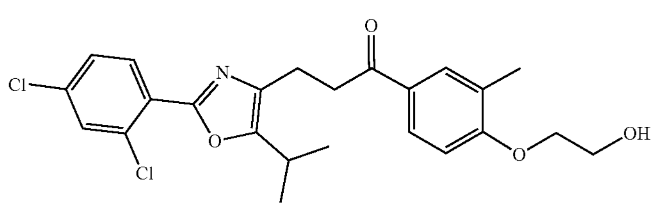 [SMILES: Cc1cc(C(=O)CCc2nc(-c3ccc(Cl)cc3Cl)oc2C(C)C)ccc1OCCO] | 3-(2-(4-chloro-2-hydroxyphenyl)-5-isopropyloxazol-4-yl)-1-(4-(2-hydroxyethoxy)-3-methylphenyl)propan-1-one |
| 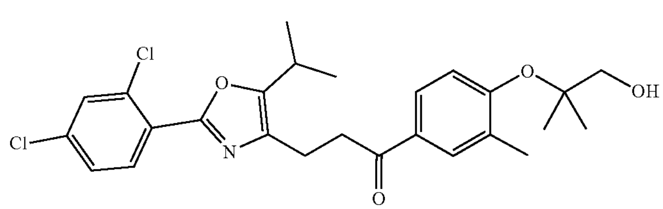 [SMILES: Cc1cc(C(=O)CCc2nc(-c3ccc(Cl)cc3Cl)oc2C(C)C)ccc1OC(C)(C)CO] | 3-(2-(2,4-dichlorophenyl)-5-isopropyloxazol-4-yl)-1-(4-((1-hydroxy-2-methylpropan-2-yl)oxy)-3-methylphenyl)propan-1-one |

TABLE 1-continued

| Structure | Name |
|---|---|
| 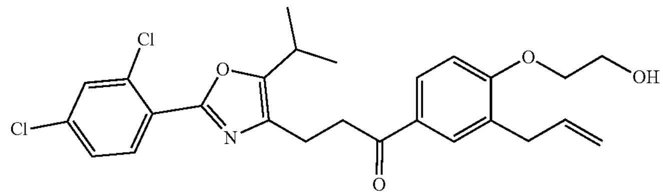 [SMILES: C=CCc1cc(C(=O)CCc2nc(-c3ccc(Cl)cc3Cl)oc2C(C)C)ccc1OCCO] | 1-(3-allyl-4-(2-hydroxyethoxy)phenyl)-3-(2-(2,4-dichlorophenyl)-5-isopropyloxazol-4-yl)propan-1-one |
| 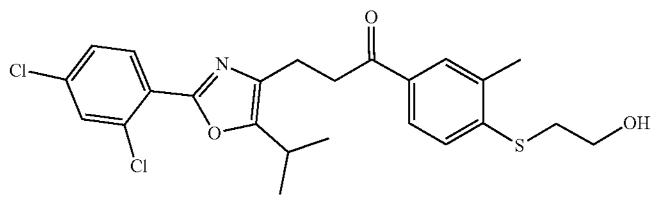 [SMILES: Cc1cc(C(=O)CCc2nc(-c3ccc(Cl)cc3Cl)oc2C(C)C)ccc1SCCO] | 3-(2-(2,4-dichlorophenyl)-5-isopropyloxazol-4-yl)-1-(4-((2-hydroxyethyl)thio)-3-methylphenyl)propan-1-one |
| 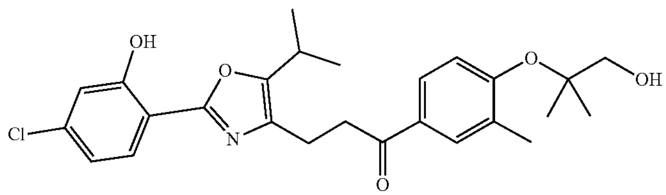 [SMILES: Cc1cc(C(=O)CCc2nc(-c3ccc(Cl)cc3O)oc2C(C)C)ccc1OC(C)(C)CO] | 3-(2-(4-chloro-2-hydroxyphenyl)-5-isopropyloxazol-4-yl)-1-(4-((1-hydroxy-2-methylpropan-2-yl)oxy)-3-methylphenyl)propan-1-one |
| 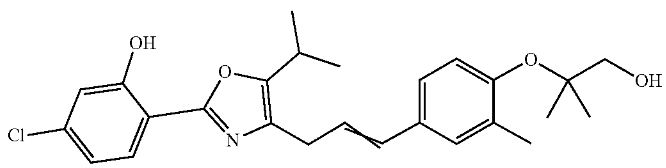 [SMILES: Cc1cc(C=CCc2nc(-c3ccc(Cl)cc3O)oc2C(C)C)ccc1OC(C)(C)CO] | 2-(4-(3-(2-(2,4-dichlorophenyl)-5-isopropyloxazol-4-yl)prop-1-en-1-yl)-2-methylphenoxy)ethan-1-ol |
| 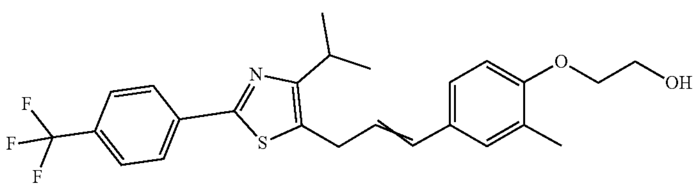 [SMILES: Cc1cc(C=CCc2sc(-c3ccc(C(F)(F)F)cc3)nc2C(C)C)ccc1OCCO] | 2-(4-(3-(4-isopropyl-2-(4-(trifluoromethyl)phenyl)thiazol-5-yl)prop-1-en-1-yl)-2-methylphenoxy)ethan-1-ol |
| 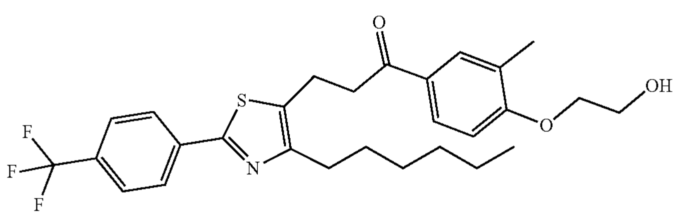 [SMILES: CCCCCCc1nc(-c2ccc(C(F)(F)F)cc2)sc1CCC(=O)c1ccc(OCCO)c(C)c1] | 3-(4-hexyl-2-(4-(trifluoromethyl)phenyl)thiazol-5-yl)-1-(4-(2-hydroxyethoxy)-3-methylphenyl)propan-1-one |
| 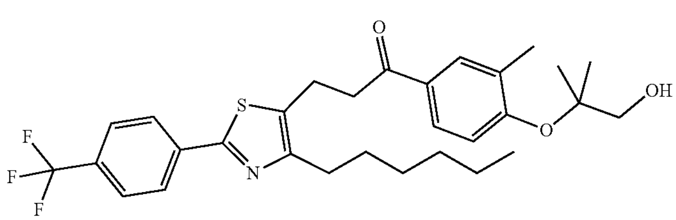 [SMILES: CCCCCCc1nc(-c2ccc(C(F)(F)F)cc2)sc1CCC(=O)c1ccc(OC(C)(C)CO)c(C)c1] | 3-(4-hexyl-2-(4-(trifluoromethyl)phenyl)thiazol-5-yl)-1-(4-((1-hydroxy-2-methylpropan-2-yl)oxy)-3-methylphenyl)propan-1-one |
| 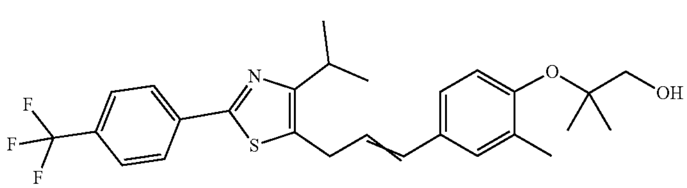 [SMILES: Cc1cc(C=CCc2sc(-c3ccc(C(F)(F)F)cc3)nc2C(C)C)ccc1OC(C)(C)CO] | 2-(4-(3-(4-isopropyl-2-(4-(trifluoromethyl)phenyl)thiazol-5-yl)prop-1-en-1-yl)-2-methylphenoxy)-2-methylpropan-1-ol |

TABLE 1-continued

| Structure | Name |
|---|---|
| 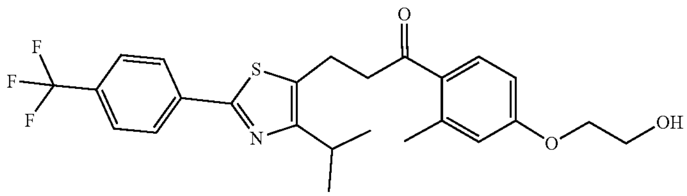 [SMILES: Cc1cc(OCCO)ccc1C(=O)CCc1sc(-c2ccc(C(F)(F)F)cc2)nc1C(C)C] | 1-(4-(2-hydroxyethoxy)-2-methylphenyl)-3-(4-isopropyl-2-(4-(trifluoromethyl)phenyl)thiazol-5-yl)propan-1-one |
| 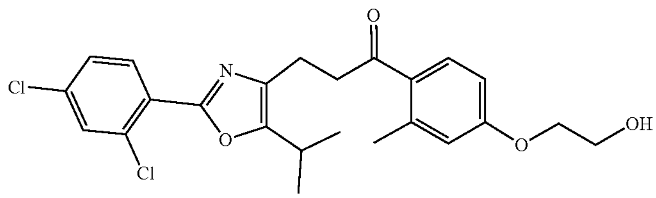 [SMILES: Cc1cc(OCCO)ccc1C(=O)CCc1nc(-c2ccc(Cl)cc2Cl)oc1C(C)C] | 3-(2-(2,4-dichlorophenyl)-5-isopropyloxazol-4-yl)-1-(4-(2-hydroxyethoxy)-2-methylphenyl)propan-1-one |
| 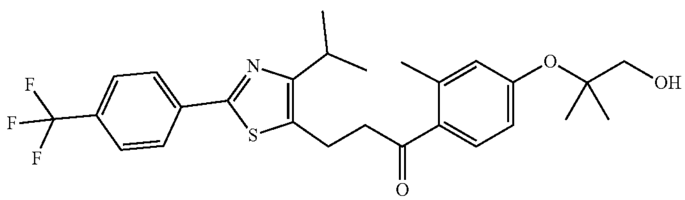 [SMILES: Cc1cc(OC(C)(C)CO)ccc1C(=O)CCc1sc(-c2ccc(C(F)(F)F)cc2)nc1C(C)C] | 1-(4-((1-hydroxy-2-methylpropan-2-yl)oxy)-2-methylphenyl)-3-(4-isopropyl-2-(4-(trifluoromethyl)phenyl)thiazol-5-yl)propan-1-one |
| 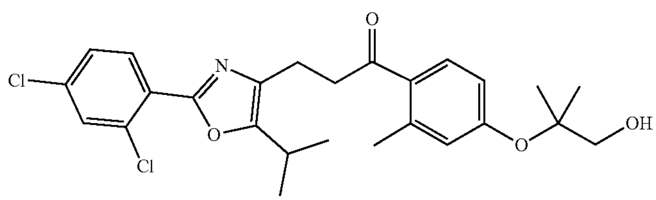 [SMILES: Cc1cc(OC(C)(C)CO)ccc1C(=O)CCc1nc(-c2ccc(Cl)cc2Cl)oc1C(C)C] | 3-(2-(2,4-dichlorophenyl)-5-isopropyloxazol-4-yl)-1-(4-((1-hydroxy-2-methylpropan-2-yl)oxy)-2-methylphenyl)propan-1-one |
| 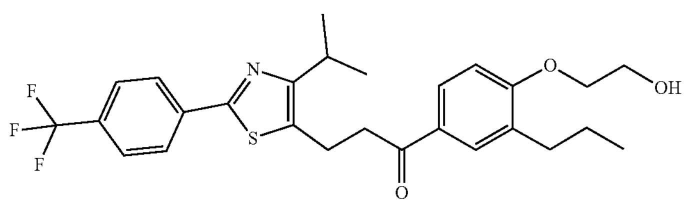 [SMILES: CCCc1cc(C(=O)CCc2sc(-c3ccc(C(F)(F)F)cc3)nc2C(C)C)ccc1OCCO] | 1-(4-(2-hydroxyethoxy)-3-propylphenyl)-3-(4-isopropyl-2-(4-(trifluoromethyl)phenyl)thiazol-5-yl)propan-1-one |
| 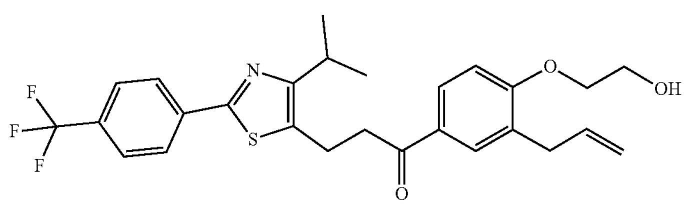 [SMILES: C=CCc1cc(C(=O)CCc2sc(-c3ccc(C(F)(F)F)cc3)nc2C(C)C)ccc1OCCO] | 1-(3-allyl-4-(2-hydroxyethoxy)phenyl)-3-(4-isopropyl-2-(4-(trifluoromethyl)phenyl)thiazol-5-yl)propan-1-one |
| 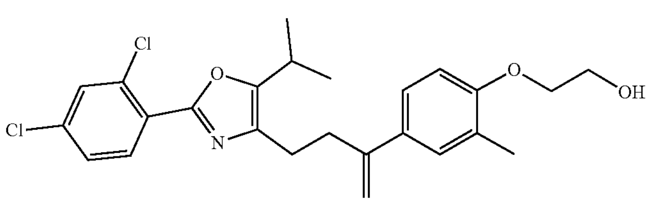 [SMILES: C=C(CCc1nc(-c2ccc(Cl)cc2Cl)oc1C(C)C)c1ccc(OCCO)c(C)c1] | 2-(4-(4-(2-(2,4-dichlorophenyl)-5-isopropyloxazol-4-yl)but-1-en-2-yl)-2-methylphenoxy)ethan-1-ol |

TABLE 1-continued

| Structure | Name |
|---|---|
| 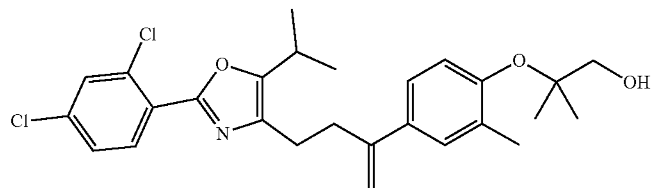 [SMILES: C=C(CCc1nc(-c2ccc(Cl)cc2Cl)oc1C(C)C)c1ccc(OC(C)(C)CO)c(C)c1] | 2-(4-(4-(2-(2,4-dichlorophenyl)-5-isopropyloxazol-4-yl)but-1-en-2-yl)-2-methylphenoxy)-2-methylpropan-1-ol |
| 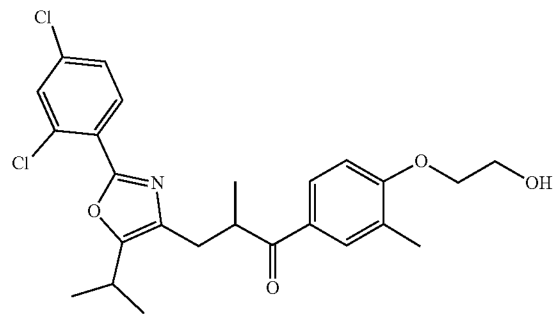 [SMILES: Cc1cc(C(=O)C(C)Cc2nc(-c3ccc(Cl)cc3Cl)oc2C(C)C)ccc1OCCO] | 3-(2-(2,4-dichlorophenyl)-5-isopropyloxazol-4-yl)-1-(4-(2-hydroxyethoxy)-3-methylphenyl)-2-methylpropan-1-one |
| 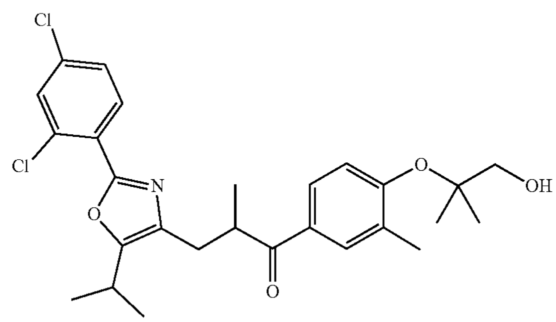 [SMILES: Cc1cc(C(=O)C(C)Cc2nc(-c3ccc(Cl)cc3Cl)oc2C(C)C)ccc1OC(C)(C)CO] | 3-(2-(2,4-dichlorophenyl)-5-isopropyloxazol-4-yl)-1-(4-((1-hydroxy-2-methylpropan-2-yl)oxy)-3-methylphenyl)-2-methylpropan-1-one |
| 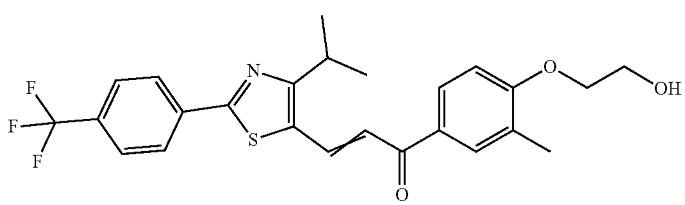 [SMILES: Cc1cc(C(=O)C=Cc2sc(-c3ccc(C(F)(F)F)cc3)nc2C(C)C)ccc1OCCO] | 1-(4-(2-hydroxyethoxy)-3-methylphenyl)-3-(4-isopropyl-2-(4-(trifluoromethyl)phenyl)thiazol-5-yl)prop-2-en-1-one |
| 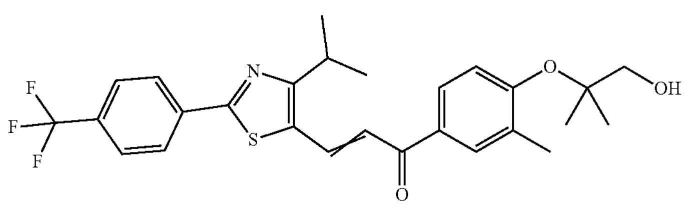 [SMILES: Cc1cc(C(=O)C=Cc2sc(-c3ccc(C(F)(F)F)cc3)nc2C(C)C)ccc1OC(C)(C)CO] | 1-(4-((1-hydroxy-2-methylpropan-2-yl)oxy)-3-methylphenyl)-3-(4-isopropyl-2-(4-(trifluoromethyl)phenyl)thiazol-5-yl)prop-2-en-1-one |
| 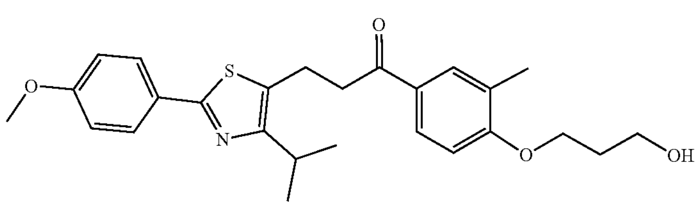 [SMILES: COc1ccc(-c2nc(C(C)C)c(CCC(=O)c3ccc(OCCCO)c(C)c3)s2)cc1] | 1-(4-(3-hydroxypropoxy)-3-methylphenyl)-3-(4-isopropyl-2-(4-methoxyphenyl)thiazol-5-yl)propan-1-one |

TABLE 1-continued

| Structure | Name |
| --- | --- |
| 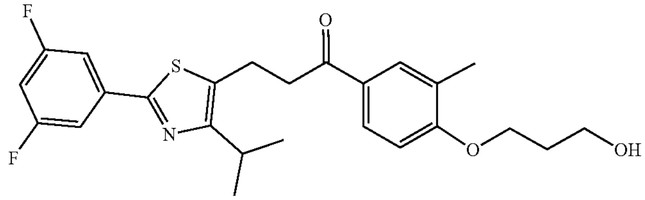 [SMILES: Cc1cc(C(=O)CCc2sc(-c3cc(F)cc(F)c3)nc2C(C)C)ccc1OCCCO] | 3-(2-(3,5-difluorophenyl)-4-isopropylthiazol-5-yl)-1-(4-(2-hydroxyethoxy)-3-methylphenyl)propan-1-one |
| 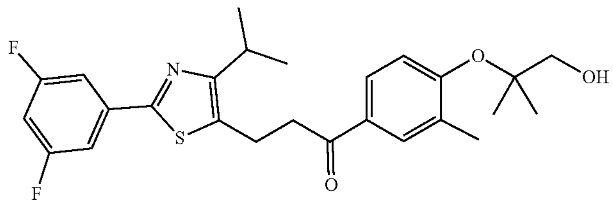 [SMILES: Cc1cc(C(=O)CCc2sc(-c3cc(F)cc(F)c3)nc2C(C)C)ccc1OC(C)(C)CO] | 3-(2-(3,5-difluorophenyl)-4-isopropylthiazol-5-yl)-1-(4-((1-hydroxy-2-methylpropan-2-yl)oxy)-3-methylphenyl)propan-1-one |
| 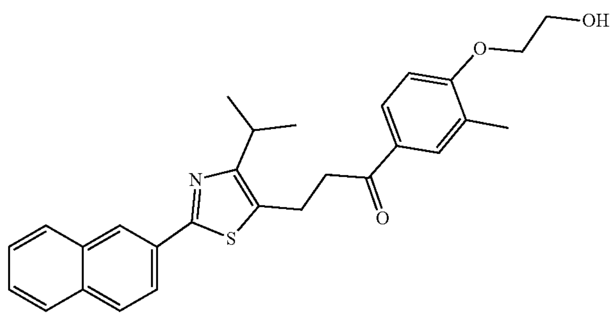 [SMILES: Cc1cc(C(=O)CCc2sc(-c3ccc4ccccc4c3)nc2C(C)C)ccc1OCCO] | 1-(4-(2-hydroxyethoxy)-3-methylphenyl)-3-(4-isopropyl-2-(naphthalen-2-yl)thiazol-5-yl)propan-1-one |
| 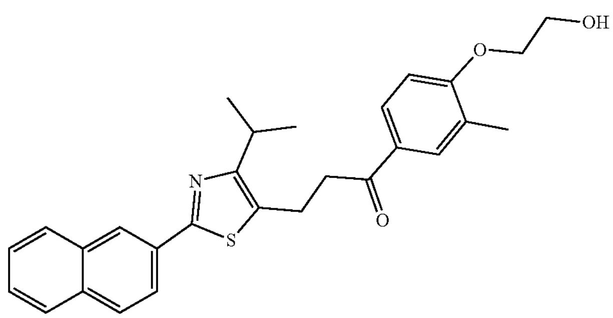 [SMILES: Cc1cc(C(=O)CCc2sc(-c3ccc4ccccc4c3)nc2C(C)C)ccc1OCCO] | 1-(4-((1-hydroxy-2-methylpropan-2-yl)oxy)-3-methylphenyl)-3-(4-isopropyl-2-(naphthalen-2-yl)thiazol-5-yl)propan-1-one |
| 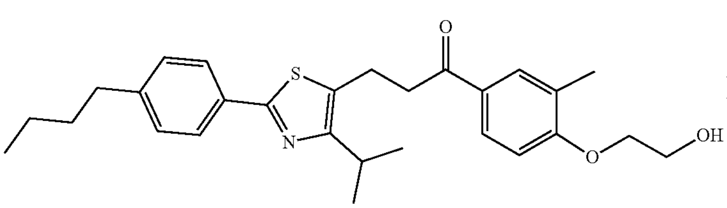 [SMILES: CCCCc1ccc(-c2nc(C(C)C)c(CCC(=O)c3ccc(OCCO)c(C)c3)s2)cc1] | 3-(2-(4-butylphenyl)-4-isopropylthiazol-5-yl)-1-(4-(2-hydroxyethoxy)-3-methylphenyl)propan-1-one |
| 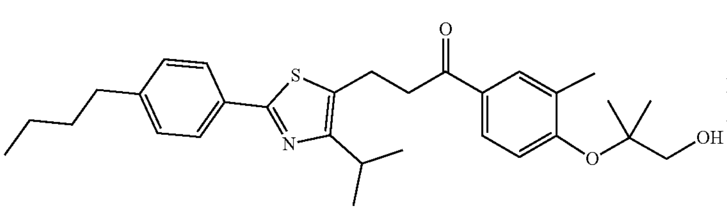 [SMILES: CCCCc1ccc(-c2nc(C(C)C)c(CCC(=O)c3ccc(OC(C)(C)CO)c(C)c3)s2)cc1] | 3-(2-(4-butylphenyl)-4-isopropylthiazol-5-yl)-1-(4-((1-hydroxy-2-methylpropan-2-yl)oxy)-3-methylphenyl)propan-1-one |

TABLE 1-continued

| Structure | Name |
|---|---|
| 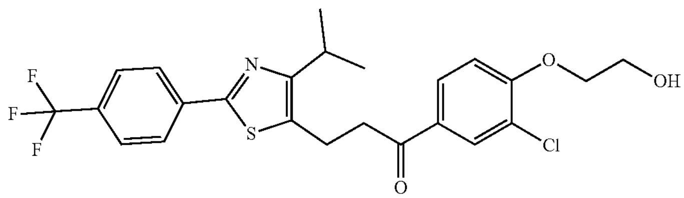 [SMILES: CC(C)c1nc(-c2ccc(C(F)(F)F)cc2)sc1CCC(=O)c1ccc(OCCO)c(Cl)c1] | 1-(3-chloro-4-(2-hydroxyethoxy)phenyl)-3-(4-isopropyl-2-(4-(trifluoromethyl)phenyl)thiazol-5-yl)propan-1-one |
| 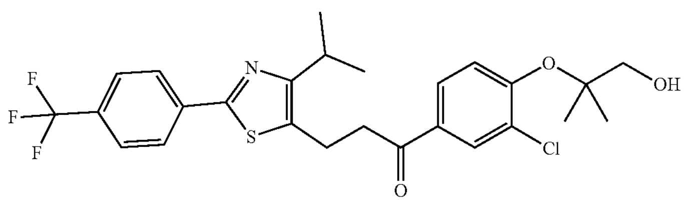 [SMILES: CC(C)c1nc(-c2ccc(C(F)(F)F)cc2)sc1CCC(=O)c1ccc(OC(C)(C)CO)c(Cl)c1] | 1-(3-chloro-4-((1-hydroxy-2-methylpropan-2-yl)oxy)phenyl)-3-(4-isopropyl-2-(4-(trifluoromethyl)phenyl)thiazol-5-yl)propan-1-one |
| 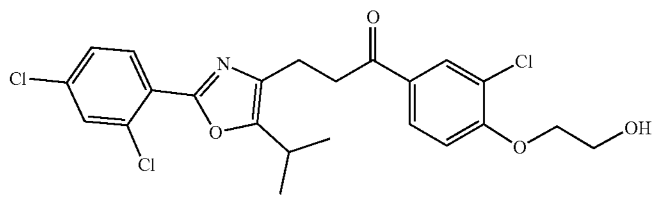 [SMILES: CC(C)c1oc(-c2ccc(Cl)cc2Cl)nc1CCC(=O)c1ccc(OCCO)c(Cl)c1] | 1-(3-chloro-4-(2-hydroxyethoxy)phenyl)-3-(2-(2,4-dichlorophenyl)-5-isopropyloxazol-4-yl)propan-1-one |
| 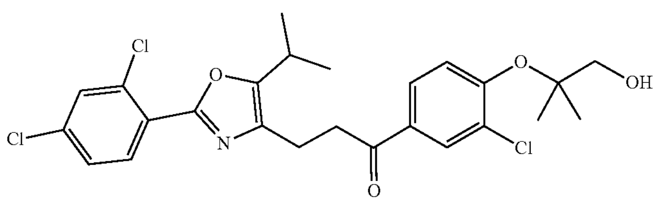 [SMILES: CC(C)c1oc(-c2ccc(Cl)cc2Cl)nc1CCC(=O)c1ccc(OC(C)(C)CO)c(Cl)c1] | 1-(3-chloro-4-((1-hydroxy-2-methylpropan-2-yl)oxy)phenyl)-3-(2-(2,4-dichlorophenyl)-5-isopropyloxazol-4-yl)propan-1-one |
| 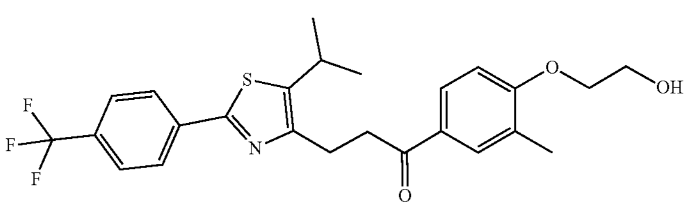 [SMILES: Cc1cc(C(=O)CCc2nc(-c3ccc(C(F)(F)F)cc3)sc2C(C)C)ccc1OCCO] | 1-(4-(2-hydroxyethoxy)-3-methylphenyl)-3-(5-isopropyl-2-(4-(trifluoromethyl)phenyl)thiazol-4-yl)propan-1-one |
| 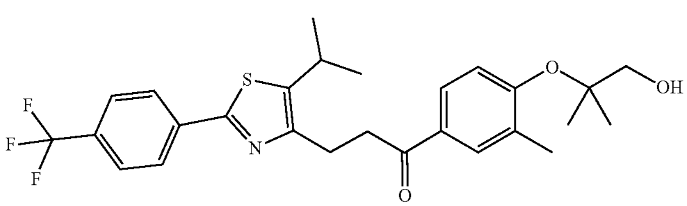 [SMILES: Cc1cc(C(=O)CCc2nc(-c3ccc(C(F)(F)F)cc3)sc2C(C)C)ccc1OC(C)(C)CO] | 1-(4-((1-hydroxy-2-methylpropan-2-yl)oxy)-3-methylphenyl)-3-(5-isopropyl-2-(4-(trifluoromethyl)phenyl)thiazol-4-yl)propan-1-one |
| 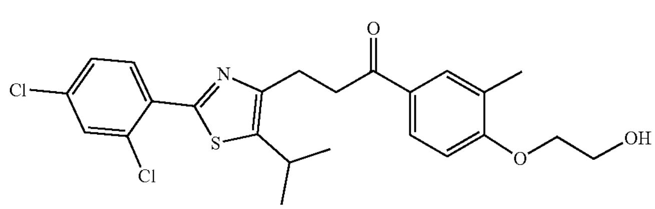 [SMILES: Cc1cc(C(=O)CCc2nc(-c3ccc(Cl)cc3Cl)sc2C(C)C)ccc1OCCO] | 3-(2-(2,4-dichlorophenyl)-5-isopropylthiazol-4-yl)-1-(4-(2-hydroxyethoxy)-3-methylphenyl)propan-1-one |

TABLE 1-continued

| Structure | Name |
|---|---|
| 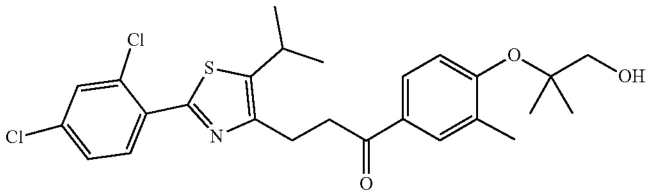 [SMILES: Cc1cc(C(=O)CCc2nc(-c3ccc(Cl)cc3Cl)sc2C(C)C)ccc1OC(C)(C)CO] | 3-(2-(2,4-dichlorophenyl)-5-isopropylthiazol-4-yl)-1-(4-((1-hydroxy-2-methylpropan-2-yl)oxy)-3-methylphenyl)propan-1-one |
| 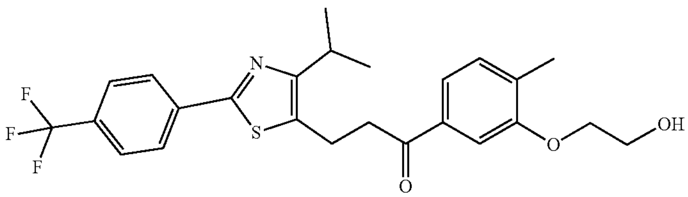 [SMILES: Cc1ccc(C(=O)CCc2sc(-c3ccc(C(F)(F)F)cc3)nc2C(C)C)cc1OCCO] | 1-(3-(2-hydroxyethoxy)-4-methylphenyl)-3-(4-isopropyl-2-(4-(trifluoromethyl)phenyl)thiazol-5-yl)propan-1-one |
| 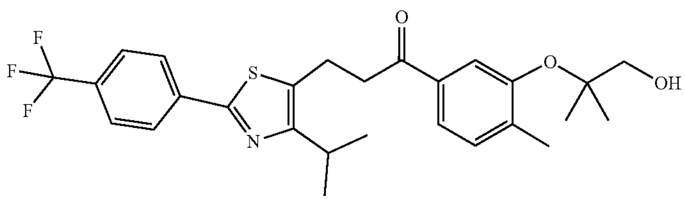 [SMILES: Cc1ccc(C(=O)CCc2sc(-c3ccc(C(F)(F)F)cc3)nc2C(C)C)cc1OC(C)(C)CO] | 1-(3-((1-hydroxy-2-methylpropan-2-yl)oxy)-4-methylphenyl)-3-(4-isopropyl-2-(4-(trifluoromethyl)phenyl)thiazol-5-yl)propan-1-one |
| 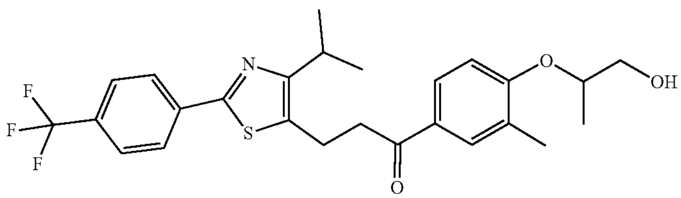 [SMILES: Cc1cc(C(=O)CCc2sc(-c3ccc(C(F)(F)F)cc3)nc2C(C)C)ccc1OC(C)CO] | 1-(4-((1-hydroxypropan-2-yl)oxy)-3-methylphenyl)-3-(4-isopropyl-2-(4-(trifluoromethyl)phenyl)thiazol-5-yl)propan-1-one |
| 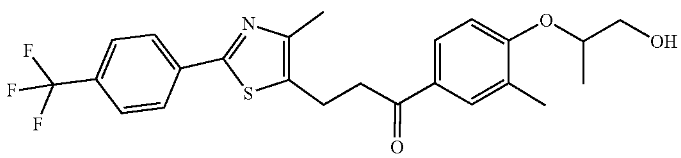 [SMILES: Cc1cc(C(=O)CCc2sc(-c3ccc(C(F)(F)F)cc3)nc2C)ccc1OC(C)CO] | 1-(4-(2-hydroxyethoxy)-3-methylphenyl)-3-(4-methyl-2-(4-(trifluoromethyl)phenyl)thiazol-5-yl)propan-1-one |
| 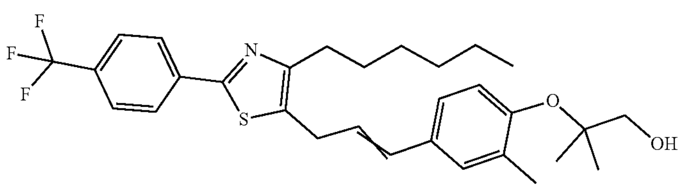 [SMILES: CCCCCCc1nc(-c2ccc(C(F)(F)F)cc2)sc1CC=Cc1ccc(OC(C)(C)CO)c(C)c1] | 2-(4-(3-(4-hexyl-2-(4-(trifluoromethyl)phenyl)thiazol-5-yl)prop-1-en-1-yl)-2-methylphenoxy)-2-methylpropan-1-ol |
| 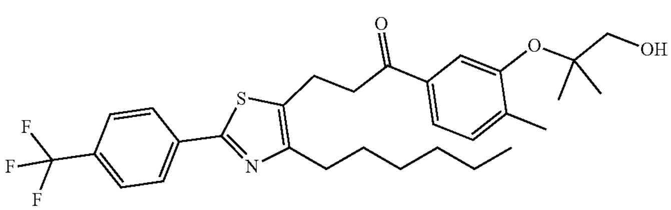 [SMILES: CCCCCCc1nc(-c2ccc(C(F)(F)F)cc2)sc1CCC(=O)c1ccc(C)c(OC(C)(C)CO)c1] | 3-(4-hexyl-2-(4-(trifluoromethyl)phenyl)thiazol-5-yl)-1-(3-((1-hydroxy-2-methylpropan-2-yl)oxy)-4-methylphenyl)propan-1-one |
| 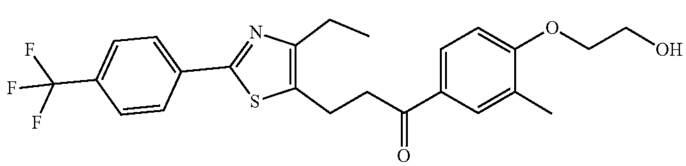 [SMILES: CCc1nc(-c2ccc(C(F)(F)F)cc2)sc1CCC(=O)c1ccc(OCCO)c(C)c1] | 3-(4-ethyl-2-(4-(trifluoromethyl)phenyl)thiazol-5-yl)-1-(4-(2-hydroxyethoxy)-3-methylphenyl)propan-1-one |

TABLE 1-continued

| Structure | Name |
|---|---|
| 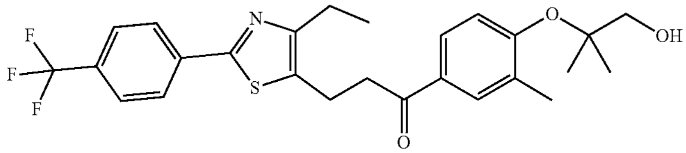 [SMILES: CCc1nc(-c2ccc(C(F)(F)F)cc2)sc1CCC(=O)c1ccc(OC(C)(C)CO)c(C)c1] | 3-(4-ethyl-2-(4-(trifluoromethyl)phenyl)thiazol-5-yl)-1-(4-((1-hydroxy-2-methylpropan-2-yl)oxy)-3-methylphenyl)propan-1-one |
| 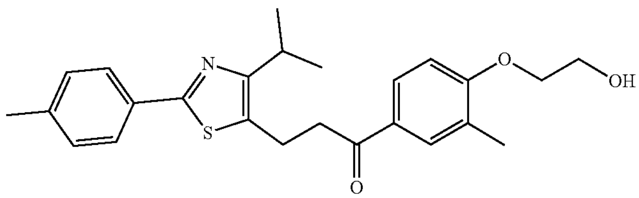 [SMILES: Cc1ccc(-c2nc(C(C)C)c(CCC(=O)c3ccc(OCCO)c(C)c3)s2)cc1] | 1-(4-(2-hydroxyethoxy)-3-methylphenyl)-3-(4-isopropyl-2-(p-tolyl)thiazol-5-yl)propan-1-one |
| 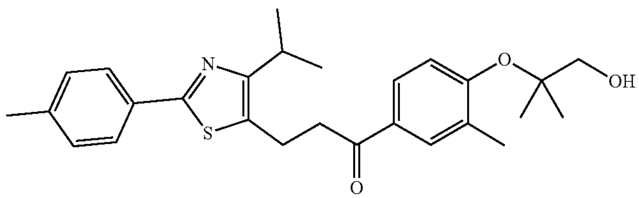 [SMILES: Cc1ccc(-c2nc(C(C)C)c(CCC(=O)c3ccc(OC(C)(C)CO)c(C)c3)s2)cc1] | 1-(4-((1-hydroxy-2-methylpropan-2-yl)oxy)-3-methylphenyl)-3-(4-isopropyl-2-(p-tolyl)thiazol-5-yl)propan-1-one |
| 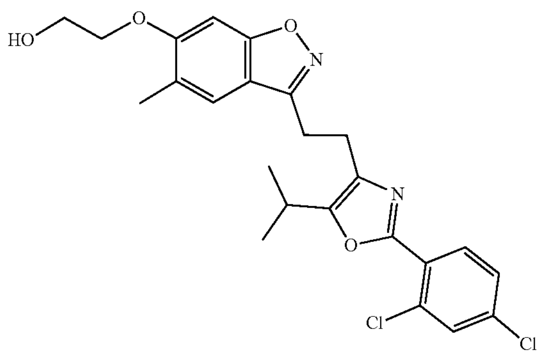 [SMILES: Cc1cc2c(CCc3nc(-c4ccc(Cl)cc4Cl)oc3C(C)C)noc2cc1OCCO] | 2-((3-(2-(2-(2,4-dichlorophenyl)-5-isopropyloxazol-4-yl)ethyl)-5-methylbenzo[d]isoxazol-6-yl)oxy)ethan-1-ol |
| 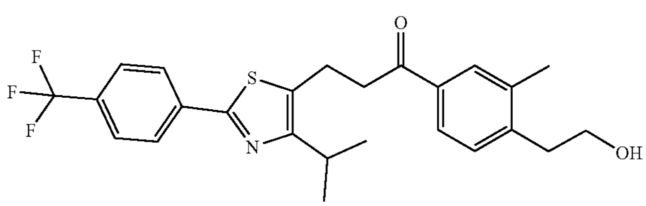 [SMILES: Cc1cc(C(=O)CCc2sc(-c3ccc(C(F)(F)F)cc3)nc2C(C)C)ccc1CCO] | 1-(4-(2-hydroxyethyl)-3-methylphenyl)-3-(4-isopropyl-2-(4-(trifluoromethyl)phenyl)thiazol-5-yl)propan-1-one |
| 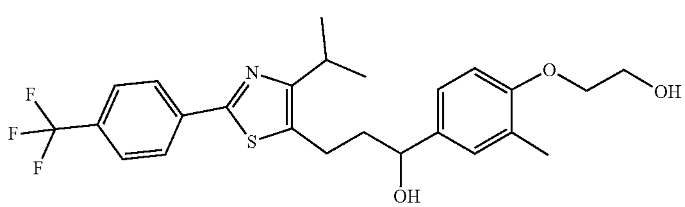 [SMILES: Cc1cc(C(O)CCc2sc(-c3ccc(C(F)(F)F)cc3)nc2C(C)C)ccc1OCCO] | 1-(4-(2-hydroxyethoxy)-3-methylphenyl)-3-(4-isopropyl-2-(4-(trifluoromethyl)phenyl)thiazol-5-yl)propan-1-ol |
| 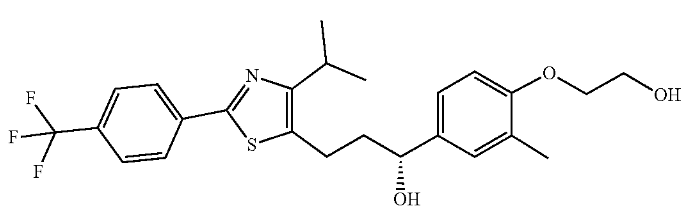 | (R)-1-(4-(2-hydroxyethoxy)-3-methylphenyl)-3-(4-isopropyl-2-(4-(trifluoromethyl)phenyl)thiazol-5-yl)propan-1-ol |

TABLE 1-continued

| Structure | Name |
|---|---|
| 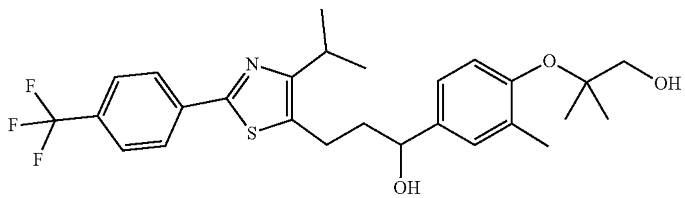 [SMILES: Cc1cc(C(O)CCc2sc(-c3ccc(C(F)(F)F)cc3)nc2C(C)C)ccc1OC(C)(C)CO] | 1-(4-((1-hydroxy-2-methylpropan-2-yl)oxy)-3-methylphenyl)-3-(4-isopropyl-2-(4-(trifluoromethyl)phenyl)thiazol-5-yl)propan-1-ol |
| 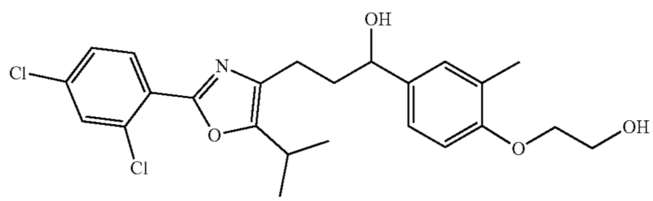 [SMILES: Cc1cc(C(O)CCc2nc(-c3ccc(Cl)cc3Cl)oc2C(C)C)ccc1OCCO] | 3-(2-(2,4-dichlorophenyl)-5-isopropyloxazol-4-yl)-1-(4-(2-hydroxyethoxy)-3-methylphenyl)propan-1-ol |
| 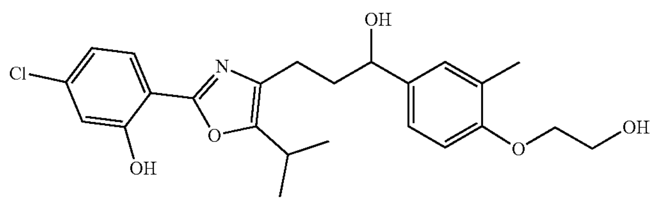 | 5-chloro-2-(4-(3-hydroxy-3-(4-(2-hydroxyethoxy)-3-methylphenyl)propyl)-5-isopropyloxazol-2-yl)phenol |
| 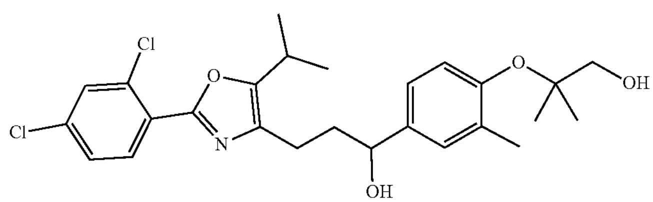 [SMILES: Cc1cc(C(O)CCc2nc(-c3ccc(Cl)cc3Cl)oc2C(C)C)ccc1OC(C)(C)CO] | 3-(2-(2,4-dichlorophenyl)-5-isopropyloxazol-4-yl)-1-(4-((1-hydroxy-2-methylpropan-2-yl)oxy)-3-methylphenyl)propan-1-ol |
| 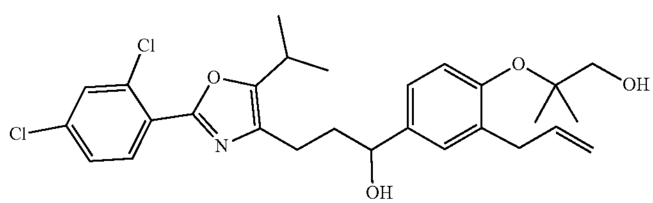 [SMILES: C=CCc1cc(C(O)CCc2nc(-c3ccc(Cl)cc3Cl)oc2C(C)C)ccc1OC(C)(C)CO] | 1-(3-allyl-4-(2-hydroxyethoxy)phenyl)-3-(2-(2,4-dichlorophenyl)-5-isopropyloxazol-4-yl)propan-1-ol |
| 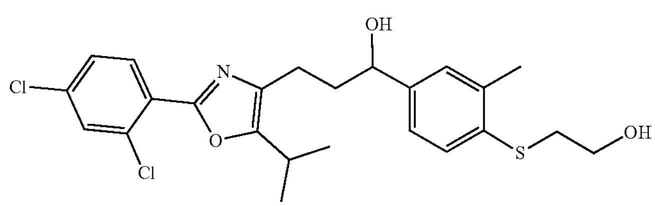 [SMILES: Cc1cc(C(O)CCc2nc(-c3ccc(Cl)cc3Cl)oc2C(C)C)ccc1SCCO] | 3-(2-(2,4-dichlorophenyl)-5-isopropyloxazol-4-yl)-1-(4-((2-hydroxyethyl)thio)-3-methylphenyl)propan-1-ol |
| 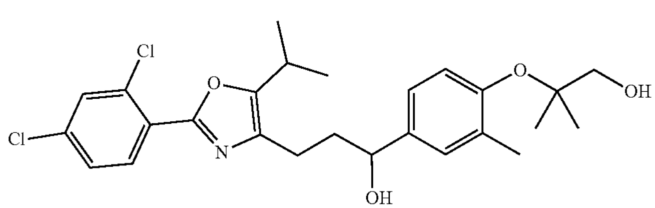 [SMILES: Cc1cc(C(O)CCc2nc(-c3ccc(Cl)cc3Cl)oc2C(C)C)ccc1OC(C)(C)CO] | 5-chloro-2-(4-(3-hydroxy-3-(4-((1-hydroxy-2-methylpropan-2-yl)oxy)-3-methylphenyl)propyl)-5-isopropyloxazol-2-yl)phenol |

TABLE 1-continued

| Structure | Name |
|---|---|
| 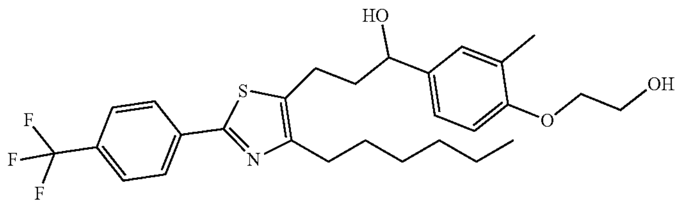 [SMILES: CCCCCCc1nc(-c2ccc(C(F)(F)F)cc2)sc1CCC(O)c1ccc(OCCO)c(C)c1] | 3-(4-hexyl-2-(4-(trifluoromethyl)phenyl)thiazol-5-yl)-1-(4-(2-hydroxyethoxy)-3-methylphenyl)propan-1-ol |
| 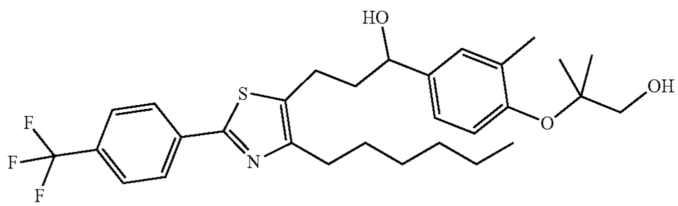 [SMILES: CCCCCCc1nc(-c2ccc(C(F)(F)F)cc2)sc1CCC(O)c1ccc(OC(C)(C)CO)c(C)c1] | 3-(4-hexyl-2-(4-(trifluoromethyl)phenyl)thiazol-5-yl)-1-(4-((1-hydroxy-2-methylpropan-2-yl)oxy)-3-methylphenyl)propan-1-ol |
| 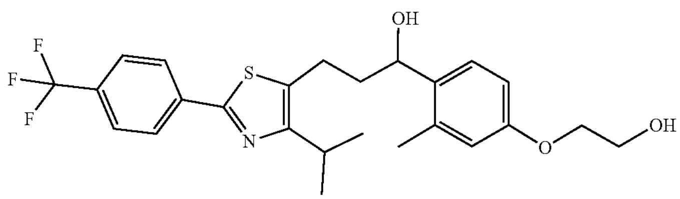 [SMILES: Cc1cc(OCCO)ccc1C(O)CCc1sc(-c2ccc(C(F)(F)F)cc2)nc1C(C)C] | 1-(4-(2-hydroxyethoxy)-2-methylphenyl)-3-(4-isopropyl-2-(4-(trifluoromethyl)phenyl)thiazol-5-yl)propan-1-ol |
| 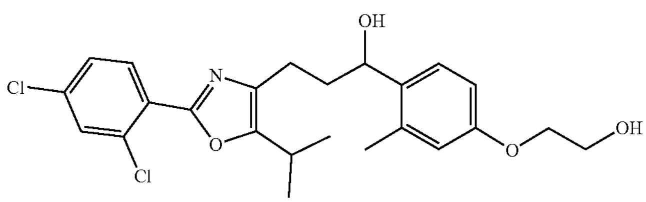 [SMILES: Cc1cc(OCCO)ccc1C(O)CCc1nc(-c2ccc(Cl)cc2Cl)oc1C(C)C] | 3-(2-(2,4-dichlorophenyl)-5-isopropyloxazol-4-yl)-1-(4-(2-hydroxyethoxy)-2-methylphenyl)propan-1-ol |
| 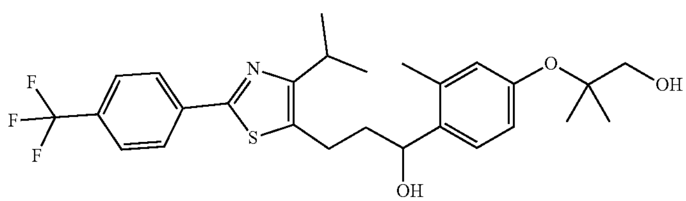 [SMILES: Cc1cc(OC(C)(C)CO)ccc1C(O)CCc1sc(-c2ccc(C(F)(F)F)cc2)nc1C(C)C] | 1-(4-((1-hydroxy-2-methylpropan-2-yl)oxy)-2-methylphenyl)-3-(4-isopropyl-2-(4-(trifluoromethyl)phenyl)thiazol-5-yl)propan-1-ol |
| 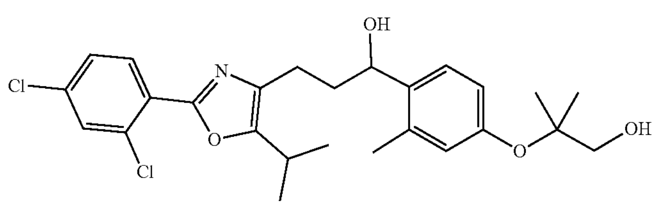 [SMILES: Cc1cc(OC(C)(C)CO)ccc1C(O)CCc1nc(-c2ccc(Cl)cc2Cl)oc1C(C)C] | 3-(2-(2,4-dichlorophenyl)-5-isopropyloxazol-4-yl)-1-(4-((1-hydroxy-2-methylpropan-2-yl)oxy)-2-methylphenyl)propan-1-ol |
| 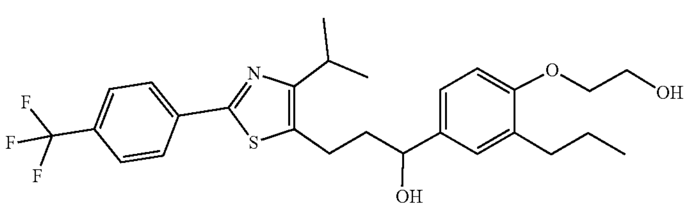 [SMILES: CCCc1cc(C(O)CCc2sc(-c3ccc(C(F)(F)F)cc3)nc2C(C)C)ccc1OCCO] | 1-(4-(2-hydroxyethoxy)-3-propylphenyl)-3-(4-isopropyl-2-(4-(trifluoromethyl)phenyl)thiazol-5-yl)propan-1-one |

TABLE 1-continued

| Structure | Name |
|---|---|
| 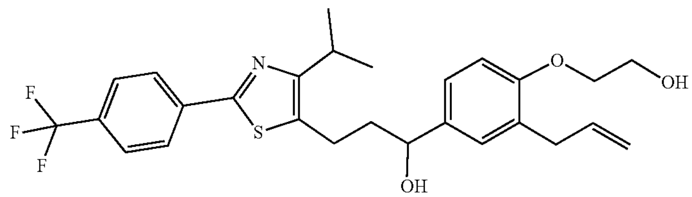 [SMILES: C=CCc1cc(C(O)CCc2sc(-c3ccc(C(F)(F)F)cc3)nc2C(C)C)ccc1OCCO] | 1-(3-allyl-4-(2-hydroxyethoxy)phenyl)-3-(4-isopropyl-2-(4-(trifluoromethyl)phenyl)thiazol-5-yl)propan-1-ol |
| 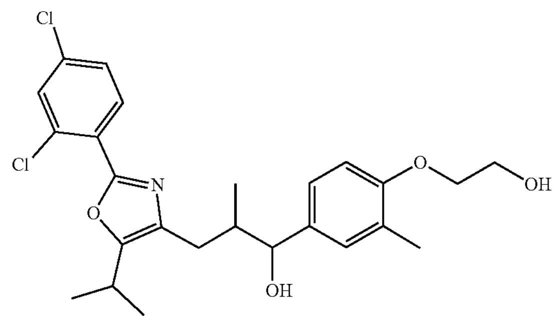 | 3-(2-(2,4-dichlorophenyl)-5-isopropyloxazol-4-yl)-1-(4-(2-hydroxyethoxy)-3-methylphenyl)-2-methylpropan-1-ol |
| 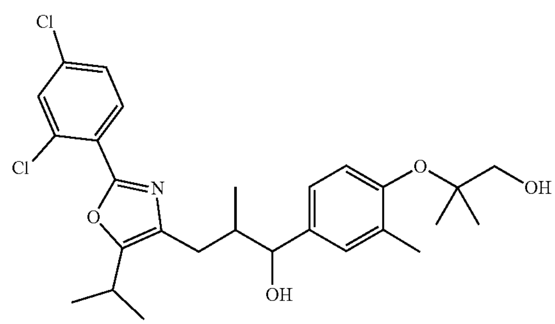 [SMILES: Cc1cc(C(O)C(C)Cc2nc(-c3ccc(Cl)cc3Cl)oc2C(C)C)ccc1OC(C)(C)CO] | 3-(2-(2,4-dichlorophenyl)-5-isopropyloxazol-4-yl)-1-(4-((1-hydroxy-2-methylpropan-2-yl)oxy)-3-methylphenyl)-2-methylpropan-1-ol |
| 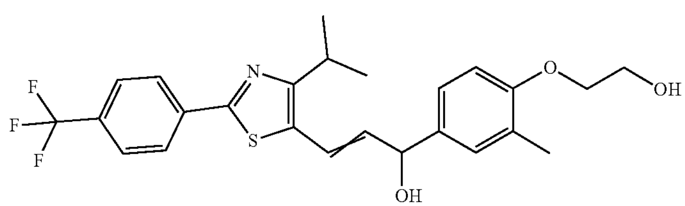 [SMILES: Cc1cc(C(O)C=Cc2sc(-c3ccc(C(F)(F)F)cc3)nc2C(C)C)ccc1OCCO] | 1-(4-(2-hydroxyethoxy)-3-methylphenyl)-3-(4-isopropyl-2-(4-(trifluoromethyl)phenyl)thiazol-5-yl)prop-2-en-1-ol |
| 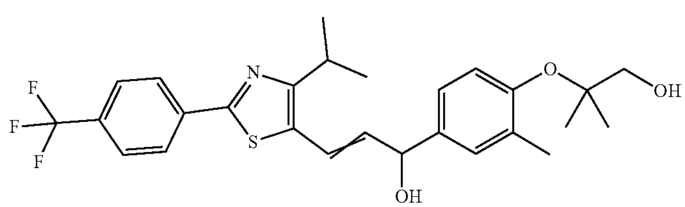 [SMILES: Cc1cc(C(O)C=Cc2sc(-c3ccc(C(F)(F)F)cc3)nc2C(C)C)ccc1OC(C)(C)CO] | 1-(4-((1-hydroxy-2-methylpropan-2-yl)oxy)-3-methylphenyl)-3-(4-isopropyl-2-(4-(trifluoromethyl)phenyl)thiazol-5-yl)prop-2-en-1-ol |
| 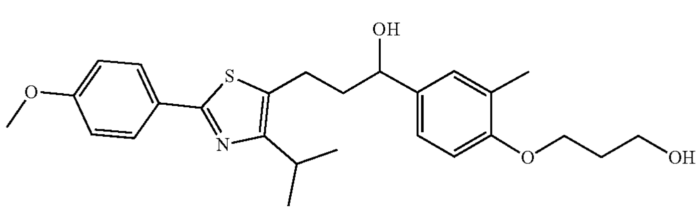 [SMILES: COc1ccc(-c2nc(C(C)C)c(CCC(O)c3ccc(OCCCO)c(C)c3)s2)cc1] | 1-(4-(3-hydroxypropoxy)-3-methylphenyl)-3-(4-isopropyl-2-(4-methoxyphenyl)thiazol-5-yl)propan-1-ol |

TABLE 1-continued

| Structure | Name |
|---|---|
| 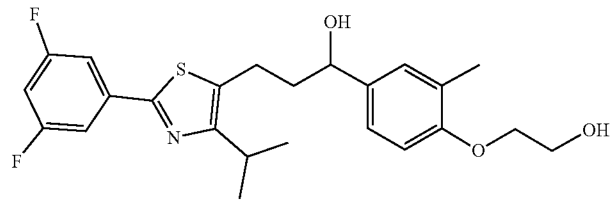 [SMILES: Cc1cc(C(O)CCc2sc(-c3cc(F)cc(F)c3)nc2C(C)C)ccc1OCCO] | 3-(2-(3,5-difluorophenyl)-4-isopropylthiazol-5-yl)-1-(4-(2-hydroxyethoxy)-3-methylphenyl)propan-1-ol |
| 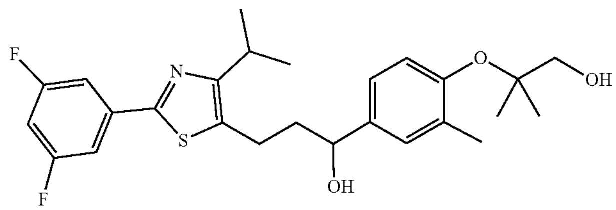 [SMILES: Cc1cc(C(O)CCc2sc(-c3cc(F)cc(F)c3)nc2C(C)C)ccc1OC(C)(C)CO] | 3-(2-(3,5-difluorophenyl)-4-isopropylthiazol-5-yl)-1-(4-((1-hydroxy-2-methylpropan-2-yl)oxy)-3-methylphenyl)propan-1-ol |
| 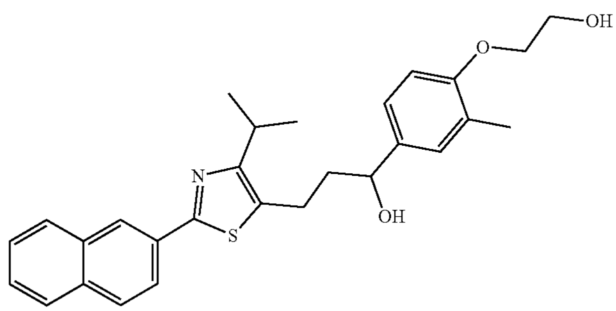 [SMILES: Cc1cc(C(O)CCc2sc(-c3ccc4ccccc4c3)nc2C(C)C)ccc1OCCO] | 1-(4-(2-hydroxyethoxy)-3-methylphenyl)-3-(4-isopropyl-2-(naphthalen-2-yl)thiazol-5-yl)propan-1-ol |
| 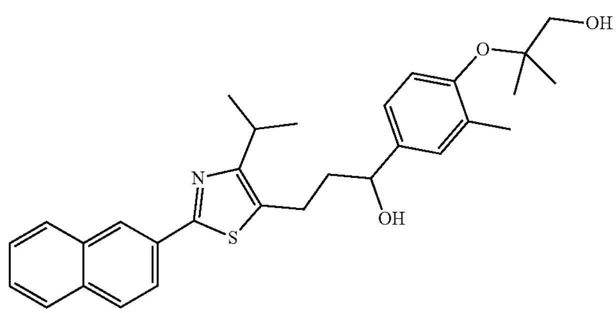 [SMILES: Cc1cc(C(O)CCc2sc(-c3ccc4ccccc4c3)nc2C(C)C)ccc1OC(C)(C)CO] | 1-(4-((1-hydroxy-2-methylpropan-2-yl)oxy)-3-methylphenyl)-3-(4-isopropyl-2-(naphthalen-2-yl)thiazol-5-yl)propan-1-ol |
| 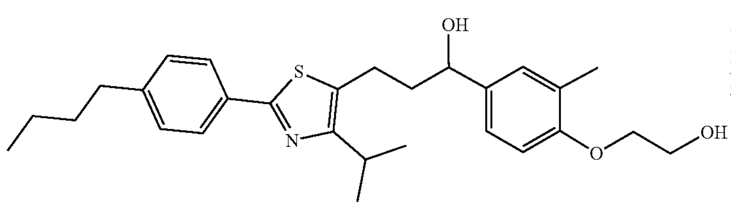 [SMILES: CCCCc1ccc(-c2nc(C(C)C)c(CCC(O)c3ccc(OCCO)c(C)c3)s2)cc1] | 3-(2-(4-butylphenyl)-4-isopropylthiazol-5-yl)-1-(4-(2-hydroxyethoxy)-3-methylphenyl)propan-1-ol |
| 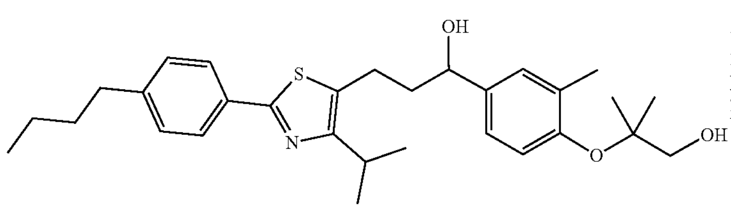 [SMILES: CCCCc1ccc(-c2nc(C(C)C)c(CCC(O)c3ccc(OC(C)(C)CO)c(C)c3)s2)cc1] | 3-(2-(4-butylphenyl)-4-isopropylthiazol-5-yl)-1-(4-((1-hydroxy-2-methylpropan-2-yl)oxy)-3-methylphenyl)propan-1-ol |

TABLE 1-continued

| Structure | Name |
|---|---|
| 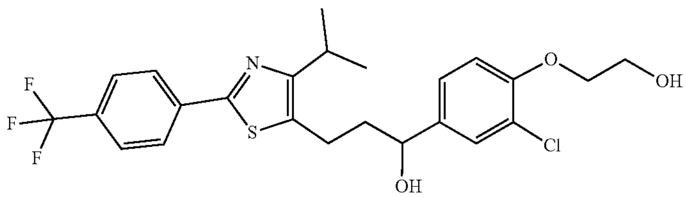 [SMILES: CC(C)c1nc(-c2ccc(C(F)(F)F)cc2)sc1CCC(O)c1ccc(OCCO)c(Cl)c1] | 1-(3-chloro-4-(2-hydroxyethoxy)phenyl)-3-(4-isopropyl-2-(4-(trifluoromethyl)phenyl)thiazol-5-yl)propan-1-ol |
| 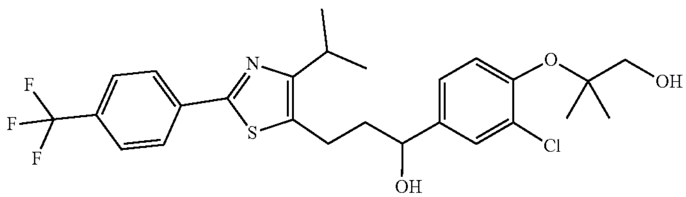 [SMILES: CC(C)c1nc(-c2ccc(C(F)(F)F)cc2)sc1CCC(O)c1ccc(OC(C)(C)CO)c(Cl)c1] | 1-(3-chloro-4-((1-hydroxy-2-methylpropan-2-yl)oxy)phenyl)-3-(4-isopropyl-2-(4-(trifluoromethyl)phenyl)thiazol-5-yl)propan-1-ol |
| 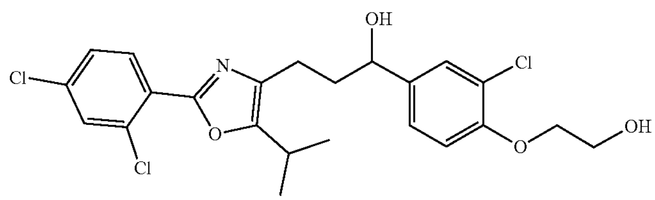 [SMILES: CC(C)c1oc(-c2ccc(Cl)cc2Cl)nc1CCC(O)c1ccc(OCCO)c(Cl)c1] | 1-(3-chloro-4-(2-hydroxyethoxy)phenyl)-3-(2-(2,4-dichlorophenyl)-5-isopropyloxazol-4-yl)propan-1-ol |
| 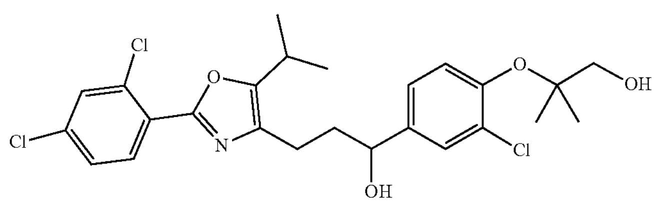 [SMILES: CC(C)c1oc(-c2ccc(Cl)cc2Cl)nc1CCC(O)c1ccc(OC(C)(C)CO)c(Cl)c1] | 1-(3-chloro-4-((1-hydroxy-2-methylpropan-2-yl)oxy)phenyl)-3-(2-(2,4-dichlorophenyl)-5-isopropyloxazol-4-yl)propan-1-ol |
| 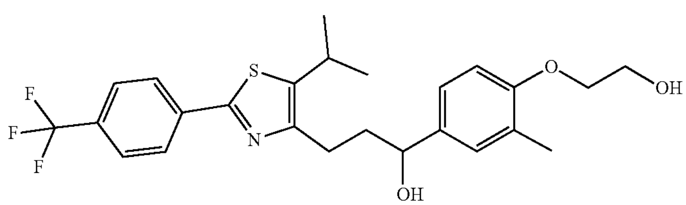 [SMILES: Cc1cc(C(O)CCc2nc(-c3ccc(C(F)(F)F)cc3)sc2C(C)C)ccc1OCCO] | 1-(4-(2-hydroxyethoxy)-3-methylphenyl)-3-(5-isopropyl-2-(4-(trifluoromethyl)phenyl)thiazol-4-yl)propan-1-ol |
| 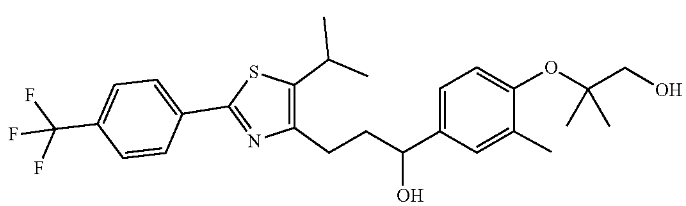 [SMILES: Cc1cc(C(O)CCc2nc(-c3ccc(C(F)(F)F)cc3)sc2C(C)C)ccc1OC(C)(C)CO] | 1-(4-((1-hydroxy-2-methylpropan-2-yl)oxy)-3-methylphenyl)-3-(5-isopropyl-2-(4-(trifluoromethyl)phenyl)thiazol-4-yl)propan-1-ol |
| 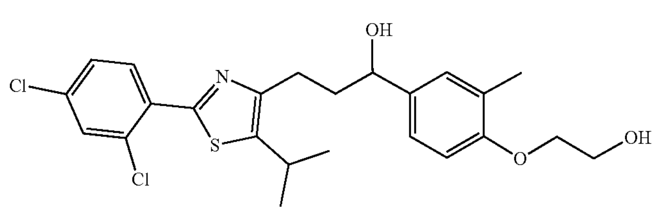 [SMILES: Cc1cc(C(O)CCc2nc(-c3ccc(Cl)cc3Cl)sc2C(C)C)ccc1OCCO] | 3-(2-(2,4-dichlorophenyl)-5-isopropylthiazol-4-yl)-1-(4-(2-hydroxyethoxy)-3-methylphenyl)propan-1-ol |

TABLE 1-continued

| Structure | Name |
|---|---|
| 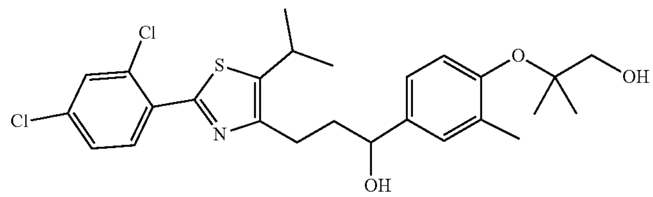 [SMILES: Cc1cc(C(O)CCc2nc(-c3ccc(Cl)cc3Cl)sc2C(C)C)ccc1OC(C)(C)CO] | 3-(2-(2,4-dichlorophenyl)-5-isopropylthiazol-4-yl)-1-(4-((1-hydroxy-2-methylpropan-2-yl)oxy)-3-methylphenyl)propan-1-ol |
| 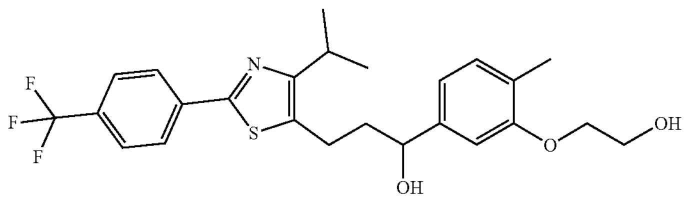 [SMILES: Cc1ccc(C(O)CCc2sc(-c3ccc(C(F)(F)F)cc3)nc2C(C)C)cc1OCCO] | 1-(3-(2-hydroxyethoxy)-4-methylphenyl)-3-(4-isopropyl-2-(4-(trifluoromethyl)phenyl)thiazol-5-yl)propan-1-ol |
| 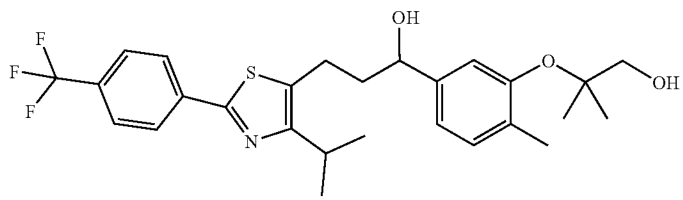 [SMILES: Cc1ccc(C(O)CCc2sc(-c3ccc(C(F)(F)F)cc3)nc2C(C)C)cc1OC(C)(C)CO] | 1-(3-((1-hydroxy-2-methylpropan-2-yl)oxy)-4-methylphenyl)-3-(4-isopropyl-2-(4-(trifluoromethyl)phenyl)thiazol-5-yl)propan-1-ol |
| 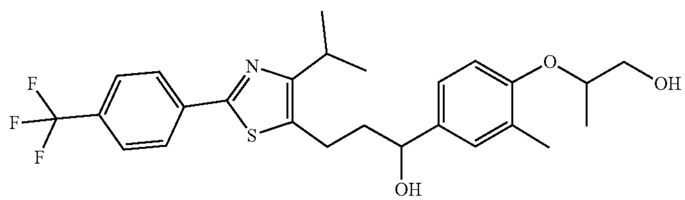 [SMILES: Cc1cc(C(O)CCc2sc(-c3ccc(C(F)(F)F)cc3)nc2C(C)C)ccc1OC(C)CO] | 1-(4-((1-hydroxypropan-2-yl)oxy)-3-methylphenyl)-3-(4-isopropyl-2-(4-(trifluoromethyl)phenyl)thiazol-5-yl)propan-1-ol |
| 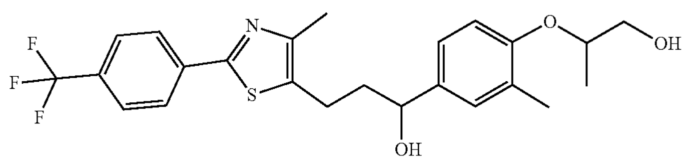 [SMILES: Cc1cc(C(O)CCc2sc(-c3ccc(C(F)(F)F)cc3)nc2C)ccc1OC(C)CO] | 1-(4-(2-hydroxyethoxy)-3-methylphenyl)-3-(4-methyl-2-(4-(trifluoromethyl)phenyl)thiazol-5-yl)propan-1-one |
| 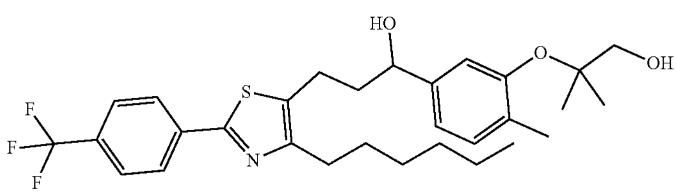 [SMILES: CCCCCCc1nc(-c2ccc(C(F)(F)F)cc2)sc1CCC(O)c1ccc(C)c(OC(C)(C)CO)c1] | 3-(4-hexyl-2-(4-(trifluoromethyl)phenyl)thiazol-5-yl)-1-(3-((1-hydroxy-2-methylpropan-2-yl)oxy)-4-methylphenyl)propan-1-ol |
| 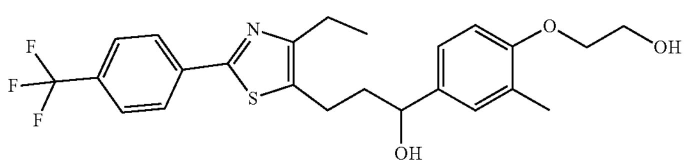 [SMILES: CCc1nc(-c2ccc(C(F)(F)F)cc2)sc1CCC(O)c1ccc(OCCO)c(C)c1] | 3-(4-ethyl-2-(4-(trifluoromethyl)phenyl)thiazol-5-yl)-1-(4-(2-hydroxyethoxy)-3-methylphenyl)propan-1-ol |
| 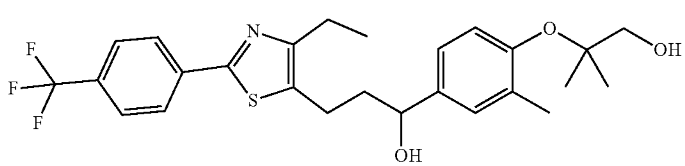 [SMILES: CCc1nc(-c2ccc(C(F)(F)F)cc2)sc1CCC(O)c1ccc(OC(C)(C)CO)c(C)c1] | 3-(4-ethyl-2-(4-(trifluoromethyl)phenyl)thiazol-5-yl)-1-(4-((1-hydroxy-2-methylpropan-2-yl)oxy)-3-methylphenyl)propan-1-ol |

TABLE 1-continued

| Structure | Name |
|---|---|
| 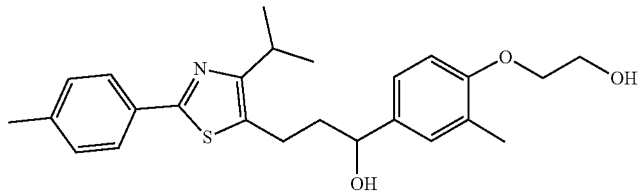 [SMILES: Cc1ccc(-c2nc(C(C)C)c(CCC(O)c3ccc(OCCO)c(C)c3)s2)cc1] | 1-(4-(2-hydroxyethoxy)-3-methylphenyl)-3-(4-isopropyl-2-(p-tolyl)thiazol-5-yl)propan-1-ol |
| 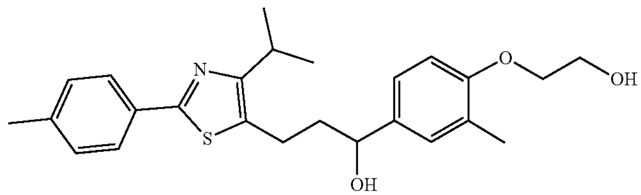 [SMILES: Cc1ccc(-c2nc(C(C)C)c(CCC(O)c3ccc(OCCO)c(C)c3)s2)cc1] | 1-(4-((1-hydroxy-2-methylpropan-2-yl)oxy)-3-methylphenyl)-3-(4-isopropyl-2-(p-tolyl)thiazol-5-yl)propan-1-ol |
| 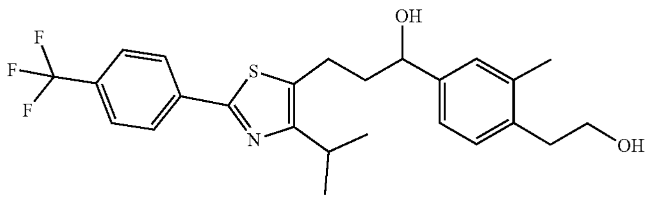 [SMILES: Cc1cc(C(O)CCc2sc(-c3ccc(C(F)(F)F)cc3)nc2C(C)C)ccc1CCO] | 1-(4-(2-hydroxyethyl)-3-methylphenyl)-3-(4-isopropyl-2-(4-(trifluoromethyl)phenyl)thiazol-5-yl)propan-1-ol |

5.2.4. Compounds of Formula (D)

In some embodiments, the compounds of the invention are compounds of Formula (D):

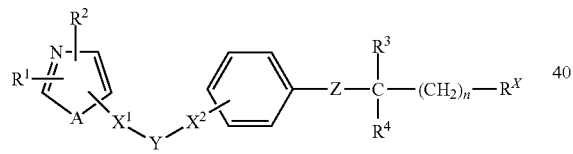

(D)

or a pharmaceutically acceptable salt, solvate, ester, amide, or prodrug thereof, wherein:

each of $R^1$ and $R^2$ independently is a hydrogen, a halogen, nitro, $C_{1-8}$ alkyl, $C_{1-8}$ alkoxy, $C_{1-8}$ haloalkyl having 1 to 3 halogens, $C_{1-8}$ haloalkoxy having 1 to 3 halogens, $C_{2-8}$ alkenyl, $C_{2-8}$ alkynyl, 3-7 membered cycloalkyl, $C_{1-8}$ alkyl substituted with 3-7 membered cycloalkyl, $C_{6-10}$ aryl which is optionally substituted, arylalkyl group which has a $C_{6-10}$ aryl moiety and $C_{1-8}$ alkyl moiety, a heterocyclic group or a heterocyclic-alkyl group having a $C_{1-8}$ alkyl group;

each occurrence of $R^3$, $R^4$, and $R^5$ is independently a hydrogen or $C_{1-8}$ alkyl;

A is an oxygen atom, a sulfur atom, or $NR^3$;

each of $X^1$, $X^2$, and Z independently is C(=O), C(=O)NH, C(=N—$OR^4$), CH($OR^5$), NH(C=O), $NHSO_2$, $SO_2NH$, CH=CH, C≡C, or a bond; and Y is $C_{1-8}$ alkylene;

$R^X$ is $CH_2OH$, COH, $COOCH_2CONR^{X4}R^{X5}$, $SO_3H$,

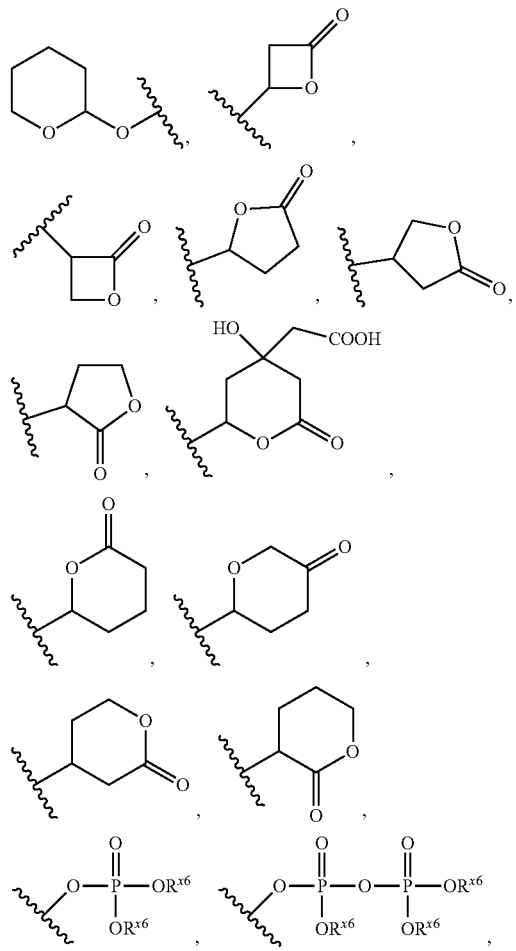

-continued

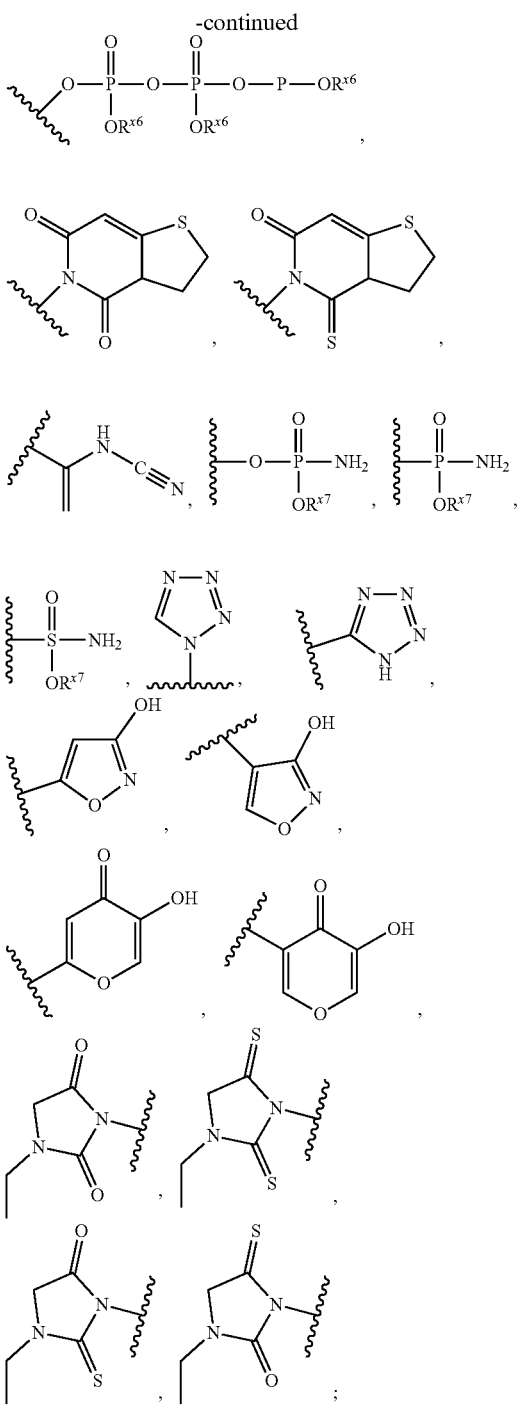

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

Examples of the halogen atom for $R^1$ and $R^2$ include fluorine, chlorine, and bromine.

Examples of alkyl groups having 1-8 carbon atoms for $R^1$, $R^2$, $R^3$, $R^4$ and $R^5$ include methyl, ethyl, propyl, isopropyl, butyl, isobutyl, t-butyl, and pentyl.

Examples of alkoxy groups having 1-8 carbon atoms for $R^1$ and $R^2$ include methoxy, ethoxy, propyloxy, isopropyloxy, butyloxy, isobutyloxy, t-butyloxy, and pentyloxy.

Examples of alkyl groups having 1-8 carbon atoms which has 1-3 halogen substituents for $R^1$ and $R^2$ include chloromethyl, fluoromethyl, bromomethyl, chloroethyl, 2-fluoroethyl, and trifluoromethyl.

Examples of alkoxy groups having 1-8 carbon atoms which has 1-3 halogen substituents for $R^1$ and $R^2$ include chloromethoxy, fluoromethoxy, bromomethoxy, 2-chloroethoxy, 2-fluoroethoxy, and trifluoroethoxy.

Examples of alkenyl groups having 2-8 carbon atoms for $R^1$ and $R^2$ include vinyl or allyl. The alkynyl group having 2-8 carbon atoms can be, for example, propargyl. The cycloalkyl group having 3-7 carbon atoms can be, for example, cyclohexyl or cyclopentyl. The alkyl group having a 3-7 membered cycloalkyl substituent can be, for example, cyclohexylmethyl or cyclopentylmethyl.

The aryl group for the aryl group optionally having a substituent for $R^1$ and $R^2$ can be, for example, phenyl or naphthyl.

Examples of arylalkyl groups optionally having a substituent include benzyl and phenethyl.

Example of heterocyclic groups for the heterocyclic group optionally having a substituent include a 5-7 membered cyclic group having ring-forming 1-4 hetero atoms such as nitrogen, oxygen and sulfur. For instance, pyridyl, thienyl and furyl can be included. Further, a benzene ring condensed with the heterocyclic group such as quinolyl or benzothienyl can be included.

Examples of heterocyclic groups for the heterocyclic ring-alkyl group (the alkyl moiety has 1-8 carbon atoms) optionally having a substituent can be the same as that described hereinbefore for the heterocyclic group optionally having a substituent. The alkyl group preferably has 1-3 carbon atoms.

The substituent for the substituents of the aryl group optionally having a substituent, the arylalkyl group (the aryl moiety has 6-10 carbon atoms, and the alkyl moiety has 1-8 carbon atoms) optionally having a substituent, the heterocyclic group optionally having a substituent, and a heterocyclic ring-alkyl group (the alkyl moiety has 1-8 carbon atoms) optionally having a substituent can be a halogen atom such as chlorine, bromine, or fluorine, nitro, hydroxyl, amino, an alkyl amino group having 1-8 carbon atoms such as methylamino, or ethylamino, a dialkylamino group having 2-10 carbon atoms such as dimethylamino, an alkyl group having 1-8 carbon atoms such as methyl, ethyl, propyl, isopropyl, or butyl, an alkoxy group having 1-8 carbon atoms such as methoxy, ethoxy, propoxy, isopropoxy, or butoxy, an alkyl group having 1-8 carbon atoms which has 1-3 halogen substituents such as chloromethyl, fluoromethyl, bromomethyl, 2-chloroethyl, 2-fluoroethyl, or trifluoromethyl, an alkoxy group having 1-8 carbon atoms which has 1-3 halogen substituents such as chloromethoxy, fluoromethoxy, bromomethoxy, 2-chloroethoxy, 2-fluoroethoxy, or trifluoromethoxy, an alkyenyl group having 2-8 carbon atoms such as vinyl or allyl, an alkynyl group having 2-8 carbon atoms such as propargyl, a cycloalkyl group having 3-7 carbon atoms such as cyclohexyl or cyclopentyl, an alkyl group having a cycloalkyl group of 3-7 carbon atoms such as cyclohexylmethyl or cyclopentylmethyl, phenyl, or pyridyl.

In some embodiments, the compound of Formula (D) is a compound shown in Table 2 or pharmaceutically acceptable salt, solvate, ester, amide, or prodrug thereof.

TABLE 2

| Structure | Name |
|---|---|
| 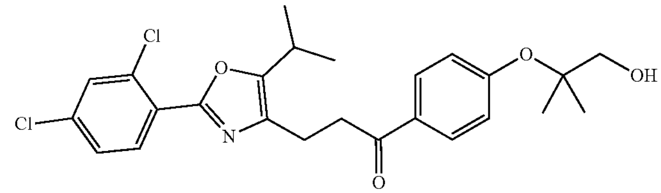 [SMILES: CC(C)c1oc(-c2ccc(Cl)cc2Cl)nc1CCC(=O)c1ccc(OC(C)(C)CO)cc1] | 3-(2-(2,4-dichlorophenyl)-5-isopropyloxazol-4-yl)-1-(4-((1-hydroxy-2-methylpropan-2-yl)oxy)phenyl)propan-1-one |
| 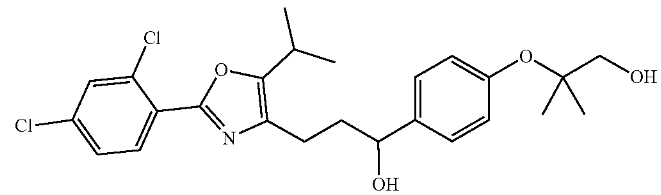 [SMILES: CC(C)c1oc(-c2ccc(Cl)cc2Cl)nc1CCC(O)c1ccc(OC(C)(C)CO)cc1] | 3-(2-(2,4-dichlorophenyl)-5-isopropyloxazol-4-yl)-1-(4-((1-hydroxy-2-methylpropan-2-yl)oxy)phenyl)propan-1-ol |
| 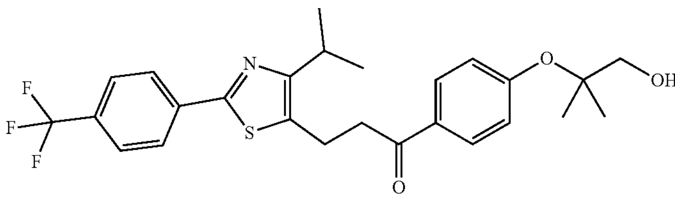 [SMILES: CC(C)c1nc(-c2ccc(C(F)(F)F)cc2)sc1CCC(=O)c1ccc(OC(C)(C)CO)cc1] | 1-(4-((1-hydroxy-2-methylpropan-2-yl)oxy)phenyl)-3-(4-isopropyl-2-(4-(trifluoromethyl)phenyl)thiazol-5-yl)propan-1-one |
| 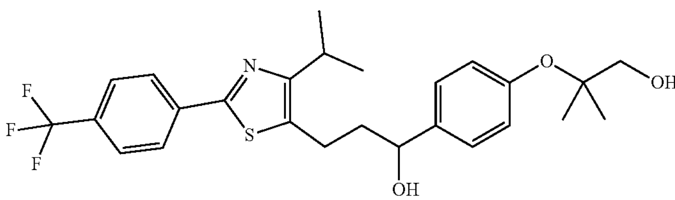 [SMILES: CC(C)c1nc(-c2ccc(C(F)(F)F)cc2)sc1CCC(O)c1ccc(OC(C)(C)CO)cc1] | 1-(4-((1-hydroxy-2-methylpropan-2-yl)oxy)phenyl)-3-(4-isopropyl-2-(4-(trifluoromethyl)phenyl)thiazol-5-yl)propan-1-ol |

5.2.5. Compounds of Formula (E)

In some embodiments, the compounds of the invention are compounds of Formula (E):

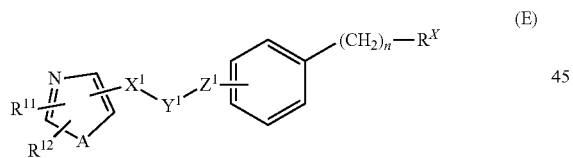

(E)

or a pharmaceutically acceptable salt, solvate, ester, amide, or prodrug thereof, wherein:

each of $R^{11}$ and $R^{12}$ independently is hydrogen, halogen, nitro, hydroxyl, amino, $C_{1-8}$ alkyl, an $C_{1-8}$ alkoxy, $C_{1-8}$ haloalkyl group having 1 to 3 halogens, $C_{1-8}$ haloalkoxy group having 1 to 3 halogens, $C_{2-8}$ alkenyl, $C_{2-8}$ alkynyl, a 3-7 membered cycloalkyl, $C_{1-8}$ alkyl having a 3-7 membered cycloalkyl substituent, or phenyl, naphthyl, benzyl, phenethyl, pyridyl, thienyl, furyl, quinolyl, or benzothienyl group which optionally has a substituent which is a halogen atom, nitro, hydroxyl, amino, $C_{1-8}$ alkyl, $C_{1-8}$ alkoxy, $C_{1-8}$ haloalkyl having 1 to 3 halogens, $C_{1-8}$ haloalkoxy having 1 to 3 halogens, $C_{2-8}$ alkenyl, $C_{2-8}$ alkynyl, 3-7 membered cycloalkyl group, $C_{1-8}$ alkyl group having a 3-7 membered cycloalkyl substituent, phenyl or pyridyl;

each of $X^1$ and $Z^1$ independently is C(=O), C(=O)NH, C(=N—OR$^{14}$), CH(OR$^{15}$), NH(C=O), NHSO$_2$, SO$_2$NH, CH=CH, C≡C, or a bond, wherein each of $R^{14}$ and $R^{15}$ is a hydrogen or $C_{1-8}$ alkyl;

$Y^1$ is $C_{1-8}$ alkylene;

$R^X$ is CH$_2$OH, COH, COOCH$_2$CONR$^{X4}$R$^{X5}$, SO$_3$H,

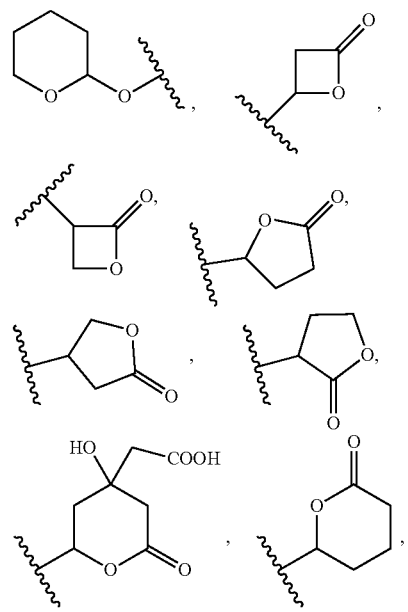

-continued

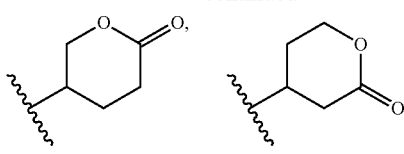

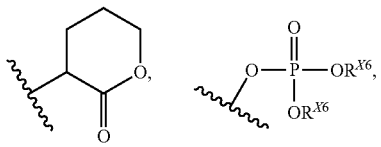

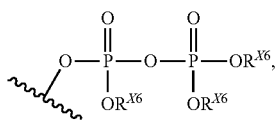

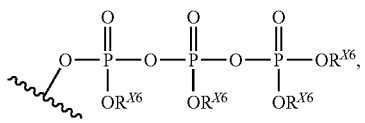

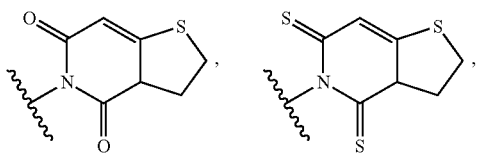

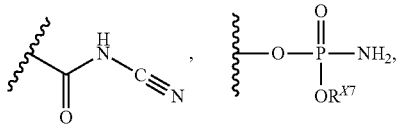

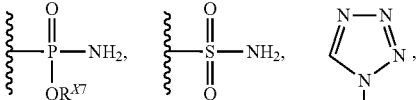

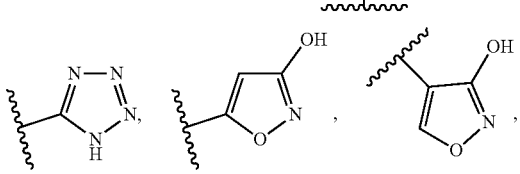

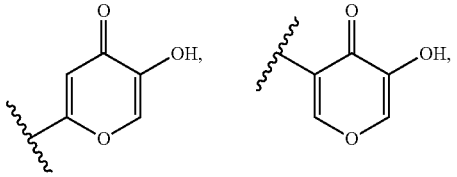

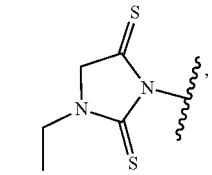

-continued

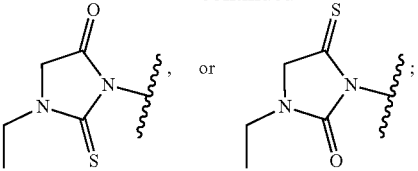

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the halogen atom, alkoxy groups having 1-8 carbon atoms, alkyl group having 1-8 carbon atoms which has 1-3 halogen substituents, alkoxy group having 1-8 carbon atoms which has 1-3 halogen substituents, alkenyl group having 2-8 carbon atoms, alkynyl group having 2-8 carbon atoms, cycloalkyl group having 3-7 carbon atoms, alkyl group having 1-8 carbon atoms which has a cycloalkyl group of 3-7 carbon atoms for $R^{11}$ and $R^{12}$ can be those described for the halogen atom, alkoxy group, alkyl group having 1-8 carbon atoms which has a halogen substituent, alkoxy group having 1-8 carbon atoms which has a halogen substituent, alkenyl, alkynyl, cycloalkyl group, and alkyl group having 1-8 carbon atoms which has a cycloalkyl group of 3-7 carbon atoms for $R^1$ and $R^2$ of Formula (D).

In some embodiments, the alkyl group having 1-8 carbon atoms for $R^{11}$, $R^{12}$, $R^{14}$, and $R^{15}$ can be an alkyl group described for $R^1$, $R^2$, $R^3$, $R^4$ and $R^5$ of Formula (D).

In the case that $R^{11}$ or $R^{12}$ is phenyl, naphthyl, benzyl, phenethyl, pyridyl, thienyl, furyl, quinolyl, or benzothienyl, these rings can in some embodiments have such substituents a halogen atom such as chlorine, bromine, or fluorine, nitro, hydroxyl, amino, an alkyl amino group having 1-8 carbon atoms such as methylamino, or ethylamino, a dialkylamino group having 2-10 carbon atoms such as dimethylamino, an alkyl group having 1-8 carbon atoms such as methyl, ethyl, propyl, isopropyl, or butyl, an alkoxy group having 1-8 carbon atoms such as methoxy, ethoxy, propoxy, isopropoxy, or butoxy, an alkyl group having 1-8 carbon atoms which has 1-3 halogen substituents such as chloromethyl, fluoromethyl, bromomethyl, 2-chloroethyl, 2-fluoroethyl, or trifluoromethyl, an alkoxy group having 1-8 carbon atoms which has 1-3 halogen substituents such as chloromethoxy, fluoromethoxy, bromomethoxy, 2-chloroethoxy, 2-fluoroethoxy, or trifluoromethoxy, an alkenyl group having 2-8 carbon atoms such as vinyl or allyl, an alkynyl group having 2-8 carbon atoms such as propargyl, a cycloalkyl group having 3-7 carbon atoms such as cyclohexyl or cyclopentyl, an alkyl group having a cycloalkyl group of 3-7 carbon atoms such as cyclohexylmethyl or cyclopentylmethyl, phenyl, or pyridyl.

The compound provided can be a stereoisomer such as cis or trans, or an optical isomer. These isomers are included in the invention.

The compound provided includes a pharmaceutically acceptable salt such as an alkali metal salt, e.g., sodium salt or potassium salt. Further, the compounds provided can be in the form of pharmaceutically acceptable salts such as alkali metal salts, e.g., sodium salt and potassium salt.

In some embodiments, the compound of Formula (E) is a compound shown in Table 3 or pharmaceutically acceptable salt, solvate, ester, amide, or prodrug thereof.

TABLE 3

| Structure | Name |
|---|---|
| 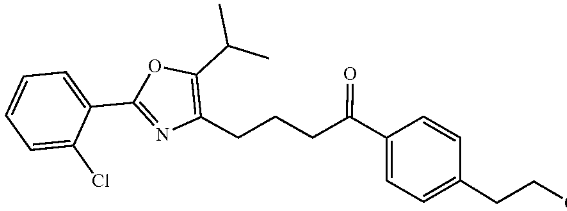 | 4-(2-(2-chlorophenyl)-5-isopropyloxazol-4-yl)-1-(4-(2-hydroxyethyl)phenyl)butan-1-one |
| 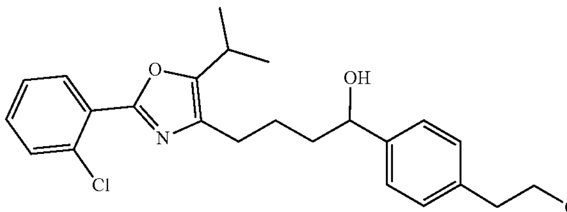 | 4-(2-(2-chlorophenyl)-5-isopropyloxazol-4-yl)-1-(4-(2-hydroxyethyl)phenyl)butan-1-ol |

5.2.6. Compounds of Formula (F)

In some embodiments, the compounds of the invention are compounds of Formula (F):

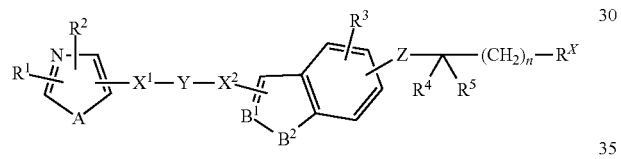

(F)

or a pharmaceutically acceptable salt, solvate, ester, amide, or prodrug thereof, wherein:

A is O, S or $NR^7$ in which $R^7$ is hydrogen or $C_{1-8}$ alkyl;

$B^1$ is CW or N in which W is hydrogen or a bond; $B^2$ is O, S or $NR^3$ in which $R^8$ is hydrogen or $C_{1-8}$ alkyl;

each of $X^1$ and $X^2$ is O, S, NH, NHC(=O), C(=O), C(=N—$OR^9$), CH($OR^{10}$), C≡C, C=C or a bond, wherein each of $R^9$ and $R^{10}$ is hydrogen or $C_{1-8}$ alkyl;

Y is $C_{1-8}$ alkylene, which is unsubstituted or substituted with $C_{1-8}$ alkyl or $C_{1-8}$ haloalkyl having 1-3 halogens;

Z is NH, O or S;

$R^1$ is aryl, which is unsubstituted or substituted with $C_{1-8}$ alkyl, $C_{1-8}$ alkoxy, $C_{1-8}$ haloalkyl having 1-3 halogens, hydroxyl, nitro, amino, phenyl, pyridyl or halogen, or a heterocyclic group having a five to eight membered ring comprising one to three hetero atoms each of which is independently nitrogen, oxygen or sulfur and the other atoms are carbon, optionally wherein a benzene ring is condensed with the heterocyclic ring;

$R^2$ is $C_{2-8}$ alkyl, $C_{1-8}$ haloalkyl having with 1-3 halogens, $C_{3-7}$ cycloalkyl, $C_{2-8}$ alkenyl, $C_{2-8}$ alkynyl, $C_{1-4}$ alkyl substituted with aryl, which is unsubstituted or substituted with $C_{1-8}$ alkyl, $C_{1-8}$ alkoxy, $C_{1-8}$ haloalkyl having 1-3 halogens, hydroxyl, nitro, amino, phenyl, pyridyl or halogen, or $C_{1-4}$ alkyl substituted with a heterocyclic group having five to eight membered ring having one to three heteroatoms each of which is independently nitrogen, oxygen or sulfur;

$R^3$ is halogen, trifluoromethyl, $C_{1-8}$ alkyl, $C_{2-8}$ alkenyl or $C_{2-8}$ alkynyl;

each of $R^4$ and $R^5$ is hydrogen, $C_{1-8}$ alkyl or $C_{1-8}$ haloalkyl having 1-3 halogens;

each of Z and $R^3$ is attached to the benzene ring, and $X^2$ is not attached to the benzene ring;

$R^X$ is $CH_2OH$, COH, $COOCH_2CONR^{X4}R^{X5}$, $SO_3H$,

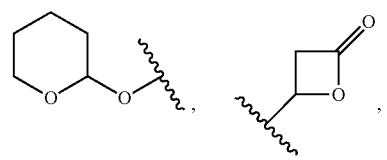

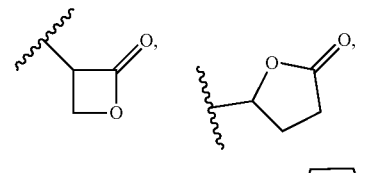

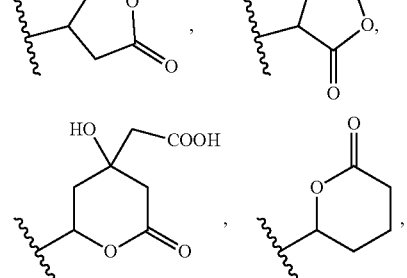

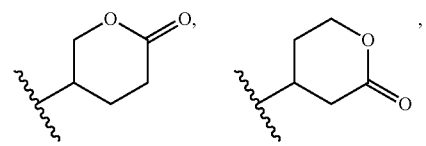

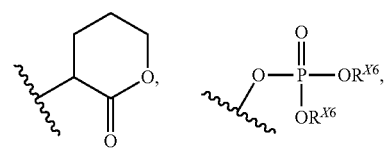

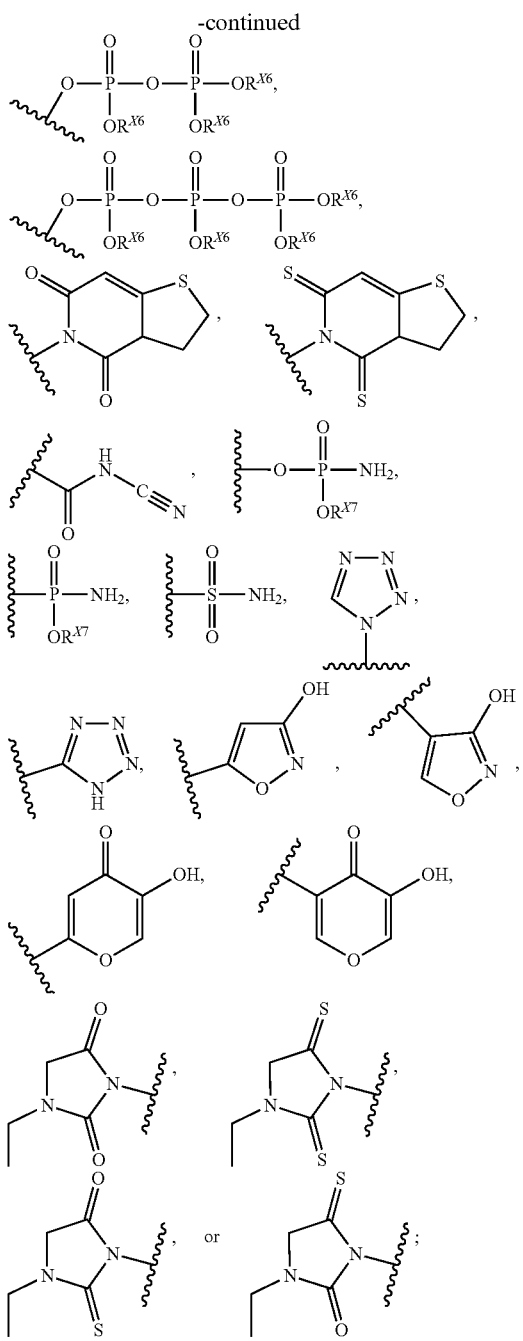

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In the Formula (F), $R^3$, $R^4$, $R^5$, $R^6$, $R^7$, $R^8$, $R^9$, $R^{10}$, the substituent of the alkylene chain of Y, the substituent of the aryl and the heterocyclic group of $R^3$, the substituent of the alkyl group substituted with aryl of $R^2$, and the substituent of the alkyl group substituted with a heterocyclic group of $R^2$ can in some embodiments be an alkyl group having 1-8 carbon atoms. Examples of the alkyl groups include methyl, ethyl, propyl, isopropyl, butyl, isobutyl, t-butyl, pentyl and hexyl.

In some embodiments, $R^2$ can be an alkyl group having 2-8 carbon atoms. Examples of the alkyl groups include ethyl, propyl, iso-propyl, butyl, isobutyl, t-butyl, pentyl and hexyl.

In some embodiments, $R^2$, $R^4$, $R^5$, the substituent of the alkylene chain of Y, the substituent of the aryl or heterocyclic group of $R^1$, the substituent of the alkyl group substituted with aryl of $R^2$, and the substituent of the alkyl group substituted with a heterocyclic group of $R^2$ can be an alkyl groups having 1-8 carbon atoms substituted with 1-3 halogens. Examples of the haloalkyl groups include methyl, ethyl, propyl, isopropyl, butyl, and t-butyl which are substituted with 1-3 halogens such as fluorine, chlorine, and bromine. In some embodiments, the group is trifluoromethyl, chloromethyl, 2-chloroethyl, 2-bromoethyl or 2-fluoroethyl.

In some embodiments, $R^2$ and $R^3$ can be an alkenyl group having 2-8 carbon atoms. Examples of the alkenyl groups include vinyl and allyl. $R^2$ and $R^3$ can be an alkynyl group having 2-8 carbon atoms. Examples of the alkynyl groups include propargyl.

In some embodiments, $R^3$ can be a halogen atom. Examples of the halogen atoms include fluorine, chlorine and bromine.

In some embodiments, $R^2$ can be a cycloalkyl group having 3-7 carbon atoms. Examples of the cycloalkyl groups include cyclopropyl, cyclopentyl and cyclohexyl.

In some embodiments, the substituent of the aryl or heterocyclic group of $R^1$, the substituent of the alkyl group substituted with aryl of $R^2$, and the substituent of the alkyl group substituted with a heterocyclic group of $R^2$ can be an alkoxy groups having 1-8 carbon atoms. Examples of the alkoxy groups include methoxy, ethoxy, propoxy, isopropoxy, butoxy, isobutoxy, t-butoxy, pentyloxy and hexyloxy.

In some embodiments, $R^1$ and the aryl moiety of the aryl substituted with alkyl of $R^2$ can be an aryl group. Examples of the aryl groups include phenyl and naphthyl. $R^1$ and the substituent of the alkyl group of $R^2$ can be a heterocyclic group having five to eight membered ring. Examples of the heterocyclic groups include pyridyl, thienyl, furyl, thiazolyl and quinolyl.

In some embodiments, $R^1$ can be a heterocyclic group having five to eight membered ring comprising one to three hetero atoms selected from the group consisting of nitrogen, oxygen and sulfur and the other atoms consisting of carbon. A benzene ring can be condensed with the heterocyclic ring. Examples of the condensed rings include quinoline ring and benzothiophene ring In some embodiments, Y can be an alkylene chain having 1 to 8 carbon atoms. Examples of the alkylene chains include methylene and ethylene.

In some embodiments, $R^3$ can be one to three groups. In some embodiments, two or three groups of $R^3$ can be different from each other.

In some embodiments, $R^6$ can be an alkyl group having 1-8 carbon atoms substituted with amino. Examples of the aminoalkyl groups include methyl, ethyl, propyl, isopropyl, butyl, isobutyl, t-butyl, pentyl and hexyl which are substituted with an amino group such as piperidino, pyrrolidino, dimethylamino, and diethylamino.

In some embodiments, the compounds of the Formula (F) can be in the form of pharmaceutically acceptable salts such as alkali metal salts, e.g., sodium salt and potassium salt.

In some embodiments, the compound of Formula (F) is a compound shown in Table 4 or pharmaceutically acceptable salt, solvate, ester, amide, or prodrug thereof.

TABLE 4

| Structure | Name |
|---|---|
| 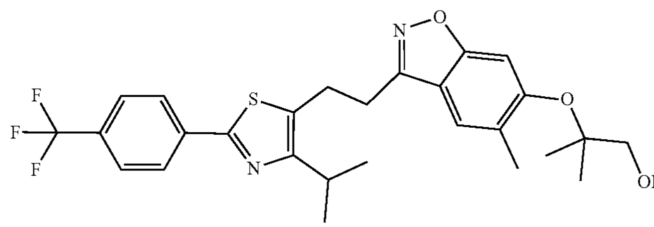 | 2-((3-(2-(4-isopropyl-2-(4-(trifluoromethyl)phenyl)thiazol-5-yl)ethyl)-5-methylbenzo[d]isoxazol-6-yl)oxy)-2-methylpropan-1-ol |
| 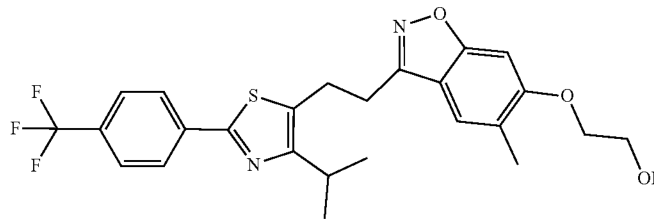 | 2-((3-(2-(4-isopropyl-2-(4-(trifluoromethyl)phenyl)thiazol-5-yl)ethyl)-5-methylbenzo[d]isoxazol-6-yl)oxy)ethan-1-ol |
| 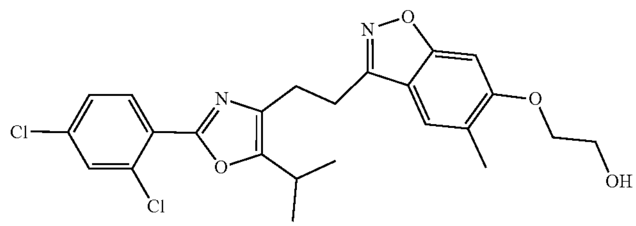 [SMILES: Cc1cc2c(CCc3nc(-c4ccc(Cl)cc4Cl)oc3C(C)C)noc2cc1OCCO] | 2-((3-(2-(2-(2,4-dichlorophenyl)-5-isopropyloxazol-4-yl)ethyl)-5-methylbenzo[d]isoxazol-6-yl)oxy)ethan-1-ol |

5.2.7. Compounds of Formula (G), (H), and (J)

In some embodiments, the compounds of the invention are compounds of Formula (G):

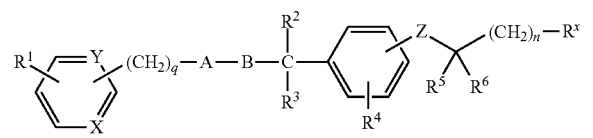

or a pharmaceutically acceptable salt, solvate, ester, amide, or prodrug thereof, wherein:

each of $R^1$ and $R^4$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

$R^2$ is hydrogen;

$R^3$ is $C_{1-8}$ alkyl, or $R^3$ is combined with $R^2$ to form =O or =C($R^7$)($R^8$) in which each of $R^7$ and $R^8$ which are the same or different, is a hydrogen or $C_{1-8}$ alkyl; each of $R^5$ and $R^6$, which are the same or different, is a hydrogen atom, $C_{1-8}$ alkyl, $C_{1-8}$ haloalkyl;

X and Y are the same or different and each represents CH or N;

Z is oxygen or sulfur;

A is a 5-membered heterocyclic group which is pyrazole, thiophene, furan or pyrrole, wherein the heterocyclic group is unsubstituted or substituted with $C_{1-8}$ alkyl having a substituent which is $C_{1-8}$ alkyl, 3- to 7-membered cycloalkyl, $C_{2-8}$ alkenyl, $C_{2-8}$ alkynyl, $C_{1-8}$ alkoxy, $C_{1-8}$ alkyl group substituted with a 3- to 7-membered cycloalkyl group, $C_{1-8}$ haloalkyl, $C_{1-8}$ haloalkoxy, $C_{6-10}$ aryl, 5- or 6-membered heterocyclic group, an aralkyl group having a $C_{6-10}$ aryl moiety and a $C_{1-8}$ alkylene moiety, or 5- or 6-membered heterocyclic group;

B is a $C_{1-8}$ alkylene chain which is unsubstituted or substituted with $C_{1-8}$ alkyl, 3- to 7-membered cycloalkyl group, $C_{2-8}$ alkenyl, $C_{2-8}$ alkynyl, $C_{1-8}$ alkoxy, halogen, $C_{1-8}$ haloalkyl or $C_{1-8}$ haloalkoxy, the alkylene group optionally having a double bond in the case that the alkylene group has 2 to 6 carbon atoms;

q is 0, 1, 2, 3, 4, or 5;

$R^x$ is $CH_2OH$, COH, $COOCH_2CONR^{X4}R^{X5}$, $SO_3H$,

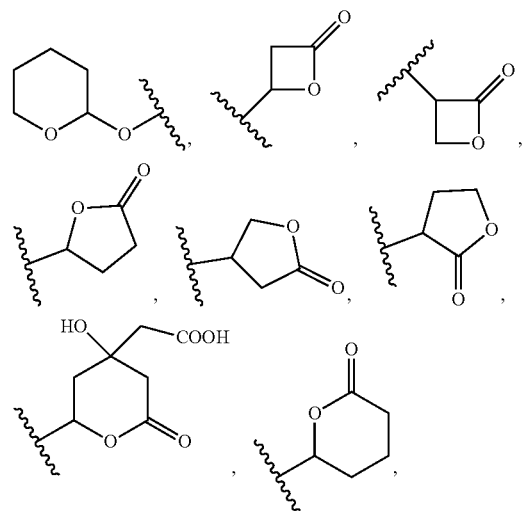

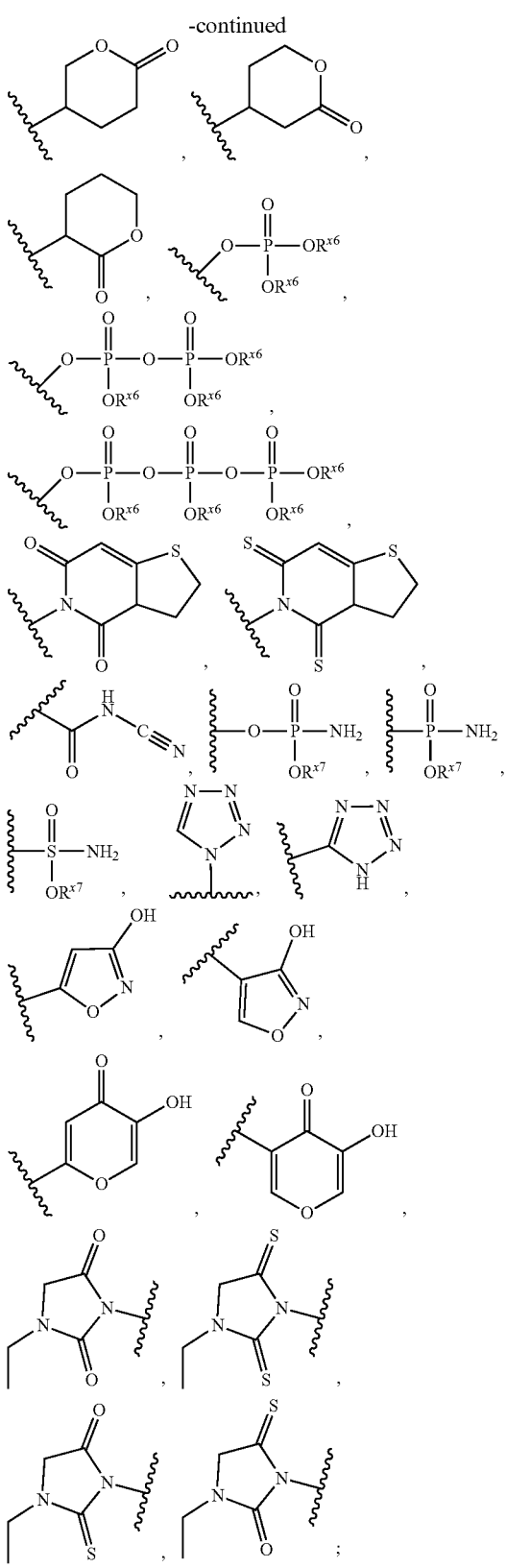

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (H):

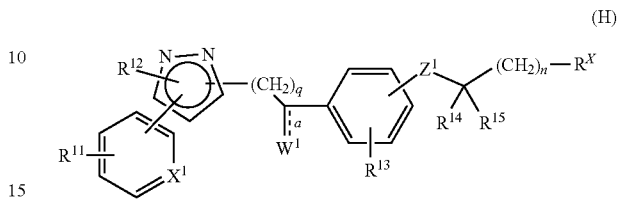

(H)

or a pharmaceutically acceptable salt, solvate, ester, amide, or prodrug thereof, wherein:

each of $R^{11}$ and $R^{13}$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

$R^{12}$ is hydrogen, $C_{1-8}$ alkyl, a 3- to 7-membered cycloalkyl, $C_{2-8}$ alkenyl, $C_{2-8}$ alkynyl, $C_{1-8}$ alkoxy, $C_{1-8}$ alkyl having a 3- to 7-membered cycloalkyl group substituent, $C_{1-8}$ haloalkyl, $C_{1-8}$ haloalkoxy, $C_{6-10}$ aryl, a 5- or 6-membered heterocyclic group, an aralkyl group having a $C_6$-10 aryl moiety and a $C_{1-8}$ alkylene moiety, or a $C_{1-8}$ alkyl group having a 5- or 6-membered heterocyclic substituent;

$R^{14}$ and $R^{15}$ are the same or different and each is a hydrogen atom, $C_{1-8}$ alkyl, or $C_{1-8}$ haloalkyl;

$X^1$ is CH or N;

$Z^1$ is oxygen or sulfur;

$W^1$ is oxygen or $CH_2$ when bond a is present and OH when bond a is absent;

q is 2, 3, or 4.

$R^X$ is $CH_2OH$, COH, $COOCH_2CONR^{X4}R^{X5}$, $SO_3H$,

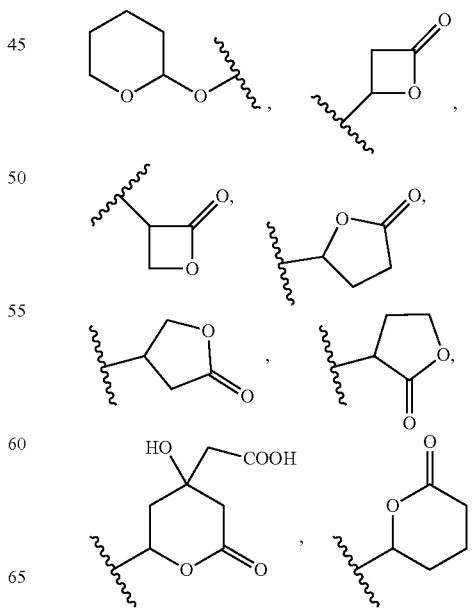

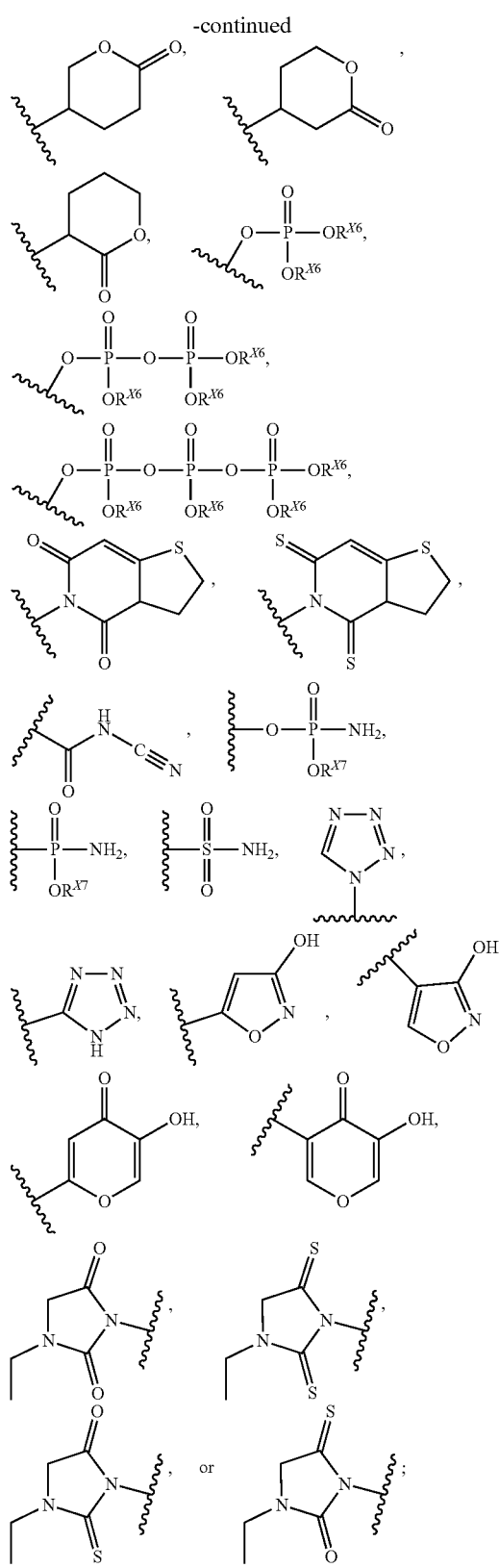

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (J):

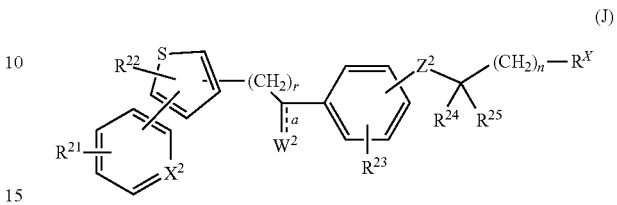

(J)

or a pharmaceutically acceptable salt, solvate, ester, amide, or prodrug thereof, wherein:

each of $R^{21}$ and $R^{23}$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

$R^{22}$ is hydrogen, $C_{1-8}$ alkyl, a 3- to 7-membered cycloalkyl, $C_{2-8}$ alkenyl, $C_{2-8}$ alkynyl, $C_{1-8}$ alkoxy, $C_{1-8}$ alkyl having a 3- to 7-membered cycloalkyl group substituent, $C_{1-8}$ haloalkyl, $C_{1-8}$ haloalkoxy, $C_{6-10}$ aryl, a 5- or 6-membered heterocyclic group, an aralkyl group having a $C_6$-10 aryl moiety and a $C_{1-8}$ alkylene moiety, or a $C_{1-8}$ alkyl group having a 5- or 6-membered heterocyclic substituent;

$R^{24}$ and $R^{25}$ are the same or different and each is a hydrogen atom, $C_{1-8}$ alkyl, or $C_{1-8}$ haloalkyl;

$X^2$ is CH or N;

$Z^2$ is oxygen or sulfur;

$W^2$ is oxygen or $CH_2$ when bond a is present and OH when bond a is absent;

r is 2, 3, or 4.

$R^X$ is $CH_2OH$, COH, $COOCH_2CONR^{X4}R^{X5}$, $SO_3H$,

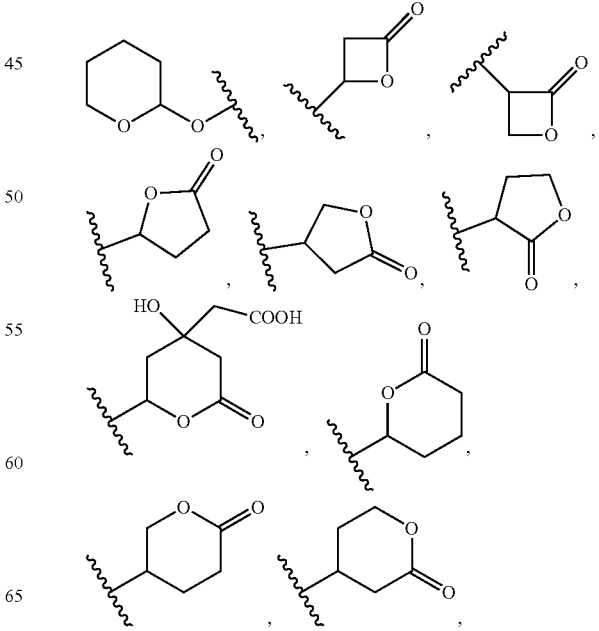

-continued

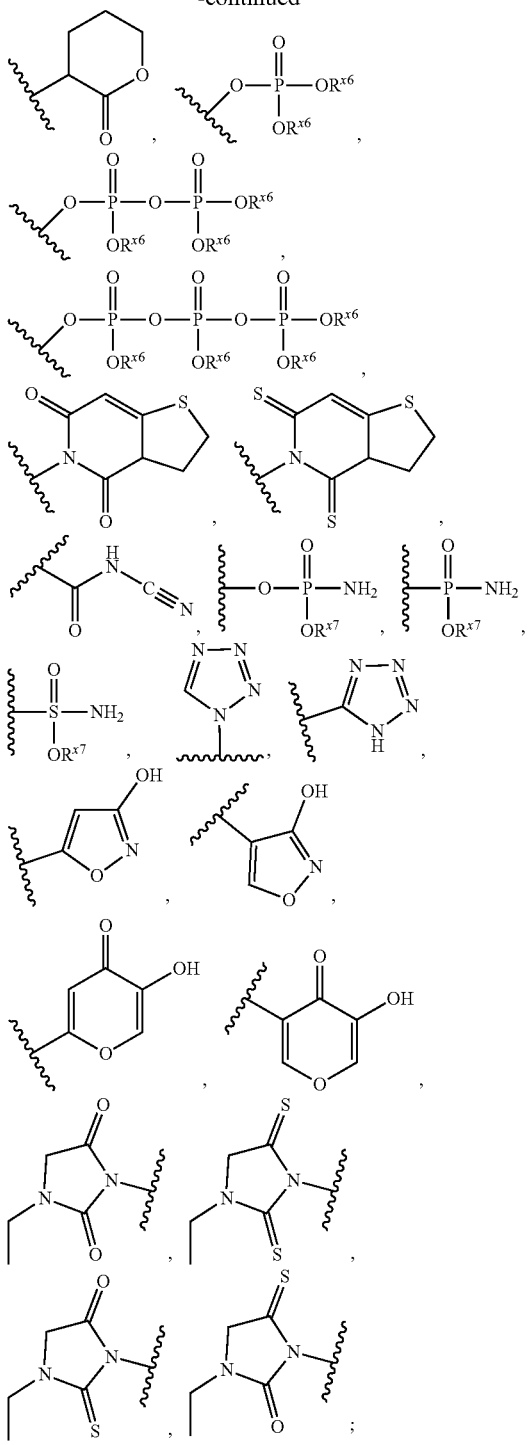

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

Regarding the Formula (G), examples of the alkyl groups having 1 to 8 carbon atoms which can be $R^1$, $R^3$, $R^4$, $R^5$, $R^6$, $R^7$, the substituent of the 5-membered heterocyclic group for A, or the substituent of the alkylene chain having 2 to 6 carbon atoms for B include methyl, ethyl, propyl, isopropyl, butyl, i-butyl, t-butyl, pentyl and hexyl.

Examples of the alkenyl groups having 2 to 8 carbon atoms which can be $R^1$, $R^4$, the substituent of the 5-membered heterocyclic group for A, or the substituent of the alkylene chain having 2 to 6 carbon atoms for B include vinyl and allyl.

Examples of the alkynyl groups having 2 to 8 carbon atoms which can be $R^1$, $R^4$, the substituent of the 5-membered heterocyclic group for A, or the substituent of the alkylene chain having 2 to 6 carbon atoms for B include propargyl.

Examples of the 3- to 7-membered cycloalkyl groups which can be the substituent of the 5-membered heterocyclic group for A, or the substituent of the alkylene chain having 2 to 6 carbon atoms for B include cyclopropyl, cyclopentyl and cyclohexyl.

Examples of the alkoxy groups having 1 to 8 carbon atoms which can be $R^1$, $R^4$, the substituent of the 5-membered heterocyclic group for A, or the substituent of the alkylene chain having 2 to 6 carbon atoms for B include methoxy, ethoxy, propoxy, isopropoxy, butoxy, i-butoxy, t-butoxy, pentyloxy and hexyloxy.

Examples of the halogen atoms which can be $R^1$, $R^4$, or the substituent of the alkylene chain having 2 to 6 carbon atoms for B include fluorine, chlorine, and bromine.

Examples of the alkyl groups having 1 to 8 carbon atoms and a halogen atom substituent which can be $R^1$, $R^4$, $R^5$, $R^6$, the substituent of the 5-membered heterocyclic group for A, or the substituent of the alkylene chain having 2 to 6 carbon atoms for B include methyl, ethyl, propyl, isopropyl, butyl and t-butyl which have substituents such as 1 to 3 fluorine, chlorine or bromine atoms. In some embodiments, the alkyl group having 1 to 8 carbon atoms and a halogen atom substituent is trifluoromethyl, chloromethyl, chloroethyl, 2-bromoethyl, or 2-fluoroethyl.

Examples of the alkoxy groups having 1 to 8 carbon atoms and a halogen atom substituent which can be $R^1$, $R^4$, the substituent of the 5-membered heterocyclic group for A, or the substituent of the alkylene chain having 2 to 6 carbon atoms for B include methoxy, ethoxy, propoxy, isopropyloxy, butyloxy and t-butyloxy which have substituents such as 1 to 3 fluorine, chlorine or bromine atoms. In some embodiments, the alkoxy group having 1 to 8 carbon atoms and a halogen atom substituent is trifluoromethyloxy, chloromethyloxy, 2-chloroethyloxy, 2-bromoethyloxy, or 2-fluoroethyloxy.

Examples of the acyl groups having 2 to 8 carbon atoms which can be $R^1$ or $R^4$, include acetyl and propionyl.

Examples of the aryl groups having 6 to 10 carbon atoms which can be $R^1$, $R^4$, or the substituent of the 5-membered heterocyclic group for A, include phenyl.

Examples of the 5- or 6-membered heterocyclic groups which can be $R^1$, $R^4$, or the substituent of the 5-membered heterocyclic group for A, include pyridyl.

Examples of the alkyl groups having 1 to 8 carbon atoms and a 3- to 7-cycloalkyl group substituent which can be the substituent of the 5-membered heterocyclic group for A, include methyl, ethyl, propyl, isopropyl, butyl, i-butyl, t-butyl, pentyl and hexyl which have cyclopropyl, cyclopentyl, or cyclophexyl substituent.

Examples of the aralkyl groups (which have an aryl moiety of 6 to 10 carbon atoms and an alkylene moiety of 1 to 8 carbon atoms) which can be the substituent of the 5-membered heterocyclic group for A, include benzyl and phenethyl.

Examples of the alkyl groups having 1 to 8 carbon atoms and a 5- or 6-membered heterocyclic group which can be the substituent of the 5-membered heterocyclic group for A, include methyl, ethyl, propyl, isopropyl, butyl, i-butyl, t-butyl, pentyl and hexyl which have a pyridyl substituent.

Examples of the alkyl groups having 1 to 8 carbon atoms, alkenyl groups having 2 to 8 carbon atoms, alkynyl groups having 2 to 8 carbon atoms, alkoxy groups having 1 to 8 carbon atoms, halogen atoms, alkyl groups having 1 to 8 carbon atoms and a halogen atom substituent, alkoxy groups having 1 to 8 carbon atoms and a halogen atom substituent, acyl groups having 2 to 8 carbon atoms, aryl groups having 6 to 10 carbon atoms, and 5- or 6-membered heterocyclic groups which can be $R^{11}$ or $R^{13}$ of the Formula (H) or $R^{21}$ or $R^{23}$ of the Formula (J) are those described hereinabove for $R^1$ and $R^4$ of the Formula (G).

Examples of the alkyl groups having 1 to 8 carbon atoms, 3- to 7-membered cycloalkyl groups, alkenyl groups having 2 to 8 carbon atoms, alkynyl groups having 2 to 8 carbon atoms, alkoxy groups having 1 to 8 carbon atoms, alkyl groups having 1 to 8 carbon atoms and a 3- to 7-membered cycloalkyl group substituent, alkyl groups having 1 to 8 carbon atoms and a halogen atom substituent, alkoxy groups having 1 to 8 carbon atoms and a halogen atom substituent, aryl groups having 6 to 10 carbon atoms, 5- or 6-membered heterocyclic groups, aralkyl groups having an aryl moiety of 6 to 10 carbon atoms and an alkylene moiety of 1 to 8 carbon atoms, and alkyl groups having 1 to 8 carbon atoms and a 5- or 6-membered heterocyclic substituent which can be $R^{12}$ of the Formula (H) or $R^{22}$ of the formula (J) include those described hereinabove for the substituent of the 5-membered heterocyclic group for A of the Formula (G).

Examples of the alkyl groups having 1 to 8 carbon atoms and alkyl groups having 1 to 8 carbon atoms and a halogen atom substituent which can be $R^{14}$ or $R^{15}$ of the Formula (H) or $R^{24}$ or $R^{25}$ of the Formula (J) include those described hereinabove for $R^5$ and $R^6$ of the Formula (G).

$R^1$ in the Formula (G), $R^{11}$ in the formula (H), and $R^{21}$ in the formula (J) can be attached to the benzene ring or the like in a single or plural number (1 to 3). If each of $R^1$, $R^{11}$ and $R^{21}$ is present in a plural number, the plural groups can be the same or different.

$R^4$ in the Formula (G), $R^{13}$ in the Formula (H), and $R^{23}$ in the Formula (J) can be attached to the benzene ring or the like in a single or plural number (1 to 3). If each of $R^4$, $R^{13}$ and $R^{23}$ is present in a plural number, the plural groups can be the same or different.

The substituent group of the 5-membered heterocyclic group for A in the Formula (G), $R^{12}$ in the formula (H), and $R^{22}$ in the Formula (J) can be attached to the heterocyclic ring in a single or plural number (1 or 2). If each of the substituent group of the 5-membered heterocyclic group for A, $R^{12}$ and $R^{22}$ is present in plural number, the plural groups can be the same or different.

The compounds of the Formulas (G), (H) and (J) can be pharmacologically acceptable salts such as alkali metal salts, for example, sodium salts, potassium salts, or lithium salts.

The compounds of the Formulas (G), (H) and (J) can be present in the optically active forms, and in the form of optical isomers such as compounds of a racemic form or geometric isomers such as compounds of a cis- or trans form.

In some embodiments, the compound of Formula (G), (H), or (J) is a compound shown in Table 5 or pharmaceutically acceptable salt, solvate, ester, amide, or prodrug thereof.

TABLE 5

| Structure | Name |
| --- | --- |
| 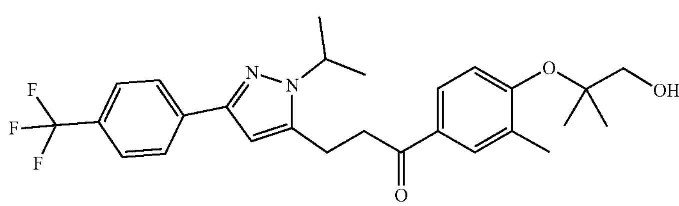 [SMILES: Cc1cc(C(=O)CCc2cc(-c3ccc(C(F)(F)F)cc3)nn2C(C)C)ccc1OC(C)(C)CO] | 1-(4-((1-hydroxy-2-methylpropan-2-yl)oxy)-3-methylphenyl)-3-(1-isopropyl-3-(4-(trifluoromethyl)phenyl)-1H-pyrazol-5-yl)propan-1-one |
| 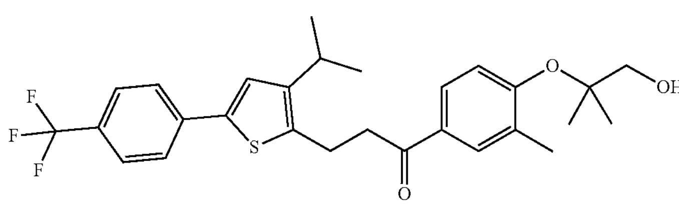 [SMILES: Cc1cc(C(=O)CCc2sc(-c3ccc(C(F)(F)F)cc3)cc2C(C)C)ccc1OC(C)(C)CO] | 1-(4-((1-hydroxy-2-methylpropan-2-yl)oxy)-3-methylphenyl)-3-(3-isopropyl-5-(4-(trifluoromethyl)phenyl)thiophen-2-yl)propan-1-one |
| 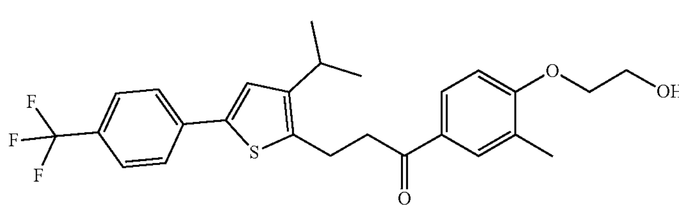 [SMILES: Cc1cc(C(=O)CCc2sc(-c3ccc(C(F)(F)F)cc3)cc2C(C)C)ccc1OCCO] | 1-(4-(2-hydroxyethoxy)-3-methylphenyl)-3-(3-isopropyl-5-(4-(trifluoromethyl)phenyl)thiophen-2-yl)propan-1-one |

TABLE 5-continued

| Structure | Name |
|---|---|
| | 1-(4-((1-hydroxy-2-methylpropan-2-yl)oxy)-3-methylphenyl)-3-(1-isopropyl-5-(4-(trifluoromethyl)phenyl)-1H-pyrazol-5-yl)propan-1-ol |
| 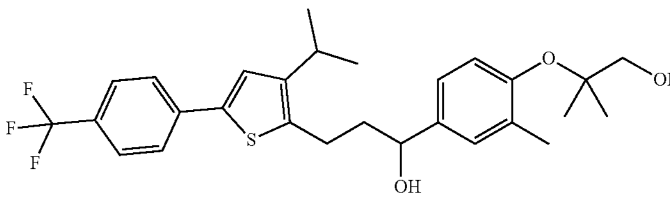 | 1-(4-((1-hydroxy-2-methylpropan-2-yl)oxy)-3-methylphenyl)-3-(3-isopropyl-5-(4-(trifluoromethyl)phenyl)thiophen-2-yl)propan-1-ol |
| 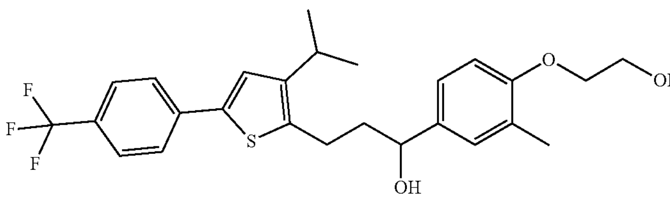 | 1-(4-(2-hydroxyethoxy)-3-methylphenyl)-3-(3-isopropyl-5-(4-(trifluoromethyl)phenyl)thiophen-2-yl)propan-1-ol |

5.2.8. Compounds of Formula (K)

In some embodiments, the compounds of the invention are compounds of Formula (K):

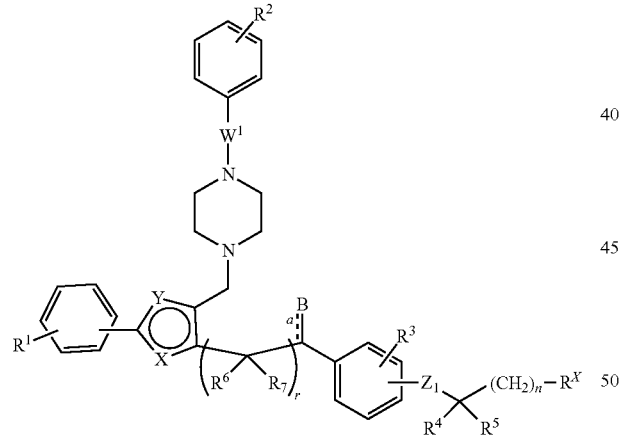

(K)

or a pharmaceutically acceptable salt, solvate, ester, amide, or prodrug thereto, wherein:

A is CH or nitrogen;
B, when bond a is present, is oxygen or C(R$^8$)(R$^9$) in which each of R$^8$ and R$^9$ is independently hydrogen or C$_{1-8}$ alkyl; B, when bond a is absent, is OH;
W$^1$ is a bond, C(=O), or (C(R$^{1'}$)(R$^{11}$))$_m$ in which each of R$^{10}$ and R$^{11}$ is independently a hydrogen or C$_{1-8}$ alkyl group and m is 1, 2, or 3;
X and Y differ from each other, and each is an oxygen atom, a sulfur atom, a nitrogen atom, or CR$^{12}$ in which R$^{12}$ is a hydrogen or C$_{1-8}$ alkyl;
Z$^1$ is a bond, oxygen, sulfur, or C(R$^{13}$)(R$^{14}$) in which each of R$^{13}$ and R$^{14}$ is independently a hydrogen or C$_{1-8}$ alkyl;

each of R$^1$, R$^2$, and R$^3$, is independently a hydrogen, C$_{1-8}$ alkyl, C$_{2-8}$ alkenyl, C$_{2-8}$ alkynyl, C$_{1-8}$ alkoxy, halogen, C$_{1-8}$ haloalkyl; C$_{1-8}$ haloalkoxy; hydroxyl, nitro, C$_{2-8}$ acyl group, C$_{6-10}$ aryl, or a 5- or 6-membered heterocyclic group;

each of R$^4$ and R$^5$ is independently hydrogen, C$_{1-8}$ alkyl, C$_{1-8}$ haloalkyl;

each of R$^6$ and R$^7$ is independently hydrogen, C$_{1-8}$ alkyl, C$_{2-8}$ alkenyl, C$_{2-8}$ alkynyl, or C$_{1-8}$ haloalkyl r is 1, 2, 3, 4, or 5;

R$^X$ is CH$_2$OH, COH, COOCH$_2$CONR$^{X4}$R$^{X5}$, SO$_3$H,

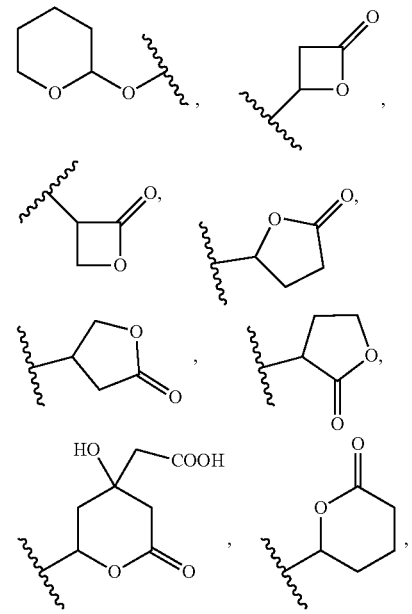

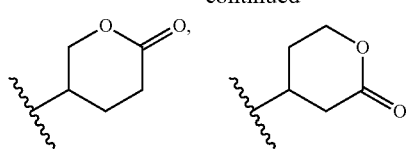

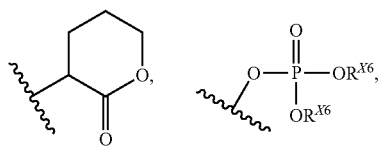

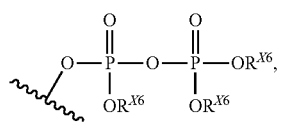

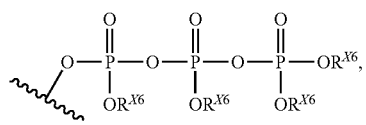

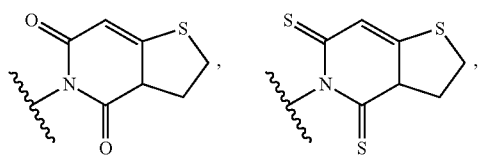

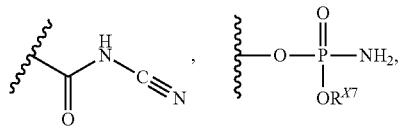

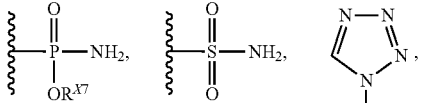

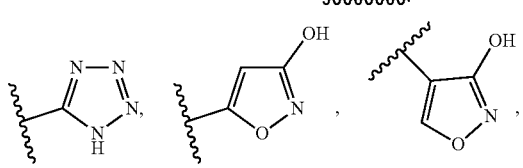

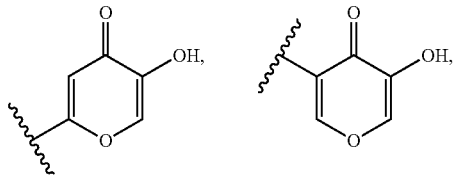

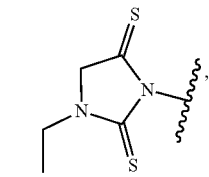

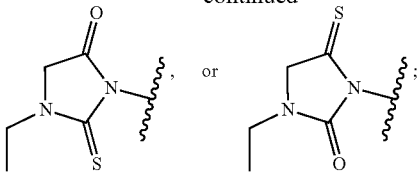

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In the Formula (K), examples of the alkyl groups having 1 to 8 carbon atoms for $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ include methyl, ethyl, propyl, isopropyl, butyl, i-butyl, t-butyl, pentyl and hexyl.

Examples of the alkenyl groups having 2 to 8 carbon atoms for $R^1$, $R^2$, $R^3$, $R^6$ and $R^7$ include vinyl and allyl.

Examples of the alkynyl groups having 2 to 8 carbon atoms for $R^1$, $R^2$, $R^3$, $R^6$ and $R^7$ include propargyl.

Examples of the alkoxy groups having 1 to 8 carbon atoms for $R^1$, $R^2$, and $R^3$ include methoxy, ethoxy, propoxy, isopropoxy, butoxy, i-butoxy, t-butoxy, pentyloxy and hexyloxy.

Examples of the halogen atoms for $R^1$, $R^2$, and $R^3$ include fluorine, chlorine, and bromine.

Examples of the alkyl groups having 1 to 8 carbon atoms which are substituted with a halogen atom for $R^1$, $R^2$, $R^3$, $R^4$, $R^5$, $R^6$, and $R^7$ include methyl, ethyl, propyl, isopropyl, butyl, and t-butyl which are substituted with 1 to 3 halogen atoms such as fluorine, chlorine, and bromine. In one embodiment, substituents are trifluoromethyl, chloromethyl, 2-chloroethyl, 2-bromoethyl, or 2-flouroethyl.

Examples of the alkoxy groups having 1 to 8 carbon atoms which are substituted with a halogen atom for $R^1$, $R^2$, and $R^3$ include methoxy, ethoxy, propoxy, isopropoxy, butoxy, and t-butoxy which are substituted with 1 to 3 halogen atoms such as fluorine, chlorine, or bromine. In one embodiment, substituents are tritluoromethyloxy, chloromethyloxy, 2-chloroethyloxy, 2-bromoethyloxy, or 2-flouroethyloxy.

Examples of the acyl groups having 2 to 8 carbon atoms for $R^1$, $R^2$ and $R^3$ include acetyl and propionyl.

Examples of the aryl groups having 6 to 10 carbon atoms for $R^1$, $R^2$ and $R^3$ include phenyl.

Examples of the 5- or 6-membered heterocyclic groups for $R^1$, $R^2$ and $R^3$ include pyridyl.

$R^1$, $R^2$ and $R^3$ in the Formula (K) can be attached to the benzene ring or the like in numbers of 1 to 3 in which the same or different groups can be attached to the same ring.

The compounds provided herein which are represented by the Formula (K) can be in the form of a pharmacologically acceptable salts such as alkali metal salts, e.g., salts of sodium, potassium and lithium.

The compounds provided herein can be in the optically active forms, and in the form of optical isomers such as compounds of a racemic form or geometric isomers such as compounds of a cis- or trans form.

In some embodiments, the compound of Formula (K) is a compound shown in Table 6 or pharmaceutically acceptable salt, solvate, ester, amide, or prodrug thereof.

TABLE 6

| Structure | Name |
|---|---|
| 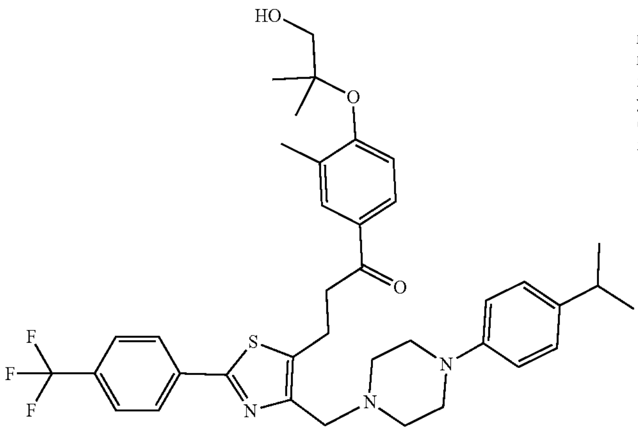 [SMILES: Cc1cc(C(=O)CCc2sc(-c3ccc(C(F)(F)F)cc3)nc2CN2CCN(c3ccc(C(C)C)cc3)CC2)ccc1OC(C)(C)CO] | 1-(4-((1-hydroxy-2-methylpropan-2-yl)oxy)-3-methylphenyl)-3-(4-((4-(4-isopropylphenyl)piperazin-1-yl)methyl)-2-(4-(trifluoromethyl)phenyl)thiazol-5-yl)propan-1-one |
| 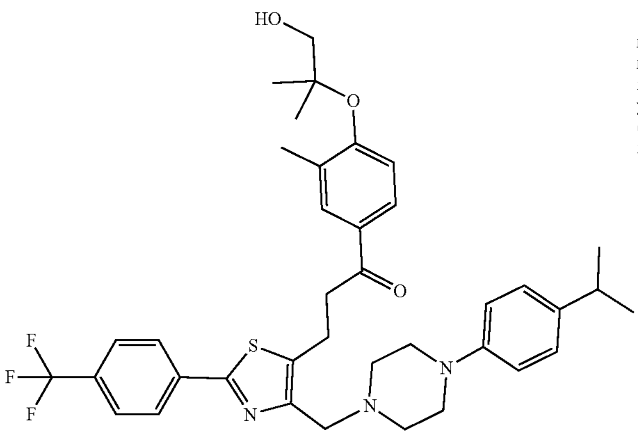 [SMILES: Cc1cc(C(=O)CCc2sc(-c3ccc(C(F)(F)F)cc3)nc2CN2CCN(c3ccc(C(C)C)cc3)CC2)ccc1OC(C)(C)CO] | 1-(4-((1-hydroxy-2-methylpropan-2-yl)oxy)-3-methylphenyl)-3-(4-((4-(4-isopropylphenyl)piperazin-1-yl)methyl)-2-(4-(trifluoromethyl)phenyl)thiazol-5-yl)propan-1-ol |

5.2.9. Compounds of Formula (L)

In some embodiments, the compounds of the invention are compounds of Formula (L):

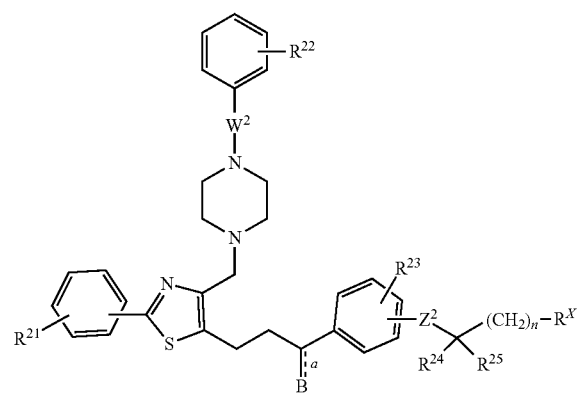

(L)

or a pharmaceutically acceptable salt, solvate, ester, amide, or prodrug thereof, wherein:

B, when bond a is present, is oxygen; B, when bond a is absent, is OH;

$W^2$ is a bond, C(=O), or $CH_2$;

$Z^2$ is oxygen or sulfur;

each of $R^{21}$, $R^{22}$, and $R^{23}$ is independently a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

each of $R^{24}$ and $R^{25}$ is independently hydrogen, $C_{1-8}$ alkyl, $C_{1-8}$ haloalkyl;

$R^X$ is $CH_2OH$, COH, $COOCH_2CONR^{X4}R^{X5}$, $SO_3H$,

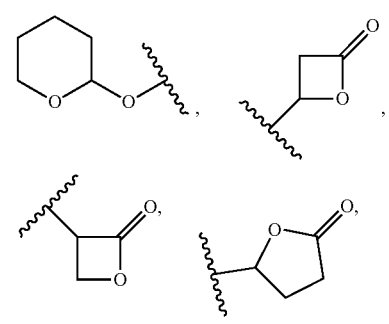

-continued

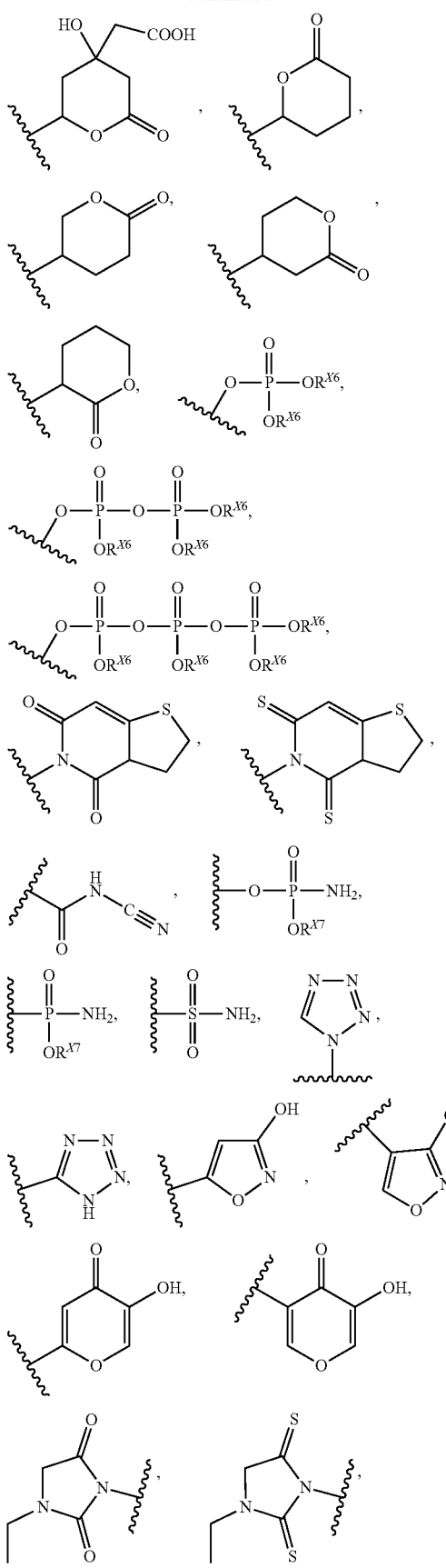

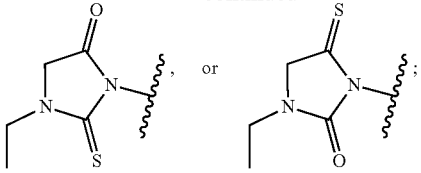

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In the Formula (L), the alkyl groups having 1 to 8 carbon atoms, alkenyl groups having 2 to 8 carbon atoms, alkynyl groups having 2 to 8 carbon atoms, alkoxy groups having 1 to 8 carbon atoms, halogen atoms, alkyl groups having 1 to 8 carbon atoms which are substituted with a halogen atom, alkoxy groups having 1 to 8 carbon atoms which are substituted with a halogen atom, hydroxyls, nitros, acyl groups having 2 to 8 carbon atoms, aryl groups having 6 to 10 carbon atoms, and 5- or 6-membered heterocyclic groups for $R^{21}$, $R^{22}$ and $R^{23}$ can in some embodiments be those described for $R^{1}$, $R^{2}$ and $R^{3}$ in the Formula (K).

In the Formula (L), the alkyl groups having 1 to 8 carbon atoms and alkyl groups having 1 to 8 carbon atoms which are substituted with a halogen atom for $R^{24}$ and $R^{25}$ can in some embodiments be those described for $R^{4}$ and $R^{5}$ in the Formula (K).

$R^{21}$, $R^{22}$ and $R^{23}$ in the Formula (L) can be attached to the benzene ring or the like in numbers of 1 to 3 in which the same or different groups can be attached to the same ring.

The compounds provided herein which are represented by the Formula (L) can be in the form of a pharmacologically acceptable salts such as alkali metal salts, e.g., salts of sodium, potassium and lithium.

The compounds provided herein can be in the optically active forms, and in the form of optical isomers such as compounds of a racemic form or geometric isomers such as compounds of a cis- or trans form.

5.2.10. Compounds of Formula (M) and (N)

In some embodiments, the compounds of the invention are compounds of Formula (M):

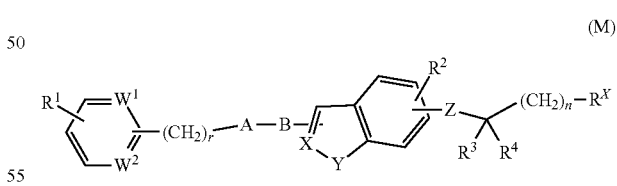

(M)

or a pharmaceutically acceptable salt, solvate, ester, amide, or prodrug thereof, wherein:

each of $W^1$ and $W^2$ is independently nitrogen or CH;

X is nitrogen or CH;

Y is oxygen or sulfur;

Z is a bond, oxygen, sulfur or $NR^5$, in which $R^5$ is hydrogen or $C_{1-8}$ alkyl;

each of $R^1$ and $R^2$ is independently hydrogen, halogen, hydroxyl, nitro, amino, $C_{1-8}$ alkyl, 3- to 7-membered cycloalkyl group, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ haloalkoxy, $C_{6-10}$ aryl, 5- or 6-membered heterocyclic group, an aralkyl group having $C_{6-10}$ aryl moiety and a $C_{1-8}$ alkylene, or $C_{1-8}$ alkyl having a 5- or 6-membered heterocyclic substituent;

each of $R^3$ and $R^4$ is independently hydrogen, $C_{1-8}$ alkyl, or $C_{1-8}$ haloalkyl;

A is a 5-membered heterocycle which is pyrazole, thiophene, furan, isoxazole, isothiazole or pyrrole, in which the 5-membered heterocycle is unsubstituted or substituted with halogen, hydroxyl, nitro, amino, $C_{1-8}$ alkyl, 3- to 7-membered cycloalkyl group, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ haloalkoxy, $C_{6-10}$ aryl, a 5- or 6-membered heterocyclic group, an aralkyl group having a $C_{6-10}$ aryl moiety and $C_{1-8}$ alkylene moiety, or $C_{1-8}$ alkyl group having a 5- or 6-membered heterocyclic substituent;

B is a bond or $C_{1-8}$ alkylene which is unsubstituted or substituted with $C_{1-8}$ alkyl, 3- to 7-membered cycloalkyl, $C_{1-8}$ alkoxy or a halogen substituent, optionally wherein the $C_{1-8}$ alkylene has a double or triple bond;

r is 0, 1, 2, or 3;

$R^X$ is $CH_2OH$, $COH$, $COOCH_2CONR^{X4}R^{X5}$, $SO_3H$,

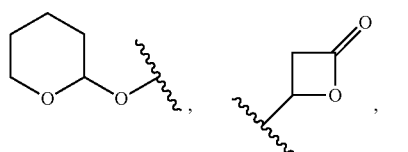

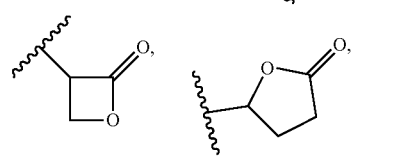

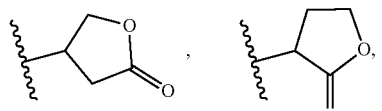

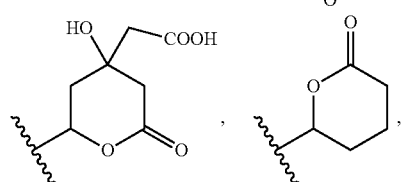

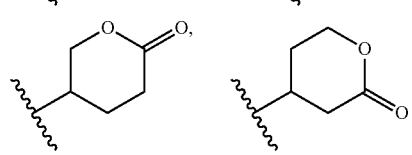

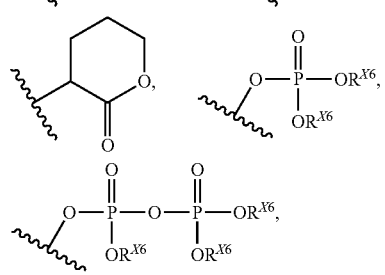

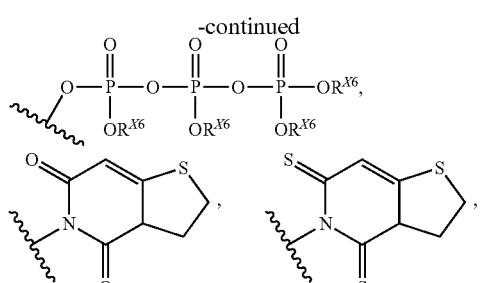

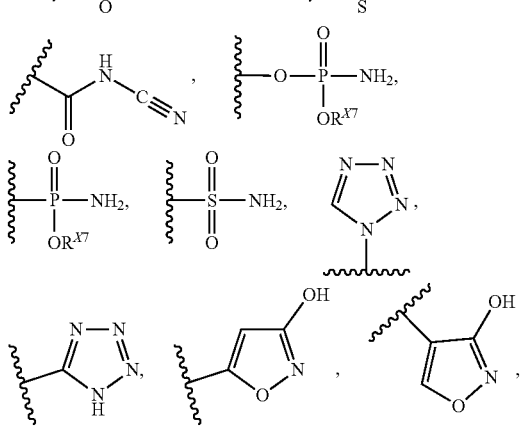

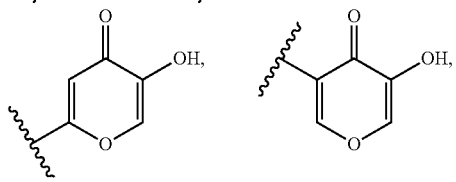

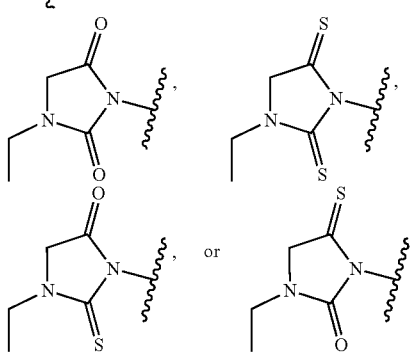

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (N):

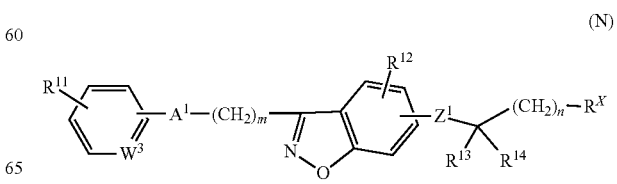

(N)

a or a pharmaceutically acceptable salt, solvate, ester, amide, or prodrug thereof, wherein:

$W^3$ is nitrogen or CH;

$Z^1$ is oxygen or sulfur;

each of $R^{11}$ and $R^{12}$ is independently hydrogen, halogen, hydroxyl, nitro, amino, $C_{1-8}$ alkyl, $C_{1-8}$ alkoxy, $C_{1-8}$ haloalkyl, or $C_{1-8}$ haloalkoxy' each of $R^{13}$ and $R^{14}$ is independently hydrogen or $C_{1-8}$ alkyl;

$A^1$ is a 5-membered heterocycle which is pyrazole or thiophene, in which the 5-membered heterocycle is unsubstituted or substituted with halogen, hydroxyl, nitro, amino, $C_{1-8}$ alkyl, $C_{1-8}$ alkoxy, $C_{1-8}$ haloalkyl, or $C_{1-8}$ haloalkoxy;

m is 2, 3, or 4;

$R^X$ is $CH_2OH$, COH, $COOCH_2CONR^{X4}R^{X5}$, $SO_3H$,

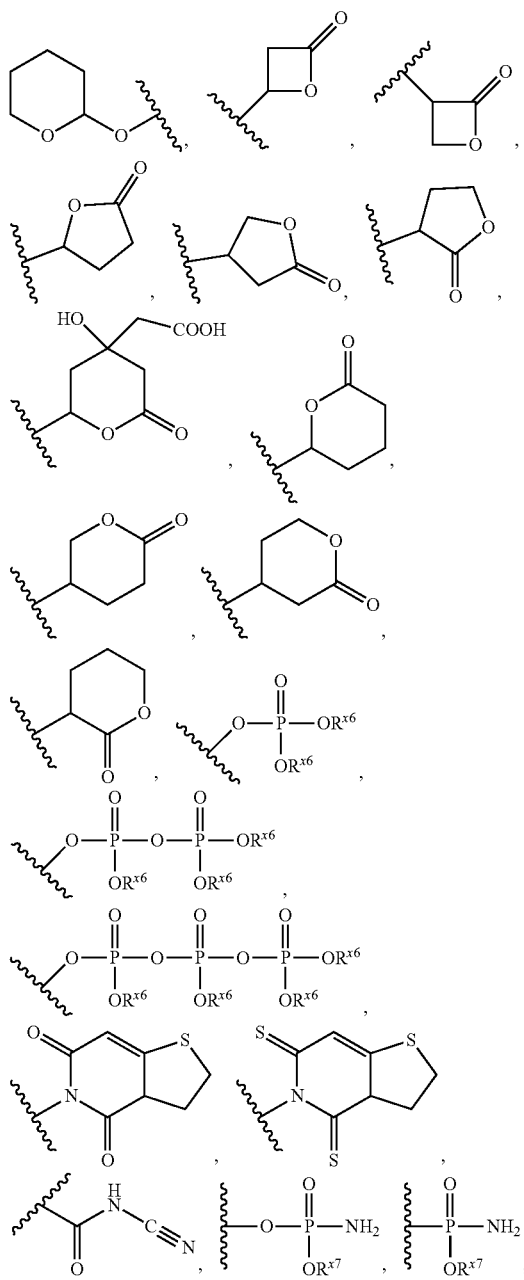

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments of compounds of Formula (M), the alkyl group having 1 to 8 carbon atoms for $R^1$, $R^2$, $R^3$, $R^4$, $R^5$, a substituent attached to the 5-membered hetero ring of A (when present), and a substituent attached to an alkylene chain having 1 to 8 carbon atoms can be methyl, ethyl, propyl, isopropyl, butyl, i-butyl, t-butyl, pentyl, or hexyl.

In one embodiment, the alkenyl group having 2 to 8 carbon atoms for $R^1$, $R^2$ and a substituent is attached to the 5-membered hetero ring of A and is vinyl or allyl.

In one embodiment, the alkynyl 1 group having 2 to 8 carbon atoms for $R^1$, $R^2$, wherein a substituent is attached to the 5-membered hetero ring of A and is propargyl.

In one embodiment, the 3- to 7-membered cycloalkyl group for $R^1$, $R^2$, wherein a substituent is attached to the 5-membered hetero ring of A. In another embodiment, a substituent is attached to the alkylene chain having 1 to 8 carbon atoms and is cyclopentyl or cyclohexyl.

In one embodiment, the alkoxy group having 1 to 8 carbon atoms for $R^1$, $R^2$, wherein a substituent is attached to the 5-membered hetero ring of A. In another embodiment, a substituent is attached to the alkylene chain having 1 to 8 carbon atoms and is methoxy, ethoxy, propoxy, isopropoxy, butoxy, i-butoxy, t-butoxy, pentyloxy, or hexyloxy.

In one embodiment, $R^1$ and $R^2$ is halogen, a substituent is attached to the 5-membered hetero ring of A. In another embodiment, a substituent is attached to the alkylene chain having 1 to 8 carbon atoms and is fluorine, chlorine, or bromine.

In one embodiment, the alkyl group having 1 to 8 carbon atoms and a halogen substituent for $R^1$, $R^2$, $R^5$, wherein a substituent is attached to the 5-membered hetero ring of A and is methyl, ethyl, propyl, isopropyl, butyl or t-butyl which has 1 to 3 halogen substituents such as fluorine, chlorine or bromine. In another embodiment, the substituents are selected from trifluoromethyl, chloromethyl, 2-chloroethyl, 2-bromoethyl, and 2-fluoroethyl.

In one embodiment, the alkoxy group having 1 to 8 carbon atoms and a halogen substituent for $R^1$, $R^2$, wherein a substituent is attached to the 5-membered hetero ring of A and is methoxy, ethoxy, propoxy, isopropoxy, butyloxy or t-butyloxy which has 1 to 3 halogen substituents such as fluorine, chlorine or bromine. In one embodiment, the substituents are selected from trifluoromethyloxy, chloromethyloxy, 2-chloroethyloxy, 2-bromoethyloxy, and 2-fluoroethyloxy.

In one embodiment, the aryl group having 6 to 10 carbon atoms for $R^1$, $R^2$, and a substituent is attached to the 5-membered hetero ring of A and is phenyl.

In one embodiment, the 5- or 6-membered heterocyclic group for $R^1$, $R^2$, and a substituent is attached to the 5-membered hetero ring of A and is pyridyl.

In one embodiment, the alkyl group having 1 to 8 carbon atoms and 3- to 7-membered cycloalkyl group for $R^1$, $R^2$, and a substituent is attached to the 5-membered hetero ring of A and is methyl, ethyl, propyl, isopropyl, butyl, i-butyl, t-butyl, pentyl, or hexyl which has a cyclopropyl substituent, a cyclopentyl substituent, or a cyclohexyl substituent.

In one embodiment, the aralkyl having an aryl moiety of 6 to 10 carbon atoms and an alkylene moiety of 1 to 8 carbon atoms for $R^1$, $R^2$, and a substituent is attached to the 5-membered hetero ring of A and is benzyl or phenethyl.

In one embodiment, the alkyl group having 1 to 8 carbon atoms and 5- or 6-membered heterocyclic group for $R^1$, $R^2$, and a substituent is attached to the 5-membered hetero ring of A and is methyl, ethyl, propyl, isopropyl, butyl, i-butyl, t-butyl, pentyl, or hexyl which has a pyridyl substituent.

In one embodiment, the 5-membered hetero ring, which may have a substituent for A, is pyrazole or thiophene having a substituent. In another embodiment, pyrazole is having a substituent.

In one embodiment, the alkylene chain having 1 to 8 carbon atoms which has substituent for B is an alkylene chain having 1 to 4 carbon atoms. In another embodiment, the alkylene chain is an ethylene chain or a propylene chain.

In one embodiment, n is 0.

In some embodiment of the compounds of Formula (N), the halogen atom, alkyl group having 1 to 8 carbon atoms, alkoxy group having 1 to 8 carbon atoms, alkyl group having 1 to 8 carbon atoms and a halogen substituent, and alkoxy group having 1 to 8 carbon atoms and a halogen substituent for $R^{11}$ and $R^{12}$ can be those described hereinbefore for $R^1$ and $R^2$ of the Formula (M).

In one embodiment, the alkyl group having 1 to 8 carbon atoms for $R^{13}$ and $R^{14}$ can be those described hereinbefore for $R^3$ and $R^4$ of the Formula (M).

In one embodiment, the halogen atom, alkyl group having 1 to 8 carbon atoms, alkoxy group having 1 to 8 carbon atoms, alkyl group having 1 to 8 carbon atoms and a halogen substituent, and alkoxy group having 1 to 8 carbon atoms and a halogen substituent which is attached to pyrazole or thiophene for $A^1$ in the Formula (N) are those described hereinbefore for the substituents attached to the 5-membered hetero ring of A of the Formula (M).

In one embodiment, $R^1$ of the Formula (M) and $R^{11}$ of the Formula (N), the benzene ring or the like can have 1 to 3 number of $R^1$ or $R^{11}$ which are the same or different from each other. In another embodiment, the benzene ring or the like can have 1 to 3 substituents other than a hydrogen atom.

In one embodiment, $R^2$ of the Formula (M) and $R^{12}$ of the Formula (N), the benzene ring of the benzisoxazole ring or the like can have 1 to 3 number of $R^2$ or $R^{12}$ which are the same or different from each other. In another embodiment, the benzene ring of the benzisoxazole ring or the like can have 1 to 3 substituents other than a hydrogen atom.

In one embodiment, the substituent attached to the 5-membered hetero ring for A of the Formula (M) and the substituent attached to pyrazole or thiophene for $A^1$ of the Formula (N) can be present in 1 or 2 number which can be the same or different from each other.

The compounds provided herein which are represented by the Formula (M) and (N) can be in the form of a pharmacologically acceptable salts such as alkali metal salts, e.g., salts of sodium, potassium and lithium.

The compounds provided herein can be in the optically active forms, and in the form of optical isomers such as compounds of a racemic form or geometric isomers such as compounds of a cis- or trans form.

In some embodiments, the compound of Formula (M) or (N) is a compound shown in Table 7 or pharmaceutically acceptable salt, solvate, ester, amide, or prodrug thereof.

TABLE 7

| Structure | Name |
|---|---|
| 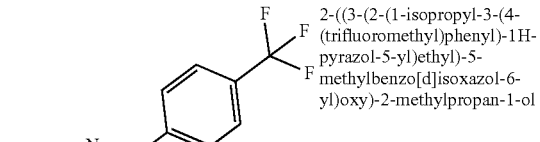 | 2-((3-(2-(1-isopropyl-3-(4-(trifluoromethyl)phenyl)-1H-pyrazol-5-yl)ethyl)-5-methylbenzo[d]isoxazol-6-yl)oxy)-2-methylpropan-1-ol |

TABLE 7-continued

| Structure | Name |
|---|---|
| 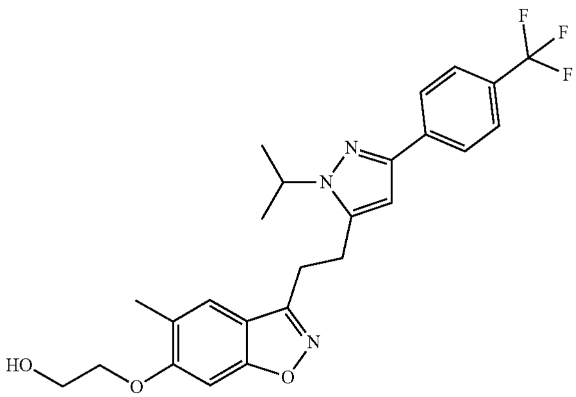 [SMILES: Cc1cc2c(CCc3cc(-c4ccc(C(F)(F)F)cc4)nn3C(C)C)noc2cc1OCCO] | 2-((3-(2-(1-isopropyl-3-(4-(trifluoromethyl)phenyl)-1H-pyrazol-5-yl)ethyl)-5-methylbenzo[d]isoxazol-6-yl)oxy)ethan-1-ol |

5.2.11. Compounds of Formula (O), (P) and (Q)

In some embodiments, the compounds of the invention are compounds of Formula (O):

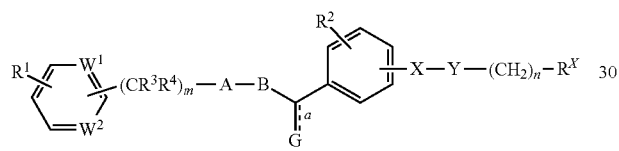
(O)

or a pharmaceutically acceptable salt, solvate, ester, amide, or prodrug thereof, wherein:

each of $W^1$ and $W^2$ independently is CH or nitrogen;

X is $NR^5$ or $CR^6R^7$; wherein $R^5$ is hydrogen, $C_{1-8}$ alkyl, $C_{1-8}$ haloalkyl, $C_{1-8}$ alkyl substituted with $C_{1-8}$ alkoxy, $C_{3-7}$ cycloalkyl, $C_{1-8}$ alkyl substituted with $C_{3-7}$ cycloalkyl, $C_{1-8}$ alkyl substituted with phenyl, $C_{2-8}$ acyl, or $C_{2-8}$ alkenyl, and each of $R^6$ and $R^7$ independently is hydrogen or $C_{1-8}$ alkyl;

Y is $(CR^8R^9)_r$, wherein each of $R^8$ and $R^9$ independently is hydrogen or $C_{1-8}$ alkyl, and r is 1, 2, 3, or 4; or X and Y are combined to form $CR^{10}=CR^{11}$ or ethynylene, wherein each of $R^{10}$ and $R^{11}$ independently is hydrogen or $C_{1-8}$ alkyl;

G, when bond a is present, is O, S or $CR^{12}R^{13}$, wherein each of $R^{12}$ and $R^{13}$ independently is hydrogen or $C_{1-8}$ alkyl; G, when bond a is absent, is OH;

A is a five-membered heterocyclic ring which is thiazole, oxazole, imidazole, pyrazole, thiophene, furan, or pyrrole, wherein the heterocyclic ring is unsubstituted or substituted with $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, hydroxyl, nitro, $C_{2-8}$ acyl, $C_{6-10}$ aryl, or a five-membered or six-membered heterocyclic group;

B is a $C_{1-8}$ alkylene, $C_{2-8}$ alkenylene or $C_{2-8}$ alkynylene chain, wherein the chain is unsubstituted or substituted with $C_{1-8}$ alkyl, $C_{3-7}$ cycloalkyl, $C_{1-8}$ alkoxy, or halogen;

each of $R^1$ and $R^2$ independently is hydrogen, $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, hydroxyl, nitro, $C_{2-8}$ acyl, $C_{6-10}$ aryl, or a five-membered or six-membered heterocyclic group;

each of $R^3$ and $R^4$ independently is hydrogen or $C_{1-8}$ alkyl;

m is 0, 1, 2, or 3;

$R^X$ is $CH_2OH$, COH, $COOCH_2CONR^{X4}R^{X5}$, $SO_3H$,

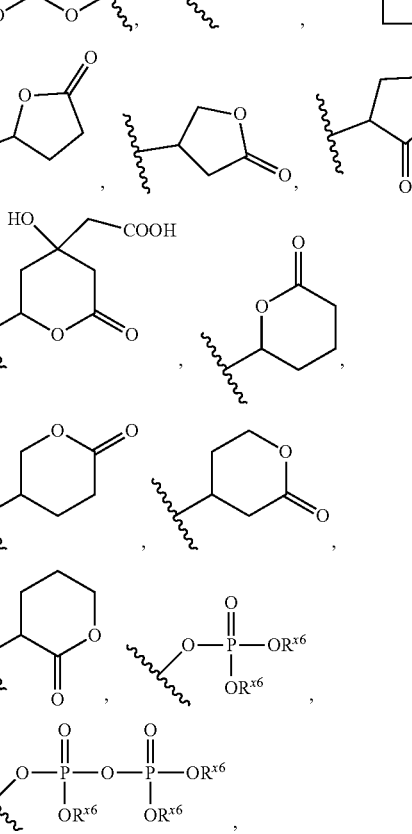

-continued

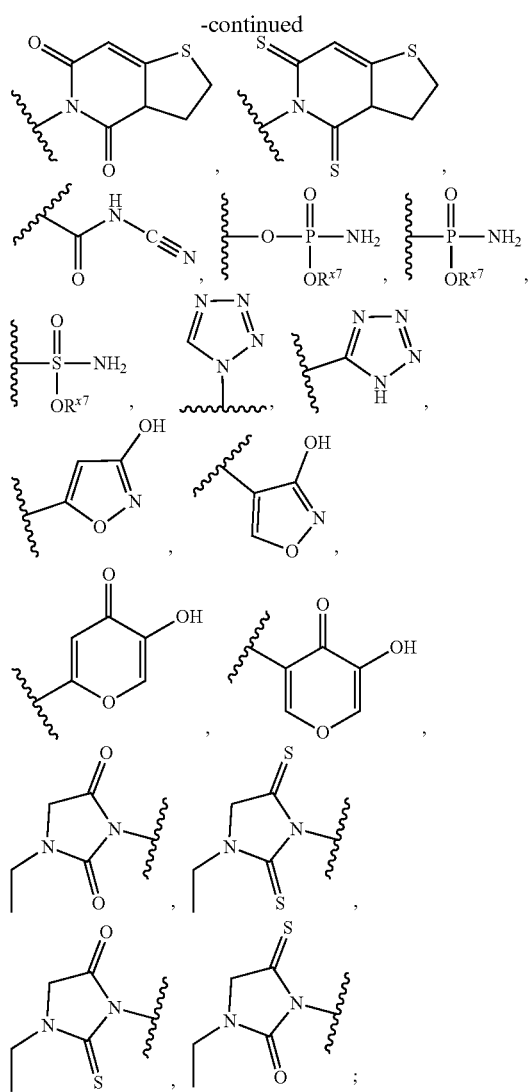

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (P):

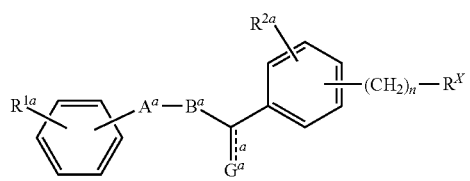

(P)

or a pharmaceutically acceptable salt, solvate, ester, amide, or prodrug thereof, wherein:

$G^a$, when bond a is present, is O, S or $CH_2$; $G^a$, when bond a is absent, is OH.

$A^a$ is five-membered heterocyclic ring which is thiazole, oxazole, or thiophene, wherein the five-membered heterocyclic ring is unsubstituted or is substituted with $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$B^a$ is a $C_{1-8}$ alkylene or $C_{2-8}$ alkenylene chain;

each of $R^{1a}$ and $R^{2a}$ independently is hydrogen, $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$R^X$ is $CH_2OH$, COH, $COOCH_2CONR^{X4}R^{X5}$, $SO_3H$,

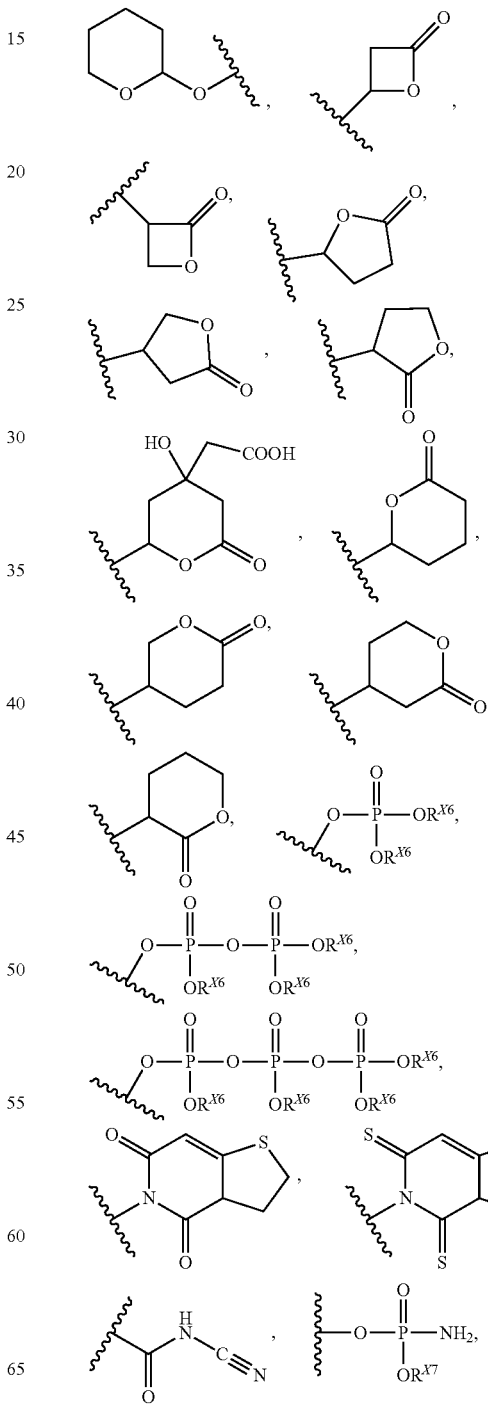

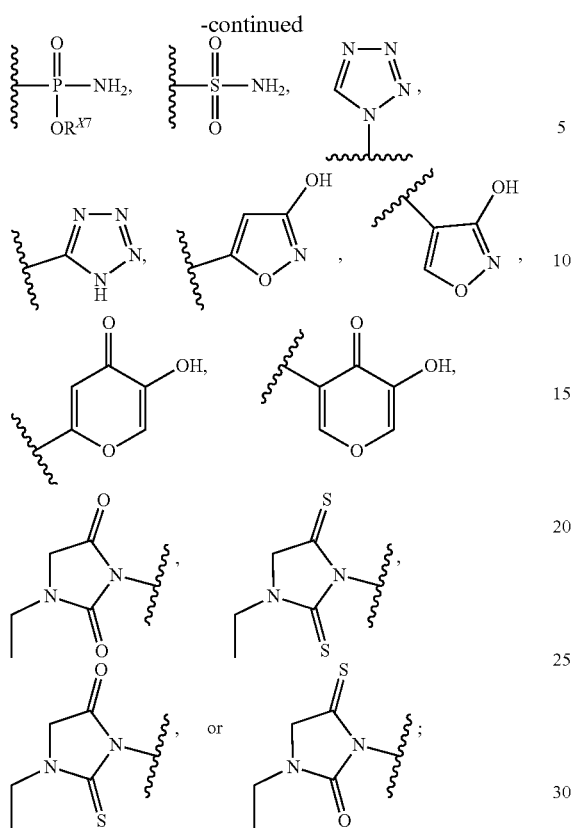

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (Q):

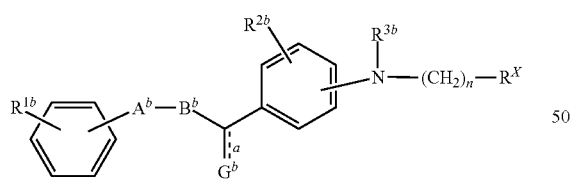

(Q)

or a pharmaceutically acceptable salt, solvate, ester, amide, or prodrug thereof, wherein:

$G^b$, when bond a is present, is O, S or $CH_2$; $G^b$, when bond a is absent, is OH;

$A^b$ is five-membered heterocyclic ring which is thiazole, oxazole, or thiophene, wherein the five-membered heterocyclic ring is unsubstituted or is substituted with $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$B^b$ is a $C_{1-8}$ alkylene or $C_{2-8}$ alkenylene chain;

each of $R^{1b}$ and $R^{2b}$ independently is hydrogen, $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$R^{3b}$ is hydrogen or $C_{1-8}$ alkyl;

$R^X$ is $CH_2OH$, COH, $COOCH_2CONR^{X4}R^{X5}$, $SO_3H$,

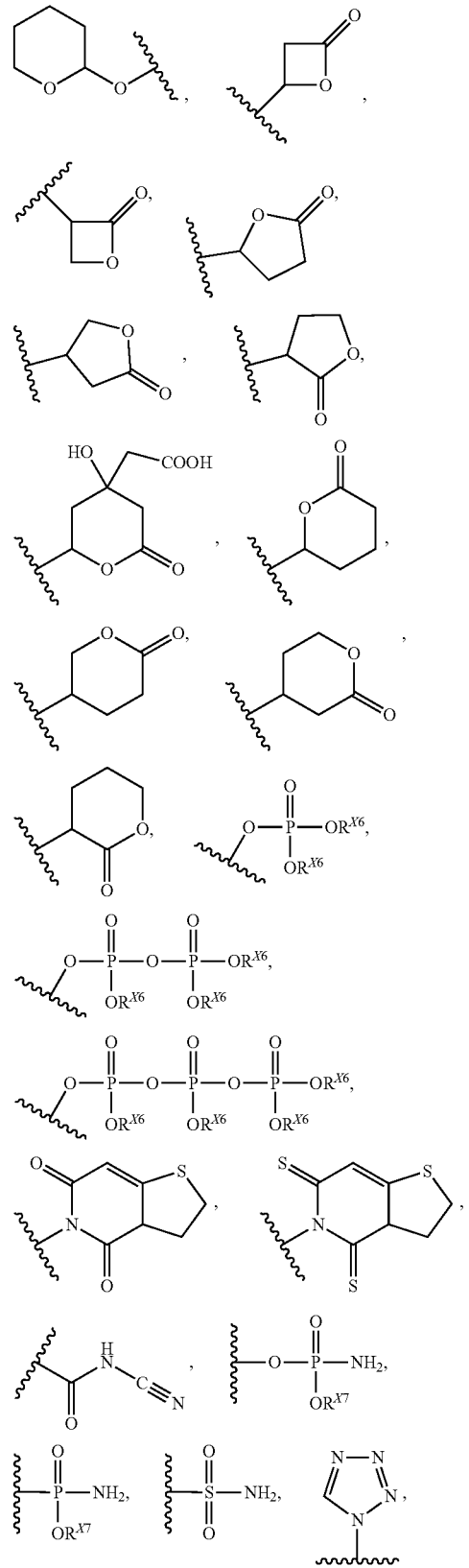

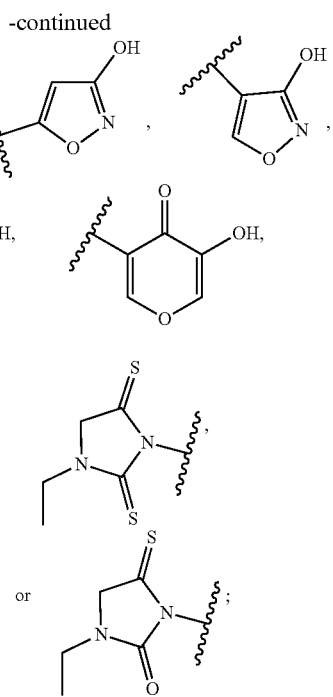

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, in the Formula (O), $R^1$, $R^2$, $R^3$, $R^4$, $R^5$, $R^6$, $R^7$, $R^8$, $R^9$, $R^{10}$, R, $R^{12}$, $R^{13}$, a substituent of the five-membered heterocyclic ring represented by A, and a substituent of the $C_{1-8}$ alkylene, $C_{2-8}$ alkenylene or $C_{2-8}$ alkynylene chain represented by B can be $C_{1-8}$ alkyl. Examples of the $C_{1-8}$ alkyl include methyl, ethyl, propyl, isopropyl, butyl, isobutyl, t-butyl, pentyl and hexyl.

In one embodiment, $R^1$, $R^2$, $R^5$, and a substituent of the five-membered heterocyclic ring represented by A can be $C_{2-8}$ alkenyl. Examples of the $C_{2-8}$ alkenyl include vinyl and allyl.

In one embodiment, $R^1$, $R^2$, and a substituent of the five-membered heterocyclic ring represented by A can be $C_{2-8}$ alkynyl. Examples of the $C_{2-8}$ alkynyl include propargyl.

In one embodiment, $R^1$, $R^2$, a substituent of the five-membered heterocyclic ring represented by A, and a substituent of the $C_{1-8}$ alkylene, $C_{2-8}$ alkenylene or $C_{2-8}$ alkynylene chain represented by B can be $C_{1-8}$ alkoxy. Examples of the $C_{1-8}$ alkoxy include methoxy, ethoxy, propoxy, isopropoxy, butoxy, isobutoxy, t-butoxy, pentyloxy, and hexyloxy.

In one embodiment, $R^1$, $R^2$, a substituent of the five-membered heterocyclic ring represented by A, and a substituent of the $C_{1-8}$ alkylene, $C_{2-8}$ alkenylene or $C_{2-8}$ alkynylene chain represented by B can be halogen. Examples of the halogen include fluorine, chlorine, and bromine.

In one embodiment, $R^1$, $R^2$, $R^5$, and a substituent of the five-membered heterocyclic ring represented by A can be $C_{1-8}$ alkyl substituted with halogen. Examples of the $C_{1-8}$ alkyl substituted with halogen include methyl, ethyl, propyl, isopropyl, butyl, and t-butyl which are substituted with 1-3 halogens such as fluorine, chlorine, and bromine. Preferred are trifluoromethyl, chloromethyl, 2-chloroethyl, 2-bromoethyl, and 2-fluoroethyl.

In one embodiment, $R^1$, $R^2$, and a substituent of the five-membered heterocyclic ring represented by A can be $C_{1-8}$ alkoxy substituted with halogen.

Examples of the $C_{1-8}$ alkoxy substituted with halogen include methoxy, ethoxy, propoxy, isopropoxy, butoxy, and t-butoxy which are substituted with 1-3 halogen atoms such as fluorine atom, chlorine atom, or bromine atom. In one embodiment, $R^1$, $R^2$, and a substituent of the five-membered heterocyclic ring are trifluoromethoxy, chloromethoxy, 2-chloroethoxy, 2-bromoethoxy, and 2-fluoroethoxy.

In one embodiment, $R^1$, $R^2$, $R^5$, and a substituent of the five-membered heterocyclic ring represented by A can be $C_{2-8}$ acyl. Examples of the $C_{2-8}$ acyl include acetyl and propionyl.

In one embodiment, $R^1$, $R^2$, and a substituent of the five-membered heterocyclic ring represented by A can be $C^\cdot.\backslash Q$ aryl. Examples of the $C_{6-10}$ aryl include phenyl.

In one embodiment, $R^1$, $R^2$, and a substituent of the five-membered heterocyclic ring represented by A can be a five-membered or six-membered heterocyclic group. Examples of the five-membered or six-membered heterocyclic group include pyridyl.

In one embodiment, $R^5$ can be $C_{1-8}$ alkyl substituted with $C_{1-8}$ alkoxy.

Examples of the $C_{1-8}$ alkyl substituted with $C_{1-8}$ alkoxy include methyl, ethyl, propyl, isopropyl, butyl, isobutyl, t-butyl, pentyl and hexyl which are substituted with methoxy, ethoxy, propoxy, isopropoxy, butoxy, isobutoxy, t-butoxy, pentyloxy, or hexyloxy.

In one embodiment, $R^5$ can be cycloalkyl of three-membered to seven-membered ring. Examples of the cycloalkyl of three-membered to seven-membered ring include cyclopropyl, cyclobutyl, cyclopentyl, and cyclohexyl.

In one embodiment, $R^5$ can be $C_{1-8}$ alkyl substituted with cycloalkyl of three-membered to seven-membered ring. Examples of the $C_{1-8}$ alkyl substituted with cycloalkyl of three-membered to seven-membered ring include methyl, ethyl, propyl, isopropyl, butyl, isobutyl, t-butyl, pentyl and hexyl which are substituted with cyclopropyl, cyclobutyl, cyclopentyl, or cyclohexyl.

In one embodiment, $R^5$ can be $C_{1-8}$ alkyl substituted with phenyl.

Examples of the $C_{1-8}$ alkyl substituted with phenyl include benzyl and phenethyl.

In one embodiment, a substituent of the $C_{1-8}$ alkylene, $C_{2-8}$ alkenylene or $C_{2-8}$ alkynylene chain represented by B can be cycloalkyl of three-membered to seven-membered ring. Examples of the cycloalkyl of three-membered to seven-membered ring include cyclopropyl, cyclobutyl, cyclopentyl, and cyclohexyl.

In some embodiments, in the Formula (P), $R^{13}$, $R^{2a}$, and a substituent of five-membered heterocyclic ring represented by A can be $C_{1-8}$ alkyl, $C_{1-8}$ alkoxy, halogen, $C_{1-8}$ alkyl substituted with halogen, $C_{1-8}$ alkoxy substituted with halogen, and $C_{2-8}$ acyl. Examples of them are the same as the examples of $R^1$, $R^2$, and the substituent of the five-membered heterocyclic ring represented by A in the Formula (O).

In some embodiments, in the Formula (Q), $R^{1a}$, $R^{2a}$, and a substituent of five-membered heterocyclic ring represented by $A^a$ can be $C_{1-8}$ alkyl, $C_{1-8}$ alkoxy, halogen, $C_{1-8}$ alkyl substituted with halogen, $C_{1-8}$ alkoxy substituted with halogen, and $C_{2-8}$ acyl. Examples of them are the same as the examples of $R^1$, $R^2$, and the substituent of the five-membered heterocyclic ring represented by A in the Formula (O).

In one embodiment, in the Formula (Q), $R^{3b}$ can be $C_{1-8}$ alkyl. Examples are the same as the examples of $R^5$ in the Formula (O).

In one embodiment, each of $R^1$, $R^2$ in the Formula (O), $R^{1a}$, $R^{2a}$ in the Formula (P), $R^{1b}$ and $R^{2b}$ in the Formula (Q) can be one to three groups attached to the rings, such as benzene ring. The two or three groups can be different from each other.

The compounds having the Formulae (O), (P), and (Q) can be present in the form of a pharmaceutically acceptable salt. Examples of the salt include an alkali metal salt, such as sodium salt, potassium salt and lithium salt.

The compounds having the Formulae (O), (P), and (Q) can also be present in the form of an optical isomer such as enantiomer or racemic body, or a geometrical isomer such as cis or trans. Also provided are isomers of these compounds.

In some embodiments, the compound of Formula (O), (P), or (Q) is a compound shown in Table 8 or pharmaceutically acceptable salt, solvate, ester, amide, or prodrug thereof.

unsubstituted or substituted with $C_{1-8}$ alkyl, 3-7 membered cycloalkyl, $C_{2-8}$ alkenyl, $C_{2-8}$ alkynyl, $C_{1-8}$ alkoxyl, $C_{1-8}$ alkyl group substituted with a 3-7 membered cycloalkyl group, $C_{1-8}$ haloalkyl, $C_{1-8}$ haloalkoxy, $C_{6-10}$ aryl, a 5 or 6-membered heterocyclic group, aralkyl group comprising a $C_{6-10}$ aryl group and a $C_{1-8}$ alkyl group, or $C_{1-8}$ alkyl group substituted with a 5 or 6-membered heterocyclic group;

B is a bond or $C_{1-8}$ alkylene which is unsubstituted or substituted with $C_{1-8}$ alkyl, a 3-7 membered cycloalkyl group, $C_{1-8}$ alkoxy or a halogen, and which may have a double bond or triple bond when the carbon number of the alkylene chain is 2 or more;

D is N or CH;

E is O or S;

each of $R^1$ and $R^2$ is independently H, $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, nitro, $C_{2-8}$ acyl, $C_{6-10}$ aryl, or a 5 or 6-membered heterocyclic group;

TABLE 8

| Structure | Name |
| --- | --- |
| 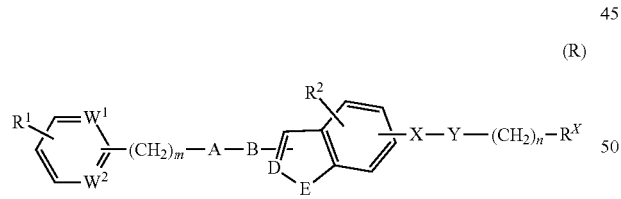 | 1-(4-(3-hydroxypropyl)-3-methylphenyl)-3-(4-isopropyl-2-(4-(trifluoromethyl)phenyl)thiazol-5-yl)propan-1-one |
| 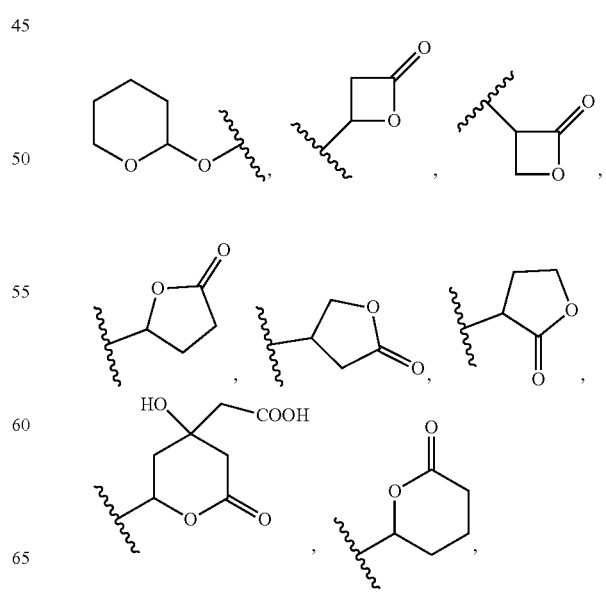 | 1-(4-((2-hydroxyethyl)(methyl)amino)-phenyl)-3-(4-isopropyl-2-(4-(trifluoromethyl)phenyl)thiazol-5-yl)propan-1-one |

5.2.12. Compounds of Formula (R) and (S)

In some embodiments, the compounds of the invention are compounds of Formula (R):

(R)

or a pharmaceutically acceptable salt, solvate, ester, amide, or prodrug thereof, wherein:

each of $W^1$ and $W^2$ is independently CH or N;

X is $NR^3$ or $CR^4R^5$, in which $R^3$ is $C_{1-8}$ alkyl, $C_{1-8}$ haloalkyl, $C_{1-8}$ alkyl substituted with $C_{1-8}$ alkoxy, $C_{1-8}$ alkyl substituted with a 3-7 membered cycloalkyl, $C_{1-8}$ alkyl substituted with a phenyl group, $C_{2-8}$ acyl, or $C_{2-8}$ alkenyl;

each of $R^4$ and $R^5$ is independently hydrogen or $C_{1-8}$ alkyl;

Y is $(CR^6R^7)_r$, in which each of $R^6$ and $R^7$ is independently hydrogen or $C_{1-8}$ alkyl and r is 1, 2, 3, or 4;

A is a 5 or 6-membered heterocyclic group which is thiazole, oxazole, imidazole, pyrazole, thiophene, furan, pyrrole, pyridine or pyrimidine, or a phenyl group, wherein the 5 or 6-membered heterocyclic group or phenyl group is m 0, 1, 2, or 3;

$R^X$ is $CH_2OH$, $COH$, $COOCH_2CONR^{X4}R^{X5}$, $SO_3H$,

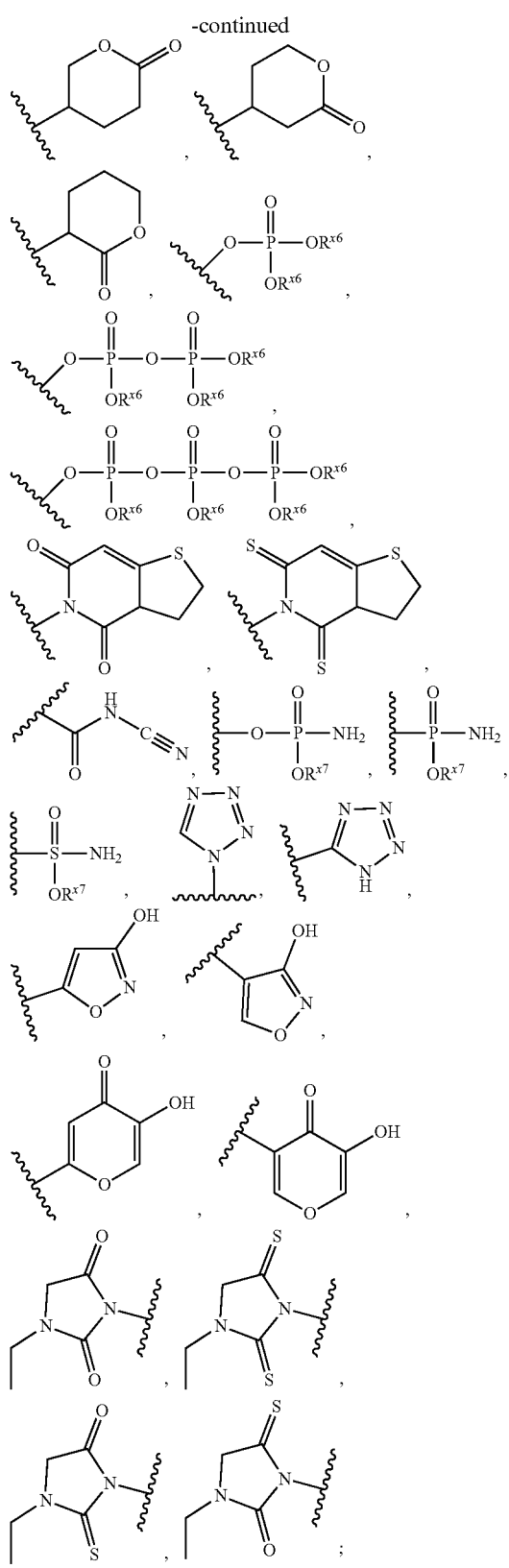

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, the compounds of the invention are compounds of Formula (S):

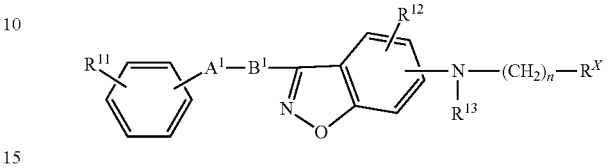

(S)

or a pharmaceutically acceptable salt, solvate, ester, amide, or prodrug thereof, wherein:

$A^1$ is a 5 or 6-membered heterocyclic group which is thiazole, oxazole, pyridine or pyrimidine, or a phenyl group, wherein the 5 or 6-membered heterocyclic group or phenyl group is unsubstituted or substituted with $C_{1-8}$ alkyl or $C_{1-8}$ haloalkyl;

$B^1$ is $C_{2-4}$ alkylene;

each of $R^{11}$ and $R^{12}$ is independently H, $C_{1-8}$ alkyl, halogen, or $C_{1-8}$ haloalkyl;

$R^{13}$ is $C_{1-8}$ alkyl or $C_{1-8}$ haloalkyl, optionally wherein the N to which $R^{13}$ is attached is attached to the 6th position of benzisoxazole;

$R^X$ is $CH_2OH$, $COH$, $COOCH_2CONR^{X4}R^{X5}$, $SO_3H$,

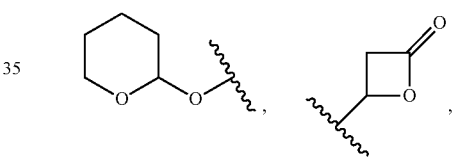

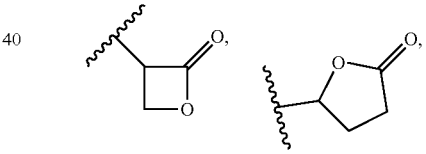

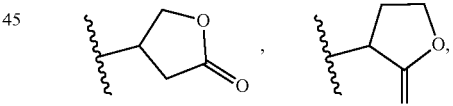

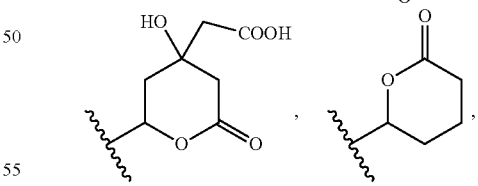

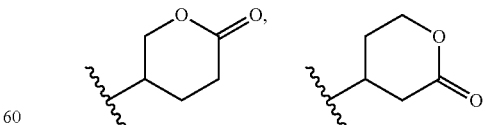

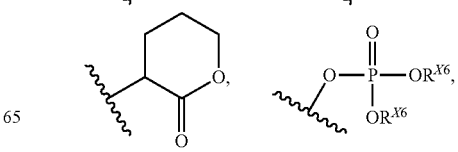

-continued

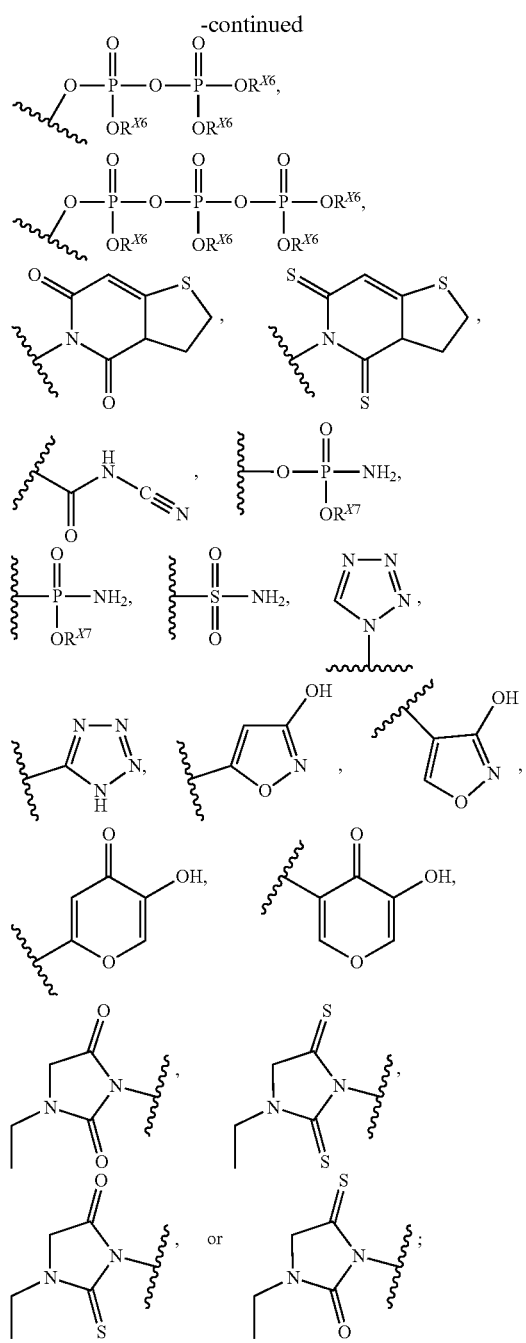

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, of the compounds having the Formula (R), both $W^1$ and $W^2$ are CH.

In some embodiments of the compounds having the Formula (R), X is $CR^4R^5$, $CH_2$, or $NR^3$, and $R^3$ is an alkyl group having 1 to 8 carbon atoms. In another embodiment, $R^3$ is a methyl group.

In some embodiments of the compounds having the Formula (R), Y is $CH_2$.

In some embodiments of the compounds having the Formula (R), Z is a carboxylic group.

In some embodiments of the compounds, having the Formula (R), A is thiazole or oxazole which may have a substituent selected from the group consisting of an alkyl group having 1 to 8 carbon atoms, an alkenyl group having 2 to 8 carbon atoms, an alkynyl group having 2 to 8 carbon atoms, an alkyl group having 1 to 8 carbon atoms and a halogen atom substituent, an aryl group having 6 to 10 carbon atoms or a 5 or 6-membered heterocyclic group; pyrazole which may have a substituent selected from the group consisting of an alkyl group having 1 to 8 carbon atoms, an alkenyl group having 2 to 8 carbon atoms, an alkynyl group having 2 to 8 carbon atoms, an alkyl group having 1 to 8 carbon atoms and a halogen atom substituent, an aryl group having 6 to 10 carbon atoms or a 5 or 6-membered heterocyclic group.

In some embodiments of the compounds having the Formula (R), B is an ethylene chain.

In some embodiments of the compounds having the Formula (R), D is N.

In some embodiments of the compounds having the Formula (R), E is O.

In some embodiments of the compounds having the Formula (R), each of $R^1$ and $R^2$ is independently H, an alkyl group having 1 to 8 carbon atoms, an alkenyl group having 2 to 8 carbon atoms, an alkoxy group having 1 to 8 carbon atoms, a halogen atom, an alkyl group having 1 to 8 carbon atoms and a halogen atom substituent or an alkoxy group having 1 to 8 carbon atoms and a halogen atom substituent.

In some embodiments of the compounds having the Formula (R), m is 0.

In some embodiments of the compounds having the Formula (S), $R^{13}$ is an alkyl group having 1 to 8 carbon atoms. In another embodiment, $R^{13}$ is a methyl group.

In some embodiments of the compounds having the Formula (S), p is 1.

In some embodiments of the compounds having the Formula (S), $A^1$ is thiazole, oxazole or phenyl which may have a substituent selected from the group consisting of an alkyl group having 1 to 8 carbon atoms or an alkyl group having 1 to 8 carbon atoms and a halogen atom substituent. In another embodiment, $A^1$ is thiazole which may have an alkyl group having 1 to 8 carbon atoms as a substituent.

In some embodiments of the compounds having the Formula (S), $B^1$ is an ethylene chain.

In some embodiments of the compounds having the Formula (S), $R^{11}$ is an alkyl group having 1 to 8 carbon atoms, a halogen atom or an alkyl group having 1 to 8 carbon atoms and a halogen atom substituent.

In some embodiments of the compounds having the Formula (S), $R^{12}$ is H, an alkyl group having 1 to 8 carbon atoms or an alkyl group having 1 to 8 carbon atoms and a halogen atom substituent.

The compounds having the Formulae (R) and (S) can also be present in the form of an optical isomer such as enantiomer or racemic body, or a geometrical isomer such as cis or trans. Also provided are isomers of these compounds.

The compounds having the Formulae (R) and (S) can be present in the form of a pharmaceutically acceptable salt. Examples of the salt include an alkali metal salt, such as sodium salt, potassium salt and lithium salt.

In some embodiments, the compound of Formula (R) or (S) is a compound shown in Table 9 or pharmaceutically acceptable salt, solvate, ester, amide, or prodrug thereof.

TABLE 9

| Structure | Name |
|---|---|
| 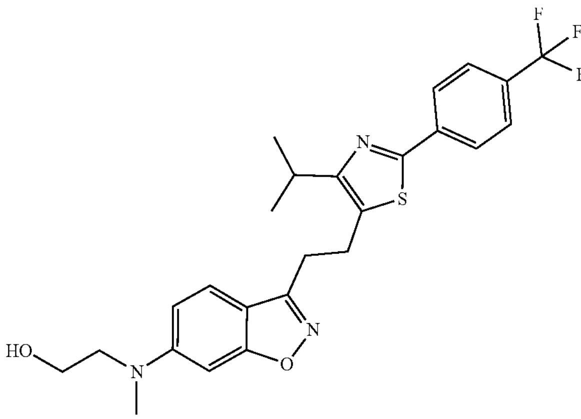 [SMILES: CC(C)c1nc(-c2ccc(C(F)(F)F)cc2)sc1CCc1noc2cc(N(C)CCO)ccc12] | 2-((3-(2-(4-isopropyl-2-(4-(trifluoromethyl)phenyl)thiazol-5-yl)ethyl)benzo[d]isoxazol-6-yl)(methyl)amino)ethan-1-ol |
| 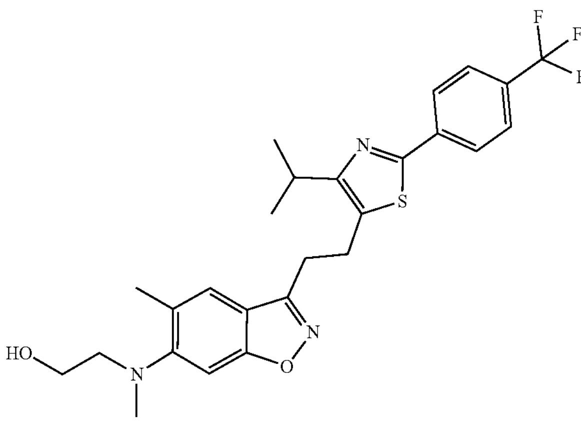 [SMILES: Cc1cc2c(CCc3sc(-c4ccc(C(F)(F)F)cc4)nc3C(C)C)noc2cc1N(C)CCO] | 2-((3-(2-(4-isopropyl-2-(4-(trifluoromethyl)phenyl)thiazol-5-yl)ethyl)-5-methylbenzo[d]isoxazol-6-yl)(methyl)amino)ethan-1-ol |

5.2.13. Compounds of Formula (T)

In some embodiments, the compounds of the invention are compounds of Formula (T):

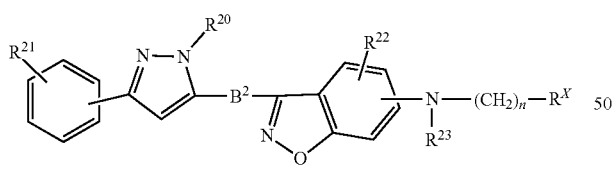

(T)

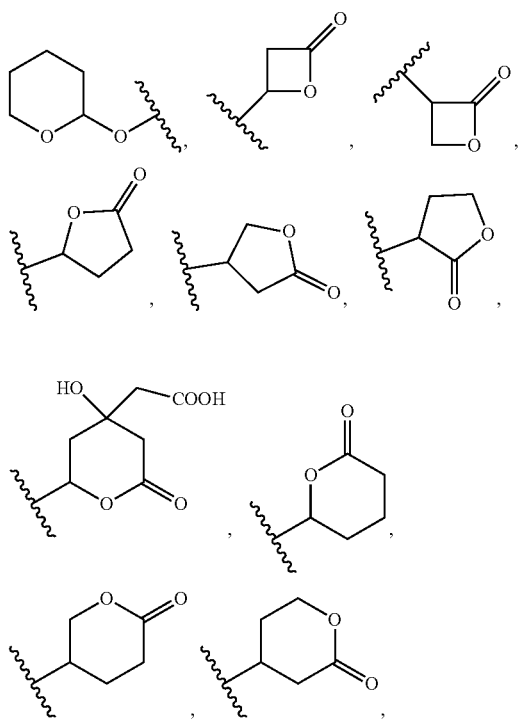

or a pharmaceutically acceptable salt, solvate, ester, amide, or prodrug thereof, wherein:

$B^2$ is $C_{2-4}$ alkylene;

$R^{20}$ is $C_{1-8}$ alkyl;

each of $R^{21}$ and $R^{22}$ is independently H, $C_{1-8}$ alkyl, halogen, or $C_{1-8}$ haloalkyl;

$R^{23}$ is $C_{1-8}$ alkyl or $C_{1-8}$ haloalkyl, optionally wherein the N to which $R^{23}$ is attached is attached to the 6th position of benzisoxazole;

$R^X$ is $CH_2OH$, COH, $COOCH_2CONR^{X4}R^{X5}$, $SO_3H$,

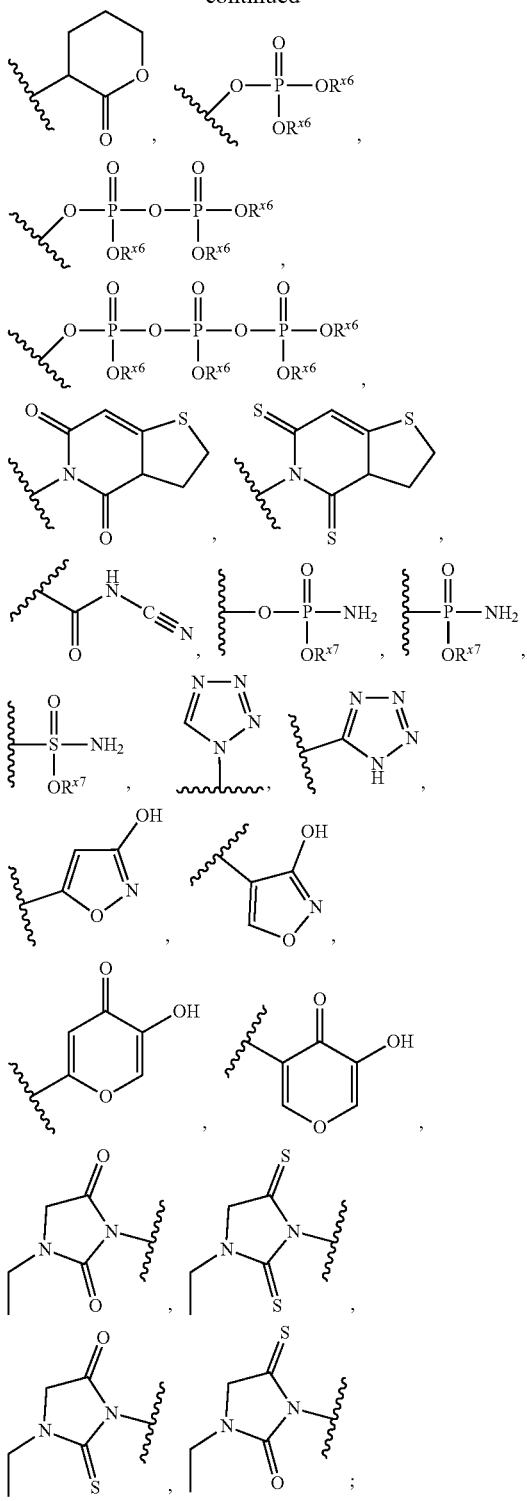

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

In some embodiments, $R^{23}$ is an alkyl group having 1 to 8 carbon atoms or an alkyl group having 1 to 8 carbon atoms and a halogen atom substituent. In another embodiment, $R^{23}$ is a methyl group.

In some embodiments, n is an integer of 1 to 4. In some embodiments, n is 1.

In some embodiments, $R^{20}$ is an alkyl group having 1 to 8 carbon atoms. In another embodiment, $R^{20}$ is methyl.

In some embodiments, $B^2$ is an alkylene chain having 2 to 4 carbon atoms. In another embodiment, $B^2$ is an ethylene chain.

In some embodiments, each of $R^{21}$ and $R^{22}$ is independently H, an alkyl group having 1 to 8 carbon atoms, a halogen atom, an alkyl group having 1 to 8 carbon atoms and a halogen atom substituent. In another embodiment, $R^{21}$ is an alkyl group having 1 to 8 carbon atoms, a halogen atom or an alkyl group having 1 to 8 carbon atoms and a halogen atom substituent. In yet another embodiment, $R^{22}$ is H, an alkyl group having 1 to 8 carbon atoms or an alkyl group having 1 to 8 carbon atoms and a halogen atom substituent.

In some embodiments, $N(R^{23})((CH_2)_n—R^x)$ is attached to the 6th position of benzisoxazole.

The compounds having the Formula (T) can also be present in the form of an optical isomer such as enantiomer or racemic body, or a geometrical isomer such as cis or trans. Also provided are isomers of these compounds.

The compounds having the Formula (T) can be present in the form of a pharmaceutically acceptable salt. Examples of the salt include an alkali metal salt, such as sodium salt, potassium salt and lithium salt.

5.2.14. Compounds of Formula (U)

In some embodiments, the compounds of the invention are compounds of Formula (U):

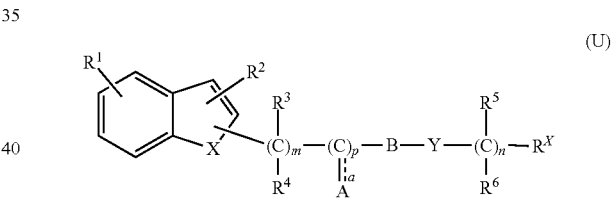

or a pharmaceutically acceptable salt, solvate, ester, amide, or prodrug thereof, wherein:

$R^1$ is hydrogen, halogen, hydroxyl, nitro, amino, cyano, carboxyl, $C_{1-8}$ alkyl, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_{6-10}$ aryl moiety and a $C_{1-8}$ alkylene moiety, or a $C_{1-8}$ alkyl group having a 5- or 6-membered heterocyclic substituent;

$R^2$ is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety;

each of $R^3$, $R^4$, $R^5$ and $R^6$ independently is hydrogen, $C_{1-8}$ alkyl, or $C_{1-8}$ haloalkyl;

X is oxygen, sulfur or $NR^7$; where $R^7$ is hydrogen, $C_{1-8}$ alkyl, $C_{1-8}$ haloalkyl, an aralkyl group having a $C_{6-10}$ aryl moiety and a $C_{1-8}$ alkylene moiety, $C_{2-8}$ acyl, or $C_{2-8}$ alkenyl;

Y is oxygen, sulfur, $NR^8$ or a bond, where $R^8$ is hydrogen, $C_{1-8}$ alkyl, $C_{1-8}$ haloalkyl, $C_{2-8}$ acyl, or $C_{2-8}$ alkenyl;

p is 0 or 1;

A, when bond a is present, is oxygen $CH_2$, N—$NH_2$ or N—$OR^9$, where $R^9$ is hydrogen, $C_{1-8}$ alkyl, $C_{1-8}$ haloalkyl, $C_{2-8}$ acyl, $C_{2-8}$ alkenyl, or an aralkyl group having a $C_{6-10}$ aryl moiety and a $C_{1-8}$ alkylene moiety; A, when bond a is absent, is OH;

B is, in the case of p=1, a benzene ring having or not having a substituent which is halogen, hydroxyl, nitro, amino, $C_{1-8}$ alkyl, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, or an aralkyl group having a $C_{6-10}$ aryl moiety and a $C_1$-$C_8$ alkylene moiety of 1-8 carbon atoms, and, in the case of p=0, a condensed ring which is indole, benzofuran, benzisoxazole or 1,2-benzisothiazole, in which said condensed ring has or does not have a substituent which is halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_1$-$C_8$ alkoxy substituent, $C_{1-8}$ haloalkoxy group, $C_{2-8}$ acyl, $C_{6-10}$ aryl, or an aralkyl group having a $C_{6-10}$ aryl moiety and a $C_{1-8}$ alkylene moiety;

Y is bonded to the benzene ring of B;

$(C(R^3)(R^4))_m$ is bonded to the condensed ring of B at its 3-position;

m is an integer of 1 to 4;

n is 0, 1, 2, 3, 4, or 5;

Y is a bond in the case of n=0;

$R^X$ is $CH_2OH$, COH, $COOCH_2CONR^{X4}R^{X5}$, $SO_3H$,

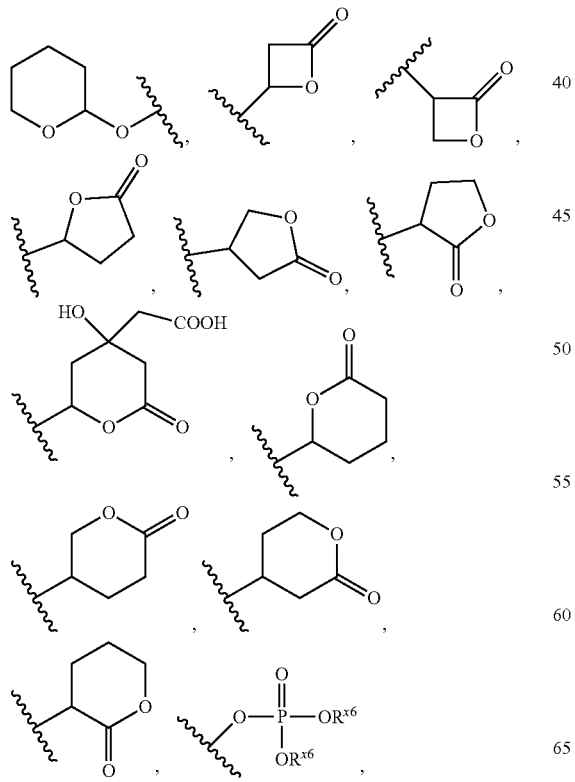

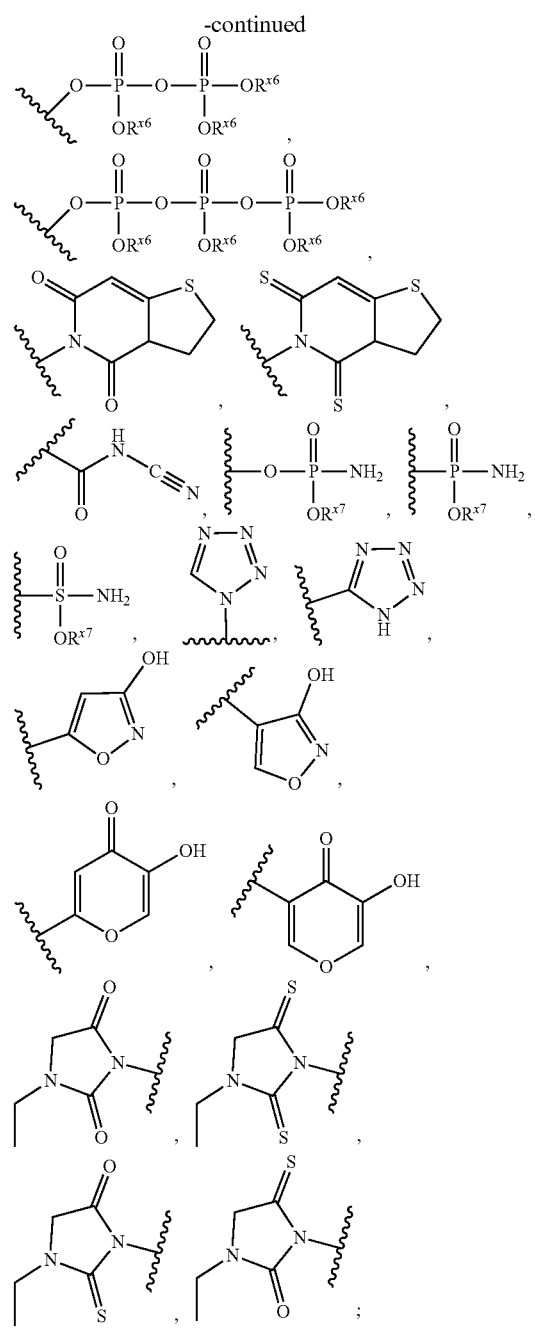

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl.

In some embodiments, $R^1$ represents hydrogen, halogen, hydroxyl, nitro, amino, cyano, carboxyl, an alkyl group having 1-8 carbon atoms, a 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and an alkoxy substituent having 1-8 carbon atoms, an alkoxy group having 1-8 carbon atoms and having a halogen substituent, an acyl group having 2-8 carbon atoms, an aryl group having 6-10 carbon atoms, a 5- or 6-membered heterocyclic group, an aralkyl group having an aryl moiety of 6-10 carbon atoms and an alkylene moiety of 1-8 carbon atoms, or an alkyl group having 1-8 carbon atoms and a 5- or 6-membered heterocyclic substituent.

In some embodiments, $R^2$ represents hydrogen, an alkyl group having 1-8 carbon atoms, an alkenyl group having 2-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and having an alkoxy substituent having 1-8 carbon atoms, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, each of $R^3$, $R^4$, $R^5$ and $R^6$ independently represents hydrogen, an alkyl group having 1-8 carbon atoms, or an alkyl group having 1-8 carbon atoms and having a halogen substituent.

In some embodiments, X is oxygen, sulfur or $NR^7$, $R^7$ representing hydrogen, an alkyl group having 1-8 carbon atoms, an alkyl group having 1-8 carbon atoms and having a halogen substituent, an aralkyl group having an aryl moiety of 6-10 carbon atoms and an alkylene moiety of 1-8 carbon atoms, an acyl group having 2-8 carbon atoms, or an alkenyl group having 2-8 carbon atoms.

In some embodiments, Y is oxygen, sulfur, NR or a bond, $R^8$ representing hydrogen, an alkyl group having 1-8 carbon atoms, an alkyl group having 1-8 carbon atoms and having a halogen substituent, an acyl group having 2-8 carbon atoms, or an alkenyl group having 2-8 carbon atoms.

In some embodiments, p is 0 or 1.

In some embodiments, A is oxygen, $CH_2$, $N-NH_2$ or $N-OR^9$, $R^9$ representing hydrogen, an alkyl group having 1-8 carbon atoms, an alkyl group having 1-8 carbon atoms and having a halogen substituent, an acyl group having 2-8 carbon atoms, an alkenyl group having 2-8 carbon atoms, or an aralkyl group having an aryl moiety of 6-10 carbon atoms and an alkylene moiety of 1-8 carbon atoms.

In some embodiments, B represents, in the case of p=1, a benzene ring having or not having a substituent selected from the group consisting of halogen, hydroxyl, nitro, amino, an alkyl group having 1-8 carbon atoms, 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and having an alkoxy substituent having 1-8 carbon atoms, an alkoxy group having 1-8 carbon atoms and having a halogen substituent, an acyl group having 2-8 carbon atoms, an aryl group having 6-10 carbon atoms, or an aralkyl group having an aryl moiety of 6-10 carbon atoms and an alkylene moiety of 1-8 carbon atoms, and, in the case of p=0, a condensed ring selected from the group consisting of indole, benzofuran, benz-isoxazole and 1,2-benzisothiazole, in which said condensed ring has or does not have a substituent selected from the group consisting of halogen, hydroxyl, nitro, amino, an alkyl group having 1-8 carbon atoms, 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and having an alkoxy substituent having 1-8 carbon atoms, an alkoxy group having 1-8 carbon atoms and having a halogen substituent, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, Y is bonded to the benzene ring of B.

In some embodiments, $-(C(R^3)(R^4))_m-$ is bonded to the condensed ring of B at its 3-position.

In some embodiments, m is an integer of 1 to 4.

In some embodiments, n is an integer of 0 to 5.

In some embodiments, Y is a bond in the case of n=0.

The compounds having the Formula (U) can also be present in the form of an optical isomer such as enantiomer or racemic body, or a geometrical isomer such as cis or trans. Also provided are isomers of these compounds.

The compounds having the Formula (U) can be present in the form of a pharmaceutically acceptable salt. Examples of the salt include an alkali metal salt, such as sodium salt, potassium salt and lithium salt.

5.2.15. Compounds of Formula (V)

In some embodiments, the compounds of the invention are compounds of Formula (V):

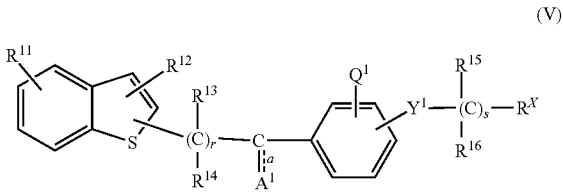

(V)

or a pharmaceutically acceptable salt, solvate, ester, amide, or prodrug thereof, wherein:

$R^{11}$ is hydrogen, halogen, hydroxyl, nitro, amino, cyano, carboxyl, $C_{1-8}$ alkyl, $C_{3-7}$ cycloalkyl, $C_2$-$C_8$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_{6-10}$ aryl moiety and a $C_{1-8}$ alkylene moiety, or a $C_{1-8}$ alkyl group having a 5- or 6-membered heterocyclic substituent;

$R^{12}$ is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety; each of $R^{13}$, $R^{14}$, $R^{15}$ and $R^{1-6}$ independently is hydrogen, $C_{1-8}$ alkyl, or $C_{1-8}$ haloalkyl;

$Y^1$ is oxygen, sulfur, $NR^{18}$ or a bond, where $R^{18}$ is hydrogen, $C_{1-8}$ alkyl, $C_{1-8}$ haloalkyl, $C_{2-8}$ acyl, or $C_{2-8}$ alkenyl;

$A^1$, when bond a is present, is oxygen $CH_2$, $N-NH_2$ or $N-OR^{19}$, where $R^{19}$ is hydrogen, $C_{1-8}$ alkyl, $C_{1-8}$ haloalkyl, $C_{2-8}$ acyl, $C_{2-8}$ alkenyl, or an aralkyl group having a $C_{6-10}$ aryl moiety and a $C_{1-8}$ alkylene moiety; $A^1$, when bond a is absent, is OH;

$Q^1$ is hydrogen, halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl, or an aralkyl group having a $C_{6-10}$ aryl moiety and a $C_{1-8}$ alkylene moiety;

r is 1, 2, 3, or 4;

s is 1, 2, 3, 4, or 5;

$R^X$ is $CH_2OH$, $COH$, $COOCH_2CONR^{X4}R^{X5}$, $SO_3H$,

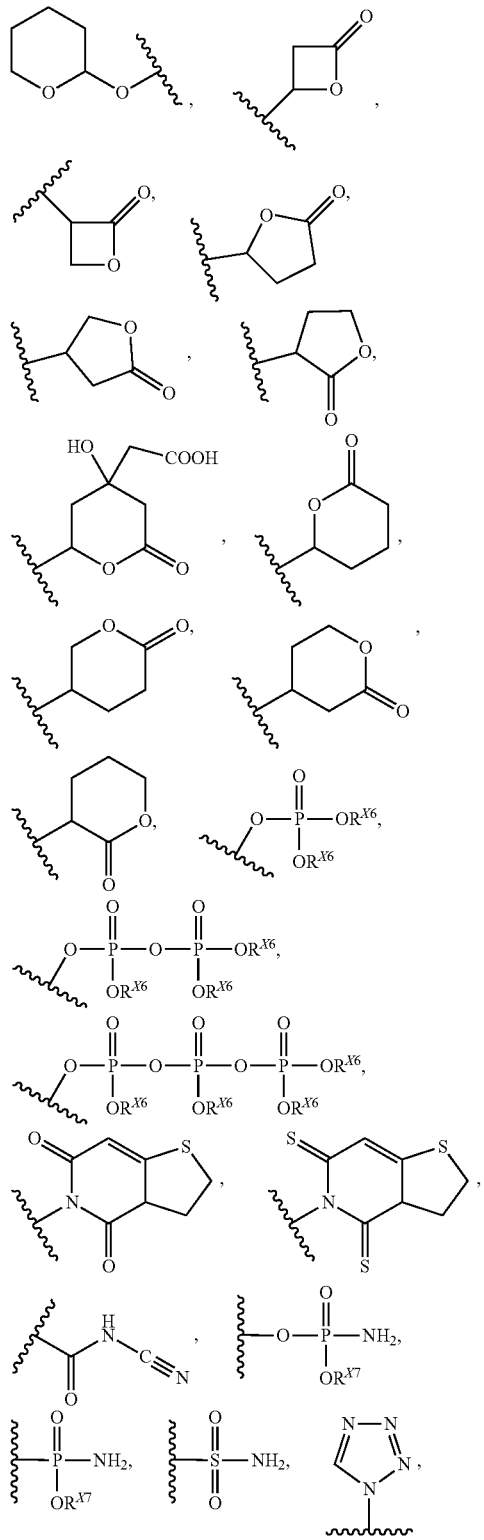

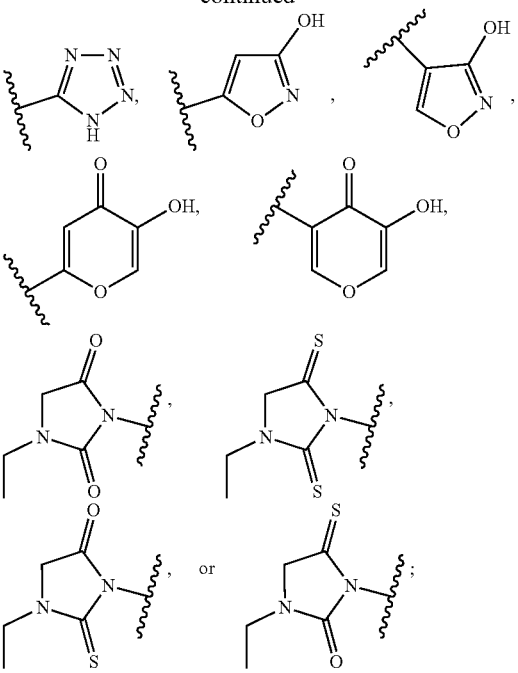

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl.

In some embodiments, $R^{11}$ represents hydrogen, halogen, hydroxyl, nitro, amino, cyano, carboxyl, an alkyl group having 1-8 carbon atoms, a 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and an alkoxy substituent having 1-8 carbon atoms, an alkoxy group having 1-8 carbon atoms and having a halogen substituent, an acyl group having 2-8 carbon atoms, an aryl group having 6-10 carbon atoms, a 5- or 6-membered heterocyclic group, an aralkyl group having an aryl moiety of 6-10 carbon atoms and an alkylene moiety of 1-8 carbon atoms, or an alkyl group having 1-8 carbon atoms and a 5- or 6-membered heterocyclic substituent.

In some embodiments, $R^{12}$ represents hydrogen, an alkyl group having 1-8 carbon atoms, an alkenyl group having 2-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and having an alkoxy substituent having 1-8 carbon atoms, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, each of $R^{13}$, $R^{14}$, $R^{15}$ and $R^{16}$ independently represents hydrogen, an alkyl group having 1-8 carbon atoms, or an alkyl group having 1-8 carbon atoms and having a halogen substituent.

In some embodiments, Y¹ is oxygen, sulfur, NR¹⁸ or a bond, R¹⁸ representing hydrogen, an alkyl group having 1-8 carbon atoms, an alkyl group having 1-8 carbon atoms and having a halogen substituent, an acyl group having 2-8 carbon atoms, or an alkenyl group having 2-8 carbon atoms.

the salt include an alkali metal salt, such as sodium salt, potassium salt and lithium salt.

In some embodiments, the compound of Formula (V) is a compound shown in Table 10 or pharmaceutically acceptable salt, solvate, ester, amide, or prodrug thereof.

TABLE 10

| Structure | Name |
|---|---|
|  | OH1-(4-(3-hydroxypropyl)-3-methylphenyl)-3-(3-isopropyl-6-(trifluoromethyl)benzo[b]thiophen-2-yl)propan-1-one |
|  | OH1-(4-(3-hydroxypropyl)-3-methylphenyl)-3-(3-isopropyl-6-(trifluoromethyl)benzo[b]thiophen-2-yl)propan-1-ol |

In some embodiments, A¹ is oxygen CH₂, N—NH₂ or N—OR¹⁹, R¹⁹ representing hydrogen, an alkyl group having 1-8 carbon atoms, an alkyl group having 1-8 carbon atoms and having a halogen substituent, an acyl group having 2-8 carbon atoms, an alkenyl group having 2-8 carbon atoms, or an aralkyl group having an aryl moiety of 6-10 carbon atoms and an alkylene moiety of 1-8 carbon atoms.

In some embodiments, Q¹ represents hydrogen, halogen, hydroxyl, nitro, amino, an alkyl group having 1-8 carbon atoms, a 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and an alkoxy substituent having 1-8 carbon atoms, an alkoxy group having 1-8 carbon atoms and having a halogen substituent, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, r is an integer of 1 to 4.

In some embodiments, s is an integer of 1 to 5.

The compounds having the Formula (V) can also be present in the form of an optical isomer such as enantiomer or racemic body, or a geometrical isomer such as cis or trans. Also provided are isomers of these compounds.

The compounds having the Formula (V) can be present in the form of a pharmaceutically acceptable salt. Examples of 5.2.16. Compounds of Formula (W)

In some embodiments, the compounds of the invention are compounds of Formula (W):

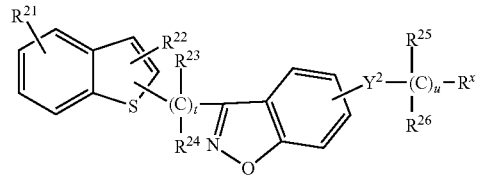

or a pharmaceutically acceptable salt, solvate, ester, amide, or prodrug thereof, wherein:

R²¹ is hydrogen, halogen, hydroxyl, nitro, amino, cyano, carboxyl, $C_{1-8}$ alkyl, $C_{3-7}$ cycloalkyl, C2-C8 alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_{6-10}$ aryl moiety and a $C_{1-8}$ alkylene moiety, or a $C_{1-8}$ alkyl group having a 5- or 6-membered heterocyclic substituent;

R²² is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety;

each of $R^{23}$, $R^{24}$, $R^{25}$ and $R^{26}$ independently is hydrogen, $C_{1-8}$ alkyl, or $C_{1-8}$ haloalkyl;

$Y^2$ is oxygen, sulfur, $NR^{28}$ or a bond, where $R^{28}$ is hydrogen, $C_{1-8}$ alkyl, $C_{1-8}$ haloalkyl, $C_{2-8}$ acyl, or $C_{2-8}$ alkenyl;

$Q^2$ is hydrogen, halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl, or an aralkyl group having a $C_{6-10}$ aryl moiety and a $C_{1-8}$ alkylene moiety;

t is 1, 2, 3, or 4;

u is 1, 2, 3, 4, or 5;

$R^X$ is $CH_2OH$, $COH$, $COOCH_2CONR^{X4}R^{X5}$, $SO_3H$,

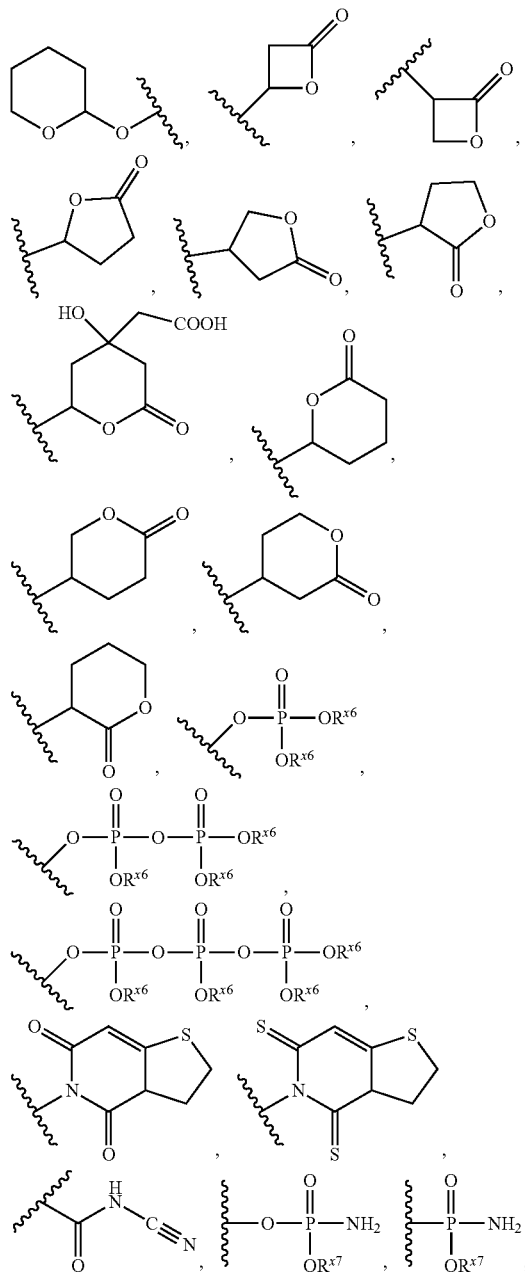

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl.

In some embodiments, $R^{21}$ represents hydrogen, halogen, hydroxyl, nitro, amino, cyano, carboxyl, an alkyl group having 1-8 carbon atoms, a 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and an alkoxy substituent having 1-8 carbon atoms, an alkoxy group having 1-8 carbon atoms and having a halogen substituent, an acyl group having 2-8 carbon atoms, an aryl group having 6-10 carbon atoms, a 5- or 6-membered heterocyclic group, an aralkyl group having an aryl moiety of 6-10 carbon atoms and an alkylene moiety of 1-8 carbon atoms, or an alkyl group having 1-8 carbon atoms and a 5- or 6-membered heterocyclic substituent.

In some embodiments, $R^{22}$ represents hydrogen, an alkyl group having 1-8 carbon atoms, an alkenyl group having 2-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and having an alkoxy substituent having 1-8 carbon atoms, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, each of $R^{23}$, $R^{24}$, $R^{25}$ and $R^{26}$ independently represents hydrogen, an alkyl group having 1-8 carbon atoms, or an alkyl group having 1-8 carbon atoms and having a halogen substituent.

In some embodiments, $Y^2$ is oxygen, sulfur, $NR^{28}$ or a bond, $R^{28}$ representing hydrogen, an alkyl group having 1-8 carbon atoms, an alkyl group having 1-8 carbon atoms and having a halogen substituent, an acyl group having 2-8 carbon atoms, or an alkenyl group having 2-8 carbon atoms.

In some embodiments, $Q^2$ represents hydrogen, halogen, hydroxyl, nitro, amino, an alkyl group having 1-8 carbon atoms, a 3- to 7-membered cycloalkyl group, an alkenyl group having 2-8 carbon atoms, an alkynyl group having 2-8 carbon atoms, an alkoxy group having 1-8 carbon atoms, an alkyl group having 1-8 carbon atoms and having a 3- to 7-membered cycloalkyl substituent, an alkyl group having 1-8 carbon atoms and having a halogen substituent, an alkyl group having 1-8 carbon atoms and an alkoxy substituent having 1-8 carbon atoms, an alkoxy group having 1-8 carbon atoms and having a halogen substituent, an acyl group having 2-8 carbon atoms, an aryl group having 6-10 carbon atoms, or an aralkyl group having an aryl moiety of 6-10 carbon atoms and an alkylene moiety of 1-8 carbon atoms.

In some embodiments, t is an integer of 1 to 4.

In some embodiments, u is an integer of 1 to 5.

The compounds having the Formula (W) can also be present in the form of an optical isomer such as enantiomer or racemic body, or a geometrical isomer such as cis or trans. Also provided are isomers of these compounds.

The compounds having the Formula (W) can be present in the form of a pharmaceutically acceptable salt. Examples of the salt include an alkali metal salt, such as sodium salt, potassium salt and lithium salt.

In some embodiments, the compound of Formula (W) is a compound shown in Table 11 or pharmaceutically acceptable salt, solvate, ester, amide, or prodrug thereof.

TABLE 11

| Structure | Name |
| --- | --- |
| 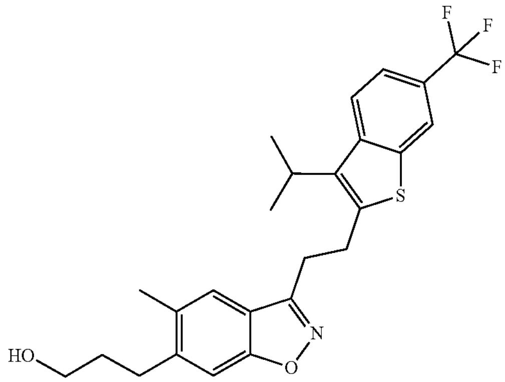 [SMILES: Cc1cc2c(CCc3sc4cc(C(F)(F)F)ccc4c3C(C)C)noc2cc1CCCO] | 3-(3-(2-(3-isopropyl-6-(trifluoromethyl)benzo[b]thiophen-2-yl)ethyl)-5-methylbenzo[d]isoxazol-6-yl)propan-1-ol |
| 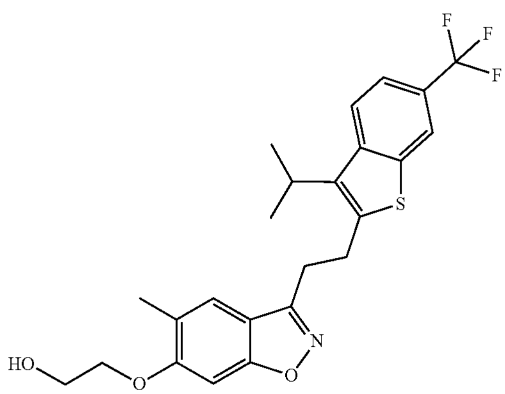 [SMILES: Cc1cc2c(CCc3sc4cc(C(F)(F)F)ccc4c3C(C)C)noc2cc1OCCO] | 2-((3-(2-(3-isopropyl-6-(trifluoromethyl)benzo[b]thiophen-2-yl)ethyl)-5-methylbenzo[d]isoxazol-6-yl)oxy)ethan-1-ol |

5.2.17. Compounds of Formula (X)

In some embodiments, the compounds of the invention are compounds of Formula (X):

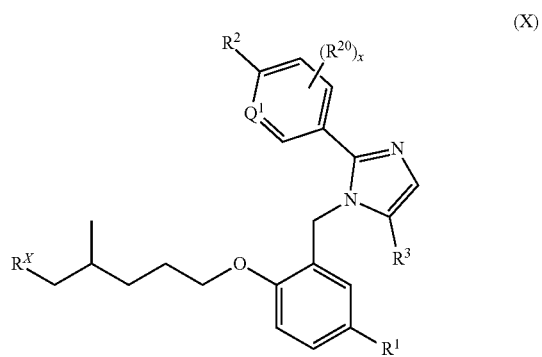

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, $S(C_{1-4}$ alkyl), $SO_2(C_{1-4}$-alkyl), 5- or 6-membered heterocycle, aryl, 5-membered heteroaryl, $C\equiv C-R^{2A}$, $O(CH_2)_mR^{2B}$, $NH(C_{1-4}$ alkyl), $N(C_{1-4}$ alkyl)$_2$, or $C(O)(C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

$R^{2A}$ and $R^{2B}$ are each independently $C_{1-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CD_3$;

$R^X$ is $CH_2OH$, $COH$, $COOCH_2CONR^{X4}R^{X5}$, $SO_3H$,

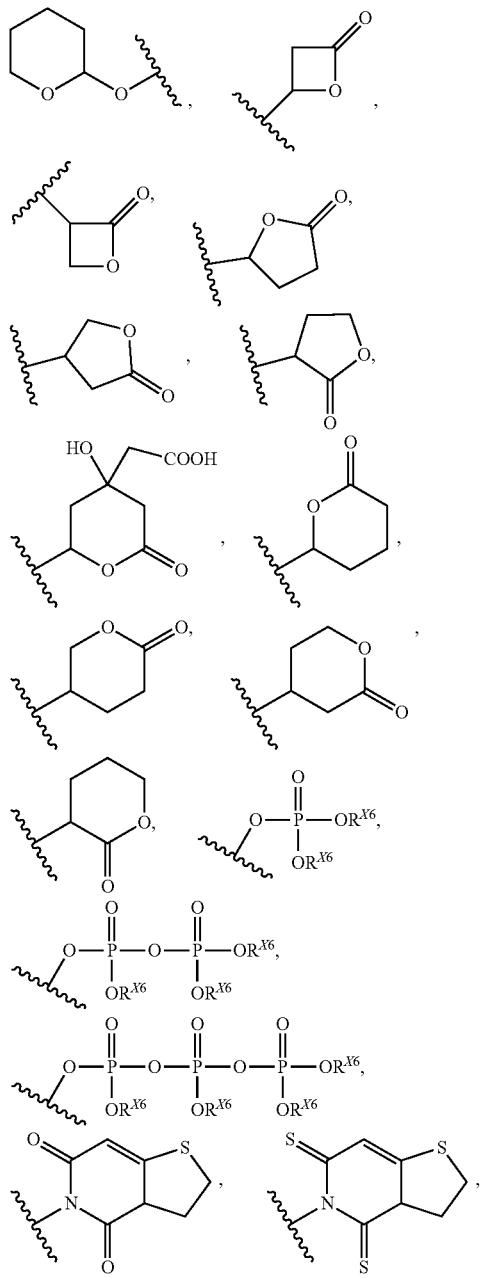

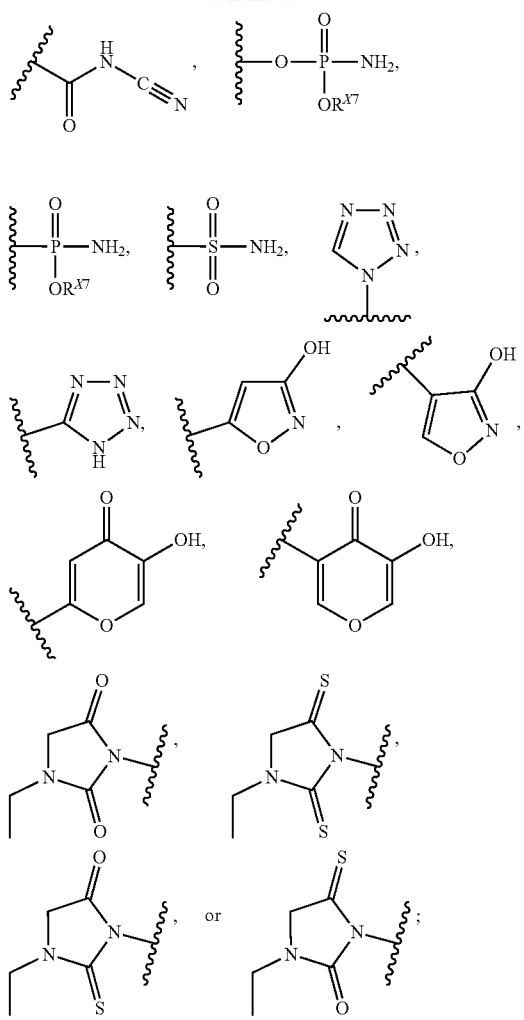

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

In some embodiments, the compound is

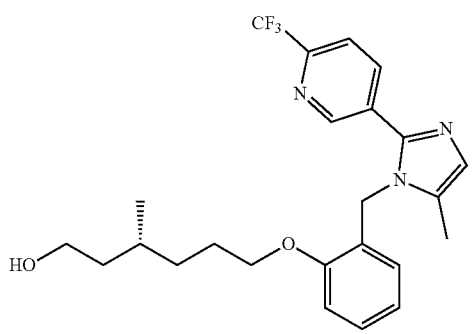 [SMILES: Cc1cnc(-c2ccc(C(F)(F)F)nc2)n1Cc1ccccc1OCCC[C@@H](C)CCO]

("Compound VI"), or pharmaceutically acceptable salt, solvate, ester, amide, or prodrug thereof.

5.2.18. Compounds of Formula (Y)

In some embodiments, the compounds of the invention are compounds of Formula (Y):

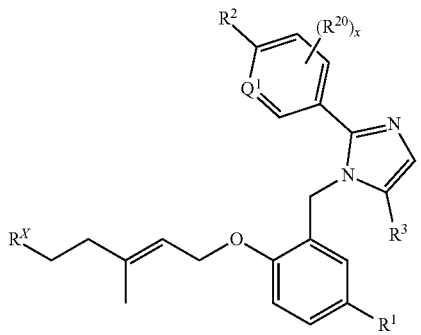

(Y)

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, $S(C_{1-4}$ alkyl), $SO_2(C_{1-4}$-alkyl), 5- or 6-membered heterocycle, aryl, 5-membered heteroaryl, C≡C—$R^{2A}$, $O(CH_2)_m R^{2B}$, $NH(C_{1-4}$ alkyl), $N(C_{1-4}$ alkyl)$_2$, or $C(O)(C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

$R^{2A}$ and $R^{2B}$ are each independently $C_{1-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CO_3$;

$R^X$ is $CH_2OH$, COH, $COOCH_2CONR^{X4}R^{X5}$, $SO_3H$,

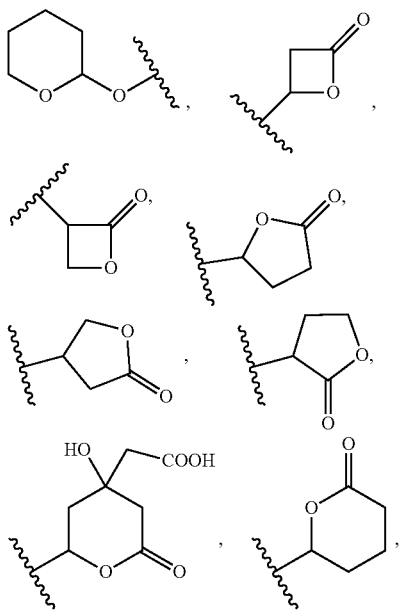

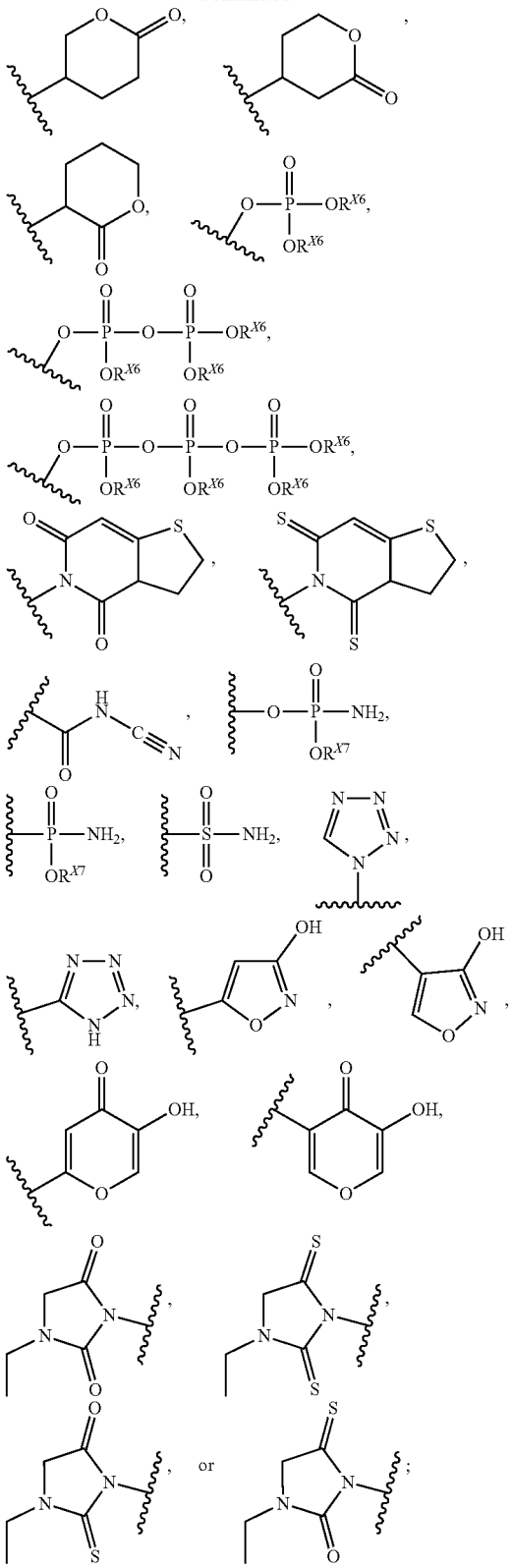

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

5.2.19. Compounds of Formula (Z)

In some embodiments, the compounds of the invention are compounds of Formula (Z):

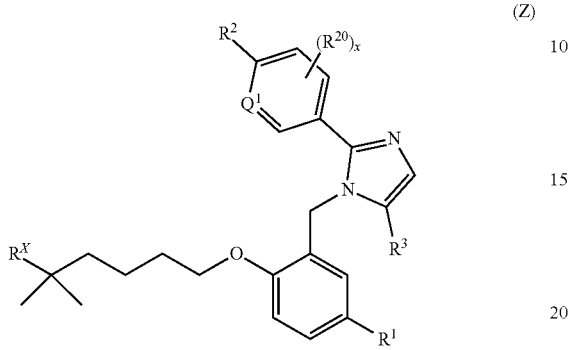

(Z)

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, $S(C_{1-4}$ alkyl), $SO_2(C_{1-4}$-alkyl), 5- or 6-membered heterocycle, aryl, 5-membered heteroaryl, C≡C—$R^{2A}$, $O(CH_2)_m R^{2B}$, $NH(C_{1-4}$ alkyl), $N(C_{1-4}$ alkyl)$_2$, or $C(O)(C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

$R^{2A}$ and $R^{2B}$ are each independently $C_{1-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CD_3$;

$R^X$ is $CH_2OH$, COH, $COOCH_2CONR^{X4}R^{X5}$, $SO_3H$,

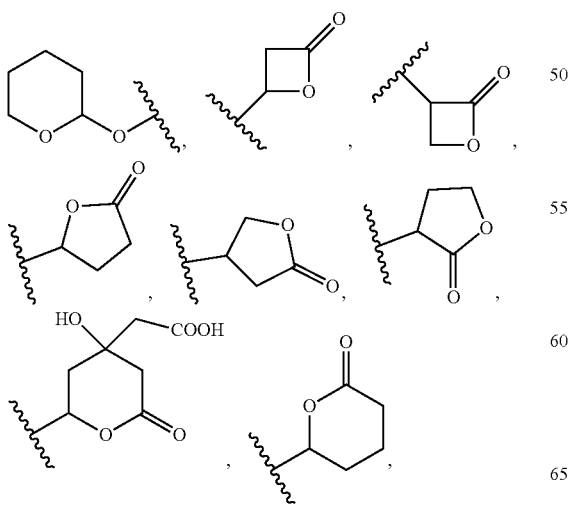

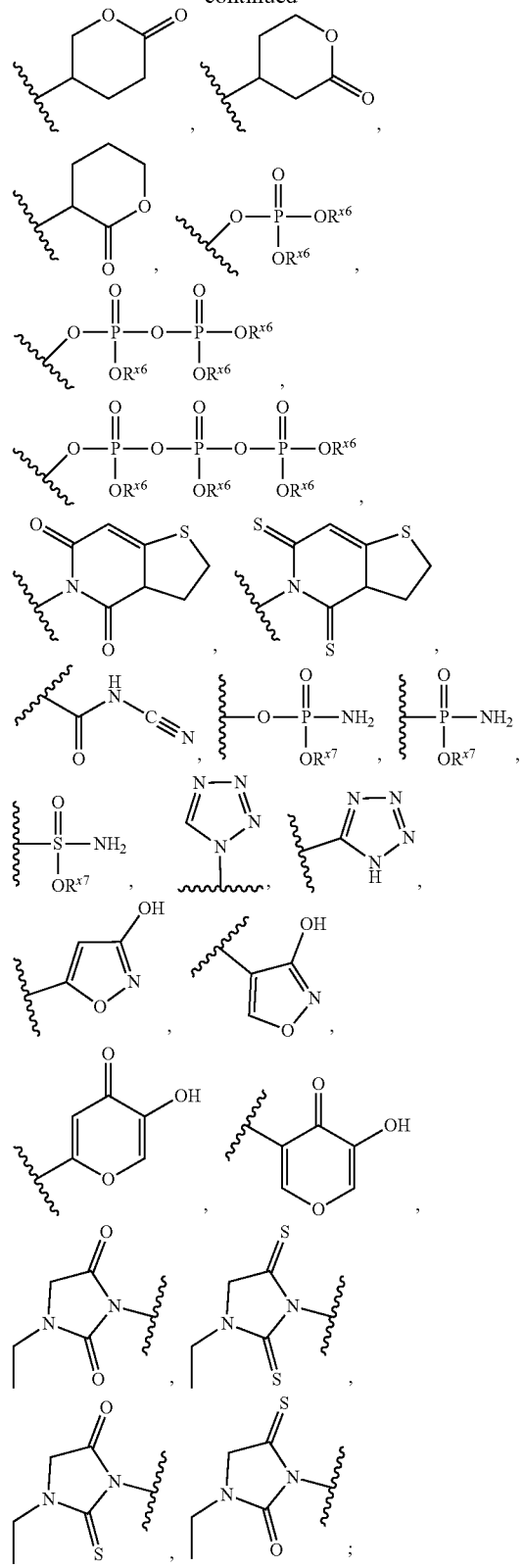

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

5.2.20. Compounds of Formula (AA)

In some embodiments, the compounds of the invention are compounds of Formula (AA):

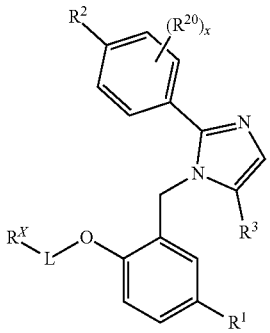

(AA)

or a pharmaceutically acceptable salt, solvate, ester, amide, or prodrug thereof, wherein:

L is $(CH_2)_5$, which is unsubstituted or substituted by one methyl group;

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, $S(C_{1-4}$ alkyl), $SO_2(C_{1-4}$-alkyl), 5- or 6-membered heterocycle, aryl, 5-membered heteroaryl, $C\equiv C—R^{2A}$, $O(CH_2)_mR^{2B}$, $NH(C_{1-4}$ alkyl), $N(C_{1-4}$ alkyl)$_2$, or $C(O)(C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 0 or 1;

$R^{2A}$ and $R^{2B}$ are each independently $C_{1-4}$ alkyl, $C_{1-4}$ haloalkyl, or $C_{3-6}$ cycloalkyl;

$R^3$ is $C_{1-4}$ haloalkyl, $NO_2$, CN, halogen, or $C(O)O(C_{1-4}$ alkyl);

$R^{20}$ is hydrogen, halogen, $C_{1-4}$ alkyl, CN, or $C_{1-4}$ alkoxy;

$R^X$ is $CH_2OH$, COH, $COOCH_2CONR^{X4}R^{X5}$, $SO_3H$,

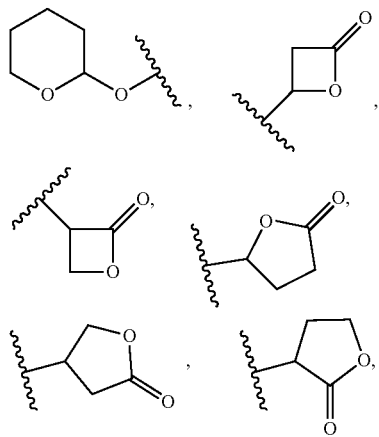

-continued

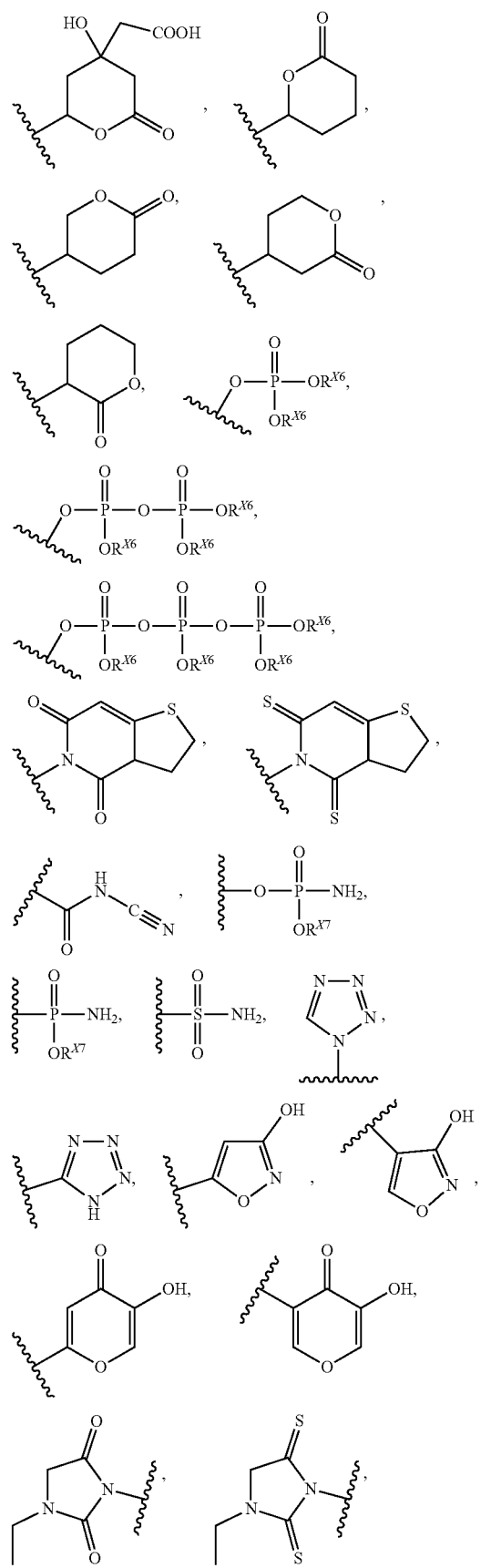

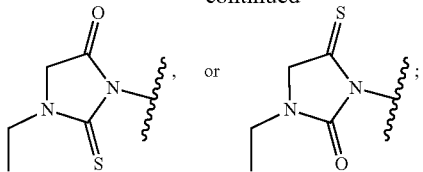

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

5.2.21. Additional Compounds

In some embodiments, the compound of the invention is

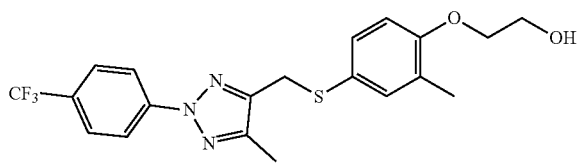 [SMILES: Cc1cc(SCc2nn(-c3ccc(C(F)(F)F)cc3)nc2C)ccc1OCCO]

("Compound VII") or a pharmaceutically acceptable salt, solvate, ester, amide, or prodrug thereof.

In some embodiments, the compound of the invention is

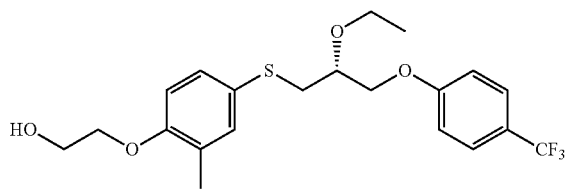 [SMILES: CCO[C@H](COc1ccc(C(F)(F)F)cc1)CSc1ccc(OCCO)c(C)c1]

("Compound VIII") or a pharmaceutically acceptable salt, solvate, ester, amide, or prodrug thereof.

5.3. Compositions of the Invention

In some embodiments, the compositions of the invention comprise (i) an effective amount of a compound of the invention and (ii) a pharmaceutically acceptable carrier or vehicle.

In some embodiments, the compositions of the invention comprise (i) an effective amount of Compound I or a pharmaceutically acceptable salt, solvate, ester, amide, or prodrug thereof and (ii) a pharmaceutically acceptable carrier or vehicle. In some embodiments, the compositions of the invention comprise (i) an effective amount of a racemate of Compound I or a pharmaceutically acceptable salt, solvate, ester, amide, or prodrug thereof and (ii) a pharmaceutically acceptable carrier or vehicle. In some embodiments, the compositions of the invention comprise (i) an effective amount of a mixture of enantiomers of Compound I or a pharmaceutically acceptable salt, solvate, ester, amide, or prodrug thereof and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I has an hydroxyl-bearing allylic carbon atom having an (R)-enantiomer, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I has an hydroxyl-bearing allylic carbon atom having an (R)-enantiomer, and (ii) a pharmaceutically acceptable carrier or vehicle, wherein the compositions are substantially free of the (S)-enantiomer of Compound I or a pharmaceutically acceptable salt or thereof. In some embodiments, the compositions of the invention comprise (i) an effective amount of Compound I or a pharmaceutically acceptable salt, solvate, ester, amide, or prodrug thereof, wherein Compound I has an hydroxyl-bearing allylic carbon atom having an (S)-enantiomer, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I has an hydroxyl-bearing allylic carbon atom having an (S)-enantiomer, and (ii) a pharmaceutically acceptable carrier or vehicle, wherein the compositions are substantially free of the (R)-enantiomer of Compound I or a pharmaceutically acceptable salt, solvate, ester, amide, or prodrug thereof. In some embodiments, the compositions of the invention comprise (i) an effective amount of a non-racemic mixture of an (R)-enantiomer and an (S)-enantiomer of Compound I or a pharmaceutically acceptable salt, solvate, ester, amide, or prodrug thereof and (ii) a pharmaceutically acceptable carrier or vehicle. In some embodiments, the non-racemic mixture has an excess of (R)-enantiomer relative to (S)-enantiomer. In some embodiments, the non-racemic mixture has an excess of (S)-enantiomer relative to (R)-enantiomer.

In some embodiments, the compositions of the invention comprise (i) an effective amount of a (Z)-isomer of Compound I or a pharmaceutically acceptable salt, solvate, ester, amide, or prodrug thereof and (ii) a pharmaceutically acceptable carrier or vehicle. In some embodiments, the compositions of the invention comprise (i) an effective amount of a (Z)-isomer of Compound I or a pharmaceutically acceptable salt, solvate, ester, amide, or prodrug thereof and (ii) a pharmaceutically acceptable carrier or vehicle, wherein the compositions are substantially free of the (E)-isomer of Compound I or a pharmaceutically acceptable salt or thereof. In some embodiments, the compositions of the invention comprise (i) an effective amount of an (E)-isomer of Compound I or a pharmaceutically acceptable salt, solvate, ester, amide, or prodrug thereof and (ii) a pharmaceutically acceptable carrier or vehicle. In some embodiments, the compositions of the invention comprise (i) an effective amount of an (E)-isomer of Compound I or a pharmaceutically acceptable salt, solvate, ester, amide, or prodrug thereof and (ii) a pharmaceutically acceptable carrier or vehicle, wherein the compositions are substantially free of the (Z)-isomer of Compound I or a pharmaceutically acceptable salt, solvate, ester, amide, or prodrug thereof. In some embodiments, the compositions of the invention comprise (i) an effective amount of a non-equal mixture of a (Z)-isomer and an (E)-isomer of Compound I or a pharmaceutically acceptable salt, solvate, ester, amide, or prodrug thereof and (ii) a pharmaceutically acceptable carrier or vehicle. In some embodiments, the non-equal mixture has an excess of (Z)-isomer relative to (E)-isomer. In some embodiments, the non-equal mixture has an excess of (E)-isomer relative to (Z)-isomer.

In some embodiments, the compositions of the invention comprise (i) an effective amount of Compound I or a pharmaceutically acceptable salt, solvate, ester, amide, or prodrug thereof, wherein Compound I is an (Z)-isomer and has an hydroxyl-bearing allylic carbon atom having an (R)-stereochemistry, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I is an (Z)-isomer and has an hydroxyl-bearing allylic carbon atom having an (R)-stereochemistry, and (ii) a pharmaceutically acceptable carrier or vehicle, wherein the compositions are substantially free of Compounds ((Z)-(S)-I), ((E)-(R)-I), or ((E)-(S)-I), or a pharmaceutically acceptable salt or thereof. In some embodiments, the compositions of the invention comprise (i) an effective amount of Compound I or a pharmaceutically acceptable salt, solvate, ester, amide, or prodrug thereof, wherein Compound I is an (Z)-isomer and has an hydroxyl-bearing allylic carbon atom having an (S)-stereochemistry, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I is an (Z)-isomer and has an hydroxyl-bearing allylic carbon atom having an (S)-stereochemistry, and (ii) a pharmaceutically acceptable carrier or vehicle, wherein the compositions are substantially free of Compounds ((Z)-(R)-I), ((E)-(R)-I), or ((E)-(S)-I), or a pharmaceutically acceptable salt or thereof. In some embodiments, the compositions of the invention comprise (i) an effective amount of Compound I or a pharmaceutically acceptable salt, solvate, ester, amide, or prodrug thereof, wherein Compound I is an (E)-isomer and has an hydroxyl-bearing allylic carbon atom having an (R)-stereochemistry, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I is an (E)-isomer and has an hydroxyl-bearing allylic carbon atom having an (R)-stereochemistry, (ii) a pharmaceutically acceptable carrier or vehicle, wherein the compositions are substantially free of Compounds (E)-(S)-I), ((Z)-(R)-I), or ((Z)-(S)-I), or a pharmaceutically acceptable salt or thereof. In some embodiments, the compositions of the invention comprise (i) an effective amount of Compound I or a pharmaceutically acceptable salt, solvate, ester, amide, or prodrug thereof, wherein Compound I is an (E)-isomer and has an hydroxyl-bearing allylic carbon atom having an (S)-stereochemistry, and (ii) a pharmaceutically acceptable carrier or vehicle. In some embodiments, the compositions of the invention comprise (i) an effective amount of Compound I or a pharmaceutically acceptable salt, solvate, ester, amide, or prodrug thereof, wherein Compound I is an (E)-isomer and has an hydroxyl-bearing allylic carbon atom having an (S)-stereochemistry, and (ii) a pharmaceutically acceptable carrier or vehicle, wherein the compositions are substantially free of Compounds ((E)-(R)-I), ((Z)-(R)-I), or ((Z)-(S)-I), or a pharmaceutically acceptable salt or thereof.

In some embodiments, the composition of the invention comprises (i) an effective amount of Compound II or a pharmaceutically acceptable salt, solvate, ester, amide, or prodrug thereof and (ii) a pharmaceutically acceptable carrier or vehicle. In some embodiments, the composition of the invention comprises (i) an effective amount of a (Z)-isomer of Compound II or a pharmaceutically acceptable salt, solvate, ester, amide, or prodrug thereof and (ii) a pharmaceutically acceptable carrier or vehicle. In some embodiments, the composition of the invention comprises (i) an effective amount of a (Z)-isomer of Compound II or a pharmaceutically acceptable salt, solvate, ester, amide, or prodrug thereof and (ii) a pharmaceutically acceptable carrier or vehicle, wherein the compositions are substantially free of the (E)-isomer of Compound II or a pharmaceutically acceptable salt or thereof. In some embodiments, the composition of the invention comprises (i) an effective amount of an (E)-isomer of Compound II or a pharmaceutically acceptable salt, solvate, ester, amide, or prodrug thereof and (ii) a pharmaceutically acceptable carrier or vehicle. In some embodiments, the composition of the invention comprises (i) an effective amount of an (E)-isomer of Compound II or a pharmaceutically acceptable salt, solvate, ester, amide, or prodrug thereof and (ii) a pharmaceutically acceptable carrier or vehicle, wherein the compositions are substantially free of the (Z)-isomer of Compound II or a pharmaceutically acceptable salt or thereof. In some embodiments, the compositions of the invention comprise (i) an effective amount of a non-equal mixture of a (Z)-isomer and an (E)-isomer of Compound II or a pharmaceutically acceptable salt, solvate, ester, amide, or prodrug thereof and (ii) a pharmaceutically acceptable carrier or vehicle. In some embodiments, the non-equal mixture has an excess of (Z)-isomer relative to (E)-isomer. In some embodiments, the non-equal mixture has an excess of (E)-isomer relative to (Z)-isomer.

In some embodiments, the compositions of the invention comprise (i) an effective amount of Compound III or a pharmaceutically acceptable salt, solvate, ester, amide, or prodrug thereof and (ii) a pharmaceutically acceptable carrier or vehicle. In some embodiments, the compositions of the invention comprise (i) an effective amount of a racemate of Compound III or a pharmaceutically acceptable salt, solvate, ester, amide, or prodrug thereof and (ii) a pharmaceutically acceptable carrier or vehicle. In some embodiments, the compositions of the invention comprise (i) an effective amount of a mixture of enantiomers of Compound III or a pharmaceutically acceptable salt, solvate, ester, amide, or prodrug thereof and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III has an hydroxyl-bearing allylic carbon atom having an (R)-enantiomer, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III has an hydroxyl-bearing allylic carbon atom having an (R)-enantiomer, and (ii) a pharmaceutically acceptable carrier or vehicle, wherein the compositions are substantially free of the (S)-enantiomer of Compound III or a pharmaceutically acceptable salt or thereof. In some embodiments, the compositions of the invention comprise (i) an effective amount of Compound III or a pharmaceutically acceptable salt, solvate, ester, amide, or prodrug thereof, wherein Compound III has an hydroxyl-bearing allylic carbon atom having an (S)-enantiomer, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III has an hydroxyl-bearing allylic carbon atom having an (S)-enantiomer, and (ii) a pharmaceutically acceptable carrier or vehicle, wherein the compositions are substantially free of the (R)-enantiomer of Compound III or a pharmaceutically acceptable salt, solvate, ester, amide, or prodrug thereof. In some embodiments, the compositions of the invention comprise (i) an effective amount of a non-racemic mixture of an (R)-enantiomer and an (S)-enantiomer of Compound III or a pharmaceutically acceptable salt, solvate, ester, amide, or prodrug thereof and (ii) a pharmaceutically acceptable carrier or vehicle. In some embodiments, the non-racemic mixture has an excess of (R)-enantiomer relative to (S)-enantiomer. In some embodiments, the non-racemic mixture has an excess of (S)-enantiomer relative to (R)-enantiomer.

In some embodiments, the compositions of the invention comprise (i) an effective amount of a (Z)-isomer of Compound III or a pharmaceutically acceptable salt, solvate, ester, amide, or prodrug thereof and (ii) a pharmaceutically acceptable carrier or vehicle. In some embodiments, the compositions of the invention comprise (i) an effective amount of a (Z)-isomer of Compound III or a pharmaceutically acceptable salt, solvate, ester, amide, or prodrug thereof and (ii) a pharmaceutically acceptable carrier or vehicle, wherein the compositions are substantially free of the (E)-isomer of Compound III or a pharmaceutically acceptable salt or thereof. In some embodiments, the compositions of the invention comprise (i) an effective amount of an (E)-isomer of Compound III or a pharmaceutically acceptable salt, solvate, ester, amide, or prodrug thereof and (ii) a pharmaceutically acceptable carrier or vehicle. In some embodiments, the compositions of the invention comprise (i) an effective amount of an (E)-isomer of Compound III or a pharmaceutically acceptable salt, solvate, ester, amide, or prodrug thereof and (ii) a pharmaceutically acceptable carrier or vehicle, wherein the compositions are substantially free of the (Z)-isomer of Compound III or a pharmaceutically acceptable salt, solvate, ester, amide, or prodrug thereof. In some embodiments, the compositions of the invention comprise (i) an effective amount of a non-equal mixture of a (Z)-isomer and an (E)-isomer of Compound III or a pharmaceutically acceptable salt, solvate, ester, amide, or prodrug thereof and (ii) a pharmaceutically acceptable carrier or vehicle. In some embodiments, the non-equal mixture has an excess of (Z)-isomer relative to (E)-isomer. In some embodiments, the non-equal mixture has an excess of (E)-isomer relative to (Z)-isomer.

In some embodiments, the compositions of the invention comprise (i) an effective amount of Compound III or a pharmaceutically acceptable salt, solvate, ester, amide, or prodrug thereof, wherein Compound III is an (Z)-isomer and has an hydroxyl-bearing allylic carbon atom having an (R)-stereochemistry, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III is an (Z)-isomer and has an hydroxyl-bearing allylic carbon atom having an (R)-stereochemistry, and (ii) a pharmaceutically acceptable carrier or vehicle, wherein the compositions are substantially free of Compounds ((Z)-(S)-III), ((E)-(R)-III), or ((E)-(S)-III), or a pharmaceutically acceptable salt or thereof. In some embodiments, the compositions of the invention comprise (i) an effective amount of Compound III or a pharmaceutically acceptable salt, solvate, ester, amide, or prodrug thereof, wherein Compound III is an (Z)-isomer and has an hydroxyl-bearing allylic carbon atom having an (S)-stereochemistry, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III is an (Z)-isomer and has an hydroxyl-bearing allylic carbon atom having an (S)-stereochemistry, and (ii) a pharmaceutically acceptable carrier or vehicle, wherein the compositions are substantially free of Compounds ((Z)-(R)-III), ((E)-(R)-III), or ((E)-(S)-III), or a pharmaceutically acceptable salt or thereof. In some embodiments, the compositions of the invention comprise (i) an effective amount of Compound III or a pharmaceutically acceptable salt, solvate, ester, amide, or prodrug thereof, wherein Compound III is an (E)-isomer and has an hydroxyl-bearing allylic carbon atom having an (R)-stereochemistry, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III is an (E)-isomer and has an hydroxyl-bearing allylic carbon atom having an (R)-stereochemistry, (ii) a pharmaceutically acceptable carrier or vehicle, wherein the compositions are substantially free of Compounds (E)-(S)-III), ((Z)-(R)-III), or ((Z)-(S)-III), or a pharmaceutically acceptable salt or thereof. In some embodiments, the compositions of the invention comprise (i) an effective amount of Compound III or a pharmaceutically acceptable salt, solvate, ester, amide, or prodrug thereof, wherein Compound III is an (E)-isomer and has an hydroxyl-bearing allylic carbon atom having an (S)-stereochemistry, and (ii) a pharmaceutically acceptable carrier or vehicle. In some embodiments, the compositions of the invention comprise (i) an effective amount of Compound III or a pharmaceutically acceptable salt, solvate, ester, amide, or prodrug thereof, wherein Compound III is an (E)-isomer and has an hydroxyl-bearing allylic carbon atom having an (S)-stereochemistry, and (ii) a pharmaceutically acceptable carrier or vehicle, wherein the compositions are substantially free of Compounds ((E)-(R)-III), ((Z)-(R)-III), or ((Z)-(S)-III), or a pharmaceutically acceptable salt or thereof.

In some embodiments, the compositions of the invention comprise (i) an effective amount of Compound IV or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound V or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound VI or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound VIa or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound VIb or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound VII or a pharmaceutically acceptable salt, solvate, ester, amide, or prodrug thereof and (ii) a pharmaceutically acceptable carrier or vehicle.

In some embodiments, the compositions of the invention comprise (i) an effective amount of Compound VIII or a pharmaceutically acceptable salt, solvate, ester, amide, or prodrug thereof and (ii) a pharmaceutically acceptable carrier or vehicle.

In some embodiments, the compositions of the invention further comprise another therapeutically active agent.

A composition of the invention further comprising another therapeutically active agent is a "combination of the invention." The present invention provides combinations of the invention. The combination of the invention can comprise one or more therapeutically active agents.

In some embodiments, the other therapeutically active agent is a lipid lowering drug, a statin, a cholesterol absorption inhibitor, an antibody against PCSK9, an siRNA PCSK9, an anti-fibrotic agent, a thyroid hormone, a selective thyroid receptor-β agonist, apoptosis signal-regulating kinase 1 (ASK1) inhibitor, acetyl-CoA carboxylase (ACC) inhibitor, an integrin antagonist, or a non-steroidal Farnesoid X receptor (FXR) agonist.

In some embodiments, the lipid lowering drug is gemfibrozil, fenofibrate, bezafibrate, clofibrate, ciprofibrate, clinofibrate, etofylline, pirifibrate, simfibrate, tocofibrate, or pemafibrate. In some embodiments, the lipid lowering drug is gemfibrozil, fenofibrate, bezafibrate, or pemafibrate.

In some embodiments, statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt or solvate thereof. In some embodiments, statin is atorvastatin, simvastatin, pravastatin or rosuvastatin, or a pharmaceutically acceptable salt or solvate thereof.

In some embodiments, the cholesterol absorption inhibitor is ezetimibe.

In some embodiments, the antibody against PCSK9 is evolocumab alirocumab, bococizumab, 1D05-IgG2 (Merck), RG7652 (Genentech), LY3015014 (Eli Lilly), or LGT-209 (Novartis/Cyon Therapeutics). In some embodiments, the antibody against PCSK9 is evolocumab or alirocumab.

In some embodiments, the siRNA PCSK9 is an siRNA interfering with production of PCSK9 such as inclisiran.

In some embodiments, the anti-fibrotic agent is nitazoxamide, tizoxanide, or tizoxanide glucuronide, nintedanib, imatinib, or a pharmaceutically acceptable salt or solvate thereof.

In some embodiments, the selective thyroid receptor-β agonist is VK2809 (Viking Therapeutics), MGL-3196 (Madrigal Pharmaceuticals), MGL-3745 (Madrigal Pharmaceuticals), SKL-14763, sobetirome, BCT304 (ITL Pharma), ZYT1 (Zydus Cadila), MB-0781 (Metabasis), or eprotirome.

In some embodiments, the ASK1 inhibitor is selonsertib.

In some embodiments, the ACC inhibitor is firsocostat.

In some embodiments, the integrin antagonist is an α5β1 inhibitor or a pan integrin inhibitor. In some embodiments, the integrin antagonist is IDL-2965 (Indalo Therapeutics). In some embodiments, the integrin antagonist is CLT-28643 (ClanoTech AB).

In some embodiments, the integrin antagonist is 3-(6-Methoxypyridin-3-yl)-3-(4-(3-(5,6,7,8-tetrahydro-1,8-naphthyridin-2-yl)propyl)-1H-indazol-1-yl)propanoic acid; 3-(6-Methoxypyridin-3-yl)-3-(5-(2-(5,6,7,8-tetrahydro-1,8-naphthyridin-2-yl)ethyl)-1H-indazol-1-yl)propanoic acid; 3-(6-Methoxypyridin-3-yl)-3-(4-(2-(5,6,7,8-tetrahydro-1,8-naphthyridin-2-yl)ethoxy)-1H-indazol-1-yl)propanoic acid; (S)-2-(((Benzyloxy)carbonyl)amino)-3-(5-(2-(5,6,7,8-tetrahydro-1,8-naphthyridin-2-yl)ethoxy)-2H-indazol-2-yl)propanoic acid; 3-Phenyl-3-(5-(3-(5,6,7,8-tetrahydro-1,8-naphthyridin-2-yl)propoxy)-1H-indazol-1-yl)propanoic acid; (S)-3-(6-Methoxypyridin-3-yl)-3-(5-(2-(5,6,7,8-tetrahydro-1,8-naphthyridin-2-yl)ethoxy)-2H-indazol-2-yl)propanoic acid; (S)-3-(6-Methoxypyridin-3-yl)-3-(6-(2-(5,6,7,8-tetrahydro-1,8-naphthyridin-2-yl)ethyl)-2H-indazol-2-yl)propanoic acid; (S)-3-(6-Methoxypyridin-3-yl)-3-(6-((2-methyl-5,6,7,8-tetrahydro-1,8-naphthyridin-3-yl)methyl)-2H-indazol-2-yl)propanoic acid; (S)-3-(6-Methoxypyridin-3-yl)-3-(6-(3-(5,6,7,8-tetrahydro-1,8-naphthyridin-2-yl)propyl)-2H-indazol-2-yl)propanoic acid; (S)-3-(6-Methoxypyridin-3-yl)-3-(6-(2-(2-methyl-5,6,7,8-tetrahydro-1,8-naphthyridin-3-yl)ethyl)-2H-indazol-2-yl)propanoic acid; 3-(6-Methoxypyridin-3-yl)-3-(5-(2-(5,6,7,8-tetrahydro-1,8-naphthyridin-2-yl)ethoxy)pyrazolo[4,3-b]pyridin-1-yl)propanoic acid; 3-(5-(2-((4,5-Dihydroimidazol-2-yl)amino)ethoxy)-1H-indazol-1-yl)-3-(6-methoxypyridin-3-yl)propanoic acid; 3-(5-(2-(5,6,7,8-Tetrahydro-1,8-naphthyridin-2-yl)ethoxy)-1H-indazol-1-yl-)-2-((2,4,6-trimethylphenyl)sulfonamido)propanoic acid; 2-(((Benzyloxy)carbonyl)amino)-3-(5-(2-(5,6,7,8-tetrahydro-1,8-naphthyridin-2-yl)ethoxy)-1H-indazol-1-yl)propanoic acid; 3-(Quinoxalin-2-yl)-3-(5-(2-(5,6,7,8-tetrahydro-1,8-naphthyridin-2-yl)ethoxy)-1H-indazol-1-yl) propanoic acid; (R)-3-(Quinoxalin-2-yl)-3-(5-(2-(5,6,7,8-tetrahydro-1,8-naphthyridin-2-yl-)ethoxy)-1H-indazol-1-yl) propanoic acid; (S)-3-(Quinoxalin-2-yl)-3-(5-(2-(5,6,7,8-tetrahydro-1,8-naphthyridin-2-yl-)ethoxy)-1H-indazol-1-yl) propanoic acid; 3-(3,5-Dichlorophenyl)-3-(4-(3-(5,6,7,8-tetrahydro-1,8-naphthyridin-2-yl)-propyl)-1H-indazol-1-yl) propanoic acid; 3-(Quinoxalin-2-yl)-3-(4-(3-(5,6,7,8-tetrahydro-1,8-naphthyridin-2-yl)propyl)-1H-indazol-1-yl) propanoic acid; 3-(6-Methoxypyridin-3-yl)-3-(5-(3-(5,6,7,8-tetrahydro-1,8-naphthyridin-2-yl)propyl)-1H-indazol-1-yl)propanoic acid; 3-(3,5-Dichlorophenyl)-3-(5-(3-(5,6,7,8-tetrahydro-1,8-naphthyridin-2-yl)-propyl)-1H-indazol-1-yl) propanoic acid; 3-(Quinoxalin-2-yl)-3-(5-(3-(5,6,7,8-tetrahydro-1,8-naphthyridin-2-yl)propyl)-1H-indazol-1-yl) propanoic acid; 3-(3-(Dimethylcarbamoyl)phenyl)-3-(5-(3-(5,6,7,8-tetrahydro-1,8-naphthyridin-2-yl)propyl)-1H-indazol-1-yl)propanoic acid; 3-(3-(Dimethylcarbamoyl)phenyl)-3-(5-(2-(5,6,7,8-tetrahydro-1,8-naphthyridin-2-yl)ethyl)-1H-indazol-1-yl)propanoic acid; 3-(Dibenzo[b,d]furan-3-yl)-3-(5-(2-(5,6,7,8-tetrahydro-1,8-naphthyridin-2-yl)ethyl)-1H-indazol-1-yl)propanoic acid; 3-(3-((Dimethylamino)methyl)phenyl)-3-(5-(2-(5,6,7,8-tetrahydro-1,8-naphthyridin-2-yl)ethyl)-1H-indazol-1-yl) propanoic acid; 3-(Quinoxalin-2-yl)-3-(5-(2-(5,6,7,8-tetrahydro-1,8-naphthyridin-2-yl)eth-yl)-1H-indazol-1-yl) propanoic acid; 3-(3,5-Dichlorophenyl)-3-(5-(2-(5,6,7,8-tetrahydro-1,8-naphthyridin-2-yl)-ethyl)-1H-indazol-1-yl) propanoic acid; 3-(3-(Dimethylcarbamoyl)phenyl)-3-(4-(2-(5,6,7,8-tetrahydro-1,8-naphthyridin-2-yl)ethoxy)-1H-indazol-1-yl)propanoic acid; 3-(Dibenzo[b,d]furan-3-yl)-3-(4-(2-(5,6,7,8-tetrahydro-1,8-naphthyridin-2-yl)ethoxy)-1H-indazol-1-yl)propanoic acid; 6,6,6-Trifluoro-3-(4-(3-(5,6,7,8-tetrahydro-1,8-naphthyridin-2-yl)propyl)-1H-indazol-1-yl)hexanoic acid; 3-(3,5-Dichlorophenyl)-3-(4-(2-(5,6,7,8-tetrahydro-1,8-naphthyridin-2-yl)-ethoxy)-1H-indazol-1-yl)propanoic acid; 3-(Quinoxalin-2-yl)-3-(4-(2-(5,6,7,8-tetrahydro-1,8-naphthyridin-2-yl)eth-oxy)-1H-indazol-1-yl) propanoic acid; 3-(6-Methoxypyridin-3-yl)-3-(5-(2-(5,6,7,8-tetrahydro-1,8-naphthyridin-2-yl)ethoxy)-1H-indazol-1-yl)propanoic acid; 3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid; (S)-2-(((Benzyloxy)carbonyl)amino)-3-(5-(3-(5,6,7,8-tetrahydro-1,8-naphthyridin-2-yl)

propyl)-1H-indazol-1-yl)propanoic acid; (R)-3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid; (S)-3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid; 2-(((Benzyloxy)carbonyl)amino)-3-(4-(2-(5,6,7,8-tetrahydro-1,8-naphthyridin-2-yl)ethoxy)-1H-indazol-1-yl)propanoic acid; (R)-3-(6-Methoxypyridin-3-yl)-3-(5-(2-(5,6,7,8-tetrahydro-1,8-naphthyridin-2-yl)ethoxy)-1H-indazol-1-yl)propanoic acid; (S)-3-(6-Methoxypyridin-3-yl)-3-(5-(2-(5,6,7,8-tetrahydro-1,8-naphthyridin-2-yl)ethoxy)-1H-indazol-1-yl)propanoic acid; 3-(5-Chloropyridin-3-yl)-3-(5-(2-(5,6,7,8-tetrahydro-1,8-naphthyridin-2-y-l)ethoxy)-1H-indazol-1-yl)propanoic acid; 3-(3,5-Dichlorophenyl)-3-(5-(2-(5,6,7,8-tetrahydro-1,8-naphthyridin-2-yl)-ethoxy)-1H-indazol-1-yl)propanoic acid; 3-(3-Fluoro-4-methoxyphenyl)-3-(5-(2-(5,6,7,8-tetrahydro-1,8-naphthyridin-2-yl)ethoxy)-1H-indazol-1-yl)propanoic acid; 3-Cyclopropyl-3-(5-(2-(5,6,7,8-tetrahydro-1,8-naphthyridin-2-yl)ethoxy)-1-H-indazol-1-yl)propanoic acid; 3-(5-(2-(5,6,7,8-Tetrahydro-1,8-naphthyridin-2-yl)ethoxy)-1H-indazol-1-yl-)octanoic acid; 3-(2,3-Dihydrobenzofuran-5-yl)-3-(5-(2-(5,6,7,8-tetrahydro-1,8-naphthyridin-2-yl)ethoxy)-1H-indazol-1-yl)propanoic acid; 3-(Quinolin-3-yl)-3-(5-(2-(5,6,7,8-tetrahydro-1,8-naphthyridin-2-yl)ethoxy)-1H-indazol-1-yl)propanoic acid (48); 3-(5-(2-(5,6,7,8-Tetrahydro-1,8-naphthyridin-2-yl)ethoxy)-1H-indazol-1-yl-)-3-(thiophen-2-yl)propanoic acid; 3-(Pyridin-3-yl)-3-(5-(2-(5,6,7,8-tetrahydro-1,8-naphthyridin-2-yl)ethoxy-)-1H-indazol-1-yl)propanoic acid; 3-(5-(2-(5,6,7,8-Tetrahydro-1,8-naphthyridin-2-yl)ethoxy)-1H-indazol-1-yl-)propanoic acid; 3-(3-Cyanophenyl)-3-(5-(2-(5,6,7,8-tetrahydro-1,8-naphthyridin-2-yl)ethoxy)-1H-indazol-1-yl)propanoic acid; 3-(5-Fluoropyridin-2-yl)-3-(5-(2-(5,6,7,8-tetrahydro-1,8-naphthyridin-2-y-l)ethoxy)-1H-indazol-1-yl)propanoic acid; 3-(Dibenzo[b,d]furan-2-yl)-3-(5-(2-(5,6,7,8-tetrahydro-1,8-naphthyridin-2-yl)ethoxy)-1H-indazol-1-yl)propanoic acid; 3-(4,6-Dimethylpyrimidin-2-yl)-3-(5-(2-(5,6,7,8-tetrahydro-1,8-naphthyridin-2-yl)ethoxy)-1H-indazol-1-yl)propanoic acid; 3-(2-Methylbenzo[d]thiazol-5-yl)-3-(5-(2-(5,6,7,8-tetrahydro-1,8-naphthyridin-2-yl)ethoxy)-1H-indazol-1-yl)propanoic acid; 3-(4-Phenoxyphenyl)-3-(5-(2-(5,6,7,8-tetrahydro-1,8-naphthyridin-2-yl)eth-oxy)-1H-indazol-1-yl)propanoic acid; 3-(3-Morpholinophenyl)-3-(5-(2-(5,6,7,8-tetrahydro-1,8-naphthyridin-2-yl)-ethoxy)-1H-indazol-1-yl)propanoic acid; 3-(3-(1H-Pyrrol-1-yl)phenyl)-3-(5-(2-(5,6,7,8-tetrahydro-1,8-naphthyridin-2-yl)ethoxy)-1H-indazol-1-yl)propanoic acid; 3-(3-((Dimethylamino)methyl)phenyl)-3-(5-(2-(5,6,7,8-tetrahydro-1,8-naphthyridin-2-yl)ethoxy)-1H-indazol-1-yl)propanoic acid; 3-(Pyridin-2-yl)-3-(5-(2-(5,6,7,8-tetrahydro-1,8-naphthyridin-2-yl)ethoxy-)-1H-indazol-1-yl)propanoic acid; 3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid; 3-(1-Propylpyrazol-4-yl)-3-(5-(2-(5,6,7,8-tetrahydro-1,8-naphthyridin-2-y-l)ethoxy)-1H-indazol-1-yl)propanoic acid; (S)-3-(6-Methoxypyridin-3-yl)-3-(5-(2-(5,6,7,8-tetrahydro-1,8-naphthyridin-2-yl)ethyl)-2H-indazol-2-yl)propanoic acid; (S)-3-(6-Methoxypyridin-3-yl)-3-(6-(2-(5,6,7,8-tetrahydro-1,8-naphthyridin-2-yl)ethoxy)-2H-indazol-2-yl)propanoic acid; 3-(2-Methylpyrimidin-5-yl)-3-(5-(2-(5,6,7,8-tetrahydro-1,8-naphthyridin-2-yl)ethoxy)-1H-indazol-1-yl)propanoic acid; (S)-3-(6-Methoxypyridin-3-yl)-3-(5-(3-(5,6,7,8-tetrahydro-1,8-naphthyridin-2-yl)propyl)-2H-indazol-2-yl)propanoic acid; 3-(3-(3,5-Dimethylpyrazol-1-yl)phenyl)-3-(5-(2-(5,6,7,8-tetrahydro-1,8-naphthyridin-2-yl)ethoxy)-1H-indazol-1-yl)propanoic acid; 4-(4-(Benzyloxy)phenyl)-3-(5-(2-(5,6,7,8-tetrahydro-1,8-naphthyridin-2-yl-)ethoxy)-1H-indazol-1-yl)butanoic acid; 3-(6-Methoxypyridin-3-yl)-3-(3-methyl-5-(2-(5,6,7,8-tetrahydro-1,8-naphthyridin-2-yl)ethoxy)-1H-indazol-1-yl)propanoic acid; 3-(1-Methyl-2-oxo-1,2-dihydropyridin-4-yl)-3-(5-(2-(5,6,7,8-tetrahydro-1,-8-naphthyridin-2-yl)ethoxy)-1H-indazol-1-yl)propanoic acid; (3S)-3-(6-Methoxypyridin-3-yl)-3-(6-(2-(1,2,3,4-tetrahydro-1,8-naphthyridin-2-yl)ethyl)-2H-indazol-2-yl)propanoic acid; 4-Phenyl-2-((5-(2-(5,6,7,8-tetrahydro-1,8-naphthyridin-2-yl)ethoxy)-1H-indazol-1-yl)methyl)butanoic acid; 3-(1-(tert-Butoxycarbonyl)piperidin-4-yl)-3-(5-(2-(5,6,7,8-tetrahydro-1,8-naphthyridin-2-yl)ethoxy)-1H-indazol-1-yl)propanoic acid; 3-(Pyridin-4-yl)-3-(5-(2-(5,6,7,8-tetrahydro-1,8-naphthyridin-2-yl)ethoxy-)-1H-indazol-1-yl)propanoic acid; 2-(1-(5-(2-(5,6,7,8-Tetrahydro-1,8-naphthyridin-2-yl)ethoxy)-1H-indazol-1-yl)cyclopropyl)acetic acid; 3-(2-Ethoxypyrimidin-5-yl)-3-(5-(2-(5,6,7,8-tetrahydro-1,8-naphthyridin-2-yl)ethoxy)-1H-indazol-1-yl)propanoic acid; 4-(4-Fluorophenyl)-3-(5-(2-(5,6,7,8-tetrahydro-1,8-naphthyridin-2-yl)ethoxy)-1H-indazol-1-yl)butanoic acid; 3-(5-Methoxypyrazin-2-yl)-3-(5-(2-(5,6,7,8-tetrahydro-1,8-naphthyridin-2-yl)ethoxy)-1H-indazol-1-yl)propanoic acid; 3-(Quinoxalin-6-yl)-3-(5-(2-(5,6,7,8-tetrahydro-1,8-naphthyridin-2-yl)eth-oxy)-1H-indazol-1-yl)propanoic acid; (S)-3-(Quinolin-3-yl)-3-(6-(2-(5,6,7,8-tetrahydro-1,8-naphthyridin-2-yl)ethyl)-2H-indazol-2-yl)propanoic acid; (S)-3-(6-((2-Methyl-5,6,7,8-tetrahydro-1,8-naphthyridin-3-yl)methyl)-2H-indazol-2-yl)-3-(quinolin-3-yl)propanoic acid; (3S)-3-(Quinolin-3-yl)-3-(6-(2-(1,2,3,4-tetrahydro-1,8-naphthyridin-2-yl)-ethyl)-2H-indazol-2-yl)propanoic acid; (S)-3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid; (R)-3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid; 3-(5-Fluoro-6-methoxypyridin-3-yl)-3-(5-(2-(5,6,7,8-tetrahydro-1,8-naphthyridin-2-yl)ethoxy)-1H-indazol-1-yl)propanoic acid; (S)-3-(Quinolin-3-yl)-3-(6-(3-(5,6,7,8-tetrahydro-1,8-naphthyridin-2-yl)propyl)-2H-indazol-2-yl)propanoic acid; (3S)-3-(Quinolin-3-yl)-3-(6-(3-(1,2,3,4-tetrahydro-1,8-naphthyridin-2-yl)-propyl)-2H-indazol-2-yl)propanoic acid; 3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid; 3-(6-(2-Hydroxy-2-methylpropoxy)-5-methylpyridin-3-yl)-3-(5-(2-(5,6,7,8-tetrahydro-1,8-naphthyridin-2-yl)ethoxy)-1H-indazol-1-yl)propanoic acid; 3-(3,4-Dihydro-2H-pyrido[3,2-b][1,4]oxazin-6-yl)-3-(5-(2-(5,6,7,8-tetrahydro-1,8-naphthyridin-2-yl)ethoxy)-1H-indazol-1-yl)propanoic acid; 3-(2-Methoxypyrimidin-5-yl)-3-(5-(2-(5,6,7,8-tetrahydro-1,8-naphthyridin-2-yl)ethoxy)-1H-indazol-1-yl)propanoic acid; 3-(2-(2-Oxopyrrolidin-1-yl)pyridin-4-yl)-3-(5-(2-(5,6,7,8-tetrahydro-1,8-naphthyridin-2-yl)ethoxy)-1H-indazol-1-yl)propanoic acid; 3-(Isoquinolin-6-yl)-3-(5-(2-(5,6,7,8-tetrahydro-1,8-naphthyridin-2-yl)ethoxy)-1H-indazol-1-yl)propanoic acid; 3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid; 3-(1,8-Naphthyridin-2-yl)-3-(5-(2-(5,6,7,8-tetrahydro-1,8-naphthyridin-2-yl)ethoxy)-1H-indazol-1-yl)propanoic acid; 3-(3,4-Dihydro-2H-pyrido[3,2-b][1,4]oxazin-7-yl)-3-(5-(2-(5,6,7,8-tetrahydro-1,8-naphthyridin-2-yl)ethoxy)-1H-indazol-1-yl)propanoic acid; (S)-2-(((Benzyloxy)carbonyl)amino)-3-(5-(((5,6,7,8-tetrahydro-1,8-naphthyridin-2-yl)methoxy)-2H-indazol-2-yl)propanoic acid; (R)-3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid; (S)-3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid; 3-(1,8-Naphthyridin-3-yl)-3-(5-(2-(5,6,7,8-tetrahydro-1,8-naphthyridin-2-yl)ethoxy)-1H-indazol-1-yl)propanoic acid; 3-(5-(2-Oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid; 3-(5-(2-(5,6,7,8-Tetrahydro-1,8-naphthyridin-2-yl)ethoxy)-1H-indazol-1-yl-)-3-(1-(tetrahydro-2H-pyran-2-yl)pyrazolo[3,4-b]pyridin-5-yl)propanoic acid; 3-(5-(1,3-Dioxolan-2-yl)pyridin-3-yl)-3-(5-(2-(5,6,7,8-tetrahydro-1-,8-naphthyridin-2-yl)ethoxy)-1H-indazol-1-yl)propanoic acid; 3-(5-((Dimethylamino)methyl)pyridin-3-yl)-3-(5-(2-(5,6,7,8-tetrahydro-1,8-naphthyridin-2-yl)ethoxy)-1H-indazol-1-yl)propanoic acid; 3-(1H-Pyrazolo[3,4-b]pyridin-5-yl)-3-(5-(2-(5,6,7,8-tetrahydro-1,8-naphthyridin-2-yl)ethoxy)-1H-indazol-1-yl)propanoic acid; (S)-3-(2-Ethoxypyrimidin-5-yl)-3-(5-(2-(5,6,7,8-tetrahydro-1,8-naphthyridin-2-yl)ethoxy)-1H-indazol-1-yl)propanoic acid; (R)-3-(2-Ethoxypyrimidin-5-yl)-3-(5-(2-(5,6,7,8-tetrahydro-1,8-naphthyridin-2-yl)ethoxy)-1H-indazol-1-yl)propanoic acid; 3-(2,3-Dihydro-[1,4]dioxino[2,3-b]pyridin-7-yl)-3-(5-(2-(5,6,7,8-tetrahydro-1,8-naphthyridin-2-yl)ethoxy)-1H-indazol-1-yl)propanoic acid; 3-(Benzo[d]thiazol-6-yl)-3-(5-(2-(5,6,7,8-tetrahydro-1,8-naphthyridin-2-y-I)ethoxy)-1H-indazol-1-yl)propanoic acid; 3-(2-Morpholinopyrimidin-5-yl)-3-(5-(2-(5,6,7,8-tetrahydro-1,8-naphthyridin-2-yl)ethoxy)-1H-indazol-1-yl)propanoic acid; 3-(2-(Methylamino)pyrimidin-5-yl)-3-(5-(2-(5,6,7,8-tetrahydro-1,8-naphthyridin-2-yl)ethoxy)-1H-indazol-1-yl)propanoic acid; 3-(6-Methoxypyridin-3-yl)-3-(5-(3-(5,6,7,8-tetrahydro-1,8-naphthyridin-2-yl)propyl)-1H-pyrazolo[4,3-b]pyridin-1-yl)propanoic acid; 3-(6-Methoxypyridazin-3-yl)-3-(5-(2-(5,6,7,8-tetrahydro-1,8-naphthyridin-2-yl)ethoxy)-1H-indazol-1-yl)propanoic acid; 3-([1,2,4]Triazolo[4,3-a]pyridin-6-yl)-3-(5-(2-(5,6,7,8-tetrahydro-1,8-naphthyridin-2-yl)ethoxy)-1H-indazol-1-yl)propanoic acid; 3-(5,6,7,8-Tetrahydro-1,8-naphthyridin-2-yl)-3-(5-(2-(5,6,7,8-tetrahydro-1,8-naphthyridin-2-yl)ethoxy)-1H-indazol-1-yl)propanoic acid; 3-(1-Methyl-1H-pyrazolo[3,4-b]pyridin-5-yl)-3-(5-(2-(5,6,7,8-tetrahydro-1-,8-naphthyridin-2-yl)ethoxy)-1H-indazol-1-yl)propanoic acid; (S)-3-(2-Methoxypyrimidin-5-yl)-3-(6-(2-(5,6,7,8-tetrahydro-1,8-naphthyridin-2-yl)ethyl)-2H-indazol-2-yl)propanoic acid; 3-(2-(Azetidin-1-yl)pyrimidin-5-yl)-3-(5-(2-(5,6,7,8-tetrahydro-1,8-naphthyridin-2-yl)ethoxy)-1H-indazol-1-yl)propanoic acid; 3-(2-Methyl-2H-pyrazolo[3,4-b]pyridin-5-yl)-3-(5-(2-(5,6,7,8-tetrahydro-1-,8-naphthyridin-2-yl)ethoxy)-1H-indazol-1-yl)propanoic acid; 3-(5-(Oxazol-5-yl)pyridin-3-yl)-3-(5-(2-(5,6,7,8-tetrahydro-1,8-naphthyridin-2-yl)ethoxy)-1H-indazol-1-yl)propanoic acid; 3-(7-Ethyl-5,6,7,8-tetrahydroimidazo[1,2-a]pyrazin-3-yl)-3-(5-(2-(5,6,7,8-tetrahydro-1,8-naphthyridin-2-yl)ethoxy)-1H-indazol-1-yl)propanoic acid; 3-(5-(((tert-Butoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid; 3-(5-Morpholinopyridin-3-yl)-3-(5-(2-(5,6,7,8-tetrahydro-1,8-naphthyridin-2-yl)ethoxy)-1H-indazol-1-yl)propanoic acid; 3-(5-(Methylsulfonyl)pyridin-3-yl)-3-(5-(2-(5,6,7,8-tetrahydro-1,8-naphthyridin-2-yl)ethoxy)-1H-indazol-1-yl)propanoic acid; 3-(3-Methyl-3H-imidazo[4,5-b]pyridin-6-yl)-3-(5-(2-(5,6,7,8-tetrahydro-1,-8-naphthyridin-2-yl)ethoxy)-1H-indazol-1-yl)propanoic acid; 3-(5-(Pyrrolidin-1-yl)pyridin-3-yl)-3-(5-(2-(5,6,7,8-tetrahydro-1,8-naphthyridin-2-yl)ethoxy)-1H-indazol-1-yl)propanoic acid; (R)-3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid; (S)-3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid; 3-([1,2,4]Triazolo[4,3-a]pyridin-7-yl)-3-(5-(2-(5,6,7,8-tetrahydro-1,8-naphthyridin-2-yl)ethoxy)-1H-indazol-1-yl)propanoic acid; 3-(5-(Aminomethyl)pyridin-3-yl)-3-(5-(2-(5,6,7,8-tetrahydro-1,8-naphthyridin-2-yl)ethoxy)-1H-indazol-1-yl)propanoic acid; 3-([1,3]Dioxolo[4,5-b]pyridin-6-yl)-3-(5-(2-(5,6,7,8-tetrahydro-1,8-naphthyridin-2-yl)ethoxy)-1H-indazol-1-yl)propanoic acid; 3-(5-(1,3-Dioxolan-2-yl)-6-methoxypyridin-3-yl)-3-(5-(2-(5,6,7,8-tetrahydro-1,8-naphthyridin-2-yl)ethoxy)-1H-indazol-1-yl)propanoic acid; 3-(6-(1H-Pyrazol-1-yl)pyridin-2-yl)-3-(5-(2-(5,6,7,8-tetrahydro-1,8-naphthyridin-2-yl)ethoxy)-1H-indazol-1-yl)propanoic acid; 3-(1-(Pyridin-4-yl)-1H-pyrazol-4-yl)-3-(5-(2-(5,6,7,8-tetrahydro-1,8-naphthyridin-2-yl)ethoxy)-1H-indazol-1-yl)propanoic acid; 3-(2-Methyl-2H-pyrazolo[4,3-b]pyridin-6-yl)-3-(5-(2-(5,6,7,8-tetrahydro-1-,8-naphthyridin-2-yl)ethoxy)-1H-indazol-1-yl)propanoic acid; 3-(1-Methyl-1H-pyrazolo[4,3-b]pyridin-6-yl)-3-(5-(2-(5,6,7,8-tetrahydro-1-,8-naphthyridin-2-yl)ethoxy)-1H-indazol-1-yl)propanoic acid; (R)-3-(5-(1,3-dioxolan-2-yl)pyridin-3-yl)-3-(5-(2-(5,6,7,8-tetrahydro-1,8-naphthyridin-2-yl)ethoxy)-1H-indazol-1-yl)propanoic acid; (S)-3-(5-(1,3-dioxolan-2-yl)pyridin-3-yl)-3-(5-(2-(5,6,7,8-tetrahydro-1,8-naphthyridin-2-yl)ethoxy)-1H-indazol-1-yl)propanoic acid; 3-(1-methyl-1H-imidazo[4,5-b]pyridin-6-yl)-3-(5-(2-(5,6,7,8-tetrahydro-1,-8-naphthyridin-2-yl)ethoxy)-1H-indazol-1-yl)propanoic acid; 3-(5-(1H-pyrazol-5-yl)pyridin-3-yl)-3-(5-(2-(5,6,7,8-tetrahydro-1,8-naphthyridin-2-yl)ethoxy)-1H-indazol-1-yl)propanoic acid; 3-(6-morpholinopyrazin-2-yl)-3-(5-(2-(5,6,7,8-tetrahydro-1,8-naphthyridin-2-yl)ethoxy)-1H-indazol-1-yl)propanoic acid; 3-(5-(1-methyl-1H-pyrazol-4-yl)pyridin-3-yl)-3-(5-(2-(5,6,7,8-tetrahydro-1,8-naphthyridin-2-yl)ethoxy)-1H-indazol-1-yl)propanoic acid; 3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid; (R)-3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid; (S)-3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid; (R)-3-(2-methoxypyrimidin-5-yl)-3-(5-(2-(5,6,7,8-tetrahydro-1,8-naphthyridin-2-yl)ethoxy)-1H-indazol-1-yl)propanoic acid; (S)-3-(2-methoxypyrimidin-5-yl)-3-(5-(2-(5,6,7,8-tetrahydro-1,8-naphthyridin-2-yl)ethoxy)-1H-indazol-1-yl)propanoic acid; 3-(6-methoxypyrazin-2-yl)-3-(5-(2-(5,6,7,8-tetrahydro-1,8-naphthyridin-2-yl)ethoxy)-1H-indazol-1-yl)propanoic acid; (R)-3-(5-(2-oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid; (S)-3-(5-(2-oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid; 3-(5-(morpholine-4-carbonyl)pyridin-3-yl)-3-(5-(2-(5,6,7,8-tetrahydro-1,8-naphthyridin-2-yl)ethoxy)-1H-indazol-1-yl)propanoic acid; 3-(5-(dimethylcarbamoyl)pyridin-3-yl)-3-(5-(2-(5,6,7,8-tetrahydro-1,8-naphthyridin-2-yl)ethoxy)-1H-indazol-1-yl)propanoic acid; 3-(5-(4-methylpiperazine-1-carbonyl)pyridin-3-yl)-3-(5-(2-(5,6,7,8-tetrahydro-1,8-naphthyridin-2-yl)ethoxy)-1H-indazol-1-yl)propanoic acid; 3-(5-cyclopropylpyridin-3-yl)-3-(5-(2-(5,6,7,8-tetrahydro-1,8-naphthyridin-2-yl)ethoxy)-1H-indazol-1-yl)propanoic acid; 3-(5-(4-methylpiperazin-1-yl)pyridin-3-yl)-3-(5-(2-(5,6,7,8-tetrahydro-1,-8-naphthyridin-2-yl)ethoxy)-1H-indazol-1-yl)propanoic acid; 3-(5-(azetidine-1-carbonyl)pyridin-3-yl)-3-(5-(2-(5,6,7,8-tetrahydro-1,8-naphthyridin-2-yl)ethoxy)-1H-indazol-1-yl)propanoic acid; 3-(5-((2-(dimethylamino)

ethyl)carbamoyl)pyridin-3-yl)-3-(5-(2-(5,6,7,8-tetrahydro-1,8-naphthyridin-2-yl)ethoxy)-1H-indazol-1-yl)propanoic acid; (S)-3-(2-methylpyrimidin-5-yl)-3-(5-(2-(5,6,7,8-tetrahydro-1,8-naphthyridin-2-yl)ethoxy)-1H-indazol-1-yl)propanoic acid; (R)-3-(2-methylpyrimidin-5-yl)-3-(5-(2-(5,6,7,8-tetrahydro-1,8-naphthyridin-2-yl)ethoxy)-1H-indazol-1-yl)propanoic acid; 3-(5-(1H-pyrazol-1-yl)pyridin-3-yl)-3-(5-(2-(5,6,7,8-tetrahydro-1,8-naphthyridin-2-yl)ethoxy)-1H-indazol-1-yl)propanoic acid; 3-(5-(2-(5,6,7,8-tetrahydro-1,8-naphthyridin-2-yl)ethoxy)-1H-indazol-1-yl-)hexanoic acid; 3-(5-(dimethylamino)pyridin-3-yl)-3-(5-(2(5,6,7,8-tetrahydro-1,8-naphthyridin-2-yl)ethoxy)-1H-indazol-1-yl)propanoic acid; 3-cyclohexyl-3-(5-(2-(5,6,7,8-tetrahydro-1,8-naphthyridin-2-yl)ethoxy)-1H-indazol-1-yl)propanoic acid; (R)-3-(5-(methylsulfonyl)pyridin-3-yl)-3-(5-(2-(5,6,7,8-tetrahydro-1,8-naphthyridin-2-yl)ethoxy)-1H-indazol-1-yl)propanoic acid; (S)-3-(5-(methyl sulfonyl)pyridin-3-yl)-3-(5-(2-(5,6,7,8-tetrahydro-1,8-naphthyridin-2-yl)-ethoxy)-1H-indazol-1-yl)propanoic acid; 3-(5-(((methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid; (R)-3-(5-(((methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid; (S)-3-(5-(((methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid; 3-(5-(methylsulfonamidomethyl)pyridin-3-yl)-3-(5-(2-(5,6,7,8-tetrahydro-1,-8-naphthyridin-2-yl)ethoxy)-1H-indazol-1-yl)propanoic acid; 3-(5-(acetamidomethyl)pyridin-3-yl)-3-(5-(2-(5,6,7,8-tetrahydro-1,8-naphthyridin-2-yl)ethoxy)-1H-indazol-1-yl)propanoic acid; 3-(5-(2-(5,6,7,8-Tetrahydro-1,8-naphthyridin-2-yl)ethoxy)-1H-indazol-1-yl-)-3-(5,6,7,8-tetrahydro-1,8-naphthyridin-3-yl)propanoic acid; 4-((6-(2-Carboxy-1-(5-(2-(5,6,7,8-tetrahydro-1,8-naphthyridin-2-yl)ethoxy-)-1H-indazol-1-yl)ethyl)pyrazin-2-yl)amino)butanoic acid; 3-(6-Methoxypyridin-3-yl)-3-(4-(2-(5,6,7,8-tetrahydro-1,8-naphthyridin-2-yl)ethyl)-1H-indazol-1-yl)propanoic acid; (R)-3-(5-(2-((R)-7-methyl-5,6,7,8-tetrahydro-1,8-naphthyridin-2-yl)ethoxy-)-1H-indazol-1-yl)-3-(2-methylpyrimidin-5-yl)propanoic acid; (S)-3-(5-(2-((R)-7-methyl-5,6,7,8-tetrahydro-1,8-naphthyridin-2-yl)ethoxy-)-1H-indazol-1-yl)-3-(2-methylpyrimidin-5-yl)propanoic acid; (R)-3-(5-(2-((S)-7-methyl-5,6,7,8-tetrahydro-1,8-naphthyridin-2-yl)ethoxy-)-1H-indazol-1-yl)-3-(2-methylpyrimidin-5-yl)propanoic acid; (S)-3-(5-(2-((S)-7-methyl-5,6,7,8-tetrahydro-1,8-naphthyridin-2-yl)ethoxy-)-1H-indazol-1-yl)-3-(2-methylpyrimidin-5-yl)propanoic acid; 3-(6-Methoxypyridin-3-yl)-3-(5-(2-(1-methyl-1,2,3,4-tetrahydropyrido[2,3-b]pyrazin-6-yl)ethoxy)-1H-indazol-1-yl)propanoic acid; (S)-3-(5-(2-(3,4-dihydro-2H-pyrido[3,2-b][1,4]oxazin-6-yl)ethoxy)-1H-indazol-1-yl)-3-(6-methoxypyridin-3-yl)propanoic acid; and (R)-3-(5-(2-(3,4-dihydro-2H-pyrido[3,2-b][1,4]oxazin-6-yl)ethoxy)-1H-indazol-1-yl)-3-(6-methoxypyridin-3-yl)propanoic acid; or a pharmaceutically acceptable salt thereof. See US 2019/0256496, which is hereby incorporated by reference it its entirety.

In some embodiments, the integrin antagonist is (S)-3-(3-(2-methoxyethoxy)phenyl)-4-((R)-3-(2-(5,6,7,8-tetrahydro-1,8-naphthyridin-2-yl)ethyl)pyrrolidin-1-yl)butanoic acid; (S)-3-(3-((R)-2-methoxypropoxylphenyl)-4-((R)-3-(2-(5,6,7,8-tetrahydro-1,-8-naphthyridin-2-yl)ethyl)pyrrolidin-1-yl)butanoic acid; (S)-3-(3-((S)-2-methoxypropoxylphenyl)-4-4R)-3-(2-(5,6,7,8-tetrahydro-1,8-naphthyridin-2-yl)ethyl)pyrrolidin-1-yl)butanoic acid; (S)-3-(3-(2-methoxy-2-methylpropoxy)phenyl)-44(R)-3-(2-(5,6,7,8-tetrahydro-1,8-naphthyridin-2-yl)ethyl)pyrrolidin-1-yl)butanoic acid; 3-(3-(((S)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid; (S)-4-((R)-3-(2-(5,6,7,8-tetrahydro-1,8-naphthyridin-2-yl)ethyl)pyrrolidin-1-yl)-3-(3-(((S)-tetrahydrofuran-3-yl)oxy)phenyl)butanoic acid; (S)-4-((R)-3-(2-(5,6,7,8-tetrahydro-1,8-naphthyridin-2-yl)ethyl)pyrrolidin-1-yl)-3-(3-(((R)-tetrahydrofuran-3-yl)oxy)phenyl)butanoic acid; (S)-3-(3,5-Bis(2-methoxyethoxy)phenyl)-4-((R)-3-(2-(5,6,7,8-tetrahydro-1,-8-naphthyridin-2-yl)ethyl)pyrrolidin-1-yl)butanoic acid; (3S)-4-((R)-3-(2-(5,6,7,8-Tetrahydro-1,8-naphthyridin-2-yl)ethyl)pyrrolidin-1-yl)-3-(3-(tetrahydrofuran-3-yl)phenyebutanoic acid; (3S)-4-((R)-3-(2-(5,6,7,8-Tetrahydro-1,8-naphthyridin-2-yl)ethyl)pyrrolidin-1-yl)-3-(3-(tetrahydrofuran-3-yl)phenyebutanoic acid; (S)-3-(3-((1-methoxy-2-methylpropan-2-yl)oxy)phenyl)-4-4R)-3-(2-(5,6,7,8-tetrahydro-1,8-naphthyridin-2-yl)ethyl)pyrrolidin-1-yl)butanoic acid; (S)-3-(3-(((R)-1-methoxypropan-2-yl)oxy)phenyl)-4-((R)-3-(2-(5,6,7,8-tetrahydro-1,8-naphthyridin-2-yl)ethyl)pyrrolidin-1-yl)butanoic acid; (S)-3-(3-(2-Isopropoxyethoxy)phenyl)-4-((R)-3-(2-(5,6,7,8-tetrahydro-1,8-naphthyridin-2-yl)ethyl)pyrrolidin-1-yl)butanoic acid; (S)-4-((R)-3-(2-(5,6,7,8-Tetrahydro-1,8-naphthyridin-2-yl)ethyl)pyrrolidin-1-yl)-3-(3-(((R)-tetrahydrofuran-2-yl)methoxy)phenyl)butanoic acid; (S)-4-((R)-3-(2-(5,6,7,8-tetrahydro-1,8-naphthyridin-2-yl)ethyl)pyrrolidin-1-yl)-3-(3-(((S)-tetrahydrofuran-2-yl)methoxy)phenyl)butanoic acid; (S)-3-(2-Fluoro-5-(2-methoxyethoxy)phenyl)-4-((R)-3-(2-(5,6,7,8-tetrahydro-1,8-naphthyridin-2-yl)ethyl)pyrrolidin-1-yl)butanoic acid; 3-(3-((1,3-Dimethoxypropan-2-yeoxy)phenyl)-4-((R)-3-(2-(5,6,7,8-tetrahydro-1,8-naphthyridin-2-yl)ethyl)pyrrolidin-1-yl)butanoic acid; 3-(3-(2-Fluoroethoxy)-5-(2-methoxyethoxy)phenyl)-4-((R)-3-(2-(5,6,7,8-tetrahydro-1,8-naphthyridin-2-yl)ethyl)pyrrolidin-1-yl)butanoic acid; 3-(3-(3-Methoxypropoxy)phenyl)-4-((R)-3-(2-(5,6,7,8-tetrahydro-1,8-naphthyridin-2-yl)ethyl)pyrrolidin-1-yl)butanoic acid; or 3-(3-(Oxetan-3-ylmethoxy)phenyl)-4-((R)-3-(2-(5,6,7,8-tetrahydro-1,8-naphthyridin-2-yl)ethyl)pyrrolidin-1-yl)butanoic acid; or a pharmaceutically acceptable salt thereof. See US 2019/0112306, which is hereby incorporated by reference it its entirety.

In some embodiments, the integrin antagonist has the structure

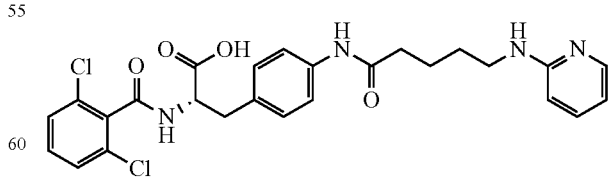

or a pharmaceutically acceptable salt thereof. See U.S. Pat. No 10,214,522, which is hereby incorporated by reference it its entirety.

In some embodiments, the integrin antagonist has the structure
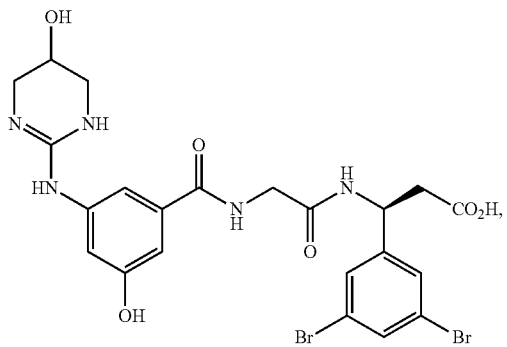
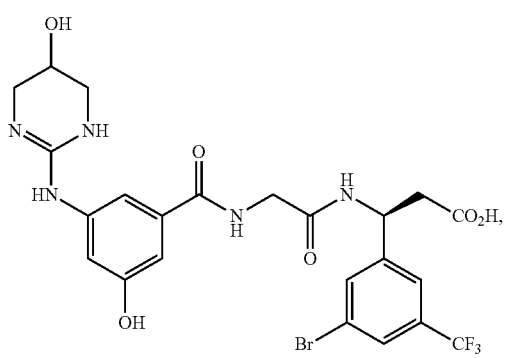
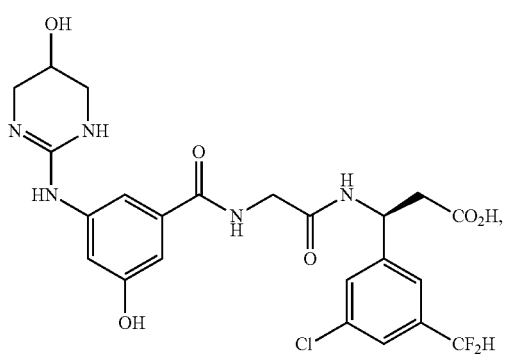
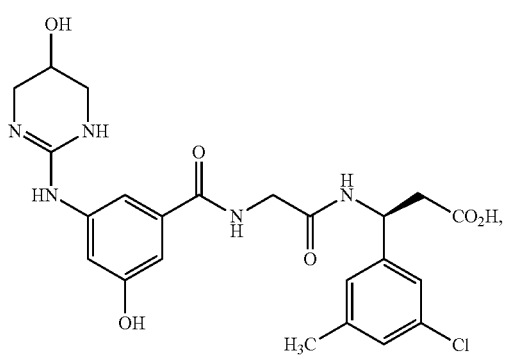
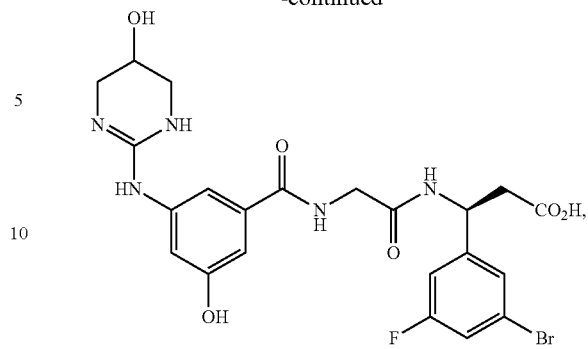
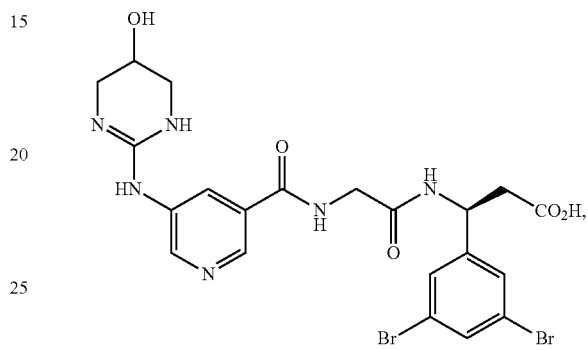
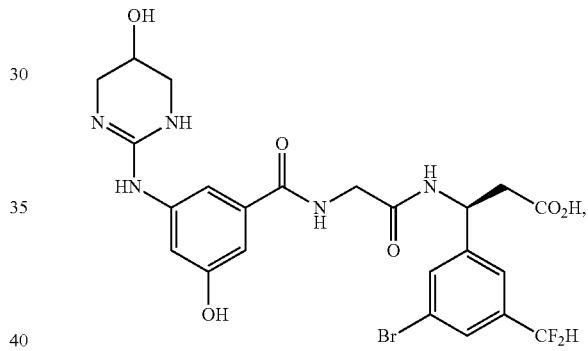
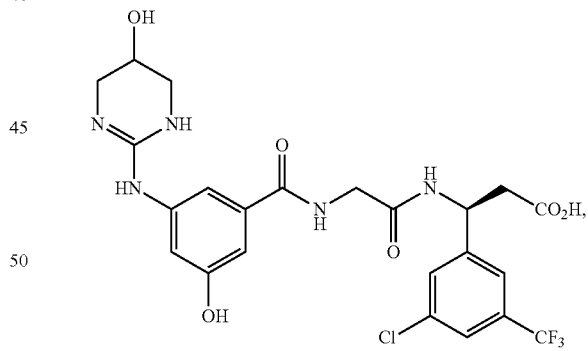
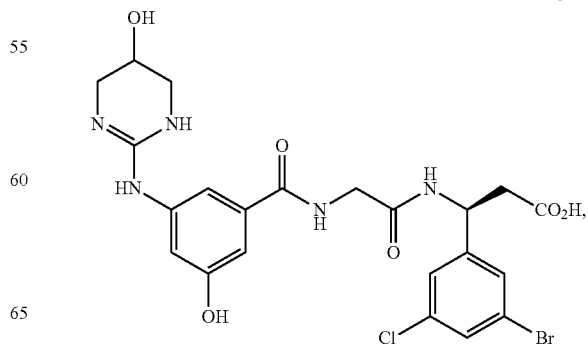

153
-continued
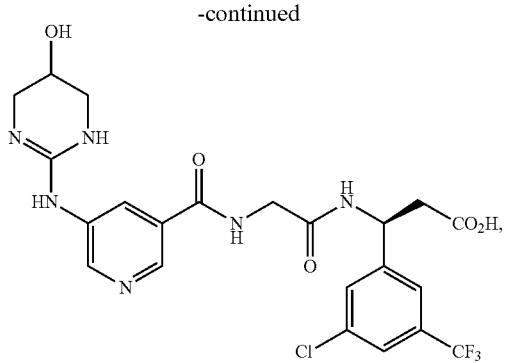
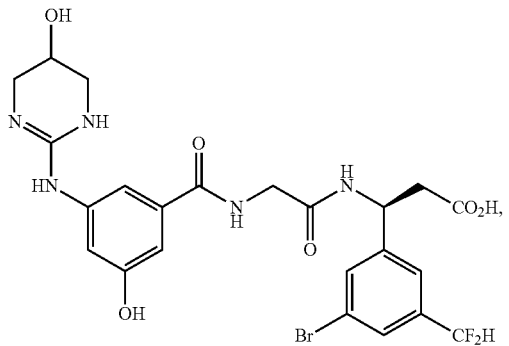
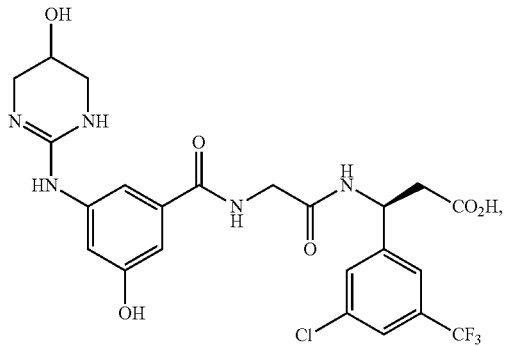
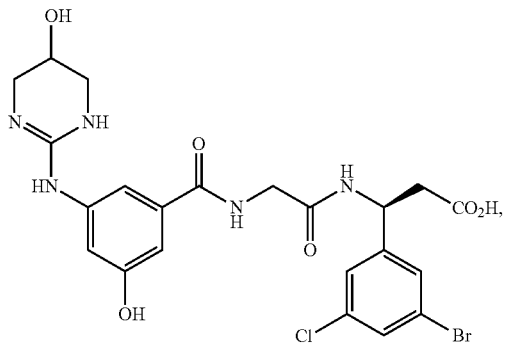
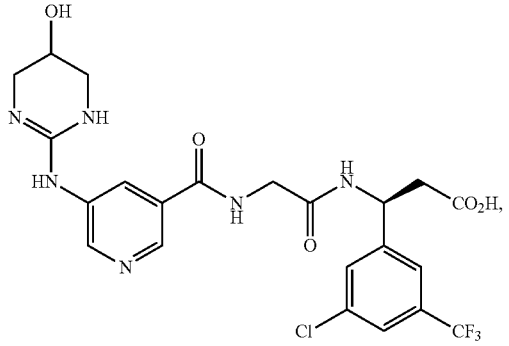
154
-continued
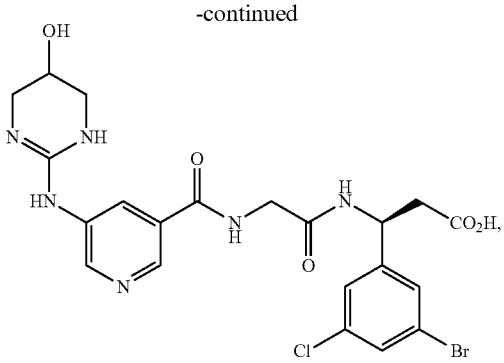
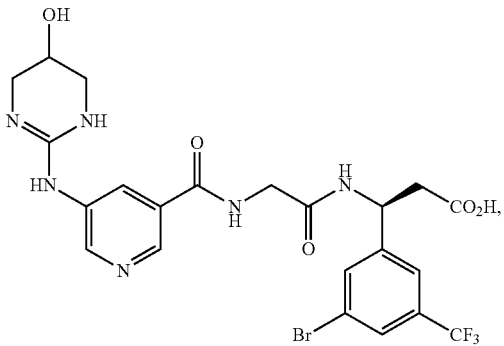
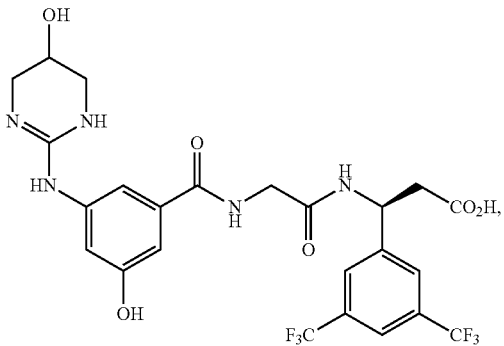
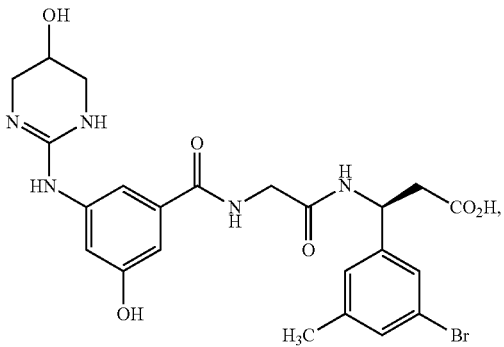
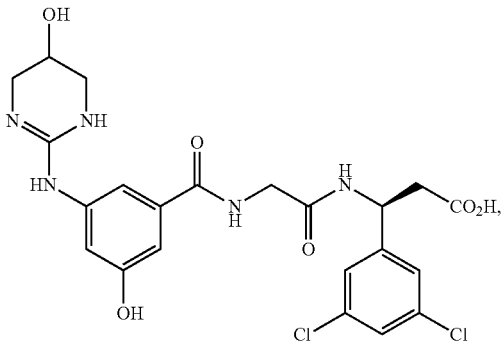

-continued

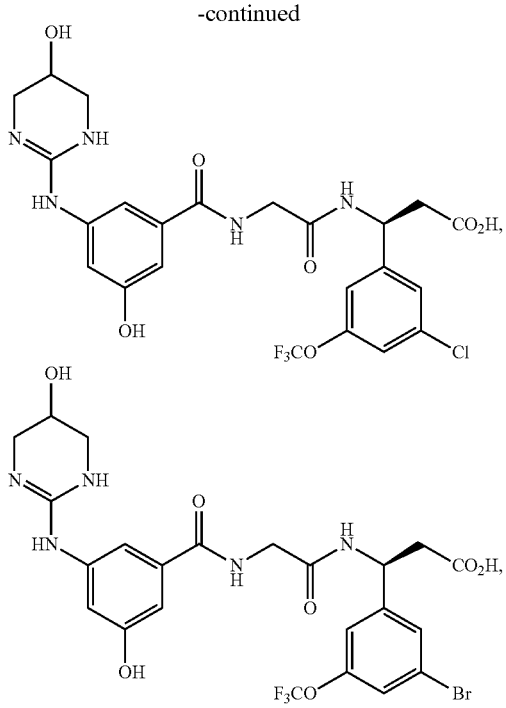

or a pharmaceutically acceptable salt thereof. See US 2018/0072684, which is hereby incorporated by reference it its entirety.

In some embodiments, the non-steroidal Farnesoid X receptor (FXR) agonist is cilofexor.

In some embodiments, the combinations of the invention comprise selonsertib, firsocostat or cilofexor. In some embodiments, the combinations of the invention comprise selonsertib and firsocostat. In some embodiments, the combinations of the invention comprises selonsertib and cilofexor. In some embodiments, the combinations of the invention comprises fircosostat and cilofexor. In some embodiments, the combinations of the invention comprise selonsertib, firsocostat and cilofexor.

In some embodiments, the pharmaceutically acceptable carrier or vehicle includes, but is not limited to, a binder, filler, diluent, disintegrant, wetting agent, lubricant, glidant, coloring agent, dye-migration inhibitor, sweetening agent or flavoring agent.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof.

Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In some embodiments, the binder is hydroxypropylcellulose.

The binder or filler can be present from about 2% to about 49% by weight of the compositions of the invention provided herein or any range within these values. In some embodiments, the binder or filler is present in the composition of the invention from about 5% to about 15% by weight. In some embodiments, the binder or filler is present in the composition of the invention at about 5%, about 6%, about 7%, about 8%, about 9%, about 8%, about 10%, about 11%, about 12%, about 13%, about 14%, or about 15% by weight or any range within any of these values.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. In some embodiments, the diluent is lactose monohydrate. In some embodiments, the diluent is lactose monohydrate Fast-Flo 316 NF.

The compositions of the invention can comprise a diluent, e.g., from about 5% to about 49% of a diluent by weight of composition or any range between any of these values. In some embodiments, the diluent is present in the compositions of the invention from about 15% to about 30% by weight. In some embodiments, the diluent is present in the composition of the invention at about 15%, about 16%, about 17%, about 18%, about 19%, about 18%, about 20%, about 21%, about 22%, about 23%, about 24%, about 25%, about 26%, about 27%, about 28%, about 29%, or about 30% by weight or any range within any of these values.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the compositions of the invention can vary. In some embodiments, the disintegrant is croscarmellose sodium. In some embodiments, the disintegrant is croscarmellose sodium NF (Ac-Di-Sol).

The compositions of the invention can comprise a disintegrant, e.g., from about 0.5% to about 15% or from about 1% to about 10% by weight of a disintegrant. In some embodiments, the compositions of the invention comprise a disintegrant in an amount of about 5%, about 6%, about 7%, about 8%, about 9%, about 8%, about 10%, about 11%, about 12%, about 13%, about 14%, or about 15% by weight of the composition or in any range within any of these values.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. In some embodiments, the lubricant is magnesium stearate.

The compositions of the invention can comprise a lubricant, e.g., about 0.1 to about 5% by weight of a lubricant. In some embodiments, the compositions of the invention comprise a lubricant in an amount of about 0.5%, 0.6%, 0.7%, 0.8%, 0.9%, 0.8%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, or 3.0%, by weight of the composition or in any range within any of these values.

Suitable glidants include colloidal silicon dioxide, CAB-O-SIL® (Cabot Co. of Boston, Mass.), and talc, including asbestos-free talc.

Coloring agents include any of the approved, certified, water soluble FD&C dyes, and water insoluble FD&C dyes suspended on alumina hydrate, and color lakes and mixtures thereof.

Flavoring agents include natural flavors extracted from plants, such as fruits, and synthetic blends of compounds that provide a pleasant taste sensation, such as peppermint and methyl salicylate.

Sweetening agents include sucrose, lactose, mannitol, syrups, glycerin, sucralose, and artificial sweeteners, such as saccharin, stevioside (*Stevia*) and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether.

Solvents include glycerin, sorbitol, ethyl alcohol, and syrup.

Examples of non-aqueous liquids utilized in emulsions include mineral oil and cottonseed oil. Organic acids include citric and tartaric acid. Sources of carbon dioxide include sodium bicarbonate and sodium carbonate.

The compounds of the invention and the compositions of the invention can be formulated for administration by a variety of means including orally, parenterally, by inhalation spray, topically, or rectally in formulations containing pharmaceutically acceptable carriers, adjuvants and vehicles. The term "parenteral" as used here includes subcutaneous, intravenous, intramuscular, and intraarterial injections with a variety of infusion techniques. Intraarterial and intravenous injection as used herein includes administration through catheters.

The compounds of the invention and the compositions of the invention can be formulated in accordance with the routine procedures adapted for desired administration route. Accordingly, the compositions of the invention can take such forms as suspensions, solutions or emulsions in oily or aqueous vehicles, and can contain formulatory agents such as suspending, stabilizing and/or dispersing agents. The compounds of the invention and the compositions of the invention can be formulated as a preparation suitable for implantation or injection. Thus, for example, the compositions of the invention can be formulated with suitable polymeric or hydrophobic materials (e.g., as an emulsion in an acceptable oil) or ion exchange resins, or as sparingly soluble derivatives (e.g., as a sparingly soluble salt). The compounds of the invention and the compositions of the invention can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In some embodiments, the compositions of the invention are suitable for oral administration. These compositions can comprise solid, semisolid, gelmatrix or liquid dosage forms suitable for oral administration. As used herein, oral administration includes buccal, lingual, and sublingual administration. Suitable oral dosage forms include, without limitation, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups or any combination thereof. In some embodiments, compositions of the invention suitable for oral administration are in the form of a tablet or a capsule. In some embodiments, the composition of the invention is in a form of a tablet. In some embodiments, the composition of the invention is in a form of a capsule. In some embodiments, the compound of the invention is contained in a capsule.

In some embodiments, capsules are immediate release capsules. Non-limiting example of a capsule is a Conisnap® hard gelatin capsule.

The compositions of the invention can be in the form of compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which can be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. A film coating can impart the same general characteristics as a sugar coating. Multiple compressed tablets are compressed tablets made by more than one compression cycle, including layered tablets, and press-coated or dry-coated tablets.

In some embodiments, the coating is a film coating. In some embodiments, the film coating comprises Opadry White and simethicone emulsion 30% USP.

In some embodiments, the compound of the invention is contained in a tablet. In some embodiments, the compound of the invention is contained in a compressed tablet. In some embodiments, the compound of the invention is contained in a film-coated compressed tablet. In some embodiments, the compositions of the invention are in the form of film-coated compressed tablets.

In some embodiments, the compositions of the invention is prepared by fluid bed granulation of the compound of the invention with one or more pharmaceutically acceptable carrier, vehicle, or excipients. In some embodiments, the compositions of the invention prepared by fluid bed granulation process can provide tablet formulation with good flowability, good compressibility, fast dissolution, good stability, and/or minimal to no cracking. In some embodiments, the fluid bed granulation process allows preparation of formulations having high drug loading, such as over 70% or over 75% of a compound of the invention.

The compositions of the invention can be in the form of soft or hard capsules, which can be made from gelatin, methylcellulose, starch, or calcium alginate. The hard gelatin capsule, also known as the dry-filled capsule (DFC), can comprise of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells can contain a preservative to prevent the growth of microorganisms. Suitable preservatives are those as described herein, including methyl- and propyl-parabens, and sorbic acid. The liquid, semisolid, and solid dosage forms provided herein can be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules can also be coated as known by those of skill in the art in order to modify or sustain dissolution of the active ingredient.

The compositions of the invention can be in liquid or semisolid dosage forms, including emulsions, solutions, suspensions, elixirs, and syrups. An emulsion can be a two-phase system, in which one liquid is dispersed in the form of small globules throughout another liquid, which can be oil-in-water or water-in-oil. Emulsions can include a pharmaceutically acceptable non-aqueous liquids or solvent, emulsifying agent, and preservative. Suspensions can include a pharmaceutically acceptable suspending agent and preservative. Aqueous alcoholic solutions can include a pharmaceutically acceptable acetal, such as a di-(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs can be clear, sweetened, and hydroalcoholic solutions. Syrups can be concentrated aqueous solutions of a sugar, for example, sucrose, and can comprise a preservative. For a liquid dosage form, for example, a solution in a polyethylene glycol can be diluted with a sufficient quantity of a pharmaceutically acceptable liquid carrier, e.g., water, to be measured conveniently for administration.

The compositions of the invention for oral administration can be also provided in the forms of liposomes, micelles, microspheres, or nanosystems. Micellar dosage forms can be prepared as described in U.S. Pat. No. 6,350,458.

The compositions of the invention can be provided as non-effervescent or effervescent, granules and powders, to be reconstituted into a liquid dosage form. Pharmaceutically acceptable carriers and excipients used in the non-effervescent granules or powders can include diluents, sweeteners, and wetting agents. Pharmaceutically acceptable carriers and excipients used in the effervescent granules or powders can include organic acids and a source of carbon dioxide.

Coloring and flavoring agents can be used in all of the above dosage forms. And, flavoring and sweetening agents are especially useful in the formation of chewable tablets and lozenges.

The compositions of the invention can be formulated as immediate or modified release dosage forms, including delayed-, extended, pulsed-, controlled, targeted-, and programmed-release forms.

In some embodiments, the compositions of the invention comprise a film-coating.

The compositions of the invention can comprise another active ingredient that does not impair the composition's therapeutic or prophylactic efficacy or can comprise a substance that augments or supplements the composition's efficacy.

The tablet dosage forms can comprise the compound of the invention in powdered, crystalline, or granular form, and can further comprise a carrier or vehicle described herein, including binder, disintegrant, controlled-release polymer, lubricant, diluent, or colorant.

In some embodiments, the compositions of the invention can further comprise an excipient such as a diluent, a disintegrant, a wetting agent, a binder, a glidant, a lubricant, or any combination thereof. In some embodiments, a tablet comprises a binder. And, in some embodiments, the binder comprises microcrystalline cellulose, dibasic calcium phosphate, sucrose, corn starch, polyvinylpyrridone, hydroxypropyl cellulose, hydroxymethyl cellulose, or any combination thereof. In other embodiments, the tablet comprises a disintegrant. In other embodiments, the disintegrant comprises sodium croscarmellose, sodium starch glycolate, or any combination thereof. In other embodiments, the tablet comprises a lubricant. And, in some embodiments, the lubricant comprises magnesium stearate stearic acid, hydrogenated oil, sodium stearyl fumarate, or any combination thereof.

In some embodiments, the compositions of the invention are in the form of a tablet that comprises a binder such as any of the binders described herein.

In some embodiments, the compositions of the invention are in the form of a tablet that comprises a disintegrant such as any of the disintegrants described herein.

In some embodiments, the compositions of the invention are in the form of a tablet that comprises a lubricant such as any of the lubricants described herein.

In some embodiments, the compositions of the invention can be in a modified release or a controlled release dosage form. In some embodiments, the compositions of the invention can comprise particles exhibiting a particular release profile. For example, the composition of the invention can comprise a compound of the invention in an immediate release form while also comprising a statin or a pharmaceutically acceptable salt, solvate, ester, amide, or prodrug thereof in a modified release form, both compressed into a single tablet. Other combination and modification of release profile can be achieved as understood by one skilled in the art. Examples of modified release dosage forms suited for pharmaceutical compositions of the instant invention are described, without limitation, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

In some embodiments, the compositions of the invention are a matrix-controlled release dosage form. In some embodiments, the release profile of the compound of the invention and of the other pharmaceutically active agent is the same or different. Suitable matrix-controlled release dosage forms are described, for example, in Takada et al in "Encyclopedia of Controlled Drug Delivery," Vol. 2, Mathiowitz ed., Wiley, 1999.

In some embodiments, the matrix-controlled release form comprises an erodible matrix comprising water-swellable, erodible, or soluble polymers, including synthetic polymers, and naturally occurring polymers and derivatives, such as polysaccharides and proteins.

In some embodiments, the erodible matrix of the matrix-controlled release form comprises chitin, chitosan, dextran, or pullulan; gum agar, gum arabic, gum karaya, locust bean gum, gum tragacanth, carrageenans, gum ghatti, guar gum, xanthan gum, or scleroglucan; starches, such as dextrin or maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), carrrboxymethyl ethyl cellulose (CMEC) hydroxyethyl cellulose (HEC), hydroxypropyl cellulose (HPC), cellulose acetate (CA), cellulose propionate (CP), cellulose butyrate (CB), cellulose acetate butyrate (CAB), cellulose acetate phthalate (CAP), cellulose acetate trimellitate (CAT), hydroxypropyl methyl cellulose (HPMC), HPMCP, HPMCAS, hydroxypropyl methyl cellulose acetate trimellitate (HPMCAT), or ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; or other acrylic acid derivatives, such as homopolymers and copolymers of butylmethacrylate, methylmethacrylate, ethylmethacrylate, ethylacrylate, (2-dimethylaminoethyl)methacrylate, or (trimethylaminoethyl)methacrylate chloride; or any combination thereof.

In other embodiments, the compositions of the invention are in a matrix-controlled modified release form comprising a non-erodible matrix. In some embodiments, the statin, the compound of the invention is dissolved or dispersed in an inert matrix and is released primarily by diffusion through the inert matrix once administered. In some embodiments, the non-erodible matrix of the matrix-controlled release form comprises an insoluble polymer, such as polyethylene, polypropylene, polyisoprene, polyisobutylene, polybutadiene, polymethylmethacrylate, polybutylmethacrylate, chlorinated polyethylene, polyvinylchloride, a methyl acrylate-methyl methacrylate copolymer, an ethylene-vinylacetate copolymer, an ethylene/propylene copolymer, an ethylene/ethyl acrylate copolymer, a vinylchloride copolymer with vinyl acetate, a vinylidene chloride, an ethylene or a propylene, an ionomer polyethylene terephthalate, a butyl rubber epichlorohydrin rubber, an ethylene/vinyl alcohol copolymer, an ethylene/vinyl acetate/vinyl alcohol terpolymer, an ethylene/vinyloxyethanol copolymer, a polyvinyl chloride, a plasticized nylon, a plasticized polyethyleneterephthalate, a natural rubber, a silicone rubber, a polydimethylsiloxane, a silicone carbonate copolymer, or a hydrophilic polymer, such as an ethyl cellulose, a cellulose acetate, a crospovidone, or a cross-linked partially hydrolyzed polyvinyl acetate; a fatty compound, such as a carnauba wax, a microcrystalline wax, or a triglyceride; or any combination thereof.

The compositions of the invention that are in a modified release dosage form can be prepared by methods known to those skilled in the art, including direct compression, dry or wet granulation followed by compression, melt-granulation followed by compression.

In some embodiments, the compositions of the invention comprise a tablets-in-capsule system, which can be a multifunctional and multiple unit system comprising versatile mini-tablets in a hard gelatin capsule. The mini-tablets can be rapid-release, extended-release, pulsatile, delayed-onset extended-release minitablets, or any combination thereof. In some embodiments, combinations of mini-tablets or combinations of mini-tablets and minibeads comprising multiple active pharmaceutical agents can each have specific lag times, of release multiplied pulsatile drug delivery system (DDS), site-specific DDS, slow-quick DDS, quick/slow DDS and zero-order DDS.

In some embodiments, the compositions of the invention are in an osmotic-controlled release dosage form.

In some embodiments, the osmotic-controlled release device comprises a one-chamber system, a two-chamber system, asymmetric membrane technology (AMT), an extruding core system (ECS), or any combination thereof. In some embodiments, such devices comprise at least two components: (a) the core which contains the active pharmaceutical agent(s); and (b) a semipermeable membrane with at least one delivery port, which encapsulates the core. The semipermeable membrane controls the influx of water to the core from an aqueous environment of use so as to cause drug release by extrusion through the delivery port(s).

In some embodiments, the core of the osmotic device optionally comprises an osmotic agent, which creates a driving force for transport of water from the environment of use into the core of the device. One class of osmotic agents useful in the compositions of invention comprises water-swellable hydrophilic polymers, which are also referred to as "osmopolymers" or "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly(acrylic) acid, poly (methacrylic) acid, polyvinylpyrrolidone (PVP), cross-linked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

Another class of osmotic agents useful in the compositions of the invention comprises osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the compound of the invention dissolves following administration. For example, an amorphous sugar, such as Mannogeme EZ (SPI Pharma, Lewes, Del.) can be included to provide faster delivery during the first couple of hours (e.g., about 1 to about 5 hrs) to promptly produce prophylactic or therapeutic efficacy, and gradually and continually release of the remaining amount to maintain the desired level of therapeutic or prophylactic effect over an extended period of time. In some embodiments, the compound of the invention is released from the compositions of the invention at such a rate to replace the amount of the compound of the invention metabolized or excreted by the subject.

The core can also include a wide variety of other excipients and carriers as described herein to enhance the performance of the dosage form or to promote stability or processing.

Materials useful for forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

The semipermeable membranes can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the compound of the invention released and the release rate can substantially be modulated via the thickness and porosity of the semipermeable membrane, the composition of the core, and the number, size, and position of the delivery ports.

In some embodiments, the pharmaceutical composition in an osmotic controlled-release dosage form can further comprise additional conventional excipients as described herein to promote performance or processing of the formulation.

The osmotic controlled-release dosage forms can be prepared according to conventional methods and techniques known to those skilled in the art (see, Remington: The Science and Practice of Pharmacy, supra; Santus and Baker, J. Controlled Release 1995, 35, 1-21; Verma et al., Drug Development and Industrial Pharmacy 2000, 26, 695-708; Verma et al., J. Controlled Release 2002, 79, 7-27).

In some embodiments, the pharmaceutical composition provided herein is formulated as asymmetric membrane technology (AMT) controlled-release dosage form that comprises an asymmetric osmotic membrane that coats a core comprising the active ingredient(s) and other pharmaceutically acceptable excipients. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In some embodiments, the pharmaceutical composition provided herein is formulated as ESC controlled-release dosage form that comprises an osmotic membrane that coats a core comprising the compound of the invention, hydroxylethyl cellulose, and other pharmaceutically acceptable excipients.

In some embodiments, the compositions of the invention are a modified release dosage form that is fabricated as a multiparticulate-controlled release dosage form that comprises a plurality of particles, granules, or pellets, microparticulates, beads, microcapsules and microtablets, ranging from about 10 µm to about 3 mm, about 50 µm to about 2.5 mm, or from about 100 µm to 1 mm in diameter.

The multiparticulate-controlled release dosage forms can provide a prolonged release dosage form with an improved bioavailability. Suitable carriers to sustain the release rate of the compound of the invention include, without limitation, ethyl cellulose, HPMC, HPMC-phtalate, colloidal silicondioxide and Eudragit-RSPM.

Compositions of the invention in pellet form can comprise 50-80% (w/w) of a drug and 20-50% (w/w) of microcrystalline cellulose or other polymers. Suitable polymers include, but are not limited to, microcrystalline wax, pregelatinized starch and maltose dextrin.

Beads can be prepared in capsule and tablet dosage forms. Beads in tablet dosage form can demonstrate a slower dissolution profile than microparticles in capsule form. Microparticle fillers suitable for compositions and therapeutic or prophylactic methods of the invention include, without limitation, sorbitan monooleate (Span 80), HPMC, or any combination thereof. Suitable dispersions for controlled release latex include, for example, ethyl-acrylate and methyl-acrylate.

In some embodiments, the compositions of the invention are in the form or microcapsules and/or microtablets. In some embodiments, microcapsules comprise extended release polymer microcapsules containing a statin and a compound of the invention with various solubility characteristics. Extended release polymer microcapsules can be prepared with colloidal polymer dispersion in an aqueous environment. In other embodiments, microcapsules suitable for the compositions and methods provided herein can be prepared using conventional microencapsulating techniques (Bodmeier & Wang, 1993).

Such multiparticulates can be made by the processes known to those skilled in the art, including wet- and dry-granulation, extrusion/spheronization, roller-compaction, melt-congealing, and by spray-coating seed cores. See, for example, Multiparticulate Oral Drug Delivery; Marcel Dekker: 1994; and Pharmaceutical Pelletization Technology; Marcel Dekker: 1989. Excipients for such technologies are commercially available and described in US Pharmacopeia.

Other excipients as described herein can be blended with the compositions of the invention to aid in processing and forming the multiparticulates. The resulting particles can themselves constitute the multiparticulate dosage form or can be coated by various film-forming materials, such as enteric polymers, water-swellable, or water-soluble polymers. The multiparticulates can be further processed as a capsule or a tablet.

In other embodiments, the compositions of the invention are in a dosage form that has an instant releasing component and at least one delayed releasing component, and is capable of giving a discontinuous release of the compound in the form of at least two consecutive pulses separated in time from 0.1 hr to 24 hrs.

In some embodiments, the compositions of the invention comprise from about 1 mg to about 1000 mg of a compound of the invention or any amount ranging from and to these values. In some embodiments, the compositions of the invention comprise from about 1 mg to about 500 mg of a compound of the invention or any amount ranging from and to these values. In some embodiments, the compositions of the invention comprise from about 1 mg to about 400 mg of a compound of the invention or any amount ranging from and to these values.

In other embodiments, the compositions of the invention comprise a compound of the invention in an amount that is a molar equivalent to about 1 mg to about 1000 mg of a compound of the invention or any amount ranging from and to these values. In other embodiments, the compositions of the invention comprise a compound of the invention in an amount that is a molar equivalent to about 1 mg to about 500 mg of a compound of the invention or any amount ranging from and to these values. In other embodiments, the compositions of the invention comprise a compound of the invention in an amount that is a molar equivalent to about 1 mg to about 400 mg of a compound of the invention or any amount ranging from and to these values.

In some embodiments, the compositions of the invention comprise a compound of the invention in an amount of about 10 wt % to about 99 wt % of the total weight of the composition of the invention.

5.4. Methods of the Invention

The present invention provides methods for treating or preventing a liver disorder, dyslipidemia, dyslipoproteinemia, a renal disease, a disorder of glucose metabolism, a disorder of lipid metabolism, a disorder of glucid metabolism, a cardiovascular disease, a vascular disease, a metabolic syndrome, a complication associated with metabolic syndrome, a PPAR-associated disorder, septicemia, a thrombotic disorder, obesity, diabetic nephropathy, diabetic retinopathy, atherosclerosis, pancreatitis, a cerebrovascular disease, a disorder related to neovascularization, hypertension, cancer, inflammation, an inflammatory disease, a neurodegenerative disease, an autoimmune disease, a neoplastic disease, muscle atrophy, cholestasis, mitochondrial dysfunction, an ocular disease, a lysosomal storage disease, or impotence, comprising administering to a subject in need thereof an effective amount of a compound of the invention or a composition of the invention. The present invention provides methods for treating or preventing a kidney disease (e.g., acute kidney injury), comprising administering to a subject in need thereof an effective amount of a compound of the invention or a composition of the invention.

In some embodiments, the present invention provides methods for treating or preventing a liver disorder, comprising administering to a subject in need thereof an effective amount of a compound of the invention or a composition of the invention. In some embodiments, the liver disorder involves pathological disruption, inflammation, degeneration, apoptosis, or proliferation of liver cells. In some embodiments, the liver disorder is liver fibrosis, fatty liver disease, non-alcoholic fatty liver disease (NAFLD) or non-alcoholic steatohepatitis (NASH).

In some embodiments, the present invention provides methods for reducing an abnormally high concentration of alanine transaminase (ALT), aspartate transaminase (AST), alkaline phosphatase (ALP), bilirubin, gamma-glutamyl-transferase (GGT), L-lactate dehydrogenase (LD), prothrombin time (PT), creatinine, or total protein in a subject's blood plasma or blood serum, comprising administering to a subject in need thereof an effective amount of a compound of the invention or a composition of the invention. In some embodiments, the present invention provides methods for elevating an abnormally low concentration of albumin or total protein, in a subject's blood plasma or blood serum, comprising administering to a subject in need thereof an effective amount of a compound of the invention or a composition of the invention.

An "abnormally high concentration" of ALT in a subject's blood plasma or blood serum is greater than 56 units/liter. In some embodiments, the reducing is to a normal concentration. In some embodiments, the normal concentration of ALT in a subject's blood plasma or blood serum ranges from about 7 units/liter to about 56 units/liter.

An "abnormally high concentration" of AST in a subject's blood plasma or blood serum is greater than 48 units/liter. In some embodiments, the reducing is to a normal concentration. In some embodiments, the normal concentration of AST in a subject's blood plasma or blood serum ranges from about 8 units/liter to about 48 units/liter.

An "abnormally high concentration" of ALP in a subject's blood plasma or blood serum is greater than 129 units/liter. In some embodiments, the reducing is to a normal concentration. In some embodiments, the normal concentration of ALP in a subject's blood plasma or blood serum ranges from about 40 units/liter to about 129 units/liter.

An "abnormally low concentration" of albumin in a subject's blood plasma or blood serum is less than 3.5 g/dL. In some embodiments, the elevating is to a normal concentration. In some embodiments, the normal concentration of albumin in a subject's blood plasma or blood serum ranges from about 3.5 g/dL to about 5.0 g/dL.

An "abnormally high concentration" of bilirubin in a subject's blood plasma or blood serum is greater than 1.2 mg/dL. In some embodiments, the reducing is to a normal concentration. In some embodiments, the normal concentration of bilirubin in a subject's blood plasma or blood serum ranges from about 0.1 mg/dL to about 1.2 mg/dL.

An "abnormally high concentration" of GGT in a subject's blood plasma or blood serum is greater than 61 units/liter. In some embodiments, the reducing is to a normal concentration. In some embodiments, the normal concentration of GGT in a subject's blood plasma or blood serum ranges from about 8 units/liter to about 61 units/liters.

An "abnormally high concentration" of LD in a subject's blood plasma or blood serum is greater than 222 units/liter. In some embodiments, the reducing is to a normal concentration. In some embodiments, the normal concentration of LD in a subject's blood plasma or blood serum ranges from about 122 units/liter to about 222 units/liters.

An "abnormally high concentration" of PT in a subject's blood plasma or blood serum is greater than 12.5 seconds. In some embodiments, the reducing is to a normal concentration. In some embodiments, the normal concentration of PT in a subject's blood plasma or blood serum ranges from about 9.4 seconds to about 12.5 seconds.

An "abnormally high concentration" of creatinine in a subject's blood plasma or blood serum is greater than 1.5 mg/dL, which corresponds to a glomerular filtration rate (GFR) of approximately 30 mL/min and indicative of renal failure. In some embodiments, the reducing is to a normal concentration. In some embodiments, the normal concentration of creatinine in a subject's blood plasma or blood serum ranges from about 0.84 mg/dL to about 1.21 mg/dL. (about 74.3 µmol/L to about 107 µmol/L).

An "abnormally high concentration" of total protein in a subject's blood plasma or blood serum is greater than 7.9 g/dL. An "abnormally low concentration" of total protein in a subject's blood plasma or blood serum is less than 6.3 g/dL. In some embodiments, the reducing is to a normal concentration. In some embodiments, the elevating is to a normal concentration. In some embodiments, the normal concentration of total protein in a subject's blood plasma or blood serum ranges from about 6.3 g/dL to about 7.9 g/dL.

In some embodiments, the present invention provides methods for treating or preventing NAFLD or NASH, comprising administering to a subject in need thereof an effective amount of a compound of the invention or the composition of the invention.

In some embodiments, the present invention provides methods for treating or preventing dyslipidemia, comprising administering to a subject in need thereof an effective amount of the compound of the invention or the composition of the invention. In some embodiments, the dyslipidemia is hyperlipidemia or an abnormally low concentration of high density lipoprotein cholesterol (HDL-C) in the subject's blood plasma or blood serum. The term "dyslipidemia" refers to a disorder that leads to or is manifested by an aberrant level of circulating lipids.

In some embodiments, the present invention provides methods for restoring blood plasma or blood serum concentration of total-cholesterol, low density lipoprotein cholesterol (LDL-C), HDL-C, non-HDL-C or free triglycerides to a normal or recommended concentration or ratio. Accordingly, to the extent that levels of lipids in the blood plasma or blood serum are abnormally high, the compounds of the invention or the compositions of the invention can be administered to a patient to restore normal levels. Normal levels of lipids are well known to those skilled in the art. For example, normal blood levels of total-cholesterol, low density lipoprotein cholesterol (LDL-C), HDL-C, non-HDL-C, free triglycerides and others parameters relating to lipid metabolism can be found at the web site of the American Heart Association, The National Lipid Association and that of the National Cholesterol Education Program of the National Heart, Lung and Blood Institute. In some embodiments, a recommended concentration of HDL-C in the blood plasma or the blood serum is above 35 mg/dl. In some embodiments, a recommended concentration of LDL-C in the blood plasma or the blood serum is below 100 mg/dl. In some embodiments, a recommended LDL-C:HDL-C ratio in the blood plasma or in the blood serum is below 5:1, in some embodiments, 3.5:1. In some embodiments, a recommended concentration of free triglycerides in the blood plasma or the blood serum is less than 200 mg/dl.

In some embodiments, the present invention provides methods for treating or preventing hyperlipidemia, comprising administering to a subject in need thereof an effective amount of a compound of the invention or a composition of the invention. In some embodiments, hyperlipidemia is hypercholesterolemia, familial hypercholesterolemia, hypertriglyceridemia, or familial combined hyperlipidemia. In some embodiments, hyperlipidemia is characterized by an abnormally reduced or deficient lipoprotein lipase level or activity in the subject's blood plasma or blood serum, or an abnormally high concentration of ketone bodies, lipoprotein (a) cholesterol (Lp(a)-C), low density lipoprotein (LDL), very low density lipoproteins cholesterol (VLDL-C) or non-esterified fatty acids (NEFA) in the subject's blood plasma or blood serum. In some embodiments, the reduced or deficient lipoprotein lipase level or activity is a result of a lipoprotein lipase mutation. In some embodiments, the reduced or deficient lipoprotein lipase level or activity is a result of a mutation in a gene encoding a lipoprotein lipase.

Non-limiting examples of ketone bodies include acetoacetate, beta-hydroxybutyrate, and acetone. An "abnormally high concentration" of ketone bodies in a subject's blood plasma or blood serum is 1 mg/dL or greater (<0.1 mmol/L). In some embodiments, the present invention provides methods for reducing an abnormally high concentration of ketone bodies in a subject's blood plasma or blood serum, wherein the concentration is 1 mg/dL or greater. In some embodiments, the reducing is to a normal level. In some embodiments, the normal level is less than 1 mg/dL (<0.1 mmol/L). See Devkota, B. P. et al. Medscape emedicine, updated Oct. 30, 2015.

An "abnormally high concentration" of VLDL-C in a subject's blood plasma or blood serum is greater than 30 mg/dL (1.7 mmol/L). In some embodiments, the present invention provides methods for reducing VLDL-C concentration in a subject's blood plasma or blood serum, wherein the VLDL-C concentration is greater than 30 mg/dL. In some embodiments, the reducing is to a normal level. In some embodiments, the normal level ranges from 2 mg/dL to 30 mg/dL (0.1 to 1.7 mmol/L).

An "abnormally high concentration" of NEFA is in a subject's blood plasma or blood serum in a non-fasting state is 0.9 mM or greater. An "abnormally high concentration" of NEFA in a subject's blood plasma or blood serum in a fasting state is greater than 1.8 mM at a fasting state. An "abnormally high concentration" of NEFA in a subject's blood plasma or blood serum at 15-hour fasting is greater than 1.1 nM. An "abnormally high concentration" of NEFA in a subject's blood plasma or blood serum at 20-hour fasting is greater than 1.3 mM. An "abnormally high concentration" of NEFA in a subject's blood plasma or blood serum at 15-hour fasting is greater than 1.1 nM. An "abnormally high concentration" of NEFA in a subject's blood plasma or blood serum at 24-hour fasting is greater than 1.8 mM. In some embodiments, the present invention provides methods for reducing NEFA concentration in a subject's blood plasma or blood serum, wherein the NEFA concentration is greater than 0.9 mM, in some embodiments greater than 1.1 mM, in some embodiments greater than 1.5 mM and in some embodiments greater than 1.8 mM. In some embodiments, the reducing is to a normal level. In some embodiments, the normal level is 1.8 mM or less, in some embodiments 1.5 mM or less, in some embodiments 1.1 mM or less and in some embodiments 0.9 mM or less. See Horowitz, G. L. et al. Medscape emedicine, updated Jul. 25, 2019.

In some embodiments, the present invention provides methods for treating or preventing dyslipoproteinemia, comprising administering to a subject in need thereof an effective amount of a compound of the invention or a composition of the invention. In some embodiments, the dyslipoproteinemia is characterized by an abnormally high concentration of LDL, apolipoprotein (a) or VLDL in a subject's blood plasma or blood serum, or an abnormally low concentration of high density lipoprotein (HDL) or lipoprotein lipase in a subject's blood plasma or blood serum. In some embodiments, the abnormally low concentration of the lipoprotein lipase is associated with: a lipoprotein lipase mutation, hypoalphalipoproteinemia, a lipoprotein abnormality associated with diabetes, a lipoprotein abnormality associated with obesity, a lipoprotein abnormality associated with Alzheimer's disease, or familial combined hyperlipidemia. The term "dyslipoproteinemia" refers to a disorder that leads to or is manifested by an aberrant concentration of circulating lipoproteins in a subject's blood plasma or blood serum. To the extent that the concentrations of lipoproteins in the blood plasma or blood serum are too high, the compounds of the invention or the compositions of the invention can be administered to the subject to restore to normal concentrations of lipoproteins. Conversely, to the extent that the concentrations of lipoproteins in the blood plasma or blood serum are too low, the compounds of the invention or the compositions of the invention can be administered to the subject to restore to normal concentrations. Normal concentrations of lipoproteins are reported in medical treatises known to those of skill in the art.

In some embodiments, the present invention provides methods for treating or preventing a renal disease, comprising administering to a subject in need thereof an effective amount of a compound of the invention or a composition of the invention. In some embodiments, the renal disease is a glomerular disease, a tubular disease, a tubulointerstitial disease, acute or rapidly progressive renal failure, chronic renal failure, nephrolithiasis, or a tumor. In some embodiments, the renal disease is hypertension, nephrosclerosis, microangiopathic hemolytic anemia, atheroembolic renal disease, diffuse cortical necrosis, or a renal infarct.

In some embodiments, the glomerular disease is an acute glomerulonephritis, a chronic glomerulonephritis, a rapidly progressive glomerulonephritis, a nephrotic syndrome, a focal proliferative glomerulonephritis, a glomerular lesion associated with systemic disease, Goodpasture syndrome, multiple myeloma, diabetes, neoplasia, sickle cell disease or a chronic inflammatory disease. In some embodiments, the glomerular lesion associated with systemic disease is systemic lupus erythematosus.

In some embodiments, the tubular disease is an acute tubular necrosis, an acute renal failure, a polycystic renal disease, medullary sponge kidney, a medullary cystic disease, nephrogenic diabetes, or a renal tubular acidosis.

In some embodiments, the tubulointerstitial disease is pyelonephritis, a drug- or toxin-induced tubulointerstitial nephritis, a hypercalcemic nephropathy, or a hypokalemic nephropathy.

In some embodiments, the tumor is renal cell carcinoma or nephroblastoma.

In some embodiments, the renal disease is hypertension. In some embodiments, the hypertension is an essential hypertension, hyperpiesa, hyperpiersis, a malignant hypertension, a secondary hypertension, or a white-coat hypertension.

In some embodiments, the renal disease is a kidney disease.

In some embodiments, the present invention provides methods for treating or preventing a disorder of glucose metabolism, comprising administering to a subject in need thereof an effective amount of a compound of the invention or a composition of the invention. The term "disorder of glucose metabolism" refers to a disorder that leads to or is manifested by aberrant glucose storage and/or utilization. To the extent that indicia of glucose metabolism (i.e. insulin, glucose, or glycated hemoglobin in a subject's blood plasma or blood serum) are too high, the compounds of the invention or the compositions of the invention can be administered to a subject to restore to normal levels. Normal indicia of glucose metabolism are reported in medical treatises known to those of skill in the art. See U.S. Pat. No. 7,709,682 B2.

In some embodiments, the present invention provides methods for reducing an abnormally high concentration of glucose in a subject's blood plasma or blood serum, comprising administering to a subject in need thereof an effective amount of a compound of the invention or a composition of the invention. An "abnormally high concentration" of glucose in a subject's blood plasma or blood serum at a fasted state (10-16 hours without eating) is greater than 5.6 mmol/L (100 mg/dL). In some embodiments, the reducing is to a normal concentration. In some embodiments, the normal concentration of glucose is less than 5.6 mmol/L at fasted state. In some embodiments, a fasted glucose blood plasma or blood serum concentration in the range of 5.6 mmol/L to 6 mmol/L (100-109 mg/dL) may indicate prediabetes. In some embodiments, a fasted glucose blood plasma or blood serum concentration in the range of 6.1 mmol/L to 6.9 mmol/L (110-125 mg/dL) can indicate diabetes. In some embodiments, a fasted glucose blood plasma or blood serum concentration of 7 mmol/L (126 mg/dL) and above indicates diabetes.

In some embodiments, the abnormally high concentration of glucose in a subject's blood plasma or blood serum is measured in a glucose tolerance test (GTT).

An "abnormally high concentration" of glucose in a subject's blood plasma or blood serum in a one-hour GTT is greater than 10 mmol/L (180 mg/dL). In some embodiments, the reducing is to a normal concentration. In some embodiments, the normal concentration in a one-hour GTT is less than 10 mmol/L (180 mg/dL).

An "abnormally high concentration" of glucose in a subject's blood plasma or blood serum in a two-hour GTT with 75 g intake is greater than 7.8 mmol/L (140 mg/dL), which indicates hyperglycemia. In some embodiments, the reducing is to a normal concentration. In some embodiments, the normal concentration in two-hour GTT with 75 g intake is less than 7.8 mmol/L (140 mg/dL). In some embodiments, a glucose concentration in a subject's blood plasma or blood serum between 7.8 mmol/L (140 mg/dL) and 11.1 mmol/L (200 mg/dL) in two-hour GTT with 75 g intake indicates impaired glucose tolerance. In some embodiments, a glucose concentration above 11.1 mmol/L in two-hour GTT with 75 g intake indicates diabetes.

In some embodiments, the present invention provides methods for increasing abnormally low glucose metabolism in a subject, wherein the subject's glucose concentration in the subject's blood plasma or blood serum is greater than 7.8 mmol/L (140 mg/dL) in a two-hour GTT. In some embodiments, the present invention provides methods treating or preventing a disorder of glucose metabolism in a subject, wherein the subject's glucose concentration in the subject's blood plasma or blood serum is in the range of 7.8 mmol/L (140 mg/dL) to 11.1 mmol/L (200 mg/dL) in a two-hour GTT. In some embodiments, the present invention provides methods for treating or preventing a disorder of glucose metabolism in a subject, wherein the subject's glucose concentration in the subject's blood plasma or blood serum is greater than 11.1 mmol/L (200 mg/dL) in a two-hour GTT.

In some embodiments, the present invention provides methods for reducing an abnormally high level of $HbA_{1c}$ in a subject's blood plasma or blood serum, comprising administering to a subject in need thereof an effective amount of a compound of the invention or a composition of the invention. An "abnormally high level" of hemoglobin A1c ($HbA_{1c}$) in a subject's blood plasma or blood serum is 6.5% or greater (expressed in % NGSP units). In some embodiments, the reducing is to a normal level. In some embodiments, the normal levels of $HbA_{1c}$ is in the range of about 4% to about 5.9%. In some embodiments, the present invention provides methods for reducing $HbA_{1c}$ level in a subject's blood plasma or blood serum, wherein the $HbA_{1c}$ level is greater than 7%, greater than 8%, or greater than 9%. See Horowitz, G. L. et al. Medscape emedicine, updated Jul. 25, 2019.

In some embodiments, the present invention provides methods for increasing abnormally low glucose metabolism in a subject, wherein the subject's $HbA_{1c}$ level is 6.5% or greater and the subject's fasting glucose concentration is 126 mg/dL or greater (≥7.0 mmol/L), in the subject's blood plasma or blood serum. See Selvin, E. et al. *Ann Intern Med*. Published online Jun. 18, 2018.

In some embodiments, the present invention provides methods for treating or preventing a disorder of glucose metabolism in a subject, wherein the subject has $HbA_{1c}$ greater than or equal to 6.5%. In some embodiments, the present invention provides methods for treating or preventing a disorder of glucose metabolism in a subject, wherein the subject has $HbA_{1c}$ greater than or equal to 6.5% and fasting glucose concentration greater than or equal to 126 mg/dL (7.0 mmol/L) in the subject's blood plasma or blood serum.

In some embodiments, the present invention provides methods for reducing an abnormally high concentration of glucose in a subject's blood plasma or blood serum, comprising administering to a subject in need thereof an effective amount of a compound of the invention or a composition of the invention, wherein the subject is pregnant. An "abnormally high concentration" of glucose in a pregnant subject's blood plasma or blood serum at fasted state is greater than 5.3 mmol/L (95 mg/dL).

In some embodiments, the present invention provides methods for reducing an abnormally high concentration of glucose in a subject's blood plasma or blood serum, comprising administering to a subject in need thereof (i) a glucose solution as part of a two-step gestational diabetes test and (ii) an effective amount of a compound of the invention or a composition of the invention. An "abnormally high concentration" of glucose in a subject's blood plasma or blood serum at 1 hour after drinking the glucose solution in a two-step gestational diabetes test is greater than 10 mmol/L (180 mg/dL). In the two-step procedure, the first step is a 50 g glucose dose. If it results in a blood glucose level of more than 7.8 mmol/L (140 mg/dL), it is followed by a 100 g glucose dose. An "abnormally high concentration: of glucose in a subject's blood plasma or blood serum at 2 hour after drinking the glucose solution in a two-step gestational diabetes test is greater than 8.6 mmol/L (155 mg/dL). An "abnormally high concentration: of glucose in a subject's blood plasma or blood serum at 3 hour after drinking the glucose solution in a two-step gestational diabetes test is greater than 7.8 mmol/L (140 mg/dL).

In some embodiments, the present invention provides methods for treating or preventing a disorder of glucose metabolism in a subject, wherein the subject has impaired glucose tolerance. In some embodiments, the present invention provides methods for treating or preventing a disorder of glucose metabolism in a subject, wherein the subject has diabetes. In some embodiments, the present invention provides methods for treating or preventing a disorder of glucose metabolism in a subject, wherein the subject has confirmed undiagnosed diabetes. In some embodiments, the present invention provides methods for treating or preventing a disorder of glucose metabolism in a subject, wherein the subject has gestational diabetes.

In some embodiments, the present invention provides methods for reducing abnormally high concentration of insulin in a subject's blood plasma or blood serum, comprising administering to a subject in need thereof an effective amount of a compound of the invention or a composition of the invention. An "abnormally high concentration" of insulin in a subject's blood plasma or blood serum at a fasted state is greater than 25 mIU/L (>174 µmol/L). In some embodiments, the reducing is to a normal concentration. In some embodiments, the normal concentration of insulin in a subject's blood plasma or blood serum at a fasted state is less than 25 mIU/L (<174 µmol/L). See Buppajarntham, S. et al. Medscape emedicine, updated Jan. 2, 2019.

In some embodiments, the present invention provides methods for reducing abnormally high concentration of insulin in a subject's blood plasma or blood serum, comprising administering to a subject in need thereof an effective amount of a compound of the invention or a composition of the invention.

In some embodiments, the methods further comprise administering glucose to the subject. In some embodiments, the methods do not comprise administering glucose to the subject. In some embodiments, the subject is in a fasted state.

In some embodiments, the subject has an abnormally concentration of insulin in the subject's blood plasma or blood glucose at 30 minutes after glucose administration. An "abnormally high concentration" of insulin in a subject's blood plasma or blood serum at 30 minutes after glucose administration is greater than 230 mIU/L (>1597 µmol/L). In some embodiments, the reducing is to a normal concentration. In some embodiments, the normal concentration of insulin in a subject's blood plasma or blood serum at 30 minutes after glucose administration is in the range of about 30 mIU/L to about 230 mIU/L (208-1597 µmol/L). See Buppajarntham, 2019.

In some embodiments, the subject has an abnormally concentration of insulin in the subject's blood plasma or blood serum at 1 hour after glucose administration. An "abnormally high concentration" of insulin in a subject's blood plasma or blood serum at 1 hour after glucose administration is greater than 276 mIU/L (>1917 µmol/L). In some embodiments, the present invention provides methods for reducing abnormally high concentration of insulin in a subject's blood plasma or blood serum, comprising administering to a subject in need thereof an effective amount of a compound of the invention or a composition of the invention. In some embodiments, the reducing is to a normal concentration. In some embodiments, the normal concentration of insulin in a subject's blood plasma or blood serum at 1 hour after glucose administration is in the range of about 18 mIU/L to about 276 mIU/L (125-1917 µmol/L). See Buppajarntham, 2019.

In some embodiments, the subject has an abnormally concentration of insulin in the subject's blood plasma or blood glucose at 2 hours after glucose administration. An "abnormally high concentration" of insulin in a subject's blood plasma or blood serum at 2 hour after glucose administration is greater than 166 mIU/L (>1153 µmol/L). In some embodiments, the present invention provides methods for reducing an abnormally high concentration of insulin in a subject's blood plasma or blood serum, comprising administering to a subject in need thereof an effective amount of a compound of the invention or a composition of the invention. In some embodiments, the normal concentration of insulin in a subject's blood plasma or blood serum at 2 hours after glucose administration is in the range of about 16 mIU/L to about 166 mIU/L (111-1153 µmol/L). See Buppajarntham, 2019.

In some embodiments, the subject has an abnormally concentration of insulin in the subject's blood plasma or blood glucose at 3 hours after glucose administration. An "abnormally high concentration" of insulin in a subject's blood plasma or blood serum at 3 hours after glucose administration is greater than 25 mIU/L (>174 µmol/L). In some embodiments, the present invention provides methods for reducing an abnormally high concentration of insulin in a subject's blood plasma or blood serum, comprising administering to a subject in need thereof an effective amount of a compound of the invention or a composition of the invention. In some embodiments, the normal concentration of insulin in a subject's blood plasma or blood serum at 3 hours or later after glucose administration is less than 25 mIU/L (<174 µmol/L). See Buppajarntham, 2019.

In some embodiments, the present invention provides methods for treating or preventing a disorder of glucose metabolism in a subject, wherein the subject has insulin concentration in the subject's blood plasma or blood serum above 25 mIU/L at a fasted state or after 3 hours after glucose administration. See Buppajarntham, 2019.

In some embodiments, the disorder of glucose metabolism is an impaired glucose tolerance; an insulin resistance; an insulin resistance-related breast, colon or prostate cancer; diabetes; pancreatitis; hypertension; polycystic ovarian disease; or an abnormally high concentration of blood insulin or glucose in the subject's blood plasma or blood serum. In some embodiments, the diabetes is non-insulin dependent diabetes mellitus (NIDDM), insulin dependent diabetes mellitus (IDDM), gestational diabetes mellitus (GDM), or maturity onset diabetes of the young (MODY).

In some embodiments, the present invention provides methods for treating or preventing a metabolic syndrome (syndrome X), comprising administering to a subject in need thereof an effective amount of a compound of the invention or a composition of the invention. In some embodiments, the present invention provides methods for treating or preventing a symptom of a metabolic syndrome (syndrome X), comprising administering to a subject in need thereof an effective amount of a compound of the invention or a composition of the invention. In some embodiments, the symptom is impaired glucose tolerance, hyper tension, dyslipidemia, or dyslipoproteinemia.

In some embodiments, the present invention provides methods for treating or preventing a vascular disease or cardiovascular disease, comprising administering to a subject in need thereof an effective amount of a compound of the invention or a composition of the invention. The term "cardiovascular disease" refers to a disease of the heart or circulatory system. In some embodiments, the vascular disease or the cardiovascular disease is a peripheral vascular disease, a coronary heart disease, stroke, restenosis, arteriosclerosis, ischemia, an endothelium dysfunction, an ischemia-reperfusion injury, a myocardial infarction, or a cerebral infarction.

In some embodiments, the present invention provides methods for treating or preventing a PPAR-associated disorder, comprising administering to a subject in need thereof an effective amount of a compound of the invention or a composition of the invention. In some embodiments, the PPAR-associated disorder is rheumatoid arthritis, multiple sclerosis, psoriasis, an inflammatory bowel disease, breast cancer, colon cancer, or prostate cancer. In some embodiments, the PPAR-associated disorder is a vascular disease, a muscular disease, a demyelinating disease, a muscle structure disorder, a neuronal activation disorder, a muscle fatigue disorder, a muscle mass disorder, a mitochondrial disease, a mitochondrial dysfunction, a beta oxidation disease, or a metabolic disease. In some embodiments, the PPAR-associated disorder is an abnormally low concentration of HDL, an abnormally low concentration of apolipoprotein A-I (apo A-I), an abnormally high concentration of VLDL-C, an abnormally high concentration of low density lipoprotein cholesterol (LDL-C), an abnormally high concentration of triglyceride, an abnormally high concentration of apolipoprotein B (apo B), an abnormally high concentration of apolipoprotein C-III (apo C-III) or an abnormally reduced ratio of post-heparin hepatic lipase to lipoprotein lipase activity in the subject's blood plasma or blood serum. In some embodiments, the PPAR-associated disorder is an abnormally high concentration of HDL or an abnormally low concentration of apo A-I in the subject's lymph or cerebral fluid.

In some embodiments, the PPAR-associated disorder is abnormally low concentration of lipoprotein lipase activity in the post-heparin plasma in a subject (subject's blood plasma after intravenous injection of heparin). In some embodiments, the present invention provides methods for elevating an abnormally low concentration of lipoprotein lipase activity in the post-heparin plasma, comprising administering to a subject in need thereof an effective amount of a compound of the invention or a composition of the invention. An "abnormally low concentration" of lipoprotein lipase activity in the post-heparin plasma is less than 30 U/L. In some embodiments, the elevating is to a normal concentration. In some embodiments, the normal concentration is in the range from about 30 U/L to about 153 U/L (See Nakajima et al. *Clin Chim Acta*. 2018 December; 487:54-59).

In some embodiments, the present invention provides methods for treating or preventing a PPAR-associated disorder in a subject, wherein the subject has lipoprotein lipase activity in the post-heparin plasma of less than 30 U/L.

In some embodiments, the subject is a male subject. An "abnormally high concentration" of HDL in a male subject is greater than 75 mg/dL.

In some embodiments, the subject is a female subject. An "abnormally high concentration" of HDL for a female subject is greater than 90 mg/dL.

In some embodiments, the present invention provides methods for reducing an abnormally high concentration of HDL in a subject's blood plasma or blood serum, comprising administering to a subject in need thereof an effective amount of a compound of the invention or a composition of the invention. In some embodiments, the reducing is to a normal concentration. In some embodiments, the normal concentration for a male subject is less than 75 mg/dL. In some embodiments, the normal concentration for a female subject is less than 90 mg/dL. In some embodiments, the present invention provides methods for treating or preventing a PPAR-associated disorder in a male subject, wherein the subject has HDL concentration in the subject's blood plasma or blood serum greater than 75 mg/dL. In some embodiments, the present invention provides methods for treating or preventing a PPAR-associated disorder in a female subject, wherein the subject has HDL concentration in the subject's blood plasma or blood serum greater than 90 mg/dL. See Hassan, M. et. al. Glob Cardiol Sci Pract. 2016 Dec. 30; 2016(4): e201634.

In some embodiments, the muscular disease is a muscular dystrophy disease. In some embodiments, the muscular dystrophy disease is Duchenne muscular dystrophy, Becker muscular dystrophy, a limb-girdle muscular dystrophy, congenital muscular dystrophy, facioscapulohumeral muscular dystrophy, myotonic muscular dystrophy, oculopharyngeal muscular dystrophy, distal muscular dystrophy, or Emery-Dreifuss muscular dystrophy.

In some embodiments, the demyelinating disease is multiple sclerosis, Charcot-Marie-Tooth disease, Pelizaeus-Merzbacher disease, encephalomyelitis, neuromyelitis optica, adrenoleukodystrophy, or Guillian-Barre syndrome.

In some embodiments, the muscle structure disorder is Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorder, myotonic chondrodystrophy, myotonic dystrophy, myotubular myopathy, nemaline body disease, oculopharyngeal MD, or stress urinary incontinence.

In some embodiments, the neuronal activation disorder is amyotrophic lateral sclerosis, Charcot-Marie-Tooth disease, Guillain-Barre syndrome, Lambert-Eaton syndrome, multiple sclerosis, myasthenia gravis, a nerve lesion, peripheral neuropathy, spinal muscular atrophy, tardy ulnar nerve palsy, or toxic myoneural disorder.

In some embodiments, the muscle fatigue disorder is chronic fatigue syndrome, diabetes (type I or II), a glycogen storage disease, fibromyalgia, Friedreich's ataxia, intermittent claudication, lipid storage myopathy, MELAS (mitochondrial encephalopathy, lactic acidosis, and stroke-like episodes) syndrome, mucopolysaccharidosis, Pompe disease, or thyrotoxic myopathy.

In some embodiments, the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus.

In some embodiments, the mitochondrial disease is Alpers's disease, chronic progressive external ophthalmoplegia (CPEO), Kearns-Sayra syndrome (KSS), Leber hereditary optic neuropathy (LHON), MELAS, myoclonic epilepsy and ragged-red fiber disease (MERRF), neurogenic muscle weakness (NARP), ataxia, retinitis pigmentosa, Pearson syndrome, a mitochondrial malfunction, or a mitochondrial loss of functionality (for example, due to a drug affecting mitochondrial functions).

In some embodiments, the mitochondrial dysfunction is a drug induced mitochondrial dysfunction.

In some embodiments, the beta oxidation disease is systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, or riboflavin-responsive disorders of β-oxidation (RR-MADD).

In some embodiments, the metabolic disease is hyperlipidemia, dyslipidemia, hyperchlolesterolemia, hypertriglyceridemia, HDL hypocholesterolemia, LDL hypercholesterolemia, HLD non-cholesterolemia, VLDL hyperproteinemia, dyslipoproteinemia, apolipoprotein A-I hypoproteinemia, atherosclerosis, a disease of arterial sclerosis, a disease of cardiovascular system, cerebrovascular disease, peripheral circulatory disease, metabolic syndrome, syndrome X, obesity, diabetes, type I diabetes, type II diabetes, hyperglycemia, insulin resistance, impaired glucose tolerance, hyperinsulinism, a diabetic complication, cardiac insufficiency, cardiac infarction, cardiomyopathy, hypertension, non-alcoholic fatty liver disease (NAFLD), non-alcoholic steatohepatitis (NASH), a thrombus, Alzheimer disease, a neurodegenerative disease, a demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, or pancreatitis.

In some embodiments, the present invention provides methods for treating or preventing septicemia, comprising administering to a subject in need thereof an effective amount of a compound of the invention or a composition of the invention. In some embodiments, septicemia is septic shock.

In some embodiments, the present invention provides methods for treating or preventing a thrombotic disorder, comprising administering to a subject in need thereof an effective amount of a compound of the invention or a composition of the invention. In some embodiments, the thrombotic disorder is high concentration of fibrinogen in the subject's blood plasma or blood serum, or promotion of fibrinolysis.

In some embodiments, the present invention provides methods for treating or preventing obesity, comprising administering to a subject in need thereof an effective amount of a compound of the invention or a composition of the invention. In some embodiments, the obesity is abdominal obesity. In some embodiments, the methods for treating or preventing obesity further comprise promoting weight reduction in the subject.

In some embodiments, the present invention provides methods for treating or preventing diabetic nephropathy, comprising administering to a subject in need thereof an effective amount of a compound of the invention or a composition of the invention. In some embodiments, the methods for treating or preventing diabetic nephropathy further comprise treating or preventing a kidney disease that develops as a result of diabetes mellitus. In some embodiments, the present invention provides methods for treating or preventing diabetes mellitus, comprising administering to a subject in need thereof an effective amount of a compound of the invention or a composition of the invention.

In some embodiments, the present invention provides methods for treating or preventing diabetic retinopathy, comprising administering to a subject in need thereof an effective amount of a compound of the invention or a composition of the invention. In some embodiments, the methods for treating or preventing diabetic retinopathy result in treating or preventing a complication of diabetes that can lead to or cause blindness.

In some embodiments, the present invention provides methods for treating or preventing a cerebrovascular disease, comprising administering to a subject in need thereof an effective amount of a compound of the invention or a composition of the invention. In some embodiments, the cerebrovascular disease is cerebral ischemia.

In some embodiments, the present invention provides methods for treating or preventing a disorder related to neovascularization, comprising administering to a subject in need thereof an effective amount of a compound of the invention or a composition of the invention. In some embodiments, the disorder related to neovascularization is retinopathy or diabetes.

In some embodiments, the present invention provides methods for treating or preventing hypertension, comprising administering to a subject in need thereof an effective amount of a compound of the invention or a composition of the invention. In some embodiments, the methods for treating or preventing hypertension result in treating or preventing blood flow that occurs through the subject's vessels at a greater than normal force.

In some embodiments, the present invention provides methods for treating or preventing cancer, comprising administering to a subject in need thereof an effective amount of a compound of the invention or a composition of the invention. In some embodiments, the cancer is a human sarcoma or human carcinoma. In some embodiments, the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, bone cancer, breast cancer, ovarian cancer, prostate cancer, esophageal cancer, oral cancer, nasal cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, leukemia, acute lymphoblastic B-cell leukemia, acute lymphoblastic T-cell leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, hairy cell leukemia, lymphoblastic leukemia, myelogenous leukemia, lymphocyticleukemia, myelocytic leukemia, polycythemia vera, multiple myeloma, lymphoma, Hodgkin's disease, non-Hodgkin's lymphoma, Waldenstrom's macroglobulinemia, or a heavy chain disease.

In some embodiments, the leukemia is acute or chronic lymphoblastic leukemia, myelogenous leukemia, lymphocyticleukemia, lymphocytic leukemia, or myelocytic leukemia. In some embodiments, the myelocytic leukemia is acute and is myeloblastic, promyclocytic, myelomonocytic, monocytic or erythroleukemia In some embodiments, the lymphoma is Hodgkin's lymphoma or non-Hodgkin's lymphoma.

In some embodiments, the present invention provides methods for treating or preventing an inflammatory disease, comprising administering to a subject in need thereof an effective amount of a compound of the invention or a composition of the invention. In some embodiments, the inflammatory disease is multiple sclerosis, a chronic inflammatory disorder of a joint, arthritis, a respiratory distress syndrome, an inflammatory bowel disease, an inflammatory lung disorder, an inflammatory disorder, an inflammatory disorder of the gum, tuberculosis, leprosy, an inflammatory disease of the kidney, an inflammatory disorder of the skin, an inflammatory disease of the central nervous system, a systemic lupus erythematosus (SLE) or an inflammatory disease of the heart.

In some embodiments, the arthritis is rheumatoid arthritis or osteoarthritis.

In some embodiments, the inflammatory bowel disease is ileitis, ulcerative colitis or Crohn's disease.

In some embodiments, the inflammatory lung disorder is asthma or chronic obstructive airway disease.

In some embodiments, the inflammatory disorder of the eye is corneal dystrophy, trachoma, onchocerciasis, uveitis, sympathic ophthalmitis or endophthalmitis.

In some embodiments, the inflammatory disorder of the gum is periodontitis or gingivitis.

In some embodiments, the inflammatory disease of the kidney is glomerulonephritis or nephrosis.

In some embodiments, the inflammatory disorder of the skin is acne, sclerodermatitis, psoriasis, eczema, photoaging or wrinkles.

In some embodiments, the inflammatory disease of the central nervous system is AIDS-related neurodegeneration, stroke, neurotrauma, Alzheimer's disease, encephalomyelitis, or viral or autoimmune encephalitis.

In some embodiments, the inflammatory disease of the heart is cardiomyopathy.

In some embodiments, the present invention provides methods for treating or preventing a neurodegenerative disease, comprising administering to a subject in need thereof an effective amount of a compound of the invention or a composition of the invention. In some embodiments, the neurodegenerative disease is Alzheimer's disease or Huntington's disease.

In some embodiments, the present invention provides methods for treating or preventing an autoimmune disease, comprising administering to a subject in need thereof an effective amount of a compound of the invention or a composition of the invention. In some embodiments, the autoimmune disease is immune-complex vasculitis, systemic lupus or erythematodes.

In some embodiments, the present invention provides methods for treating or preventing a neoplastic disease, comprising administering to a subject in need thereof an effective amount of a compound of the invention or a composition of the invention. In some embodiments, the neoplastic disease is carcinogenesis.

In some embodiments, the present invention provides methods for treating or preventing cholestasis, comprising administering to a subject in need thereof an effective amount of the compound of the invention or the composition of the invention.

In some embodiments, the cholestasis is intrahepatic cholestatic disease or extrahepatic cholestatic disease. In some embodiments, the intrahepatic cholestatic disease is primary biliary cholangitis (PBC), primary sclerosing cholangitis (PSC), progressive familial intrahepatic cholestasis (PFIC), or Alagille syndrome (AS). In some embodiments, the methods for treating or preventing intrahepatic cholestatic disease result in preventing or reducing the risk of developing an intrahepatic cholestatic disease, e.g., causing the clinical symptoms of an intra hepatic cholestatic disease to not develop in a subject who may be predisposed to an intrahepatic cholestatic disease by who does not yet experience or display symptoms of the intrahepatic cholestatic disease (i.e., prophylaxis). In some embodiments, the methods for treating or preventing intrahepatic cholestatic disease comprise inhibiting an intrahepatic cholestatic disease, e.g., arresting or reducing the development of the intrahepatic cholestatic disease or reducing the number, frequency, duration or severity of one or more of its clinical symptoms.

In some embodiments, the present invention provides methods for treating or preventing an ocular disease, comprising administering to a subject in need thereof an effective amount of a compound of the invention or a composition of the invention. In some embodiments, the ocular disease is dry eye, meibomian gland dysfunction, a keratoconjunctiva epithelial disorder, a corneal epithelial disorder, or a corneal ulcer. In some embodiments, the ocular disease is dry eye syndrome, corneal ulcer, superficial punctuate keratitis, corneal epithelial erosion, an ocular allergic disease associated with corneal lesion such as vernal conjunctivitis, or atopic keratoconjunctivitis. In some embodiments, the ocular disease is hyperevaporative dry eye. In some embodiments, the ocular disease is injury of corneal epithelial cells. In some embodiments, the injury of corneal epithelial cells is associated with endogenous diseases such as Sjogren's syndrome, Stevens-Johnson syndrome, keratoconjunctivitis sicca (dry eye) or the like. In some embodiments, the injury of corneal epithelial cells is associated with exogenous diseases such as post-operation, drug use, trauma, corneal ulcer, meibomianitis, exogenous diseases during wearing contact lenses or the like. In some embodiments, the injury of corneal epithelial cells is associated with ocular allergic diseases accompanying corneal lesion such as vernal conjunctivitis, atopic keratoconjunctivitis or the like. In some embodiments, the ocular disease is superficial punctuate keratitis and corneal epithelial erosion.

In some embodiments, the methods for treating or preventing an ocular disease result in promoting proliferation of meibomian gland epithelial cells and corneal epithelial cells.

In some embodiments, the present invention provides methods for treating or preventing a lysosomal storage disorder, comprising administering to a subject in need thereof an effective amount of a compound of the invention or a composition of the invention. In some embodiments, the lysosomal storage disorder is neuronal ceroid lipofuscinosis, Alzheimer's disease, Huntington's disease, amyotrophic lateral sclerosis (ALS), Parkinson's disease, multiple system atrophy (MSA), progressive supranuclear palsy (PSP), corticobasal degeneration (CBD), dementia with Lewy bodies (DLB), a disorder of the autophagy pathway, Tay-Sach's disease, Fabry disease, Niemann-Pick disease, Gaucher disease, Hunter syndrome, alpha-mannosidosis, aspartylglucosaminuria, cholesteryl ester storage disease, chronic hexosaminidase A deficiency, cystinosis, Danon disease, Farber disease, fucosidosis, galactosialidosis, or Batten disease.

In some embodiments, the present invention provides methods for treating or preventing a kidney disease, comprising administering to a subject in need thereof an effective amount of a compound of the invention or a composition of the invention. In some embodiments, the kidney disease is renal ischemia reperfusion injury. In some embodiments, the kidney disease is acute kidney injury. In some embodiments, the methods for treating or preventing a kidney disease result in lowering the subject's risk for acute kidney injury following coronary artery bypass graft, transplantation, and/or valve surgery.

In some embodiments, the subject has AKI. In other embodiments, the subject is at risk for AKI.

AKI can be characterized by rapid decline in renal functions, which can be caused by a number of factors, such as a reduction in renal blood flow, glomerulonephritis, use of nephrotoxic antibiotics, use of anticancer agents, and sepsis.

Acute kidney injury can be diagnosed, for example, when a subject exhibits changes in one or more of serum creatinine level, glomerular filtration rate, or urine output. For example, AKI can be characterized by a serum creatinine level of at least 1.5 times baseline, wherein baseline refers to the subject's serum creatinine level no more than 7 days prior. For example, a patient having AKI can have a serum creatinine level is 1.5 to 1.9 times baseline, 2.0 to 2.9 times baseline, or 3.0 or more times baseline. Alternatively, AKI can be characterized by an increase in serum creatinine of at least 0.3 mg/dL or at least 0.4 mg/dL, for example by an increase of serum creatinine of at least 0.3 mg/dL within a 48 hour period.

Alternatively, AKI can be characterized by a glomerular filtration rate of less than 90 mL/min/1.73 m$^2$. For example, a subject having AKI can have glomerular filtration rate of 60-89 mL/min/1.73 m$^2$, 30-59 mL/min/1.73 m$^2$, 15-29 mL/min/1.73 m$^2$, or less than 15 mL/min/1.73 m$^2$.

Alternatively, AKI can be characterized by a subject having a urine output of less than 0.5 mL/Kg over 6 hours, less than 0.5 mL/Kg over 12 hours, less than 0.3 mL/Kg over 12 hours, or anuria for 12 or more hours.

AKI can be classified using the KDIGO criteria (Kidney Disease Improving Global Outcomes. KDIGO Clinical Practice Guideline for Acute Kidney Injury. Kidney International Supplements 2012; 2:1-138) shown in Table 12.

TABLE 12

KDIGO classification for AKI

| Stage | Serum creatinine | Urine output |
|---|---|---|
| 1 | 1.5-1.9 times baseline OR ≥0.3 mg/dl (≥26.5 μmol/l) increase | <0.5 ml/kg/h for 6-12 hours |
| 2 | 2.0-2.9 times baseline | <0.5 ml/kg/h for ≥12 hours |
| 3 | 3.0 times baseline OR Increase in serum creatinine to ≥4.0 mg/dl (≥353.6 μmol/l) OR Initiation of renal replacement therapy OR, in patients <18 years, decrease in eGFR to <35 ml/min per 1.73 m$^3$ | <0.3 ml/kg/h for ≥24 hours OR Anuria for ≥12 hours |

AKI can occur with specific kidney diseases (e.g., acute interstitial nephritis, acute glomerular and vasculitic renal diseases); non-specific conditions (e.g., ischemia, toxic injury); as well as extrarenal pathology (e.g., prerenal azotemia, and acute postrenal obstructive nephropathy). More than one of these conditions may coexist in the same subject and, more importantly, epidemiological evidence supports the notion that even mild, reversible AKI has important clinical consequences, including increased risk of death. Furthermore, because the manifestations and clinical consequences of AKI can be quite similar (even indistinguishable) regardless of whether the etiology is predominantly within the kidney or predominantly from outside stresses on the kidney, AKI encompasses both direct injury to the kidney as well as acute impairment of function.

In some embodiments, the subject having AKI or at risk of AKI has diabetes, underlying renal insufficiency, nephritic syndrome, atherosclerotic disease, sepsis, hypotension, hypoxia, myoglobinuria-hematuria, or liver disease. In some embodiments, the subject is elderly, pregnant, a surgical patient, or has been exposed to a nephrotoxic agent. In a specific embodiment, the subject having AKI or at risk of AKI is a surgical patient. Accordingly, in certain embodiments, a compound of the disclosure is administered to a surgical patient after surgery, e.g., after a cardiovascular procedure such as coronary artery bypass graft (CABG) surgery and/or heart valve surgery.

In some embodiments, the subject has sepsis (e.g., associated with a gram-negative bacterial infection). The sepsis can in some embodiments be caused by an intra-abdominal cavity infection or be urosepsis. Sepsis is a risk factor for AKI. Thus, in some embodiments, the subject can be at risk for AKI, for example due to sepsis.

In some embodiments, the subject has a shortened sequential organ failure assessment score (SOFA) score of 1 to 4 before treatment with a compound of the disclosure, e.g., a score of 1, 2, 3, or 4 (see, Vincent et al. 1996, Intensive Care Med, 22:707-710).

In some embodiments, the subject has AKI secondary to an infection or is at risk of AKI due to an infection, for example a viral infection, e.g., COVID-19.

In some embodiments, the subject having AKI or at risk of AKI has been exposed to a nephrotoxic agent. A nephrotoxic agent is a drug or chemical capable of causing AKI. Drugs or chemicals capable of causing AKI include, but are not limited to, cisplatin; gentamicin; cephaloridine; cyclosporine; amphotericin; carbon tetrachloride; trichloroethylene; and dichloroacetylene.

In some embodiments, the present invention provides methods for treating or preventing impotence, comprising administering to a subject in need thereof an effective amount of a compound of the invention or a composition of the invention. In some embodiments, the impotence results from damages to a nerve, artery, smooth muscles, or fibrous tissue; diabetes; kidney disease; alcoholism; multiple sclerosis; atherosclerosis; vascular disease; or neurologic disease. In some embodiments, the methods for treating or preventing impotence results in treating or preventing erectile dysfunction.

The present invention provides methods for treating or preventing hyperlipemia, hyperlipidemia, hyperlipoproteinemia, hypercholesterolemia, hypertriglyceridemia, or dyslipidemia, comprising administering to a subject in need thereof an effective amount of a compound of the invention or a composition of the invention. In some embodiments, the hypercholesterolemia is homozygous familial hypercholesterolemia.

The present invention provides methods for treating a subject having or preventing a subject from having an abnormally high concentration in a subject's blood plasma or blood serum of high low-density lipoprotein (LDL), apolipoprotein B (apo B), lipoprotein(a) (Lp(a)), apolipoprotein (a), or very low-density lipoprotein (VLDL), comprising administering to a subject in need thereof an effective amount of a compound of the invention or a composition of the invention.

An "abnormally high concentration" of lipoprotein-cholesterol can depend on the number of risk factors and whether the treatment is for a primary or a secondary prevention. As used herein a "primary prevention" refers to a treatment aimed to avoid a subject developing or getting a disease or a condition. As used herein a "secondary prevention" refers to a treatment aimed to detect a disease or a condition early and prevent the disease or condition from getting worse or advancing. Recommended lipoprotein-cholesterol concentrations can be found in guidelines published by the National Lipid Association or by the National Institute of Health National Heart, Lung, and Blood Institute such as the Third Report of the Expert Panel on Detection, Evaluation, and Treatment of High Blood Cholesterol in Adults (ATP III Final Report), 2002. The ATP III Final Report is hereby incorporated by reference in its entirety for all purposes.

In some embodiments, the present invention provides methods for reducing an abnormally high concentration of apo B in a subject's blood plasma or blood serum, comprising administering to a subject in need thereof an effective amount of a compound of the invention or a composition of the invention. In some embodiments, an "abnormally high concentration" of apo B in a subject's blood plasma or blood serum is greater than 130 mg/dL. In some embodiments, the reducing is to a normal concentration. In some embodiments, the normal concentration of apo B in a subject's blood plasma or blood serum is less than 130 mg/dL. In some embodiments, the subject is a male subject. In some embodiments, the subject is a female subject. In some embodiments, the present invention provides methods for treating a subject with apo B blood plasma or blood serum concentration of greater than 130 mg/dL. In some embodiments, the present invention provides methods for treating a subject with apo B blood plasma or blood serum concentration of greater than 130 mg/dL, when the subject is at low risk of coronary heart disease (CHD) having 0-1 CHD risk factors.

In some embodiments, the present invention provides methods for treating a subject with apo B blood plasma or blood serum concentration of greater than 110 mg/dL, when the subject is at moderate risk of CHD having 2 or more CHD risk factors. In some embodiments, an "abnormally high concentration" of apo B in a subject's blood plasma or blood serum is greater than 110 mg/dL. In some embodiments, the subject has 2 or more CHD risk factors. In some embodiments, the subject has a CHD or a CHD risk equivalent. In some embodiments, the present invention provides methods for treating a subject with apo B blood plasma or blood serum concentration of greater than 90 mg/dL, when the subject has a CHD or a CHD risk equivalent.

In some embodiments, the present invention provides methods for reducing an abnormally high concentration of Lp(a) in a subject's blood plasma or blood serum, comprising administering to a subject in need thereof an effective amount of a compound of the invention or a composition of the invention. An "abnormally high concentration" of Lp(a) in a subject's blood plasma or blood serum is greater than 10 mg/dL. In some embodiments, the abnormally high concentration of Lp(a) is associated with an increase in cardiovascular risk. In some embodiments, the reducing is to a normal concentration. In some embodiments, the normal concentration of Lp(a) in a subject's blood plasma or blood serum is less than 10 mg/dL. In some embodiments, the normal concentration of Lp(a) in a subject's blood plasma or blood serum is less than 50 mg/dL (See, Banach, M. J Am Heart Assoc. 2016 April; 5(4): e003597). In some embodiments, the present invention provides methods for treating a subject with Lp(a) blood plasma concentration of greater than 50 mg/dL, comprising administering to a subject in need thereof an effective amount of a compound of the invention or a composition of the invention.

The present invention provides methods for treating a subject having or preventing a subject from having an abnormally high apo B/apo A-1 ratio in a subject's blood plasma or blood serum, comprising administering to a subject in need thereof an effective amount of a compound of the invention or a composition of the invention. In some embodiments, the present invention provides methods for reducing an abnormally high apo B/apo A-1 ratio in a subject's blood plasma or blood serum, comprising administering to a subject in need thereof an effective amount of a compound of the invention or a composition of the invention. An "abnormally high" apo B/apo A-1 ratio in a subject's blood plasma or blood serum is greater than 0.9. In some embodiments, the reducing is to a normal level. In some embodiments, a normal apo B/apo A-1 ratio in a subject's blood plasma or blood serum is less than 0.9. In some embodiments, the normal apo B/apo A-1 ratio in a subject's blood plasma or blood serum is less than 0.7. In some embodiments, the subject has an apo B/apo A-1 ratio in a subject's blood plasma or blood serum of greater than 0.9. In some embodiments, the subject has an apo B/apo A-1 ratio in a subject's blood plasma or blood serum of greater than 0.7. See Walldius, G. et al. J Intern Med. 2006 May; 259(5):493-519.

In some embodiments, a male subject having an apo B/apo A-1 ratio in the male subject's blood plasma or blood serum of greater than 0.9 is considered for a primary prevention treatment. In some embodiments, a female subject having an apo B/apo A-1 ratio in the female subject's blood plasma or blood serum of greater than 0.8 is considered for a primary prevention treatment. In some embodiments, the subject is a male subject and has an apo B/apo A-1 ratio in the subject's blood plasma or blood serum of greater than 0.9. In some embodiments, the subject is a female subject and has an apo B/apo A-1 ratio in the subject's blood plasma or blood serum of greater than 0.8. See Walldius, 2006.

In some embodiments, a male subject having an apo B/apo A-1 ratio in the male subject's blood plasma or blood serum of greater than 0.7 is considered for a secondary prevention treatment. In some embodiments, a female subject having an apo B/apo A-1 ratio in the female subject's blood plasma or blood serum of greater than 0.6 is considered for a secondary prevention treatment. In some embodiments, the subject is a male subject and has an apo B/apo A-1 ratio in the subject's blood plasma or blood serum of greater than 0.7. In some embodiments, the subject is a female subject and has an apo B/apo A-1 ratio in the subject's blood plasma or blood serum of greater than 0.6. See Walldius, 2006.

The present invention provides methods for treating a subject having or preventing a subject from having an abnormally low concentration in a subject's blood plasma or blood serum of high-density lipoprotein (HDL), comprising administering to a subject in need thereof an effective amount of the compound of the invention or the composition of the invention.

The present invention provides methods for treating a subject having or preventing a subject from having an abnormally reduced or deficient lipoprotein lipase concentration or activity in a subject's blood plasma or blood serum, comprising administering to a subject in need thereof an effective amount of a compound of the invention or a composition of the invention. In some embodiments, the reduced or deficient lipoprotein lipase level or activity is a result of a lipoprotein lipase mutation. In some embodiments, the reduced or deficient lipoprotein lipase level or activity is a result of a mutation in a gene encoding a lipoprotein lipase.

In some embodiments, the present invention provides methods for elevating an abnormally low concentration of lipoprotein lipase in a subject's blood plasma or blood serum, comprising administering to a subject in need thereof an effective amount of a compound of the invention or a composition of the invention. An "abnormally reduced concentration" of lipoprotein lipase in a subject's blood serum is less than 46 ng/mL. In some embodiments, the subject has an increased risk for future coronary artery disease. In some embodiments, the elevating is to a normal concentration. In some embodiments, the normal concentration of lipoprotein lipase in a subject's blood serum is greater than 46 ng/mL. In some embodiments, the present invention provides methods for treating a subject with lipoprotein lipase blood plasma or blood serum concentration of less than 46 ng/mL, comprising administering to a subject in need thereof an effective amount of a compound of the invention or a composition of the invention. See Rip, J. et al. Arterioscler Thromb Vasc Biol. 2006 March; 26(3):637-42. Epub 2005 Dec. 22.

The present invention provides methods for treating a subject having or preventing a subject from having an abnormally high concentration of lipoprotein-associated phospholipase $A_2$ (Lp-PLA$_2$) in a subject's blood plasma or blood serum, comprising administering to a subject in need thereof an effective amount of a compound of the invention or a composition of the invention. An "abnormally high concentration" of Lp-PLA$_2$ in a subject's blood plasma or blood serum is greater than 200 ng/mL. In some embodiments, the subject has a risk for developing cardiovascular disease. In some embodiments, the risk is high.

In some embodiments, the present invention provides methods for reducing an abnormally high concentration of Lp-PLA$_2$ in a subject's blood plasma or blood serum, comprising administering to a subject in need thereof an effective amount of a compound of the invention or a composition of the invention. In some embodiments, the reducing is to a normal concentration. In some embodiments, the normal concentration of Lp-PLA$_2$ in a subject's blood plasma or blood serum concentration is less than 200 ng/mL. In some embodiments, the present invention provides methods for treating a subject with Lp-PLA$_2$ blood plasma or blood serum concentration of greater than 200 ng/mL. See Davidson, M. H. et al, The American Journal of Cardiology, 2008, 101, S51.

The present invention provides methods for treating or preventing hypoalphalipoproteinemia, a lipoprotein abnormality associated with diabetes, a lipoprotein abnormality associated with obesity, a lipoprotein abnormality associated with Alzheimer's Disease, or familial combined hyperlipidemia, comprising administering to a subject in need thereof an effective amount of a compound of the invention or a composition of the invention.

The present invention provides methods for reducing in a subject's blood plasma or blood serum an abnormally high concentration of triglyceride, low-density lipoprotein cholesterol (LDL-C), very low-density lipoprotein cholesterol (VLDL-C), non-high-density lipoprotein cholesterol, (non-HDL-C), lipoprotein(a) (Lp(a)), apolipoprotein B, HDL/(VLDL+LDL) ratio, apolipoprotein C-II (apo C-II) or apolipoprotein C-III (apo C-III), comprising administering to a subject in need thereof an effective amount of a compound of the invention or a composition of the invention.

An "abnormally high concentration" of triglyceride in a subject's blood serum is greater than 150 mg/dL. In some embodiments, the reducing is to a normal concentration. In some embodiments, the normal concentration of triglyceride in a subject's blood serum is less than 150 mg/dL. In some embodiments, the present invention provides methods for reducing a subject's blood serum triglyceride concentration, where the subject has a blood serum triglyceride concentration greater than or equal to 200 mg/dL. In some embodiments, the present invention provides methods for reducing a subject's blood serum triglyceride concentration, where the subject has a blood serum triglyceride concentration greater than or equal to 500 mg/dL.

An "abnormally high concentration" of LDL-C in a subject's blood plasma or blood serum for primary prevention is greater than 100 mg/dL. An "abnormally high concentration" of LDL-C in a subject's blood plasma or blood serum for secondary prevention in a subject with risk factors is greater than 70 mg/dL. In some embodiments, the reducing is to a normal concentration. In some embodiments, the normal concentration of LDL-C in a subject's blood plasma or blood serum is less than 100 mg/dL, wherein the subject is being considered for primary prevention. In some embodiments, the normal concentration of LDL-C in a subject's blood plasma or blood serum is less than 70 mg/dL. In some embodiments, the subject has risk factors and is being considered for secondary prevention. See Walldius, 2006.

In some embodiments, an "abnormally high concentration" of LDL-C in a subject's blood plasma or blood serum is greater than 160 mg/dL. In some embodiments, the reducing is to a normal concentration. In some embodiments, the normal concentration of LDL-C in a subject's blood plasma or blood serum is less than 160 mg/dL. In some embodiments, the subject has 0-1 CHD risk factors. In some embodiments, the present invention provides methods for treating a subject with LDL-C blood plasma or blood serum concentration of greater than 160 mg/dL. In some embodiments, the present invention provides methods for treating a subject with LDL-C blood plasma or blood serum concentration of greater than 160 mg/dL. In some embodiments, the subject has 0-1 CHD risk factors. See Walldius, 2006.

In some embodiments, an "abnormally high concentration" of LDL-C in a subject's blood plasma or blood serum is greater than 130 mg/dL. In some embodiments, the subject has 2 or more CHD risk factors. In some embodiments, the reducing is to a normal concentration. In some embodiments, the normal concentration of LDL-C in a subject's blood plasma or blood serum is less than 130 mg/dL. In some embodiments, the subject has 2 or more CHD risk factors. In some embodiments, the present invention provides methods for treating a subject with LDL-C blood plasma or blood serum concentration of greater than 130 mg/dL. In some embodiments, the subject has 2 or more CHD risk factors. See Walldius, 2006.

In some embodiments, an "abnormally high concentration" of LDL-C in a subject's blood plasma or blood serum is greater than 100 mg/dL. In some embodiments, the subject has a CHD or a CHD risk equivalent. In some embodiments, the reducing is to a normal concentration. In some embodiments, the normal concentration of LDL-C in a subject's blood plasma or blood serum is less than 100 mg/dL. In some embodiments, the subject has a CHD or a CHD risk equivalent. In some embodiments, the present invention provides methods for treating a subject with LDL-C blood plasma or blood serum concentration of greater than 100 mg/dL. In some embodiments, the subject has a CHD or a CHD risk equivalent. See Walldius, 2006.

An "abnormally high concentration" of apo C-III concentration in a subject's blood plasma or blood serum is greater than 7.87 mg/dL. In some embodiments, the reducing is to a normal concentration. In some embodiments, the normal concentration of apo C-III concentration in a subject's blood plasma or blood serum is less than 7.87 mg/dL. In some embodiments, the present invention provides methods for treating a subject, where the subject has an apo C-III blood plasma or blood serum concentration greater than 8 mg/dL. In some embodiments, the present invention provides methods for treating a subject, where the subject has an apo C-III blood plasma or blood serum concentration greater than 7.9 mg/dL. In some embodiments, the present invention provides methods for treating a subject, where the subject has an apo C-III blood plasma or blood serum concentration greater than 7.87 mg/dL. In some embodiments, the abnormally high concentration of apo C-III is associated with high risk of coronary artery disease. See Capelleveen et al. Arterioscler Thromb Vasc Biol. 2017 June; 37(6): 1206-1212.

The present invention provides methods for reducing in a subject's blood plasma or blood serum an abnormally high LDL-C/HDL-C ratio, comprising administering to a subject in need thereof an effective amount of a compound of the invention or a composition of the invention.

In some embodiments, an "abnormally high ratio" of LDL-C/HDL-C in a male subject's blood plasma or blood serum for primary prevention is greater than 3.0. In some embodiments, the reducing is to a normal ratio. In some embodiments, the normal ratio of LDL-C/HDL-C in a male subject's blood plasma or blood serum is less than 3.0, wherein the subject is being considered for primary prevention. In some embodiments, the present invention provides methods for treating a male subject with an LDL-C/HDL-C ratio in a subject's blood plasma or blood serum of greater than 3.0. In some embodiment, the me method is for primary prevention.

In some embodiments, an "abnormally high ratio" of LDL-C/HDL-C in a female subject's blood plasma or blood serum for primary prevention is greater than 2.5. In some embodiments, the reducing is to a normal ratio. In some embodiments, the normal ratio of LDL-C/HDL-C in a female subject's blood plasma or blood serum is less than 2.5, wherein the subject is being considered for primary prevention. In some embodiments, the present invention provides methods for treating a female subject with an LDL-C/HDL-C ratio in a subject's blood plasma or blood serum of greater than 2.5. In some embodiment, the me method is for primary prevention. See Walldius, 2006.

In some embodiments, an "abnormally high ratio" of LDL-C/HDL-C in a male subject's blood plasma or blood serum for secondary prevention is greater than 2.5. In some embodiments, the reducing is to a normal ratio. In some embodiments, the normal ratio of LDL-C/HDL-C in a male subject's blood plasma or blood serum is less than 2.5, wherein the subject is being considered for secondary prevention. In some embodiments, the present invention provides methods for treating a male subject with an LDL-C/HDL-C ratio in a subject's blood plasma or blood serum of greater than 2.5. In some embodiment, the me method is for secondary prevention. See Walldius, 2006.

In some embodiments, an "abnormally high ratio" of LDL-C/HDL-C in a female subject's blood plasma or blood serum for secondary prevention is greater than 2.0. In some embodiments, the reducing is to a normal ratio. In some embodiments, the normal ratio of LDL-C/HDL-C in a female subject's blood plasma or blood serum is less than 2.0, wherein the subject is being considered for secondary prevention. In some embodiments, the present invention provides methods for treating a female subject with an LDL-C/HDL-C ratio in a subject's blood plasma or blood serum of greater than 2.0. In some embodiment, the me method is for secondary prevention. See Walldius, 2006.

The present invention provides methods for reducing in a subject's blood plasma or blood serum an abnormally high concentration of non-HDL-C, comprising administering to a subject in need thereof an effective amount of a compound of the invention or a composition of the invention.

In some embodiments, an "abnormally high concentration" of non-HDL-C in a subject's blood plasma or blood serum is greater than 190 mg/dL. In some embodiments, the reducing is to a normal concentration. In some embodiments, the normal concentration of non-HDL-C in a subject's blood plasma or blood serum is less than 190 mg/dL. In some embodiments, the subject has 0-1 CHD risk factors. In some embodiments, the present invention provides methods for reducing a subject's non-HDL-C concentration in the subject's blood plasma or blood serum, wherein the non-HDL-C concentration is greater than 190 mg/dL. In some embodiments, the subject has 0-1 CHD risk factors. See Walldius, 2006.

In some embodiments, an "abnormally high concentration" of non-HDL-C in a subject's blood plasma or blood serum is greater than 160 mg/dL. In some embodiments, the subject has 2 or more CHD risk factors. In some embodiments, the reducing is to a normal concentration. In some embodiments, the normal concentration of non-HDL-C in a subject's blood plasma or blood serum is less than 160 mg/dL. In some embodiment, the subject has 2 or more CHD risk factors. In some embodiments, the present invention provides methods for reducing a subject's non-HDL-C concentration in the subject's blood plasma or blood serum, wherein the subject's non-HDL-C concentration is greater than 160 mg/dL. In some embodiments, the subject has 2 or more CHD risk factors. See Walldius, 2006.

In some embodiments, an "abnormally high concentration" of non-HDL-C in a subject's blood plasma or blood serum is greater than 130 mg/dL. In some embodiments, the subject has a CHD or a CHD risk equivalent. In some embodiments, the reducing is to a normal concentration. In some embodiments, the normal concentration of non-HDL-C in a subject's blood plasma or blood serum is less than 130 mg/dL. In some embodiments, the subject has a CHD or a CHD risk equivalent. In some embodiments, the present invention provides methods for reducing a subject's non-HDL-C concentration in the subject's blood plasma or blood serum, wherein the subject's non-HDL-C concentration is greater than 130 mg/dL. In some embodiments, the subject has a CHD or a CHD risk equivalent. See Walldius, 2006.

The present invention provides methods for elevating in a subject's blood plasma or blood serum an abnormally low concentration of a high-density lipoprotein (HDL)-associated protein, HDL-cholesterol (HDL-C), apolipoprotein A-I, or apolipoprotein E, comprising administering to a subject in need thereof an effective amount of a compound of the invention or a composition of the invention. In some embodiments, the HDL-associated protein is apolipoprotein A-I (apo A-I), apolipoprotein A-II (apo A-II), apolipoprotein A-IV (apo A-IV) or apolipoprotein E (apo E).

In some embodiments, an "abnormally low concentration" of HDL-C in a subject's blood plasma or blood serum is less than 40 mg/dL. In some embodiments, the elevating is to a normal concentration. In some embodiments, the normal concentration of HDL-C in a subject's blood plasma or blood serum is greater than 40 mg/dL. In some embodiments, the present invention provides methods for elevating HDL-C concentration in a subject's blood plasma or blood serum, where the subject's HDL-C concentration is less than 40 mg/dL. In some embodiments, the subject is a male subject. In some embodiments, the subject is a female subject.

In some embodiments, an "abnormally low concentration" of HDL-C in a male subject's blood plasma or blood serum is less than 45 mg/dL. In some embodiments, the normal concentration of HDL-C in a male subject's blood plasma or blood serum is greater than 45 mg/dL. In some embodiments, the present invention provides methods for elevating HDL-C concentration in a male subject's blood plasma or blood serum, where the subject's HDL-C concentration is less than 45 mg/dL.

In some embodiments, an "abnormally low concentration" of HDL-C in a female subject's blood plasma or blood serum is less than 50 mg/dL. In some embodiments, the normal concentration of HDL-C in a female subject's blood plasma or blood serum is greater than 50 mg/dL. In some embodiments, the normal concentration of HDL-C in a female subject's blood plasma or blood serum is greater than 55 mg/dL. In some embodiments, the present invention provides methods for elevating HDL-C concentration in a female subject's blood plasma or blood serum, where the subject's HDL-C concentration is less than 50 mg/dL. In some embodiments, the present invention provides methods for elevating HDL-C concentration in a female subject's blood plasma or blood serum where the subject's HDL-C concentration is lower than 55 mg/dL.

In some embodiments, the present invention provides methods for elevating HDL-C concentration in a subject's blood plasma or blood serum to 45 mg/dL or greater, where the subject's HDL-C concentration in a subject's blood plasma or blood serum is less than 40 mg/dL. In some embodiments, the present invention provides methods for elevating HDL-C concentration in a subject's blood plasma or blood serum to 50 mg/dL or greater, where the subject's HDL-C concentration in a subject's blood plasma or blood serum is less than 40 mg/dL. In some embodiments, the present invention provides methods for elevating HDL-C concentration in a subject's blood plasma or blood serum to 55 mg/dL or greater, where the subject's HDL-C concentration in a subject's blood plasma or blood serum is less than 40 mg/dL.

In some embodiments, the present invention provides methods for elevating HDL-C concentration in a male subject's blood plasma or blood serum to 50 mg/dL or greater, where the subject's HDL-C concentration in a subject's blood plasma or blood serum is less than 45 mg/dL. In some embodiments, the present invention provides methods for elevating HDL-C concentration in a female subject's blood plasma or blood serum to 50 mg/dL or greater, where the subject's HDL-C concentration in a subject's blood plasma or blood serum is less than 50 mg/dL. In some embodiments, the present invention provides methods for elevating HDL-C concentration in a female subject's blood plasma or blood serum to 55 mg/dL or greater, where the subject's HDL-C concentration in a subject's blood plasma or blood serum is less than 50 mg/dL.

The present invention provides methods for promoting clearance of triglyceride from a subject's blood plasma or blood serum, comprising administering to a subject in need thereof an effective amount of the compound of the invention or the composition of the invention.

The present invention provides methods for increasing an abnormally low glucose metabolism or increasing an abnormally low lipid metabolism in a subject, comprising administering to a subject in need thereof an effective amount of a compound of the invention or a composition of the invention. In some embodiments, the method for increasing an abnormally low glucose metabolism increases insulin sensitivity or oxygen consumption in a subject. In some embodiments, the method for increasing an abnormally low glucose metabolism reduces blood insulin, blood glucose, or glycated hemoglobin in a subject's blood plasma or blood serum. In some embodiments, the methods for increasing an abnormally low lipid metabolism reduces a concentration of LDL or free triglyceride in a subject's blood plasma or blood serum, or inhibits saponified or non-saponified fatty acid synthesis.

In some embodiments, a subject with abnormally low glucose metabolism has an abnormally high concentration of glucose or hemoglobin (Hb) in the subject's blood plasma or blood serum. In some embodiments, the present invention provides methods for reducing an abnormally high concentration of glucose or hemoglobin in a subject's blood plasma or blood serum. In some embodiments, the method increases abnormally low glucose metabolism. An "abnormally high concentration" of glucose in a subject's blood plasma or blood serum in a two-hour GTT is greater than 7.8 mmol/L (140 mg/dL). In some embodiments, reducing is to a normal concentration. In some embodiments, the normal concentration of glucose in a subject's blood plasma or blood serum in a two-hour GTT is less than 7.8 mmol/L (140 mg/dL). In some embodiments, the present invention provides methods for increasing abnormally low glucose metabolism in a subject's blood plasma or blood serum, where the subject's glucose concentration in the subject's blood plasma or blood serum in a two-hour GTT is greater than 7.8 mmol/L (140 mg/dL). In some embodiments, the present invention provides methods for increasing abnormally low glucose metabolism in a subject, where the subject's glucose concentration in the subject's blood plasma or blood serum in a two-hour GTT ranges from 7.8 mmol/L (140 mg/dL) to 11.1 mmol/L (200 mg/dL). In some embodiments, the present invention provides methods for increasing abnormally low glucose metabolism in a subject, where the subject's glucose concentration in the subject's blood plasma or blood serum in a two-hour GTT is above 11.1 mmol/L (200 mg/dL).

In some embodiments, the present invention provides methods for increasing abnormally low glucose metabolism in a subject, where the subject has impaired glucose tolerance. In some embodiments, the present invention provides methods for increasing abnormally low glucose metabolism in a subject, where the subject has diabetes. In some embodiments, the present invention provides methods for increasing abnormally low glucose metabolism in a subject, where the subject has gestational diabetes.

A low lipid metabolism can be characterized by dyslipidemia (using the LDL-C, TGs, non-HDL-chol, apo B, apo C-III or apo C-II values) but also with elevated concentration of transaminases. In some embodiments, the subject having a low lipid metabolism also has dyslipidemia.

The present invention provides methods for treating or preventing a symptom of a disease selected from inflammation, systemic lupus erythematosus, lupus nephritis, or arthritis, comprising administering to a subject in need thereof an effective amount of a compound of the invention or a composition of the invention. In some embodiments, the arthritis is adjuvant arthritis or type II collagen-induced arthritis. In some embodiments, the symptom is nephritis, kidney failure, or kidney function reduction. In some embodiments, the kidney function reduction requires renal dialysis.

The present invention provides methods for reducing fat content of meat in livestock, comprising administering to livestock an effective amount of a compound of the invention or a composition of the invention.

The present invention provides methods for reducing cholesterol content of a fowl egg, comprising administering to a fowl species an effective amount of a compound of the invention or a composition of the invention.

In some embodiments, the methods of the invention provide administering a dosage form of the compounds of the invention or the compositions of the invention hourly, daily, weekly, or monthly. The dosage forms and formulations of the present invention may be administered three times a day, twice a day or once a day. The dosage forms of the present invention can be administered with food or without food. An appropriate length of the treatment, dosages, and route of administration can be determined and/or adjusted by a physician.

In some embodiments of the methods of the invention, the subject is a human subject.

5.5. Synthesis of Compounds of the Invention

Compounds of the invention can be synthesized by conventional means. Exemplary processes for synthesizing exemplary compounds of Formula (A) and Formula (B) are described in Examples 1-3, infra. WO 2011/020001, the contents of which are incorporated herein by reference in their entireties, describes PPAR modulator compounds (described therein as compounds of Formulas (I)-(XX)) and processes for their synethesis. Compounds of Formulas (I)-(XX) described in WO 2011/020001 can be used as starting materials for synthesis of compounds of Formulas (C)-(H) and (J)-(W) of the present invention, respectively. For example, compounds of WO 2011/020001 having a ketone can be reduced with a reducing agent, such as $NaBH_4$, optionally in the presence of a Lewis acid, such as $CeCl_3$, or in an alcohol solvent, such as methanol, to provide convert the ketone group to a hydroxyl group. Similarly, carboxylic acid groups of compounds of WO 2011/020001 can be reduced to a hydroxymethyl group using a reducing reagent, such as $LiAlH_4$, followed by an aqueous acid workup to provide a compound of the invention.

WO 2017/062468, the contents of which are incorporated herein by reference in their entireties, describe PPAR modulator compounds (described therein as compounds of Formulas (I)-(III)) and processes for their synthesis. Compounds of Formulas (I)-(III) described in WO 2017/06246 can be used as starting materials for synthesis of compounds of Formulas (X)-(Z) of the present invention, respectively. Carboxylic acid groups of compounds of WO 2017/06246 can be reduced to a hydroxymethyl group using a reducing reagent, such as LiAlH$_4$, followed by an aqueous acid workup to provide a compound of the invention.

WO 2017/180818, the contents of which are incorporated herein by reference in their entireties, describe PPAR modulator compounds (described therein as compounds of Formulas (I)) and processes for their synthesis. Compounds of Formula (I) described in WO 2017/180818 can be used as starting materials for synthesis of compounds of Formula (AA) of the present invention. Carboxylic acid groups of compounds of WO 2017/180818 can be reduced to a hydroxymethyl group using a reducing reagent, such as LiAlH$_4$, followed by an aqueous acid workup to provide a compound of the invention.

WO 2018/067857, the contents of which are incorporated herein by reference in their entireties, describe PPAR modulator compounds (described therein as compounds A, B, and C) and processes for their synthesis. Compounds B and C described in WO 2018/067857 can be used as starting materials for synthesis of Compounds VII and VIII. Carboxylic acid groups of compounds of WO 2017/180818 can be reduced to a hydroxymethyl group using a reducing reagent, such as LiAlH$_4$, followed by an aqueous acid workup to provide a compound of the invention.

6. EXAMPLES

6.1. Example 1. Synthesis of Compound I

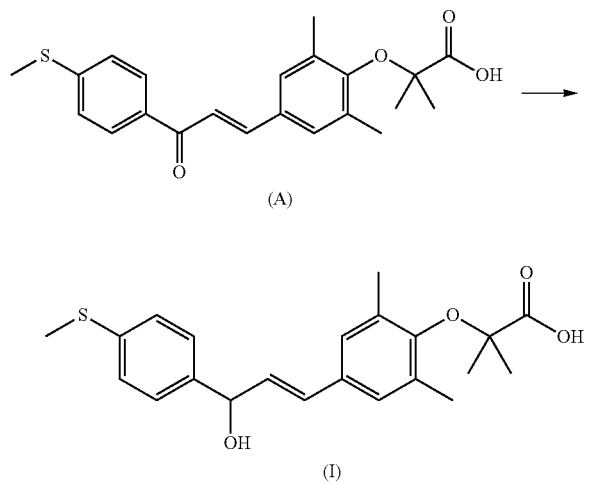

(Z)-2-(2,6-dimethyl-4-(3-(4-(methylthio)phenyl)-3-oxo-prop-1-en-1-yl)phenoxy)-2-methylpropanoic acid ("Compound A") is synthesized according to US2006/0142611. Compound A is then reduced using a reducing agent, such as NaBH$_4$, optionally in the presence of a Lewis acid, such as CeCl$_3$, or in an alcohol solvent, such as methanol, to provide Compound I racemate. Compound I racemate is then resolved to provide its (S)- and (R)-enantiomers, each being substantially free of its corresponding opposite enantiomer, using a chiral high performance liquid chromatography.

6.2. Example 2. Synthesis of Compound II

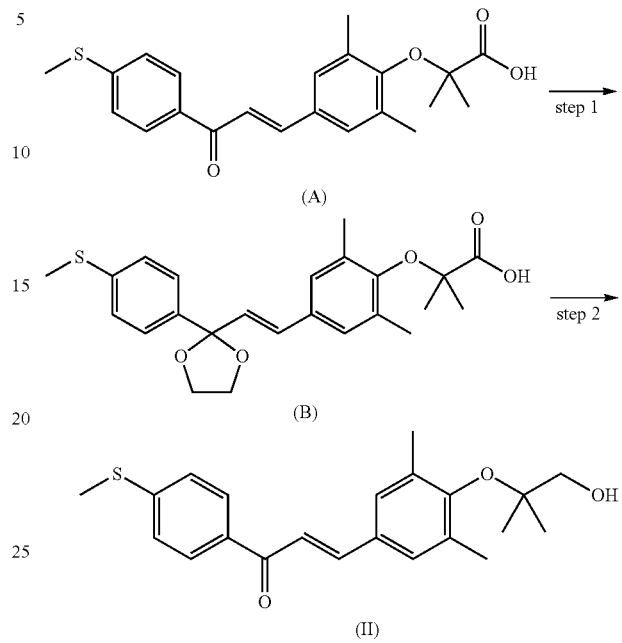

Acetal Compound is synthesized from Compound an ethylene glycol in the presence of catalytic acid, such as 0.1 M HCl. See, e.g., Dong, J-L., et al. ACS Omega, 2018, 3, 4974 for acetal formation specifically on □□□-unsaturated ketones. The carboxyl group of Compound B is subsequently reduced to a hydroxymethyl group using a reducing reagent, such as LiAlH$_4$, followed by an aqueous acid workup, which removes the acetal to provide Compound II.

6.3. Example 3. Synthesis of Compound III

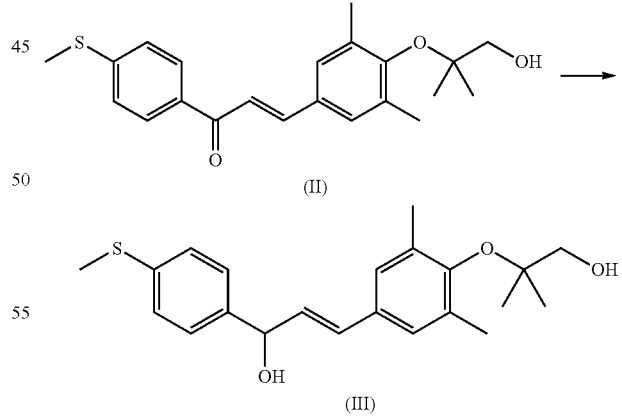

Compound II is reduced using a reducing agent, such as NaBH$_4$, optionally in the presence of a Lewis acid, such as CeCl$_3$, or in an alcohol solvent, such as methanol, to provide Compound III racemate. Compound III racemate is then resolved to provide its (S)- and (R)-enantiomers, each being substantially free of its corresponding opposite enantiomer, using a chiral high performance liquid chromatography.

6.4. Example 4. Hepatic and Peripheral Insulin Sensitive Effects in Rats Fed a High Fat/Medium Fructose Diet (Western Diet)

After 8 weeks of high fat diet, rats are treated for 5 weeks with pioglitazone (10 mg/kg), metformin (50 mg/kg), an illustrative compound of the invention (3 and 10 mg/kg), alone or in association with metformin (50 mg/kg), and GW501516 (2-[2-methyl-4-[[4-methyl-2-[4-(trifluoromethyl)phenyl]-1,3-thiazol-5-yl]methylsulfanyl]phenoxy] acetic acid) (10 mg/kg; ligand/GSK). Body weight can be decreased by metformin and this effect can be emphasized when it is associated with the illustrative compound of the invention in a dose of 10 mg/kg. After 17 days of treatment, rats are fasted for 4 hours and blood is sampled.

The glucose tolerance is assessed after 21 days of treatment by an oral glucose load performed after 6 hours of fasting.

After 5 weeks of treatment, an euglycemic-hyperinsulinemic clamp procedure is performed in awake rats. Two doses of insulin are infused with 3H-glucose: 0.2 U/kg/h to assess an effect on hepatic glucose production (HGP) and 0.8 U/kg/h to inhibit HGP and then to assess an effect on whole body glucose utilization.

6.4.1. Animal Model

Male Sprague Dawley (SD) rats (250-275 g) are first fed with the western diet during 8 weeks for inducing insulin resistance. The first set of rats undergoes an oral glucose tolerance test (OGTT) after 3 weeks of treatment (half rats/group of the clamp arm) and the second set also undergoes an OGTT after 3 weeks of treatment (half rats/group of clamp arm) and the histology study (3 rats/group).

Rats of each set are screened and randomized into the several groups according to their fasted (4 h) plasma glucose, insulin levels (for homeostatic model assessment of insulin resistance (HOMA-IR) calculation) and body weight. Rats that do not respond to the western diet are excluded from the study.

Homogenous mild obese and insulin resistant rats are allocated into the different treatment groups and western diet is continued until the end of the experiment. Given that, the 2 series started with a gap of one week.

6.4.2. Treatments

Dosage regimen: Rats are treated once daily via the oral route, in the morning. The duration of the treatment is between 5 and 5.5 weeks.

6.4.3. Test Groups

Group 1: vehicle (n=12)
Group 2: pioglitazone, 10 mg/kg (n=12)
Group 3: metformin, 50 mg/Kg (n=12)
Group 4: an illustrative compound of the invention, 3 mg/Kg (n=12)
Group 5: an illustrative compound of the invention, 10 mg/Kg (n=12)
Group 6: an illustrative compound of the invention, 3 mg/Kg+metformin 50 mg/kg (n=12)
Group 7: an illustrative compound of the invention, 10 mg/Kg+metformin 50 mg/kg (n=12)
Group 8: GW501216, 10 mg/Kg (n=12)

6.4.4. Fasting Conditions

Fasting conditions for the OGTT and the clamp procedure: food is removed from the cage and litter is changed just before lights-off (between 7:30 and 8:00 am). Then each experiment starts after about 6 hours of fasting (between 1:30 and 2:00 pm).

Fasting conditions for plasma parameters: food is removed from the cage and litter is changed 4 hours after lights-off (between 11:30 am and noon). Then blood collection starts after 4 hours of fasting (at 4:00 pm).

6.4.5. Oral Glucose Tolerance Test

After 3 weeks of treatment, rats are fasted for 6 hours and an oral glucose load (2.5 g/kg body weight) is performed. Blood glucose is measured 30 minutes before glucose load and at 0, 15, 30, 60, 90 and 120 minutes.

6.4.6. Euglycemic-Hyperinsulinemic 2 Steps Clamp with 3H-Glucose

After 4 weeks of treatment, a catheter is implanted into the femoral vein under isoflurane anesthesia and a period of 5-6 days is respected for recovery. Rats that do not recover body weight are excluded from the study. The accepted body weight loss estimated on the day of perfusion is fixed at 5% in groups where treatments should not affect body weight (as seen during body weight follow-up) (vehicle, pioglitazone and the illustrative compound of the invention, mg/kg groups) and at 10% where treatments decreases it (the 5 other groups). The morning of the clamp procedure, rats are treated and fasted for 6 hours prior to tracer, glucose and insulin infusions. The beginning of the clamp procedure is performed in the middle of the dark cycle.

The euglycemic-hyperinsulinemic 2 steps insulin clamp is performed using 0.2 U/kg/h and 0.8 U/kg/h insulin infusion associated with 3H-glucose infusion. Thereafter the following parameters are assessed:
  Whole body glucose utilization
  Hepatic glucose production
  Glucose infusion rate
  Whole body glycogen and glycolytic rates

6.4.7. In Vivo Glucose Utilization Rate

During the clamp procedure, a bolus (30 µCi) of D-[3-3H]glucose is first injected followed by 4 µCi/min/kg infusion rate during all the experiment to ensure a detectable plasma D[3-3H]glucose enrichment. A bolus of insulin (100 mU) is first injected, and insulin is then infused at a rate of 0.2 U/kg/h for the first 2 hours and 0.8 U/kg/h from 120 minutes to 210 minutes.

Throughout the infusion, glycaemia is assessed with a blood glucose meter from the tip of the tail vein when needed. Euglycemia is maintained by periodically (every 10 minutes) adjusting a variable infusion of 30% glucose. Plasma glucose concentrations and D-[3-3H]glucose specific activity are determined during stable phase in 10 µl of blood sampled from the tip of the tail vein every 20 minutes from 60 to 120 minutes during the first step and from 150 to 210 minutes during the second step.

For glucose turnover measurements, D-[3-3H]glucose enrichments are determined from total blood after deproteinization by a $Zn(OH)_2$ precipitate. Briefly, an aliquot of the supernatant is evaporated to dryness to determine the radioactivity corresponding to D-3-3H. In a second aliquot of the same supernatant, glucose concentration is assessed by the glucose oxidase method (Biomerieux, France).

6.4.8. Calculation

Calculations for glucose turnover measurements are made from parameters obtained during the infusions in steady-state condition (60-120 and 160-210 minutes). Briefly, the D-[3-3H]glucose specific activity is calculated by dividing the D-[3-3H]glucose enrichment by the plasma glucose concentration. The whole body glucose turnover rate is calculated by dividing the rate of D[3-3H]glucose by the D-[3-3H]glucose plasma specific activity. For each rat, the mean values are calculated and averaged with values from rats of the same group. The whole body glycolysis rate are measured by assessing the amount of tritiated water accumulated in the blood during the 3H-glucose infusion and the whole body glycogen synthesis rate are calculated by the difference between the whole body glucose turnover and the whole body glycolysis rate.

6.4.9. Blood, Tissue Collection and Biochemistry

At the end of the clamp procedure (9.5 hours fasting), perirenal, retroperitoneal, epididymal and inguinal fat pads and liver weights are recorded. Blood is collected from cardiac puncture and plasmas are stored at −80° C. for further assays if needed (depending on the radioactive state of samples). Liver triglyceride content is assessed (enzymatic-colorimetric method) as well as liver and adipose tissue TNF-α content (enzyme-linked immunosorbent assay (ELISA) method). See US 2011/0092517, which is hereby incorporated by reference in its entirety.

6.5. Example 5. Mouse and Rat PPAR Transcriptional Activation in Cell-Based Transactivation Assay 6.5.1. Assays with GAL4-PPAR Chimera Receptors 6.5.1.1. Receptor Expression Plasmids An established chimeric receptor system (Lehmann J M et. al. *J Biol Chem.* 1997; 272(6):3406-10) is utilized to allow comparison of the relative transcriptional activity of the receptor subtypes. The mammalian expression vectors pSG5-GAL4-PPARα, pSG5-GAL4-PPARγ and pSG5-GAL4-PPARδ from *Homo sapiens* (hs) (NM_006238, NM_015869, NM_001001928), *Macaca mulatta* (mm) (NM_001033029, XM_001116676, NM_001032860), *Mus musculus* (m) (NM_011144, U10375, NM_011146) and *Rattus norvegicus* (r) (NM_013141, NM_013196, NM_013124), which express the ligand binding domains (LBDs) of human PPARα (amino acids 167-468 for hs and m, amino acids 167-467 for mm), PPARγ1 (amino acids 176-477 for hs, amino acids 204-505 for m and mm from PPARγ) and PPARδ (amino acids 139-441 for hs and mm, amino acids 139-440 for m) each fused to the yeast transcription factor GAL4 DNA binding domain (amino acid 1-147) and the human glucocorticoid receptor (amino acids 1-76), are cloned.

Reporter plasmid: MH100×4-tk-luc (Forman B M et al. *Cell.* 1995 81(4):541-50) is used as the reporter plasmid.

6.5.1.2. Transient Transfection Assays

The African green monkey kidney cell line, CV-1 is used for the transfection assays. CV-1 cells are seeded in 24-well plates at $0.5 \times 10^5$ cells per well and are cultured for 24 hours. Transfection mixtures for chimera receptors contain 30 ng of receptor expression plasmid, 120 ng of the reporter plasmid, 350 ng of pCMX-β-galactosidase (βGAL) expression plasmid as a control for transfection efficiency, 250 ng of pGEM4 carrier plasmid and 2 µL of a lipofection reagent (Lipofectamine 2000, Invitrogen). These mixtures are added to cells and incubated for 5 hours according to the manufacturer's instructions. After the transfection, cells are incubated for an additional 40 hours in the presence of the illustrative compounds of the invention or each reference compound at different concentrations. Cell lysates are prepared with a lysis buffer (Passive Lysis Buffer, Promega) and used in the luciferase and βGAL assays. The luciferase and βGAL activity are measured with the Luciferase assay system (E4030, Promega) and with the βGAL enzyme assay system (E2000, Promega). Assays are performed in triplicate for GAL4-chimeras. Experiments are repeated at least three times.

6.5.1.3. Calculation of Relative PPAR Transactivation Activities

Each point of a relative PPAR transcriptional activity to maximal activity is calculated based on the values bellow:

Luciferase activity of cells treated with a positive control ($10^{-5}$ M GW-590735 for hPPARα, $3 \times 10^{-5}$ M rosiglitazone maleate for hPPARγ assays and $10^{-5}$ M GW-501516 for hPPARδ) as the maximal activity, and luciferase activity of cells treated with 0.1% of DMSO as the minimum activity.

6.5.1.4. Calculation of $EC_{50}$ Values $EC_{50}$ values defined as the concentration of the illustrative compound of the invention and GW-501516 to produce 50% of maximal reporter activity re calculated with Prism software (Graphpad Software).

6.5.1.5. Experiments with 10% Serum vs 0.1% Serum.

Experiments at 2 serum concentrations: 10% and 0.1%. The EC50 are calculated as previously described.

First, the assay is set up and the GAL4-chimeras/reporter plasmids are validated using homo-sapiens sequences of the different PPAR. The experiments are conducted at 10% and 0.1% serum with GW501516 (PPARδ agonist).

Plasmid Reference is as indicated in US 2011/0092517, which is hereby incorporated by reference in its entirety.

7. SPECIFIC EMBODIMENTS

7.1. Specific Embodiments, Group 1

Various aspects of the present disclosure are described in the numbered embodiments set forth in the following numbered paragraphs, where reference to a previous numbered embodiment refers to a previous numbered embodiment in this Section 7.1.

1. A compound of Formula (A):

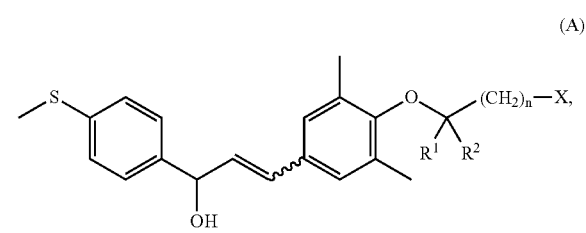

(A)

or a pharmaceutically acceptable salt, solvate, ester, amide, or prodrug thereof, wherein:

each $R^1$ and $R^2$ is independently —$C_1$-$C_6$ alkyl, —$C_2$-$C_6$ alkenyl, —$C_2$-$C_6$ alkynyl, phenyl, or benzyl; or alternatively, $R^1$ and $R^2$ together with the carbon atom to which $R^1$ and $R^2$ are attached form a $C_3$-$C_7$ cycloalkyl group;

X is —$CH_2OH$, —COOH, —COH, —$COOR^3$, —$COOCH_2CONR^4R^5$, —$SO_3H$,

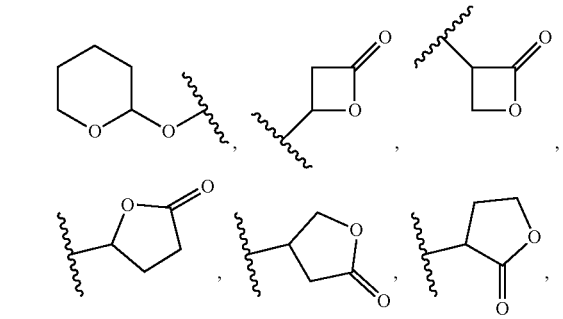

-continued

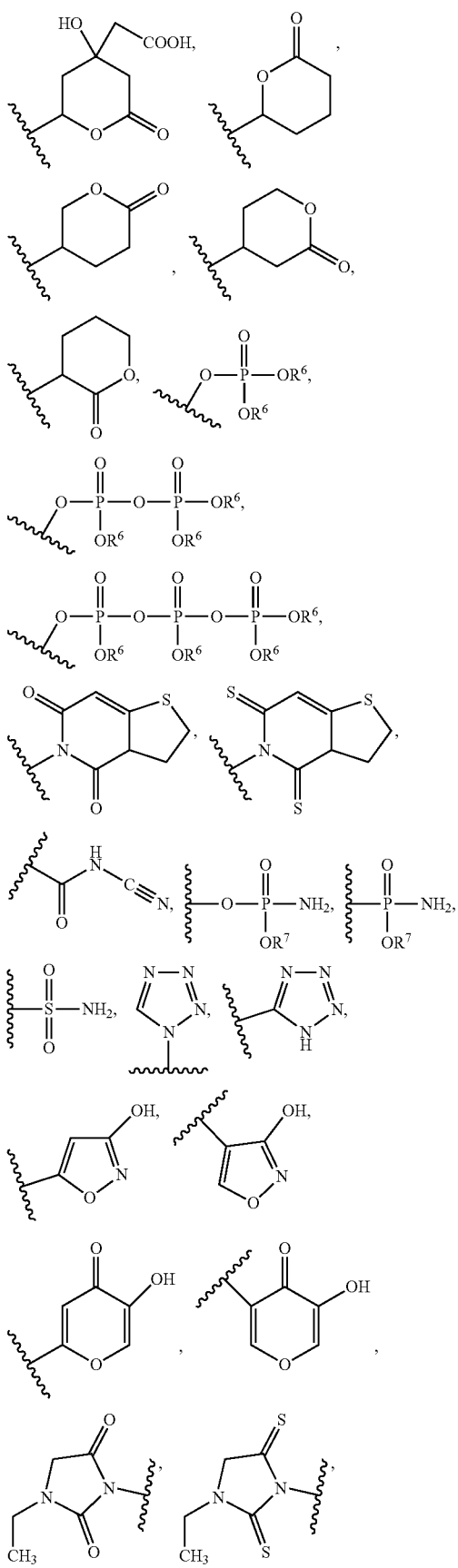

$R^3$ is —$C_1$-$C_6$ alkyl, —$C_2$-$C_6$ alkenyl, —$C_2$-$C_6$ alkynyl, phenyl, or benzyl;

each $R^4$ and $R^5$ is independently alkyl, aryl, or heteroaryl; or alternatively, $R^4$ and $R^5$ together with the carbon atom to which $R^4$ and $R^5$ are attached form a heterocycle;

each $R^6$ and $R^7$ is independently H, —$C_1$-$C_6$ alkyl, —$C_2$-$C_6$ alkenyl, or —$C_2$-$C_6$ alkynyl; and n is 0, 1, 2, 3, or 4.

2. The compound or pharmaceutically acceptable salt, solvate, ester, amide, or prodrug of the compound of embodiment 1, wherein the compound is a racemate or a mixture of enantiomers or diastereomers.

3. The compound or pharmaceutically acceptable salt, solvate, ester, amide, or prodrug of the compound of embodiment 1, wherein the compound has an hydroxyl-bearing allylic carbon atom having an (R)-stereochemistry and has the structure 4. The compound or pharmaceutically acceptable salt, solvate, ester, amide, or prodrug of the compound of embodiment 1, wherein the compound has an hydroxyl-bearing allylic carbon atom having an (S)-stereochemistry and has the structure 5. The compound or pharmaceutically acceptable salt, solvate, ester, amide, or prodrug of the compound of embodiment 3 or 4, wherein the compound is substantially free of its corresponding opposite stereoisomer.

6. The compound or pharmaceutically acceptable salt, solvate, ester, amide, or prodrug of the compound of any one of embodiments 3-5, wherein the compound has an olefin isomer configuration of (Z) or (E).

7. The compound or pharmaceutically acceptable salt, solvate, ester, amide, or prodrug of the compound of embodiment 1, wherein the compound is a (Z)-isomer and has the structure

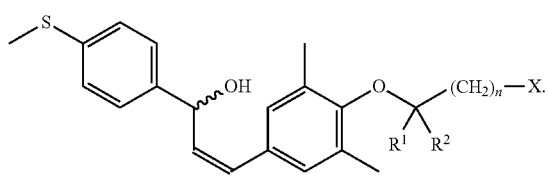

8. The compound or pharmaceutically acceptable salt, solvate, ester, amide, or prodrug of the compound of embodiment 1, wherein the compound is a (E)-isomer and has the structure

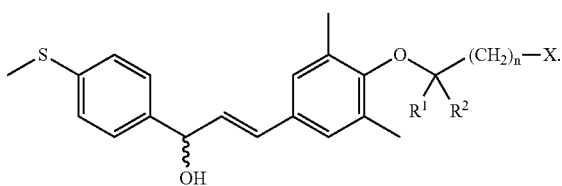

9. The compound or pharmaceutically acceptable salt, solvate, ester, amide, or prodrug of the compound of embodiment 7 or 8, wherein the compound is substantially free of its corresponding other olefin configuration.

10. The compound or pharmaceutically acceptable salt, solvate, ester, amide, or prodrug of the compound of any one of embodiments 7-9, wherein the compound has an hydroxyl-bearing allylic carbon atom having an (R)- or an (S)-stereochemistry.

11. The compound or pharmaceutically acceptable salt, solvate, ester, amide, or prodrug of any one of the compound of embodiments 1-10, wherein each $R^1$ and $R^2$ is independently —$C_1$-$C_3$ alkyl.

12. The compound or pharmaceutically acceptable salt, solvate, ester, amide, or prodrug of any one of the compound of embodiments 1-10, wherein each $R^1$ and $R^2$ is independently methyl.

13. The compound or pharmaceutically acceptable salt, solvate, ester, amide, or prodrug of any one of the compound of embodiments 1-12, wherein X is —$CH_2OH$, —COOH, —COH, —$COOR^3$, or —$COOCH_2CONR^4R^5$.

14. The compound or pharmaceutically acceptable salt, solvate, ester, amide, or prodrug of any one of the compound of embodiments 1-12, wherein X is —$CH_2OH$ or —COOH.

15. The compound or pharmaceutically acceptable salt, solvate, ester, amide, or prodrug of any one of the compound of embodiments 1-14, wherein n is 0 or 1.

16. A compound of Formula (B):

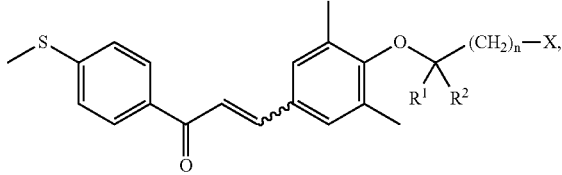

(B)

or a pharmaceutically acceptable salt, solvate, ester, amide, or prodrug thereof, wherein:

each $R^1$ and $R^2$ is independently —$C_1$-$C_6$ alkyl, —$C_2$-$C_6$ alkenyl, —$C_2$-$C_6$ alkynyl, phenyl, or benzyl; or alternatively, $R^1$ and $R^2$ together with the carbon atom to which $R^1$ and $R^2$ are attached form a $C_3$-$C_7$ cycloalkyl group;

X is —$CH_2OH$, —COH, —$COOCH_2CONR^4R^5$, —$SO_3H$,

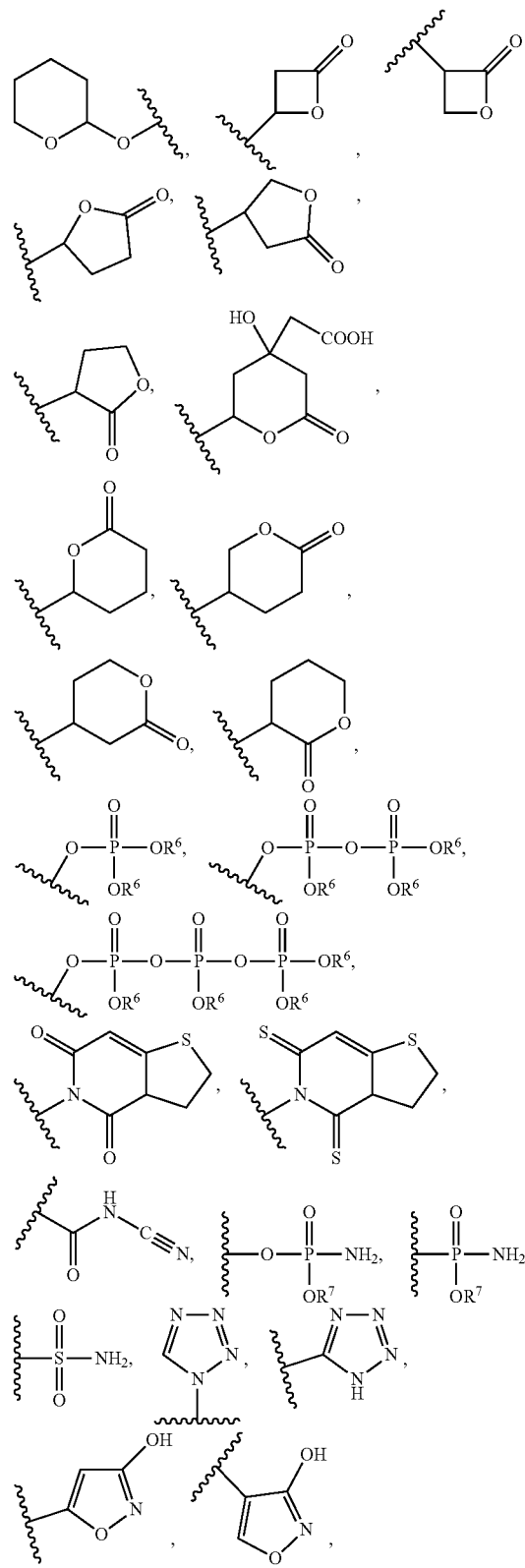

-continued

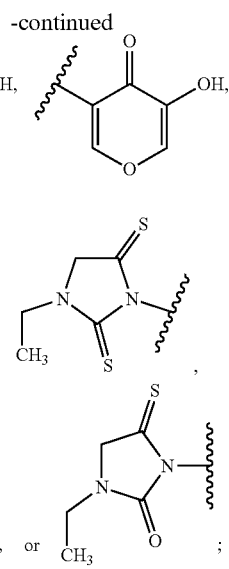

R³ is —C₁-C₆ alkyl, —C₂-C₆ alkenyl, —C₂-C₆ alkynyl, phenyl, or benzyl;

each R⁴ and R⁵ is independently alkyl, aryl, or heteroaryl; or alternatively, R⁴ and R⁵ together with the carbon atom to which R⁴ and R⁵ are attached form a heterocycle;

each R⁶ and R⁷ is independently H, —C₁-C₆ alkyl, —C₂-C₆ alkenyl, or —C₂-C₆ alkynyl; and n is 0, 1, 2, 3, or 4.

17. The compound or pharmaceutically acceptable salt, solvate, ester, amide, or prodrug of the compound of embodiment 1, wherein the compound is a mixture of (Z)- and (E)-isomers.

18. The compound or pharmaceutically acceptable salt, solvate, ester, amide, or prodrug of the compound of embodiment 16, wherein the compound is a (Z)-isomer and has the structure

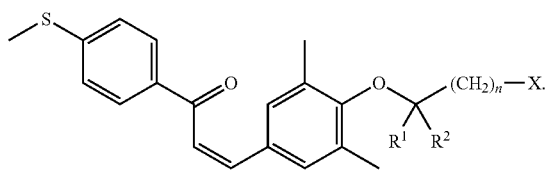

19. The compound or pharmaceutically acceptable salt, solvate, ester, amide, or prodrug of the compound of embodiment 16, wherein the compound is a (E)-isomer and has the structure

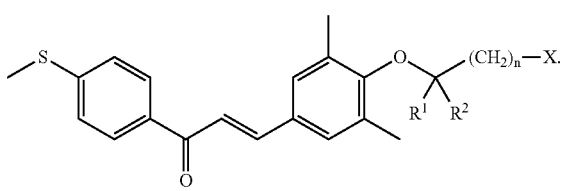

20. The compound or pharmaceutically acceptable salt, solvate, ester, amide, or prodrug of the compound of embodiment 18 or 19, wherein the compound is substantially free of its corresponding other olefin configuration.

21. The compound or pharmaceutically acceptable salt, solvate, ester, amide, or prodrug of the compound of any one of embodiments 16-20, wherein each R¹ and R² is independently —C₁-C₃ alkyl.

22. The compound or pharmaceutically acceptable salt, solvate, ester, amide, or prodrug of any one of embodiments 16-20, wherein each R¹ and R² is independently methyl.

23. The compound or pharmaceutically acceptable salt, solvate, ester, amide, or prodrug of any one of the compound of embodiments 16-22, wherein X is —CH₂OH, —COH, or —COOCH₂CONR⁴R⁵.

24. The compound or pharmaceutically acceptable salt, solvate, ester, amide, or prodrug of any one of the compound of embodiments 16-22, wherein X is —CH₂OH.

25. The compound or pharmaceutically acceptable salt, solvate, ester, amide, or prodrug of any one of the compound of embodiments 16-24, wherein n is 0 or 1.

26. A compound having the structure:

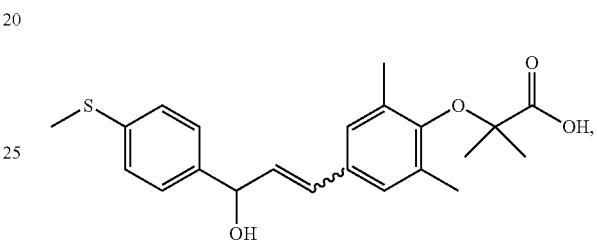

or a pharmaceutically acceptable salt, solvate, ester, amide, or prodrug thereof.

27. The compound or pharmaceutically acceptable salt, solvate, ester, amide, or prodrug of the compound of embodiment 26, wherein the compound is a racemate or a mixture of enantiomers.

28. The compound or pharmaceutically acceptable salt, solvate, ester, amide, or prodrug of the compound of embodiment 26, wherein the compound has an hydroxyl-bearing allylic carbon atom having an (R)-stereochemistry and has the structure

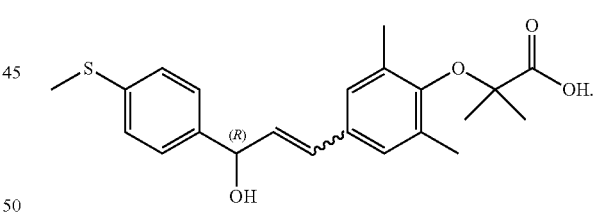

29. The compound or pharmaceutically acceptable salt, solvate, ester, amide, or prodrug of the compound of embodiment 26, wherein the compound has an hydroxyl-bearing allylic carbon atom having an (S)-stereochemistry and has the structure

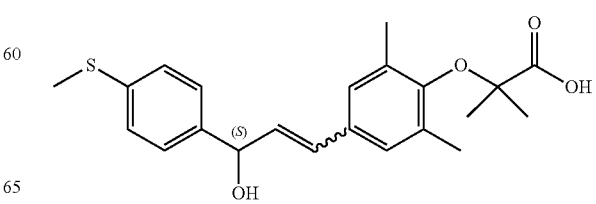

30. The compound or pharmaceutically acceptable salt, solvate, ester, amide, or prodrug of the compound of embodiment 28 or 29, wherein the compound is substantially free of its corresponding opposite enantiomer.

31. The compound or pharmaceutically acceptable salt, solvate, ester, amide, or prodrug of the compound of any one of embodiments 28-30, wherein the compound has an olefin isomer configuration of (Z) or (E).

32. The compound or pharmaceutically acceptable salt, solvate, ester, amide, or prodrug of the compound of embodiment 26, wherein the compound is a (Z)-isomer and has the structure

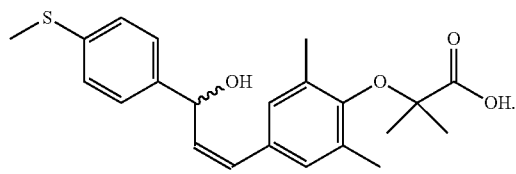 [SMILES: CSc1ccc(C(O)/C=C\c2cc(C)c(OC(C)(C)C(=O)O)c(C)c2)cc1]

33. The compound or pharmaceutically acceptable salt, solvate, ester, amide, or prodrug of the compound of embodiment 26, wherein the compound is a (E)-isomer and has the structure

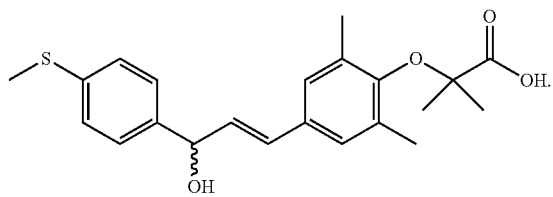 [SMILES: CSc1ccc(C(O)/C=C/c2cc(C)c(OC(C)(C)C(=O)O)c(C)c2)cc1]

34. The compound or pharmaceutically acceptable salt, solvate, ester, amide, or prodrug of the compound of embodiment 32 or 33, wherein the compound is substantially free of its corresponding other olefin configuration.

35. The compound or pharmaceutically acceptable salt, solvate, ester, amide, or prodrug of the compound of any one of embodiments 32-34, wherein the compound has an hydroxyl-bearing allylic carbon atom having an (R)- or an (S)-stereochemistry.

36. A compound having the structure:

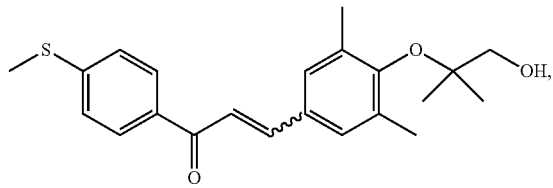 [SMILES: CSc1ccc(C(=O)C=Cc2cc(C)c(OC(C)(C)CO)c(C)c2)cc1]

or a pharmaceutically acceptable salt, solvate, ester, amide, or prodrug thereof.

37. The compound or pharmaceutically acceptable salt, solvate, ester, amide, or prodrug of the compound of embodiment 36, wherein the compound is a mixture of (Z)- and (E)-isomers.

38. The compound or pharmaceutically acceptable salt, solvate, ester, amide, or prodrug of the compound of embodiment 36, wherein the compound is a (Z)-isomer and has the structure

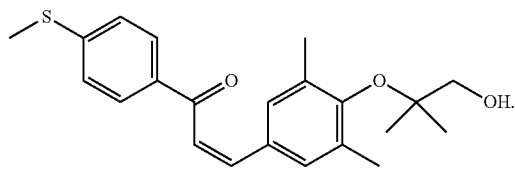 [SMILES: CSc1ccc(C(=O)/C=C\c2cc(C)c(OC(C)(C)CO)c(C)c2)cc1]

39. The compound or pharmaceutically acceptable salt, solvate, ester, amide, or prodrug of the compound of embodiment 36, wherein the compound is a (E)-isomer and has the structure

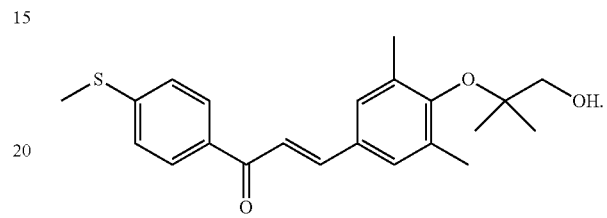

40. The compound or pharmaceutically acceptable salt, solvate, ester, amide, or prodrug of the compound of embodiment 38 or 39, wherein the compound is substantially free of its corresponding other olefin configuration.

41. A compound having the structure:

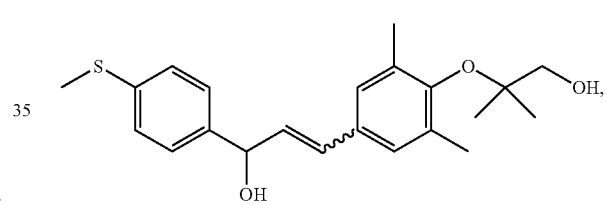

or a pharmaceutically acceptable salt, solvate, ester, amide, or prodrug thereof.

42. The compound or pharmaceutically acceptable salt, solvate, ester, amide, or prodrug of the compound of embodiment 41, wherein the compound is a racemate or a mixture of enantiomers.

43. The compound or pharmaceutically acceptable salt, solvate, ester, amide, or prodrug of the compound of embodiment 41, wherein the compound has an hydroxyl-bearing allylic carbon atom having an (R)-stereochemistry and has the structure

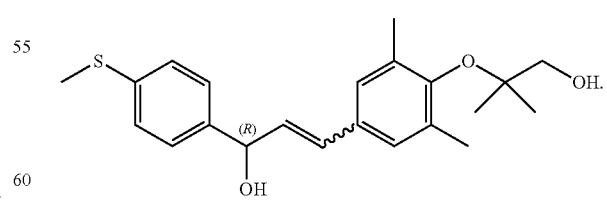

44. The compound or pharmaceutically acceptable salt, solvate, ester, amide, or prodrug of the compound of embodiment 41, wherein the compound has an hydroxyl-bearing allylic carbon atom having an (S)-stereochemistry and has the structure

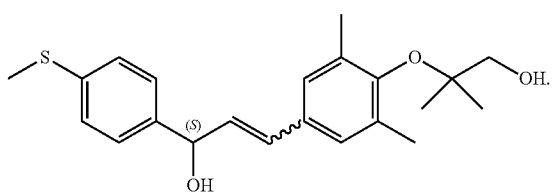

45. The compound or pharmaceutically acceptable salt, solvate, ester, amide, or prodrug of the compound of embodiment 43 or 44, wherein the compound is substantially free of its corresponding opposite enantiomer.

46. The compound or pharmaceutically acceptable salt, solvate, ester, amide, or prodrug of the compound of any one of embodiments 43-45, wherein the compound has an olefin isomer configuration of (Z) or (E).

47. The compound or pharmaceutically acceptable salt, solvate, ester, amide, or prodrug of the compound of embodiment 41, wherein the compound is a (Z)-isomer and has the structure

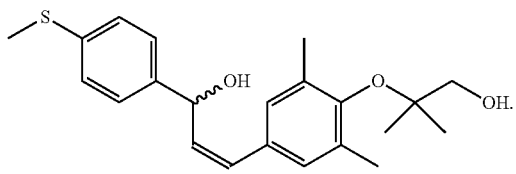 [SMILES: CSc1ccc(C(O)/C=C\c2cc(C)c(OC(C)(C)CO)c(C)c2)cc1]

48. The compound or pharmaceutically acceptable salt, solvate, ester, amide, or prodrug of the compound of embodiment 41, wherein the compound is a (E)-isomer and has the structure

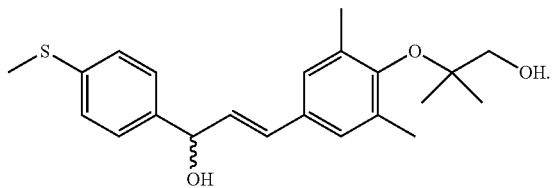 [SMILES: CSc1ccc(C(O)/C=C/c2cc(C)c(OC(C)(C)CO)c(C)c2)cc1]

49. The compound or pharmaceutically acceptable salt, solvate, ester, amide, or prodrug of the compound of embodiment 47 or 48, wherein the compound is substantially free of its corresponding other olefin configuration.

50. The compound or pharmaceutically acceptable salt, solvate, ester, amide, or prodrug of the compound of any one of embodiments 47-49, wherein the compound has an hydroxyl-bearing allylic carbon atom having an (R)- or an (S)-stereochemistry.

51. A composition comprising an effective amount of the compound or pharmaceutically acceptable salt, solvate, ester, amide, or prodrug of the compound of any one of embodiments 1-50 and a pharmaceutically acceptable carrier of vehicle.

52. The composition of embodiment 51, further comprising another therapeutically active agent.

53. The composition of embodiment 52, wherein the other therapeutically active agent is a lipid lowering drug, statin, a cholesterol absorption inhibitor, an antibody against PCSK9, an siRNA PCSK9, an anti-fibrotic agent, a thyroid hormone, a selective thyroid receptor-β agonist, apoptosis signal-regulating kinase 1 (ASK1) inhibitor, acetyl-CoA carboxylase (ACC) inhibitor, an integrin antagonist, or a non-steroidal Farnesoid X receptor (FXR) agonist.

54. The composition of embodiment 53, wherein:
the lipid lowering drug is gemfibrozil, fenofibrate, bezafibrate, clofibrate, ciprofibrate, clinofibrate, etofylline, pirifibrate, simfibrate, tocofibrate, or pemafibrate;
the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt, solvate, ester, amide, or prodrug thereof;
the cholesterol absorption inhibitor is ezetimibe;
the antibody against PCSK9 is evolocumab alirocumab, bococizumab, 1D05-IgG2, RG7652, LY3015014, or LGT-209;
the siRNA PCSK9 is inclisiran;
the anti-fibrotic agent is nitazoxamide, tizoxanide, or tizoxanide glucuronide, or a pharmaceutically acceptable salt, solvate, ester, amide, or prodrug thereof;
the selective thyroid receptor-β agonist is VK2809, MGL-3196, MGL-3745, SKL-14763, sobetirome, BCT304, ZYT1, MB-0781, or eprotirome;
the ASK1 inhibitor is selonsertib;
the ACC inhibitor is firsocostat;
the integrin antagonist is an α5β1 inhibitor or a pan integrin inhibitor; or
the FXR agonist is cilofexor.

55. A method for treating or preventing a liver disorder, dyslipidemia, dyslipoproteinemia, a renal disease, a disorder of glucose metabolism, a disorder of lipid metabolism, a disorder of glucid metabolism, a cardiovascular disease, a vascular disease, a metabolic syndrome, a complication associated with metabolic syndrome, a PPAR-associated disorder, septicemia, a thrombotic disorder, obesity, diabetic nephropathy, diabetic retinopathy, atherosclerosis, pancreatitis, a cerebrovascular disease, a disorder related to neovascularization, hypertension, cancer, inflammation, an inflammatory disease, a neurodegenerative disease, an autoimmune disease, a neoplastic disease, muscle atrophy, cholestasis, mitochondrial dysfunction, an ocular disease, a lysosomal storage disease, a kidney disease, or impotence, comprising administering to a subject in need thereof an effective amount of the compound or the pharmaceutically acceptable salt, solvate, ester, amide, or prodrug of the compound of any one of embodiments 1-50.

56. The method of embodiment 55, wherein the liver disorder involves pathological disruption, inflammation, degeneration, apoptosis, or proliferation of liver cells.

57. The method of embodiment 55, wherein the liver disorder is liver fibrosis, fatty liver disease, non-alcoholic fatty liver disease (NAFLD) or non-alcoholic steatohepatitis (NASH).

58. The method of embodiment 55, wherein the dyslipidemia is hyperlipidemia or an abnormally low concentration of high density lipoprotein cholesterol (HDL-C) in the subject's blood plasma or blood serum.

59. The method of embodiment 58, wherein the hyperlipidemia is hypercholesterolemia, familial hypercholesterolemia, hypertriglyceridemia, or familial combined hyperlipidemia.

60. The method of embodiment 58, wherein the hyperlipidemia is characterized by: an abnormally reduced or deficient lipoprotein lipase level or activity in the subject's blood plasma or blood serum, or an abnormally high concentration of ketone bodies, lipoprotein(a) cholesterol (Lp(a)-C), low density lipoprotein (LDL), very low density lipoproteins cholesterol (VLDL-C) or non-esterified fatty acids in the subject's blood plasma or blood serum.

61. The method of embodiment 60, wherein the reduced or deficient lipoprotein lipase level or activity is a result of a mutation in a gene encoding a lipoprotein lipase.

62. The method of embodiment 55, wherein the dyslipoproteinemia is characterized by an abnormally high concentration of LDL, apolipoprotein (a) or VLDL in a subject's blood plasma or blood serum, or an abnormally low concentration of high density lipoprotein (HDL) or lipoprotein lipase in a subject's blood plasma or blood serum.

63. The method of embodiment 62, wherein the abnormally low concentration of the lipoprotein lipase is associated with: a lipoprotein lipase mutation, hypoalphalipoproteinemia, a lipoprotein abnormality associated with diabetes, a lipoprotein abnormality associated with obesity, a lipoprotein abnormality associated with Alzheimer's disease, or familial combined hyperlipidemia.

64. The method of embodiment 55, wherein the renal disease is a glomerular disease, a tubular disease, a tubulointerstitial disease, acute or rapidly progressive renal failure, chronic renal failure, nephrolithiasis, or a tumor.

65. The method of embodiment 64 wherein:
the glomerular disease is an acute glomerulonephritis, a chronic glomerulonephritis, a rapidly progressive glomerulonephritis, a nephrotic syndrome, a focal proliferative glomerulonephritis, a glomerular lesion associated with systemic disease, Goodpasture syndrome, multiple myeloma, diabetes, neoplasia, sickle cell disease or a chronic inflammatory disease;
the tubular disease is an acute tubular necrosis, an acute renal failure, a polycystic renal disease, medullary sponge kidney, a medullary cystic disease, nephrogenic diabetes, or a renal tubular acidosis;
the tubulointerstitial disease is pyelonephritis, a drug- or toxin-induced tubulointerstitial nephritis, a hypercalcemic nephropathy, or a hypokalemic nephropathy; or
the tumor is renal cell carcinoma or nephroblastoma.

66. The method of embodiment 65, wherein the glomerular lesion associated with systemic disease is systemic lupus erythematosus.

67. The method of embodiment 55, wherein the renal disease is hypertension, nephrosclerosis, microangiopathic hemolytic anemia, atheroembolic renal disease, diffuse cortical necrosis, or a renal infarct.

68. The method of embodiment 67, wherein the hypertension is an essential hypertension, hyperpiesa, hyperpiersis, a malignant hypertension, a secondary hypertension, or a white-coat hypertension.

69. The method of embodiment 55, wherein the disorder of glucose metabolism is an impaired glucose tolerance; an insulin resistance; an insulin resistance-related breast, colon or prostate cancer; diabetes; pancreatitis; hypertension; polycystic ovarian disease; or an abnormally high concentration of blood insulin or glucose in the subject's blood plasma or blood serum.

70. The method of embodiment 69, wherein the diabetes is non-insulin dependent diabetes mellitus (NIDDM), insulin dependent diabetes mellitus (IDDM), gestational diabetes mellitus (GDM), or maturity onset diabetes of the young (MODY).

71. The method of embodiment 55, wherein the vascular disease or the cardiovascular disease is a peripheral vascular disease, a coronary heart disease, stroke, restenosis, arteriosclerosis, ischemia, an endothelium dysfunction, an ischemia-reperfusion injury, a myocardial infarction, or a cerebral infarction.

72. The method of embodiment 55, wherein the PPAR-associated disorder is rheumatoid arthritis, multiple sclerosis, psoriasis, an inflammatory bowel disease, breast cancer, colon cancer, or prostate cancer.

73. The method of embodiment 55, wherein the PPAR-associated disorder is a vascular disease, a muscular disease, a demyelinating disease, a muscle structure disorder, a neuronal activation disorder, a muscle fatigue disorder, a muscle mass disorder, a mitochondrial disease, a mitochondrial dysfunction, a beta oxidation disease, or a metabolic disease.

74. The method of embodiment 73, wherein:
the muscular disease is a muscular dystrophy disease;
the demyelinating disease is multiple sclerosis, Charcot-Marie-Tooth disease, Pelizaeus-Merzbacher disease, encephalomyelitis, neuromyelitis optica, adrenoleukodystrophy, or Guillian-Barre syndrome;
the muscle structure disorder is Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorder, myotonic chondrodystrophy, myotonic dystrophy, myotubular myopathy, nemaline body disease, oculopharyngeal MD, or stress urinary incontinence;
the neuronal activation disorder is amyotrophic lateral sclerosis, Charcot-Marie-Tooth disease, Guillain-Barre syndrome, Lambert-Eaton syndrome, multiple sclerosis, myasthenia gravis, a nerve lesion, peripheral neuropathy, spinal muscular atrophy, tardy ulnar nerve palsy, or toxic myoneural disorder;
the muscle fatigue disorder is chronic fatigue syndrome, diabetes (type I or II), a glycogen storage disease, fibromyalgia, Friedreich's ataxia, intermittent claudication, lipid storage myopathy, MELAS (mitochondrial encephalopathy, lactic acidosis, and stroke-like episodes) syndrome, mucopolysaccharidosis, Pompe disease, or thyrotoxic myopathy;
the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus;
the mitochondrial disease is Alpers's disease, chronic progressive external ophthalmoplegia (CPEO), Kearns-Sayra syndrome (KSS), Leber hereditary optic neuropathy (LHON), MELAS, myoclonic epilepsy and ragged-red fiber disease (MERRF), neurogenic muscle weakness (NARP), ataxia, retinitis pigmentosa, Pearson syndrome, mitochondrial malfunction, or a mitochondrial loss of functionality;
the beta oxidation disease is systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, or riboflavin-responsive disorders of β-oxidation (RR-MADD); or
the metabolic disease is hyperlipidemia, dyslipidemia, hyperchlolesterolemia, hypertriglyceridemia, HDL hypocholesterolemia, LDL hypercholesterolemia, HLD non-cholesterolemia, VLDL hyperproteinemia, dyslipoproteinemia, apolipoprotein A-1 hypoproteinemia, atherosclerosis, a disease of arterial sclerosis, a disease of cardiovascular system, cerebrovascular disease, peripheral circulatory disease, metabolic syndrome, syndrome X, obesity, diabetes, type I diabetes, type II diabetes, hyperglycemia, insulin resistance, impaired glucose tolerance, hyperinsulinism, a diabetic complication, cardiac insufficiency, cardiac infarction, cardiomyopathy, hypertension, non-alcoholic fatty liver disease (NAFLD), non-alcoholic steatohepatitis (NASH), a thrombus, Alzheimer disease, a neurodegenerative disease, a demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, or pancreatitis.

75. The method of embodiment 74, wherein the muscular dystrophy disease is Duchenne muscular dystrophy, Becker muscular dystrophy, a limb-girdle muscular dystrophy, congenital muscular dystrophy, facioscapulohumeral muscular dystrophy, myotonic muscular dystrophy, oculopharyngeal muscular dystrophy, distal muscular dystrophy, or Emery-Dreifuss muscular dystrophy.

76. The method of embodiment 55, wherein the PPAR-associated disorder is an abnormally low concentration of HDL, an abnormally low concentration of apolipoprotein A-1 (apo A-1), an abnormally high concentration of VLDL-C, an abnormally high concentration of low density lipoprotein cholesterol (LDL-C), an abnormally high concentration of triglyceride, an abnormally high concentration of apolipoprotein B (apo B), an abnormally high concentration of apolipoprotein C-III (apo C-III) or an abnormally reduced ratio of post-heparin hepatic lipase to lipoprotein lipase activity in the subject's blood plasma or blood serum.

77. The method of embodiment 55, wherein the PPAR-associated disorder is an abnormally high concentration of HDL or an abnormally low concentration of apo A-1 in the subject's lymph or cerebral fluid.

78. The method of embodiment 55, wherein the obesity is abdominal obesity.

79. The method of embodiment 55, wherein the cerebrovascular disease is cerebral ischemia.

80. The method of embodiment 55, wherein, the disorder related to neovascularization is retinopathy or diabetes.

81. The method of embodiment 55, wherein the cancer is a human sarcoma or human carcinoma.

82. The method of embodiment 55, wherein the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, bone cancer, breast cancer, ovarian cancer, prostate cancer, esophageal cancer, oral cancer, nasal cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, leukemia, acute lymphoblastic B-cell leukemia, acute lymphoblastic T-cell leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, hairy cell leukemia, lymphoblastic leukemia, myelogenous leukemia, lymphocyticleukemia, myelocytic leukemia, polycythemia vera, multiple myeloma, lymphoma, Hodgkin's disease, non-Hodgkin's lymphoma, Waldenstrom's macroglobulinemia, or a heavy chain disease.

83. The method of embodiment 82, wherein the leukemia is acute or chronic lymphoblastic leukemia, myelogenous leukemia, lymphocyticleukemia, lymphocytic leukemia, or myelocytic leukemia.

84. The method of embodiment 83, wherein the myelocytic leukemia is acute and is myeloblastic, promyclocytic, myelomonocytic, monocytic or erythroleukemia.

85. The method of embodiment 83, wherein the lymphoma is Hodgkin's lymphoma or non-Hodgkin's lymphoma.

86. The method of embodiment 55, wherein the inflammatory disease is multiple sclerosis, a chronic inflammatory disorder of a joint, arthritis, a respiratory distress syndrome, an inflammatory bowel disease, an inflammatory lung disorder, an inflammatory disorder, an inflammatory disorder of the gum, tuberculosis, leprosy, an inflammatory disease of the kidney, an inflammatory disorder of the skin, an inflammatory disease of the central nervous system, a systemic lupus erythematosus (SLE) or an inflammatory disease of the heart.

87. The method of embodiment 86, wherein:
the arthritis is rheumatoid arthritis or osteoarthritis;
the inflammatory bowel disease is ileitis, ulcerative colitis or Crohn's disease;
the inflammatory lung disorder is asthma or chronic obstructive airway disease;
the inflammatory disorder of the eye is corneal dystrophy, trachoma, onchocerciasis, uveitis, sympathic ophthalmitis or endophthalmitis;
the inflammatory disorder of the gum is periodontitis or gingivitis;
the inflammatory disease of the kidney is glomerulonephritis or nephrosis;
the inflammatory disorder of the skin is acne, sclerodermatitis, psoriasis, eczema, photoaging or wrinkles;
the inflammatory disease of the central nervous system is AIDS-related neurodegeneration, stroke, neurotrauma, Alzheimer's disease, encephalomyelitis, or viral or autoimmune encephalitis; or
the inflammatory disease of the heart is cardiomyopathy.

88. The method of embodiment 55, wherein the neurodegenerative disease is Alzheimer's disease or Huntington's disease.

89. The method of embodiment 55, wherein the autoimmune disease is immune-complex vasculitis, systemic lupus or erythematodes.

90. The method of embodiment 55, wherein, the neoplastic disease is carcinogenesis.

91. The method of embodiment 55, wherein the cholestasis is intrahepatic cholestatic disease or extrahepatic cholestatic disease.

92. The method of embodiment 91, wherein intrahepatic cholestatic disease is primary biliary cholangitis (PBC), primary sclerosing cholangitis (PSC), progressive familial intrahepatic cholestasis (PFIC), or Alagille syndrome (AS).

93. The method of embodiment 55, wherein the ocular disease is dry eye, meibomian gland dysfunction, a keratoconjunctiva epithelial disorder, a corneal epithelial disorder, or a corneal ulcer.

94. The method of embodiment 55, wherein the lysosomal storage disorder is neuronal ceroid lipofuscinosis, Alzheimer's disease, Huntington's disease, amyotrophic lateral sclerosis (ALS), Parkinson's disease, multiple system atrophy (MSA), progressive supranuclear palsy (PSP), corticobasal degeneration (CBD), dementia with Lewy bodies (DLB), a disorder of the autophagy pathway, Tay-Sach's disease, Fabry disease, Niemann-Pick disease, Gaucher disease, Hunter syndrome, alpha-mannosidosis, aspartylglucosaminuria, cholesteryl ester storage disease, chronic hexosaminidase A deficiency, cystinosis, Danon disease, Farber disease, fucosidosis, galactosialidosis, or Batten disease.

95. The method of embodiment 55, wherein the kidney disease is renal ischemia reperfusion injury.

96. The method of embodiment 55, wherein the impotence results from damages to a nerve, artery, a smooth muscle, or fibrous tissue; diabetes; kidney disease; alcoholism; multiple sclerosis; atherosclerosis; vascular disease; or neurologic disease.

97. A method for treating or preventing hyperlipemia, hyperlipidemia, hyperlipoproteinemia, hypercholesterolemia, hypertriglyceridemia, or dyslipidemia, comprising administering to a subject in need thereof an effective amount of the compound or the pharmaceutically acceptable salt, solvate, ester, amide, or prodrug of the compound of any one of embodiments 1-50.

98. The method of embodiment 97, wherein the hypercholesterolemia is homozygous familial hypercholesterolemia.

99. A method for treating a subject having or preventing a subject from having an abnormally high concentration in a subject's blood plasma or blood serum of high low-density lipoprotein (LDL), apolipoprotein B (apo B), lipoprotein(a) (Lp(a)), apolipoprotein (a), or very low-density lipoprotein (VLDL), comprising administering to a subject in need thereof an effective amount of the compound or the pharmaceutically acceptable salt, solvate, ester, amide, or prodrug of the compound of any one of embodiments 1-50.

100. A method for treating a subject having or preventing a subject from having an abnormally low concentration in a subject's blood plasma or blood serum of high-density lipoprotein (HDL), comprising administering to a subject in need thereof an effective amount of the compound or the pharmaceutically acceptable salt, solvate, ester, amide, or prodrug of the compound of any one of embodiments 1-50.

101. A method for treating a subject having or preventing a subject from having an abnormally reduced or deficient lipoprotein lipase concentration or activity in a subject's blood plasma or blood serum, comprising administering to a subject in need thereof an effective amount of the compound or the pharmaceutically acceptable salt, solvate, ester, amide, or prodrug of the compound of any one of embodiments 1-50.

102. The method of embodiment 101, wherein the reduced or deficient lipoprotein lipase level or activity is a result of a mutation in a gene encoding a lipoprotein lipase.

103. A method for treating or preventing hypoalphalipoproteinemia, a lipoprotein abnormality associated with diabetes, a lipoprotein abnormality associated with obesity, a lipoprotein abnormality associated with Alzheimer's Disease, or familial combined hyperlipidemia, comprising administering to a subject in need thereof an effective amount of the compound or the pharmaceutically acceptable salt, solvate, ester, amide, or prodrug of the compound of any one of embodiments 1-50.

104. A method for reducing in a subject's blood plasma or blood serum an abnormally high concentration of triglyceride, low-density lipoprotein cholesterol (LDL-C), very low-density lipoprotein cholesterol (VLDL-C), non-high-density lipoprotein cholesterol, (non-HDL-C), lipoprotein(a) (Lp (a)), apolipoprotein B, HDL/(VLDL+LDL) ratio, apolipoprotein C-II or apolipoprotein C-III, comprising administering to a subject in need thereof an effective amount of the compound or the pharmaceutically acceptable salt, solvate, ester, amide, or prodrug of the compound of any one of embodiments 1-50.

105. A method for elevating in a subject's blood plasma or blood serum an abnormally low concentration of a high-density lipoprotein (HDL)-associated protein, HDL-cholesterol, apolipoprotein A-1, or apolipoprotein E, comprising administering to a subject in need thereof an effective amount of the compound or the pharmaceutically acceptable salt, solvate, ester, amide, or prodrug of the compound of any one of embodiments 1-50.

106. The method of embodiment 105, wherein the HDL-associated protein is apolipoprotein A-1 (apo A-1), apolipoprotein A-II (apo A-II), apolipoprotein A-IV (apo A-IV) or apolipoprotein E (apo E).

107. A method for promoting clearance of triglyceride from a subject's blood plasma or blood serum, comprising administering to a subject in need thereof an effective amount of the compound or the pharmaceutically acceptable salt, solvate, ester, amide, or prodrug of the compound of any one of embodiments 1-50.

108. A method for increasing abnormally low glucose metabolism or lipid metabolism in a subject, comprising administering to a subject in need thereof an effective amount of the compound or the pharmaceutically acceptable salt, solvate, ester, amide, or prodrug of the compound of any one of embodiments 1-50.

109. The method of embodiment 108, wherein the method for increasing abnormally low glucose metabolism increases insulin sensitivity or oxygen consumption of a subject or decreases blood insulin, blood glucose, or glycated hemoglobin in a subject's blood plasma or blood serum.

110. The method of embodiment 108, wherein the method for increasing abnormally low lipid metabolism reduces a concentration of LDL or free triglyceride in a subject's blood plasma or blood serum, or inhibits saponified or non-saponified fatty acid synthesis.

111. A method for treating or preventing a symptom of a disease selected from inflammation, systemic lupus erythematosus, lupus nephritis, or arthritis, comprising administering to a subject in need thereof an effective amount of the compound or the pharmaceutically acceptable salt, solvate, ester, amide, or prodrug of the compound of any one of embodiments 1-50.

112. The method of embodiment 111, wherein the arthritis is adjuvant arthritis or type II collagen-induced arthritis.

113. The method of embodiment 111, wherein the symptom is nephritis, kidney failure, or kidney function reduction.

114. A method for reducing the fat content of meat in livestock, comprising administering to livestock an effective amount of the compound or the pharmaceutically acceptable salt, solvate, ester, amide, or prodrug of the compound of any one of embodiments 1-50.

115. A method for reducing cholesterol content of a fowl egg, comprising administering to a fowl species an effective amount of the compound or the pharmaceutically acceptable salt, solvate, ester, amide, or prodrug of the compound of any one of embodiments 1-50.

116. A method for treating a subject with acute kidney injury (AKI) or at risk for AKI, comprising administering to the subject an effective amount of the compound or the pharmaceutically acceptable salt, solvate, ester, amide, or prodrug of the compound of any one of embodiments 1 to 50.

117. The method of embodiment 116, wherein the compound or the pharmaceutically acceptable salt, solvate, ester, amide, or prodrug of the compound is administered intravenously, optionally wherein the method comprises once daily intravenous administration, optionally for three days.

118. The method of embodiment 116, wherein the compound or the pharmaceutically acceptable salt, solvate, ester, amide, or prodrug of the compound is administered orally.

119. The method of any one of embodiments 116 to 118, wherein the AKI is sepsis-related AKI.

120. The method of any one of embodiments 116 to 118, wherein the AKI is ischemia/reperfusion AKI.

121. The method of any one of embodiments 116 to 118, wherein the AKI is from acute interstitial nephritis.

122. The method of any one of embodiments 116 to 118, wherein the AKI is from glomerular renal disease.

123. The method of any one of embodiments 116 to 118, wherein the AKI is from acute vasculitic renal disease.

124. The method of any one of embodiments 116 to 118, wherein the AKI is from ischemia.

125. The method of any one of embodiments 116 to 118, wherein the AKI is from toxic injury.

126. The method of any one of embodiments 116 to 118, wherein the AKI is from prerenal azotemia.

127. The method of any one of embodiments 116 to 118, wherein the AKI is from acute postrenal destructive nephropathy.

128. The method of any one of embodiments 116 to 118, wherein the AKI is from diabetes.

129. The method of any one of embodiments 116 to 118, wherein the AKI is from underlying renal insufficiency.

130. The method of any one of embodiments 116 to 118, wherein the AKI is from nephritic syndrome.

131. The method of any one of embodiments 116 to 118, wherein the AKI is from atherosclerotic disease.

132. The method of any one of embodiments 116 to 118, wherein the AKI is from hypotension.

133. The method of any one of embodiments 116 to 118, wherein the AKI is from hypoxia.

134. The method of any one of embodiments 116 to 118, wherein the AKI is from myoglobinuria-hematuria.

135. The method of any one of embodiments 116 to 118, wherein the AKI is from liver disease.

136. The method of any one of embodiments 116 to 118, wherein the AKI is secondary to a viral infection, optionally wherein the viral infection is COVID-19.

137. The method of embodiment 136, wherein the subject has a viral infection, optionally wherein the viral infection is COVID-19.

138. The method of 116 to 119, wherein the subject has sepsis.

139. The method of embodiment 137, wherein the sepsis is associated with a gram-negative bacterial infection.

140. The method of embodiment 138 or embodiment 139, wherein the subject has an intra-abdominal cavity infection.

141. The method of embodiment 138 or embodiment 139, wherein the subject has urosepsis.

142. The method of any one of embodiments 116 to 141, wherein the subject is elderly.

143. The method of any one of embodiments 116 to 142, wherein the subject is a surgical patient.

144. The method of embodiment 143, wherein the surgical patient has had a cardiovascular surgery, optionally which is a coronary artery bypass graft (CABG) surgery and/or heart valve surgery.

145. The method of any one of embodiments 116 to 141, wherein the subject is pregnant.

146. The method of any one of embodiments 116 to 145, wherein the subject has been exposed to a nephrotoxic agent.

147. The method of embodiment 146, wherein the nephrotoxic agent comprises cisplatin, gentamicin, cephaloridine, cyclosporine, amphotericin, carbon tetrachloride, trichloroethylene, dichloroacetylene, or a combination thereof.

148. The method of any one of embodiments 116 to 147, wherein the subject has AKI.

149. The method of embodiment 148, wherein the effective amount is effective to reduce the severity of the AKI.

150. The method of any one of embodiments 116 to 147, wherein the subject is at risk for AKI.

151. The method of any one of embodiments 116 to 147, wherein the subject is at risk for AKI following a cardiovascular surgery, optionally which is a coronary artery bypass graft (CABG) surgery and/or heart valve surgery.

152. The method of embodiment 150 or embodiment 151, wherein the effective amount is effective to reduce the likelihood that the subject will develop AKI.

153. The method of any one of embodiments 150 to 152, wherein the effective amount is effective to delay the onset of AKI.

154. The method of any one of embodiments 150 to 152, wherein the effective amount is effective to prevent AKI.

155. The method of any one of embodiments 150 to 152, wherein if the subject develops AKI, the effective amount is effective to reduce the severity of the AKI.

156. The method of any one of embodiments 116 to 155, wherein the subject has a SOFA score of 1 to 4 prior to administration of the compound or the pharmaceutically acceptable salt, solvate, ester, amide or prodrug of the compound or the pharmaceutical composition.

157. The method of embodiment 156, wherein the subject has a SOFA score of 2 to 4 prior to administration.

158. The method of embodiment 156, wherein the subject has a SOFA score of 1 prior to administration.

159. The method of embodiment 156, wherein the subject has a SOFA score of 2 prior to administration.

160. The method of embodiment 156, wherein the subject has a SOFA score of 3 prior to administration.

161. The method of embodiment 156, wherein the subject has a SOFA score of 4 prior to administration.

162. The method of any one of embodiments 116 to 161, wherein the subject has an endotoxin activity level of >0.6 prior to administration.

163. The method of any one of embodiments 116 to 162, wherein the effective amount is effective to reduce the subject's endotoxin activity level.

7.2. Specific Embodiments, Group 2

Various aspects of the present disclosure are described in the numbered embodiments set forth in the following numbered paragraphs, where reference to a previous numbered embodiment refers to a previous numbered embodiment in this Section 7.2.

1. A compound of Formula (C):

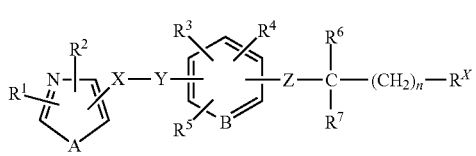

or a pharmaceutically acceptable salt, solvate, ester, amide, or prodrug thereof, wherein:

$R^1$ is phenyl, naphthyl, pyridyl, thienyl, furyl, quinolyl or benzothienyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

$R^2$ is $C_{2-8}$ alkyl, $C_{1-8}$ haloalkyl, $C_{2-8}$ alkenyl, $C_{2-8}$ alkynyl, 3-7 membered cycloalkyl, $C_{1-8}$ alkyl substituted with a 3-7 membered cycloalkyl, or $C_{1-6}$ alkyl substituted with phenyl, naphthyl or pyridyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

A is oxygen, sulfur or $NR^9$ in which $R^9$ is hydrogen or $C_{1-8}$ alkyl;

X is a $C_{1-8}$ alkylene chain which is unsubstituted or substituted with $C_{1-8}$ alkyl, $C_{1-8}$ alkoxy or hydroxyl, and which has 0 or 1 double bonds;

Y is $C(=O)$, $C(=N-OR^{10})$, $CH(OR^{11})$, $CH=CH$, $C\equiv C$, or $C(=CH_2)$ in which each of $R^{10}$ and $R^{11}$ is hydrogen or $C_{1-8}$ alkyl; each of $R^3$, $R^4$ and $R^5$ is independently hydrogen, $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl, or pyridyl; optionally wherein at least one of $R^3$, $R^4$, and $R^5$ is not hydrogen;

B is CH or nitrogen;

Z is oxygen or sulfur;

each of $R^6$ and $R^7$ is independently hydrogen, $C_{1-8}$ alkyl, or $C_{1-8}$ haloalkyl;

$R^X$ is $CH_2OH$, $COH$, $COOCH_2CONR^{X4}R^{X5}$, $SO_3H$,

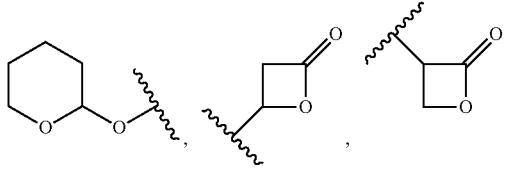

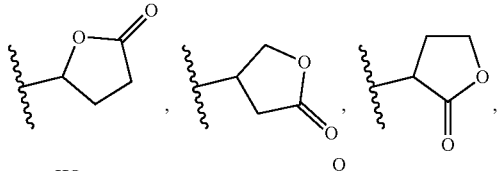

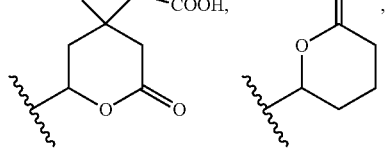

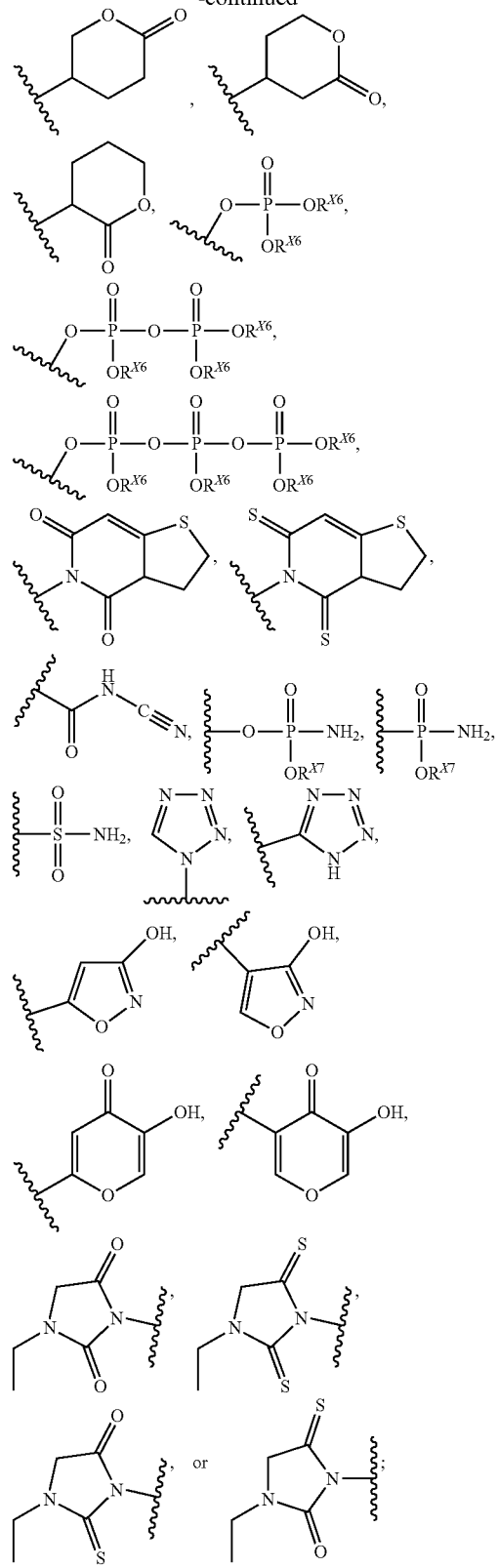

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_2$_r alkynyl; and n is 0, 1, 2, 3, or 4.

2. The compound or pharmaceutically acceptable salt, solvate, ester, amide, or prodrug of the compound of embodiment 1, wherein $R^1$ is phenyl which can have substituents selected from the group consisting of $C_{1-8}$ alkyl, $C_{1-8}$ alkyl having 1-3 halogen atoms, $C_{1-8}$ alkoxy, $C_{1-8}$ alkoxy having 1-3 halogen atoms, $C_{2-8}$ alkenyl, $C_{2-8}$ alkynyl, halogen, $C_{2-7}$ acyl, benzoyl, hydroxyl, nitro, amino, phenyl and pyridyl.

3. The compound or pharmaceutically acceptable salt, solvate, ester, amide, or prodrug of the compound of embodiment 1 or embodiment 2, wherein $R^2$ is $C_{2-8}$ alkyl.

4. The compound or pharmaceutically acceptable salt, solvate, ester, amide, or prodrug of the compound of any one of embodiments 1 to 3, wherein $R^1$ is attached to the 2nd position, and (i) $R^4$ is attached to the 4th position and —X—Y— is attached to the 5th position, or (ii) $R^4$ is attached to the 5th position and —X—Y— is attached to the 4th position.

5. The compound or pharmaceutically acceptable salt, solvate, ester, amide, or prodrug of the compound of any one of embodiments 1 to 4, wherein A is oxygen or sulfur.

6. The compound or pharmaceutically acceptable salt, solvate, ester, amide, or prodrug of the compound of any one of embodiments 1 to 5, wherein X is a $C_{1-8}$ alkylene chain.

7. The compound or pharmaceutically acceptable salt, solvate, ester, amide, or prodrug of the compound of any one of embodiments 1 to 6, wherein Y is C(=O).

8. The compound or pharmaceutically acceptable salt, solvate, ester, amide, or prodrug of the compound of any one of embodiments 1 to 7, wherein each of $R^3$, $R^4$, and $R^5$ is hydrogen, $C_{1-8}$ alkyl or $C_{1-8}$ alkyl having halogen.

9. The compound or pharmaceutically acceptable salt, solvate, ester, amide, or prodrug of the compound of any one of embodiments 1 to 8, wherein B is CH.

10. The compound or pharmaceutically acceptable salt, solvate, ester, amide, or prodrug of the compound of any one of embodiments 1 to 9, wherein Z is oxygen.

11. The compound or pharmaceutically acceptable salt, solvate, ester, amide, or prodrug of the compound of any one of embodiments 1 to 10, wherein each of $R^6$ and $R^7$ is hydrogen or $C_{1-4}$ alkyl.

12. The compound or pharmaceutically acceptable salt, solvate, ester, amide, or prodrug of the compound of embodiment 1, wherein:

$R^1$ is phenyl or naphthyl, each of which can have one or more substituents selected from the group consisting of $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl and pyridyl;

$R^2$ is $C_{2-8}$ alkyl;

A is oxygen or sulfur;

X is a $C_{1-8}$ alkylene chain which can have a $C_{1-8}$ alkyl substituent and which can contain a double bond;

Y is C(=O), CH=CH, or C(=CH$_2$); each of $R^3$, $R^4$ and $R^5$ is hydrogen, $C_{1-8}$ alkyl, $C_{1-8}$ alkyl having halogen, $C_{1-8}$ alkoxy, $C_{1-8}$ alkoxy having halogen, $C_{2-8}$ alkenyl, $C_{2-8}$ alkynyl, halogen, $C_{2-7}$ acyl, benzoyl, hydroxyl, nitro, amino, phenyl, or pyridyl;

B is CH;

Z is oxygen or sulfur; and each of $R^6$ and $R^7$ is hydrogen or $C_{1-8}$ alkyl 13. The compound or pharmaceutically acceptable salt, solvate, ester, amide, or prodrug of the compound of embodiment 12, wherein X is a $C_{1-8}$ alkylene chain.

14. The compound or pharmaceutically acceptable salt, solvate, ester, amide, or prodrug of the compound of embodiment 12, wherein $R^1$ is attached to the 2nd position.

15. The compound or pharmaceutically acceptable salt, solvate, ester, amide, or prodrug of the compound of any one of embodiments 12 to 14, wherein $R^3$, $R^4$ and $R^5$ other than hydrogens are placed at ortho-positions with respect to Z.

16. The compound or pharmaceutically acceptable salt, solvate, ester, amide, or prodrug of the compound of embodiment 1, wherein $R^1$ is phenyl substituted with $CF_3$.

17. The compound or pharmaceutically acceptable salt, solvate, ester, amide, or prodrug of the compound of embodiment 1 or embodiment 16, wherein $R^2$ is isopropyl.

18. The compound or pharmaceutically acceptable salt, solvate, ester, amide, or prodrug of the compound of any one of embodiments 1 and 16 to 17, wherein A is sulfur.

19. The compound or pharmaceutically acceptable salt, solvate, ester, amide, or prodrug of the compound of any one of embodiments 1 and 16 to 18, wherein X is $CH_2CH_2$.

20. The compound or pharmaceutically acceptable salt, solvate, ester, amide, or prodrug of the compound of any one of embodiments 1 and 16 to 19, wherein Y is C(=O).

21. The compound or pharmaceutically acceptable salt, solvate, ester, amide, or prodrug of the compound of any one of embodiments 1 and 16 to 19, wherein Y is CH(OH).

22. The compound or pharmaceutically acceptable salt, solvate, ester, amide, or prodrug of the compound of any one of embodiments 1 and 16 to 21, wherein $R^3$ is $CH_3$ and $R^4$ and $R^5$ are each hydrogen.

23. The compound or pharmaceutically acceptable salt, solvate, ester, amide, or prodrug of the compound of any one of embodiments 1 and 16 to 22, wherein B is CH.

24. The compound or pharmaceutically acceptable salt, solvate, ester, amide, or prodrug of the compound of any one of embodiments 1 and 16 to 23, wherein Z is oxygen.

25. The compound or pharmaceutically acceptable salt, solvate, ester, amide, or prodrug of the compound of any one of embodiments 1 and 16 to 24, wherein $R^6$ and $R^7$ are each hydrogen.

26. A compound of Formula (D):

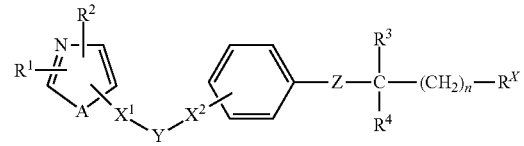

(D)

or a pharmaceutically acceptable salt, solvate, ester, amide, or prodrug thereof, wherein:

each of $R^1$ and $R^2$ independently is a hydrogen, a halogen, nitro, $C_{1-8}$ alkyl, $C_{1-8}$ alkoxy, $C_{1-8}$ haloalkyl having 1 to 3 halogens, $C_{1-8}$ haloalkoxy having 1 to 3 halogens, $C_{2-8}$ alkenyl, $C_{2-8}$ alkynyl, 3-7 membered cycloalkyl, $C_{1-8}$ alkyl substituted with 3-7 membered cycloalkyl, $C_{6-10}$ aryl which is optionally substituted, arylalkyl group which has a $C_{6-10}$ aryl moiety and $C_{1-8}$ alkyl moiety, a heterocyclic group or a heterocyclic-alkyl group having a $C_{1-8}$ alkyl group;

each occurrence of $R^3$, $R^4$, and $R^5$ is independently a hydrogen or $C_{1-8}$ alkyl;

A is an oxygen atom, a sulfur atom, or $NR^3$;

each of $X^1$, $X^2$, and Z independently is $C(=O)$, $C(=O)NH$, $C(=N-OR^4)$, $CH(OR^5)$, $NH(C=O)$, $NHSO_2$, $SO_2NH$, $CH=CH$, $C\equiv C$, or a bond; and Y is $C_{1-8}$ alkylene;

$R^X$ is $CH_2OH$, $COH$, $COOCH_2CONR^{X4}R^{X5}$, $SO_3H$,

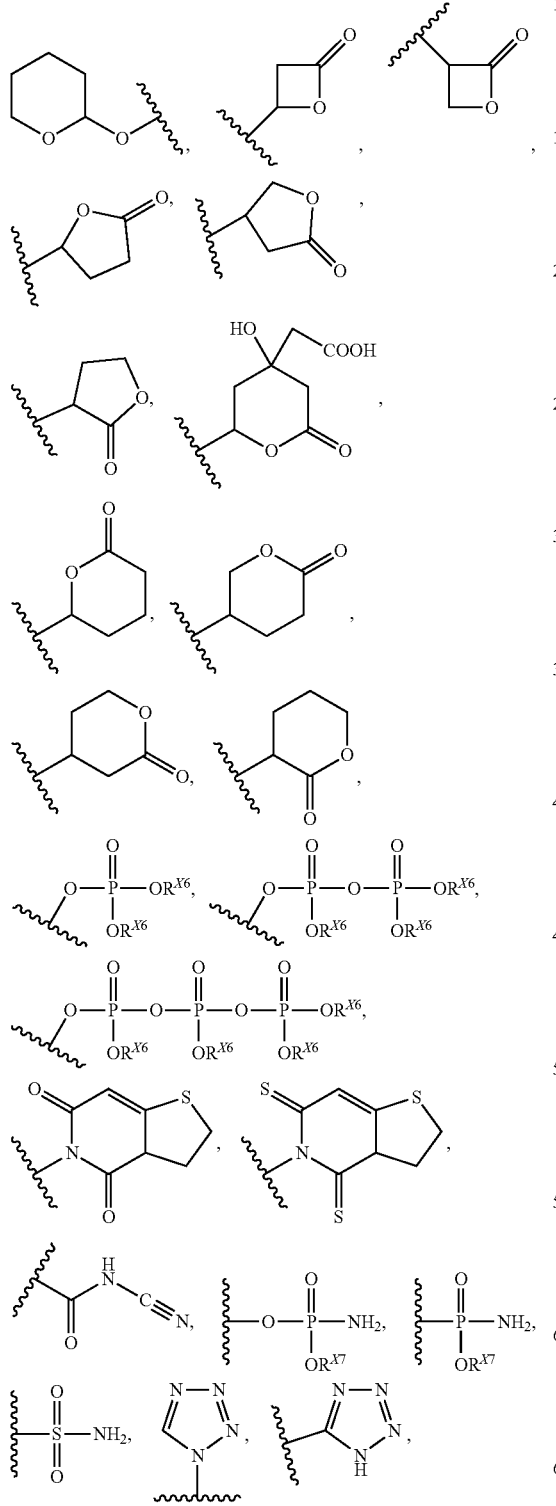

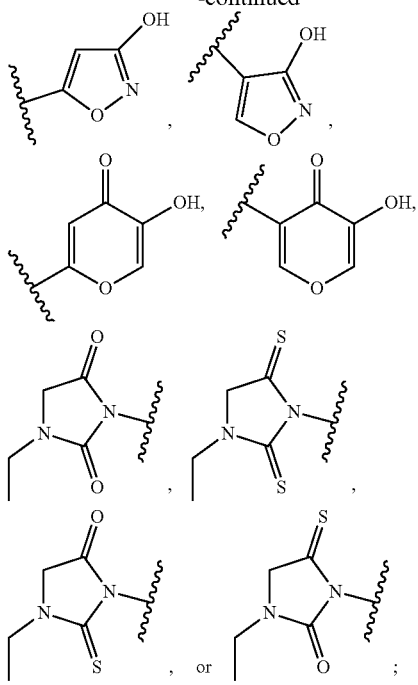

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

27. The compound or pharmaceutically acceptable salt, solvate, ester, amide, or prodrug of the compound of embodiment 26, wherein $X^1$ is $C(=O)$, $CH(OH)$, or a bond.

28. The compound or pharmaceutically acceptable salt, solvate, ester, amide, or prodrug of the compound of embodiment 26 or embodiment 27, wherein $X^2$ is $C(=O)$, $CH(OH)$, or a bond.

29. A compound of Formula (E):

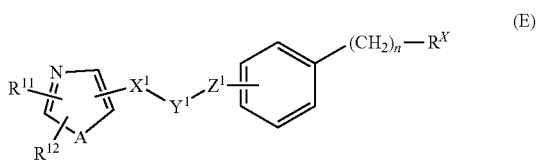

(E)

or a pharmaceutically acceptable salt, solvate, ester, amide, or prodrug thereof, wherein:

each of $R^{11}$ and $R^{12}$ independently is hydrogen, halogen, nitro, hydroxyl, amino, $C_{1-8}$ alkyl, an $C_{1-8}$ alkoxy, $C_{1-8}$ haloalkyl group having 1 to 3 halogens, $C_{1-8}$ haloalkoxy group having 1 to 3 halogens, $C_{2-8}$ alkenyl, $C_{2-8}$ alkynyl, a 3-7 membered cycloalkyl, $C_{1-8}$ alkyl having a 3-7 membered cycloalkyl substituent, or phenyl, naphthyl, benzyl, phenethyl, pyridyl, thienyl, furyl, quinolyl, or benzothienyl group which optionally has a substituent which is a halogen atom, nitro, hydroxyl, amino, $C_{1-8}$ alkyl, $C_{1-8}$ alkoxy, $C_{1-8}$ haloalkyl having 1 to 3 halogens, $C_{1-8}$ haloalkoxy having 1 to 3 halogens, $C_{2-8}$ alkenyl, $C_{2-8}$ alkynyl, 3-7 membered cycloalkyl group, $C_{1-8}$ alkyl group having a 3-7 membered cycloalkyl substituent, phenyl or pyridyl;

each of $X^1$ and $Z^1$ independently is $C(=O)$, $C(=O)NH$, $C(=N-OR^{14})$, $CH(OR^{15})$, $NH(C=O)$, $NHSO_2$, $SO_2NH$, $CH=CH$, $C\equiv C$, or a bond, wherein each of $R^{14}$ and $R^{15}$ is a hydrogen or $C_{1-8}$ alkyl;

$Y^1$ is $C_{1-8}$ alkylene;

$R^X$ is $CH_2OH$, $COH$, $COOCH_2CONR^{X4}R^{X5}$, $SO_3H$,

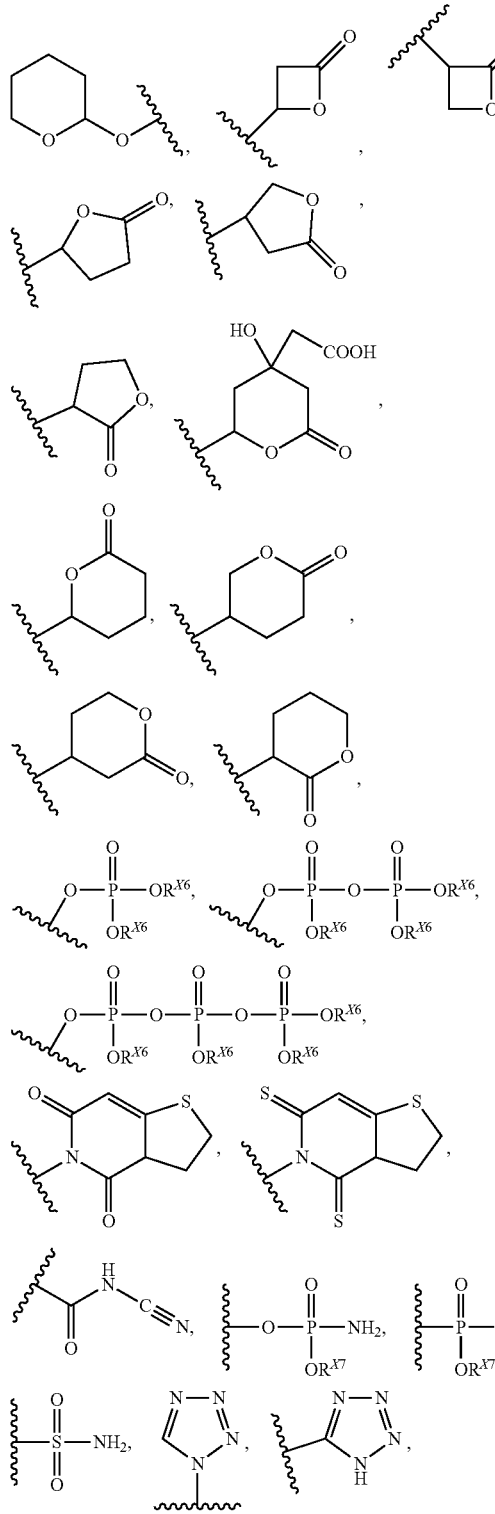

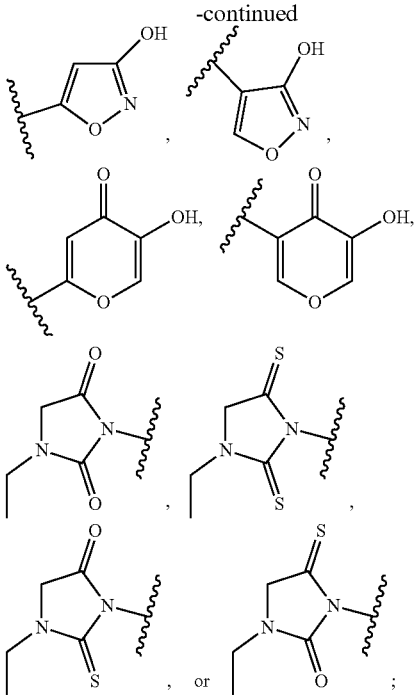

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

30. The compound or pharmaceutically acceptable salt, solvate, ester, amide, or prodrug of the compound of embodiment 29, wherein $X^1$ is $C(=O)$, $CH(OH)$, or a bond.

31. The compound or pharmaceutically acceptable salt, solvate, ester, amide, or prodrug of the compound of embodiment 29 or embodiment 30, wherein $Z^1$ is $C(=O)$, $CH(OH)$, or a bond.

32. The compound or pharmaceutically acceptable salt, solvate, ester, amide, or prodrug of the compound of any one of embodiments 29 to 31, wherein $X^1-Y^1-Z^1$ is bonded to the 3 or 4 position of the phenyl ring.

33. The compound or pharmaceutically acceptable salt, solvate, ester, amide, or prodrug of the compound of any one of embodiments 29 to 32, wherein $X^1$ is a bond and $Z^1$ is $(C=O)$.

34. The compound or pharmaceutically acceptable salt, solvate, ester, amide, or prodrug of the compound of any one of embodiments 29 to 33, wherein $X^1-Y^1-Z^1$ is bonded to the 4 position of the five membered ring.

35. The compound or pharmaceutically acceptable salt, solvate, ester, amide, or prodrug of the compound of any one of embodiments 29 to 34, wherein $R^{11}$ is a phenyl or naphthyl group which optionally has a substituent selected from the group consisting chlorine, fluorine, hydroxyl, an alkyl group having 1-5 carbon atoms, and an alkyl group having 1-5 carbon atoms, and it is bonded to the 2-position of the five membered ring.

36. The compound or pharmaceutically acceptable salt, solvate, ester, amide, or prodrug of the compound of any one of embodiments 29 to 35, wherein $R^{12}$ is an alkyl group having 3-6 carbon atoms, which is bonded to the 5-position of the 5 membered ring.

37. A compound of Formula (F):

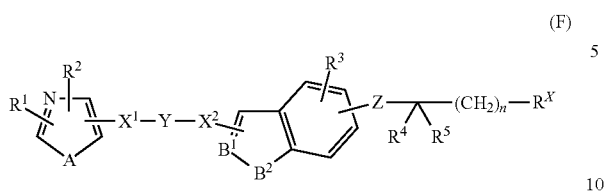

or a pharmaceutically acceptable salt, solvate, ester, amide, or prodrug thereof, wherein:

A is O, S or $NR^7$ in which $R^7$ is hydrogen or $C_{1-8}$ alkyl;
$B^1$ is CW or N in which W is hydrogen or a bond; $B^2$ is O, S or $NR^8$ in which $R^8$ is hydrogen or $C_{1-8}$ alkyl; each of $X^1$ and $X^2$ is O, S, NH, NHC(=O), C(=O), C(=N—$OR^9$), CH($OR^{10}$), C≡C, C=C or a bond, wherein each of $R^9$ and $R^{10}$ is hydrogen or $C_{1-8}$ alkyl;
Y is $C_{1-8}$ alkylene, which is unsubstituted or substituted with $C_{1-8}$ alkyl or $C_{1-8}$ haloalkyl having 1-3 halogens;
Z is NH, O or S;
$R^1$ is aryl, which is unsubstituted or substituted with $C_{1-8}$ alkyl, $C_{1-8}$ alkoxy, $C_{1-8}$ haloalkyl having 1-3 halogens, hydroxyl, nitro, amino, phenyl, pyridyl or halogen, or a heterocyclic group having a five to eight membered ring comprising one to three hetero atoms each of which is independently nitrogen, oxygen or sulfur and the other atoms are carbon, optionally wherein a benzene ring is condensed with the heterocyclic ring;
$R^2$ is $C_{2-8}$ alkyl, $C_{1-8}$ haloalkyl having with 1-3 halogens, $C_{3-7}$ cycloalkyl, $C_{2-8}$ alkenyl, $C_{2-8}$ alkynyl, $C_{1-4}$ alkyl substituted with aryl, which is unsubstituted or substituted with $C_{1-8}$ alkyl, $C_{1-8}$ alkoxy, $C_{1-8}$ haloalkyl having 1-3 halogens, hydroxyl, nitro, amino, phenyl, pyridyl or halogen, or $C_{1-4}$ alkyl substituted with a heterocyclic group having five to eight membered ring having one to three heteroatoms each of which is independently nitrogen, oxygen or sulfur;
$R^3$ is halogen, trifluoromethyl, $C_{1-8}$ alkyl, $C_{2-8}$ alkenyl or $C_{2-8}$ alkynyl;
each of $R^4$ and $R^5$ is hydrogen, $C_{1-8}$ alkyl or $C_{1-8}$ haloalkyl having 1-3 halogens;
each of Z and $R^3$ is attached to the benzene ring, and $X^2$ is not attached to the benzene ring;
$R^X$ is $CH_2OH$, COH, $COOCH_2CONR^{X4}R^{X5}$, $SO_3H$,

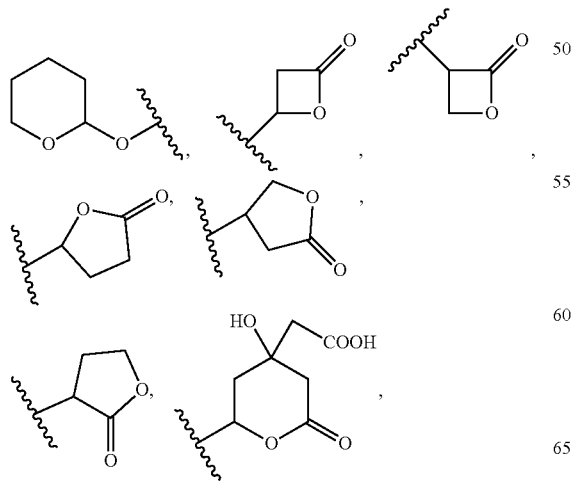

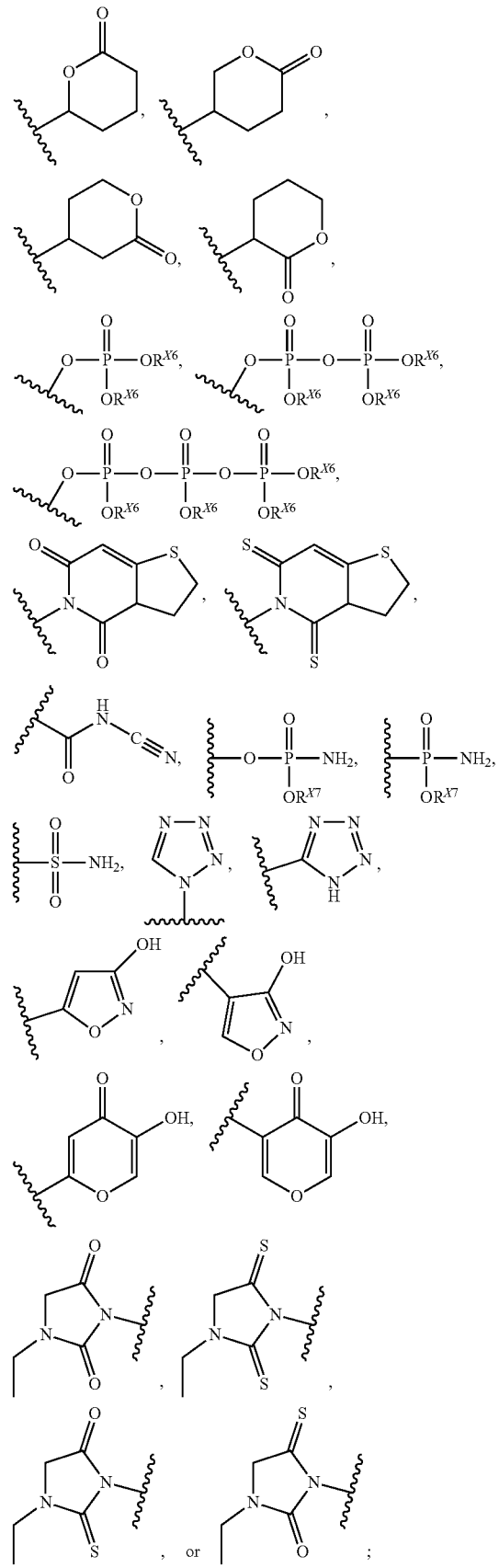

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

38. The compound or pharmaceutically acceptable salt, solvate, ester, amide, or prodrug of the compound of embodiment 37, wherein $X^1$ is C(=O), CH(OH), or a bond.

39. The compound or pharmaceutically acceptable salt, solvate, ester, amide, or prodrug of the compound of embodiment 37 or embodiment 38, wherein $X^2$ is C(=O), CH(OH), or a bond.

40. A compound of Formula (G):

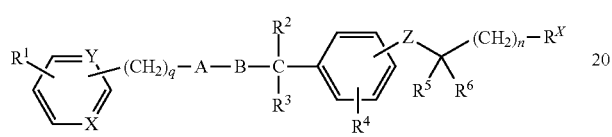

(G)

or a pharmaceutically acceptable salt, solvate, ester, amide, or pro rug thereto, wherein:

each of $R^1$ and $R^4$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

$R^2$ is hydrogen;

$R^3$ is $C_{1-8}$ alkyl, or $R^3$ is combined with $R^2$ to form =O or =C($R^7$)($R^8$) in which each of $R^7$ and $R^8$ which are the same or different, is a hydrogen or $C_{1-8}$ alkyl;

each of $R^5$ and $R^6$, which are the same or different, is a hydrogen atom, $C_{1-8}$ alkyl, $C_{1-8}$ haloalkyl;

X and Y are the same or different and each represents CH or N;

Z is oxygen or sulfur;

A is a 5-membered heterocyclic group which is pyrazole, thiophene, furan or pyrrole, wherein the heterocyclic group is unsubstituted or substituted with $C_{1-8}$ alkyl having a substituent which is $C_{1-8}$ alkyl, 3- to 7-membered cycloalkyl, $C_{2-8}$ alkenyl, $C_{2-8}$ alkynyl, $C_{1-8}$ alkoxy, $C_{1-8}$ alkyl group substituted with a 3- to 7-membered cycloalkyl group, $C_{1-8}$ haloalkyl, $C_{1-8}$ haloalkoxy, $C_{6-10}$ aryl, 5- or 6-membered heterocyclic group, an aralkyl group having a $C_{6-10}$ aryl moiety and a $C_{1-8}$ alkylene moiety, or 5- or 6-membered heterocyclic group;

B is a $C_{1-8}$ alkylene chain which is unsubstituted or substituted with $C_{1-8}$ alkyl, 3- to 7-membered cycloalkyl group, $C_{2-8}$ alkenyl, $C_{2-8}$ alkynyl, $C_{1-8}$ alkoxy, halogen, $C_{1-8}$ haloalkyl or $C_{1-8}$ haloalkoxy, the alkylene group optionally having a double bond in the case that the alkylene group has 2 to 6 carbon atoms;

q is 0, 1, 2, 3, 4, or 5;

$R^X$ is $CH_2OH$, COH, $COOCH_2CONR^{X4}R^{X5}$, $SO_3H$,

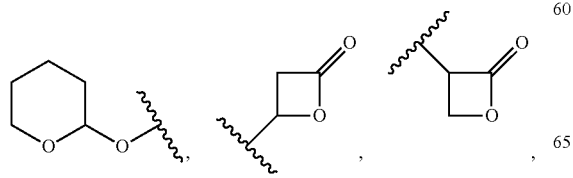

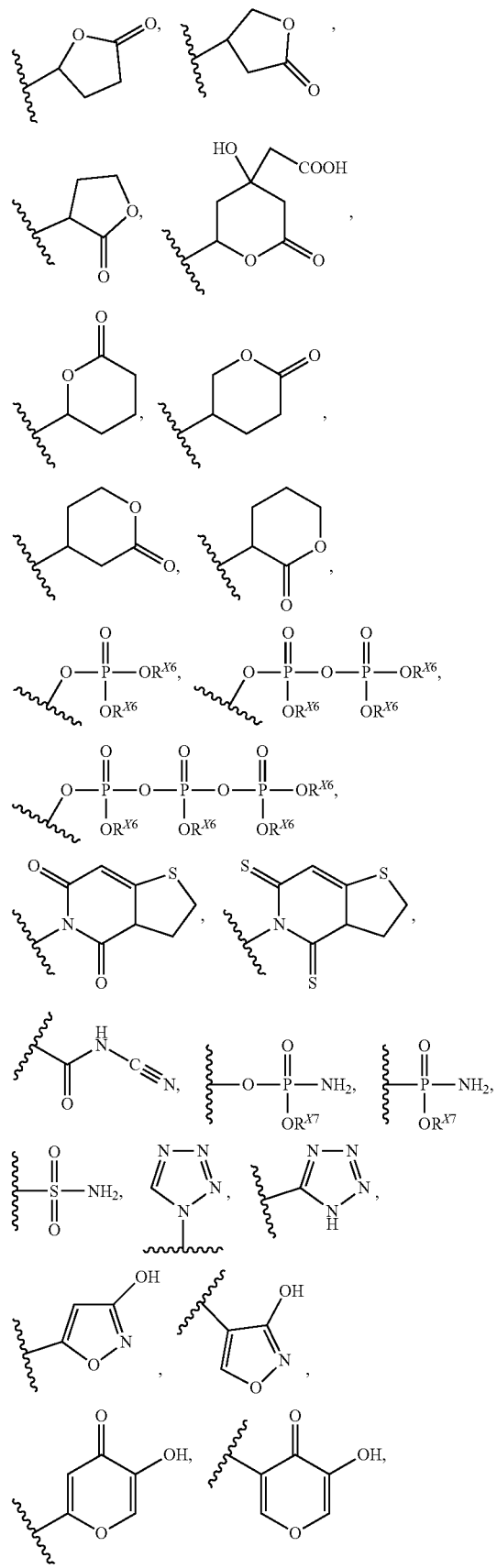

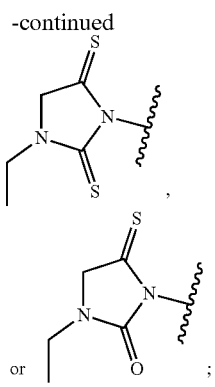

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

41. The compound or pharmaceutically acceptable salt, solvate, ester, amide, or prodrug of the compound of embodiment 40, wherein A is pyrazole.

42. The compound or pharmaceutically acceptable salt, solvate, ester, amide, or prodrug of the compound of embodiment 41, in which —$(CH_2)_q$— is attached the pyrazole at 1-position thereof.

43. The compound or pharmaceutically acceptable salt, solvate, ester, amide, or prodrug of the compound of embodiment 41, wherein —$(CH_2)_q$— is attached to the pyrazole at 3-position thereof.

44. The compound or pharmaceutically acceptable salt, solvate, ester, amide, or prodrug of the compound of embodiment 42 or 43, in which —B— is attached to the pyrazole at 4- or 5-position thereof.

45. The compound or pharmaceutically acceptable salt, solvate, ester, amide, or prodrug of the compound of embodiment 40, wherein A is thiophene, furan or pyrrole.

46. The compound or pharmaceutically acceptable salt, solvate, ester, amide, or prodrug of the compound of embodiment 45, wherein —$(CH_2)_q$— is attached the 5-membered heterocyclic group at 2-position thereof 47. The compound or pharmaceutically acceptable salt, solvate, ester, amide, or prodrug of the compound of embodiment 40, wherein A is thiophene.

48. The compound or pharmaceutically acceptable salt, solvate, ester, amide, or prodrug of the compound of embodiment 47, in which —$(CH_2)_q$— is attached the thiophene at 2-position thereof.

49. The compound or pharmaceutically acceptable salt, solvate, ester, amide, or prodrug of the compound of any one of embodiments 40 to 48, wherein q is 0.

50. The compound or pharmaceutically acceptable salt, solvate, ester, amide, or prodrug of the compound of any one of embodiments 40 to 49, wherein each of X and Y is CH.

51. The compound or pharmaceutically acceptable salt, solvate, ester, amide, or prodrug of the compound of any one of embodiments 40 to 50, in which $R^2$ is combined with $R^3$ to represent =O.

52. The compound or pharmaceutically acceptable salt, solvate, ester, amide, or prodrug of the compound of any one of embodiments 40 to 51, wherein B represents an alkylene chain having 2 to 4 carbon atoms which optionally has a substituent selected from the group consisting of an alkyl group having 1 to 8 carbon atoms and an alkyl group having 1 to 8 carbon atoms and a halogen atom substituent.

53. The compound or pharmaceutically acceptable salt, solvate, ester, amide, or prodrug of the compound of any one of embodiments 40 to 52, wherein B is an ethylene chain.

54. The compound or pharmaceutically acceptable salt, solvate, ester, amide, or prodrug of the compound of any one of embodiments 40 to 53, in which $R^1$ and $R^4$ are the same or different and each represents a hydrogen atom, an alkyl group having 1 to 8 carbon atoms, an alkoxy group having 1 to 8 carbon atoms, a halogen atom, an alkyl group having 1 to 8 carbon atoms and a halogen atom substituent, or an alkoxy group having 1 to 8 carbon atoms and a halogen atom substituent.

55. The compound or pharmaceutically acceptable salt, solvate, ester, amide, or prodrug of the compound of any one of embodiments 40 to 54, in which $R^5$ and $R^6$ are the same or different and each represents a hydrogen atom or an alkyl group having 1 to 8 carbon atoms 56. The compound or pharmaceutically acceptable salt, solvate, ester, amide, or prodrug of the compound of any one of embodiments 40 to 55, in which the substituent optionally attached to the heterocyclic group for A is an alkyl group having 1 to 8 carbon atoms or an alkyl group having 1 to 8 carbon atoms and a halogen atom substituent.

57. A compound of Formula (H):

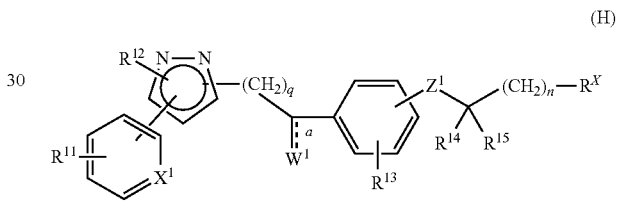

(H)

or a pharmaceutically acceptable salt, solvate, ester, amide, or prodrug thereof, wherein:

each of $R^{11}$ and $R^{13}$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

$R^{12}$ is hydrogen, $C_{1-8}$ alkyl, a 3- to 7-membered cycloalkyl, $C_{2-8}$ alkenyl, $C_{2-8}$ alkynyl, $C_{1-8}$ alkoxy, $C_{1-8}$ alkyl having a 3- to 7-membered cycloalkyl group substituent, $C_{1-8}$ haloalkyl, $C_{1-8}$ haloalkoxy, $C_{6-10}$ aryl, a 5- or 6-membered heterocyclic group, an aralkyl group having a $C_{6-10}$ aryl moiety and a $C_{1-8}$ alkylene moiety, or a $C_{1-8}$ alkyl group having a 5- or 6-membered heterocyclic substituent;

$R^{14}$ and $R^{15}$ are the same or different and each is a hydrogen atom, $C_{1-8}$ alkyl, or $C_{1-8}$ haloalkyl;

$X^1$ is CH or N;

$Z^1$ is oxygen or sulfur;

$W^1$ is oxygen or $CH_2$ when bond a is present and OH when bond a is absent;

q is 2, 3, or 4.

$R^X$ is $CH_2OH$, COH, $COOCH_2CONR^{X4}R^{X5}$, $SO_3H$,

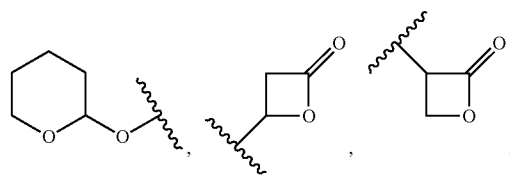

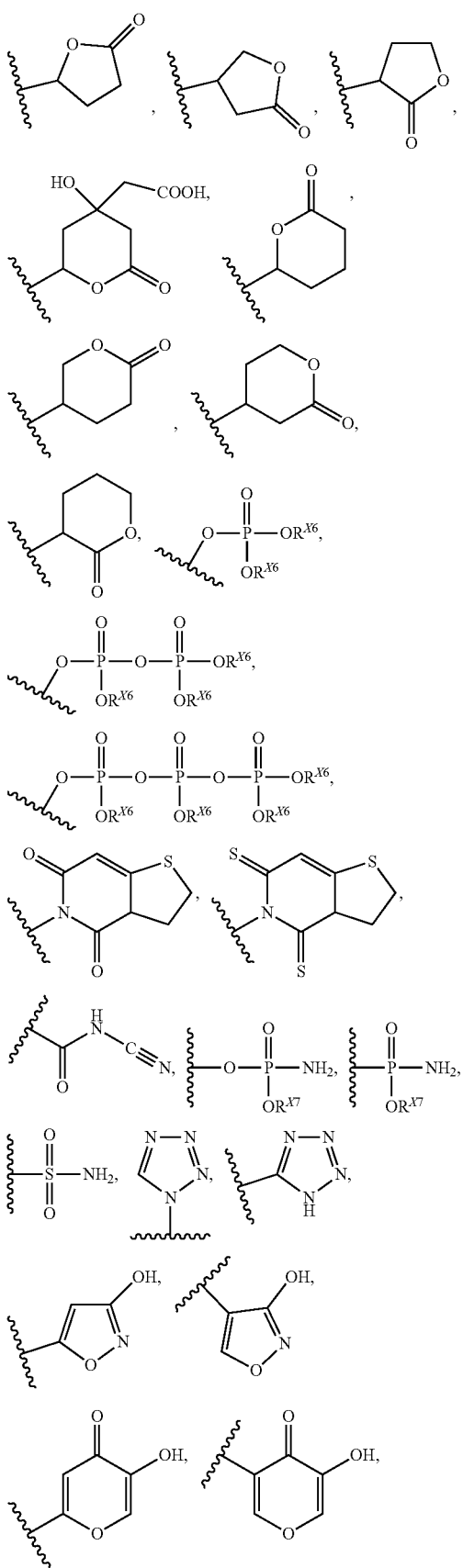

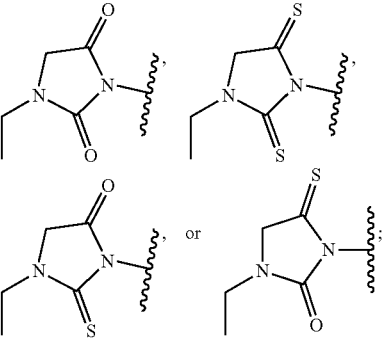

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

58. The compound or pharmaceutically acceptable salt, solvate, ester, amide, or prodrug of the compound of embodiment 57, wherein $X^1$ is CH.

59. The compound or pharmaceutically acceptable salt, solvate, ester, amide, or prodrug of the compound of embodiment 57 or 58, wherein $R^{11}$-phenyl or $R^{11}$-pyridyl is attached to the pyrazole at 1-position.

60. The compound or pharmaceutically acceptable salt, solvate, ester, amide, or prodrug of the compound of embodiment 57 or 58, wherein $R^{11}$-phenyl or $R^{11}$-pyridyl attached to the pyrazole at 3-position.

61. The compound or pharmaceutically acceptable salt, solvate, ester, amide, or prodrug of the compound of any one of embodiments 57 to 60, in which —$(CH_2)_q$— is attached to the pyrazole at 4- or 5-position.

62. The compound or pharmaceutically acceptable salt, solvate, ester, amide, or prodrug of the compound of any one of embodiments 57 to 61, in which $R^{11}$ and $R^{13}$ are the same or different and each represents a hydrogen atom, an alkyl group having 1 to 8 carbon atoms, an alkoxy group having 1 to 8 carbon atoms, a halogen atom, an alkyl group having 1 to 8 carbon atoms and a halogen atom substituent, or an alkoxy group having 1 to 8 carbon atoms and a halogen atom substituent.

63. The compound or pharmaceutically acceptable salt, solvate, ester, amide, or prodrug of the compound of any one of embodiments 57 to 61, in which $R^{11}$ and $R^{13}$ are the same or different and each represents an alkyl group having 1 to 8 carbon atoms or an alkyl group having I to 8 carbon atoms and a halogen atom substituent.

64. The compound or pharmaceutically acceptable salt, solvate, ester, amide, or prodrug of the compound of any one of embodiments 57 to 63, in which $R^{14}$ and $R^{15}$ are the same or different and each represents a hydrogen atom or an alkyl group having 1 to 8 carbon atoms.

65. The compound or pharmaceutically acceptable salt, solvate, ester, amide, or prodrug of the compound of any one of embodiments 57 to 64, in which $R^{12}$ represents a hydrogen atom, an alkyl group having 1 to 8 carbon atoms, an alkoxy group having 1 to 8 carbon atoms, an alkyl group having 1 to 8 carbon atoms and a halogen atom substituent, or an alkoxy group having 1 to 8 carbon atoms and a halogen atom substituent.

66. The compound or pharmaceutically acceptable salt, solvate, ester, amide, or prodrug of the compound of any one of embodiments 57 to 64, in which $R^{12}$ represents an alkyl group having 1 to 8 carbon atoms, or an alkyl group having 1 to 8 carbon atoms and a halogen atom substituent.

67. The compound or pharmaceutically acceptable salt, solvate, ester, amide, or prodrug of the compound of any one of embodiments 57 to 66, in which q is 2.

68. The compound or pharmaceutically acceptable salt, solvate, ester, amide, or prodrug of the compound of any one of embodiments 57 to 67, wherein bond a is absent and $W^1$ is OH.

69. The compound or pharmaceutically acceptable salt, solvate, ester, amide, or prodrug of the compound of any one of embodiments 57 to 67, wherein bond a is present and $W^1$ is oxygen.

70. A compound of Formula (J):

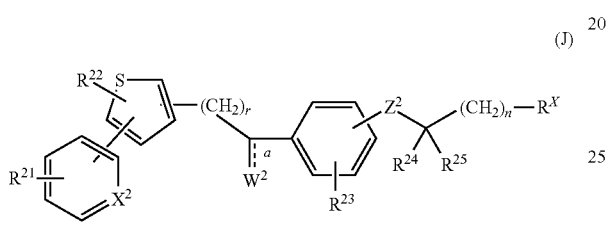

(J)

or a pharmaceutically acceptable salt, solvate, ester, amide, or prodrug thereof, wherein:

each of $R^{21}$ and $R^{23}$, which are the same or different, is a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{5-10}$ aryl, or a 5- or 6-membered heterocyclic group;

$R^{22}$ is hydrogen, $C_{1-8}$ alkyl, a 3- to 7-membered cycloalkyl, $C_{2-8}$ alkenyl, $C_{2-8}$ alkynyl, $C_{1-8}$ alkoxy, $C_{1-8}$ alkyl having a 3- to 7-membered cycloalkyl group substituent, $C_{1-8}$ haloalkyl, $C_{1-8}$ haloalkoxy, $C_{6-10}$ aryl, a 5- or 6-membered heterocyclic group, an aralkyl group having a $C_{6-10}$ aryl moiety and a $C_{1-8}$ alkylene moiety, or a $C_{1-8}$ alkyl group having a 5- or 6-membered heterocyclic substituent;

$R^{24}$ and $R^{25}$ are the same or different and each is a hydrogen atom, $C_{1-8}$ alkyl, or $C_{1-8}$ haloalkyl;

$X^2$ is CH or N;

$Z^2$ is oxygen or sulfur;

$W^2$ is oxygen or $CH_2$ when bond a is present and OH when bond a is absent;

r is 2, 3, or 4.

$R^X$ is $CH_2OH$, COH, $COOCH_2CONR^{X4}R^{X5}$, $SO_3H$,

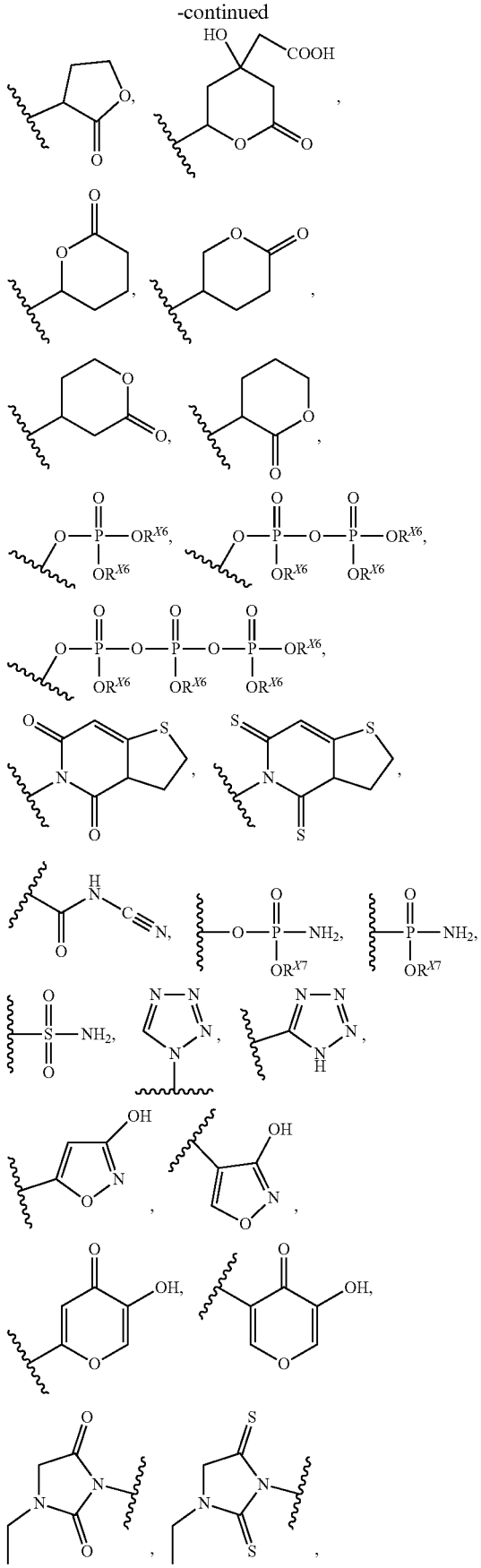

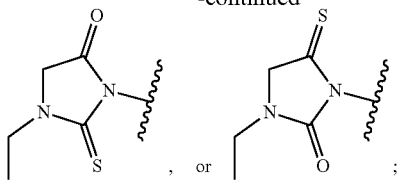, or each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

71. The compound or pharmaceutically acceptable salt, solvate, ester, amide, or prodrug of the compound of embodiment 70, in which $X^2$ is CH.

72. The compound or pharmaceutically acceptable salt, solvate, ester, amide, or prodrug of the compound of embodiment 70 or 71, in which $R^{21}$-phenyl or $R^{21}$-pyridyl is attached to the thiophene at 2-position.

73. The compound or pharmaceutically acceptable salt, solvate, ester, amide, or prodrug of the compound of any one of embodiments 70 to 72, in which $R^{21}$ and $R^{23}$ are the same or different and each represents a hydrogen atom, an alkyl group having 1 to 8 carbon atoms, an alkoxy group having 1 to 8 carbon atoms, a halogen atom, an alkyl group having 1 to 8 carbon atoms and a halogen atom substituent, or an alkoxy group having 1 to 8 carbon atoms and a halogen atom substituent.

74. The compound or pharmaceutically acceptable salt, solvate, ester, amide, or prodrug of the compound of any one of embodiments 70 to 72, in which $R^{21}$ and $R^{23}$ are the same or different and each represents an alkyl group having 1 to 8 carbon atoms or an alkyl group having 1 to 8 carbon atoms and a halogen atom substituent.

75. The compound or pharmaceutically acceptable salt, solvate, ester, amide, or prodrug of the compound of any one of embodiments 70 to 74, in which $R^{24}$ and $R^{25}$ are the same or different and each represents a hydrogen atom or an alkyl group having 1 to 8 carbon atoms.

76. The compound or pharmaceutically acceptable salt, solvate, ester, amide, or prodrug of the compound of any one of embodiments 70 to 75, in which $R^{22}$ represents a hydrogen atom, an alkyl group having 1 to 8 carbon atoms, an alkoxy group having 1 to 8 carbon atoms, an alkyl group having 1 to 8 carbon atoms and a halogen atom substituent, or an alkoxy group having 1 to 8 carbon atoms and a halogen atom substituent.

77. The compound or pharmaceutically acceptable salt, solvate, ester, amide, or prodrug of the compound of any one of embodiments 70 to 75, in which $R^{22}$ represents an alkyl group having 1 to 8 carbon atoms, or an alkyl group having 1 to 8 carbon atoms and a halogen atom substituent.

78. The compound or pharmaceutically acceptable salt, solvate, ester, amide, or prodrug of the compound of any one of embodiments 70 to 77, in which r is 2.

79. The compound or pharmaceutically acceptable salt, solvate, ester, amide, or prodrug of the compound of any one of embodiments 70 to 78, wherein bond a is absent and $W^2$ is OH.

80. The compound or pharmaceutically acceptable salt, solvate, ester, amide, or prodrug of the compound of any one of embodiments 70 to 78, wherein bond a is present and $W^2$ is oxygen.

81. A compound of Formula (K):

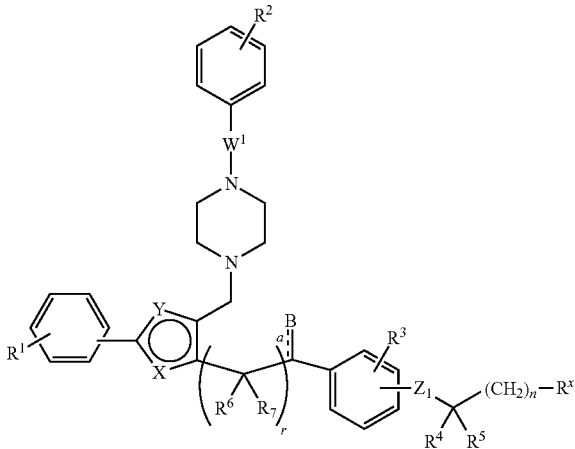

or a pharmaceutically acceptable salt, solvate, ester, amide, or prodrug thereof, wherein:

A is CH or nitrogen;

B, when bond a is present, is oxygen or $C(R^8)(R^9)$ in which each of $R^3$ and $R^9$ is independently hydrogen or $C_{1-8}$ alkyl; B, when bond a is absent, is OH;

$W^1$ is a bond, C(=O), or $(C(R^{1'})(R^{11}))_m$ in which each of $R^{10}$ and $R^{11}$ is independently a hydrogen or $C_{1-8}$ alkyl group and m is 1, 2, or 3;

X and Y differ from each other, and each is an oxygen atom, a sulfur atom, a nitrogen atom, or $CR^{12}$ in which $R^{12}$ is a hydrogen or $C_{1-8}$ alkyl;

$Z^1$ is a bond, oxygen, sulfur, or $C(R^{13})(R^{14})$ in which each of $R^{13}$ and $R^{14}$ is independently a hydrogen or $C_{1-8}$ alkyl;

each of $R^1$, $R^2$, and $R^3$, is independently a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

each of $R^4$ and $R^5$ is independently hydrogen, $C_{1-8}$ alkyl, $C_{1-8}$ haloalkyl;

each of $R^6$ and $R^7$ is independently hydrogen, $C_{1-8}$ alkyl, $C_{2-8}$ alkenyl, $C_{2-8}$ alkynyl, or $C_{1-8}$ haloalkyl r is 1, 2, 3, 4, or 5;

$R^x$ is $CH_2OH$, COH, $COOCH_2CONR^{X4}R^{X5}$, $SO_3H$,

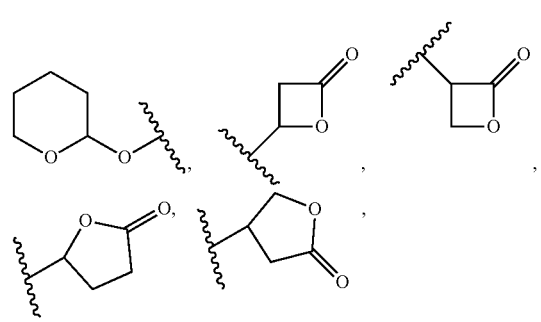

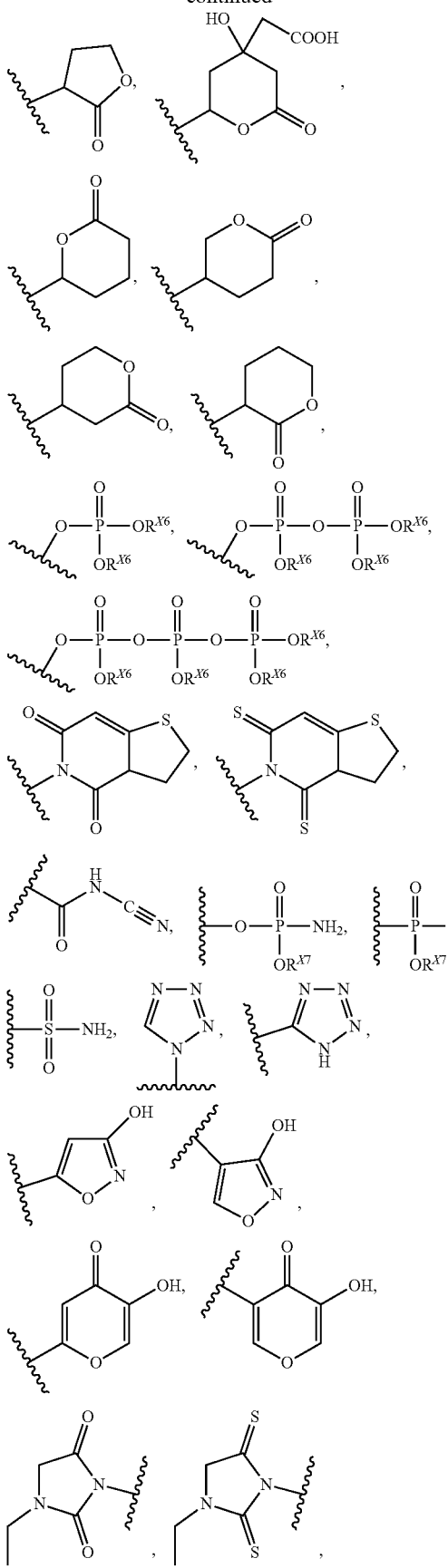

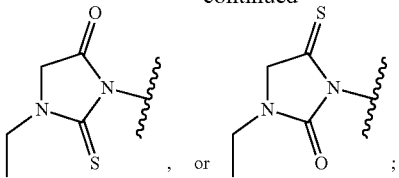, or each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

82. The compound or pharmaceutically acceptable salt, solvate, ester, amide, or prodrug of the compound of embodiment 81, wherein A is CH.

83. The compound or pharmaceutically acceptable salt, solvate, ester, amide, or prodrug of the compound of embodiment 81 or 82, in which $W^1$ is a bond.

84. The compound or pharmaceutically acceptable salt, solvate, ester, amide, or prodrug of the compound of embodiment 81 or 82, in which $W^1$ is methylene or C(=O).

85. The compound or pharmaceutically acceptable salt, solvate, ester, amide, or prodrug of the compound of any one of embodiments 81 to 84, in which X and Y are different from each other and each is an oxygen atom, a sulfur atom or a nitrogen atom.

86. The compound or pharmaceutically acceptable salt, solvate, ester, amide, or prodrug of the compound of embodiment 85, X is a sulfur atom and Y is a nitrogen atom.

87. The compound or pharmaceutically acceptable salt, solvate, ester, amide, or prodrug of the compound of any one of embodiments 81 to 86, in which $Z^1$ is an oxygen atom or a sulfur atom.

88. The compound or pharmaceutically acceptable salt, solvate, ester, amide, or prodrug of the compound of any one of embodiments 81 to 87, in which $R^1$, $R^2$ and $R^3$ independently is a hydrogen atom, an alkyl group having 1 to 8 carbon atoms, an alkenyl group having 2 to 8 carbon atoms, an alkoxy group having 1 to 8 carbon atoms, a halogen atom, an alkyl group having 1 to 8 carbon atoms which is substituted with a halogen atom, or an alkoxy group having 1 to 8 carbon atoms which is substituted with a halogen atom.

89. The compound or pharmaceutically acceptable salt, solvate, ester, amide, or prodrug of the compound of any one of embodiments 81 to 88, in which each of $R^4$ and $R^5$ independently is a hydrogen atom or methyl.

90. The compound or pharmaceutically acceptable salt, solvate, ester, amide, or prodrug of the compound of any one of embodiments 81 to 89, in which each of $R^6$ and $R^7$ independently is a hydrogen atom or an alkyl group having 1 to 8 carbon atoms 91. The compound or pharmaceutically acceptable salt, solvate, ester, amide, or prodrug of the compound of any one of embodiments 81 to 90, in which n is an integer of 2 to 4.

92. The compound or pharmaceutically acceptable salt, solvate, ester, amide, or prodrug of the compound of embodiment 91, in which n is 2.

93. The compound or pharmaceutically acceptable salt, solvate, ester, amide, or prodrug of the compound of any one of embodiments 81 to 92, wherein bond a is absent and B is OH.

94. The compound or pharmaceutically acceptable salt, solvate, ester, amide, or prodrug of the compound of any one of embodiments 81 to 92, wherein bond a is present and B is oxygen.

95. A compound of Formula (L):

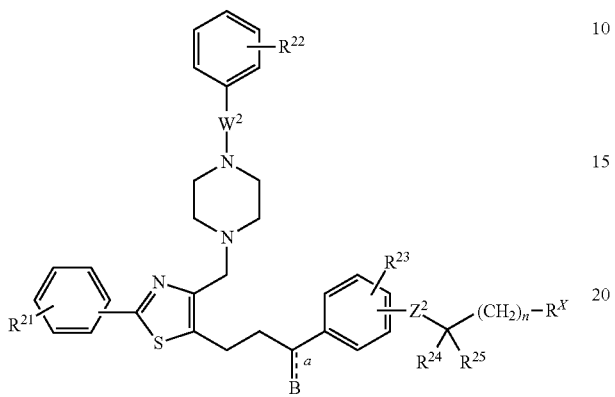

(L)

or a pharmaceutically acceptable salt, solvate, ester, amide, or prodrug thereof, wherein:

B, when bond a is present, is oxygen; B, when bond a is absent, is OH;

$W^2$ is a bond, C(=O), or $CH_2$;

$Z^2$ is oxygen or sulfur;

each of $R^{21}$, $R^{22}$, and $R^{23}$ is independently a hydrogen, $C_{1-8}$ alkyl, $C_{2-8}$ alkenyl, $C_{2-8}$ alkynyl, $C_{1-8}$ alkoxy, halogen, $C_{1-8}$ haloalkyl; $C_{1-8}$ haloalkoxy; hydroxyl, nitro, $C_{2-8}$ acyl group, $C_{6-10}$ aryl, or a 5- or 6-membered heterocyclic group;

each of $R^{24}$ and $R^{25}$ is independently hydrogen, $C_{1-8}$ alkyl, $C_{1-8}$ haloalkyl;

$R^X$ is $CH_2OH$, COH, $COOCH_2CONR^{X4}R^{X5}$, $SO_3H$,

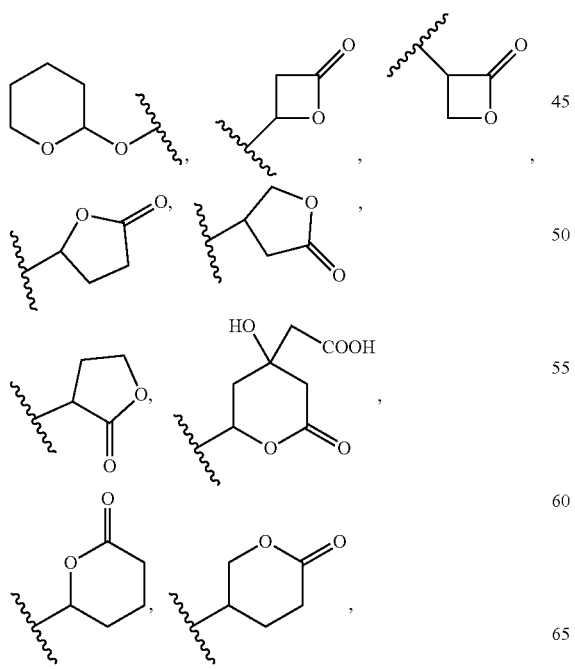

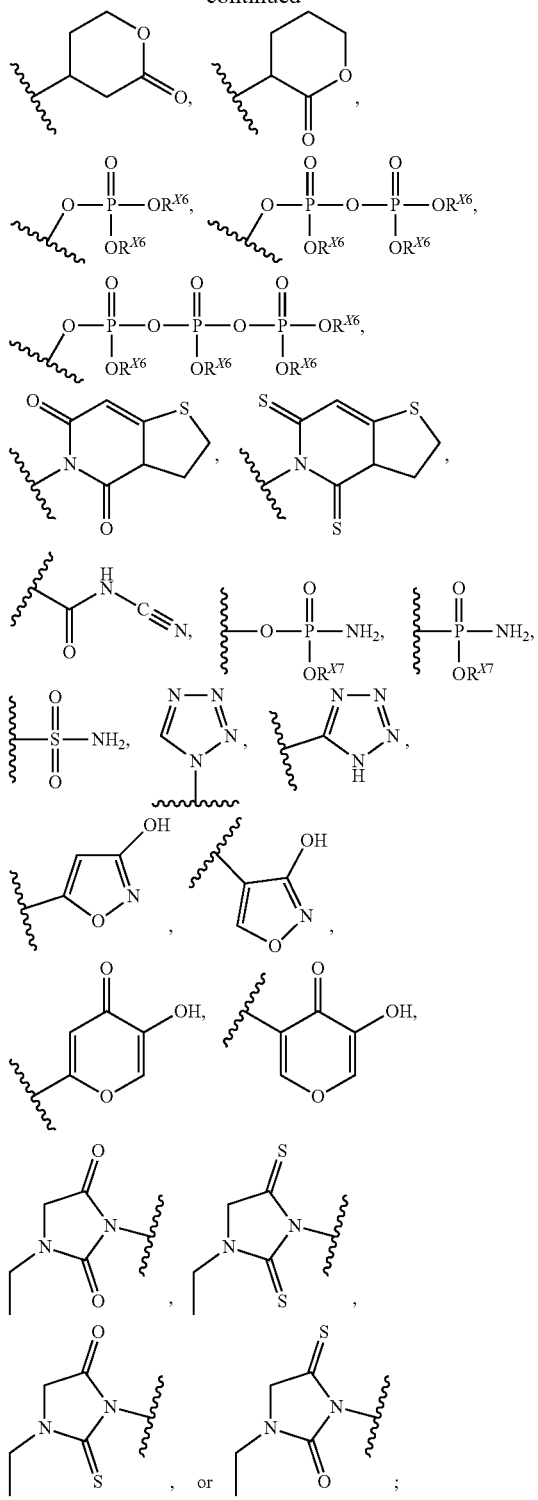

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

96. The compound or pharmaceutically acceptable salt, solvate, ester, amide, or prodrug of the compound of embodiment 95, in which W² is a bond.

97. The compound or pharmaceutically acceptable salt, solvate, ester, amide, or prodrug of the compound of any one of embodiments 95 or 96, in which $R^{21}$, $R^{22}$ and $R^{23}$ independently is a hydrogen atom, an alkyl group having 1 to 8 carbon atoms, an alkenyl group having 2 to 8 carbon atoms, an alkoxy group having 1 to 8 carbon atoms, a halogen atom, an alkyl group having 1 to 8 carbon atoms which is substituted with a halogen atom, or an alkoxy group having 1 to 8 carbon atoms which is substituted with a halogen atom.

98. The compound or pharmaceutically acceptable salt, solvate, ester, amide, or prodrug of the compound of any one of embodiments 95 to 97, in which each of $R^{24}$ and $R^{25}$ independently is a hydrogen atom or methyl.

99. The compound or pharmaceutically acceptable salt, solvate, ester, amide, or prodrug of the compound of any one of embodiments 95 to 98, wherein bond a is absent and B is OH.

100. The compound or pharmaceutically acceptable salt, solvate, ester, amide, or prodrug of the compound of any one of embodiments 95 to 98, wherein bond a is present and B is oxygen.

101. A compound of Formula (M):

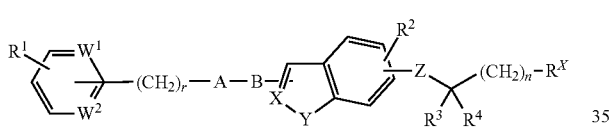

(M)

or a pharmaceutically acceptable salt, solvate, ester, amide, or prodrug thereof, wherein:
each of W¹ and W² is independently nitrogen or CH;
X is nitrogen or CH;
Y is oxygen or sulfur;
Z is a bond, oxygen, sulfur or NR⁵, in which R⁵ is hydrogen or $C_{1-8}$ alkyl; each of R¹ and R² is independently hydrogen, halogen, hydroxyl, nitro, amino, $C_{1-8}$ alkyl, 3- to 7-membered cycloalkyl group, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ haloalkoxy, $C_{6-10}$ aryl, 5- or 6-membered heterocyclic group, an aralkyl group having $C_{6-10}$ aryl moiety and a $C_{1-8}$ alkylene, or $C_{1-8}$ alkyl having a 5- or 6-membered heterocyclic substituent;
each of R³ and R⁴ is independently hydrogen, $C_{1-8}$ alkyl, or $C_{1-8}$ haloalkyl;
A is a 5-membered heterocycle which is pyrazole, thiophene, furan, isoxazole, isothiazole or pyrrole, in which the 5-membered heterocycle is unsubstituted or substituted with halogen, hydroxyl, nitro, amino, $C_{1-8}$ alkyl, 3- to 7-membered cycloalkyl group, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ haloalkoxy, $C_{6-10}$ aryl, a 5- or 6-membered heterocyclic group, an aralkyl group having a $C_{6-10}$ aryl moiety and $C_{1-8}$ alkylene moiety, or $C_{1-8}$ alkyl group having a 5- or 6-membered heterocyclic substituent;
B is a bond or $C_{1-8}$ alkylene which is unsubstituted or substituted with $C_{1-8}$ alkyl, 3- to 7-membered cycloalkyl, $C_{1-8}$ alkoxy or a halogen substituent, optionally wherein the $C_{1-8}$ alkylene has a double or triple bond;
r is 0, 1, 2, or 3;
$R^X$ is $CH_2OH$, $COH$, $COOCH_2CONR^{X4}R^{X5}$, $SO_3H$,

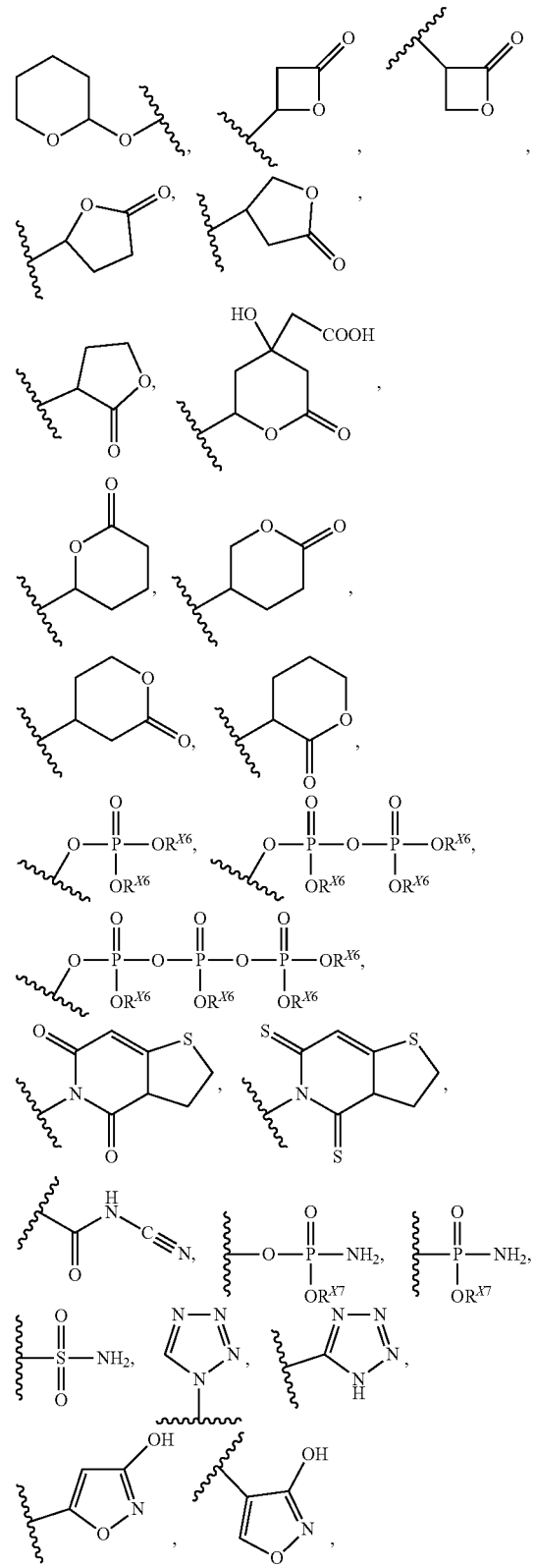

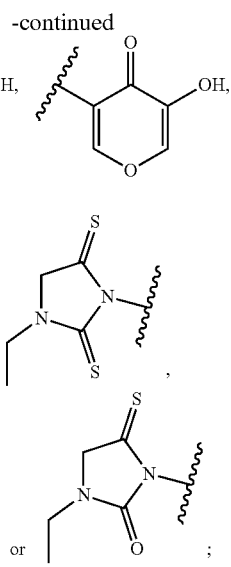

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

102. The compound or pharmaceutically acceptable salt, solvate, ester, amide, or prodrug of the compound of embodiment 101, in which each of $W^1$ and $W^2$ represents CH.

103. The compound or pharmaceutically acceptable salt, solvate, ester, amide, or prodrug of the compound of embodiment 101, in which $W^1$ represents CH and $W^2$ represents a nitrogen atom 104. The compound or pharmaceutically acceptable salt, solvate, ester, amide, or prodrug of the compound of any one of embodiments 101 to 103, in which X represents a nitrogen atom.

105. The compound or pharmaceutically acceptable salt, solvate, ester, amide, or prodrug of the compound of any one of embodiments 101 to 103, in which X represents a nitrogen atom and Y represents an oxygen atom.

106. The compound or pharmaceutically acceptable salt, solvate, ester, amide, or prodrug of the compound of any one of embodiments 101 to 103, in which X represents CH and Y represents an oxygen atom.

107. The compound or pharmaceutically acceptable salt, solvate, ester, amide, or prodrug of the compound of any one of embodiments 101 to 106, in which Z represents an oxygen atom or a sulfur atom.

108. The compound or pharmaceutically acceptable salt, solvate, ester, amide, or prodrug of the compound of any one of embodiments 101 to 107, in which each of $R^1$ and $R^2$ independently represents a hydrogen atom, a halogen atom, a hydroxyl group, a nitro group, an amino group, an alkyl group having 1 to 8 carbon atoms, an alkoxy group having 1 to 8 carbon atoms, an alkyl group having 1 to 8 carbon atoms and a halogen substituent, or an alkoxy group having 1 to 8 carbon atoms and a halogen substituent.

109. The compound or pharmaceutically acceptable salt, solvate, ester, amide, or prodrug of the compound of any one of embodiments 101 to 108, in which each of $R^3$ and $R^4$ independently represents a hydrogen atom or an alkyl group having 1 to 8 carbon atoms.

110. The compound or pharmaceutically acceptable salt, solvate, ester, amide, or prodrug of the compound of any one of embodiments 101 to 109, in which A represents pyrazole, thiophene or furan which may have a substituent selected from the group consisting of a halogen atom, a hydroxyl group, a nitro group, an amino group, an alkyl group having 1 to 8 carbon atoms, a 3- to 7-membered cycloalkyl group, an alkenyl group having 2 to 8 carbon atoms, an alkynyl group having 2 to 8 carbon atoms, an alkoxy group having 1 to 8 carbon atoms, an alkyl group having 1 to 8 carbon atoms and a 3- to 7-membered cycloalkyl substituent, an alkyl group having 1 to 8 carbon atoms and a halogen substituent, an alkoxy group having 1 to 8 carbon atoms and a halogen substituent, an aryl group having 6 to 10 carbon atoms, a 5- or 6-membered heterocyclic group, an aralkyl group having an aryl moiety of 6 to 10 carbon atoms and an alkylene moiety of 1 to 8 carbon atoms, and an alkyl group having 1 to 8 carbon atoms and a 5- or 6-membered heterocyclic substituent.

111. The compound or pharmaceutically acceptable salt, solvate, ester, amide, or prodrug of the compound of any one of embodiments 101 to 109, in which A represents pyrazole, thiophene or furan which may have a substituent selected from the group consisting of a halogen atom, a hydroxyl group, a nitro group, an amino group, an alkyl group having 1 to 8 carbon atoms, an alkoxy group having 1 to 8 carbon atoms, an alkyl group having 1 to 8 carbon atoms and a halogen substituent, or an alkoxy group having 1 to 8 carbon atoms and a halogen substituent.

112. The compound or pharmaceutically acceptable salt, solvate, ester, amide, or prodrug of the compound of any one of embodiments 101 to 109, in which A represents pyrazole which may have a substituent selected from the group consisting of a halogen atom, a hydroxyl group, a nitro group, an amino group, an alkyl group having 1 to 8 carbon atoms, an alkoxy group having 1 to 8 carbon atoms, an alkyl group having 1 to 8 carbon atoms and a halogen substituent, and an alkoxy group having 1 to 8 carbon atoms and a halogen substituent.

113. The compound or pharmaceutically acceptable salt, solvate, ester, amide, or prodrug of the compound of any one of embodiments 101 to 112, in which B represents an alkylene chain having 2 to 4 carbon atoms.

114. The compound or pharmaceutically acceptable salt, solvate, ester, amide, or prodrug of the compound of any one of embodiments 101 to 113, in which n is 0.

115. A compound of Formula (N):

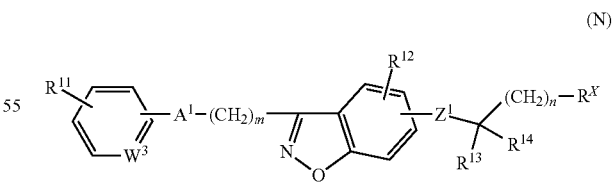

or a pharmaceutically acceptable salt, solvate, ester, amide, or prodrug thereof, wherein:

$W^3$ is nitrogen or CH;

$Z^1$ is oxygen or sulfur;

each of $R^{11}$ and $R^{12}$ is independently hydrogen, halogen, hydroxyl, nitro, amino, $C_{1-8}$ alkyl, $C_{1-8}$ alkoxy, $C_{1-8}$ haloalkyl, or $C_{1-8}$ haloalkoxy' each of $R^{13}$ and $R^{14}$ is independently hydrogen or $C_{1-8}$ alkyl;

A¹ is a 5-membered heterocycle which is pyrazole or thiophene, in which the 5-membered heterocycle is unsubstituted or substituted with halogen, hydroxyl, nitro, amino, $C_{1-8}$ alkyl, $C_{1-8}$ alkoxy, $C_{1-8}$ haloalkyl, or $C_{1-8}$ haloalkoxy;

m is 2, 3, or 4;

$R^X$ is $CH_2OH$, COH, $COOCH_2CONR^{X4}R^{X5}$, $SO_3H$,

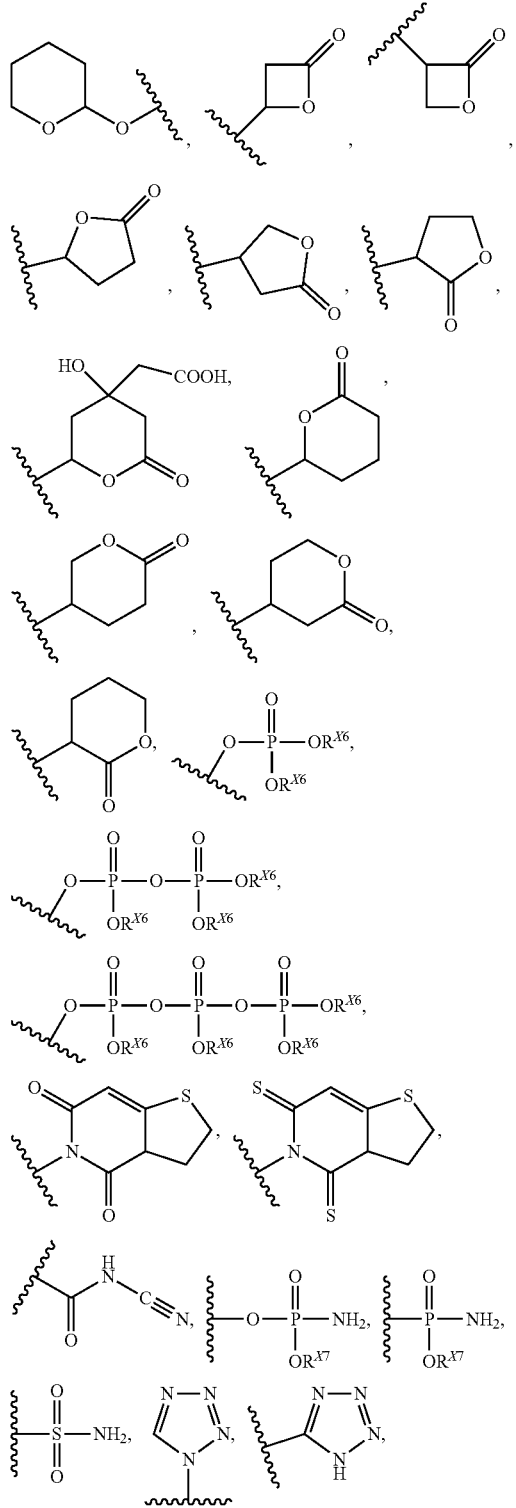
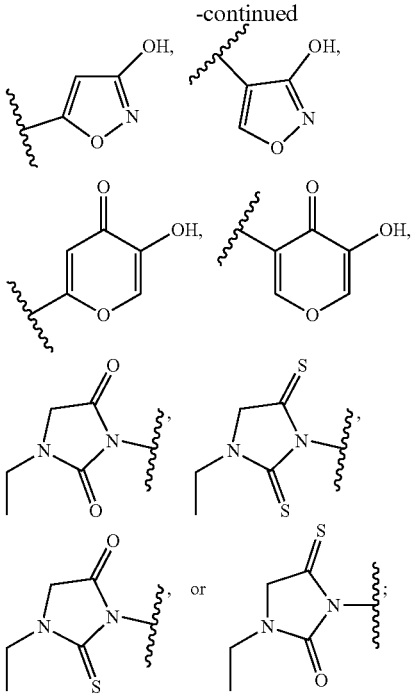

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

116. The compound or pharmaceutically acceptable salt, solvate, ester, amide, or prodrug of the compound of embodiment 115, in which $W^3$ represents CH.

117. The compound or pharmaceutically acceptable salt, solvate, ester, amide, or prodrug of the compound of embodiment 115 or 116, which A¹ represents pyrazole which may have a substituent selected from the group consisting of a halogen atom, a hydroxyl group, a nitro group, an amino group, an alkyl group having 1 to 8 carbon atoms, an alkoxy group having 1 to 8 carbon atoms, an alkyl group having 1 to 8 carbon atoms and a halogen substituent, or an alkoxy group having 1 to 8 carbon atoms and a halogen substituent.

118. The compound or pharmaceutically acceptable salt, solvate, ester, amide, or prodrug of the compound of any one of embodiments 115 to 117, in which m is 2 or 3.

119. A compound of Formula (O):

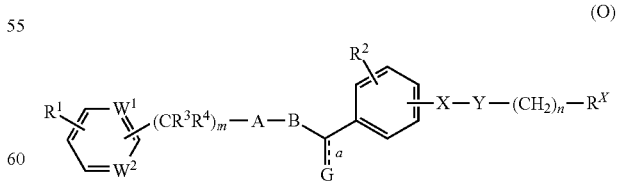

(O)

or a pharmaceutically acceptable salt, solvate, ester, amide, or prodrug thereof, wherein:

each of $W^1$ and $W^2$ independently is CH or nitrogen;

X is $NR^5$ or $CR^6R^7$; wherein $R^5$ is hydrogen, $C_{1-8}$ alkyl, $C_{1-8}$ haloalkyl, $C_{1-8}$ alkyl substituted with $C_{1-8}$ alkoxy, $C_{3-7}$ cycloalkyl, $C_{1-8}$ alkyl substituted with $C_{3-7}$ cycloalkyl, $C_{1-8}$ alkyl substituted with phenyl, $C_{2-8}$ acyl, or $C_{2-8}$ alkenyl, and each of $R^6$ and $R^7$ independently is hydrogen or $C_{1-8}$ alkyl;

Y is $(CR^8R^9)_r$, wherein each of $R^8$ and $R^9$ independently is hydrogen or $C_{1-8}$ alkyl, and r is 1, 2, 3, or 4; or X and Y are combined to form $CR^{10}=CR^{11}$ or ethynylene, wherein each of $R^{10}$ and $R^{11}$ independently is hydrogen or $C_{1-8}$ alkyl;

G, when bond a is present, is O, S or $CR^{12}R^{13}$, wherein each of $R^{12}$ and $R^{13}$ independently is hydrogen or $C_{1-8}$ alkyl; G, when bond a is absent, is OH;

A is a five-membered heterocyclic ring which is thiazole, oxazole, imidazole, pyrazole, thiophene, furan, or pyrrole, wherein the heterocyclic ring is unsubstituted or substituted with $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, hydroxyl, nitro, $C_{2-8}$ acyl, $C_{6-10}$ aryl, or a five-membered or six-membered heterocyclic group;

B is a $C_{1-8}$ alkylene, $C_{2-8}$ alkenylene or $C_{2-8}$ alkynylene chain, wherein the chain is unsubstituted or substituted with $C_{1-8}$ alkyl, $C_{3-7}$ cycloalkyl, $C_{1-8}$ alkoxy, or halogen;

each of $R^1$ and $R^2$ independently is hydrogen, $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, hydroxyl, nitro, $C_{2-8}$ acyl, $C_{6-10}$ aryl, or a five-membered or six-membered heterocyclic group;

each of $R^3$ and $R^4$ independently is hydrogen or $C_{1-8}$ alkyl;

m is 0, 1, 2, or 3;

$R^X$ is $CH_2OH$, COH, $COOCH_2CONR^{X4}R^{X5}$, $SO_3H$,

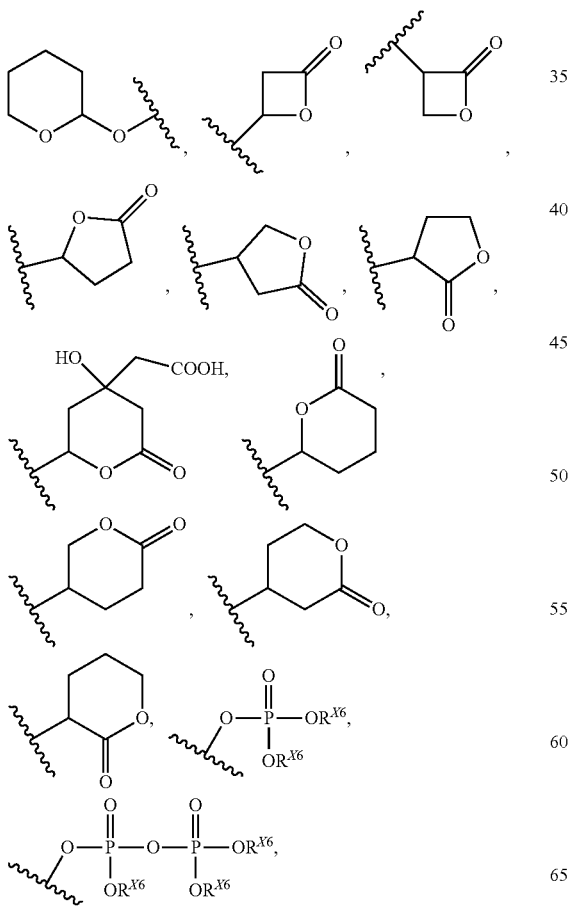

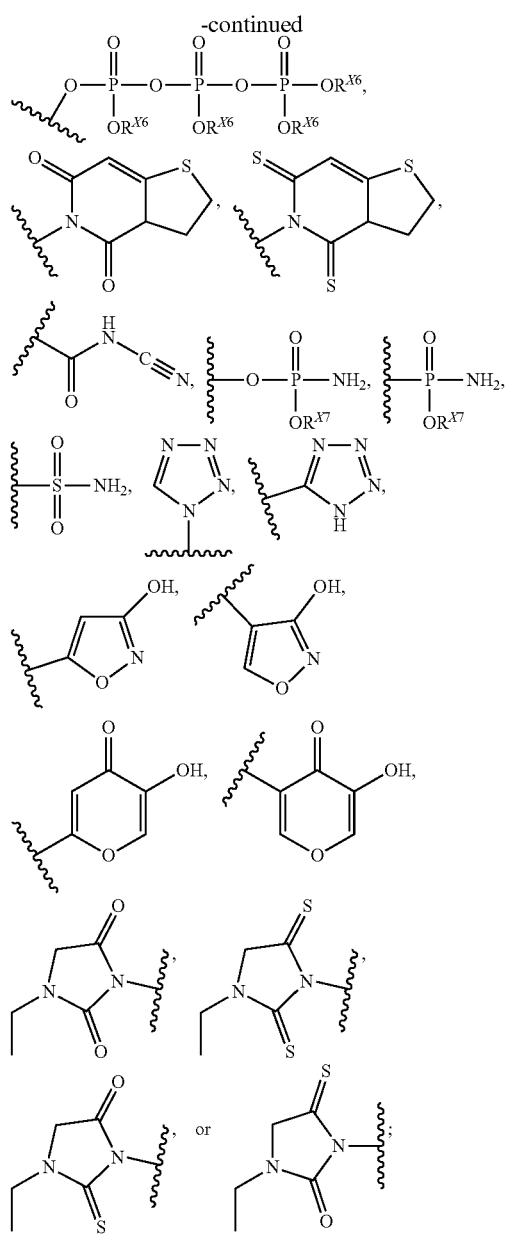

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

120. The compound or pharmaceutically acceptable salt, solvate, ester, amide, or prodrug of the compound of embodiment 119, wherein each of $W^1$ and AP is CH.

121. The compound or pharmaceutically acceptable salt, solvate, ester, amide, or prodrug of the compound of embodiment 119 or 120, wherein X is $CR^6R^7$.

122. The compound or pharmaceutically acceptable salt, solvate, ester, amide, or prodrug of the compound of embodiment 119 or 120, wherein X is $CH_2$ 123. The compound or pharmaceutically acceptable salt, solvate, ester, amide, or prodrug of the compound of embodiment 119 or 120, wherein X is $NR^5$.

124. The compound or pharmaceutically acceptable salt, solvate, ester, amide, or prodrug of the compound of embodiment 119 or 120, wherein X is NH.

125. The compound or pharmaceutically acceptable salt, solvate, ester, amide, or prodrug of the compound of embodiment 119 or 120, wherein X is $NR^3$, and $R^5$ is $C_{1-8}$ alkyl.

126. The compound or pharmaceutically acceptable salt, solvate, ester, amide, or prodrug of the compound of any one of embodiments 119 to 125, wherein Y is $CH_2$.

127. The compound or pharmaceutically acceptable salt, solvate, ester, amide, or prodrug of the compound of any one of embodiments 119 to 126, wherein Z is carboxyl.

128. The compound or pharmaceutically acceptable salt, solvate, ester, amide, or prodrug of the compound of any one of embodiments 119 to 127, wherein A is thiazole, which can be substituted with a substituent selected from the group consisting of $C_{1-8}$ alkyl, $C_{2-8}$ alkenyl, $C_{2-8}$ alkynyl, $C_{1-8}$ alkoxy, halogen, $C_{1-8}$ alkyl substituted with halogen, $C_{1-8}$ alkoxy substituted with halogen, hydroxyl, nitro, $C_{2-8}$ acyl, $C_{6-10}$ aryl, and a five-membered or six-membered heterocyclic group.

129. The compound or pharmaceutically acceptable salt, solvate, ester, amide, or prodrug of the compound of any one of embodiments 119 to 128, wherein B is ethylene chain.

130. The compound or pharmaceutically acceptable salt, solvate, ester, amide, or prodrug of the compound of any one of embodiments 119 to 129, wherein each of $R^1$ and $R^2$ independently is hydrogen, CEs alkyl, $C_{2-8}$ alkenyl, $C_{1-8}$ alkoxy, halogen, $C_{1-8}$ alkyl substituted with halogen, or $C_{1-8}$ alkoxy substituted with halogen.

131. The compound or pharmaceutically acceptable salt, solvate, ester, amide, or prodrug of the compound of any one of embodiments 119 to 129, wherein each of $R^1$ and $R^2$ independently is hydrogen, $C_{1-8}$ alkyl, halogen, or $C_{1-8}$ alkyl substituted with halogen.

132. The compound or pharmaceutically acceptable salt, solvate, ester, amide, or prodrug of the compound of any one of embodiments 119 to 131, wherein each of $R^3$ and $R^4$ is hydrogen.

133. The compound or pharmaceutically acceptable salt, solvate, ester, amide, or prodrug of the compound of any one of embodiments 119 to 132, wherein m is 0.

134. The compound or pharmaceutically acceptable salt, solvate, ester, amide, or prodrug of the compound of embodiment 119 to 133, wherein bond a is absent and G is OH.

135. The compound or pharmaceutically acceptable salt, solvate, ester, amide, or prodrug of the compound of embodiment 119 to 133, wherein bond a is present and G is oxygen.

136. A compound of Formula (P):

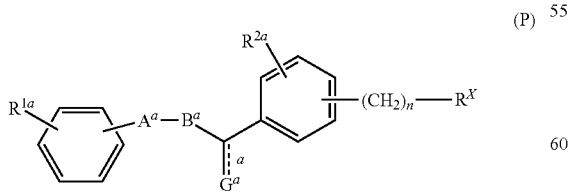

or a pharmaceutically acceptable salt, solvate, ester, amide, or prodrug thereof, wherein:
$G^a$, when bond a is present, is O, S or $CH_2$; $G^a$, when bond a is absent, is OH.

$A^a$ is five-membered heterocyclic ring which is thiazole, oxazole, or thiophene, wherein the five-membered heterocyclic ring is unsubstituted or is substituted with $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$B^a$ is a $C_{1-8}$ alkylene or $C_{2-8}$ alkenylene chain;

each of $R^{1a}$ and $R^{2a}$ independently is hydrogen, $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$R^X$ is $CH_2OH$, COH, $COOCH_2CONR^{X4}R^{X5}$, $SO_3H$,

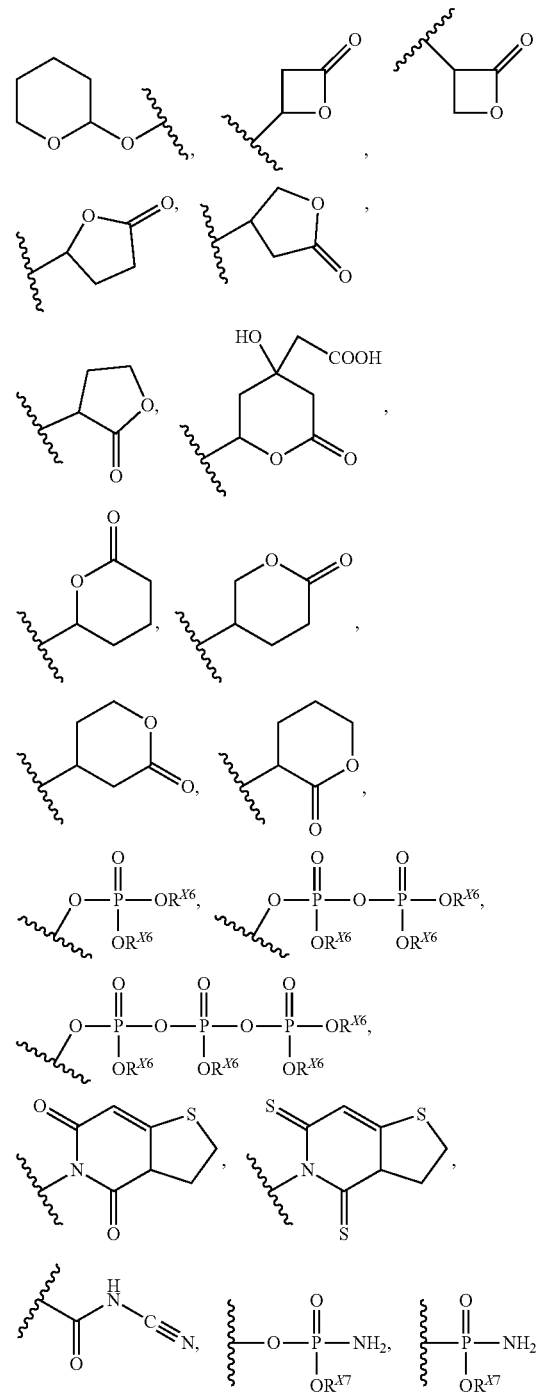

-continued

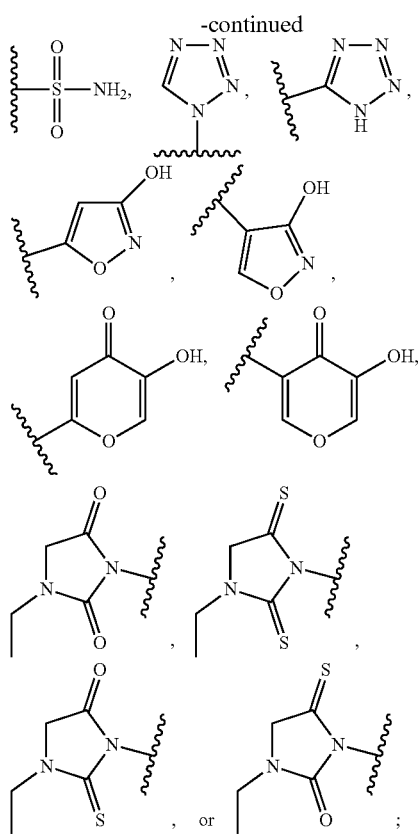

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

137. The compound or pharmaceutically acceptable salt, solvate, ester, amide, or prodrug of the compound of embodiment 136, wherein $A^a$ is thiazole, which can be substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl.

138. The compound or pharmaceutically acceptable salt, solvate, ester, amide, or prodrug of the compound of embodiment 136 or 137, wherein $B^a$ is ethylene chain.

139. The compound or pharmaceutically acceptable salt, solvate, ester, amide, or prodrug of the compound of any one of embodiments 136 to 138, wherein each of $R^{1a}$ and $R^{2a}$ independently is hydrogen, $C_{1-8}$ alkyl, $C_{1-8}$ alkoxy, halogen, $C_{1-8}$ alkyl substituted with halogen, or $C_{1-8}$ alkoxy substituted with halogen.

140. The compound or pharmaceutically acceptable salt, solvate, ester, amide, or prodrug of the compound of any one of embodiments 136 to 139, wherein bond a is absent and $G^a$ is OH.

141. The compound or pharmaceutically acceptable salt, solvate, ester, amide, or prodrug of the compound of any one of embodiments 136 to 139, wherein bond a is present and $G^a$ is oxygen.

142. A compound of Formula (Q):

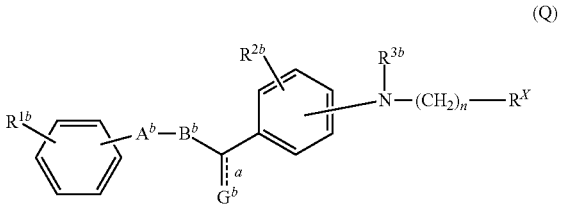

(Q)

or a pharmaceutically acceptable salt, solvate, ester, amide, or prodrug thereof, wherein:

$G^b$, when bond a is present, is O, S or $CH_2$; $G^b$, when bond a is absent, is OH;

$A^b$ is five-membered heterocyclic ring which is thiazole, oxazole, or thiophene, wherein the five-membered heterocyclic ring is unsubstituted or is substituted with $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$B^b$ is a $C_{1-8}$ alkylene or $C_{2-8}$ alkenylene chain; each of $R^{1b}$ and $R^{2b}$ independently is hydrogen, $C_{1-8}$ alkyl, $C_{1-8}$ alkoxy, halogen, $C_{1-8}$ haloalkyl, $C_{1-8}$ haloalkoxy, hydroxyl, nitro, or $C_{2-8}$ acyl;

$R^{3b}$ is hydrogen or $C_{1-8}$ alkyl;

$R^X$ is $CH_2OH$, COH, $COOCH_2CONR^{X4}R^{X5}$, $SO_3H$,

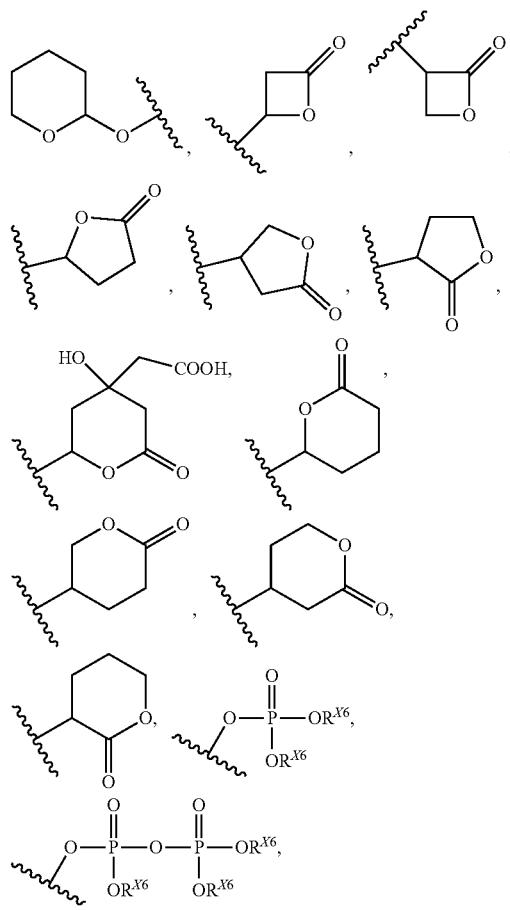

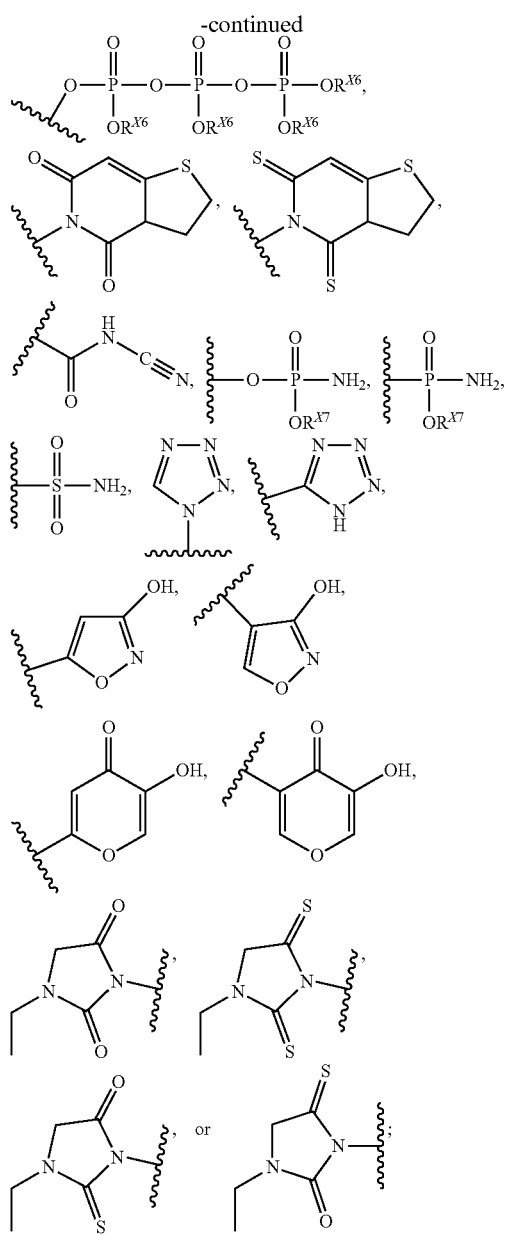

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

143. The compound or pharmaceutically acceptable salt, solvate, ester, amide, or prodrug of the compound of embodiment 142, wherein $A^b$ is thiazole, which is substituted with a substituent selected from the group consisting of $C_{1-8}$ alkyl, $C_{1-8}$ alkoxy, halogen, $C_{1-8}$ alkyl substituted with halogen, $C_{1-8}$ alkoxy substituted with halogen, hydroxyl, nitro, and $C_{2-8}$ acyl.

144. The compound or pharmaceutically acceptable salt, solvate, ester, amide, or prodrug of the compound of embodiment 142 or 143, wherein $B^b$ is ethylene chain.

145. The compound or pharmaceutically acceptable salt, solvate, ester, amide, or prodrug of the compound of any one of embodiments 142 to 144, wherein each of $R^{1b}$ and $R^{2b}$ independently is hydrogen, $C_{1-8}$ alkyl, $C_{1-8}$ alkoxy, halogen, $C_{1-8}$ alkyl substituted with halogen, or $C_{1-8}$ alkoxy substituted with halogen.

146. The compound or pharmaceutically acceptable salt, solvate, ester, amide, or prodrug of the compound of any one of embodiments 142 to 145, wherein bond a is absent and $G^b$ is OH.

147. The compound or pharmaceutically acceptable salt, solvate, ester, amide, or prodrug of the compound of any one of embodiments 142 to 145, wherein bond a is present and $G^b$ is oxygen.

148. A compound of Formula (R):

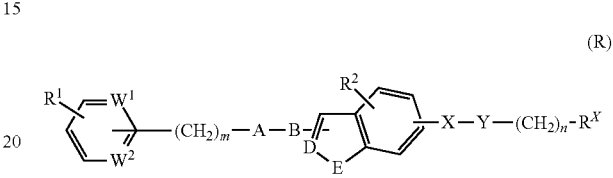

(R)

or a pharmaceutically acceptable salt, solvate, ester, amide, or prodrug thereof, wherein:

each of $W^1$ and $W^2$ is independently CH or N;

X is $NR^3$ or $CR^4R^5$, in which $R^3$ is $C_{1-8}$ alkyl, $C_{1-8}$ haloalkyl, $C_{1-8}$ alkyl substituted with $C_{1-8}$ alkoxy, $C_{1-8}$ alkyl substituted with a 3-7 membered cycloalkyl, $C_{1-8}$ alkyl substituted with a phenyl group, $C_{2-8}$ acyl, or $C_{2-8}$ alkenyl;

each of $R^4$ and $R^5$ is independently hydrogen or $C_{1-8}$ alkyl;

Y is $(CR^6R^7)_r$, in which each of $R^6$ and $R^7$ is independently hydrogen or $C_{1-8}$ alkyl and r is 1, 2, 3, or 4;

A is a 5 or 6-membered heterocyclic group which is thiazole, oxazole, imidazole, pyrazole, thiophene, furan, pyrrole, pyridine or pyrimidine, or a phenyl group, wherein the 5 or 6-membered heterocyclic group or phenyl group is unsubstituted or substituted with $C_{1-8}$ alkyl, 3-7 membered cycloalkyl, $C_{2-8}$ alkenyl, $C_{2-8}$ alkynyl, $C_{1-8}$ alkoxyl, $C_{1-8}$ alkyl group substituted with a 3-7 membered cycloalkyl group, $C_{1-8}$ haloalkyl, $C_{1-8}$ haloalkoxy, $C_{6-10}$ aryl, a 5 or 6-membered heterocyclic group, aralkyl group comprising a $C_{6-10}$ aryl group and a $C_{1-8}$ alkyl group, or $C_{1-8}$ alkyl group substituted with a 5 or 6-membered heterocyclic group;

B is a bond or $C_{1-8}$ alkylene which is unsubstituted or substituted with $C_{1-8}$ alkyl, a 3-7 membered cycloalkyl group, $C_{1-8}$ alkoxy or a halogen, and which may have a double bond or triple bond when the carbon number of the alkylene chain is 2 or more;

D is N or CH;

E is O or S;

each of $R^1$ and $R^2$ is independently H, $C_{1-8}$ alkyl, $C_{2-8}$ alkenyl, $C_{2-8}$ alkynyl, $C_{1-8}$ alkoxy, halogen, $C_{1-8}$ haloalkyl, $C_{1-8}$ haloalkoxy, nitro, $C_{2-8}$ acyl, $C_{6-10}$ aryl, or a 5 or 6-membered heterocyclic group;

m 0, 1, 2, or 3;

$R^X$ is $CH_2OH$, COH, $COOCH_2CONR^{X4}R^{X5}$, $SO_3H$,

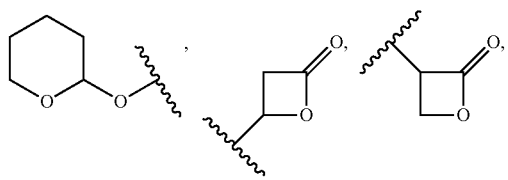

-continued

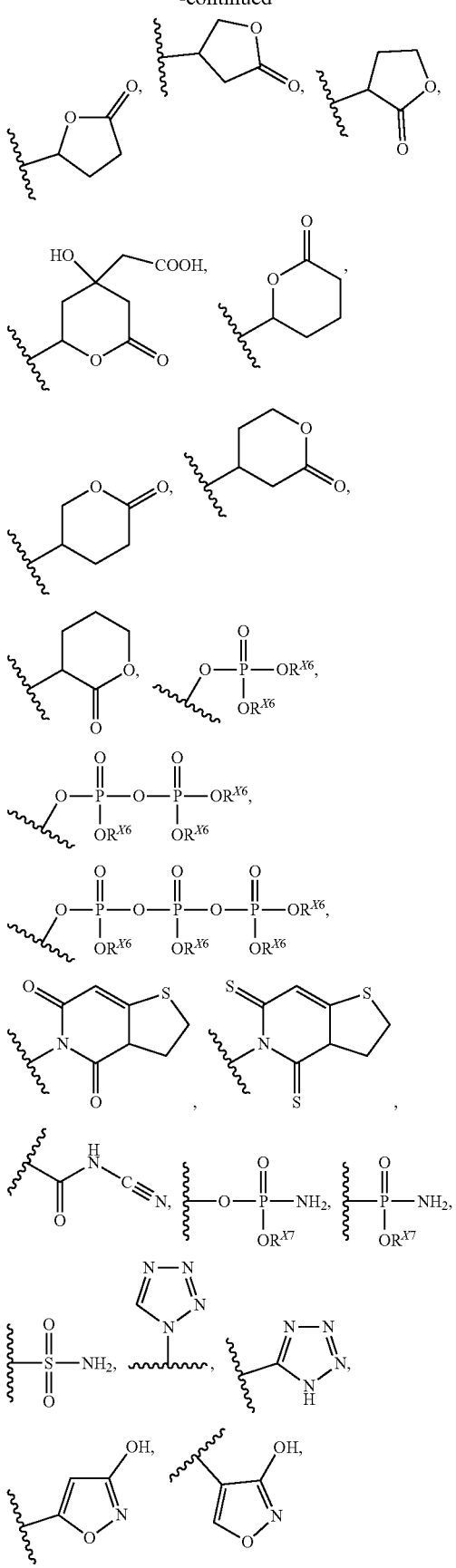

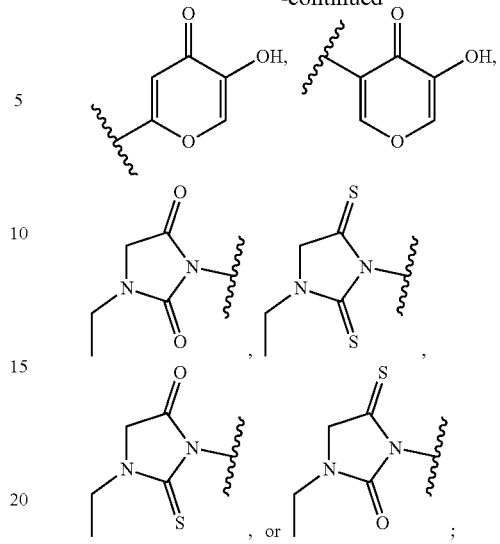

, or each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

149. A compound of Formula (S):

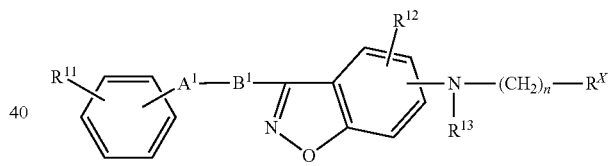

(S)

or a pharmaceutically acceptable salt, solvate, ester, amide, or prodrug thereof, wherein:

$A^1$ is a 5 or 6-membered heterocyclic group which is thiazole, oxazole, pyridine or pyrimidine, or a phenyl group, wherein the 5 or 6-membered heterocyclic group or phenyl group is unsubstituted or substituted with $C_{1-8}$ alkyl or $C_{1-8}$ haloalkyl;

$B^1$ is $C_{2-4}$ alkylene; each of $R^{11}$ and $R^{12}$ is independently H, $C_{1-8}$ alkyl, halogen, or $C_{1-8}$ haloalkyl;

$R^{13}$ is $C_{1-8}$ alkyl or $C_{1-8}$ haloalkyl, optionally wherein the N to which $R^{13}$ is attached is attached to the 6th position of benzisoxazole;

$R^X$ is $CH_2OH$, COH, $COOCH_2CONR^{X4}R^{X5}$, $SO_3H$,

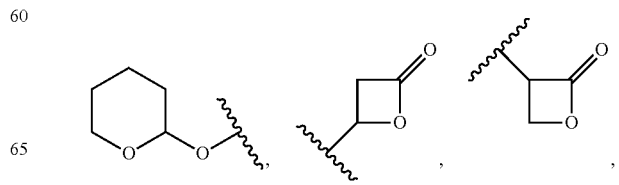

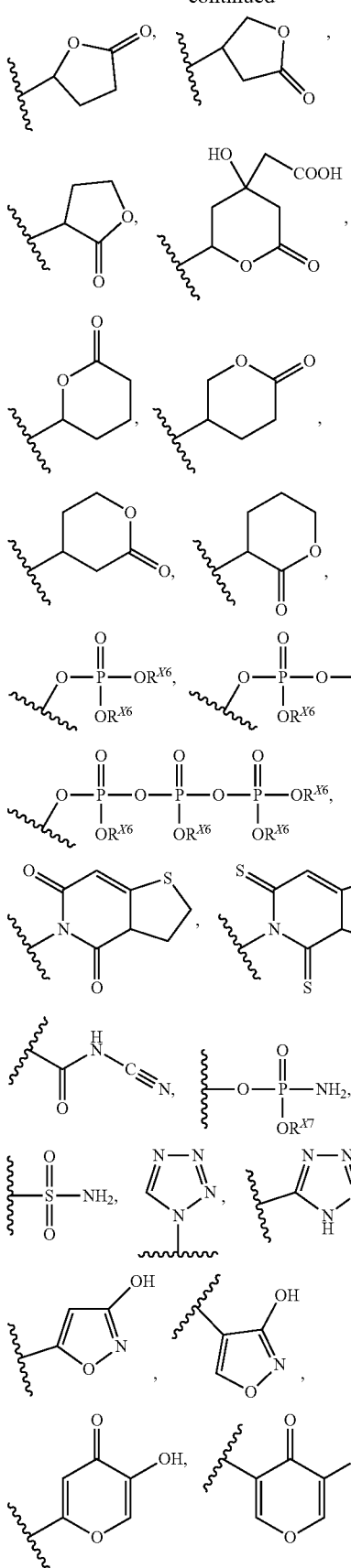

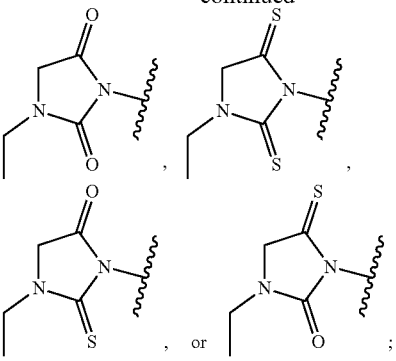

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

150. A compound of Formula (T):

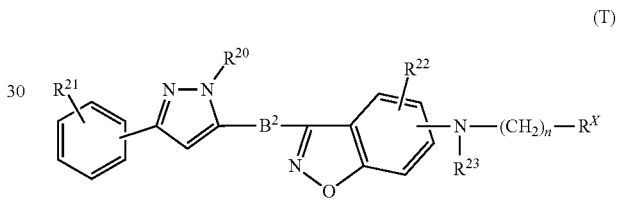

or a pharmaceutically acceptable salt, solvate, ester, amide, or prodrug thereof, wherein:

$B^2$ is $C_{2-4}$ alkylene;

$R^{20}$ is $C_{1-8}$ alkyl;

each of $R^{21}$ and $R^{22}$ is independently H, $C_{1-8}$ alkyl, halogen, or $C_{1-8}$ haloalkyl;

$R^{23}$ is $C_{1-8}$ alkyl or $C_{1-8}$ haloalkyl, optionally wherein the N to which $R^{23}$ is attached is attached to the 6th position of benzisoxazole;

$R^X$ is $CH_2OH$, COH, $COOCH_2CONR^{X4}R^{X5}$, $SO_3H$,

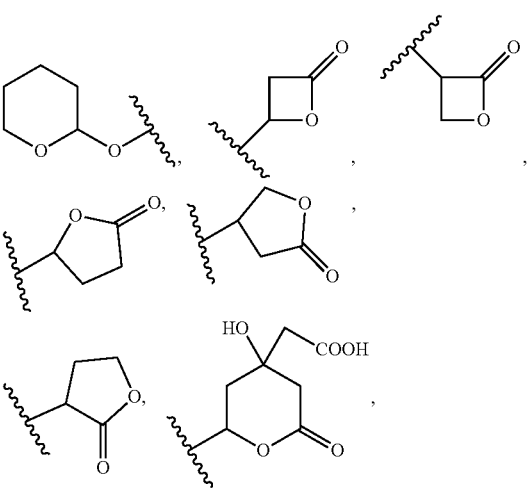

-continued

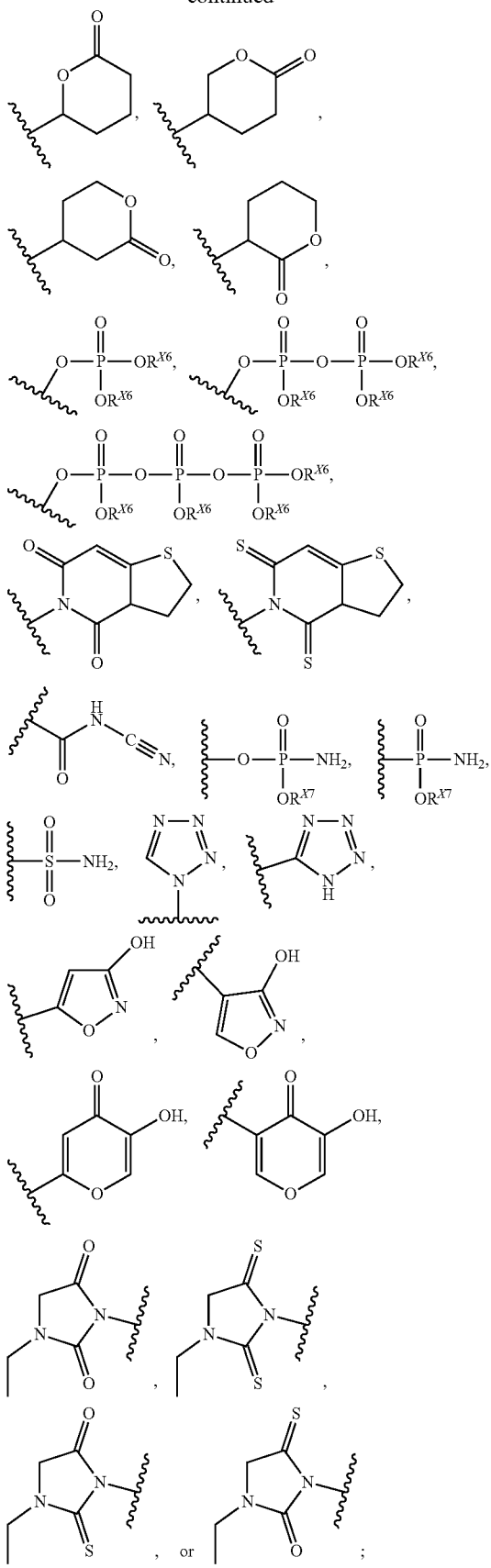

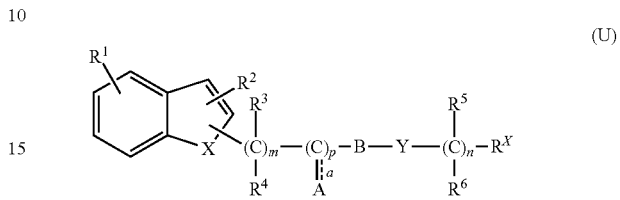

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;
each $R^{X6}$ and $R^{X7}$ is independently H, $C_{1-6}$ alkyl, $C_{2-6}$ alkenyl, or $C_{2-6}$ alkynyl; and
n is 0, 1, 2, 3, or 4.

151. A compound of Formula (U):

(U)

or a pharmaceutically acceptable salt, solvate, ester, amide, or prodrug thereof, wherein:
$R^1$ is hydrogen, halogen, hydroxyl, nitro, amino, cyano, carboxyl, $C_{1-8}$ alkyl, $C_{3-7}$ cycloalkyl, $C_2$-$C_8$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_6$-10 aryl moiety and a $C_{1-8}$ alkylene moiety, or a $C_{1-8}$ alkyl group having a 5- or 6-membered heterocyclic substituent;
$R^2$ is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety;
each of $R^3$, $R^4$, $R^5$ and $R^6$ independently is hydrogen, $C_{1-8}$ alkyl, or $C_{1-8}$ haloalkyl;
X is oxygen, sulfur or $NR^7$; where $R^7$ is hydrogen, $C_{1-8}$ alkyl, $C_{1-8}$ haloalkyl, an aralkyl group having a $C_{6-10}$ aryl moiety and a $C_{1-8}$ alkylene moiety, $C_{2-8}$ acyl, or $C_{2-8}$ alkenyl;
Y is oxygen, sulfur, $NR^8$ or a bond, where $R^8$ is hydrogen, $C_{1-8}$ alkyl, $C_{1-8}$ haloalkyl, $C_{2-8}$ acyl, or $C_{2-8}$ alkenyl;
p is 0 or 1;
A, when bond a is present, is oxygen $CH_2$, N—$NH_2$ or N—$OR^9$, where $R^9$ is hydrogen, $C_{1-8}$ alkyl, $C_{1-8}$ haloalkyl, $C_{2-8}$ acyl, $C_{2-8}$ alkenyl, or an aralkyl group having a $C_{6-10}$ aryl moiety and a $C_{1-8}$ alkylene moiety; A, when bond a is absent, is OH;
B is, in the case of p=1, a benzene ring having or not having a substituent which is halogen, hydroxyl, nitro, amino, $C_{1-8}$ alkyl, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, or an aralkyl group having a $C_{6-10}$ aryl moiety and a $C_1$-$C_8$ alkylene moiety of 1-8 carbon atoms, and, in the case of p=0, a condensed ring which is indole, benzofuran, benzisoxazole or 1,2-benzisothiazole, in which said condensed ring has or does not have a substituent which is
halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_1$-$C_8$ alkoxy substituent, $C_{1-8}$ haloalkoxy group, $C_{2-8}$ acyl, $C_{6-10}$ aryl, or an aralkyl group having a $C_{6-10}$ aryl moiety and a $C_{1-8}$ alkylene moiety;

Y is bonded to the benzene ring of B;

(C($R^3$)($R^4$))$_m$ is bonded to the condensed ring of B at its 3-position;

m is an integer of 1 to 4;

n is 0, 1, 2, 3, 4, or 5;

Y is a bond in the case of n=0;

$R^X$ is $CH_2OH$, COH, $COOCH_2CONR^{X4}R^{X5}$, $SO_3H$,

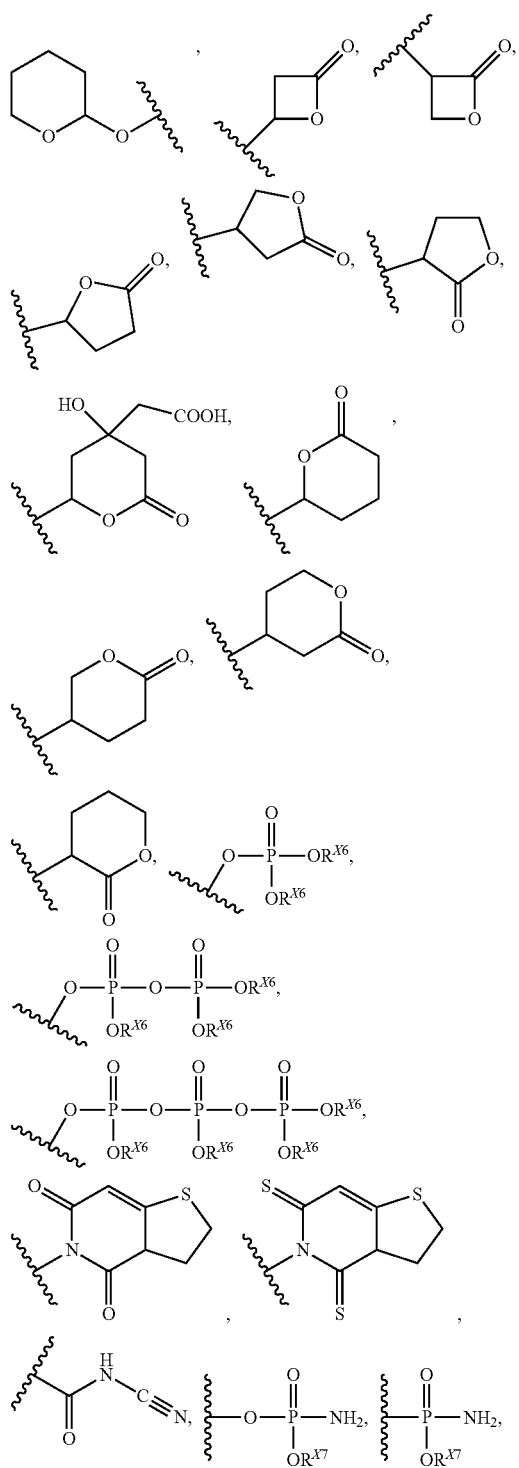

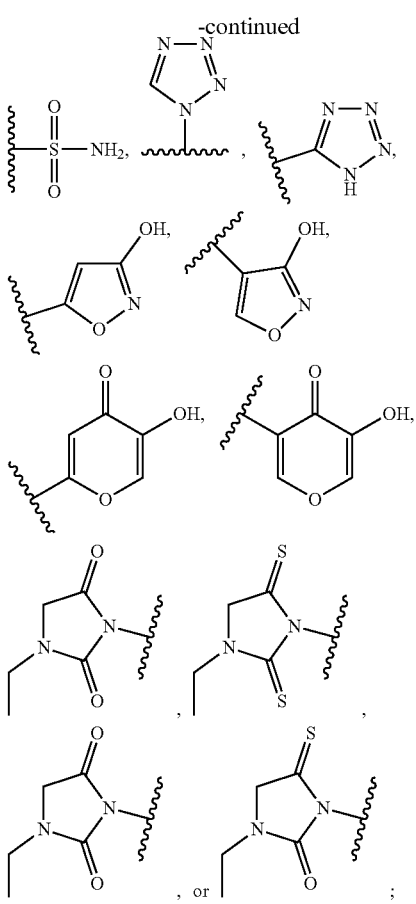

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

152. The compound or pharmaceutically acceptable salt, solvate, ester, amide, or prodrug of the compound of embodiment 151, wherein bond a is absent and A is OH.

153. The compound or pharmaceutically acceptable salt, solvate, ester, amide, or prodrug of the compound of embodiment 151, wherein bond a is present and A is oxygen.

154. A compound of Formula (V):

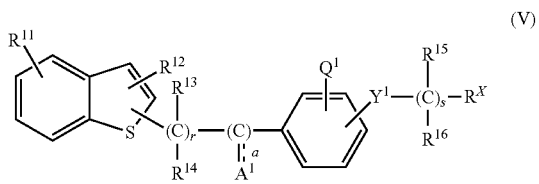

(V)

or a pharmaceutically acceptable salt, solvate, ester, amide, or prodrug thereof, wherein:

$R^{11}$ is hydrogen, halogen, hydroxyl, nitro, amino, cyano, carboxyl, $C_{1-8}$ alkyl, $C_{3-7}$ cycloalkyl, $C_2$-$C_8$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_6$-10 aryl moiety and a $C_{1-8}$ alkylene moiety, or a $C_{1-8}$ alkyl group having a 5- or 6-membered heterocyclic substituent;

$R^{12}$ is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety;

each of $R^{13}$, $R^{14}$, $R^{15}$ and $R^{16}$ independently is hydrogen, $C_{1-8}$ alkyl, or $C_{1-8}$ haloalkyl;

$Y^1$ is oxygen, sulfur, $NR^{18}$ or a bond, where $R^{18}$ is hydrogen, $C_{1-8}$ alkyl, $C_{1-8}$ haloalkyl, $C_{2-8}$ acyl, or $C_{2-8}$ alkenyl;

$A^1$, when bond a is present, is oxygen $CH_2$, N—$NH_2$ or N—$OR^{19}$, where $R^{19}$ is hydrogen, $C_{1-8}$ alkyl, $C_{1-8}$ haloalkyl, $C_{2-8}$ acyl, $C_{2-8}$ alkenyl, or an aralkyl group having a $C_{6-10}$ aryl moiety and a $C_{1-8}$ alkylene moiety; $A^1$, when bond a is absent, is OH;

$Q^1$ is hydrogen, halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl, or an aralkyl group having a $C_{6-10}$ aryl moiety and a $C_{1-8}$ alkylene moiety;

r is 1, 2, 3, or 4;

s is 1, 2, 3, 4, or 5;

$R^X$ is $CH_2OH$ COH $COOCH_2CONR^{X4}R^{X5}$ $SO_3H$

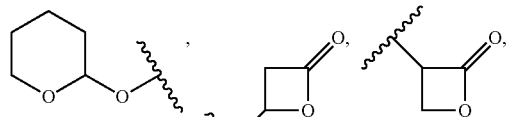

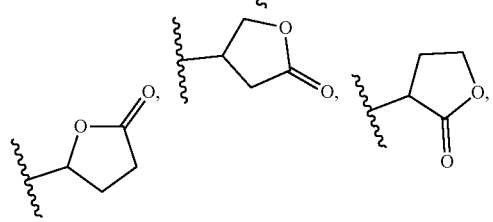

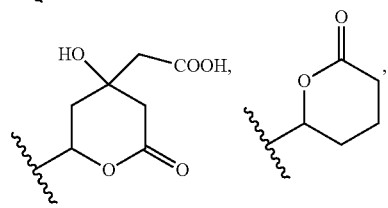

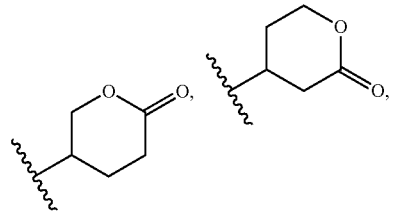

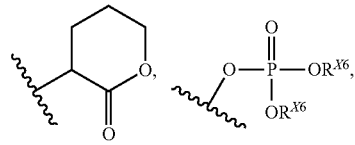

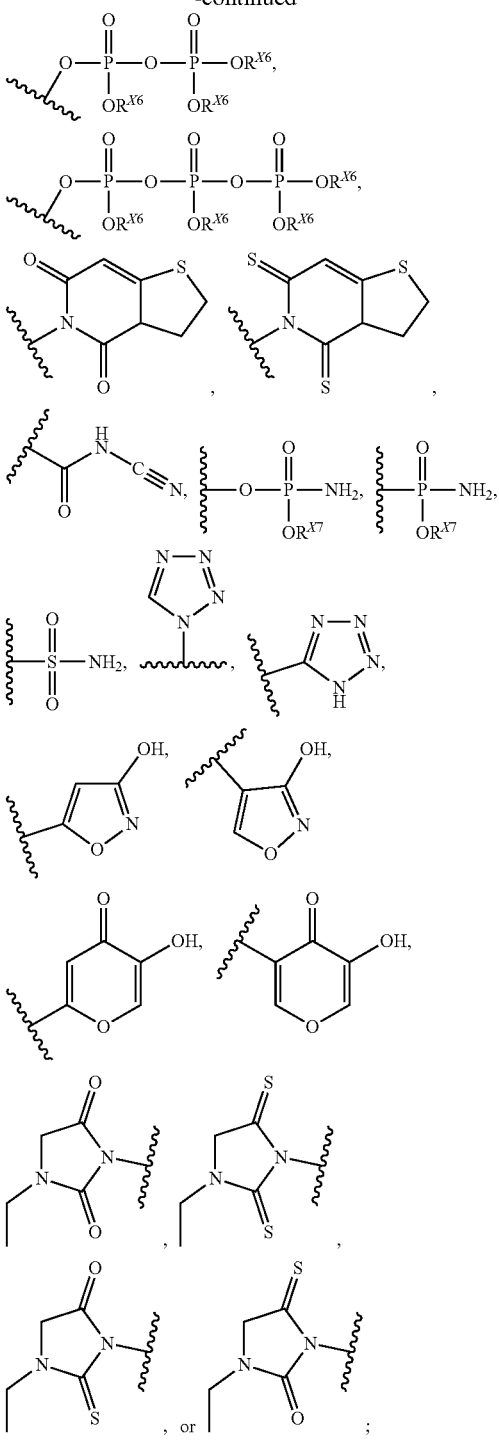

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl.

155. The compound or pharmaceutically acceptable salt, solvate, ester, amide, or prodrug of the compound of embodiment 154, wherein bond a is absent and $A^1$ is OH.

156. The compound or pharmaceutically acceptable salt, solvate, ester, amide, or prodrug of the compound of embodiment 154, wherein bond a is present and $A^1$ is oxygen.

157. A compound of Formula (N):

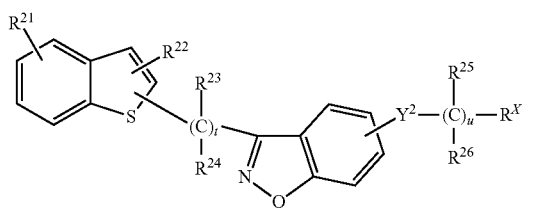

(W)

or a pharmaceutically acceptable salt, solvate, ester, amide, or prodrug thereof, wherein:

$R^{21}$ is hydrogen, halogen, hydroxyl, nitro, amino, cyano, carboxyl, $C_{1-8}$ alkyl, $C_{3-7}$ cycloalkyl, $C_2$-$C_8$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl group, a 5- or 6-membered heterocyclic group, an aralkyl group having a $C_6$-10 aryl moiety and a $C_{1-8}$ alkylene moiety, or a $C_{1-8}$ alkyl group having a 5- or 6-membered heterocyclic substituent;

$R^{22}$ is hydrogen, $C_{1-8}$ alkyl, $C_{2-8}$ alkenyl, $C_{1-8}$ alkyl having a 3- to 7-membered cycloalkyl substituent, $C_{1-8}$ haloalkyl, $C_{1-8}$ alkyl group having a $C_{1-8}$ alkoxy substituent, $C_{2-8}$ acyl, $C_{6-10}$ aryl, or an aralkyl group having a $C_{6-10}$ aryl moiety and a $C_{1-8}$ alkylene moiety;

each of $R^{23}$, $R^{24}$, $R^{25}$ and $R^{26}$ independently is hydrogen, $C_{1-8}$ alkyl, or $C_{1-8}$ haloalkyl;

$Y^2$ is oxygen, sulfur, $NR^{28}$ or a bond, where $R^{28}$ is hydrogen, $C_{1-8}$ alkyl, $C_{1-8}$ haloalkyl, $C_{2-8}$ acyl, or $C_{2-8}$ alkenyl;

$Q^2$ is hydrogen, halogen, hydroxyl, nitro, amino, $C_{1-8}$ alkyl group, $C_{3-7}$ cycloalkyl, $C_{2-8}$ alkenyl, $C_{2-8}$ alkynyl, $C_{1-8}$ alkoxy, $C_{1-8}$ alkyl having a 3- to 7-membered cycloalkyl substituent, $C_{1-8}$ haloalkyl, $C_{1-8}$ alkyl having a $C_{1-8}$ alkoxy substituent, $C_{1-8}$ haloalkoxy, $C_{2-8}$ acyl, $C_{6-10}$ aryl, or an aralkyl group having a $C_{6-10}$ aryl moiety and a $C_{1-8}$ alkylene moiety;

t is 1, 2, 3, or 4;

u is 1, 2, 3, 4, or 5;

$R^X$ is $CH_2OH$ COH $COOCH_2CONR^{X4}R^{X5}$ $SO_3H$,

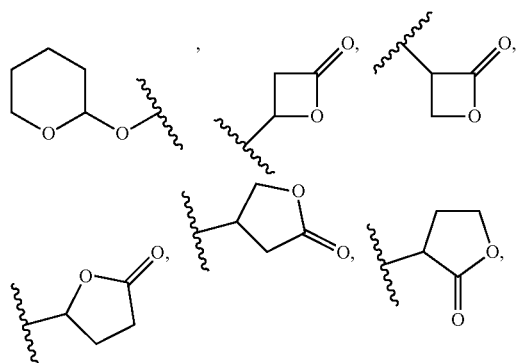

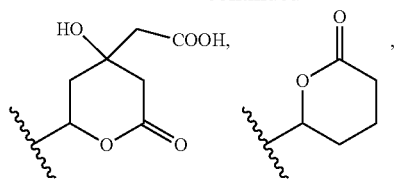

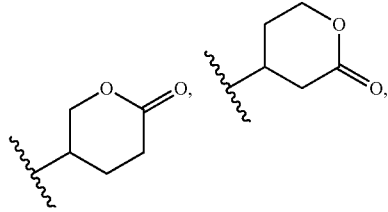

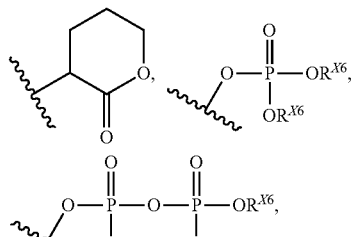

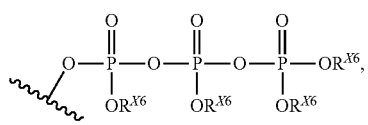

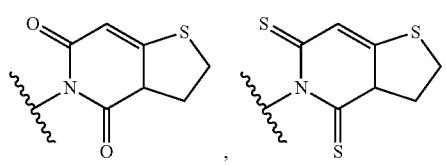

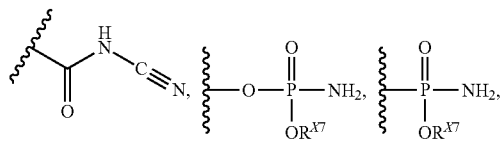

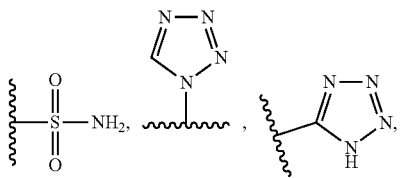

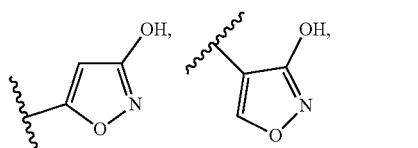

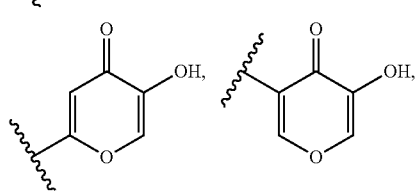

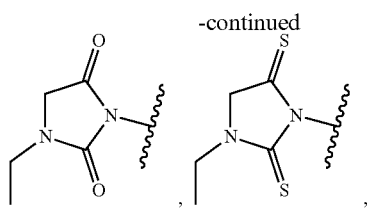, 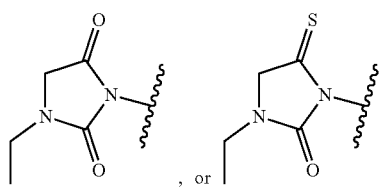

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl.

158. A compound of Formula (X):

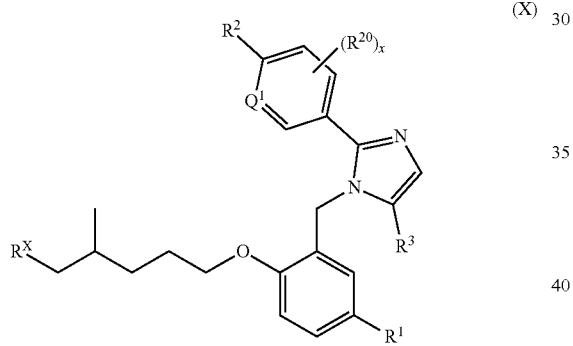

(X)

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, S($C_{1-4}$ alkyl), $SO_2$($C_{1-4}$-alkyl), 5- or 6-membered heterocycle, aryl, 5-membered heteroaryl, C≡C—$R^{2A}$, O($CH_2$)$_m R^{2B}$, NH($C_{1-4}$ alkyl), N($C_{1-4}$ alkyl)$_2$, or C(O)($C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

$R^{2A}$ and $R^{2B}$ are each independently $C_{1-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CD_3$;

$R^X$ is $CH_2OH$, COH, $COOCH_2CONR^{X4}R^{X5}$, $SO_3H$,

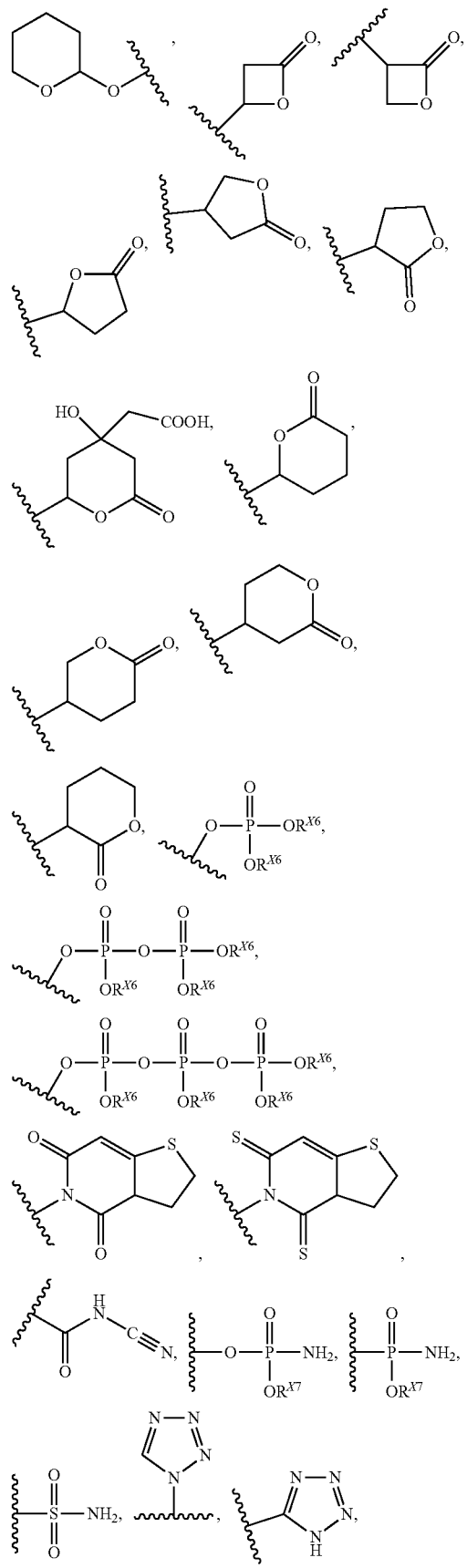

267

-continued

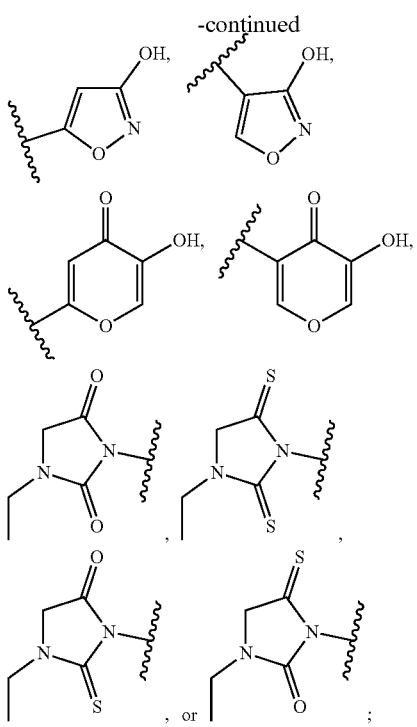

, or ;

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

159. A compound of Formula (Y):

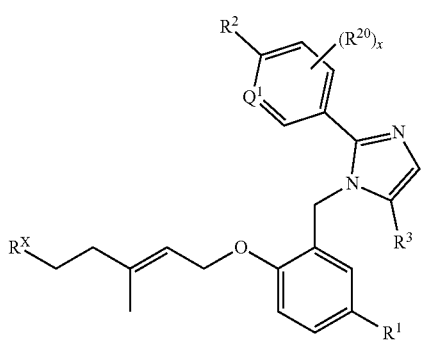

(Y)

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, S($C_{1-4}$ alkyl), $SO_2(C_{1-4}$-alkyl), 5- or 6-membered heterocycle, aryl, 5-membered heteroaryl, C≡C—$R^{2A}$, O(CH$_2$)$_m R^{2B}$, NH($C_{1-4}$ alkyl), N($C_{1-4}$ alkyl)$_2$, or C(O)($C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

268

$R^{2A}$ and $R^{2B}$ are each independently $O1_{-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CD_3$;

$R^X$ is $CH_2OH$, COH, $COOCH_2CONR^{X4}R^{X5}$, $SO_3H$,

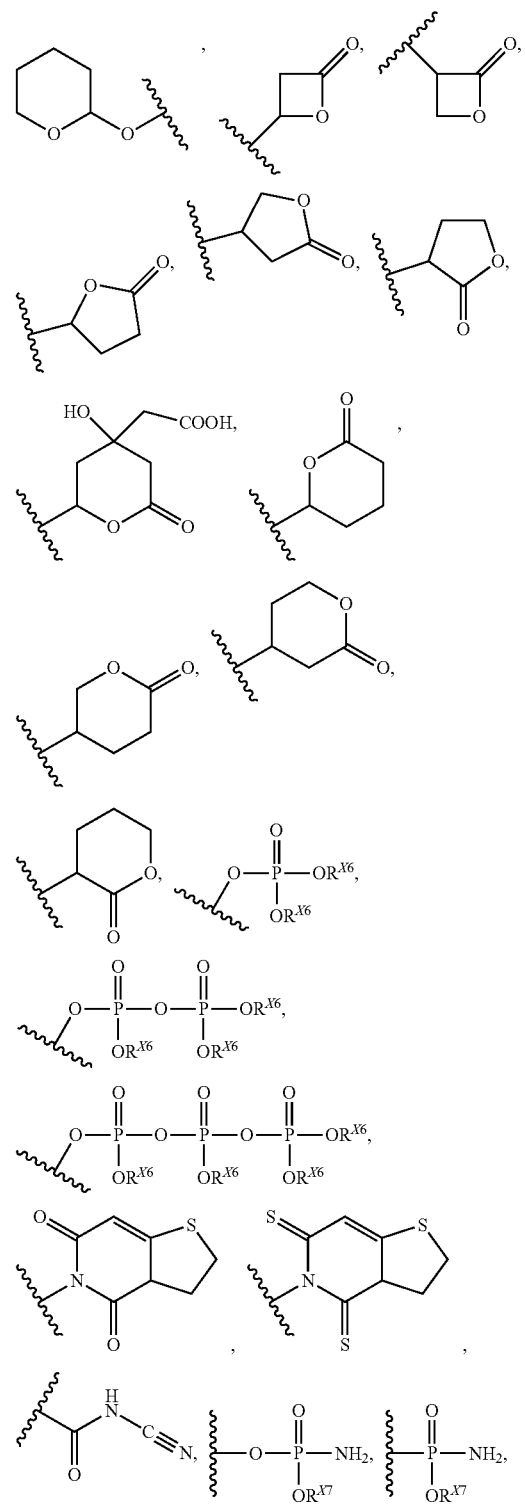

-continued

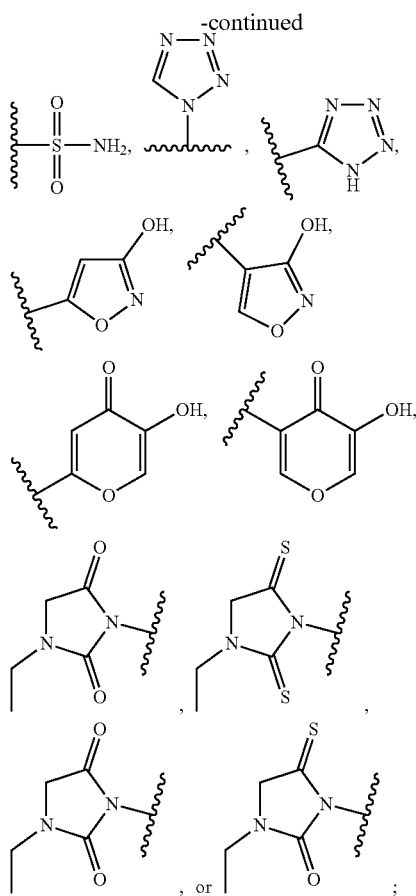

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

160. A compound of Formula (Z):

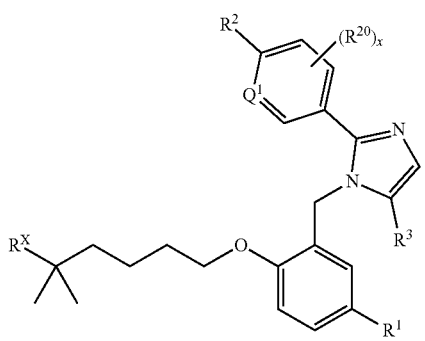

or a pharmaceutically acceptable salt, solvate, ester, amide, or prodrug thereof, wherein:

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

$Q^1$ is CH or N;

$R^2$ is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, $S(C_{1-4}$ alkyl), $SO_2(C_{1-4}$-alkyl), 5- or 6-membered heterocycle, aryl, 5-membered heteroaryl, C≡C—$R^{2A}$, $O(CH_2)_mR^{2B}$, NH($C_{1-4}$ alkyl), N($C_{1-4}$ alkyl)$_2$, or C(O)($C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 1 or 2;

$R^{2A}$ and $R^{2B}$ are each independently $C_{1-4}$ alkyl, $C_{1-4}$ haloalkyl, or $C_{3-6}$ cycloalkyl;

each $R^{20}$ is independently hydrogen, halogen, $C_{1-4}$ alkyl, CN, or $C_{1-4}$ alkoxy;

$R^3$ is $CH_3$ or $CD_3$;

$R^X$ is $CH_2OH$, COH, $COOCH_2CONR^{X4}R^{X5}$, $SO_3H$,

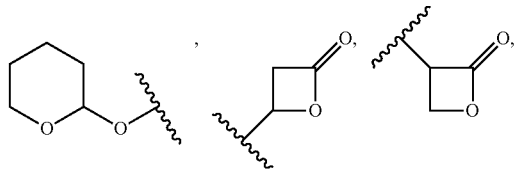

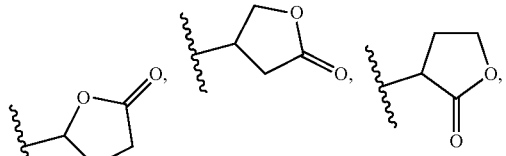

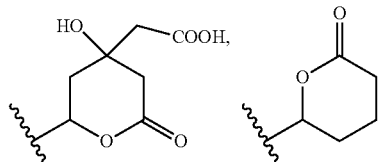

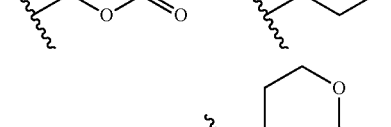

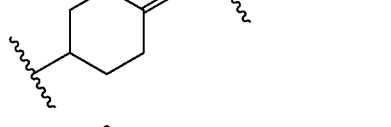

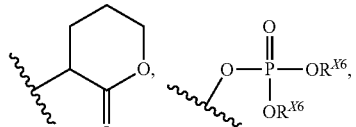

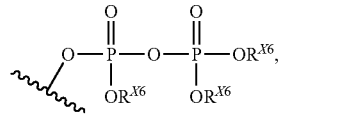

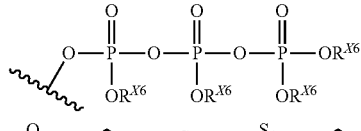

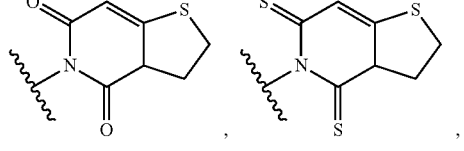

-continued

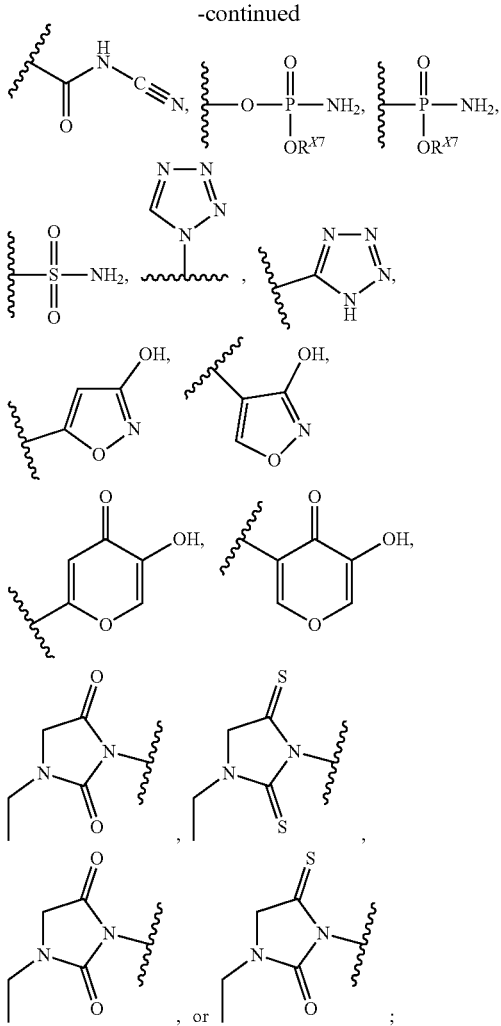

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

161. The compound or pharmaceutically acceptable salt, solvate, ester, amide, or prodrug of the compound of any one of embodiments 158 to 160, wherein $R^3$ is $CH_3$.

162. The compound or pharmaceutically acceptable salt, solvate, ester, amide, or prodrug of the compound of any one of embodiments 158 to 161, wherein $Q^1$ is CH.

163. The compound or pharmaceutically acceptable salt, solvate, ester, amide, or prodrug of the compound of any one of embodiments 158 to 161, wherein $Q^1$ N.

164. The compound or pharmaceutically acceptable salt, solvate, ester, amide, or prodrug of the compound of any one of embodiments 158 to 163, wherein $R^2$ is halogen, —$C_1$-$C_4$-alkyl, —$C_1$-$C_4$-haloalkyl, —$C_1$-$C_4$-haloalkoxy, —S($C_1$-$C_4$-alkyl), or furanyl, wherein the furanyl can be optionally substituted with —$C_1$-$C_4$-alkyl.

165. The compound or pharmaceutically acceptable salt, solvate, ester, amide, or prodrug of the compound of any one of embodiments 158 to 163, wherein $R^2$ is halogen, —$CH_3$, —$C_1$-haloalkyl, —$C_1$-haloalkoxy, —$SCH_3$, or furanyl, wherein the furanyl can be optionally substituted with —$CH_3$.

166. The compound or pharmaceutically acceptable salt, solvate, ester, amide, or prodrug of the compound of any one of embodiments 158 to 163, wherein $R^2$ is halogen, —$CH_3$, —$C_1$-haloalkyl, —$C_1$-haloalkoxy, or —$SCH_3$.

167. The compound or pharmaceutically acceptable salt, solvate, ester, amide, or prodrug of the compound of any one of embodiments 158 to 163, wherein $R^2$ is chloro, unsubstituted furanyl, —$CH_3$, —$CF_3$, —$OCF_3$, —$OCHF_2$, or —$SCH_3$.

168. The compound or pharmaceutically acceptable salt, solvate, ester, amide, or prodrug of the compound of any one of embodiments 158 to 163, wherein $R^2$ is —$CF_3$ or —$OCF_3$.

169. The compound or pharmaceutically acceptable salt, solvate, ester, amide, or prodrug of the compound of any one of embodiments 158 to 163, wherein $R^2$ is —$CF_3$.

170. The compound or pharmaceutically acceptable salt, solvate, ester, amide, or prodrug of the compound of any one of embodiments 158 to 169, wherein $R^1$ is hydrogen or halogen.

171. The compound or pharmaceutically acceptable salt, solvate, ester, amide, or prodrug of the compound of any one of embodiments 158 to 170, wherein $R^1$ is hydrogen or fluoro.

172. The compound or pharmaceutically acceptable salt, solvate, ester, amide, or prodrug of the compound of any one of embodiments 158 to 171, wherein each $R^{20}$ is independently hydrogen or halogen.

173. The compound or pharmaceutically acceptable salt, solvate, ester, amide, or prodrug of the compound of any one of embodiments 158 to 171, wherein $R^{20}$ is hydrogen or fluoro.

174. The compound or pharmaceutically acceptable salt, solvate, ester, amide, or prodrug of the compound of any one of embodiments 158 to 163, wherein $R^1$ is hydrogen or fluoro, $R^2$ is $C_1$-$C_4$-haloalkyl or $C_1$-$C_4$-haloalkoxy, $R^{20}$ is hydrogen, and x is an integer having a value of 1.

175. The compound or pharmaceutically acceptable salt, solvate, ester, amide, or prodrug of the compound of any one of embodiments 158 to 163, wherein $R^1$ is hydrogen, $R^2$ is trifluoro methyl or trifluoromethoxy, $R^{20}$ is hydrogen, and x is an integer having a value of 1.

176. A compound of Formula (AA):

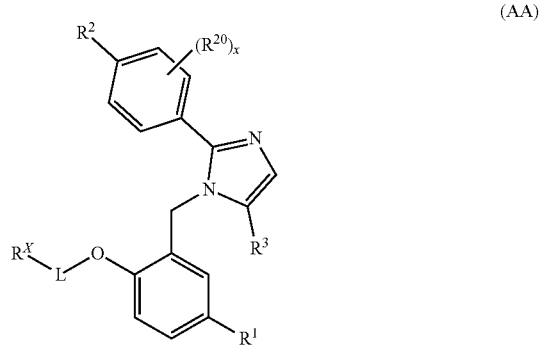

(AA)

or a pharmaceutically acceptable salt, solvate, ester, amide, or prodrug thereof, wherein:

L is $(CH_2)_5$, which is unsubstituted or substituted by one methyl group;

$R^1$ is hydrogen, halogen, $C_{1-4}$ alkyl, $C_{1-4}$ haloalkyl, CN, $C_{1-4}$ alkoxy, $C_{1-4}$ haloalkoxy, or $C_{3-6}$ cycloalkyl;

R² is hydrogen, halogen, CN, $C_{1-4}$ alkyl, $C_{1-4}$ haloalkyl, $C_{3-6}$ cycloalkyl, $C_{1-4}$ alkoxy, $C_{1-4}$ haloalkoxy, S($C_{1-4}$ alkyl), $SO_2$($C_{1-4}$-alkyl), 5- or 6-membered heterocycle, aryl, 5-membered heteroaryl, C≡C—$R^{2A}$, O($CH_2$)$_m$$R^{2B}$, NH($C_{1-4}$ alkyl), N($C_{1-4}$ alkyl)$_2$, or C(O)($C_{1-4}$ alkyl), wherein aryl and heteroaryl are unsubstituted or substituted with halogen, OH, CN, $C_{1-4}$ alkyl, formyl, acetyl, acetoxy, or carboxy, and wherein m is 1, 2, or 3;

x is 0 or 1;

$R^{2A}$ and $R^{2B}$ are each independently $C_{1-4}$ alkyl, $C_{1-4}$ haloalkyl, or $C_{3-6}$ cycloalkyl;

R³ is $C_{1-4}$ haloalkyl, $NO_2$, CN, halogen, or C(O)O($C_{1-4}$ alkyl);

R²⁰ is hydrogen, halogen, $C_{1-4}$ alkyl, CN, or $C_{1-4}$ alkoxy;

$R^X$ is $CH_2OH$, COH, $COOCH_2CONR^{X4}R^{X5}$, $SO_3H$,

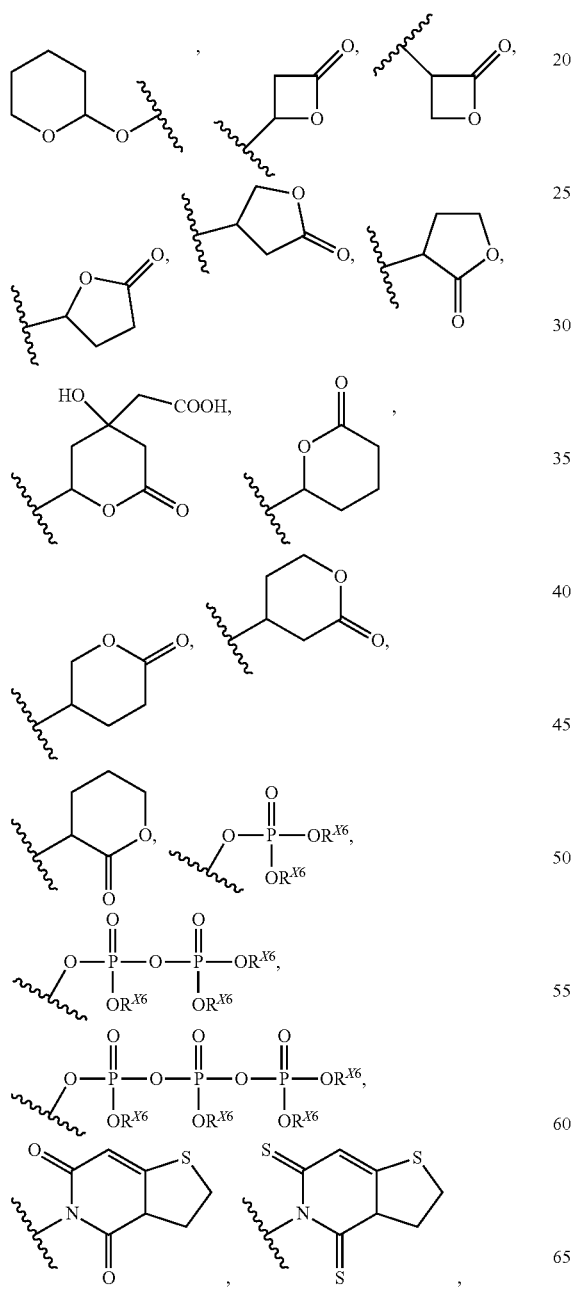

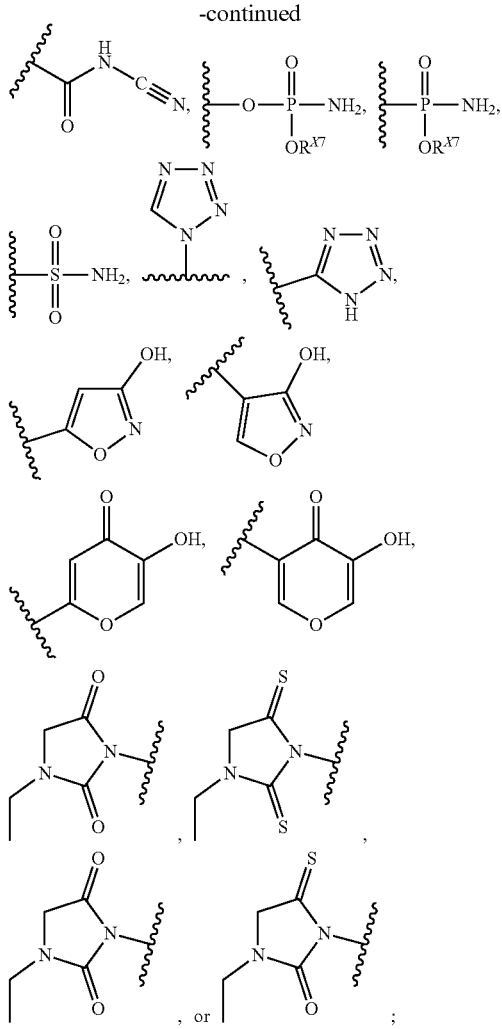

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle; and each $R^{X6}$ and $R^{X7}$ is independently H, $C_{1-6}$ alkyl, $C_{2-6}$ alkenyl, or $C_{2-6}$ alkynyl.

177. The compound or pharmaceutically acceptable salt, solvate, ester, amide, or prodrug of the compound of embodiment 176, which has the formula

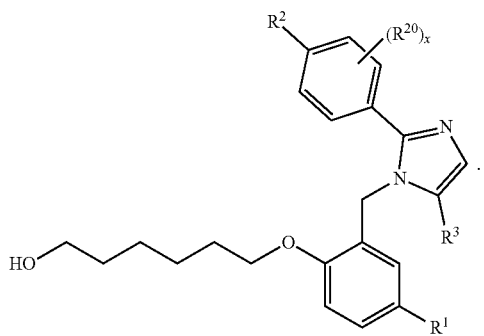

178. The compound or pharmaceutically acceptable salt, solvate, ester, amide, or prodrug of the compound of embodiment 176, which has the formula

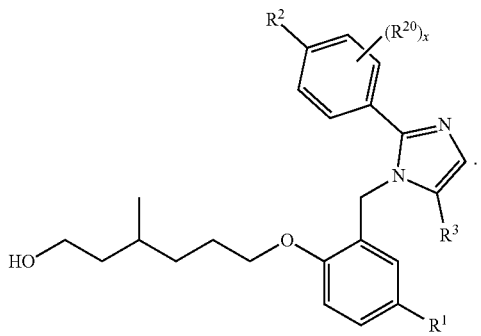

179. The compound or pharmaceutically acceptable salt, solvate, ester, amide, or prodrug of the compound of any one of embodiments 176 to 178, wherein $R^3$ is halomethyl, CN or halogen.

180. The compound or pharmaceutically acceptable salt, solvate, ester, amide, or prodrug of the compound of any one of embodiments 176 to 178, wherein $R^3$ is $CF_3$, $C_1$ or CN.

181. The compound or pharmaceutically acceptable salt, solvate, ester, amide, or prodrug of the compound of any one of embodiments 176 to 180, wherein $R^2$ is hydrogen, halogen, CN, $C_1$-$C_4$-alkyl, $C_1$-$C_4$ alkoxy, $C_1$-$C_4$-haloalkyl, $C_1$-$C_4$-haloalkyl, $S(C_1$-$C_4$-alkyl), or furanyl, wherein the furanyl can be optionally substituted with $C_1$-$C_4$-alkyl; and x is 0 or 1.

182. The compound or pharmaceutically acceptable salt, solvate, ester, amide, or prodrug of the compound of any one of embodiments 176 to 180, wherein $R^2$ is H, halogen, CN, $CH_3$, halomethyl, halomethoxy, methoxy or furanyl, wherein the furanyl can be optionally substituted with $CH_3$; and $R^{20}$ is methyl or halogen.

183. The compound or pharmaceutically acceptable salt, solvate, ester, amide, or prodrug of the compound of any one of embodiments 176 to 180, wherein $R^2$ is H, F, C, CN, $CF_3$, $OCF_3$ or furanyl; and x is 0.

184. The compound or pharmaceutically acceptable salt, solvate, ester, amide, or prodrug of the compound of any one of embodiments 176 to 183, wherein $R^1$ is hydrogen.

185. The compound or pharmaceutically acceptable salt, solvate, ester, amide, or prodrug of the compound of any one of embodiments 176 to 184, wherein $R^1$ is hydrogen or fluoro.

186. The compound or pharmaceutically acceptable salt, solvate, ester, amide, or prodrug of the compound of any one of embodiments 1 to 185, wherein $R^x$ is $CH_2OH$, COH, or $COOCH_2CONR^4R^5$.

187. The compound or pharmaceutically acceptable salt, solvate, ester, amide, or prodrug of the compound of embodiment 186, wherein $R^x$ is $CH_2OH$.

188. The compound or pharmaceutically acceptable salt, solvate, ester, amide, or prodrug of the compound of any one of embodiments 1 to 187, when depending from any one of embodiments 1 to 151, wherein n is 0.

189. The compound or pharmaceutically acceptable salt, solvate, ester, amide, or prodrug of the compound of any one of embodiments 1 to 187, when depending from any one of embodiments 1 to 151, wherein n is 1.

190. The compound or pharmaceutically acceptable salt, solvate, ester, amide, or prodrug of the compound of embodiment 1, which is

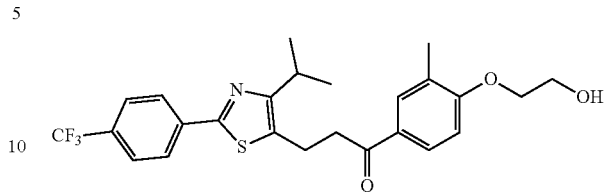

or pharmaceutically acceptable salt, solvate, ester, amide, or prodrug thereof.

191. The compound or pharmaceutically acceptable salt, solvate, ester, amide, prodrug of the compound of embodiment 1, which is

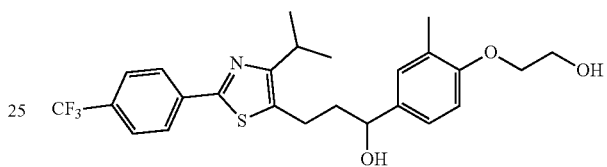

or pharmaceutically acceptable salt, solvate, ester, amide, or prodrug thereof.

192. The compound or pharmaceutically acceptable salt, solvate, ester, amide, or prodrug of the compound of embodiment 1, which is

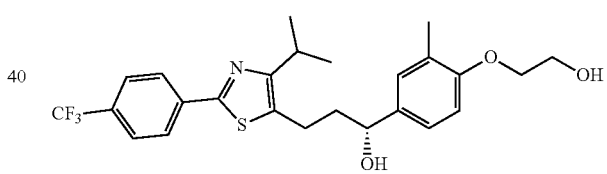

or pharmaceutically acceptable salt, solvate, ester, amide, or prodrug thereof.

193. The compound or pharmaceutically acceptable salt, solvate, ester, amide, or prodrug of the compound of embodiment 1, which is

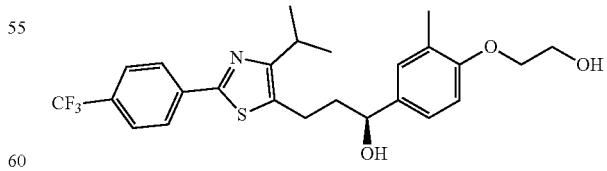

or pharmaceutically acceptable salt, solvate, ester, amide, or prodrug thereof.

194. The compound or pharmaceutically acceptable salt, solvate, ester, amide, or prodrug of the compound of embodiment 158, which is

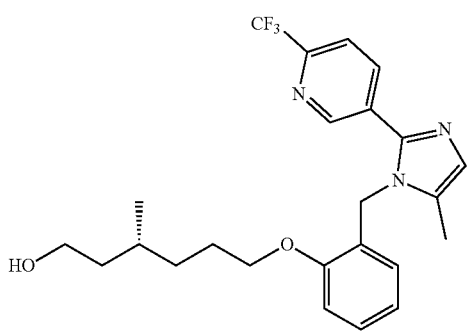 [SMILES: Cc1cnc(-c2ccc(C(F)(F)F)nc2)n1Cc1ccccc1OCCC[C@@H](C)CCO]

or pharmaceutically acceptable salt, solvate, ester, amide, or prodrug thereof.

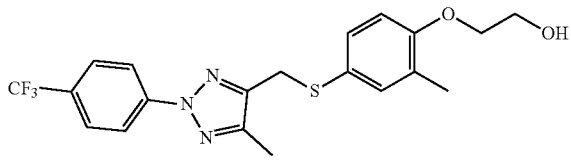 [SMILES: Cc1cc(SCc2nn(-c3ccc(C(F)(F)F)cc3)nc2C)ccc1OCCO]

195. A compound which is N or pharmaceutically acceptable salt, solvate, ester, amide, or prodrug thereof.

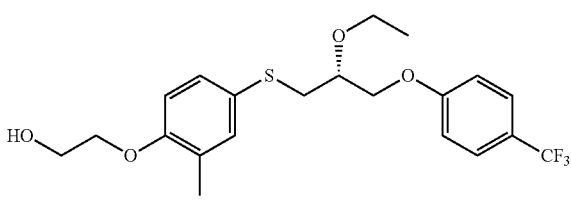 [SMILES: CCO[C@H](COc1ccc(C(F)(F)F)cc1)CSc1ccc(OCCO)c(C)c1]

196. A compound which is or pharmaceutically acceptable salt, solvate, ester, amide, or prodrug thereof.

197. A compound selected from compounds shown in Table 1, or pharmaceutically acceptable salt, solvate, ester, amide, or prodrug thereof.

198. A compound selected from compounds shown in Table 2, or pharmaceutically acceptable salt, solvate, ester, amide, or prodrug thereof.

199. A compound selected from compounds shown in Table 3, or pharmaceutically acceptable salt, solvate, ester, amide, or prodrug thereof.

200. A compound selected from compounds shown in Table 4, or pharmaceutically acceptable salt, solvate, ester, amide, or prodrug thereof.

201. A compound selected from compounds shown in Table 5, or pharmaceutically acceptable salt, solvate, ester, amide, or prodrug thereof.

202. A compound selected from compounds shown in Table 6, or pharmaceutically acceptable salt, solvate, ester, amide, or prodrug thereof.

203. A compound selected from compounds shown in Table 7, or pharmaceutically acceptable salt, solvate, ester, amide, or prodrug thereof.

204. A compound selected from compounds shown in Table 8, or pharmaceutically acceptable salt, solvate, ester, amide, or prodrug thereof.

205. A compound selected from compounds shown in Table 9, or pharmaceutically acceptable salt, solvate, ester, amide, or prodrug thereof.

206. A compound selected from compounds shown in Table 10, or pharmaceutically acceptable salt, solvate, ester, amide, or prodrug thereof 207. A compound selected from compounds shown in Table 11, or pharmaceutically acceptable salt, solvate, ester, amide, or prodrug thereof.

208. The compound or pharmaceutically acceptable salt of the compound of any one of embodiments 1 to 207.

209. The pharmaceutically acceptable salt of the compound of any one of embodiments 1 to 207, which is an alkali metal salt, optionally which is a sodium or a potassium salt.

210. A pharmaceutical composition comprising the compound or pharmaceutically acceptable salt, solvate, ester, amide, or prodrug of the compound of any one of embodiments 1 to 207 and a pharmaceutically acceptable carrier or vehicle.

211. The pharmaceutical composition of embodiment 210, further comprising a second therapeutically active agent.

212. The pharmaceutical composition of embodiment 211, wherein the second therapeutically active agent is a lipid lowering drug, statin, a cholesterol absorption inhibitor, an antibody against PCSK9, an siRNA PCSK9, an anti-fibrotic agent, a thyroid hormone, a selective thyroid receptor-β agonist, apoptosis signal-regulating kinase 1 (ASK1) inhibitor, acetyl-CoA carboxylase (ACC) inhibitor, an integrin antagonist, or a non-steroidal Farnesoid X receptor (FXR) agonist.

213. The pharmaceutical composition of embodiment 212, wherein the lipid lowering drug is gemfibrozil, fenofibrate, bezafibrate, clofibrate, ciprofibrate, clinofibrate, etofylline, pirifibrate, simfibrate, tocofibrate, or pemafibrate; the statin is atorvastatin, simvastatin, pravastatin, rosuvastatin, fluvastatin, lovastatin, pitavastatin, mevastatin, dalvastatin, dihydrocompactin, or cerivastatin, or a pharmaceutically acceptable salt, solvate, ester, amide, or prodrug thereof; the cholesterol absorption inhibitor is ezetimibe; the antibody against PCSK9 is evolocumab alirocumab, bococizumab, 1D05-IgG2, RG7652, LY3015014, or LGT-209; the siRNA PCSK9 is inclisiran; the anti-fibrotic agent is nitazoxamide, tizoxanide, or tizoxanide glucuronide, or a pharmaceutically acceptable salt, solvate, ester, amide, or prodrug thereof; the selective thyroid receptor-β agonist is VK2809, MGL-3196, MGL-3745, SKL-14763, sobetirome, BCT304, ZYT1, MB-0781, or eprotirome; the ASK1 inhibitor is selonsertib; the ACC inhibitor is firsocostat; the integrin antagonist is an α5β1 inhibitor or a pan integrin inhibitor; or the FXR agonist is cilofexor.

214. A method for treating or preventing a liver disorder, dyslipidemia, dyslipoproteinemia, a renal disease, a disorder of glucose metabolism, a disorder of lipid metabolism, a disorder of glucid metabolism, a cardiovascular disease, a vascular disease, a metabolic syndrome, a complication associated with metabolic syndrome, a PPAR-associated disorder, septicemia, a thrombotic disorder, obesity, diabetic nephropathy, diabetic retinopathy, atherosclerosis, pancreatitis, a cerebrovascular disease, a disorder related to neovascularization, hypertension, cancer, inflammation, an inflammatory disease, a neurodegenerative disease, an autoimmune disease, a neoplastic disease, muscle atrophy, cholestasis, mitochondrial dysfunction, an ocular disease, a lysosomal storage disease, a kidney disease, or impotence, comprising administering to a subject in need thereof an effective amount of the compound or the pharmaceutically acceptable salt, solvate, ester, amide, or prodrug of the compound of any one of embodiments 1 to 207.

215. The method of embodiment 214, wherein the liver disorder involves pathological disruption, inflammation, degeneration, apoptosis, or proliferation of liver cells.

216. The method of embodiment 214, wherein the liver disorder is liver fibrosis, fatty liver disease, non-alcoholic fatty liver disease (NAFLD) or non-alcoholic steatohepatitis (NASH).

217. The method of embodiment 214, wherein the dyslipidemia is hyperlipidemia or an abnormally low concentration of high density lipoprotein cholesterol (HDL-C) in the subject's blood plasma or blood serum.

218. The method of embodiment 217, wherein the hyperlipidemia is hypercholesterolemia, familial hypercholesterolemia, hypertriglyceridemia, or familial combined hyperlipidemia.

219. The method of embodiment 217, wherein the hyperlipidemia is characterized by: an abnormally reduced or deficient lipoprotein lipase level or activity in the subject's blood plasma or blood serum, or an abnormally high concentration of ketone bodies, lipoprotein(a) cholesterol (Lp(a)-C), low density lipoprotein (LDL), very low density lipoproteins cholesterol (VLDL-C) or non-esterified fatty acids in the subject's blood plasma or blood serum.

220. The method of embodiment 219, wherein the reduced or deficient lipoprotein lipase level or activity is a result of a mutation in a gene encoding a lipoprotein lipase.

221. The method of embodiment 214, wherein the dyslipoproteinemia is characterized by an abnormally high concentration of LDL, apolipoprotein (a) or VLDL in a subject's blood plasma or blood serum, or an abnormally low concentration of high density lipoprotein (HDL) or lipoprotein lipase in a subject's blood plasma or blood serum.

222. The method of embodiment 221, wherein the abnormally low concentration of the lipoprotein lipase is associated with: a lipoprotein lipase mutation, hypoalphalipoproteinemia, a lipoprotein abnormality associated with diabetes, a lipoprotein abnormality associated with obesity, a lipoprotein abnormality associated with Alzheimer's disease, or familial combined hyperlipidemia.

223. The method of embodiment 214, wherein the renal disease is a glomerular disease, a tubular disease, a tubulointerstitial disease, acute or rapidly progressive renal failure, chronic renal failure, nephrolithiasis, or a tumor.

224. The method of embodiment 223, wherein: the glomerular disease is an acute glomerulonephritis, a chronic glomerulonephritis, a rapidly progressive glomerulonephritis, a nephrotic syndrome, a focal proliferative glomerulonephritis, a glomerular lesion associated with systemic disease, Goodpasture syndrome, multiple myeloma, diabetes, neoplasia, sickle cell disease or a chronic inflammatory disease; the tubular disease is an acute tubular necrosis, an acute renal failure, a polycystic renal disease, medullary sponge kidney, a medullary cystic disease, nephrogenic diabetes, or a renal tubular acidosis; the tubulointerstitial disease is pyelonephritis, a drug- or toxin-induced tubulointerstitial nephritis, a hypercalcemic nephropathy, or a hypokalemic nephropathy; or the tumor is renal cell carcinoma or nephroblastoma.

225. The method of embodiment 224, wherein the glomerular lesion associated with systemic disease is systemic lupus erythematosus.

226. The method of embodiment 214, wherein the renal disease is hypertension, nephrosclerosis, microangiopathic hemolytic anemia, atheroembolic renal disease, diffuse cortical necrosis, or a renal infarct.

227. The method of embodiment 226, wherein the hypertension is an essential hypertension, hyperpiesia, hyperpiersis, a malignant hypertension, a secondary hypertension, or a white-coat hypertension.

228. The method of embodiment 214, wherein the disorder of glucose metabolism is an impaired glucose tolerance; an insulin resistance; an insulin resistance-related breast, colon or prostate cancer; diabetes; pancreatitis; hypertension; polycystic ovarian disease; or an abnormally high concentration of blood insulin or glucose in the subject's blood plasma or blood serum.

229. The method of embodiment 228, wherein the diabetes is non-insulin dependent diabetes mellitus (NIDDM), insulin dependent diabetes mellitus (IDDM), gestational diabetes mellitus (GDM), or maturity onset diabetes of the young (MODY).

230. The method of embodiment 214, wherein the vascular disease or the cardiovascular disease is a peripheral vascular disease, a coronary heart disease, stroke, restenosis, arteriosclerosis, ischemia, an endothelium dysfunction, an ischemia-reperfusion injury, a myocardial infarction, or a cerebral infarction.

231. The method of embodiment 214, wherein the PPAR-associated disorder is rheumatoid arthritis, multiple sclerosis, psoriasis, an inflammatory bowel disease, breast cancer, colon cancer, or prostate cancer.

232. The method of embodiment 214, wherein the PPAR-associated disorder is a vascular disease, a muscular disease, a demyelinating disease, a muscle structure disorder, a neuronal activation disorder, a muscle fatigue disorder, a muscle mass disorder, a mitochondrial disease, a mitochondrial dysfunction, a beta oxidation disease, or a metabolic disease.

233. The method of embodiment 232, wherein: the muscular disease is a muscular dystrophy disease; the demyelinating disease is multiple sclerosis, Charcot-Marie-Tooth disease, Pelizaeus-Merzbacher disease, encephalomyelitis, neuromyelitis optica, adrenoleukodystrophy, or Guillian-Barre syndrome; the muscle structure disorder is Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorder, myotonic chondrodystrophy, myotonic dystrophy, myotubular myopathy, nemaline body disease, oculopharyngeal MD, or stress urinary incontinence; the neuronal activation disorder is amyotrophic lateral sclerosis, Charcot-Marie-Tooth disease, Guillain-Barre syndrome, Lambert-Eaton syndrome, multiple sclerosis, myasthenia gravis, a nerve lesion, peripheral neuropathy, spinal muscular atrophy, tardy ulnar nerve palsy, or toxic myoneural disorder; the muscle fatigue disorder is chronic fatigue syndrome, diabetes (type I or II), a glycogen storage disease, fibromyalgia, Friedreich's ataxia, intermittent claudication, lipid storage myopathy, MELAS (mitochondrial encephalopathy, lactic acidosis, and stroke-like episodes) syndrome, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, muscular atrophy (disuse), sarcopenia, steroid myopathy, or systemic lupus erythematosus; the mitochondrial disease is Alpers's disease, chronic progressive external ophthalmoplegia (CPEO), Kearns-Sayra syndrome (KSS), Leber hereditary optic neuropathy (LHON), MELAS, myoclonic epilepsy and ragged-red fiber disease (MERRF), neurogenic muscle weakness (NARP), ataxia, retinitis pigmentosa, Pearson syndrome, mitochondrial malfunction, or a mitochondrial loss of functionality; the beta oxidation disease is systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, or riboflavin-responsive disorders of β-oxidation (RR-MADD); or the metabolic disease is hyperlipidemia, dyslipidemia, hyperchlolesterolemia, hypertriglyceridemia, HDL hypocholesterolemia, LDL hypercholesterolemia, HLD non-cholesterolemia, VLDL hyperproteinemia, dyslipoproteinemia, apolipoprotein A-1 hypoproteinemia, atherosclerosis, a disease of arterial sclerosis, a disease of cardiovascular system, cerebrovascular disease, peripheral circulatory disease, metabolic syndrome, syndrome X, obesity, diabetes, type I diabetes, type II diabetes, hyperglycemia, insulin resistance, impaired glucose tolerance, hyperinsulinism, a diabetic complication, cardiac insufficiency, cardiac infarction, cardiomyopathy, hypertension, non-alcoholic fatty liver disease (NAFLD), non-alcoholic steatohepatitis (NASH), a thrombus, Alzheimer disease, a neurodegenerative disease, a demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, or pancreatitis.

234. The method of embodiment 233, wherein the muscular dystrophy disease is Duchenne muscular dystrophy, Becker muscular dystrophy, a limb-girdle muscular dystrophy, congenital muscular dystrophy, facioscapulohumeral muscular dystrophy, myotonic muscular dystrophy, oculopharyngeal muscular dystrophy, distal muscular dystrophy, or Emery-Dreifuss muscular dystrophy.

235. The method of embodiment 214, wherein the PPAR-associated disorder is an abnormally low concentration of HDL, an abnormally low concentration of apolipoprotein A-1 (apo A-1), an abnormally high concentration of VLDL-C, an abnormally high concentration of low density lipoprotein cholesterol (LDL-C), an abnormally high concentration of triglyceride, an abnormally high concentration of apolipoprotein B (apo B), an abnormally high concentration of apolipoprotein C-III (apo C-III) or an abnormally reduced ratio of post-heparin hepatic lipase to lipoprotein lipase activity in the subject's blood plasma or blood serum.

236. The method of embodiment 214, wherein the PPAR-associated disorder is an abnormally high concentration of HDL or an abnormally low concentration of apo A-1 in the subject's lymph or cerebral fluid.

237. The method of embodiment 214, wherein the obesity is abdominal obesity.

238. The method of embodiment 214, wherein the cerebrovascular disease is cerebral ischemia.

239. The method of embodiment 214, wherein, the disorder related to neovascularization is retinopathy or diabetes.

240. The method of embodiment 214, wherein the cancer is a human sarcoma or human carcinoma.

241. The method of embodiment 214, wherein the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, bone cancer, breast cancer, ovarian cancer, prostate cancer, esophageal cancer, oral cancer, nasal cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, leukemia, acute lymphoblastic B-cell leukemia, acute lymphoblastic T-cell leukemia, acute promyelocytic leukemia, acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia, hairy cell leukemia, lymphoblastic leukemia, myelogenous leukemia, lymphocyticleukemia, myelocytic leukemia, polycythemia vera, multiple myeloma, lymphoma, Hodgkin's disease, non-Hodgkin's lymphoma, Waldenstrom's macroglobulinemia, or a heavy chain disease.

242. The method of embodiment 241, wherein the leukemia is acute or chronic lymphoblastic leukemia, myelogenous leukemia, lymphocyticleukemia, lymphocytic leukemia, or myelocytic leukemia.

243. The method of embodiment 242, wherein the myelocytic leukemia is acute and is myeloblastic, promyclocytic, myelomonocytic, monocytic or erythroleukemia.

244. The method of embodiment 242, wherein the lymphoma is Hodgkin's lymphoma or non-Hodgkin's lymphoma.

245. The method of embodiment 214, wherein the inflammatory disease is multiple sclerosis, a chronic inflammatory disorder of a joint, arthritis, a respiratory distress syndrome, an inflammatory bowel disease, an inflammatory lung disorder, an inflammatory disorder, an inflammatory disorder of the gum, tuberculosis, leprosy, an inflammatory disease of the kidney, an inflammatory disorder of the skin, an inflammatory disease of the central nervous system, a systemic lupus erythematosus (SLE) or an inflammatory disease of the heart.

246. The method of embodiment 245, wherein: the arthritis is rheumatoid arthritis or osteoarthritis; the inflammatory bowel disease is ileitis, ulcerative colitis or Crohn's disease; the inflammatory lung disorder is asthma or chronic obstructive airway disease; the inflammatory disorder of the eye is corneal dystrophy, trachoma, onchocerciasis, uveitis, sympathic ophthalmitis or endophthalmitis; the inflammatory disorder of the gum is periodontitis or gingivitis; the inflammatory disease of the kidney is glomerulonephritis or nephrosis; the inflammatory disorder of the skin is acne, sclerodermatitis, psoriasis, eczema, photoaging or wrinkles; the inflammatory disease of the central nervous system is AIDS-related neurodegeneration, stroke, neurotrauma, Alzheimer's disease, encephalomyelitis, or viral or autoimmune encephalitis; or the inflammatory disease of the heart is cardiomyopathy.

247. The method of embodiment 214, wherein the neurodegenerative disease is Alzheimer's disease or Huntington's disease.

248. The method of embodiment 214, wherein the autoimmune disease is immune-complex vasculitis, systemic lupus or erythematodes.

249. The method of embodiment 214, wherein, the neoplastic disease is carcinogenesis.

250. The method of embodiment 214, wherein the cholestasis is intrahepatic cholestatic disease or extrahepatic cholestatic disease.

251. The method of embodiment 250, wherein intrahepatic cholestatic disease is primary biliary cholangitis (PBC), primary sclerosing cholangitis (PSC), progressive familial intrahepatic cholestasis (PFIC), or Alagille syndrome (AS).

252. The method of embodiment 214, wherein the ocular disease is dry eye, meibomian gland dysfunction, a keratoconjunctiva epithelial disorder, a corneal epithelial disorder, or a corneal ulcer.

253. The method of embodiment 214, wherein the lysosomal storage disorder is neuronal ceroid lipofuscinosis, Alzheimer's disease, Huntington's disease, amyotrophic lateral sclerosis (ALS), Parkinson's disease, multiple system atrophy (MSA), progressive supranuclear palsy (PSP), corticobasal degeneration (CBD), dementia with Lewy bodies (DLB), a disorder of the autophagy pathway, Tay-Sach's disease, Fabry disease, Niemann-Pick disease, Gaucher disease, Hunter syndrome, alpha-mannosidosis, aspartylglucosaminuria, cholesteryl ester storage disease, chronic hexosaminidase A deficiency, cystinosis, Danon disease, Farber disease, fucosidosis, galactosialidosis, or Batten disease.

254. The method of embodiment 214, wherein the kidney disease is renal ischemia reperfusion injury.

255. The method of embodiment 214, wherein the impotence results from damages to a nerve, artery, a smooth muscle, or fibrous tissue; diabetes; kidney disease; alcoholism; multiple sclerosis; atherosclerosis; vascular disease; or neurologic disease.

256. A method for treating or preventing hyperlipemia, hyperlipidemia, hyperlipoproteinemia, hypercholesterolemia, hypertriglyceridemia, or dyslipidemia, comprising administering to a subject in need thereof an effective amount of the compound or the pharmaceutically acceptable salt, solvate, ester, amide, or prodrug of the compound of any one of embodiments 1 to 207.

257. The method of embodiment 256, wherein the hypercholesterolemia is homozygous familial hypercholesterolemia.

258. A method for treating a subject having or preventing a subject from having an abnormally high concentration in a subject's blood plasma or blood serum of high low-density lipoprotein (LDL), apolipoprotein B (apo B), lipoprotein(a) (Lp(a)), apolipoprotein (a), or very low-density lipoprotein (VLDL), comprising administering to a subject in need thereof an effective amount of the compound or the pharmaceutically acceptable salt, solvate, ester, amide, or prodrug of the compound of any one of embodiments 1 to 207.

259. A method for treating a subject having or preventing a subject from having an abnormally low concentration in a subject's blood plasma or blood serum of high-density lipoprotein (HDL), comprising administering to a subject in need thereof an effective amount of the compound or the pharmaceutically acceptable salt, solvate, ester, amide, or prodrug of the compound of any one of embodiments 1 to 207.

260. A method for treating a subject having or preventing a subject from having an abnormally reduced or deficient lipoprotein lipase concentration or activity in a subject's blood plasma or blood serum, comprising administering to a subject in need thereof an effective amount of the compound or the pharmaceutically acceptable salt, solvate, ester, amide, or prodrug of the compound of any one of embodiments 1 to 207.

261. The method of embodiment 260, wherein the reduced or deficient lipoprotein lipase level or activity is a result of a mutation in a gene encoding a lipoprotein lipase.

262. A method for treating or preventing hypoalphalipoproteinemia, a lipoprotein abnormality associated with diabetes, a lipoprotein abnormality associated with obesity, a lipoprotein abnormality associated with Alzheimer's Disease, or familial combined hyperlipidemia, comprising administering to a subject in need thereof an effective amount of the compound or the pharmaceutically acceptable salt, solvate, ester, amide, or prodrug of the compound of any one of embodiments 1 to 207.

263. A method for reducing in a subject's blood plasma or blood serum an abnormally high concentration of triglyceride, low-density lipoprotein cholesterol (LDL-C), very low-density lipoprotein cholesterol (VLDL-C), non-high-density lipoprotein cholesterol, (non-HDL-C), lipoprotein(a) (Lp(a)), apolipoprotein B, HDL/(VLDL+LDL) ratio, apolipoprotein C-II or apolipoprotein C-III, comprising administering to a subject in need thereof an effective amount of the compound or the pharmaceutically acceptable salt, solvate, ester, amide, or prodrug of the compound of any one of embodiments 1 to 207.

264. A method for elevating in a subject's blood plasma or blood serum an abnormally low concentration of a high-density lipoprotein (HDL)-associated protein, HDL-cholesterol, apolipoprotein A-1, or apolipoprotein E, comprising administering to a subject in need thereof an effective amount of the compound or the pharmaceutically acceptable salt, solvate, ester, amide, or prodrug of the compound of any one of embodiments 1 to 207.

265. The method of embodiment 264, wherein the HDL-associated protein is apolipoprotein A-1 (apo A-1), apolipoprotein A-II (apo A-II), apolipoprotein A-IV (apo A-IV) or apolipoprotein E (apo E).

266. A method for promoting clearance of triglyceride from a subject's blood plasma or blood serum, comprising administering to a subject in need thereof an effective amount of the compound or the pharmaceutically acceptable salt, solvate, ester, amide, or prodrug of the compound of any one of embodiments 1 to 207.

267. A method for increasing abnormally low glucose metabolism or lipid metabolism in a subject, comprising administering to a subject in need thereof an effective amount of the compound or the pharmaceutically acceptable salt, solvate, ester, amide, or prodrug of the compound of any one of embodiments 1 to 207.

268. The method of embodiment 267, wherein the method for increasing abnormally low glucose metabolism increases insulin sensitivity or oxygen consumption of a subject or decreases blood insulin, blood glucose, or glycated hemoglobin in a subject's blood plasma or blood serum.

269. The method of embodiment 267, wherein the method for increasing abnormally low lipid metabolism reduces a concentration of LDL or free triglyceride in a subject's blood plasma or blood serum, or inhibits saponified or non-saponified fatty acid synthesis.

270. A method for treating or preventing a symptom of a disease selected from inflammation, systemic lupus erythematosus, lupus nephritis, or arthritis, comprising administering to a subject in need thereof an effective amount of the compound or the pharmaceutically acceptable salt, solvate, ester, amide, or prodrug of the compound of any one of embodiments 1 to 207.

271. The method of embodiment 270, wherein the arthritis is adjuvant arthritis or type II collagen-induced arthritis.

272. The method of embodiment 270, wherein the symptom is nephritis, kidney failure, or kidney function reduction.

273. A method for reducing the fat content of meat in livestock, comprising administering to livestock an effective amount of the compound or the pharmaceutically acceptable salt, solvate, ester, amide, or prodrug of the compound of any one of embodiments 1 to 207.

274. A method for reducing cholesterol content of a fowl egg, comprising administering to a fowl species an effective amount of the compound or the pharmaceutically acceptable salt, solvate, ester, amide, or prodrug of the compound of any one of embodiments 1 to 207.

275. A method for treating a subject with acute kidney injury (AKI) or at risk for AKI, comprising administering to the subject (i) an effective amount of the compound or the pharmaceutically acceptable salt, solvate, ester, amide, or prodrug of the compound of any one of embodiments 1 to 207 or (ii) the pharmaceutical composition of embodiment 210 or embodiment 211.

276. The method of embodiment 275, wherein the (i) compound or the pharmaceutically acceptable salt, solvate, ester, amide, or prodrug of the compound or (ii) pharmaceutical composition is administered intravenously, optionally wherein the method comprises once daily intravenous administration, optionally for three days.

277. The method of embodiment 275, wherein the (i) compound or the pharmaceutically acceptable salt, solvate, ester, amide, or prodrug of the compound or (ii) pharmaceutical composition is administered orally.

278. The method of any one of embodiments 275 to 277, wherein the AKI is sepsis-related AKI.

279. The method of any one of embodiments 275 to 277, wherein the AKI is ischemia/reperfusion AKI.

280. The method of any one of embodiments 275 to 277, wherein the AKI is from acute interstitial nephritis.

281. The method of any one of embodiments 275 to 277, wherein the AKI is from glomerular renal disease.

282. The method of any one of embodiments 275 to 277, wherein the AKI is from acute vasculitic renal disease.

283. The method of any one of embodiments 275 to 277, wherein the AKI is from ischemia.

284. The method of any one of embodiments 275 to 277, wherein the AKI is from toxic injury.

285. The method of any one of embodiments 275 to 277, wherein the AKI is from prerenal azotemia.

286. The method of any one of embodiments 275 to 277, wherein the AKI is from acute postrenal destructive nephropathy.

287. The method of any one of embodiments 275 to 277, wherein the AKI is from diabetes.

288. The method of any one of embodiments 275 to 277, wherein the AKI is from underlying renal insufficiency.

289. The method of any one of embodiments 275 to 277, wherein the AKI is from nephritic syndrome.

290. The method of any one of embodiments 275 to 277, wherein the AKI is from atherosclerotic disease.

291. The method of any one of embodiments 275 to 277, wherein the AKI is from hypotension.

292. The method of any one of embodiments 275 to 277, wherein the AKI is from hypoxia.

293. The method of any one of embodiments 275 to 277, wherein the AKI is from myoglobinuria-hematuria.

294. The method of any one of embodiments 275 to 277, wherein the AKI is from liver disease.

295. The method of any one of embodiments 275 to 277, wherein the AKI is secondary to a viral infection, optionally wherein the viral infection is COVID-19.

296. The method of embodiment 295, wherein the subject has a viral infection, optionally wherein the viral infection is COVID-19.

297. The method of 275 to 278, wherein the subject has sepsis.

298. The method of embodiment 296, wherein the sepsis is associated with a gram-negative bacterial infection.

299. The method of embodiment 297 or embodiment 298, wherein the subject has an intra-abdominal cavity infection.

300. The method of embodiment 297 or embodiment 298, wherein the subject has urosepsis.

301. The method of any one of embodiments 275 to 300, wherein the subject is elderly.

302. The method of any one of embodiments 275 to 301, wherein the subject is a surgical patient.

303. The method of embodiment 302, wherein the surgical patient has had a cardiovascular surgery, optionally which is a coronary artery bypass graft (CABG) surgery and/or heart valve surgery.

304. The method of any one of embodiments 275 to 300, wherein the subject is pregnant.

305. The method of any one of embodiments 275 to 304, wherein the subject has been exposed to a nephrotoxic agent.

306. The method of embodiment 305, wherein the nephrotoxic agent comprises cisplatin, gentamicin, cephaloridine, cyclosporine, amphotericin, carbon tetrachloride, trichloroethylene, dichloroacetylene, or a combination thereof.

307. The method of any one of embodiments 275 to 306, wherein the subject has AKI.

308. The method of embodiment 307, wherein the effective amount is effective to reduce the severity of the AKI.

309. The method of any one of embodiments 275 to 306, wherein the subject is at risk for AKI.

310. The method of any one of embodiments 275 to 306, wherein the subject is at risk for AKI following a cardiovascular surgery, optionally which is a coronary artery bypass graft (CABG) surgery and/or heart valve surgery.

311. The method of embodiment 309 or embodiment 310, wherein the effective amount is effective to reduce the likelihood that the subject will develop AKI.

312. The method of any one of embodiments 309 to 311, wherein the effective amount is effective to delay the onset of AKI.

313. The method of any one of embodiments 309 to 311, wherein the effective amount is effective to prevent AKI.

314. The method of any one of embodiments 309 to 311, wherein if the subject develops AKI, the effective amount is effective to reduce the severity of the AKI.

315. The method of any one of embodiments 275 to 314, wherein the subject has a SOFA score of 1 to 4 prior to administration of the compound or the pharmaceutically acceptable salt, solvate, ester, amide or prodrug of the compound or the pharmaceutical composition.

316. The method of embodiment 315, wherein the subject has a SOFA score of 2 to 4 prior to administration.

317. The method of embodiment 315, wherein the subject has a SOFA score of 1 prior to administration.

318. The method of embodiment 315, wherein the subject has a SOFA score of 2 prior to administration.

319. The method of embodiment 315, wherein the subject has a SOFA score of 3 prior to administration.

320. The method of embodiment 315, wherein the subject has a SOFA score of 4 prior to administration.

321. The method of any one of embodiments 275 to 320, wherein the subject has an endotoxin activity level of >0.6 prior to administration.

322. The method of any one of embodiments 275 to 321, wherein the effective amount is effective to reduce the subject's endotoxin activity level.

8. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there are any inconsistencies between the teachings of one or more of the references incorporated herein and the present disclosure, the teachings of the present specification are intended.

What is claimed is:

1. A compound of Formula (C):

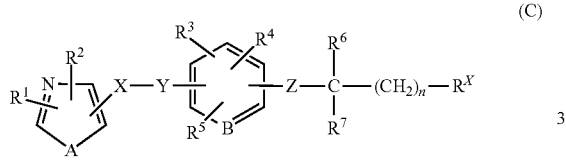

or a pharmaceutically acceptable salt, solvate, ester, amide, or prodrug thereof, wherein:

$R^1$ is phenyl, naphthyl, pyridyl, thienyl, furyl, quinolyl or benzothienyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

$R^2$ is $C_{2-8}$ alkyl, $C_{1-8}$ haloalkyl, $C_{2-8}$ alkenyl, $C_{2-8}$ alkynyl, 3-7 membered cycloalkyl, $C_{1-8}$ alkyl substituted with a 3-7 membered cycloalkyl, or $C_{1-6}$ alkyl substituted with phenyl, naphthyl or pyridyl, any of which is unsubstituted or substituted with $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl or pyridyl;

A is oxygen, sulfur or $NR^9$ in which $R^9$ is hydrogen or $C_{1-8}$ alkyl;

X is a $C_{1-8}$ alkylene chain which is unsubstituted or substituted with $C_{1-8}$ alkyl, $C_{1-8}$ alkoxy or hydroxyl, and which has 0 or 1 double bonds;

Y is C(=O), C(=N—$OR^{10}$), CH($OR^{11}$), CH=CH, C≡C, or C(=$CH_2$) in which each of $R^{10}$ and $R^{11}$ is hydrogen or $C_{1-8}$ alkyl;

each of $R^3$, $R^4$ and $R^5$ is independently hydrogen, $C_{1-8}$ alkyl, $C_{1-8}$ haloalkyl, $C_{1-8}$ alkoxy, $C_{1-8}$ haloalkoxy, $C_{2-8}$ alkenyl, $C_{2-8}$ alkynyl, halogen, $C_{2-7}$ acyl, benzoyl, hydroxyl, nitro, amino, phenyl, or pyridyl; optionally wherein at least one of $R^3$, $R^4$, and $R^5$ is not hydrogen;

B is CH or nitrogen;

Z is oxygen or sulfur;

each of $R^6$ and $R^7$ is independently hydrogen, $C_{1-8}$ alkyl, or $C_{1-8}$ haloalkyl;

$R^X$ is $CH_2OH$, COH, $COOCH_2CONR^{X4}R^{X5}$, $SO_3H$,

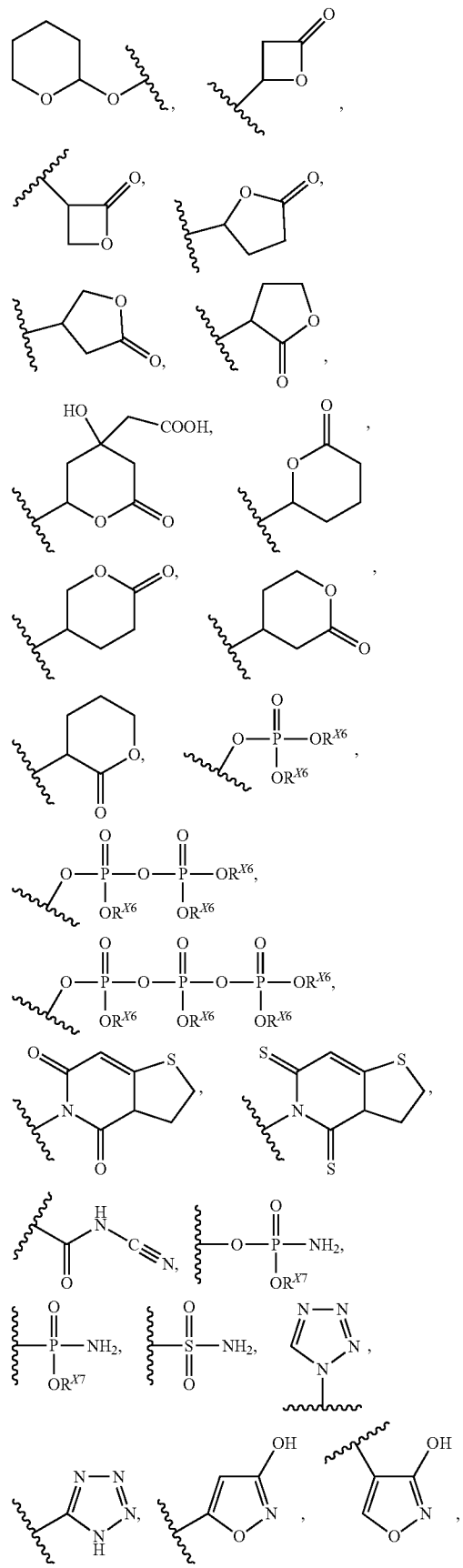

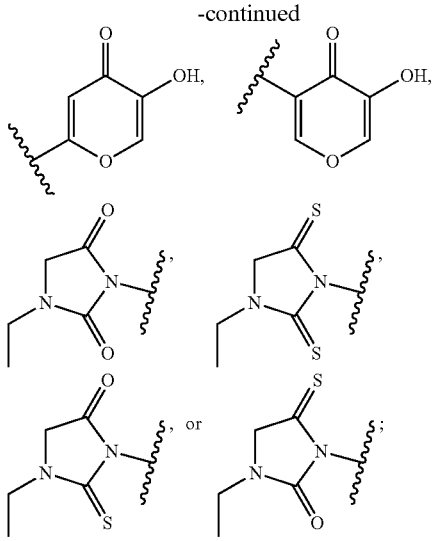

each $R^{X4}$ and $R^{X5}$ is independently alkyl, aryl, or heteroaryl; or alternatively, $R^{X4}$ and $R^{X5}$ together with the carbon atom to which $R^{X4}$ and $R^{X5}$ are attached form a heterocycle;

each $R^{X6}$ and $R^{X7}$ is independently H, $C_{1-6}$ alkyl, $C_{2-6}$ alkenyl, or $C_{2-6}$ alkynyl; and n is 0, 1, 2, 3, or 4.

2. The compound or claim 1, or a pharmaceutically acceptable salt, solvate, ester, amide, or prodrug thereof, wherein $R^1$ is phenyl which is unsubstituted or substituted with one or more substituents selected from the group consisting of $C_{1-8}$ alkyl, $C_{1-8}$ alkyl having 1-3 halogen atoms, $C_{1-8}$ alkoxy, $C_{1-8}$ alkoxy having 1-3 halogen atoms, $C_{2-8}$ alkenyl, $C_{2-8}$ alkynyl, halogen, $C_{2-7}$ acyl, benzoyl, hydroxyl, nitro, amino, phenyl and pyridyl.

3. The compound or claim 1, or a pharmaceutically acceptable salt, solvate, ester, amide, or prodrug thereof, wherein $R^1$ is phenyl substituted with $CF_3$.

4. The compound or claim 1, or a pharmaceutically acceptable salt, solvate, ester, amide, or prodrug thereof, wherein $R^2$ is $C_{2-8}$ alkyl.

5. The compound or claim 1, or a pharmaceutically acceptable salt, solvate, ester, amide, or prodrug thereof, wherein $R^2$ is isopropyl.

6. The compound or claim 1, or a pharmaceutically acceptable salt, solvate, ester, amide, or prodrug thereof, wherein $R^1$ is attached to the 2nd position, and (i) $R^4$ is attached to the 4th position and —X—Y— is attached to the 5th position, or (ii) $R^4$ is attached to the 5th position and —X—Y— is attached to the 4th position.

7. The compound or claim 1, or a pharmaceutically acceptable salt, solvate, ester, amide, or prodrug thereof, wherein A is oxygen or sulfur.

8. The compound or claim 1, or a pharmaceutically acceptable salt, solvate, ester, amide, or prodrug thereof, wherein X is a $C_{1-8}$ alkylene chain.

9. The compound or claim 1, or a pharmaceutically acceptable salt, solvate, ester, amide, or prodrug thereof, wherein X is $CH_2CH_2$.

10. The compound or claim 1, or a pharmaceutically acceptable salt, solvate, ester, amide, or prodrug thereof, wherein Y is C(=O).

11. The compound or claim 1, or a pharmaceutically acceptable salt, solvate, ester, amide, or prodrug thereof, wherein Y is CH(OH).

12. The compound or claim 1, or a pharmaceutically acceptable salt, solvate, ester, amide, or prodrug thereof, wherein each of $R^3$, $R^4$, and $R^5$ is independently hydrogen, $C_{1-8}$ alkyl or $C_{1-8}$ alkyl having halogen.

13. The compound or claim 1, or a pharmaceutically acceptable salt, solvate, ester, amide, or prodrug thereof, wherein $R^3$ is $CH_3$ and $R^4$ and $R^5$ are each hydrogen.

14. The compound or claim 1, or a pharmaceutically acceptable salt, solvate, ester, amide, or prodrug thereof, wherein B is CH.

15. The compound or claim 1, or a pharmaceutically acceptable salt, solvate, ester, amide, or prodrug thereof, wherein Z is oxygen.

16. The compound or claim 1, or a pharmaceutically acceptable salt, solvate, ester, amide, or prodrug thereof, wherein $R^6$ and $R^7$ are each hydrogen.

17. The compound or claim 1, or a pharmaceutically acceptable salt, solvate, ester, amide, or prodrug thereof, wherein $R^X$ is $CH_2OH$, COH, or $COOCH_2CONR^{X4}R^{X5}$.

18. A compound selected from the group consisting of:
1-(4-(2-hydroxyethoxy)-3-methylphenyl)-3-(4-isopropyl-2-(4-(trifluoromethyl)phenyl)thiazol-5-yl)propan-1-one;
1-(4-((1-hydroxy-2-methylpropan-2-yl)oxy)-3-methylphenyl)-3-(4-isopropyl-2-(4-(trifluoromethyl)phenyl)thiazol-5-yl)propan-1-one;
3-(2-(2,4-dichlorophenyl)-5-isopropyloxazol-4-yl)-1-(4-(2-hydroxyethoxy)-3-methylphenyl)propan-1-one;
3-(2-(4-chloro-2-hydroxyphenyl)-5-isopropyloxazol-4-yl)-1-(4-(2-hydroxyethoxy)-3-methylphenyl)propan-1-one;
3-(2-(2,4-dichlorophenyl)-5-isopropyloxazol-4-yl)-1-(4-((1-hydroxy-2-methylpropan-2-yl)oxy)-3-methylphenyl)propan-1-one;
1-(3-allyl-4-(2-hydroxyethoxy)phenyl)-3-(2-(2,4-dichlorophenyl)-5-isopropyloxazol-4-yl)propan-1-one;
3-(2-(2,4-dichlorophenyl)-5-isopropyloxazol-4-yl)-1-(4-((2-hydroxyethyl)thio)-3-methylphenyl)propan-1-one;
3-(2-(4-chloro-2-hydroxyphenyl)-5-isopropyloxazol-4-yl)-1-(4-((1-hydroxy-2-methylpropan-2-yl)oxy)-3-methylphenyl)propan-1-one;
2-(4-(3-(2-(2,4-dichlorophenyl)-5-isopropyloxazol-4-yl)prop-1-en-1-yl)-2-methylphenoxy)ethan-1-ol;
2-(4-(3-(4-isopropyl-2-(4-(trifluoromethyl)phenyl)thiazol-5-yl)prop-1-en-1-yl)-2-methylphenoxy)ethan-1-ol;
3-(4-hexyl-2-(4-(trifluoromethyl)phenyl)thiazol-5-yl)-1-(4-(2-hydroxyethoxy)-3-methylphenyl)propan-1-one;
3-(4-hexyl-2-(4-(trifluoromethyl)phenyl)thiazol-5-yl)-1-(4-((1-hydroxy-2-methylpropan-2-yl)oxy)-3-methylphenyl)propan-1-one;
2-(4-(3-(4-isopropyl-2-(4-(trifluoromethyl)phenyl)thiazol-5-yl)prop-1-en-1-yl)-2-methylphenoxy)-2-methylpropan-1-ol;
1-(4-(2-hydroxyethoxy)-2-methylphenyl)-3-(4-isopropyl-2-(4-(trifluoromethyl)phenyl)thiazol-5-yl)propan-1-one;
3-(2-(2,4-dichlorophenyl)-5-isopropyloxazol-4-yl)-1-(4-(2-hydroxyethoxy)-2-methylphenyl)propan-1-one;
1-(4-((1-hydroxy-2-methylpropan-2-yl)oxy)-2-methylphenyl)-3-(4-isopropyl-2-(4-(trifluoromethyl)phenyl)thiazol-5-yl)propan-1-one;
3-(2-(2,4-dichlorophenyl)-5-isopropyloxazol-4-yl)-1-(4-((1-hydroxy-2-methylpropan-2-yl)oxy)-2-methylphenyl)propan-1-one;

1-(4-(2-hydroxyethoxy)-3-propylphenyl)-3-(4-isopropyl-2-(4-(trifluoromethyl)phenyl)thiazol-5-yl)propan-1-one;
1-(3-allyl-4-(2-hydroxyethoxy)phenyl)-3-(4-isopropyl-2-(4-(trifluoromethyl)phenyl)thiazol-5-yl)propan-1-one;
2-(4-(4-(2-(2,4-dichlorophenyl)-5-isopropyloxazol-4-yl)but-1-en-2-yl)-2-methylphenoxy)ethan-1-ol;
2-(4-(4-(2-(2,4-dichlorophenyl)-5-isopropyloxazol-4-yl)but-1-en-2-yl)-2-methylphenoxy)-2-methylpropan-1-ol;
3-(2-(2,4-dichlorophenyl)-5-isopropyloxazol-4-yl)-1-(4-(2-hydroxyethoxy)-3-methylphenyl)-2-methylpropan-1-one;
3-(2-(2,4-dichlorophenyl)-5-isopropyloxazol-4-yl)-1-(4-((1-hydroxy-2-methylpropan-2-yl)oxy)-3-methylphenyl)-2-methylpropan-1-one;
1-(4-(2-hydroxyethoxy)-3-methylphenyl)-3-(4-isopropyl-2-(4-(trifluoromethyl)phenyl)thiazol-5-yl)prop-2-en-1-one;
1-(4-((1-hydroxy-2-methylpropan-2-yl)oxy)-3-methylphenyl)-3-(4-isopropyl-2-(4-(trifluoromethyl)phenyl)thiazol-5-yl)prop-2-en-1-one;
1-(4-(3-hydroxypropoxy)-3-methylphenyl)-3-(4-isopropyl-2-(4-methoxyphenyl)thiazol-5-yl)propan-1-one;
3-(2-(3,5-difluorophenyl)-4-isopropylthiazol-5-yl)-1-(4-(2-hydroxyethoxy)-3-methylphenyl)propan-1-one;
3-(2-(3,5-difluorophenyl)-4-isopropylthiazol-5-yl)-1-(4-((1-hydroxy-2-methylpropan-2-yl)oxy)-3-methylphenyl)propan-1-one;
1-(4-(2-hydroxyethoxy)-3-methylphenyl)-3-(4-isopropyl-2-(naphthalen-2-yl)thiazol-5-yl)propan-1-one;
1-(4-((1-hydroxy-2-methylpropan-2-yl)oxy)-3-methylphenyl)-3-(4-isopropyl-2-(naphthalen-2-yl)thiazol-5-yl)propan-1-one;
3-(2-(4-butylphenyl)-4-isopropylthiazol-5-yl)-1-(4-(2-hydroxyethoxy)-3-methylphenyl)propan-1-one;
3-(2-(4-butylphenyl)-4-isopropylthiazol-5-yl)-1-(4-((1-hydroxy-2-methylpropan-2-yl)oxy)-3-methylphenyl)propan-1-one;
1-(3-chloro-4-(2-hydroxyethoxy)phenyl)-3-(4-isopropyl-2-(4-(trifluoromethyl)phenyl)thiazol-5-yl)propan-1-one;
1-(3-chloro-4-((1-hydroxy-2-methylpropan-2-yl)oxy)phenyl)-3-(4-isopropyl-2-(4-(trifluoromethyl)phenyl)thiazol-5-yl)propan-1-one;
1-(3-chloro-4-(2-hydroxyethoxy)phenyl)-3-(2-(2,4-dichlorophenyl)-5-isopropyloxazol-4-yl)propan-1-one;
1-(3-chloro-4-((1-hydroxy-2-methylpropan-2-yl)oxy)phenyl)-3-(2-(2,4-dichlorophenyl)-5-isopropyloxazol-4-yl)propan-1-one;
1-(4-(2-hydroxyethoxy)-3-methylphenyl)-3-(5-isopropyl-2-(4-(trifluoromethyl)phenyl)thiazol-4-yl)propan-1-one;
1-(4-((1-hydroxy-2-methylpropan-2-yl)oxy)-3-methylphenyl)-3-(5-isopropyl-2-(4-(trifluoromethyl)phenyl)thiazol-4-yl)propan-1-one;
3-(2-(2,4-dichlorophenyl)-5-isopropylthiazol-4-yl)-1-(4-(2-hydroxyethoxy)-3-methylphenyl)propan-1-one;
3-(2-(2,4-dichlorophenyl)-5-isopropylthiazol-4-yl)-1-(4-((1-hydroxy-2-methylpropan-2-yl)oxy)-3-methylphenyl)propan-1-one;
1-(3-(2-hydroxyethoxy)-4-methylphenyl)-3-(4-isopropyl-2-(4-(trifluoromethyl)phenyl)thiazol-5-yl)propan-1-one;
1-(3-((1-hydroxy-2-methylpropan-2-yl)oxy)-4-methylphenyl)-3-(4-isopropyl-2-(4-(trifluoromethyl)phenyl)thiazol-5-yl)propan-1-one;
1-(4-((1-hydroxypropan-2-yl)oxy)-3-methylphenyl)-3-(4-isopropyl-2-(4-(trifluoromethyl)phenyl)thiazol-5-yl)propan-1-one;
1-(4-(2-hydroxyethoxy)-3-methylphenyl)-3-(4-methyl-2-(4-(trifluoromethyl)phenyl)thiazol-5-yl)propan-1-one;
2-(4-(3-(4-hexyl-2-(4-(trifluoromethyl)phenyl)thiazol-5-yl)prop-1-en-1-yl)-2-methylphenoxy)-2-methylpropan-1-ol;
3-(4-hexyl-2-(4-(trifluoromethyl)phenyl)thiazol-5-yl)-1-(3-((1-hydroxy-2-methylpropan-2-yl)oxy)-4-methylphenyl)propan-1-one;
3-(4-ethyl-2-(4-(trifluoromethyl)phenyl)thiazol-5-yl)-1-(4-(2-hydroxyethoxy)-3-methylphenyl)propan-1-one;
3-(4-ethyl-2-(4-(trifluoromethyl)phenyl)thiazol-5-yl)-1-(4-((1-hydroxy-2-methylpropan-2-yl)oxy)-3-methylphenyl)propan-1-one;
1-(4-(2-hydroxyethoxy)-3-methylphenyl)-3-(4-isopropyl-2-(p-tolyl)thiazol-5-yl)propan-1-one;
1-(4-((1-hydroxy-2-methylpropan-2-yl)oxy)-3-methylphenyl)-3-(4-isopropyl-2-(p-tolyl)thiazol-5-yl)propan-1-one;
2-((3-(2-(2-(2,4-dichlorophenyl)-5-isopropyloxazol-4-yl)ethyl)-5-methylbenzo[d]isoxazol-6-yl)oxy)ethan-1-ol;
1-(4-(2-hydroxyethyl)-3-methylphenyl)-3-(4-isopropyl-2-(4-(trifluoromethyl)phenyl)thiazol-5-yl)propan-1-one;
1-(4-(2-hydroxyethoxy)-3-methylphenyl)-3-(4-isopropyl-2-(4-(trifluoromethyl)phenyl)thiazol-5-yl)propan-1-ol;
(R)-1-(4-(2-hydroxyethoxy)-3-methylphenyl)-3-(4-isopropyl-2-(4-(trifluoromethyl)phenyl)thiazol-5-yl)propan-1-ol;
1-(4-((1-hydroxy-2-methylpropan-2-yl)oxy)-3-methylphenyl)-3-(4-isopropyl-2-(4-(trifluoromethyl)phenyl)thiazol-5-yl)propan-1-ol;
3-(2-(2,4-dichlorophenyl)-5-isopropyloxazol-4-yl)-1-(4-(2-hydroxyethoxy)-3-methylphenyl)propan-1-ol;
5-chloro-2-(4-(3-hydroxy-3-(4-(2-hydroxyethoxy)-3-methylphenyl)propyl)-5-isopropyloxazol-2-yl)phenol;
3-(2-(2,4-dichlorophenyl)-5-isopropyloxazol-4-yl)-1-(4-((1-hydroxy-2-methylpropan-2-yl)oxy)-3-methylphenyl)propan-1-ol;
1-(3-allyl-4-(2-hydroxyethoxy)phenyl)-3-(2-(2,4-dichlorophenyl)-5-isopropyloxazol-4-yl)propan-1-ol;
3-(2-(2,4-dichlorophenyl)-5-isopropyloxazol-4-yl)-1-(4-((2-hydroxyethyl)thio)-3-methylphenyl)propan-1-ol;
5-chloro-2-(4-(3-hydroxy-3-(4-((1-hydroxy-2-methylpropan-2-yl)oxy)-3-methylphenyl)propyl)-5-isopropyloxazol-2-yl)phenol;
3-(4-hexyl-2-(4-(trifluoromethyl)phenyl)thiazol-5-yl)-1-(4-(2-hydroxyethoxy)-3-methylphenyl)propan-1-ol;
3-(4-hexyl-2-(4-(trifluoromethyl)phenyl)thiazol-5-yl)-1-(4-((1-hydroxy-2-methylpropan-2-yl)oxy)-3-methylphenyl)propan-1-ol;
1-(4-(2-hydroxyethoxy)-2-methylphenyl)-3-(4-isopropyl-2-(4-(trifluoromethyl)phenyl)thiazol-5-yl)propan-1-ol;
3-(2-(2,4-dichlorophenyl)-5-isopropyloxazol-4-yl)-1-(4-(2-hydroxyethoxy)-2-methylphenyl)propan-1-ol;
1-(4-((1-hydroxy-2-methylpropan-2-yl)oxy)-2-methylphenyl)-3-(4-isopropyl-2-(4-(trifluoromethyl)phenyl)thiazol-5-yl)propan-1-ol;
3-(2-(2,4-dichlorophenyl)-5-isopropyloxazol-4-yl)-1-(4-((1-hydroxy-2-methylpropan-2-yl)oxy)-2-methylphenyl)propan-1-ol;
1-(4-(2-hydroxyethoxy)-3-propylphenyl)-3-(4-isopropyl-2-(4-(trifluoromethyl)phenyl)thiazol-5-yl)propan-1-one;

1-(3-allyl-4-(2-hydroxyethoxy)phenyl)-3-(4-isopropyl-2-(4-(trifluoromethyl)phenyl)thiazol-5-yl)propan-1-ol;
3-(2-(2,4-dichlorophenyl)-5-isopropyloxazol-4-yl)-1-(4-(2-hydroxyethoxy)-3-methylphenyl)-2-methylpropan-1-ol;
3-(2-(2,4-dichlorophenyl)-5-isopropyloxazol-4-yl)-1-(4-((1-hydroxy-2-methylpropan-2-yl)oxy)-3-methylphenyl)-2-methylpropan-1-ol;
1-(4-(2-hydroxyethoxy)-3-methylphenyl)-3-(4-isopropyl-2-(4-(trifluoromethyl)phenyl)thiazol-5-yl)prop-2-en-1-ol;
1-(4-((1-hydroxy-2-methylpropan-2-yl)oxy)-3-methylphenyl)-3-(4-isopropyl-2-(4-(trifluoromethyl)phenyl)thiazol-5-yl)prop-2-en-1-ol;
1-(4-(3-hydroxypropoxy)-3-methylphenyl)-3-(4-isopropyl-2-(4-methoxyphenyl)thiazol-5-yl)propan-1-ol;
3-(2-(3,5-difluorophenyl)-4-isopropylthiazol-5-yl)-1-(4-(2-hydroxyethoxy)-3-methylphenyl)propan-1-ol;
3-(2-(3,5-difluorophenyl)-4-isopropylthiazol-5-yl)-1-(4-((1-hydroxy-2-methylpropan-2-yl)oxy)-3-methylphenyl)propan-1-ol;
1-(4-(2-hydroxyethoxy)-3-methylphenyl)-3-(4-isopropyl-2-(naphthalen-2-yl)thiazol-5-yl)propan-1-ol;
1-(4-((1-hydroxy-2-methylpropan-2-yl)oxy)-3-methylphenyl)-3-(4-isopropyl-2-(naphthalen-2-yl)thiazol-5-yl)propan-1-ol;
3-(2-(4-butylphenyl)-4-isopropylthiazol-5-yl)-1-(4-(2-hydroxyethoxy)-3-methylphenyl)propan-1-ol;
3-(2-(4-butylphenyl)-4-isopropylthiazol-5-yl)-1-(4-((1-hydroxy-2-methylpropan-2-yl)oxy)-3-methylphenyl)propan-1-ol;
1-(3-chloro-4-(2-hydroxyethoxy)phenyl)-3-(4-isopropyl-2-(4-(trifluoromethyl)phenyl)thiazol-5-yl)propan-1-ol;
1-(3-chloro-4-((1-hydroxy-2-methylpropan-2-yl)oxy)phenyl)-3-(4-isopropyl-2-(4-(trifluoromethyl)phenyl)thiazol-5-yl)propan-1-ol;
1-(3-chloro-4-(2-hydroxyethoxy)phenyl)-3-(2-(2,4-dichlorophenyl)-5-isopropyloxazol-4-yl)propan-1-ol;
1-(3-chloro-4-((1-hydroxy-2-methylpropan-2-yl)oxy)phenyl)-3-(2-(2,4-dichlorophenyl)-5-isopropyloxazol-4-yl)propan-1-ol;
1-(4-(2-hydroxyethoxy)-3-methylphenyl)-3-(5-isopropyl-2-(4-(trifluoromethyl)phenyl)thiazol-4-yl)propan-1-ol;
1-(4-((1-hydroxy-2-methylpropan-2-yl)oxy)-3-methylphenyl)-3-(5-isopropyl-2-(4-(trifluoromethyl)phenyl)thiazol-4-yl)propan-1-ol;
3-(2-(2,4-dichlorophenyl)-5-isopropylthiazol-4-yl)-1-(4-(2-hydroxyethoxy)-3-methylphenyl)propan-1-ol;
3-(2-(2,4-dichlorophenyl)-5-isopropylthiazol-4-yl)-1-(4-((1-hydroxy-2-methylpropan-2-yl)oxy)-3-methylphenyl)propan-1-ol;
1-(3-(2-hydroxyethoxy)-4-methylphenyl)-3-(4-isopropyl-2-(4-(trifluoromethyl)phenyl)thiazol-5-yl)propan-1-ol;
1-(3-((1-hydroxy-2-methylpropan-2-yl)oxy)-4-methylphenyl)-3-(4-isopropyl-2-(4-(trifluoromethyl)phenyl)thiazol-5-yl)propan-1-ol;
1-(4-((1-hydroxypropan-2-yl)oxy)-3-methylphenyl)-3-(4-isopropyl-2-(4-(trifluoromethyl)phenyl)thiazol-5-yl)propan-1-ol;
1-(4-(2-hydroxyethoxy)-3-methylphenyl)-3-(4-methyl-2-(4-(trifluoromethyl)phenyl)thiazol-5-yl)propan-1-one;
3-(4-hexyl-2-(4-(trifluoromethyl)phenyl)thiazol-5-yl)-1-(3-((1-hydroxy-2-methylpropan-2-yl)oxy)-4-methylphenyl)propan-1-ol;
3-(4-ethyl-2-(4-(trifluoromethyl)phenyl)thiazol-5-yl)-1-(4-(2-hydroxyethoxy)-3-methylphenyl)propan-1-ol;
3-(4-ethyl-2-(4-(trifluoromethyl)phenyl)thiazol-5-yl)-1-(4-((1-hydroxy-2-methylpropan-2-yl)oxy)-3-methylphenyl)propan-1-ol;
1-(4-(2-hydroxyethoxy)-3-methylphenyl)-3-(4-isopropyl-2-(p-tolyl)thiazol-5-yl)propan-1-ol;
1-(4-((1-hydroxy-2-methylpropan-2-yl)oxy)-3-methylphenyl)-3-(4-isopropyl-2-(p-tolyl)thiazol-5-yl)propan-1-ol;
1-(4-(2-hydroxyethyl)-3-methylphenyl)-3-(4-isopropyl-2-(4-(trifluoromethyl)phenyl)thiazol-5-yl)propan-1-ol; and pharmaceutically acceptable salts, solvates, esters, amides, and prodrugs thereof.

19. A compound having the structure:

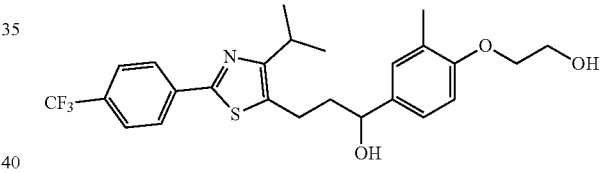

or pharmaceutically acceptable salt, solvate, ester, amide, or prodrug thereof.

20. A pharmaceutical composition comprising the compound or claim 1, or a pharmaceutically acceptable salt, solvate, ester, amide, or prodrug thereof and a pharmaceutically acceptable carrier or vehicle.

* * * * *